US012758709B2

(12) United States Patent
McLoughlin et al.

(10) Patent No.: US 12,758,709 B2
(45) Date of Patent: Oct. 13, 2026

(54) DRUG CARTRIDGE, DRUG DELIVERY DEVICE, AND METHODS FOR PREPARING THEREOF

(71) Applicant: Bristol-Myers Squibb Company, Princeton, NJ (US)

(72) Inventors: Martin John McLoughlin, Hillsborough, NJ (US); Mark Steven Howansky, Basking Ridge, NJ (US); George Tyler Currier, Somerset, NJ (US); Peter William Heyman, Florham Park, NJ (US); Yuhong Wu, Skillman, NJ (US); Erinc Sahin, East Brunswick, NJ (US); Shreya Shashank Kulkarni, North Brunswick, NJ (US); Ankur Sagar Kulshrestha, Hillsborough, NJ (US); Xiaodong Chen, Belle Mead, NJ (US); Haresh Tukaram More, Mountainside, NJ (US); Krishna Jagdish Patel, Lawrenceville, NJ (US); John Christian Knutsen, Crosswicks, NJ (US); James William Kidner Bradford, Cambridge (GB); Simon Francis Brereton, Baldock (GB); Timothy Donald Barrow-Williams, St. Albans (GB); Christopher William Rosier, Cambridge (GB); Jeffrey Nicholas Philippson, Cambridge (GB); Ryan Anthony McGinley, Cambridge (GB); Francesco Giuseppe Sasia, London (GB); Holly Charlotte Palmer, Rutland (GB); Tomas Alexander Ogg Correa, Melbourne (AU); Carys Eleri Lee, Cambridge (GB); Paul Antony Merritt, Royston (GB); Terence Zhi Seow, Royston (GB)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 356 days.

(21) Appl. No.: 18/569,136

(22) PCT Filed: Jun. 13, 2022

(86) PCT No.: PCT/US2022/033259
§ 371 (c)(1),
(2) Date: Dec. 11, 2023

(87) PCT Pub. No.: WO2022/261543
PCT Pub. Date: Dec. 15, 2022

(65) Prior Publication Data

US 2024/0390580 A1 Nov. 28, 2024

Related U.S. Application Data

(60) Provisional application No. 63/209,673, filed on Jun. 11, 2021.

(51) Int. Cl.
*A61M 5/168* (2006.01)

(52) U.S. Cl.
CPC ............................... *A61M 5/16827* (2013.01)

(58) Field of Classification Search
CPC .......... A61M 5/14248; A61M 5/16827; A61M 5/1408; A61M 5/1409; A61M 5/1407
See application file for complete search history.

(56) References Cited

U.S. PATENT DOCUMENTS 4,666,429 A * 5/1987 Stone ................. A61M 5/1408 604/83
5,088,515 A 2/1992 Kamen
(Continued)

FOREIGN PATENT DOCUMENTS

WO 9640328 A2 12/1996
WO 2020072233 A1 4/2020
WO 2020112515 A1 6/2020

OTHER PUBLICATIONS

International Search Report from PCT International Application No. PCT/US2022/033259 dated Jan. 26, 2023.

*Primary Examiner* — Laura A Bouchelle
(74) *Attorney, Agent, or Firm* — Budzyn IP Law, LLC

(57) ABSTRACT

In one aspect, a drug delivery device is provided herein including: a monolithic body having a plurality of fluid ducts and at least one outlet duct formed therein; a plurality of drug cartridges attached to the body, the drug cartridges each including a reservoir for accommodating at least one drug wherein, the plurality of fluid ducts is arranged to convey the drugs from the drug cartridges to the at least one outlet duct; and, a needle support spaced from the body, the needle
(Continued)

support including a needle configured for insertion into a patient for drug delivery, the needle support including adhesive for releasable securement to a patient, wherein, the needle support is connected to the body by a flexible tether through which passes at least one fluid passageway formed to convey drug from the at least one outlet duct to the needle.

8 Claims, 288 Drawing Sheets

(56) References Cited

U.S. PATENT DOCUMENTS

| | | | | |
|---|---|---|---|---|
| 5,190,524 | A * | 3/1993 | Wex | A61M 5/1408<br>604/83 |
| 8,257,320 | B2 * | 9/2012 | Feith | A61M 5/1408<br>604/83 |
| 2006/0241550 | A1 | 10/2006 | Kamen et al. | |
| 2010/0234805 | A1 | 9/2010 | Kaufmann et al. | |
| 2013/0010825 | A1 | 1/2013 | Kamen et al. | |
| 2013/0237947 | A1 | 9/2013 | Amirouche et al. | |
| 2014/0088549 | A1 | 3/2014 | Cole et al. | |
| 2015/0025498 | A1 | 1/2015 | Estes | |
| 2018/0064867 | A1 | 3/2018 | Crane et al. | |

* cited by examiner

- hub and primary container sub-assembly can rotate through a small rotation
- encourages 'sloshing' in primary containers to accelerate recon

Sensing a clog via premature drop in pressure at Pump OR by pressure differential between Reservoir and Pump

Flow Reversal Triggered

Clog is Broken

DRUG CARTRIDGE, DRUG DELIVERY DEVICE, AND METHODS FOR PREPARING THEREOF

FIELD OF THE INVENTION

The subject invention relates to methods of preparing drug cartridges and drug delivery devices.

BACKGROUND OF THE INVENTION

Sterilization techniques are well known in the medical arts, particularly for sterilizing drug cartridges and drug delivery devices intended for parenteral drug delivery. Techniques have been developed in the prior art involving sterilization of a drug delivery device, such as an injector, at a manufacturing facility, with the sterilized device being packaged, e.g., in a pouch, to maintain sterility till point of use. Separately, drug is prepared, maintained in a sterile state, and introduced into the drug delivery device at the point of use.

Techniques have been also developed in the prior art for preparing pre-filled drug delivery devices wherein a drug delivery device is loaded with drug at a manufacturing facility, sterilized, and packaged to maintain sterility at point of use.

It is also desirable from a convenience standpoint for a patient receiving combination drug therapy to be able to receive all of their prescribed drugs from a single injection device. This invention describes a device that can be loaded with one or several drugs, either in ready-to-use liquid or to-be-reconstituted dry format, in the prescribed ratio for that particular patient, reconstitute the dry drugs, and then automatically deliver those drugs sequentially to the patient.

SUMMARY OF THE INVENTION

In one aspect, a drug delivery device is provided herein including: a monolithic body having a plurality of fluid ducts and at least one outlet duct formed therein; a plurality of drug cartridges attached to the body, the drug cartridges each including a reservoir for accommodating at least one drug wherein, the plurality of fluid ducts is arranged to convey the drugs from the drug cartridges to the at least one outlet duct; and, a needle support spaced from the body, the needle support including a needle configured for insertion into a patient for drug delivery, the needle support including adhesive for releasable securement to a patient, wherein, the needle support is connected to the body by a flexible tether through which passes at least one fluid passageway formed to convey drug from the at least one outlet duct to the needle.

In a further aspect, a drug delivery device is provided herein including: a monolithic body having a plurality of fluid ducts and at least one outlet duct formed therein; and, a plurality of drug cartridges attached to the body, the drug cartridges each including a reservoir for accommodating at least one drug, wherein, a first of the drug cartridges includes a fluid outlet, wherein, a first of the fluid ducts, is aligned to extend from the fluid outlet, wherein, a first opening is formed in a first face of the body, the first fluid duct extending to the first opening, wherein, a second of the fluid ducts extends from the first opening and along the first face so as to be exposed along the first face, and, wherein, a second opening is formed in the first face of the body, the second fluid duct extending to the second opening, the second opening being in fluid communication with the at least one outlet duct.

In yet a further aspect, a drug delivery device is provided herein including: a body having a plurality of fluid ducts and at least one outlet duct formed therein; a plurality of drug cartridges attached to the body, the drug cartridges each including a reservoir for accommodating at least one drug; and, a displaceable actuator plate disposed adjacent to the body, wherein, a first of the drug cartridges includes a fluid outlet, wherein, a first of the fluid ducts, is aligned to extend from the fluid outlet, wherein, a displaceable seal selectively seals the fluid outlet, the seal being displaceable from a first state, where the fluid outlet is sealed, to a second state, where the fluid outlet is not sealed, and, wherein the displacement of the actuator plate causes displacement of the seal from the first state to the second state.

In still yet a further aspect, a method is provided herein of reconstituting drug in a drug delivery device, the method including: providing a reservoir of drug in a dry state; introducing a diluent into the reservoir to interact with the drug to generate an intermediate mixture, wherein pressure of the diluent is monitored during the introducing, the diluent being introduced into the reservoir until a predetermined pressure is reached; drawing the intermediate mixture from the reservoir; conveying the intermediate mixture through a vent to vent trapped gasses to generate a vented mixture; and, introducing the vented mixture into the reservoir.

Advantageously, the subject invention provides a drug delivery device useable in large volume and/or combinatorial drug delivery.

Also, advantageously, the subject invention provides a drug delivery device configured with controllable multiple flow paths, to direct flow for delivery, mixing, and reconstitution, as needed.

As used herein, a "drug" or "drug component," may be used interchangeably, and shall mean any therapeutic agent in any physical state (e.g., solid, liquid, suspension) and/or any component, in any physical state, intended to be mixed with, or otherwise co-act with, any therapeutic agent, such as a diluent and/or any combinations or mixtures thereof (e.g., a mixture of diluent and one or therapeutic agents). The drug may be prepared using any known technique, including, but not limited to, lyophilization, spray-dried dispersion (SDD), spray-freeze drying (SFD), and, melt crystallization (e.g., to form crystallized suspensions).

As used herein, "ultraviolet radiation" shall mean electromagnetic radiation with wavelengths generally found within the ultraviolet portion of the light spectrum, including within the range of 100-315 nm, suitable for decontamination. Ultraviolet radiation includes electromagnetic radiation within the ultraviolet B (UVB) range (280-315 nm) and/or electromagnetic radiation with wavelengths within the ultraviolet C (UVC) range (100-280 nm).

As used herein, an "electron-beam" shall mean a concentrated highly-charged stream of electrons suitable for decontamination. The electron beam may be characterized as "low energy," e.g., as a having a kinetic energy of 300 keV.

As used herein, "x-ray radiation" shall mean electromagnetic radiation with energy in the range of up to 10 MeV, possibly being up to 7.5 MeV. The x-ray radiation may be characterized as being within the wavelength range for "soft" x-rays, "hard" x-rays or gamma rays. The x-ray radiation may be applied to reach a dose of up to 25 kGy. Alternatively, a lower dose may be applied to achieve a sufficient sterility assurance level for a relevant bioburden.

Also used herein, "pulsed light" shall mean repeated, short bursts of electromagnetic radiation suitable for decontamination, including electromagnetic radiation within visible and invisible portions of the light spectrum. Each burst of the pulsed light may be characterized as "high energy," e.g., on the order of 300 J, with a high-power flash, e.g., on the order of 1 mW, delivered over a short duration on the order of 0.3 milliseconds. Pulsed light may include ultra-violet radiation, where ultraviolet radiation is applied in repeated short bursts, including ultraviolet radiation in the UVB and UVC ranges, as well as the ultraviolet A (UVA) range (315-400 nm). Additionally, pulsed light may include any electromagnetic radiation effective in decontamination, including, but, not limited to, x-ray radiation, light in the visible spectrum (400-770 nm) and/or infrared radiation within the infrared portion of the light spectrum (770-1100 nm). As will be understood by those skilled in the art, pulses of pulsed light may include a mix of different types of electromagnetic radiation, e.g., including visible light with ultraviolet radiation, e.g., UVC.

As used herein, "decontamination," and variants thereof, shall mean removal of germs, bacteria or other living microorganisms. High levels of such removal are achievable, including levels acceptable for sterilization.

These and other features of the subject invention shall be better understood through a study of the following detailed description and accompanying drawings.

BRIEF DESCRIPTION OF THE DRAWINGS

FIG. 40A-1 shows the initial, sealed, state of a system for accessing a drug cartridge by shifting two seals, in accordance with the subject invention.

FIG. 40A-2 shows the final, opened, state of a system of FIG. 40A-1.

FIG. 73C shows the UV threshold dose achieved after thirty seconds of ultraviolet radiation exposure.

FIG. 74 shows a drug delivery device with a further alternate barrel-configured drug cartridge, in accordance with the subject invention.

FIG. 75 shows plunger actuation in the drug delivery device of FIG. 74.

FIG. 76 shows plunger actuation in the opposing direction, following the action shown in FIG. 75.

FIG. 77 shows plunger rotation to another barrel, following the action shown in FIG. 76.

FIG. 78 shows plunger actuation, following the action shown in FIG. 77.

FIG. 79A shows a drug delivery device worn via a clip on a patient's clothing, in accordance with the subject invention.

FIG. 79B is a side view of the drug delivery device of FIG. 79A.

FIG. 80A shows a drug delivery device worn via adhesive on a patient's abdomen, in accordance with the subject invention.

FIG. 80B is a side view of the drug delivery device of FIG. 80A.

FIG. 81A shows a drug delivery device worn via a strap or belt across a patient's waist, in accordance with the subject invention.

FIG. 81B is a side view of the drug delivery device of FIG. 81A.

Figure 82B:
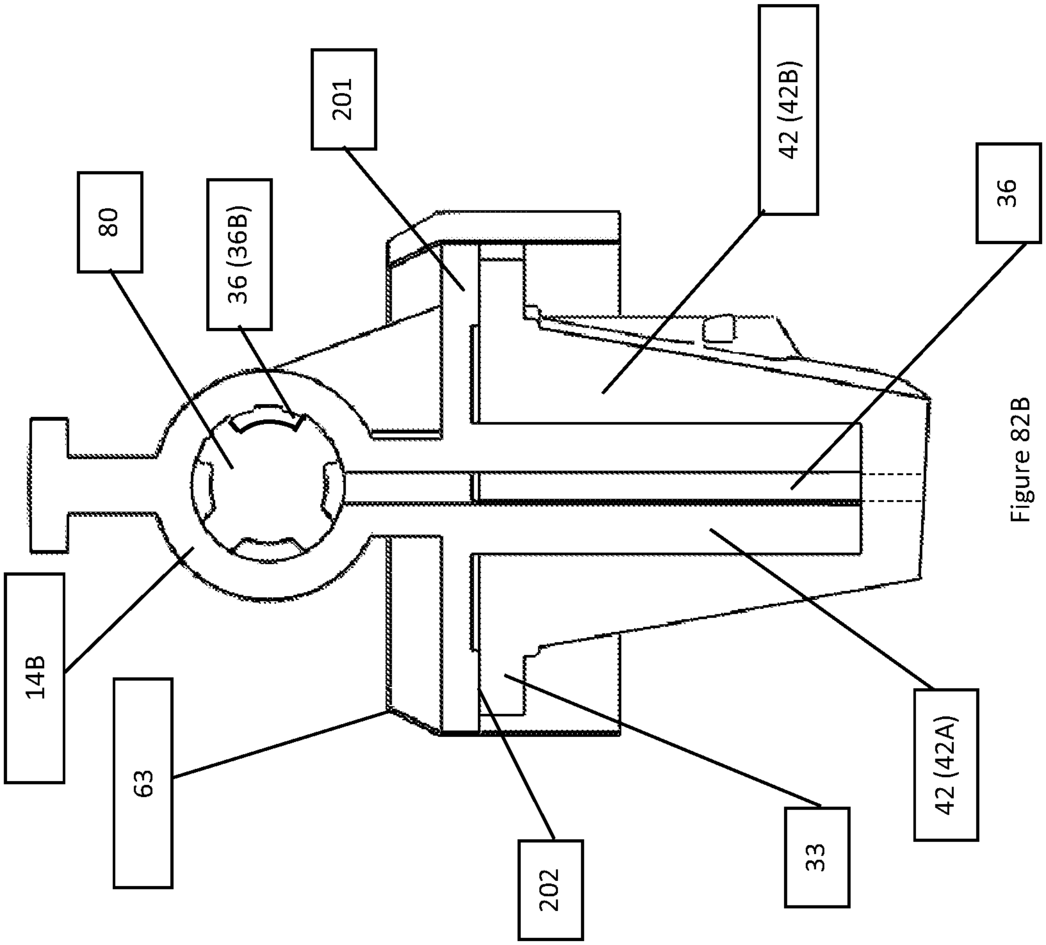
Figure 82A:
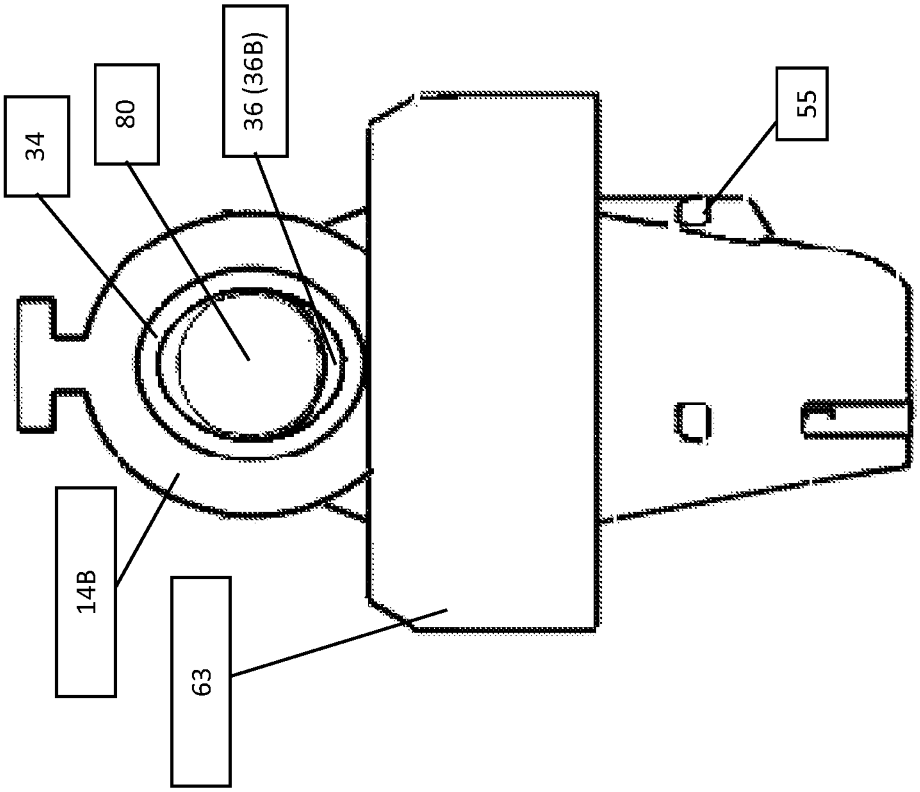

FIG. 82A is a top view of an alternative plug adapter useable with the subject invention.

FIG. 82B is a section view of the plug adapter of FIG. 82A.

Figure 83B:
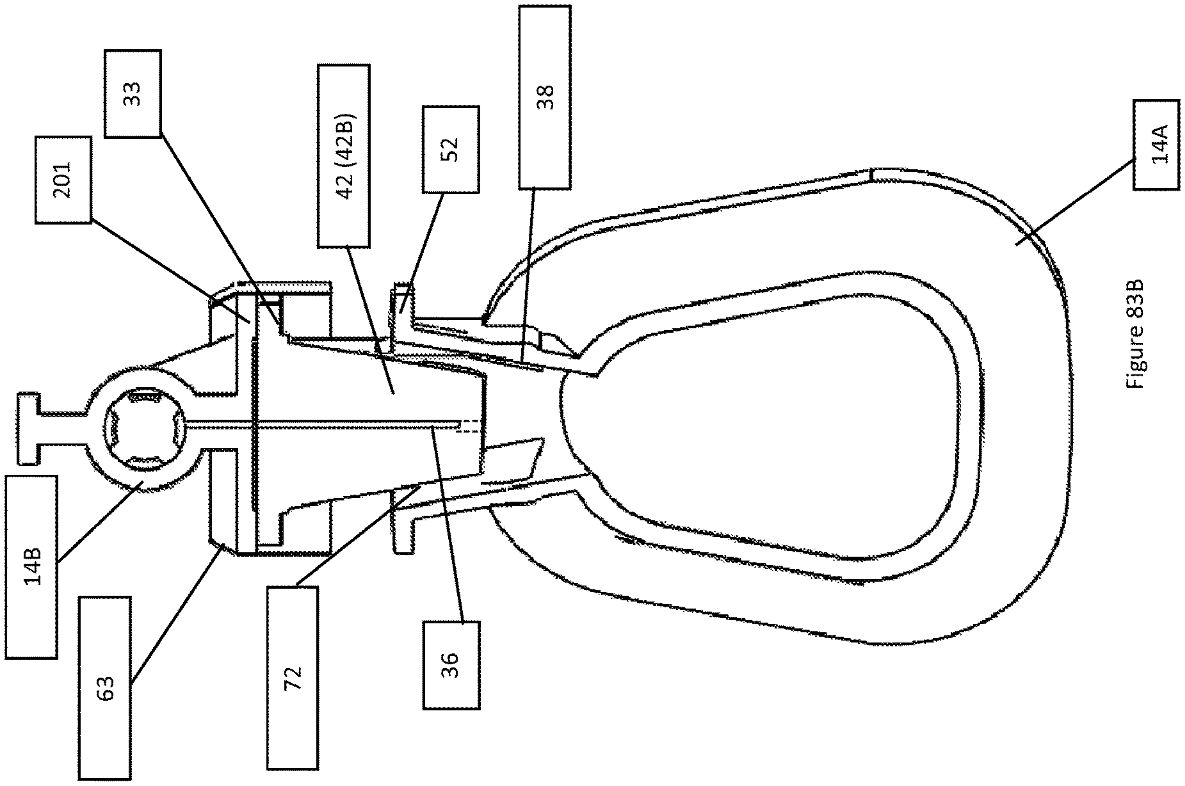
Figure 83A:
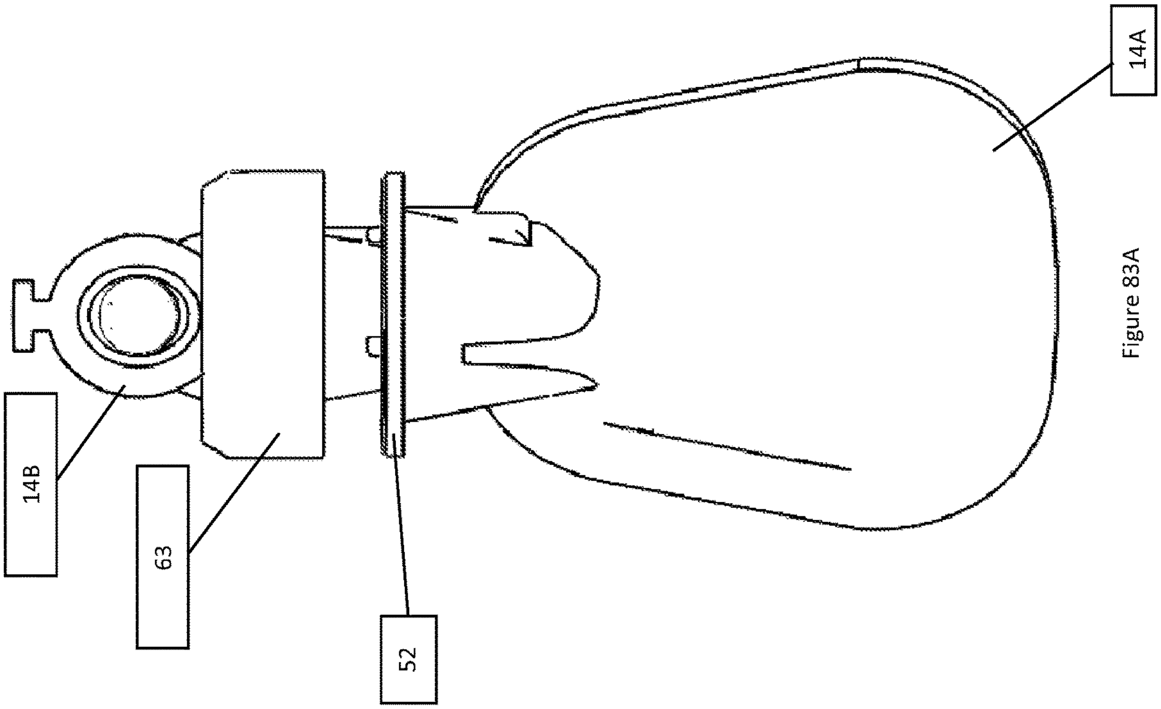

FIG. 83A is a top view of a drug cartridge including the plug adapter of FIG. 82A.

FIG. 83B is a section view of the drug cartridge of FIG. 83A, prior to assembly with a ferrule.

Figure 84B:
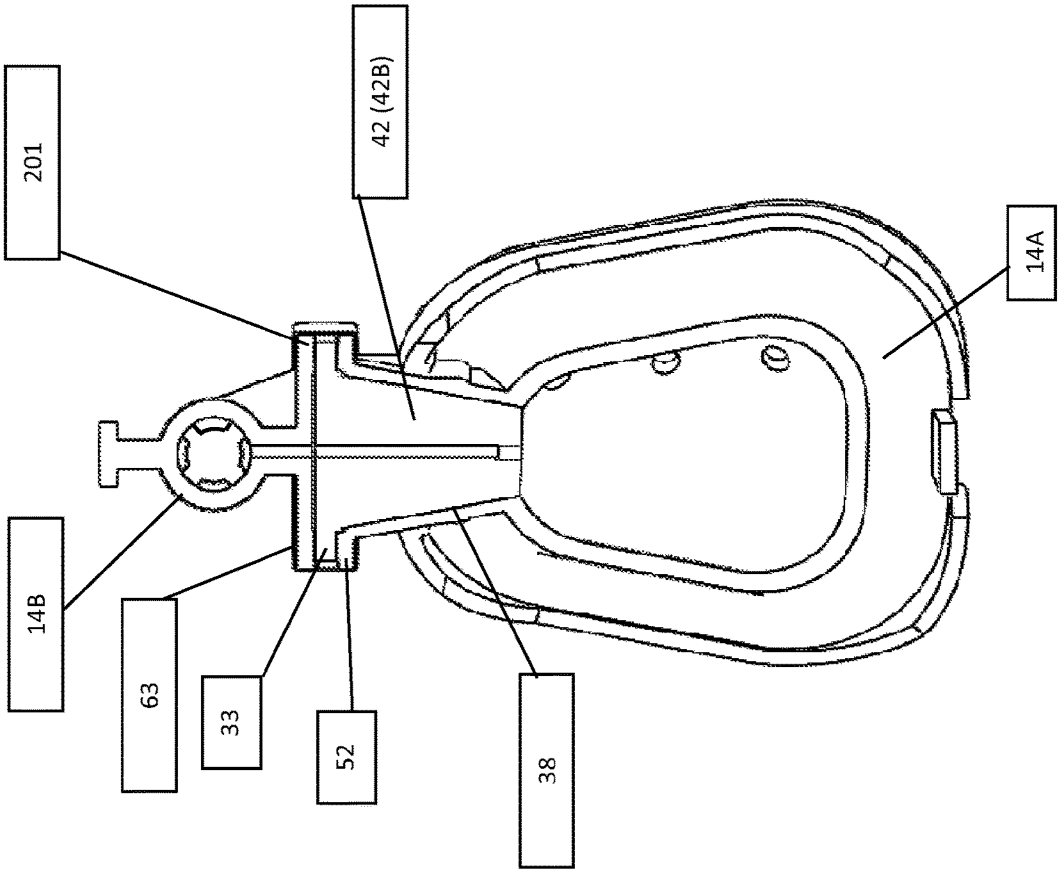
Figure 84A:
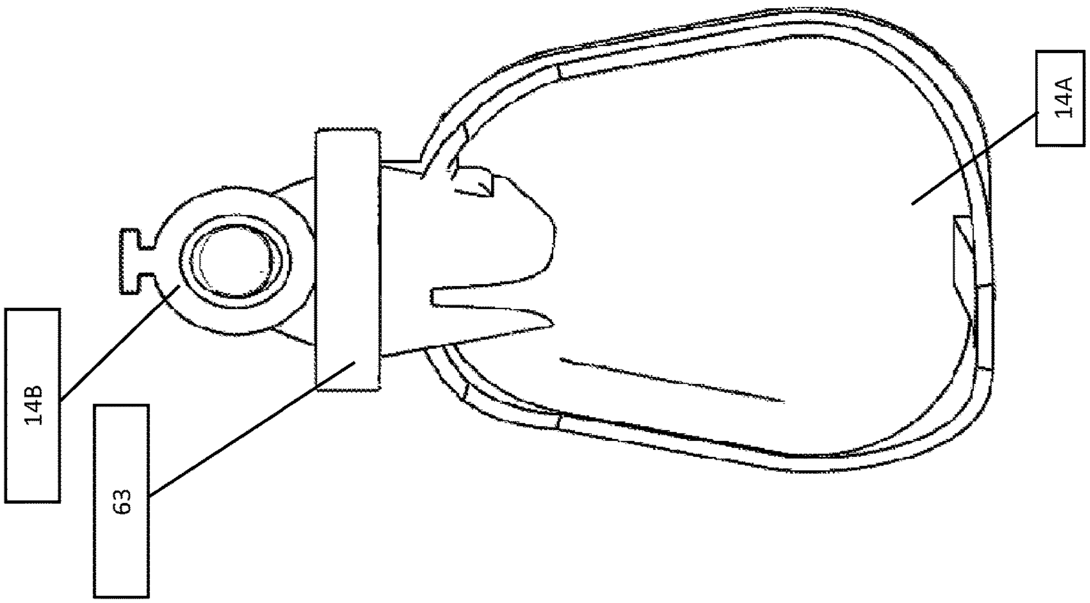

FIG. 84A is a top view of the drug cartridge of FIG. 83A, with the ferrule mounted thereto.

FIG. 84B is a section view of the drug cartridge of FIG. 84A.

Figure 85:
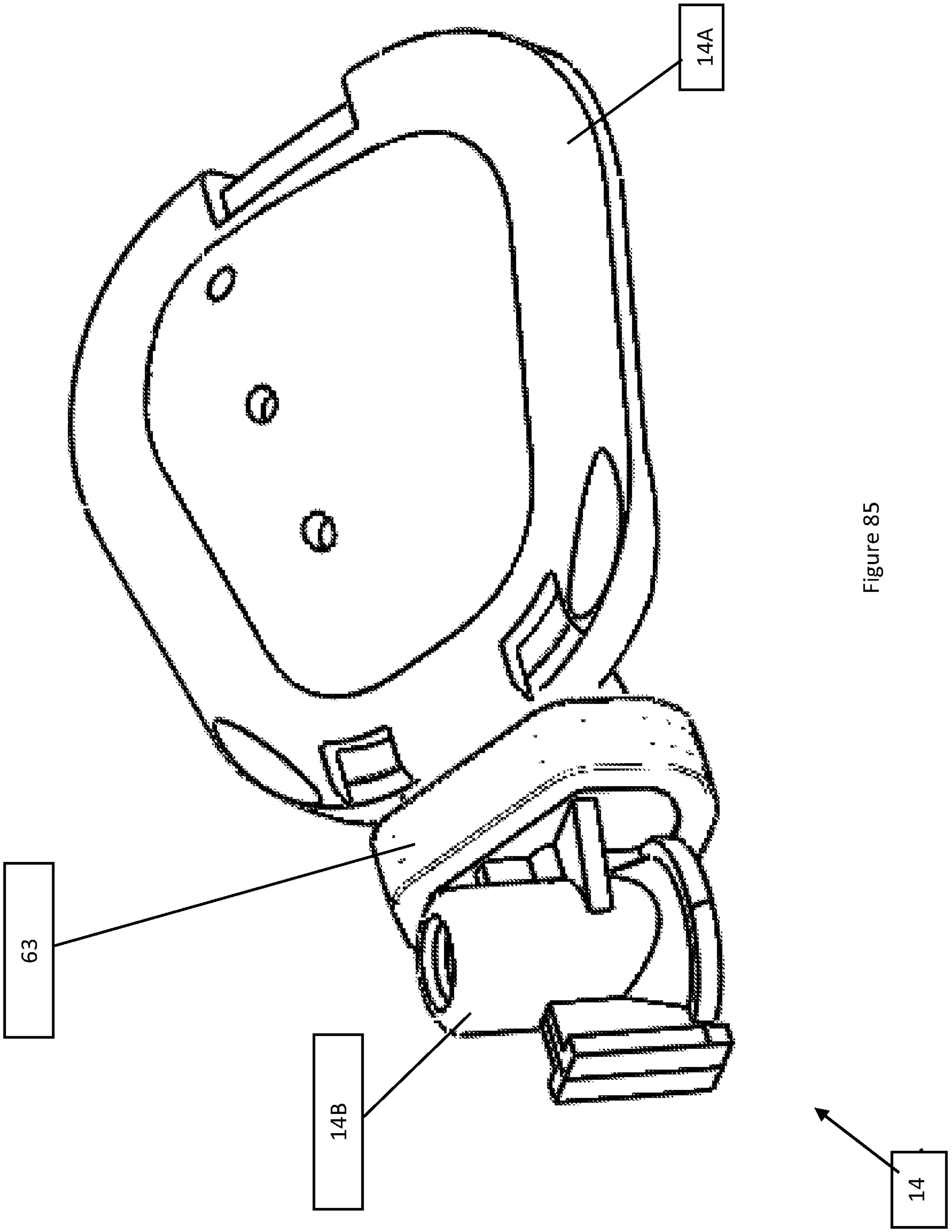

FIG. 85 is an isometric view of a drug cartridge, with a ferrule mounted thereto, in accordance with the subject invention.

Figure 86:
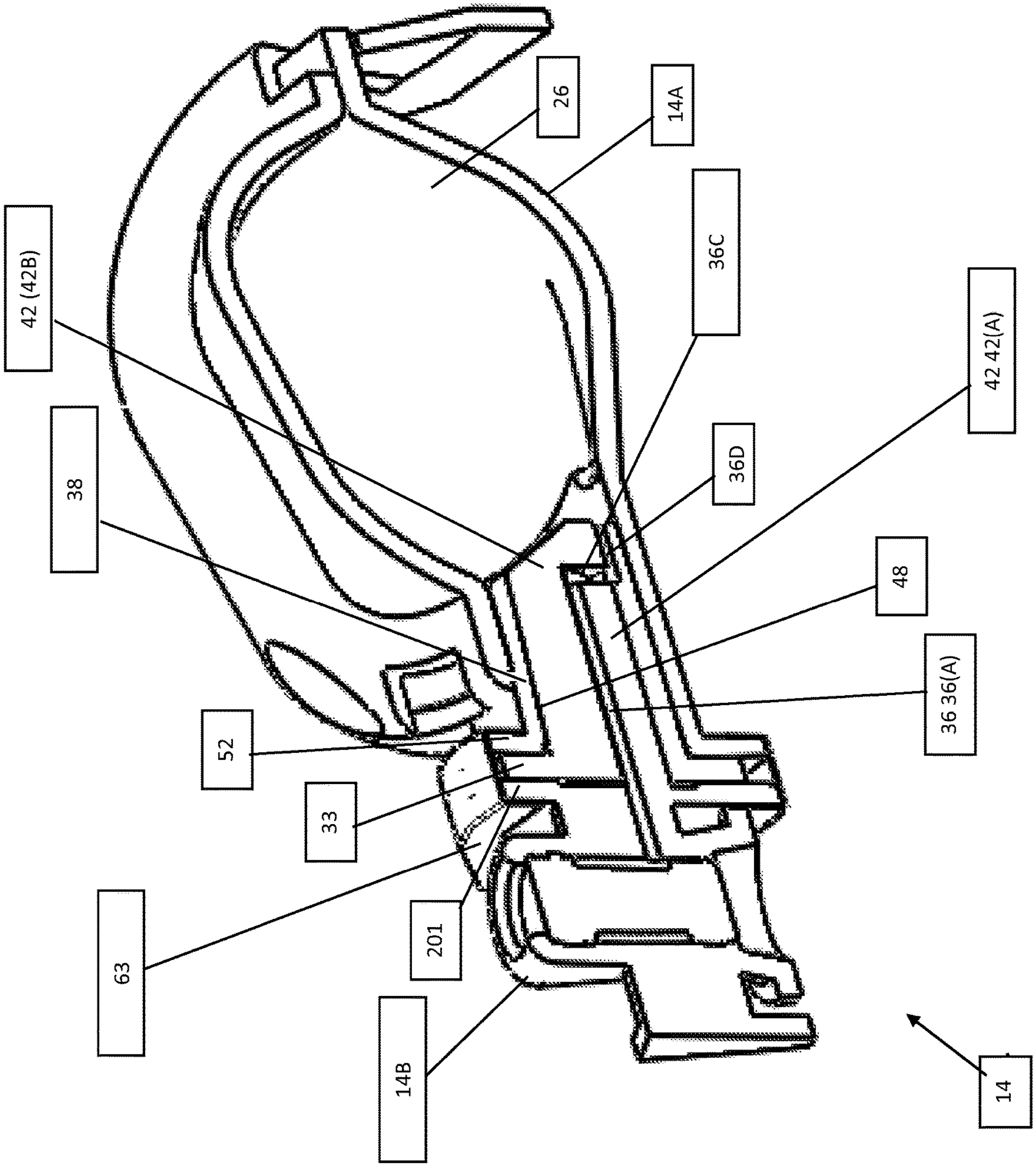

FIG. 86 is a section view of the drug cartridge of FIG. 85.

Figure 87B:
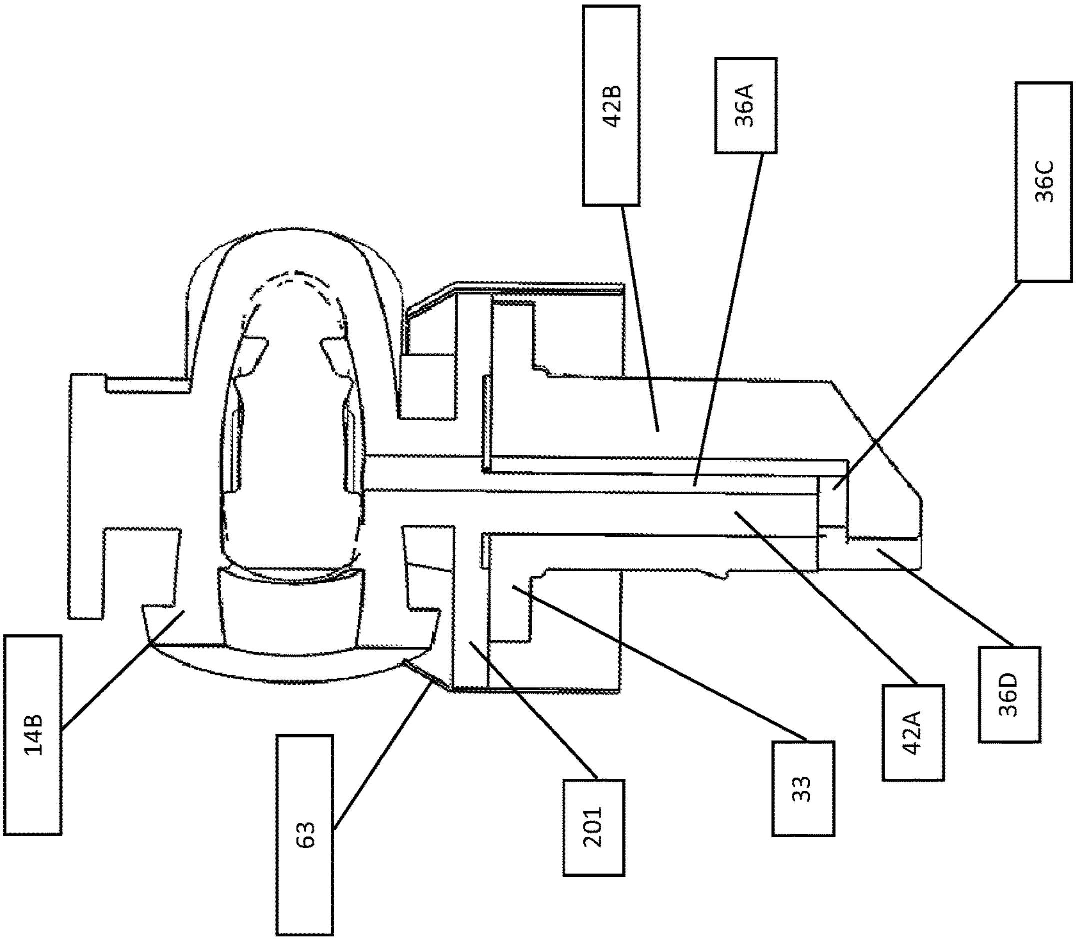
Figure 87A:
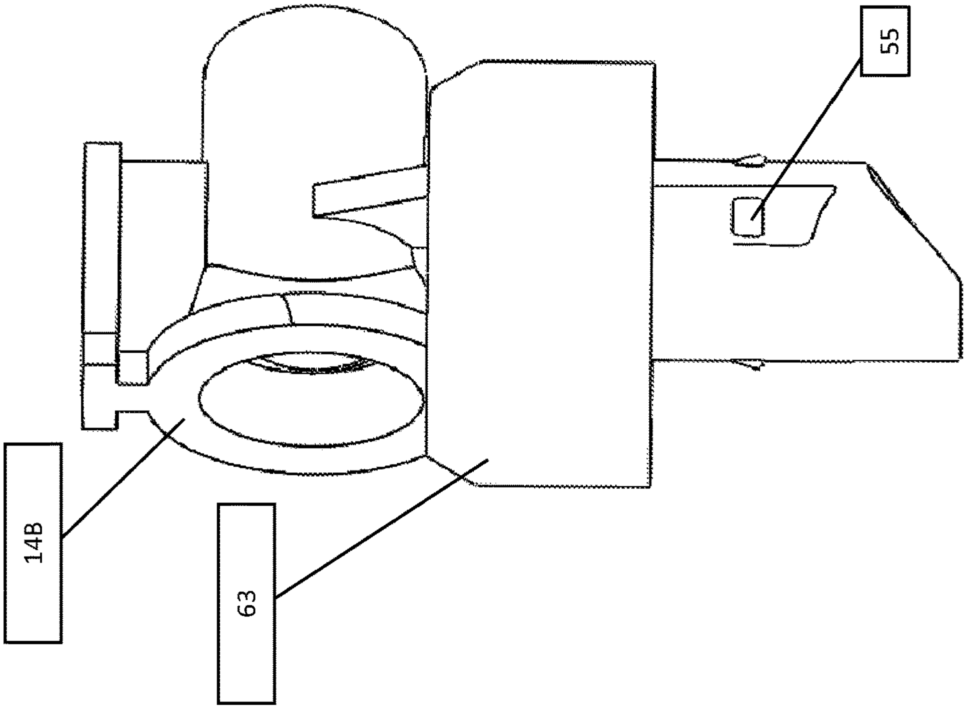

FIG. 87A is a side view of an alternative plug adapter useable with the subject invention.

FIG. 87B is a section view of the plug adapter of FIG. 87A.

Figure 88B:
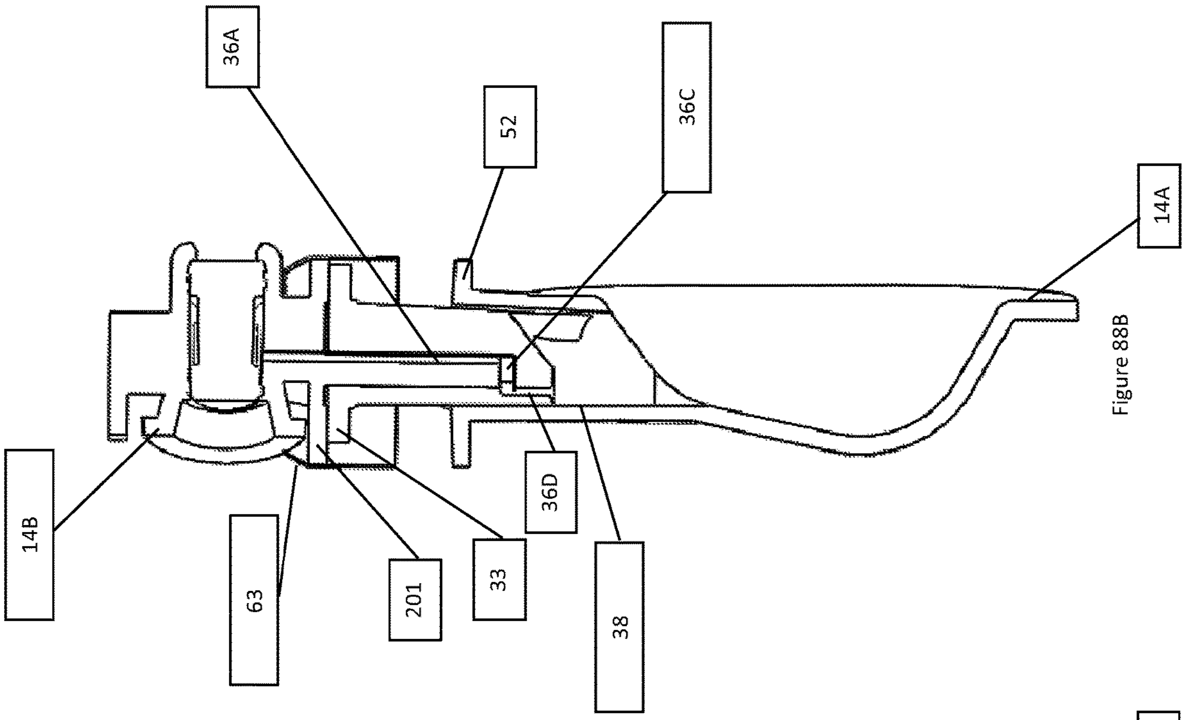
Figure 88A:
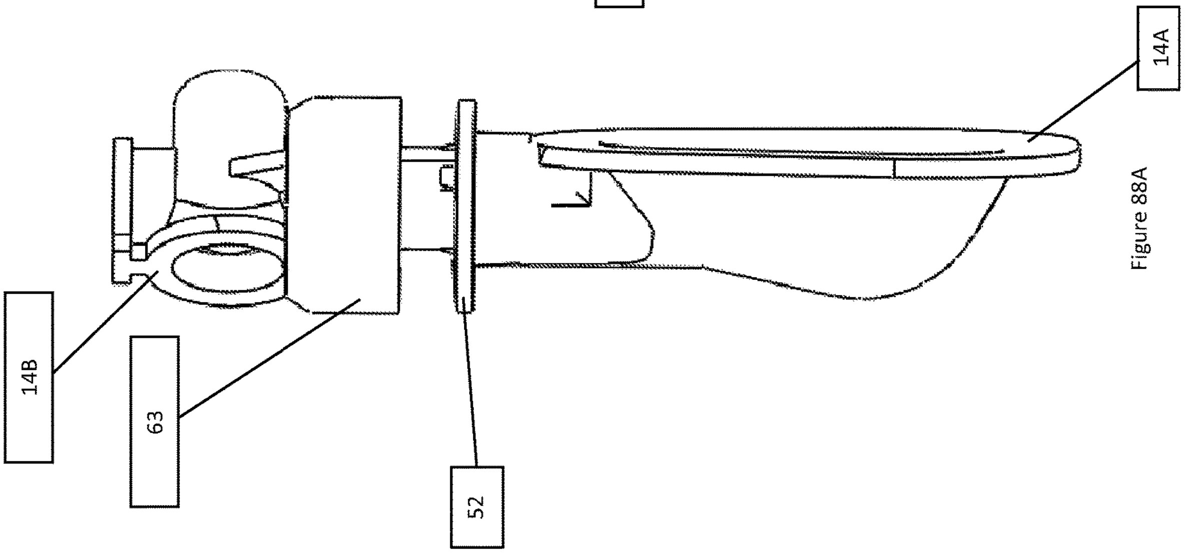

FIG. 88A is a top view of a drug cartridge including the plug adapter of FIG. 87A.

FIG. 88B is a section view of the drug cartridge of FIG. 88A, prior to assembly with a ferrule.

Figure 89B:
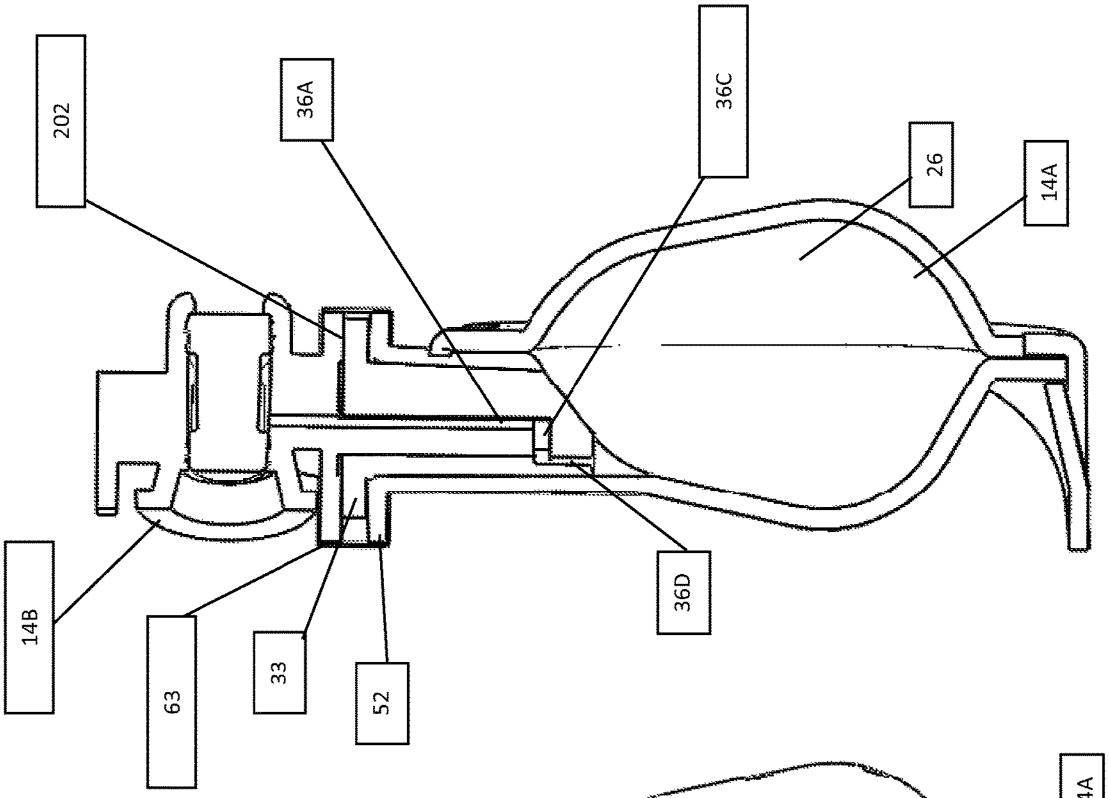
Figure 89A:
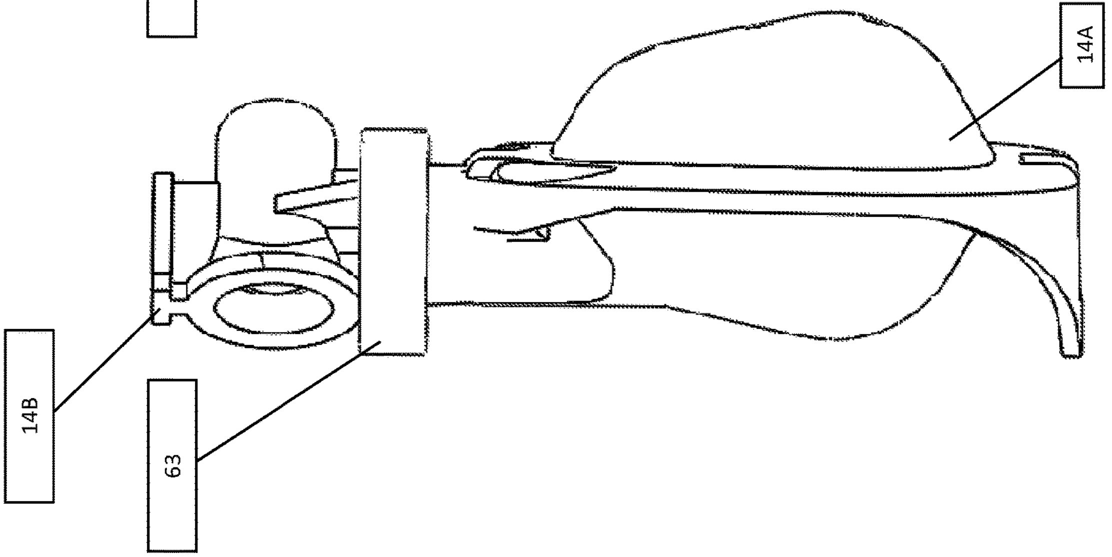

FIG. 89A is a top view of the drug cartridge of FIG. 88A, with the ferrule mounted thereto.

FIG. 89B is a section view of the drug cartridge of FIG. 89A.

FIGS. 90-94B are schematics showing various fluidic arrangements useable with the subject invention.

Figure 95:
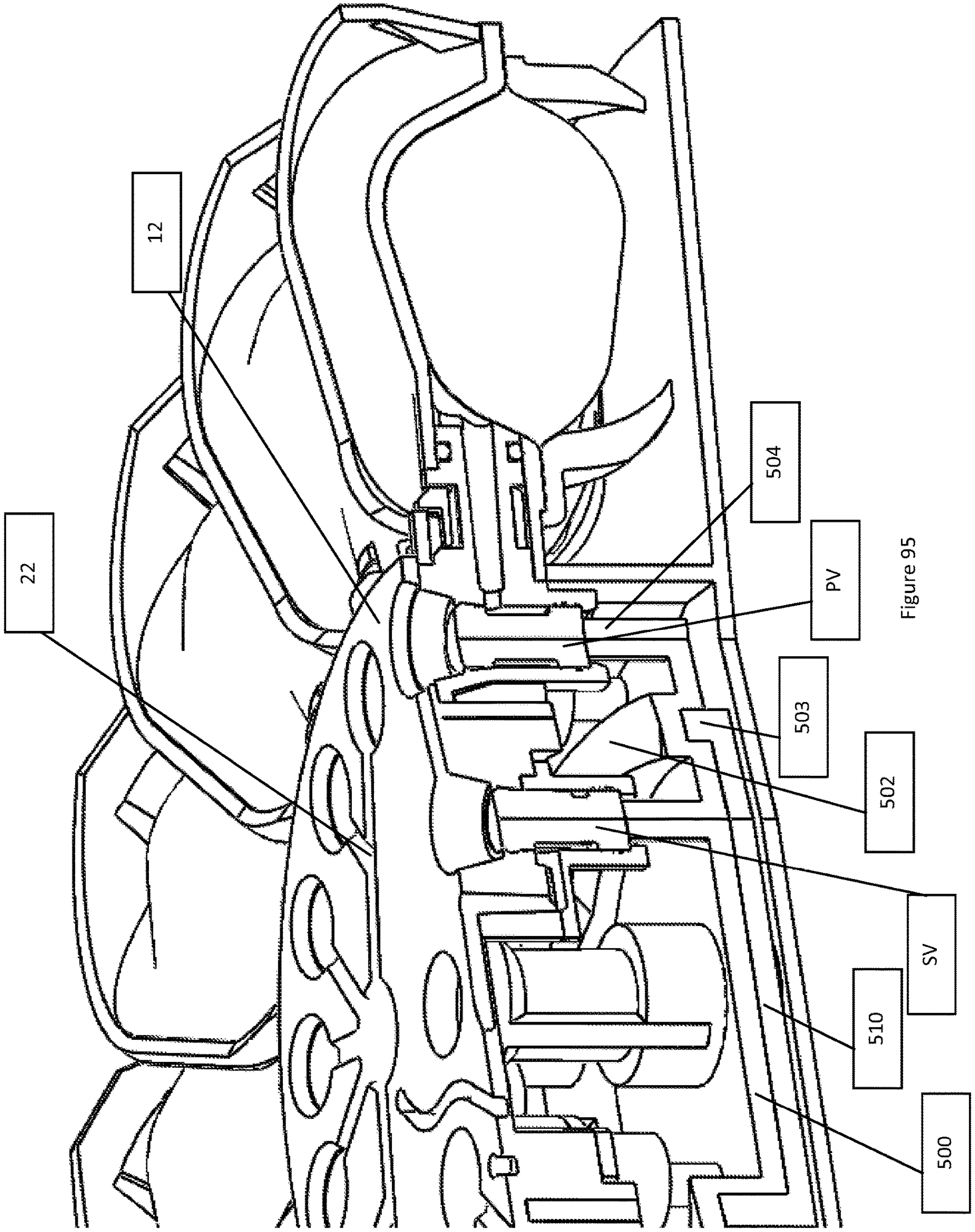

FIG. 95 is a section view of a displaceable actuator plate useable with the subject invention.

Figure 96A:
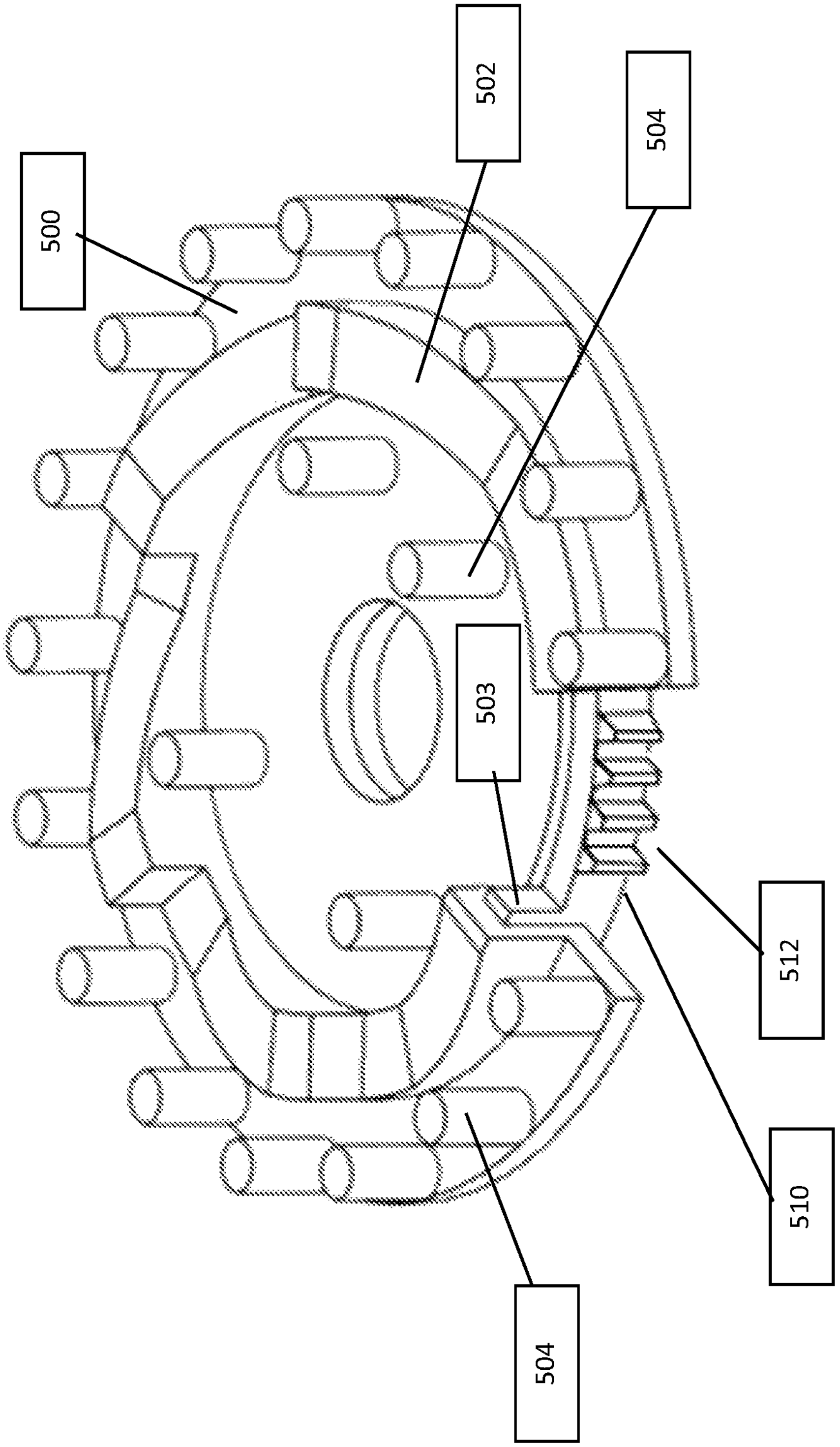

FIG. 96A is a section view of the actuator plate resting upon a gear plate.

Figure 96B:
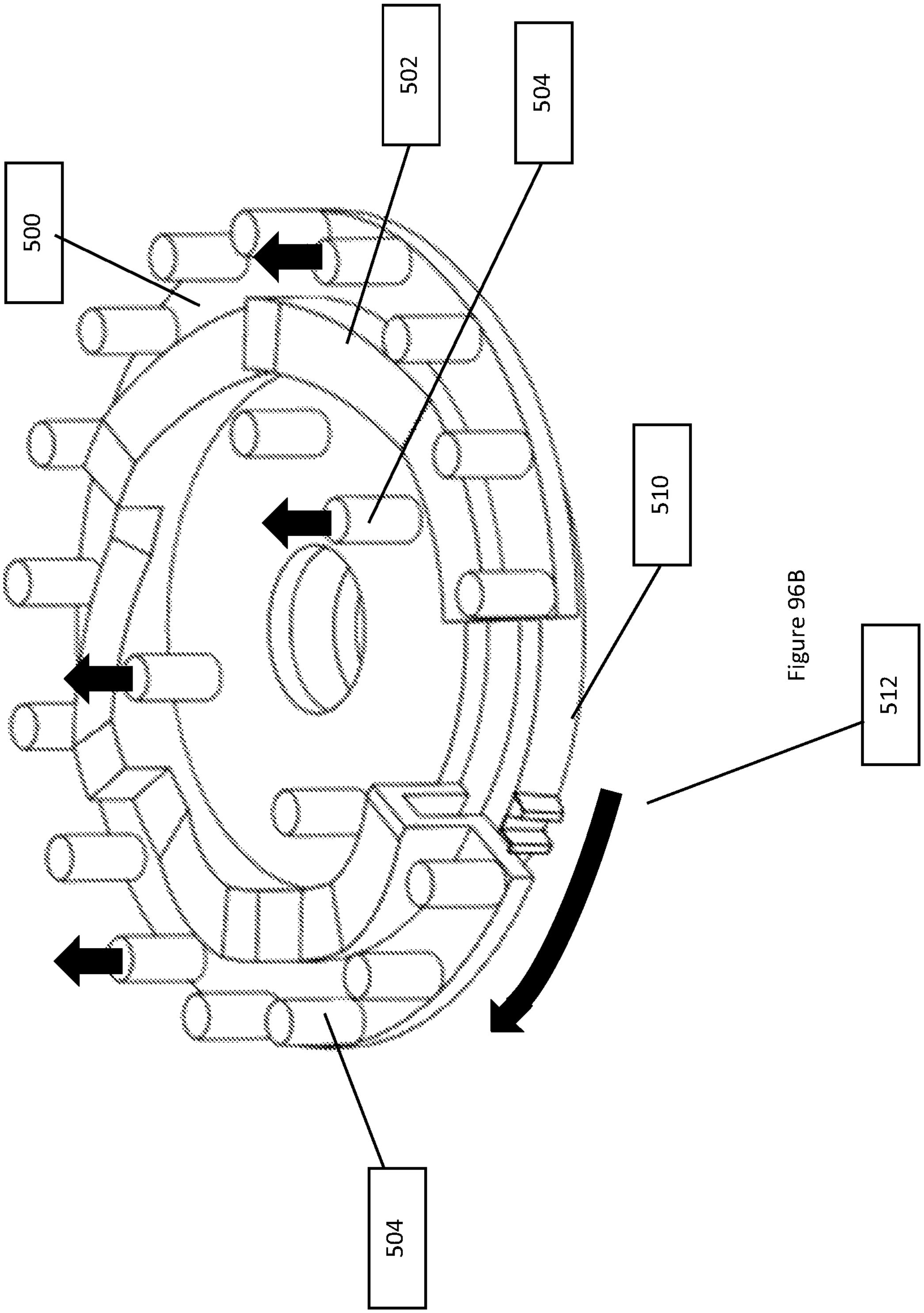

FIG. 96B is a section view similar to FIG. 96A showing the gear plate rotating resulting in lifting of the actuator plate.

Figure 96C:
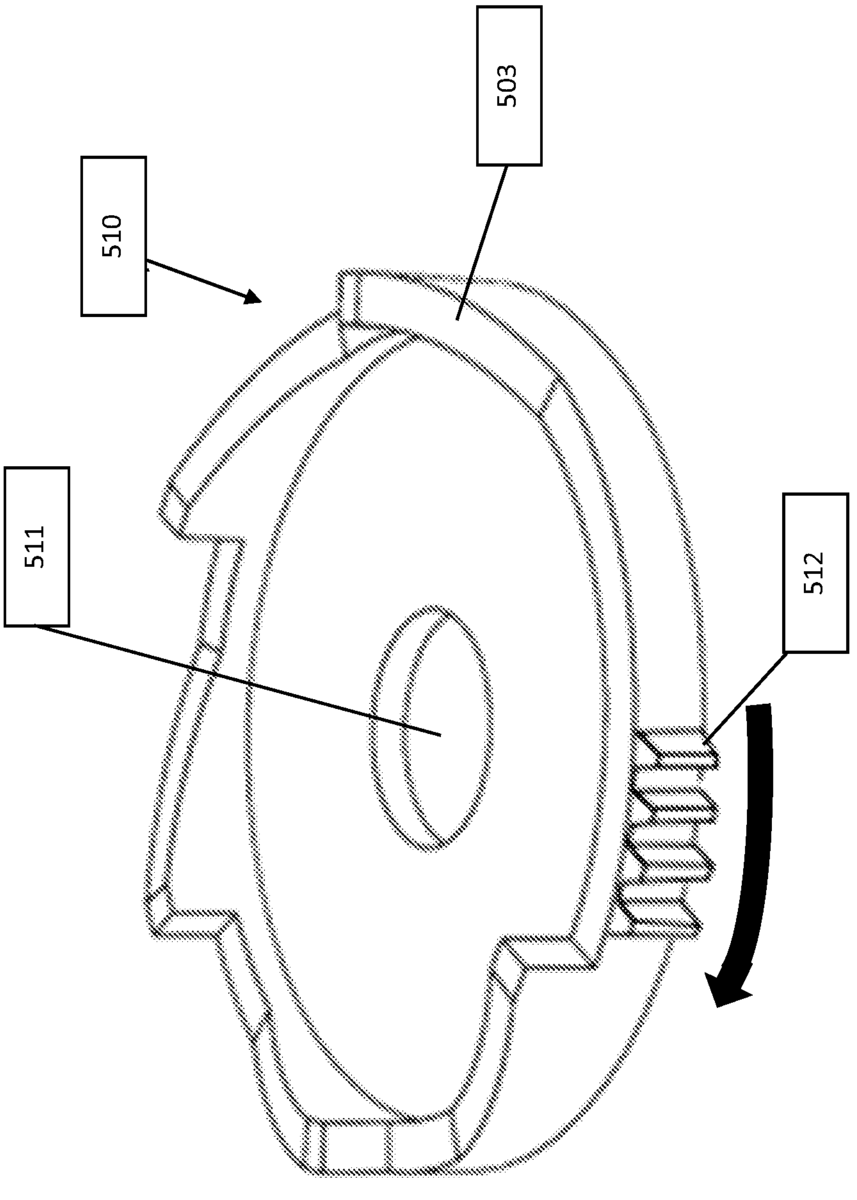

FIG. 96C is a top view of the gear plate of FIG. 96A.

Figure 96D:
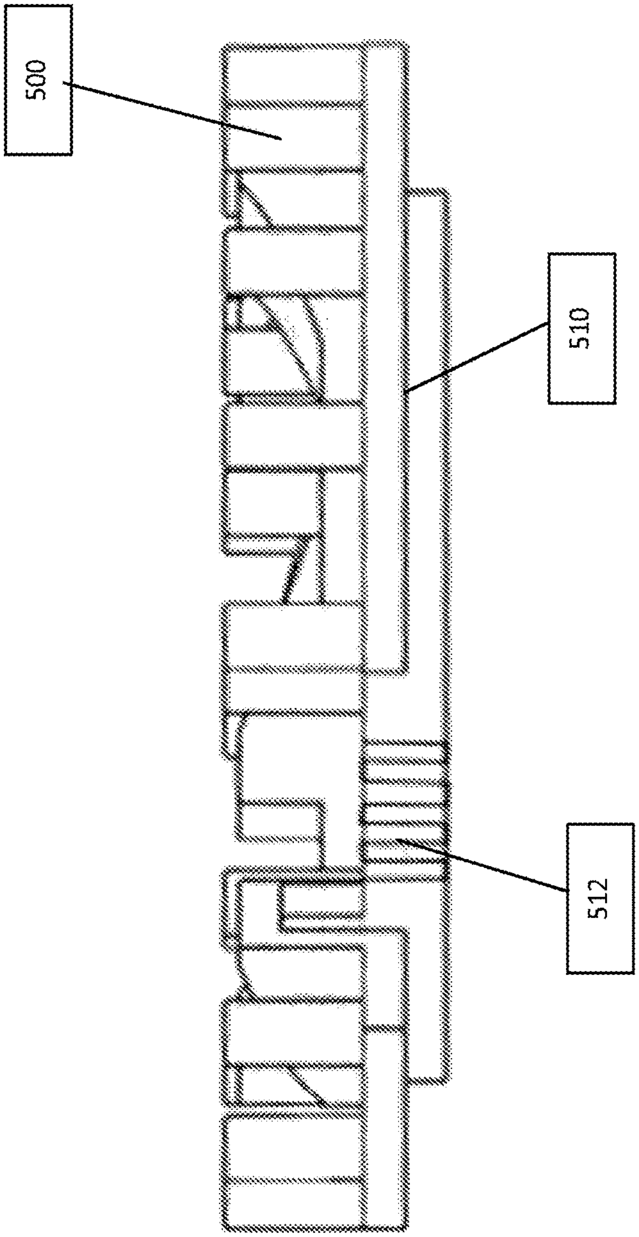

FIG. 96D is a side view of FIG. 96A.

Figure 96E:
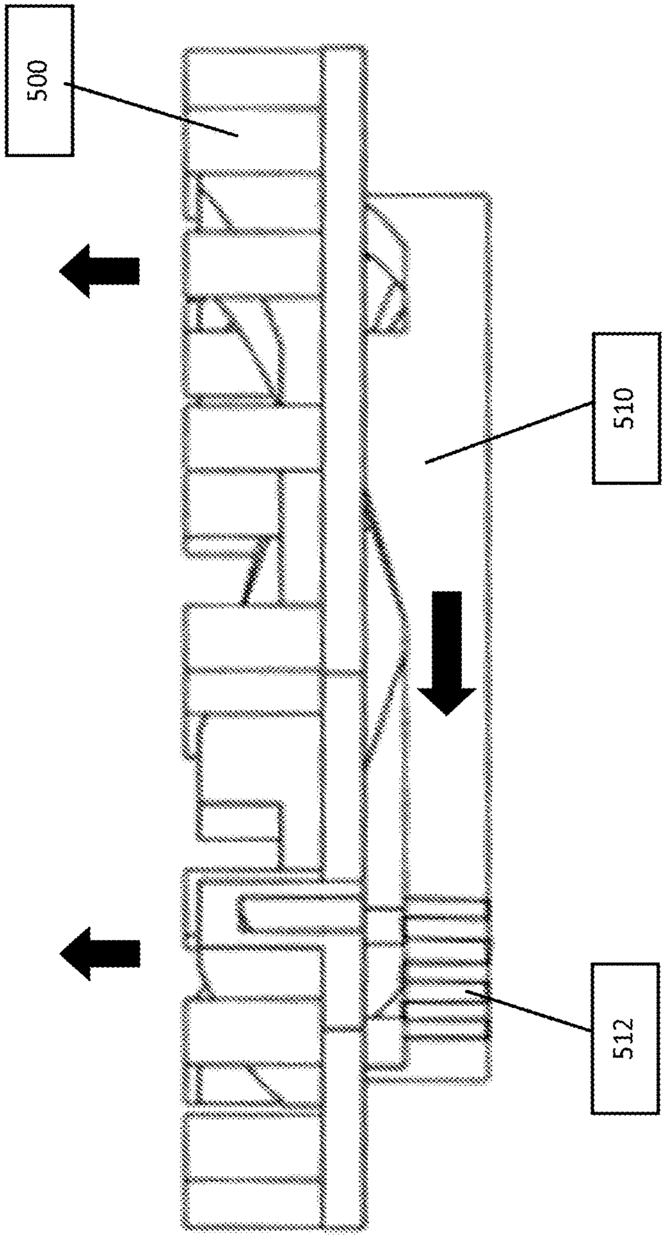

FIG. 96E is a side view of FIG. 96B.

Figure 97A:
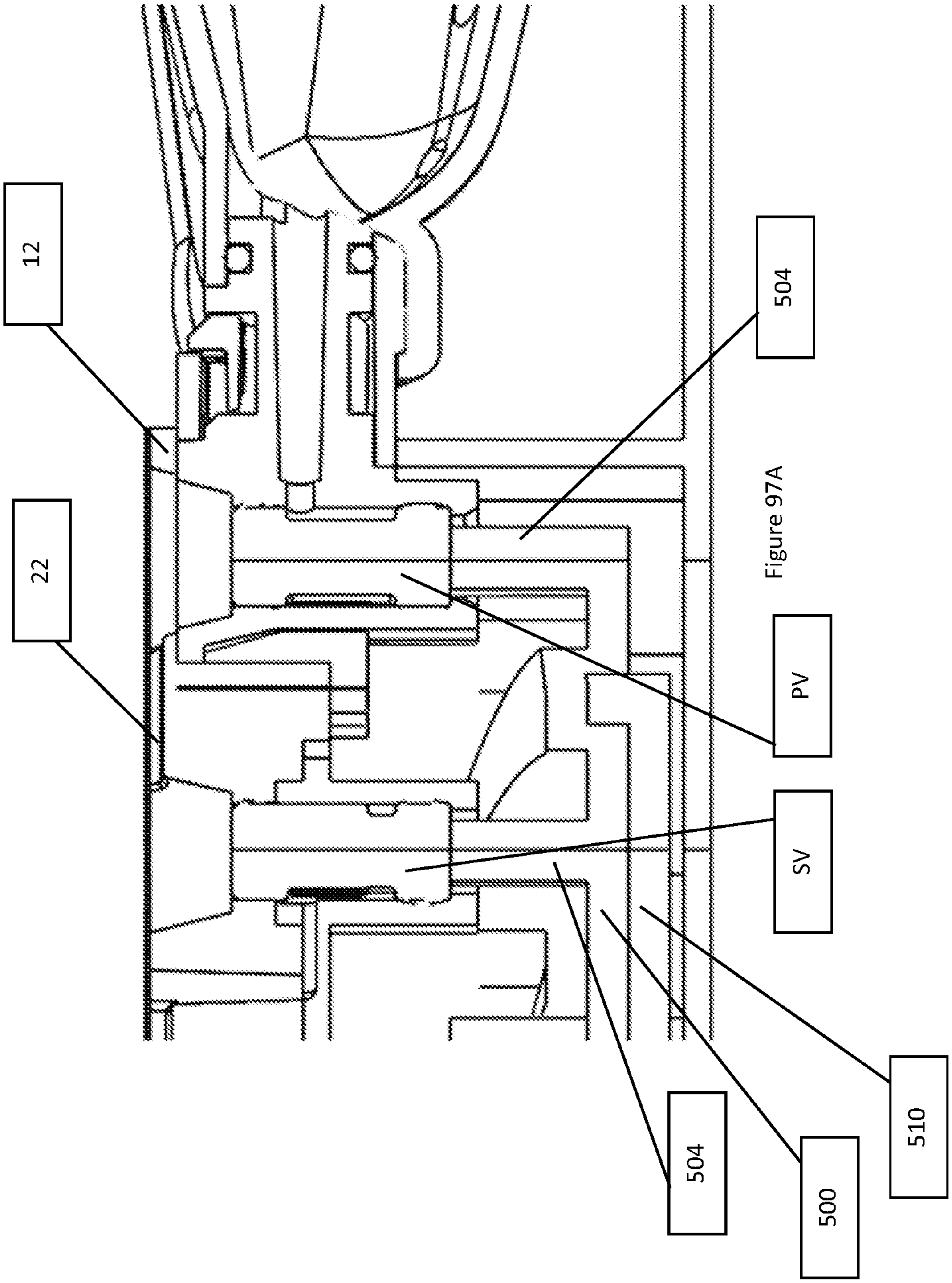

FIG. 97A is a side view with the actuator plate in a lowered position.

Figure 97B:
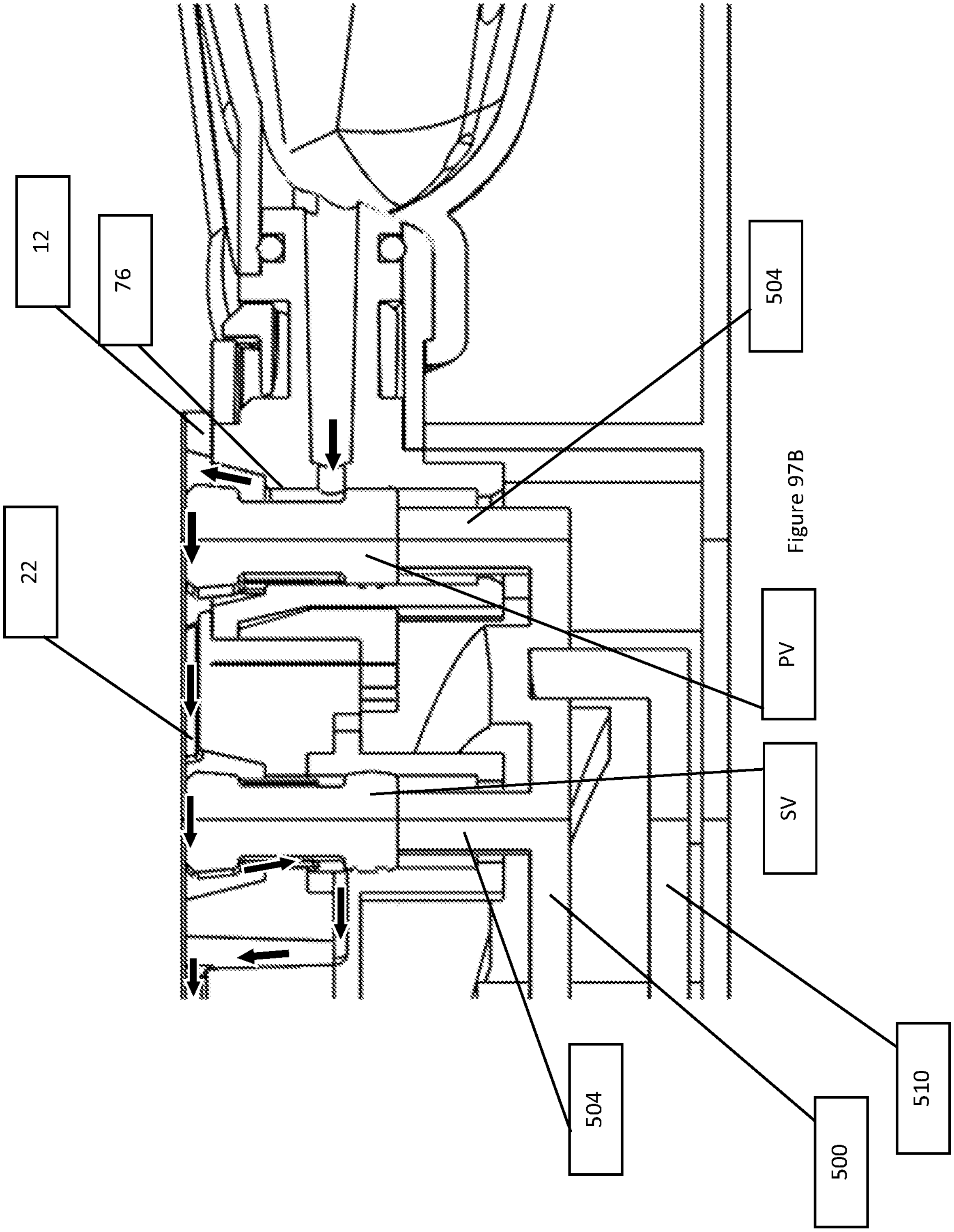

FIG. 97B is a side view showing the actuator plate lifted from the position of FIG. 97A resulting in displacement of the valves.

Figure 98:
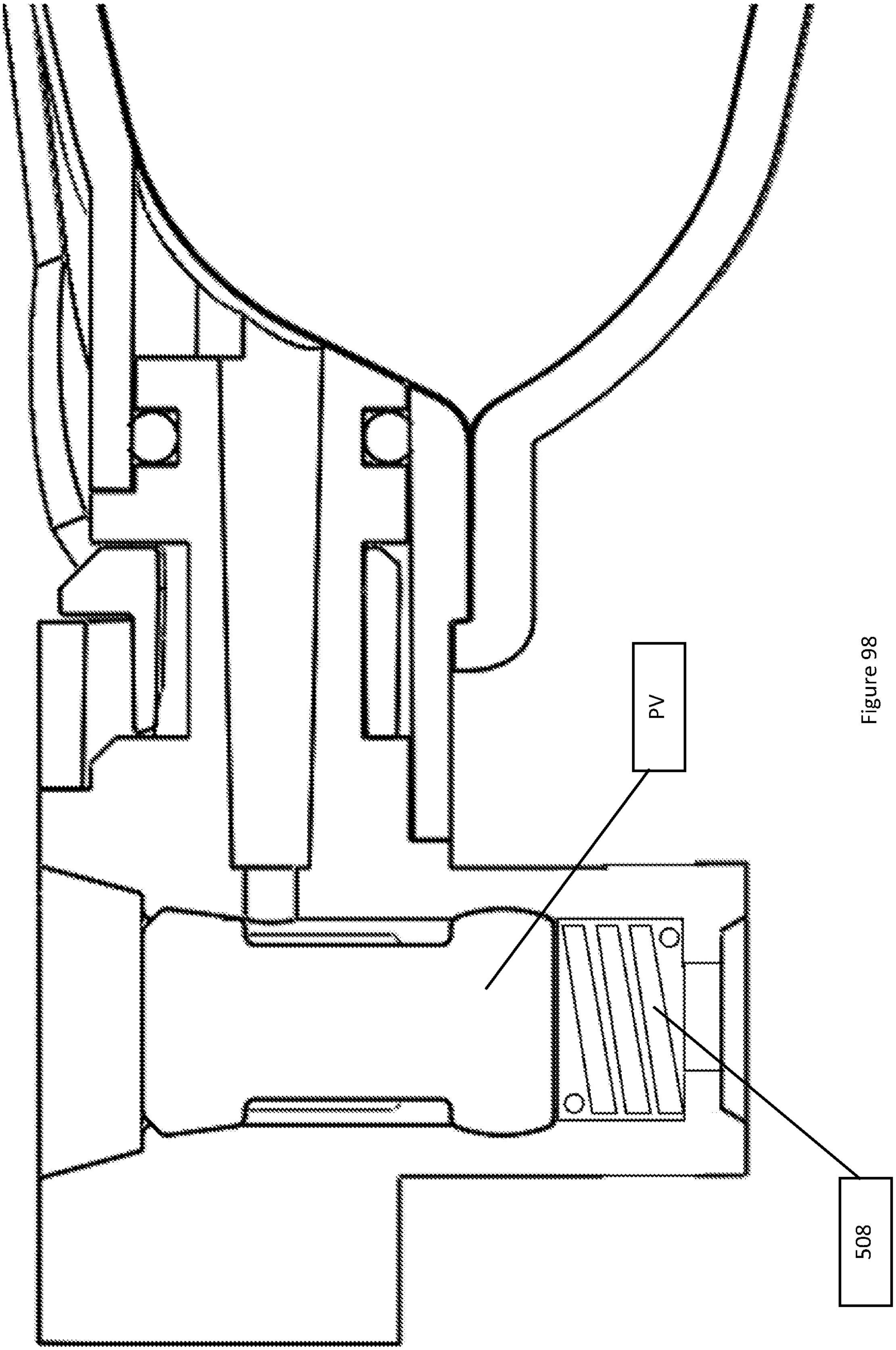

FIG. 98 is a section view of a biasing means arranged to urge a valve to the open state.

Figure 99:
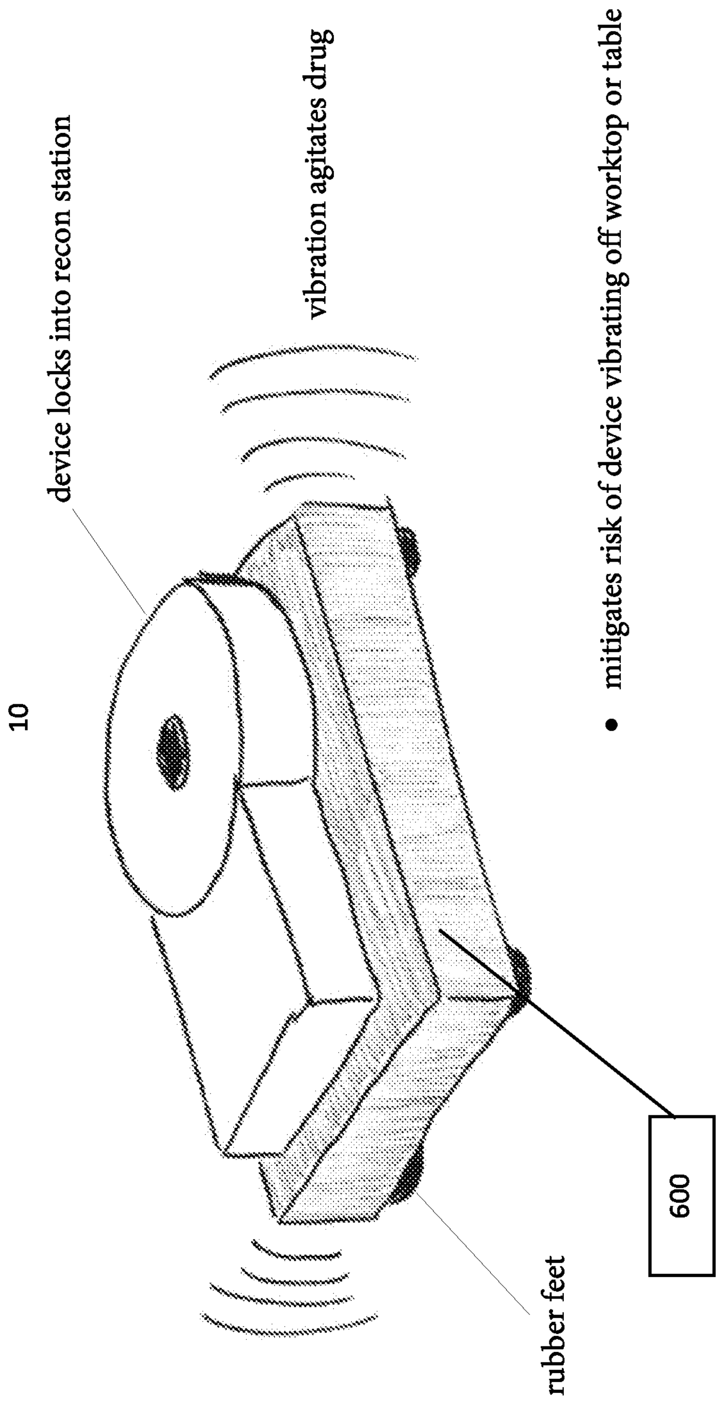

FIG. 99 is a top view of a vibrating plate useable with the subject invention.

Figure 100:
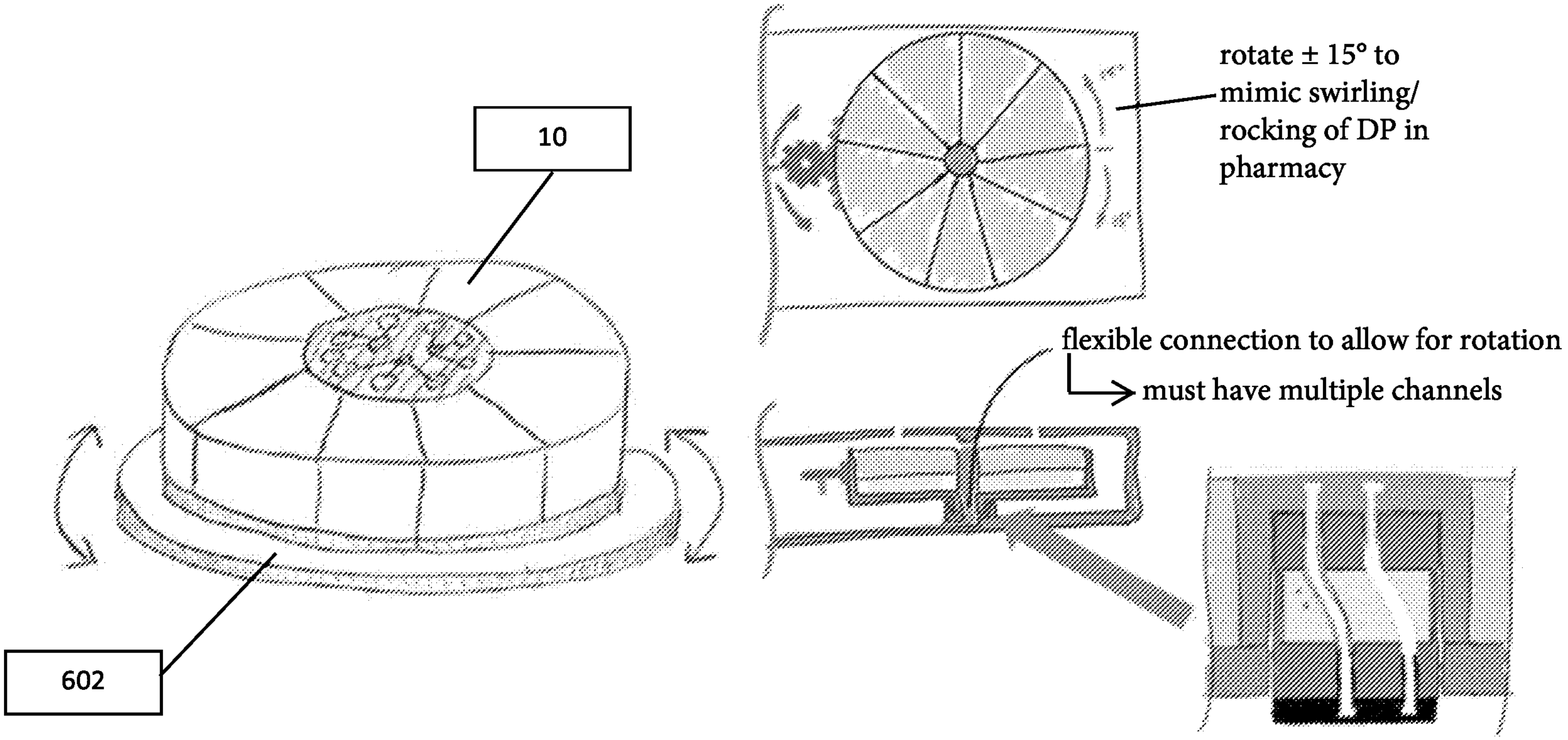

FIG. 100 is a top view of a rotating or oscillating turntable useable with the subject invention.

Figure 101:
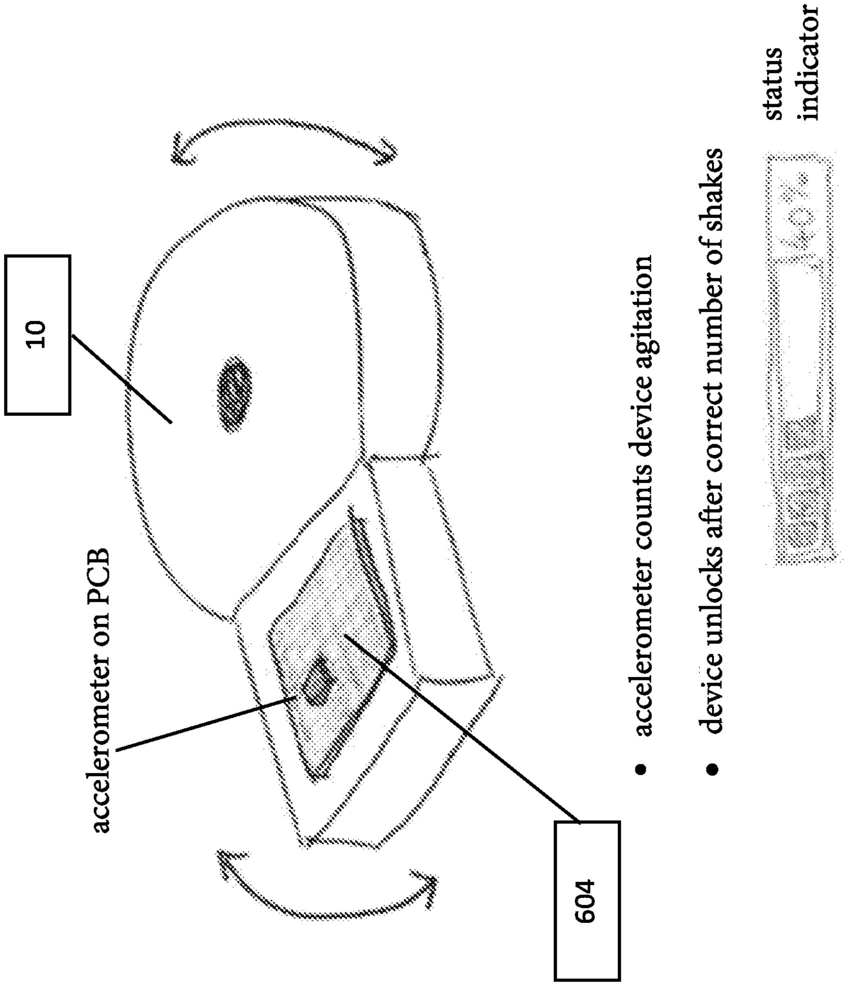

FIG. 101 is a top view of an on-board accelerometer useable with the subject invention.

Figure 102:
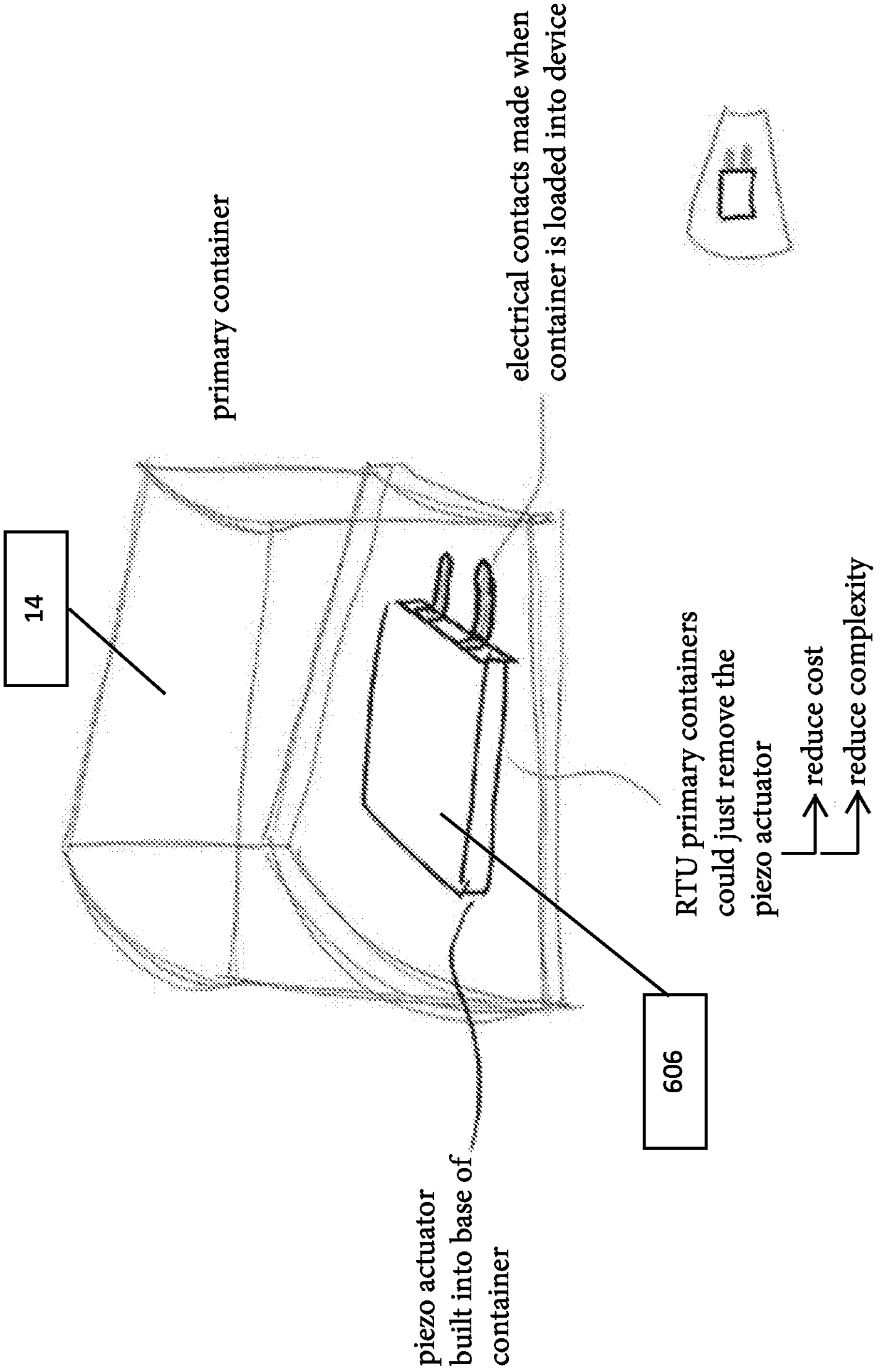

FIG. 102 is a top view of an on-board piezoelectric actuator useable with the subject invention.

Figure 103:
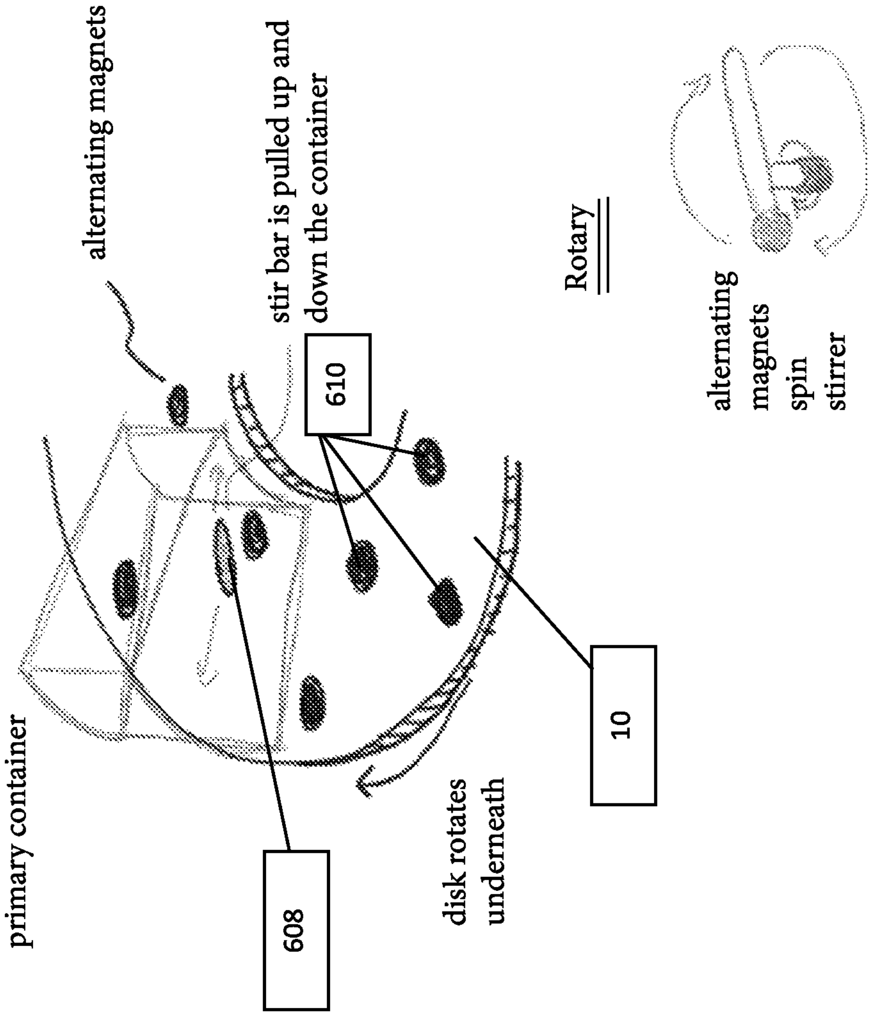

FIG. 103 shows a magnetic stirrer useable with the subject invention.

Figure 104:
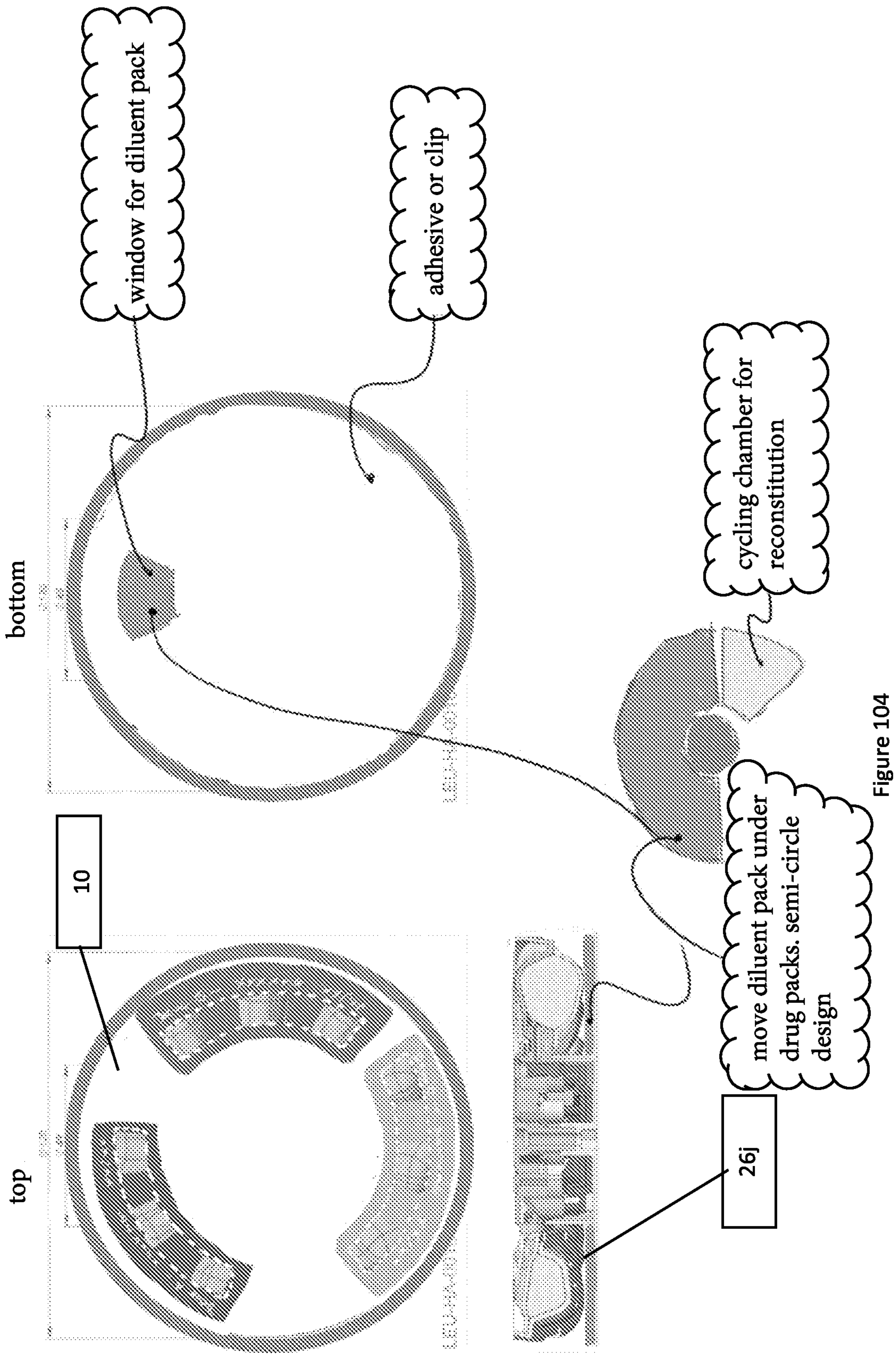

FIG. 104 shows a low-profile, collapsible reservoir, locatable below the drug cartridges of the drug delivery device, useable with the subject invention.

FIGS. 105A-112 are depictions of various arrangements for cycling of mixtures during reconstitution useable with the subject invention.

Figure 113:
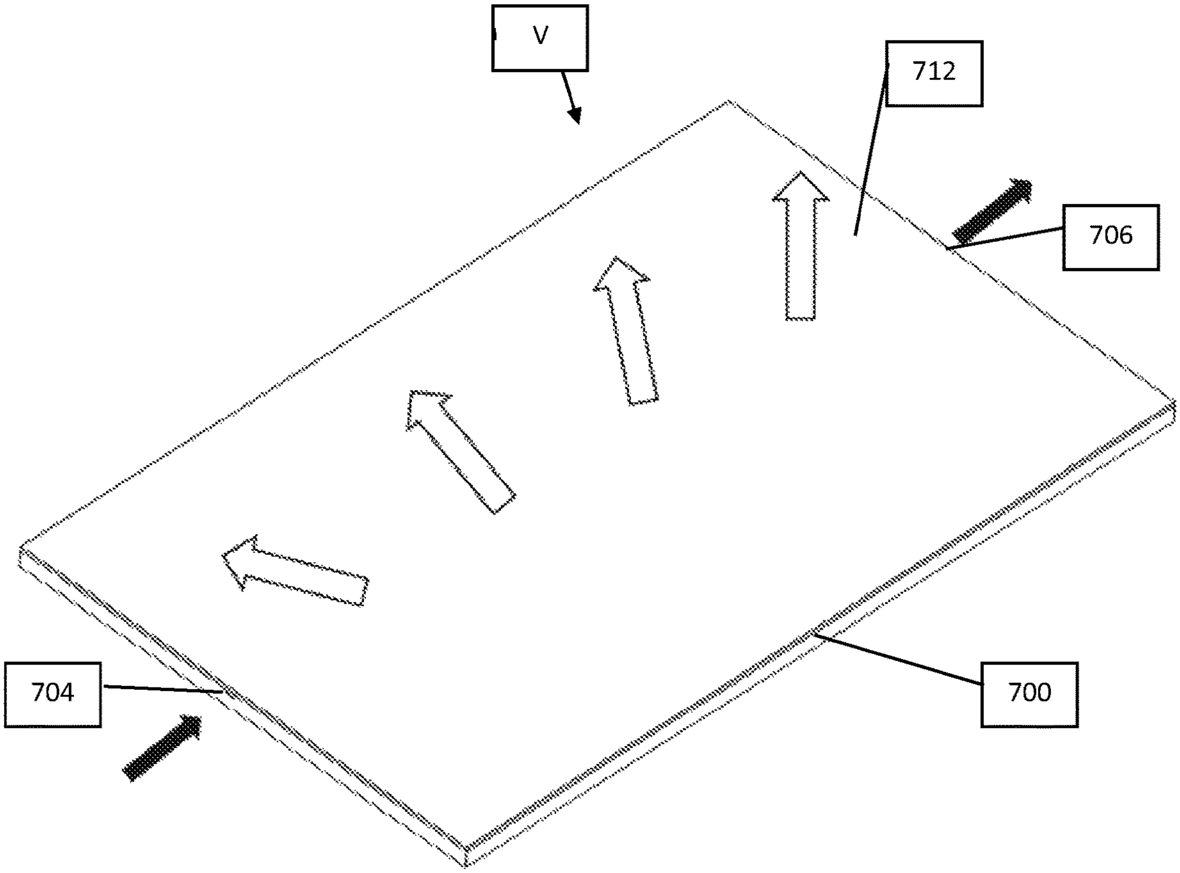

FIG. 113 is top perspective view of a vent useable with the subject invention.

Figure 114:
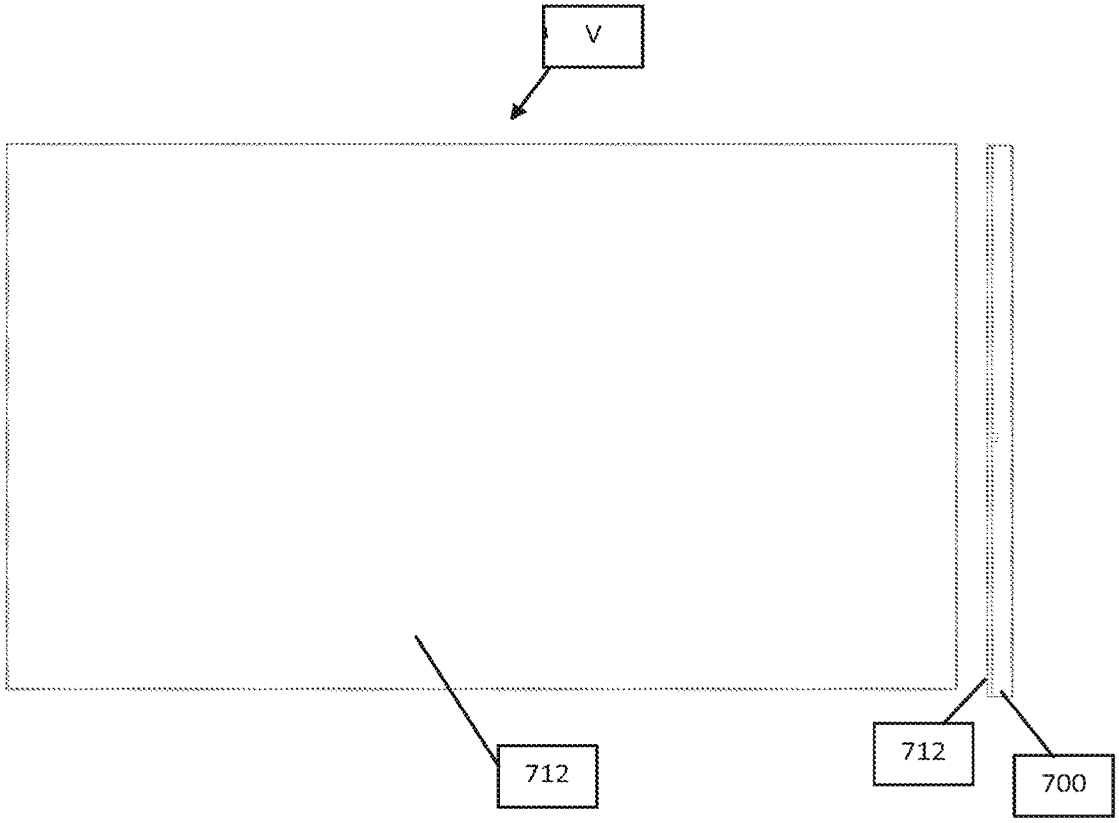

FIG. 114 includes top and side views of a vent useable with the subject invention.

Figure 115:
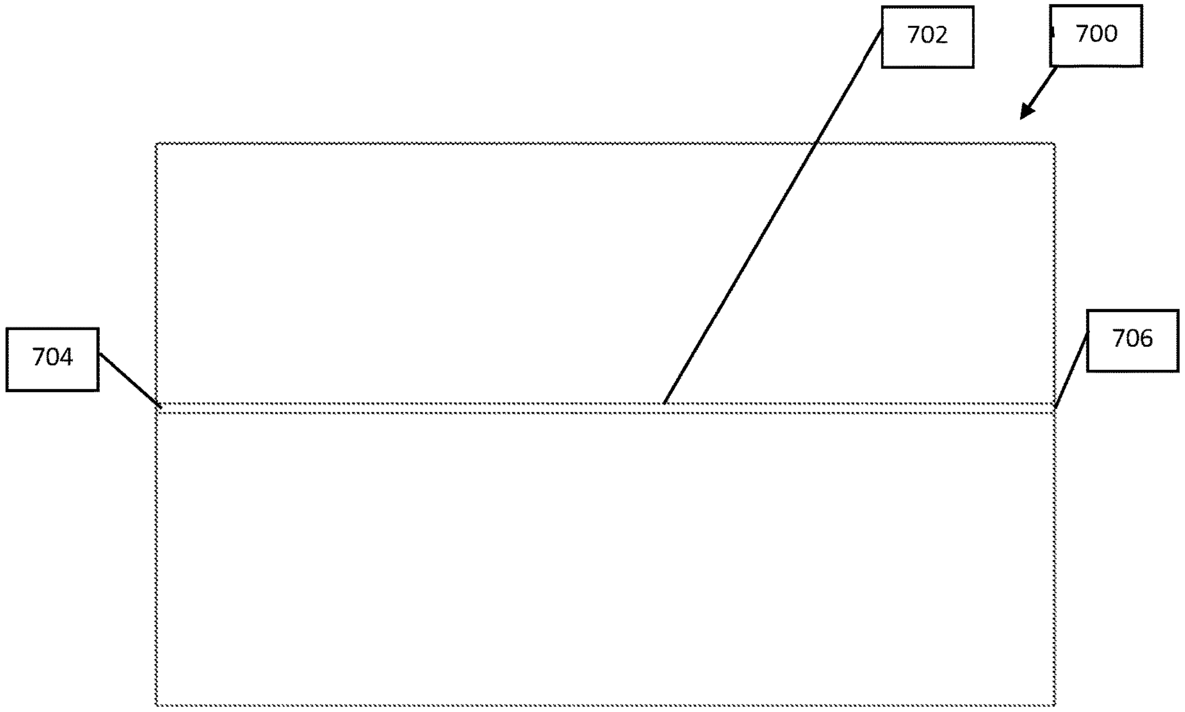

FIG. 115 is atop view of abase plate of a vent, with a straight channel formed therein, useable with the subject invention.

Figure 116:
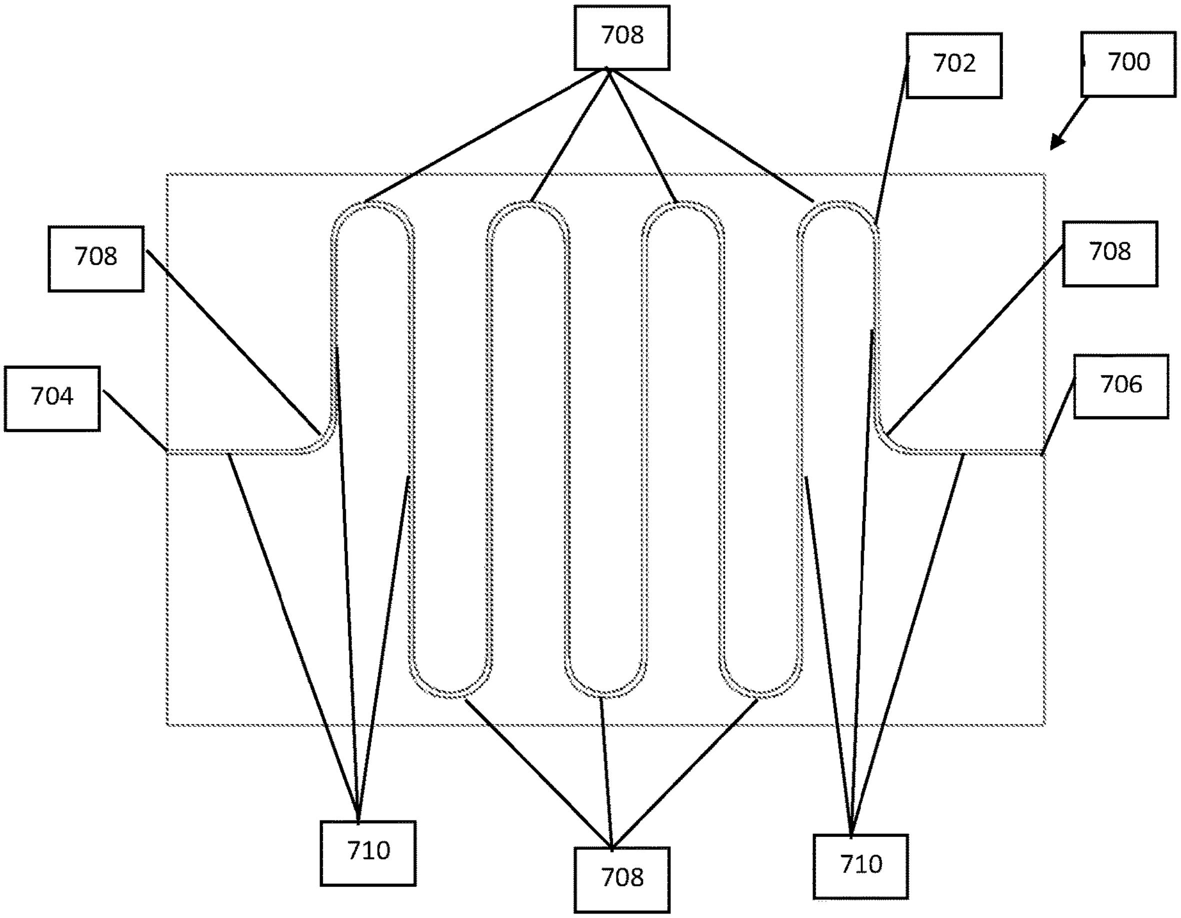

FIG. 116 is atop view of abase plate of a vent, with a channel formed therein defining a tortious pathway, useable with the subject invention.

Figure 116A:
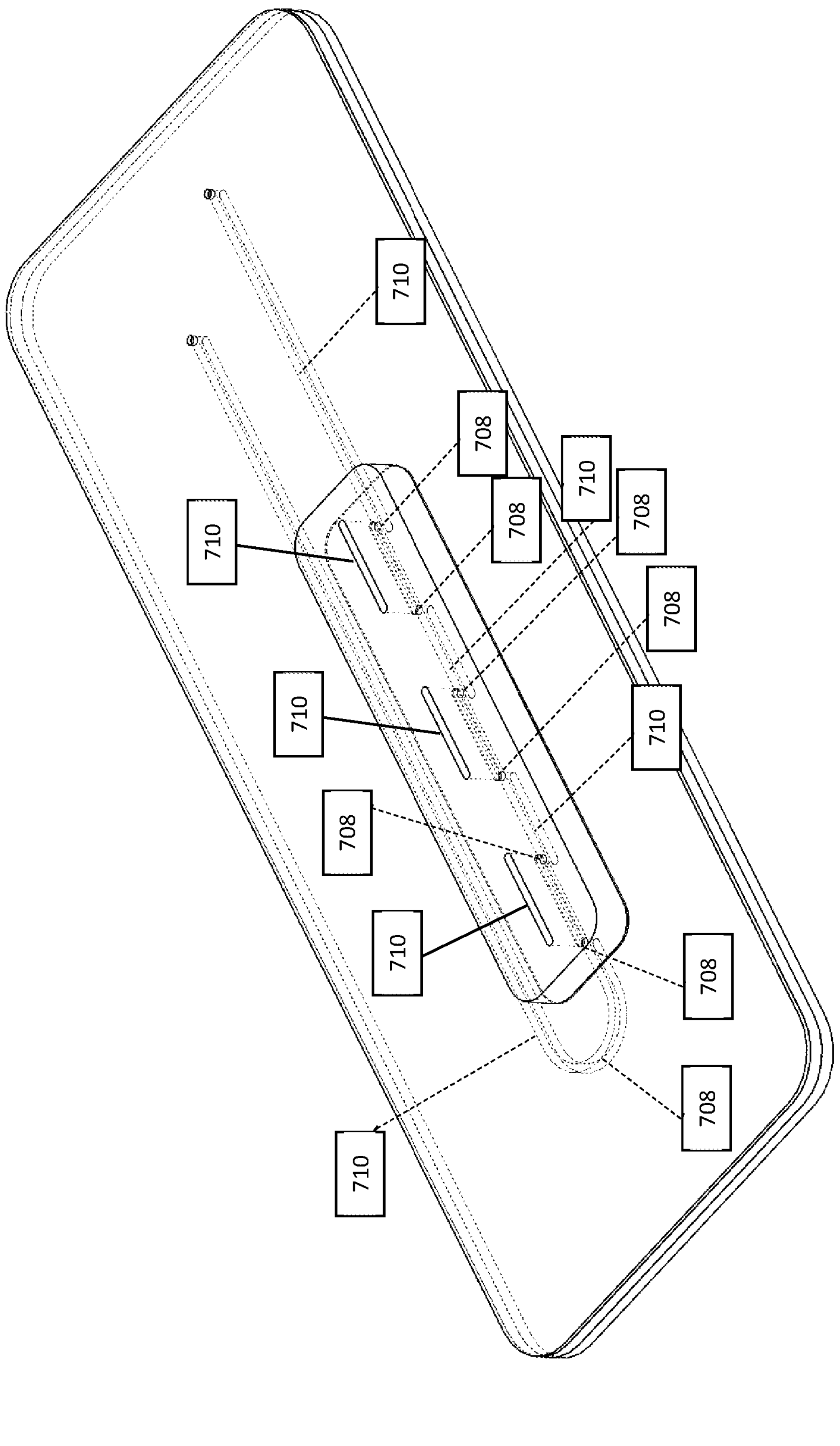
Figure 116B:
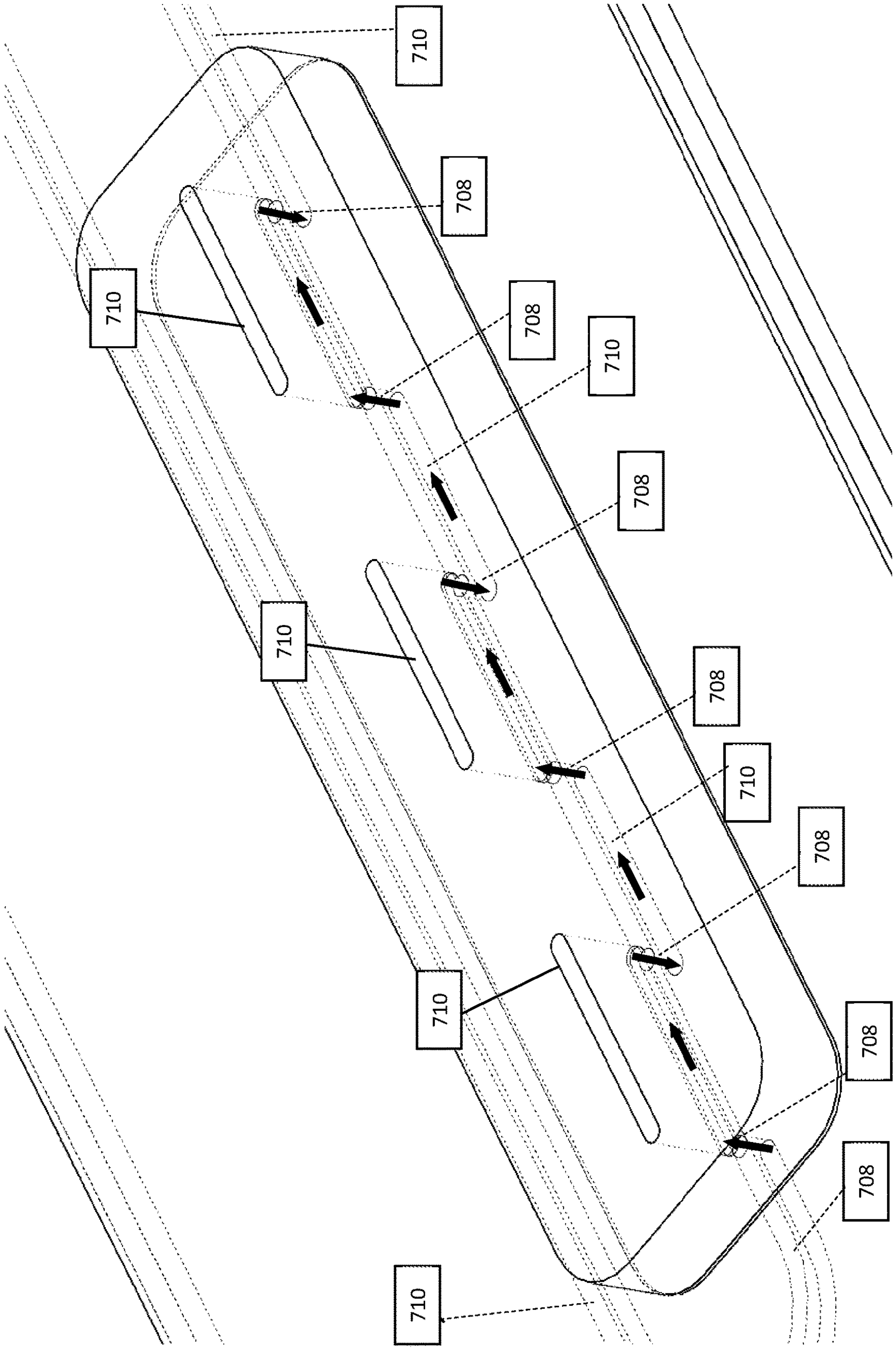
Figure 116C:
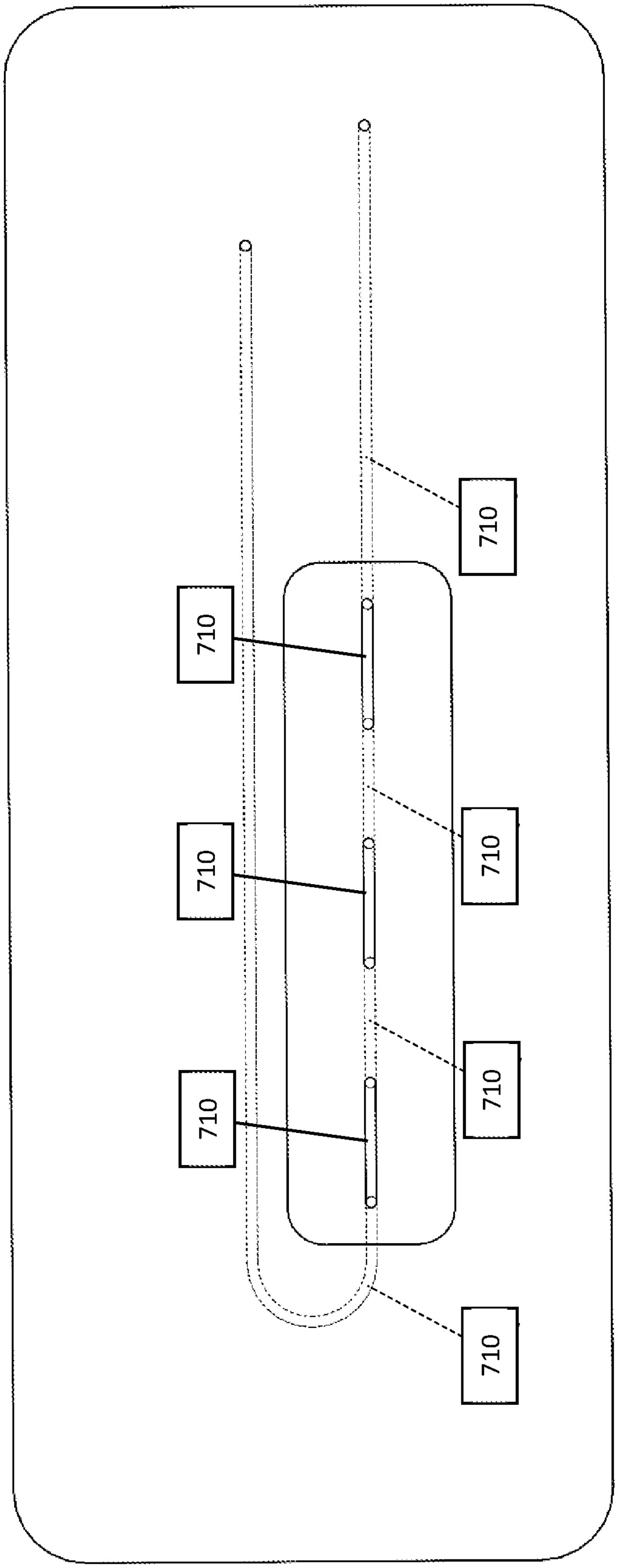

FIGS. 116A-116C show an alternative embodiment of the vent with the tortious pathway having vertical changes in direction.

Figure 117:
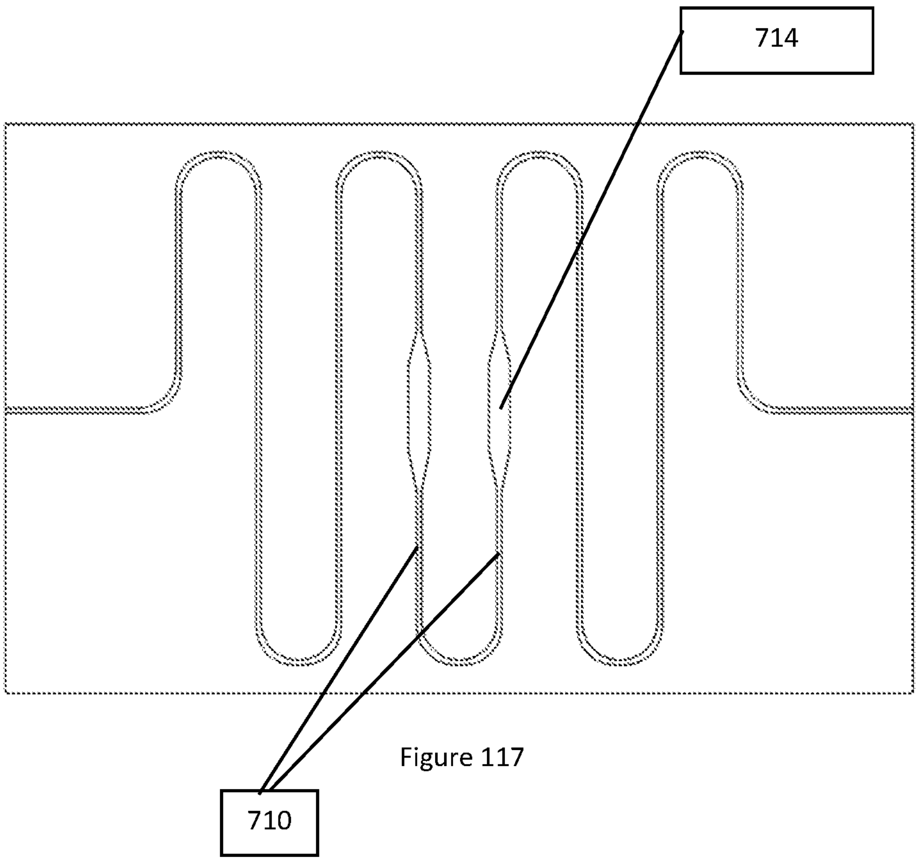

FIG. 117 is a top view of a base plate of a vent, with a channel formed therein having enlarged portions, useable with the subject invention.

Figure 117A:
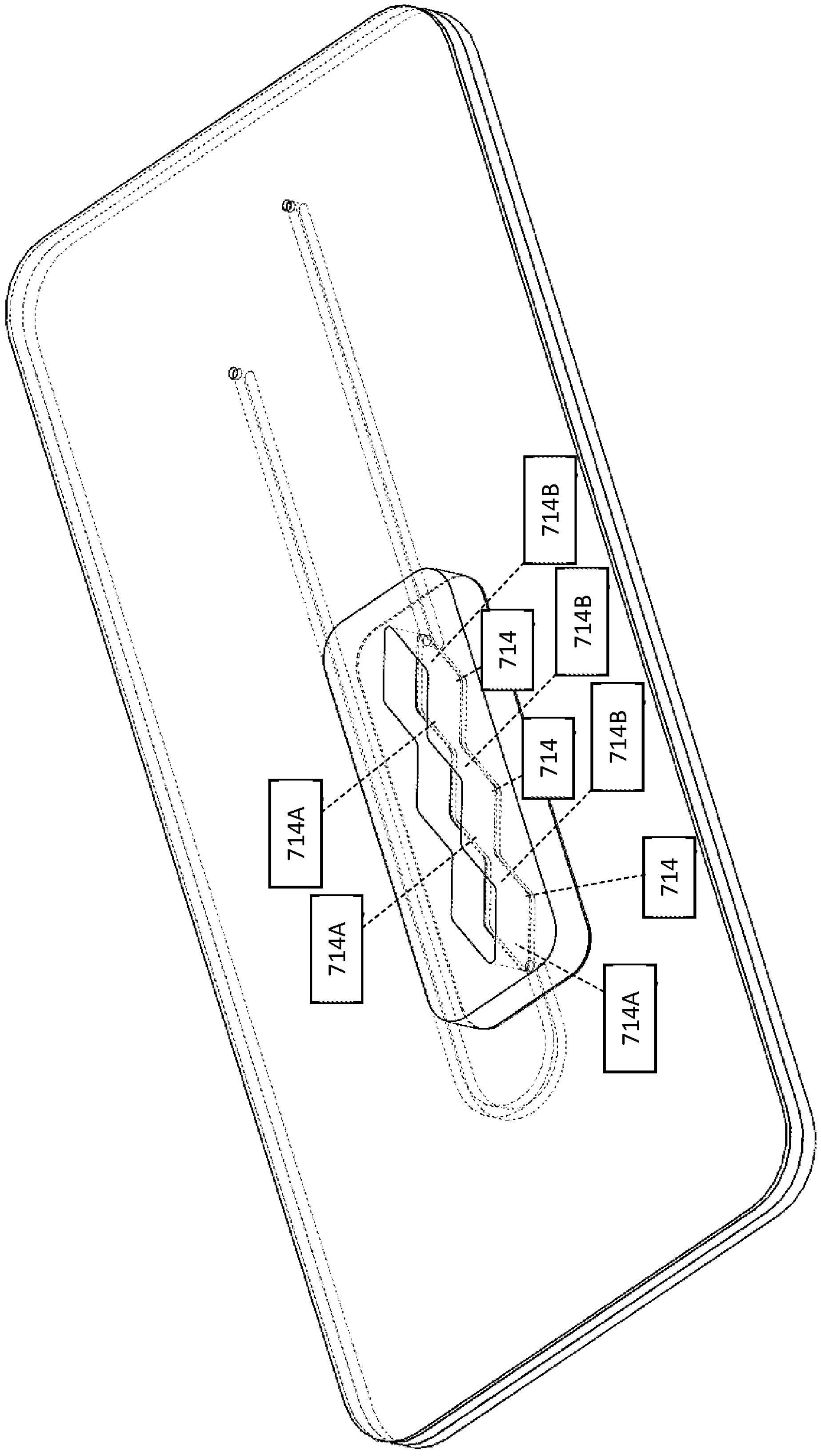
Figure 117B:
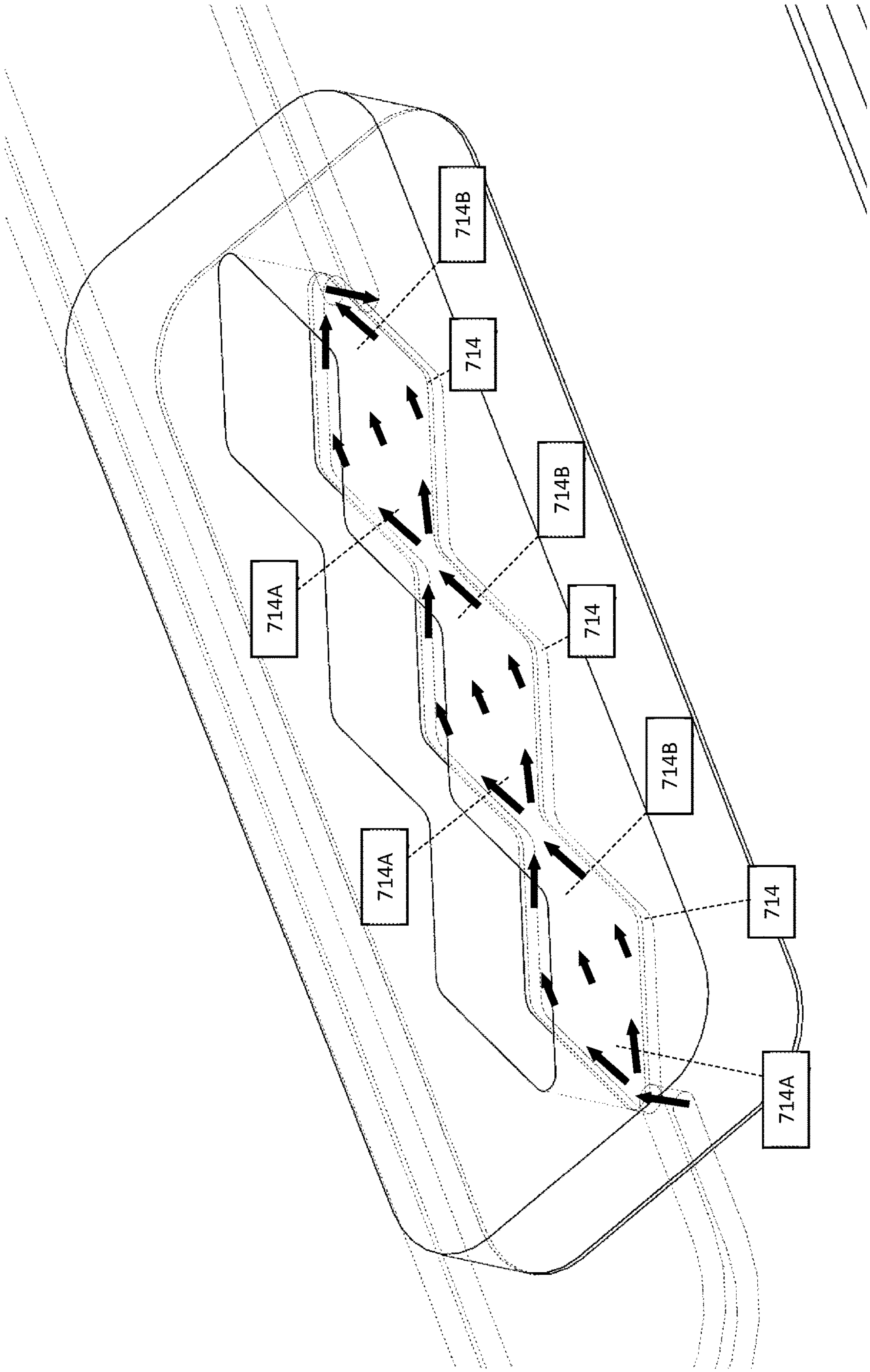

FIGS. 117A-117B show a vent with enlarged portions each having a diverging section and a converging section.

Figure 118A:
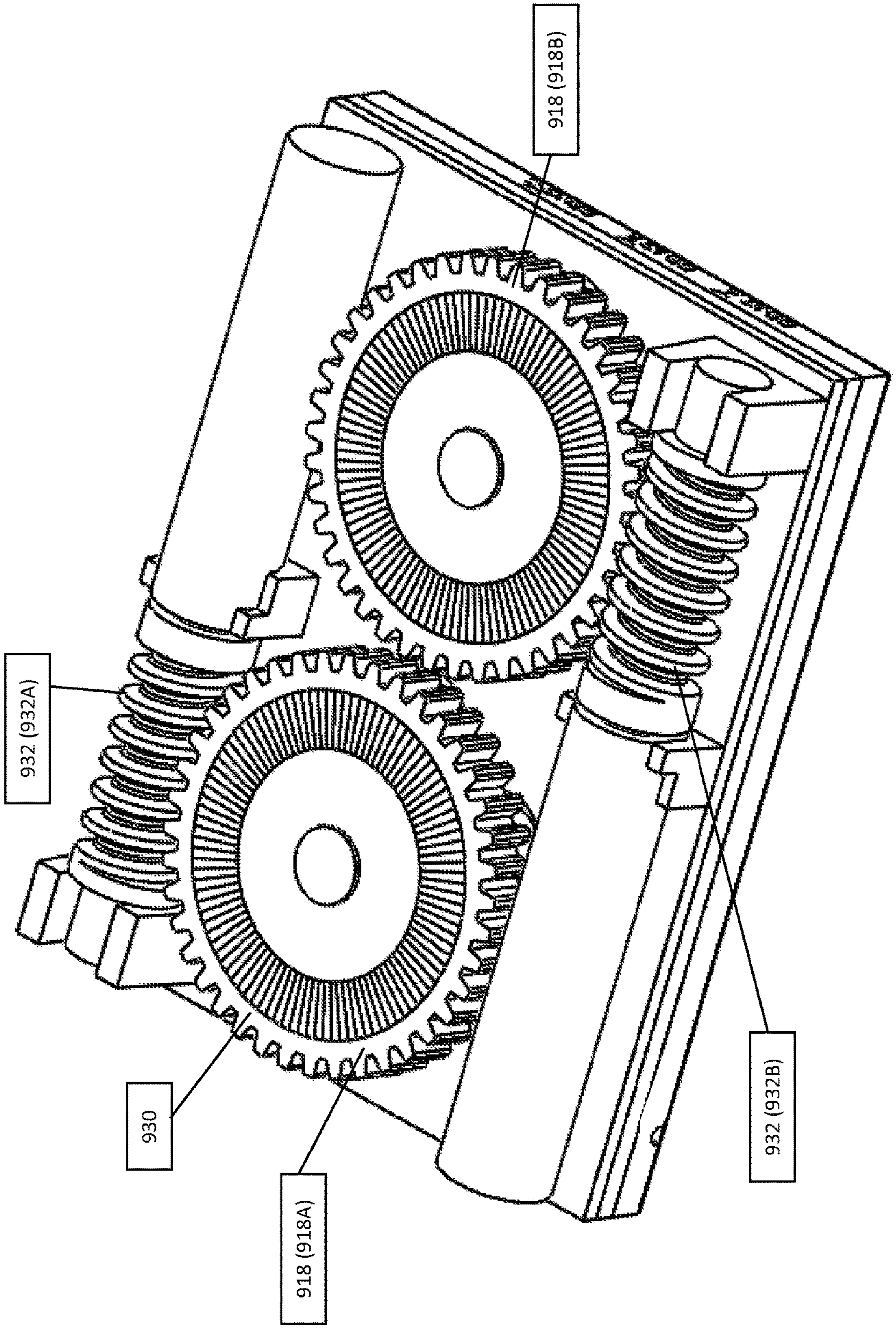

FIG. 118A is a top view of a valve module useable with the subject invention.

Figure 118B:
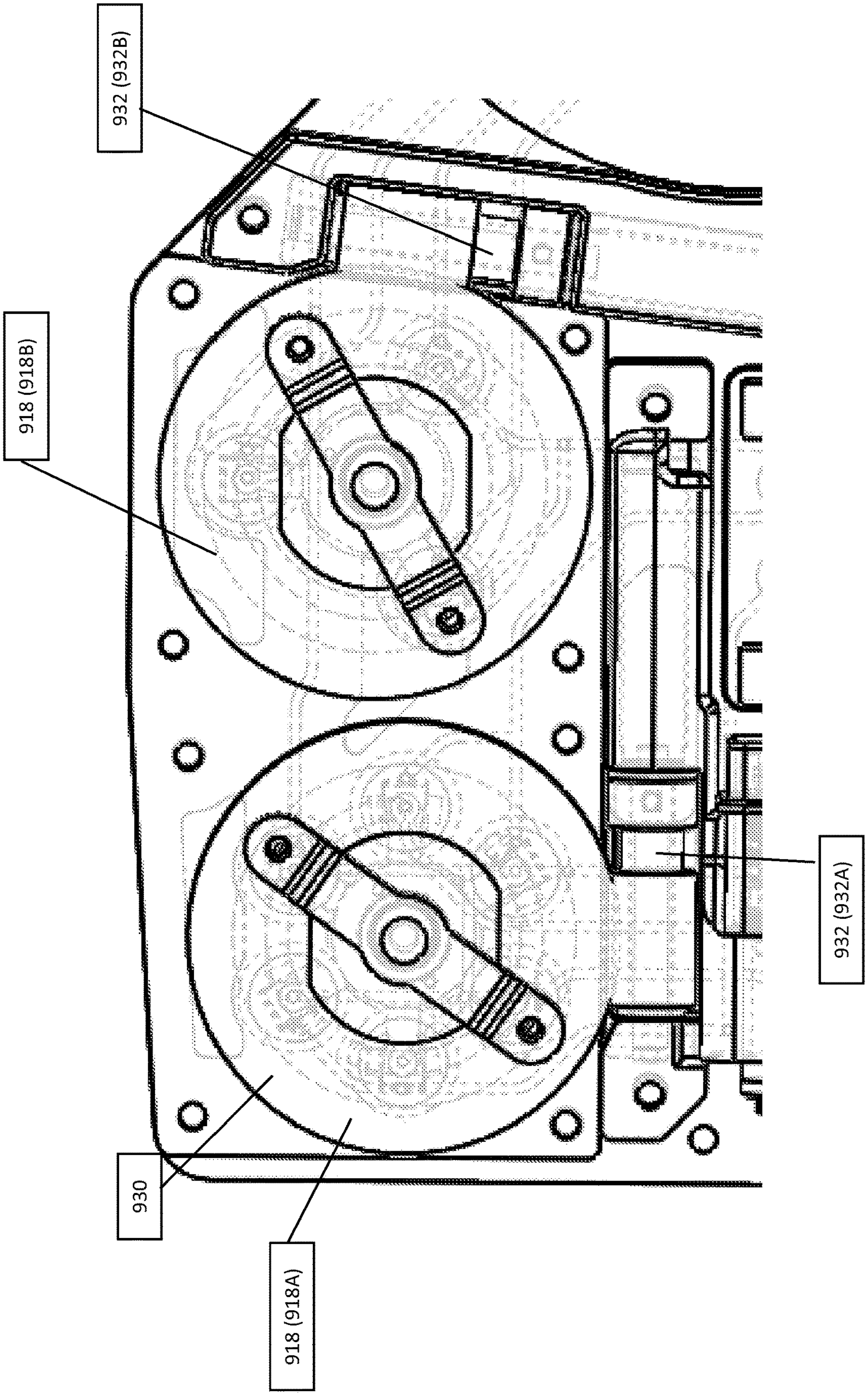

FIG. 118B is a top view of an alternate arrangement of actuator gears and worm gears useable with the subject invention.

Figure 119:
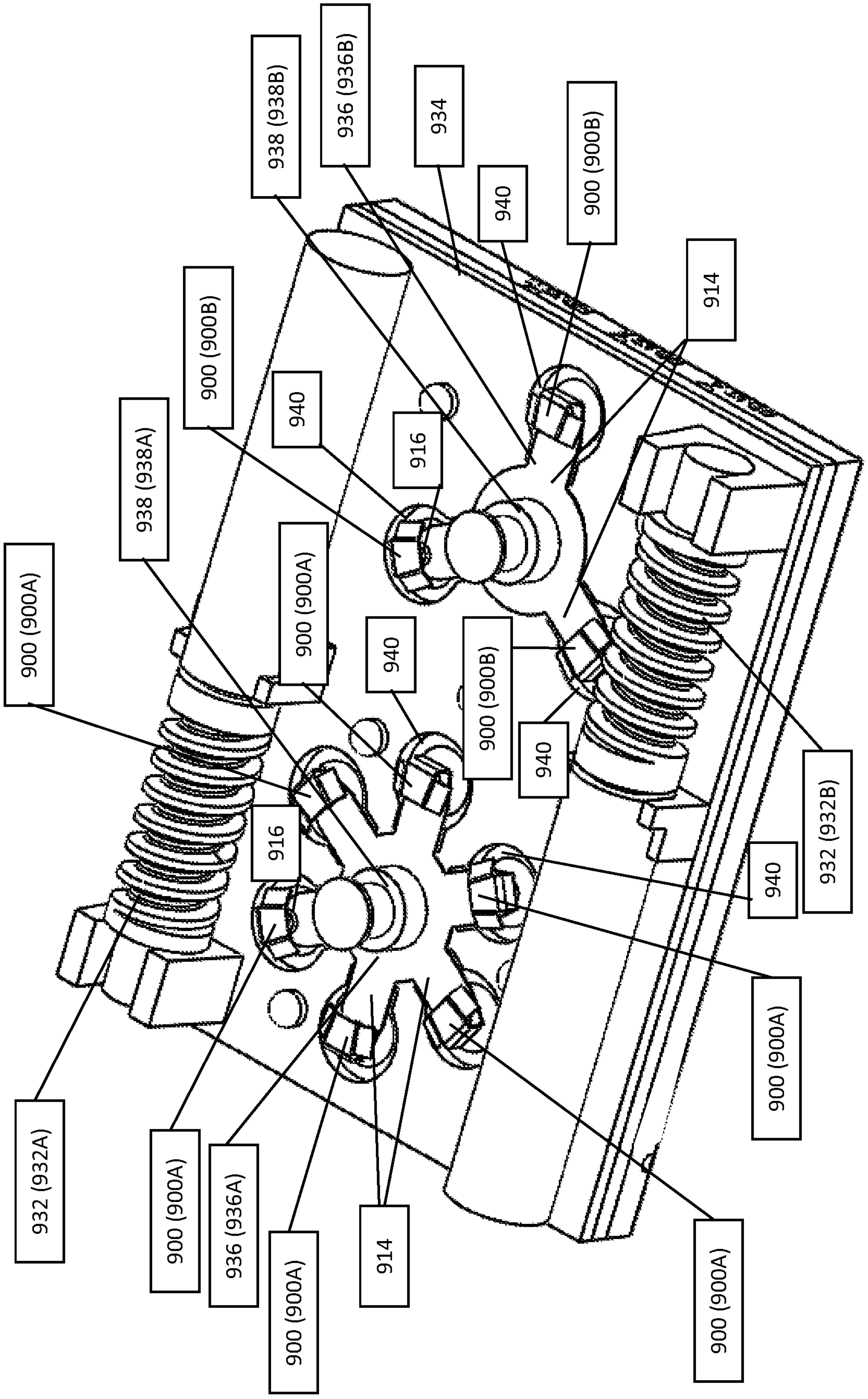

FIG. 119 is a top perspective view of the valve module of FIG. 118A with the actuator gears removed.

Figure 120:
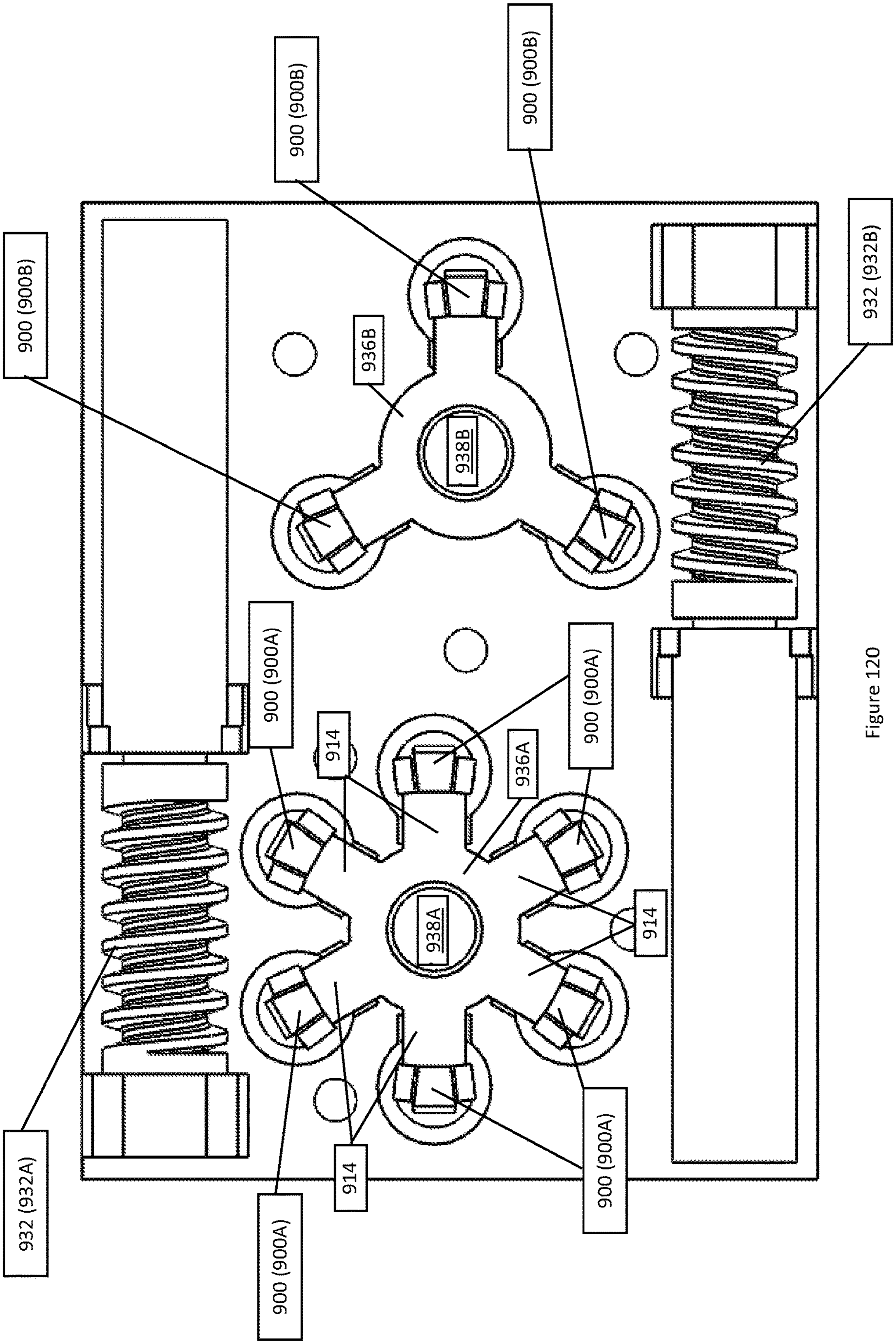

FIG. 120 is a top view of the valve module of FIG. 119.

Figure 121A:
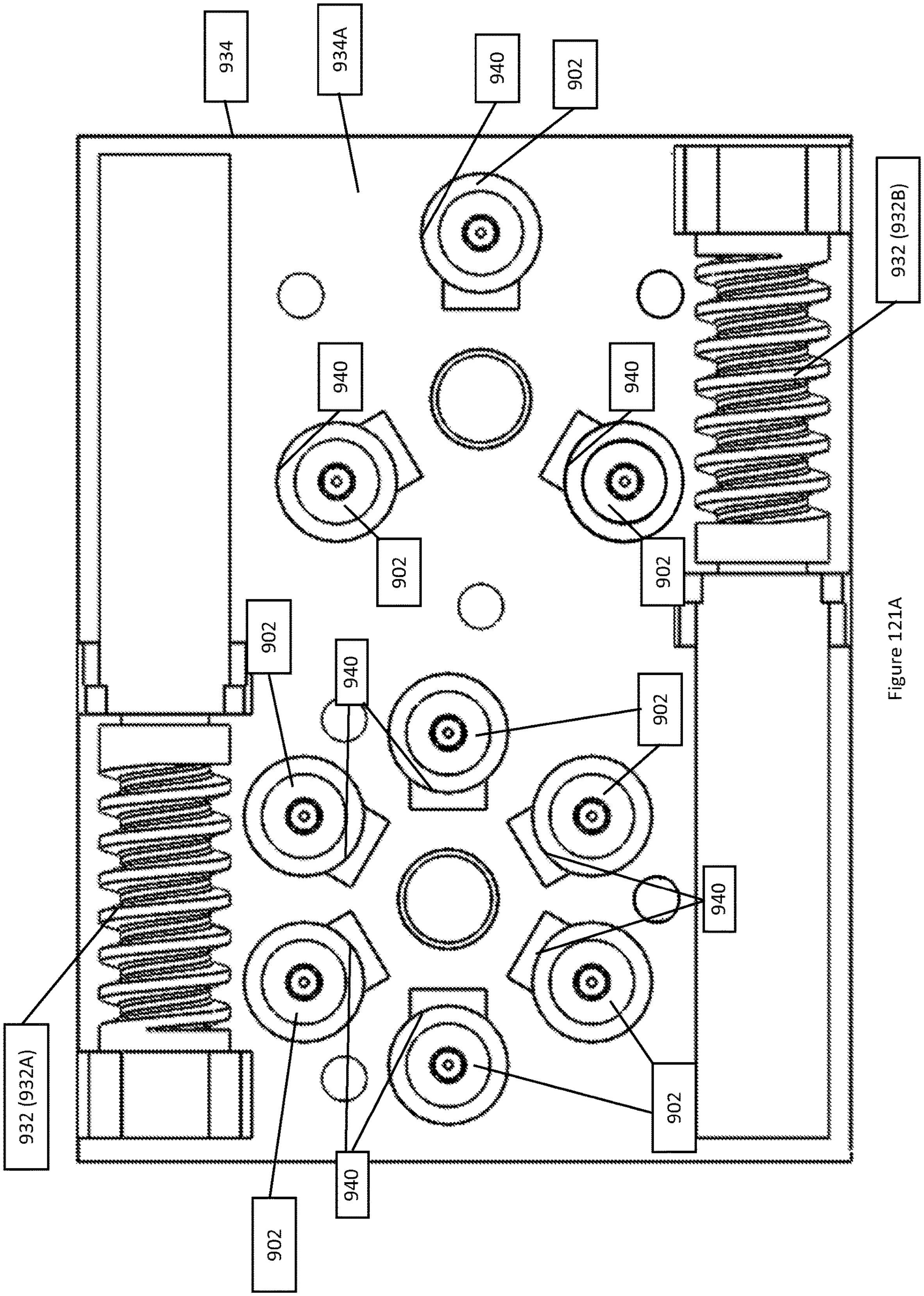

FIG. 121A is a top view of a portion of the valve module of FIG. 119 with the leaf springs removed.

Figure 121B:
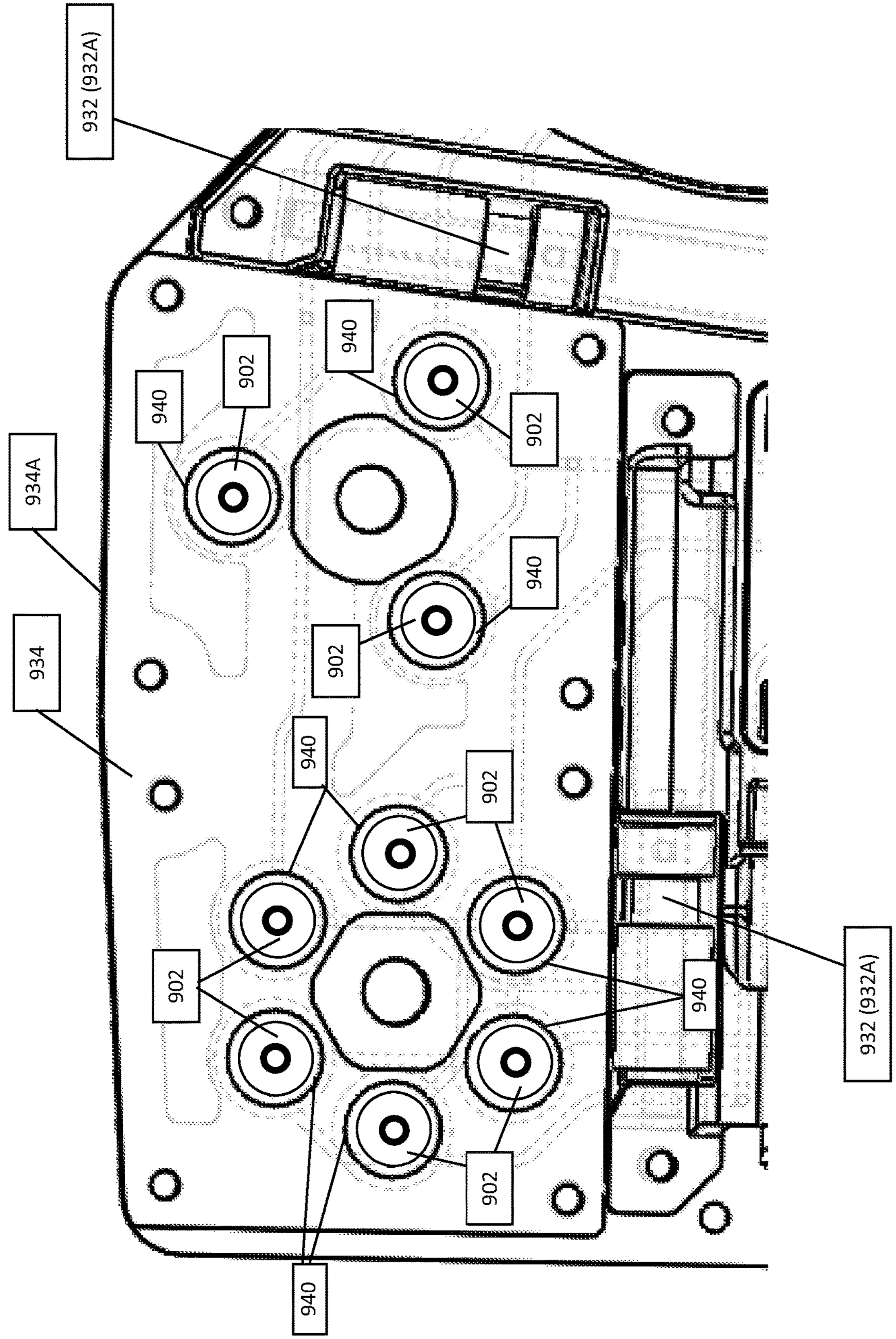

FIG. 121B is a top view of a portion of the valve module of FIG. 118 with the leaf springs and actuator gears removed.

Figure 122A:
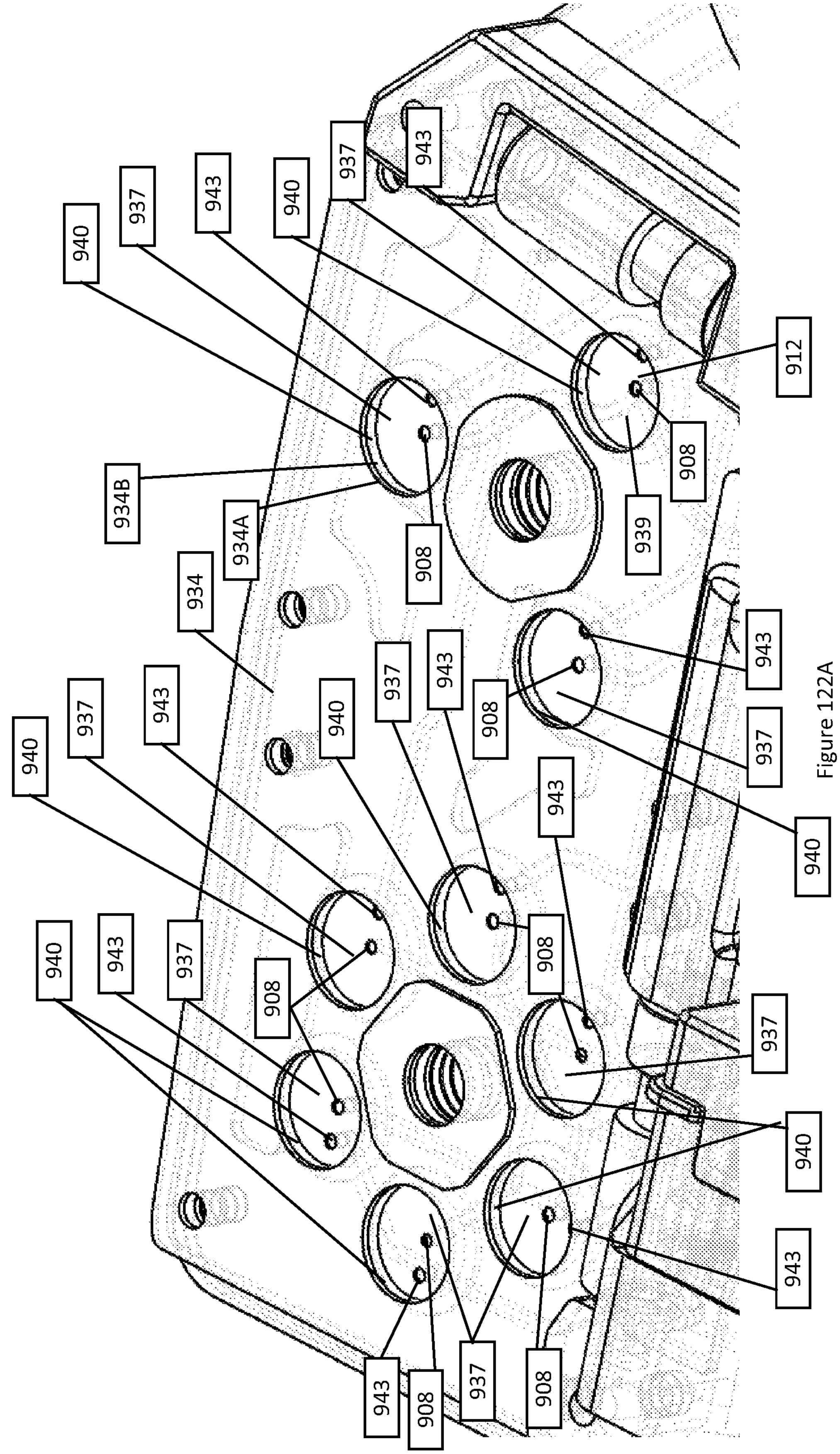

FIG. 122A is a top perspective view of the partial valve module of FIG. 121B with the flexible bodies of the valves removed.

Figure 122B:
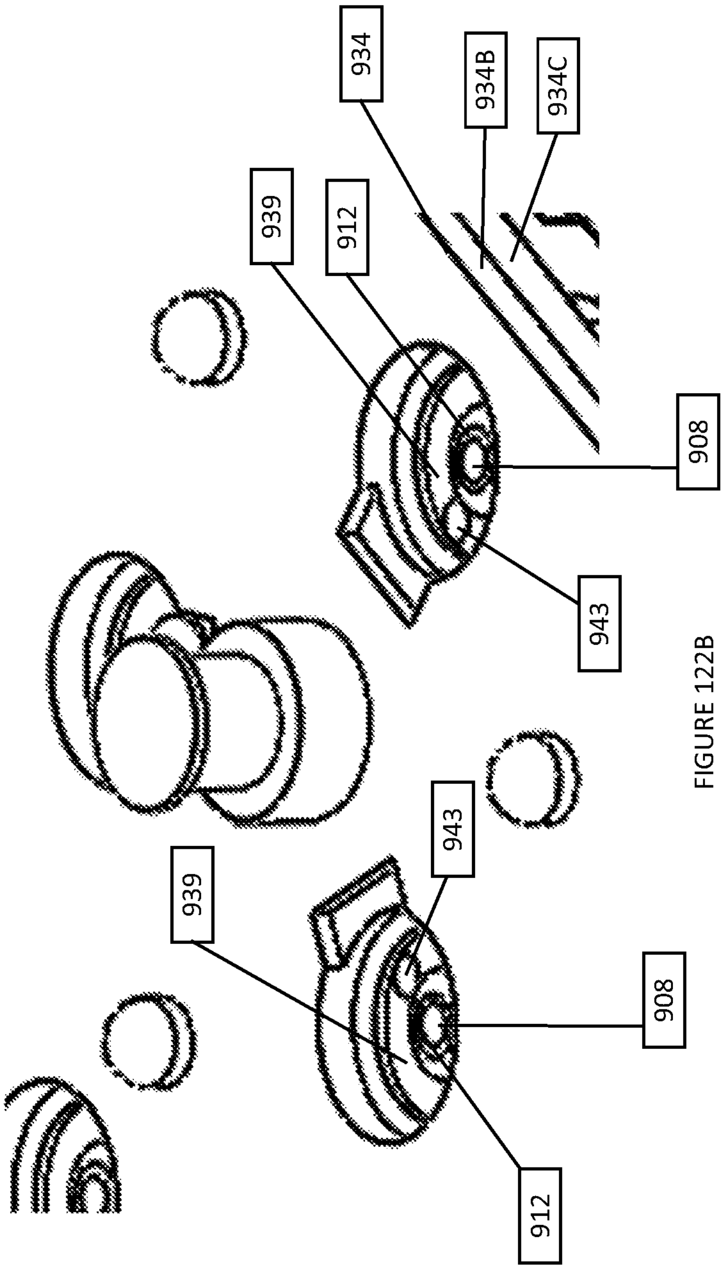

FIG. 122B is an enlarged of a portion of the partial valve module of FIG. 121A with the flexible bodies of the valves removed.

Figure 123A:
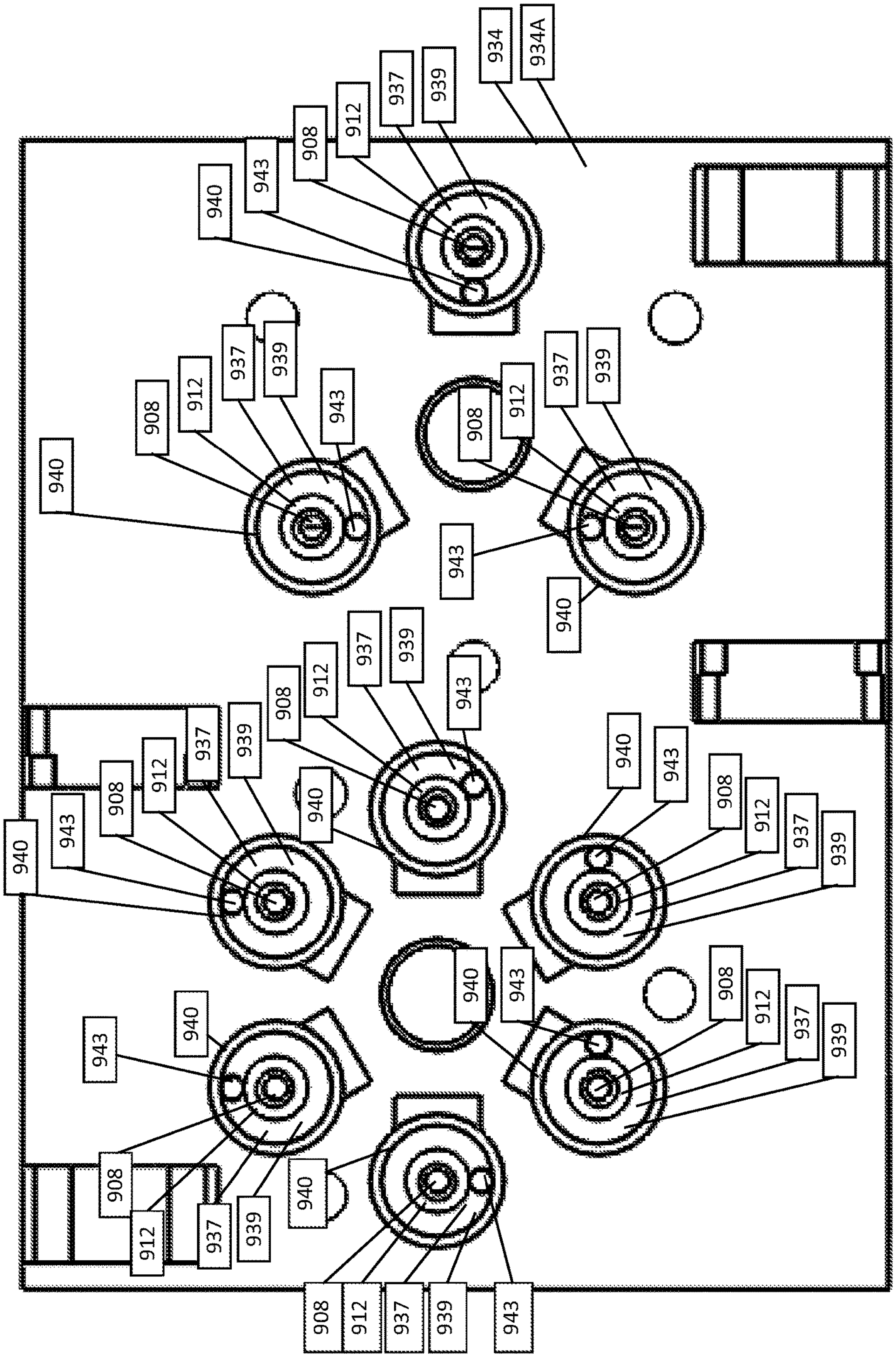

FIG. 123A is a top view of the partial valve module of FIG. 121A with the flexible bodies of the valves removed.

Figure 123B:
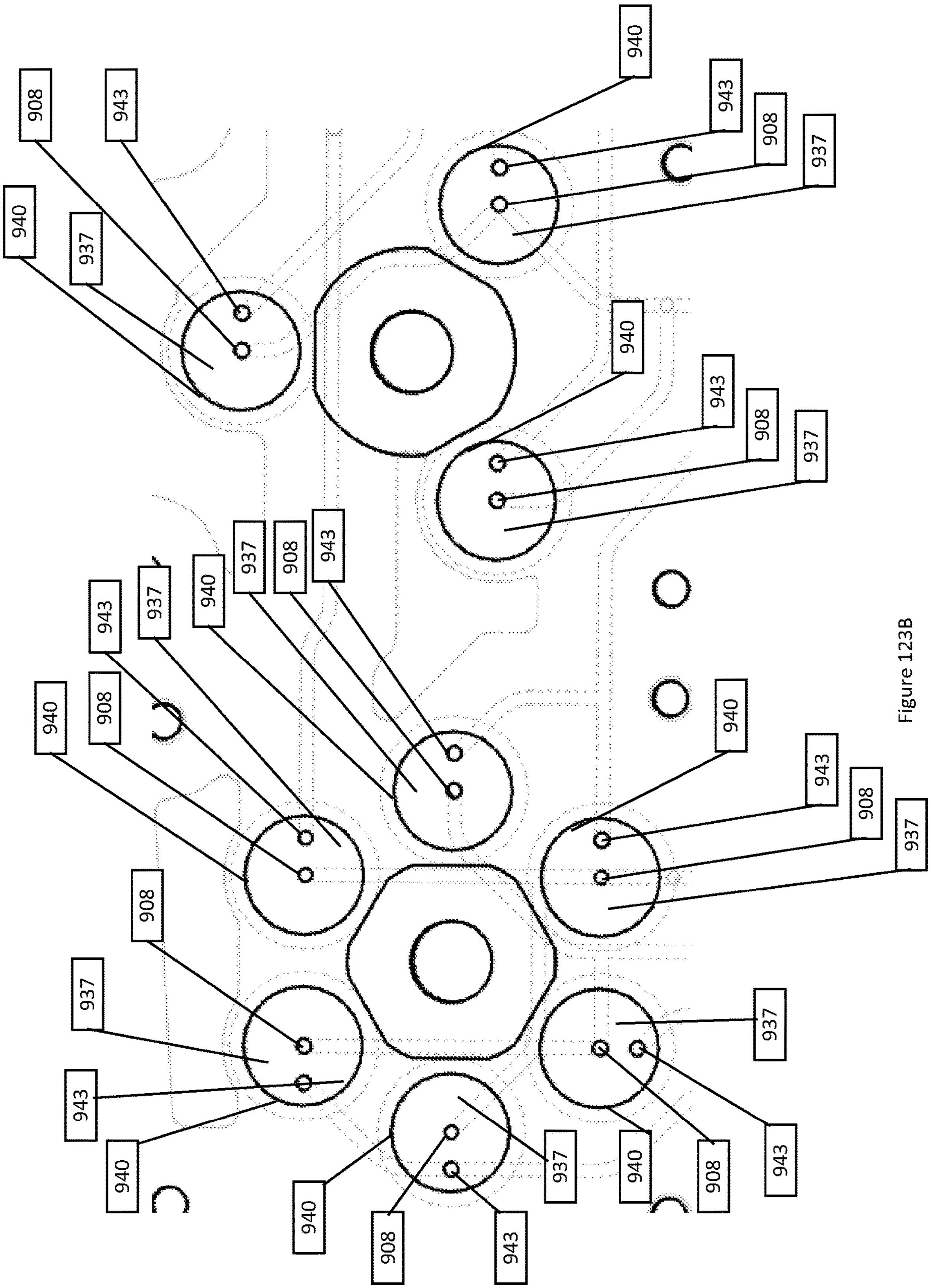

FIG. 123B is a top view of FIG. 122A with the valves superimposed over flow channels.

Figure 124:
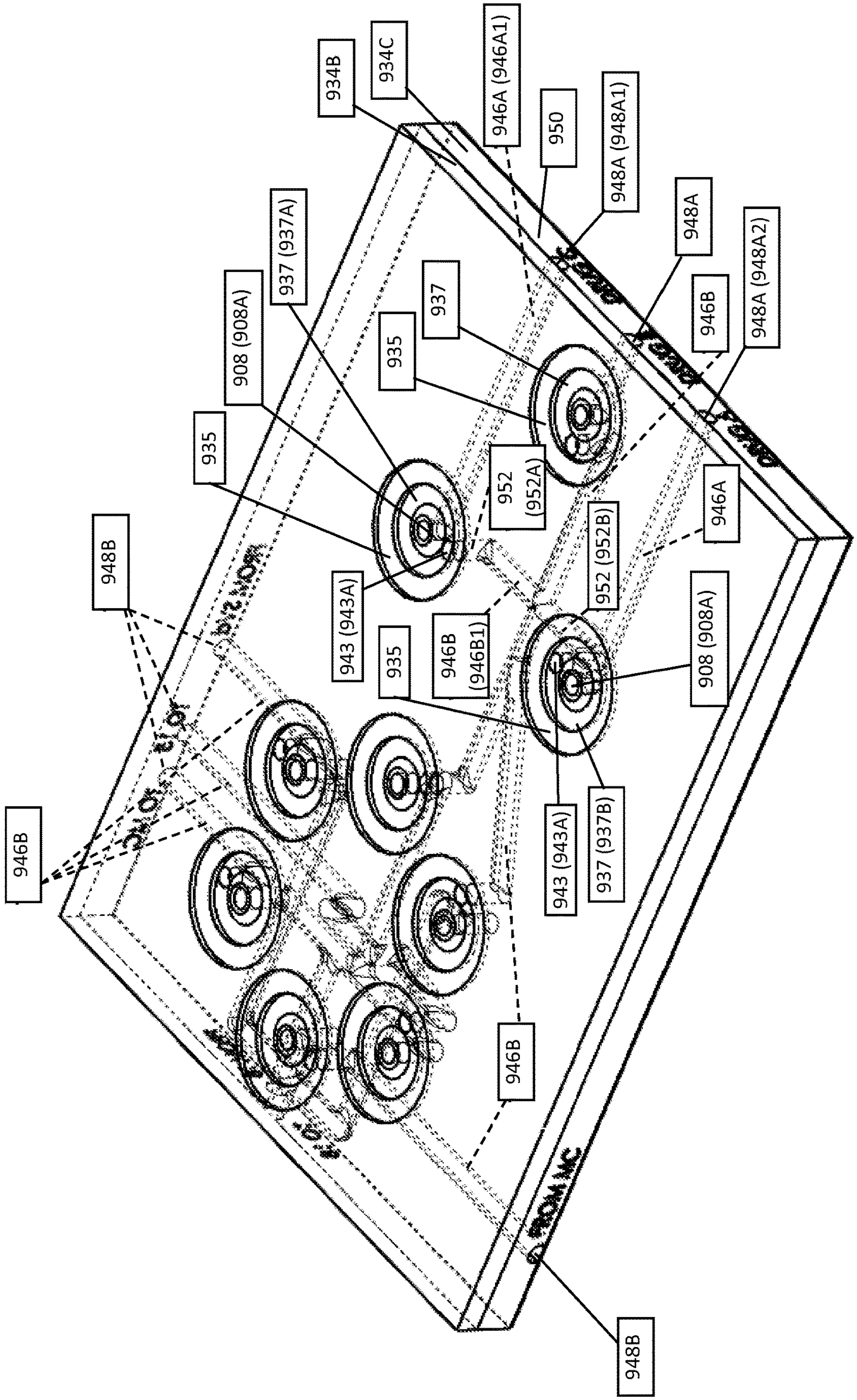

FIG. 124 is a top perspective view of the partial valve module of FIG. 123A with the top layer removed.

Figure 125:
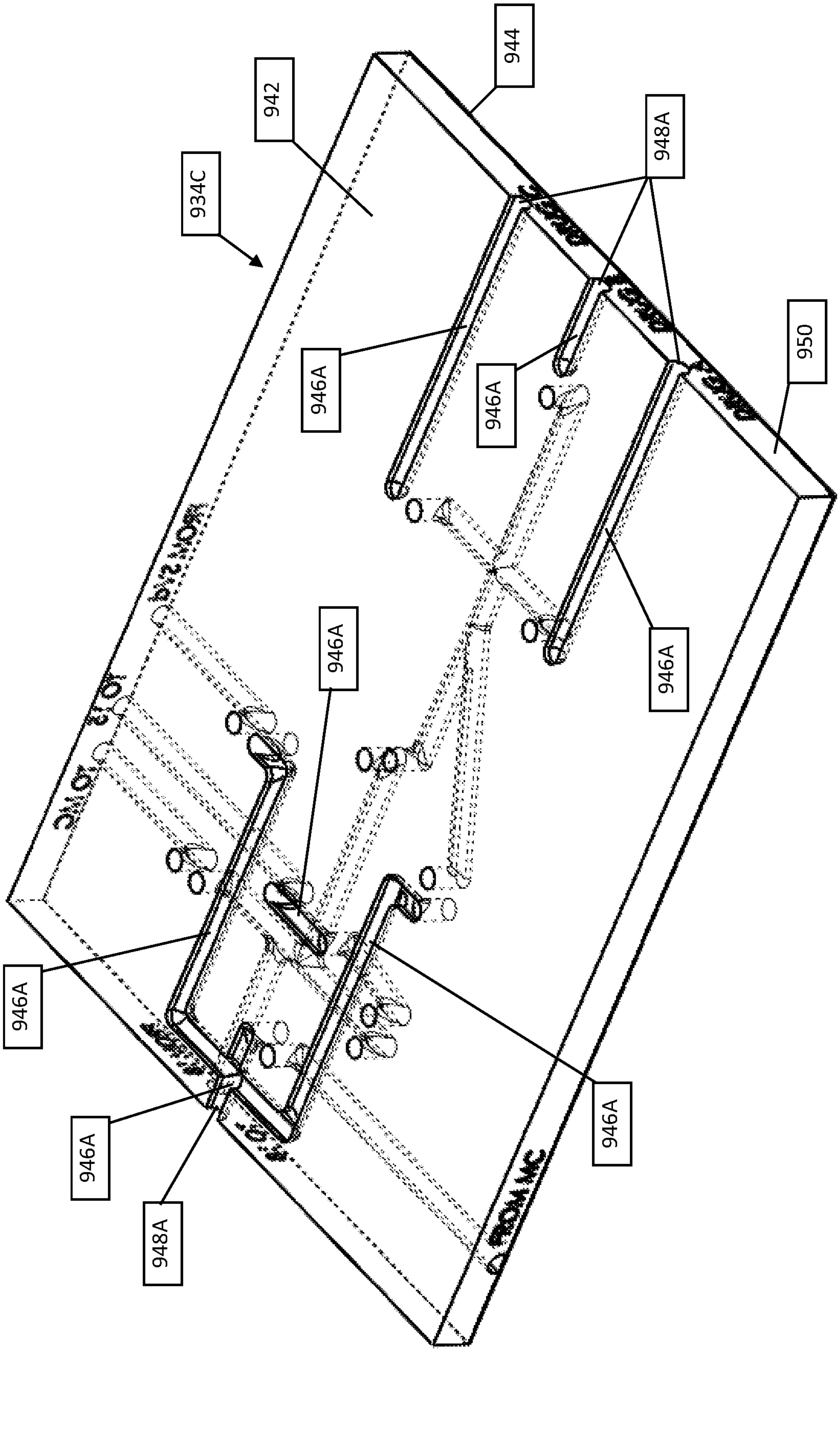

FIG. 125 is a top perspective view of a second intermediate layer useable with the partial valve module of FIG. 124.

FIGS. 126A-126D are side views of the partial valve module of FIG. 124.

Figure 126A:
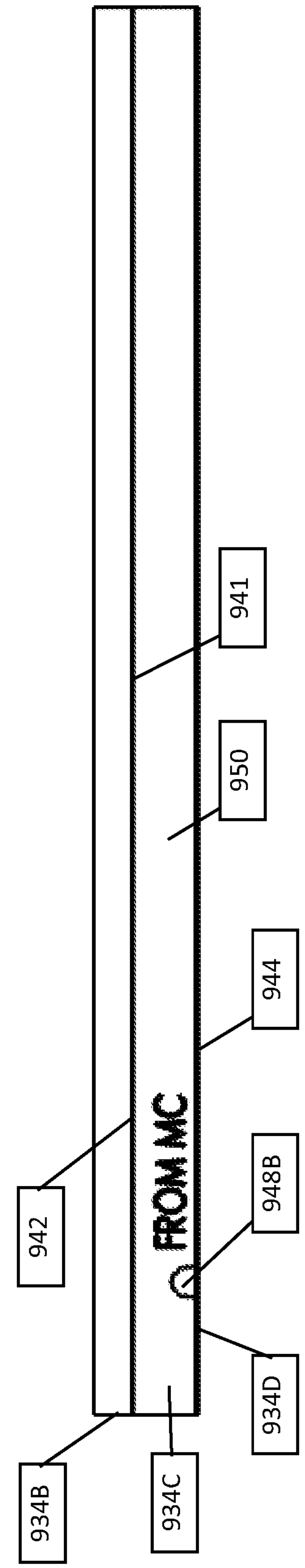
Figure 126B:
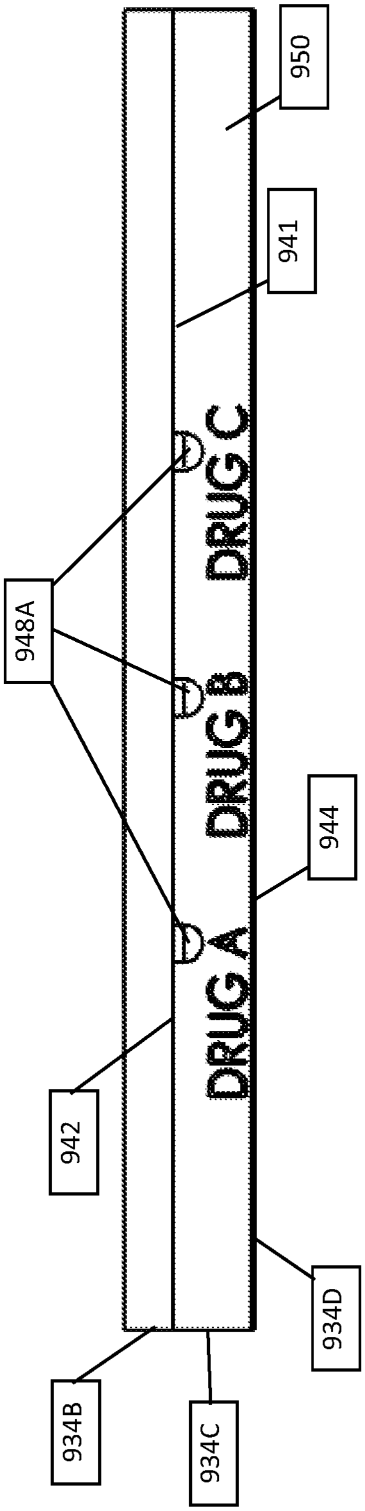
Figure 126C:
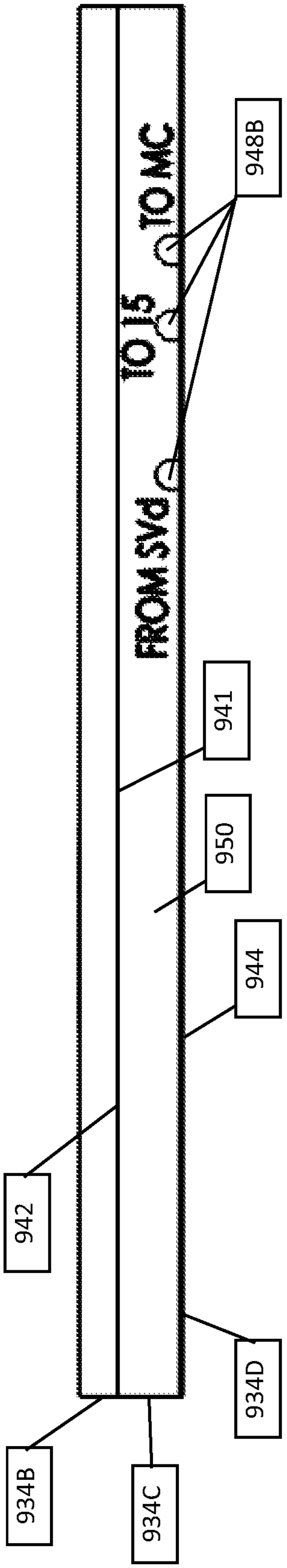
Figure 126D:
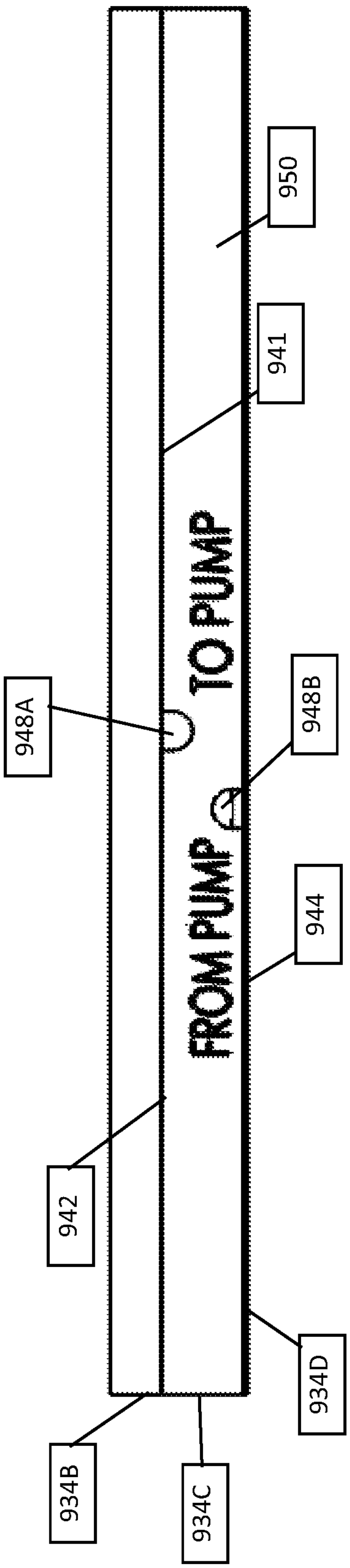
Figure 127:
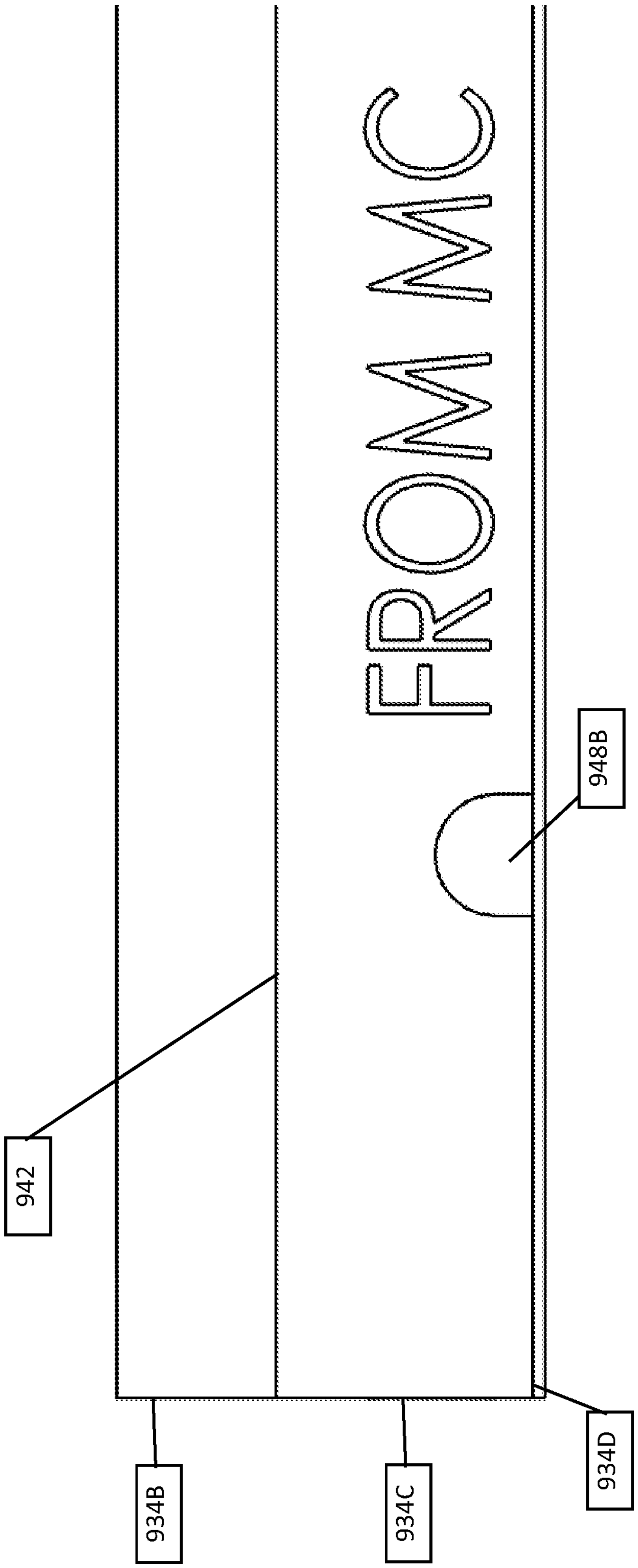

FIG. 127 is an enlarged portion of FIG. 126A.

Figure 128:
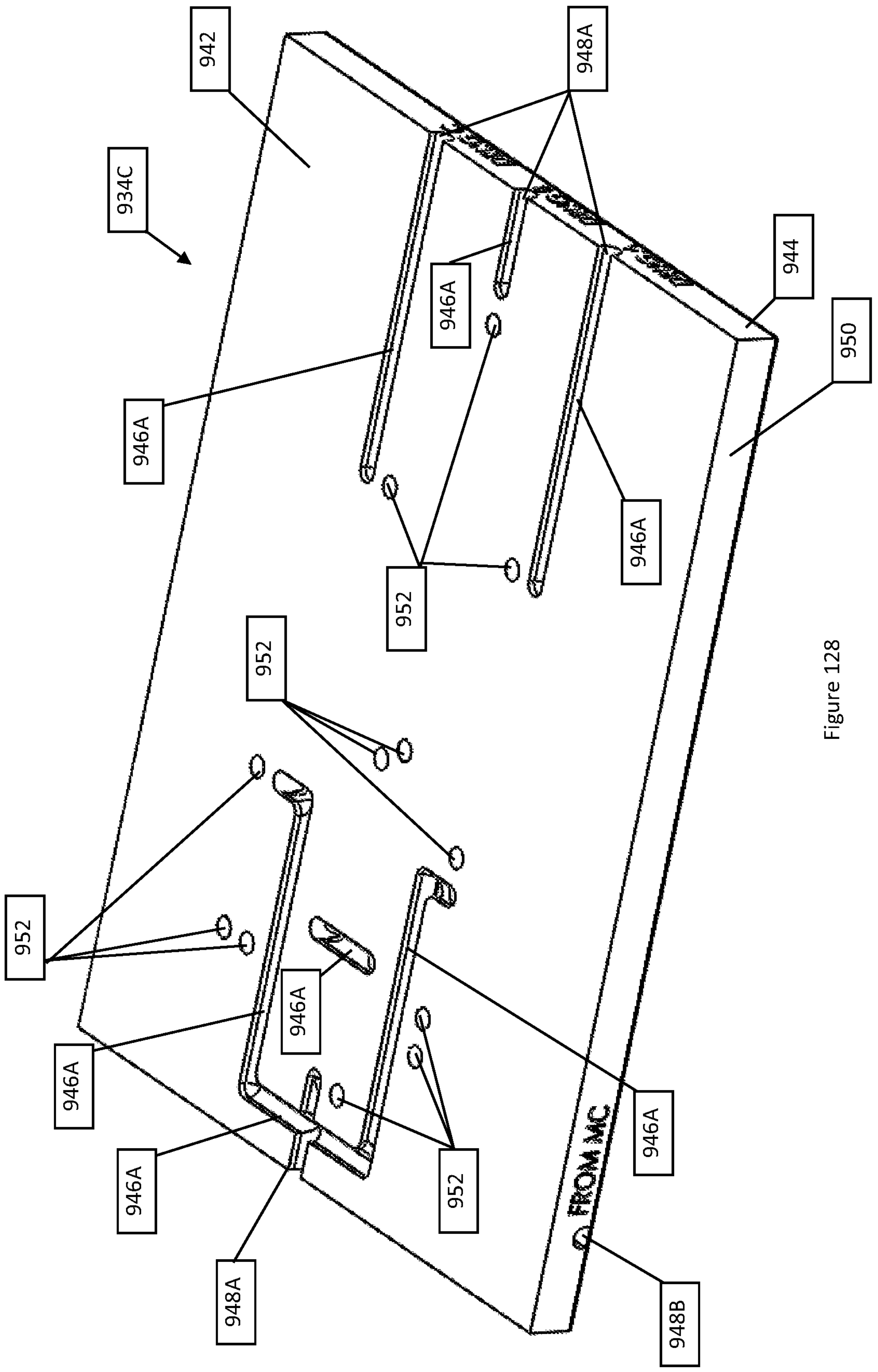

FIG. 128 is a top perspective view of the second intermediate layer of FIG. 125.

Figure 129:
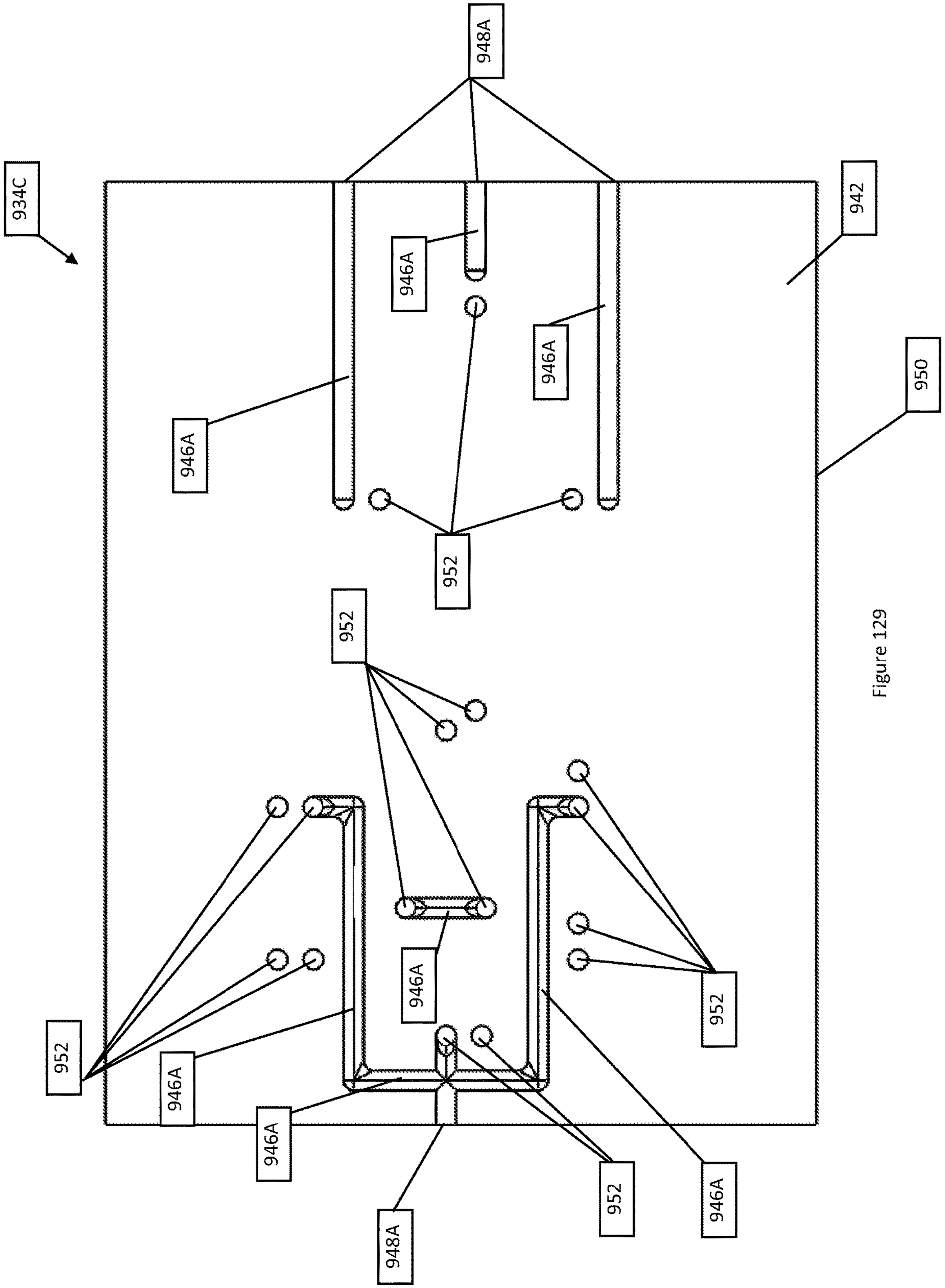

FIG. 129 is a top view of the second intermediate layer of FIG. 125.

Figure 130:
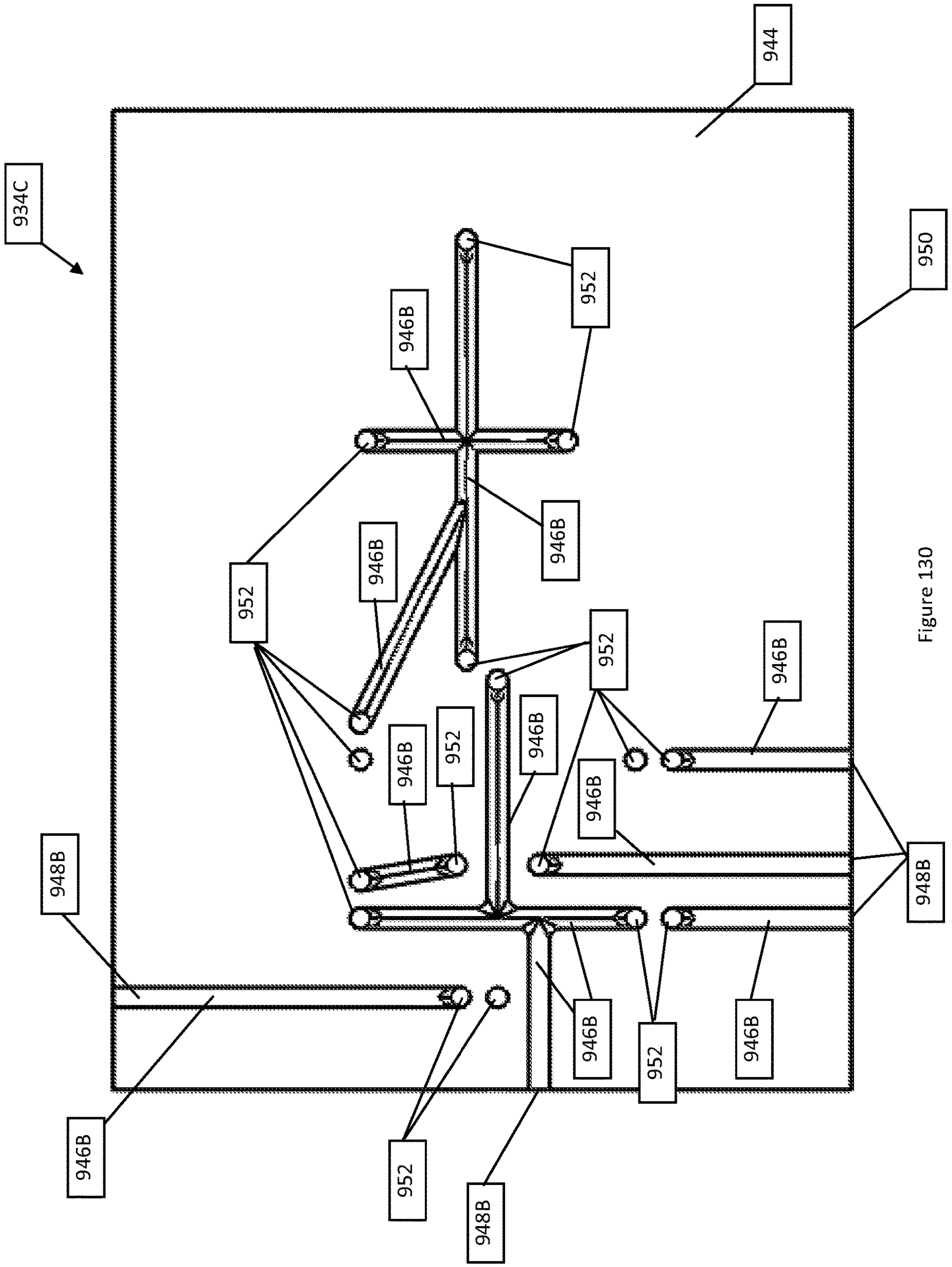

FIG. 130 is a bottom view of the second intermediate layer of FIG. 125.

Figure 131:
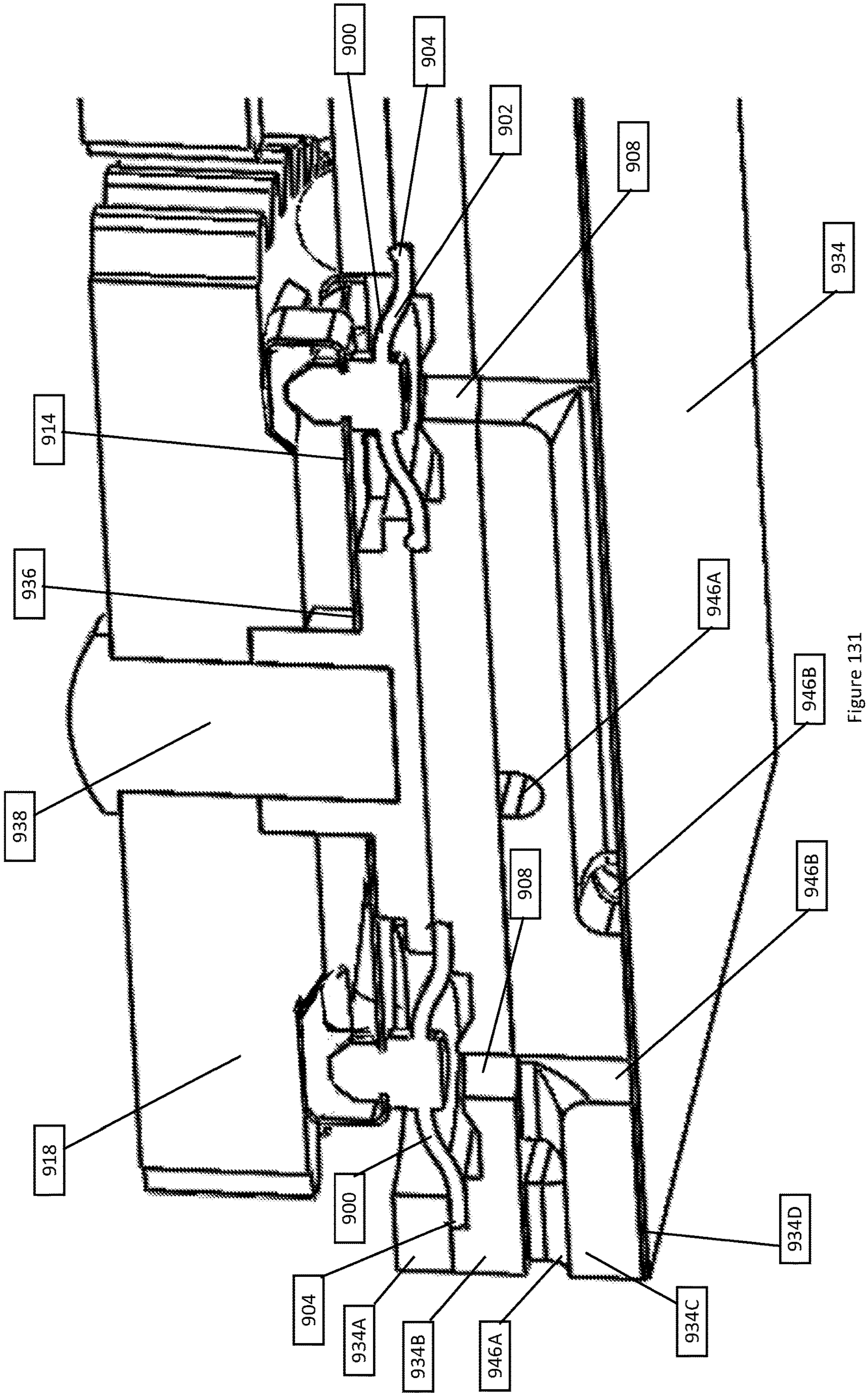

FIG. 131 is a cross-section view of the valve module of FIG. 118A.

Figure 132:
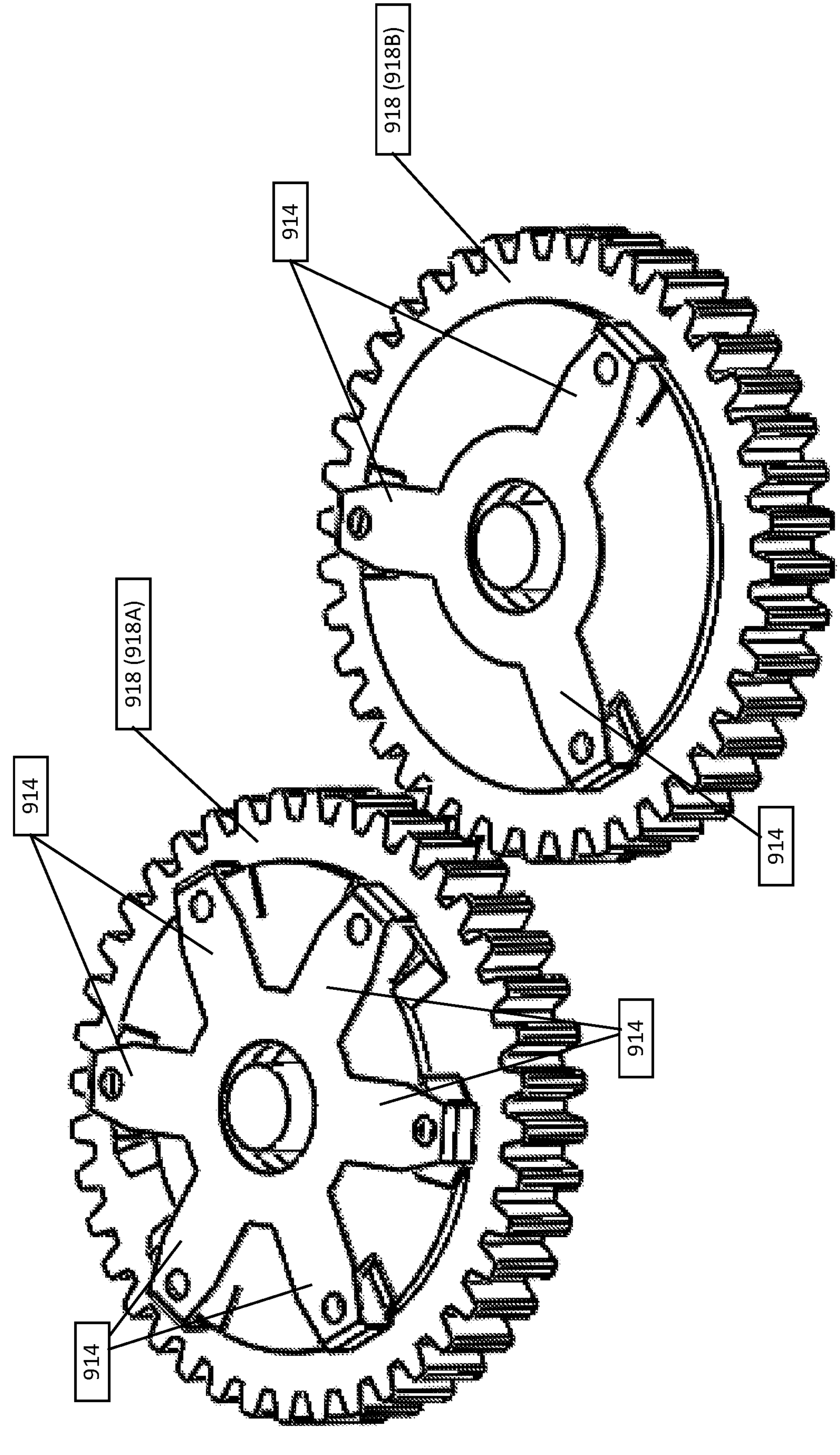

FIG. 132 is a top perspective view of an arrangement of actuator gears leaf springs useable with the subject invention.

Figure 133:
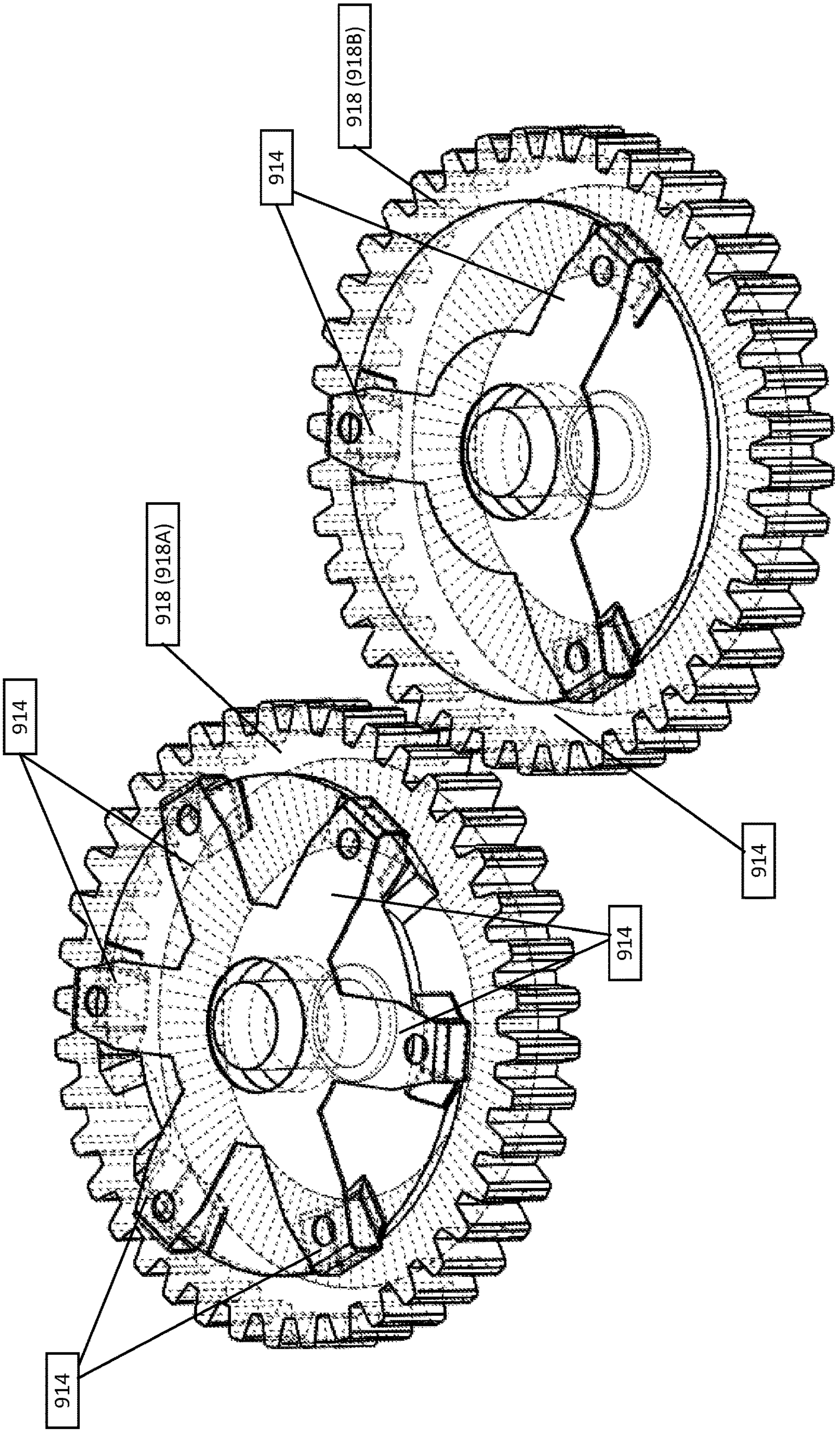

FIG. 133 is a top perspective view of the arrangement of FIG. 132 with the actuator gears shown in transparency.

Figure 134:
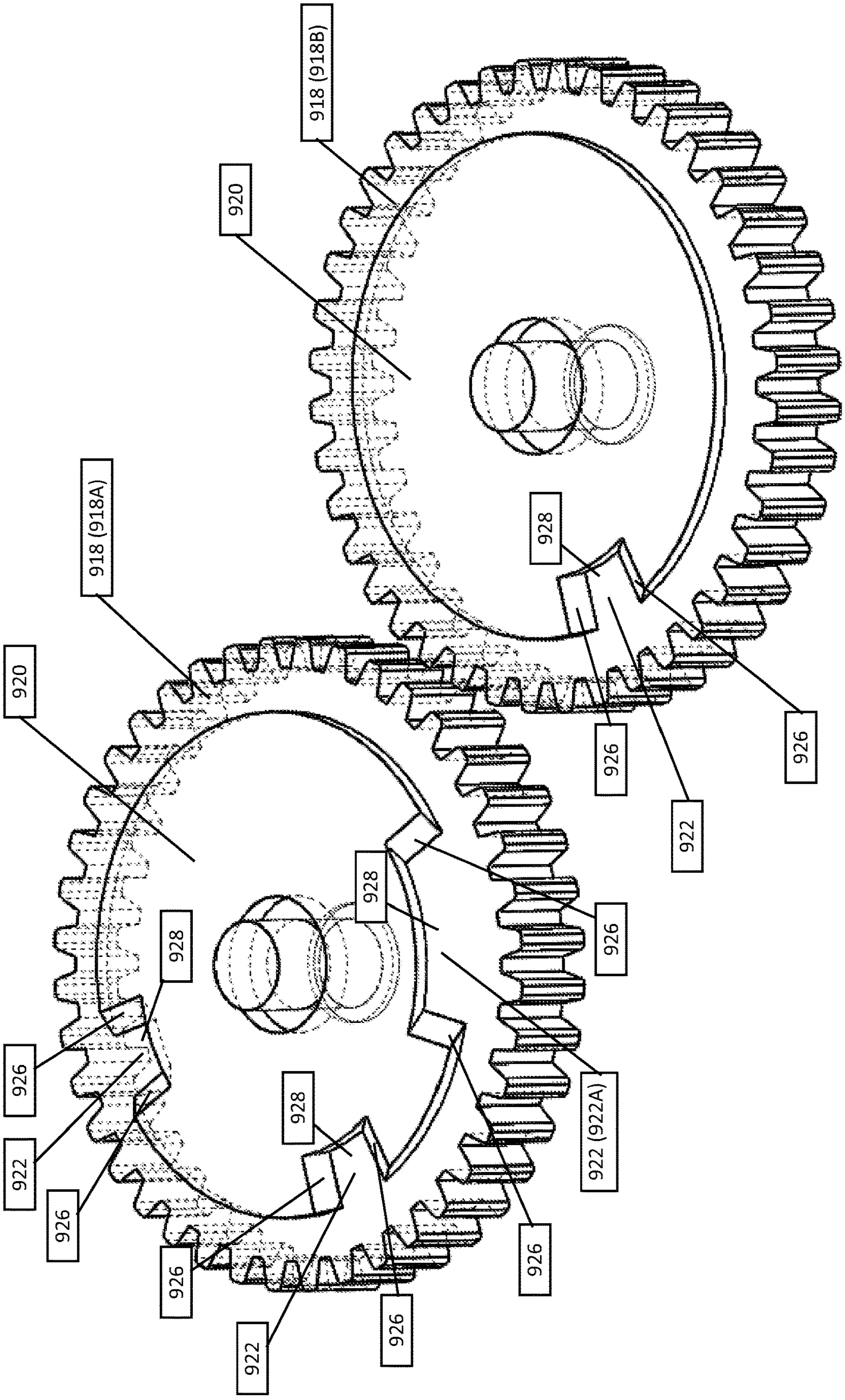

FIG. 134 is a top perspective view of the arrangement of FIG. 132 with the leaf springs removed.

Figure 135:
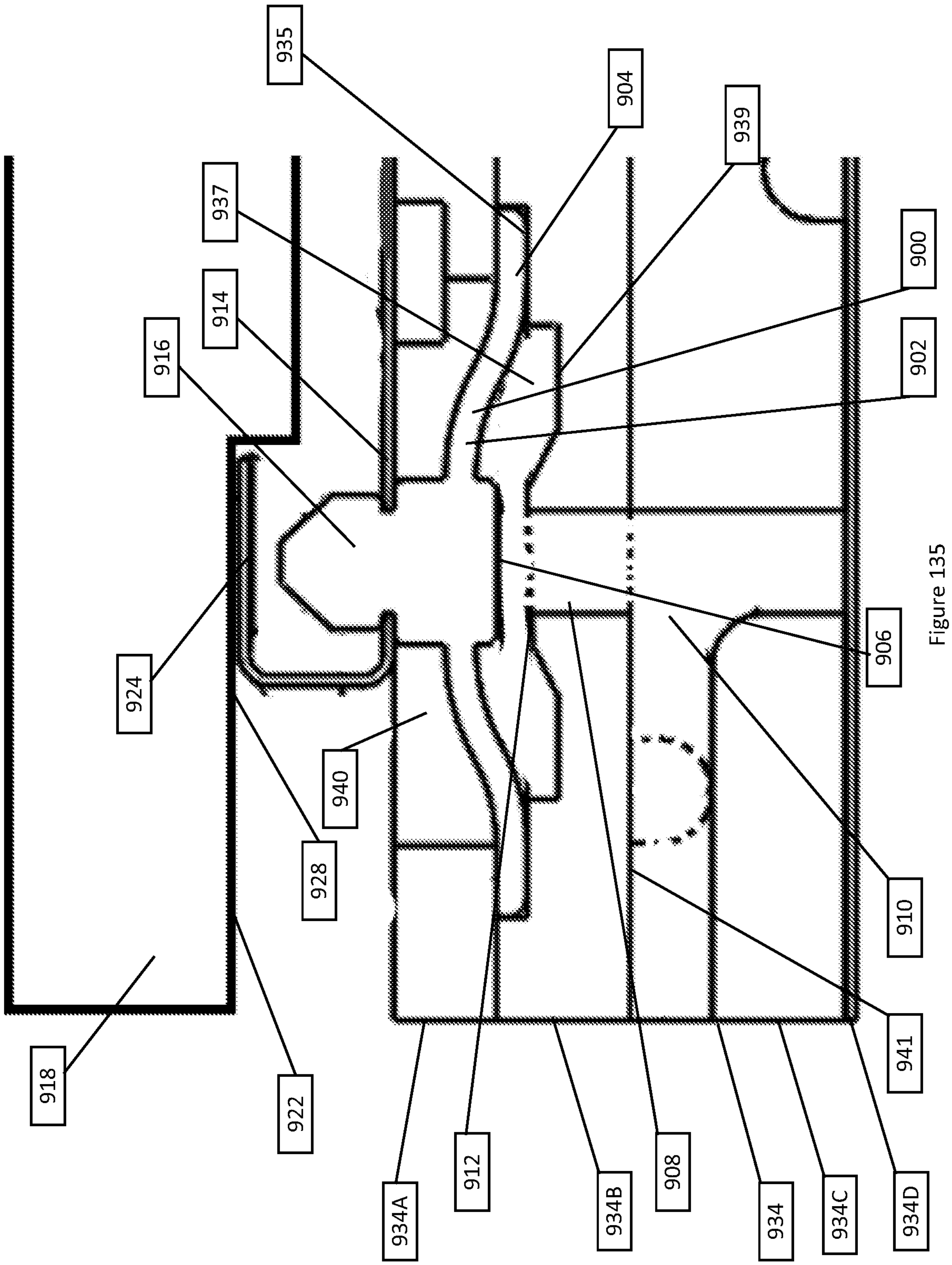

FIG. 135 is an enlarged portion of FIG. 131 showing a valve in an unbiased state.

Figure 136:
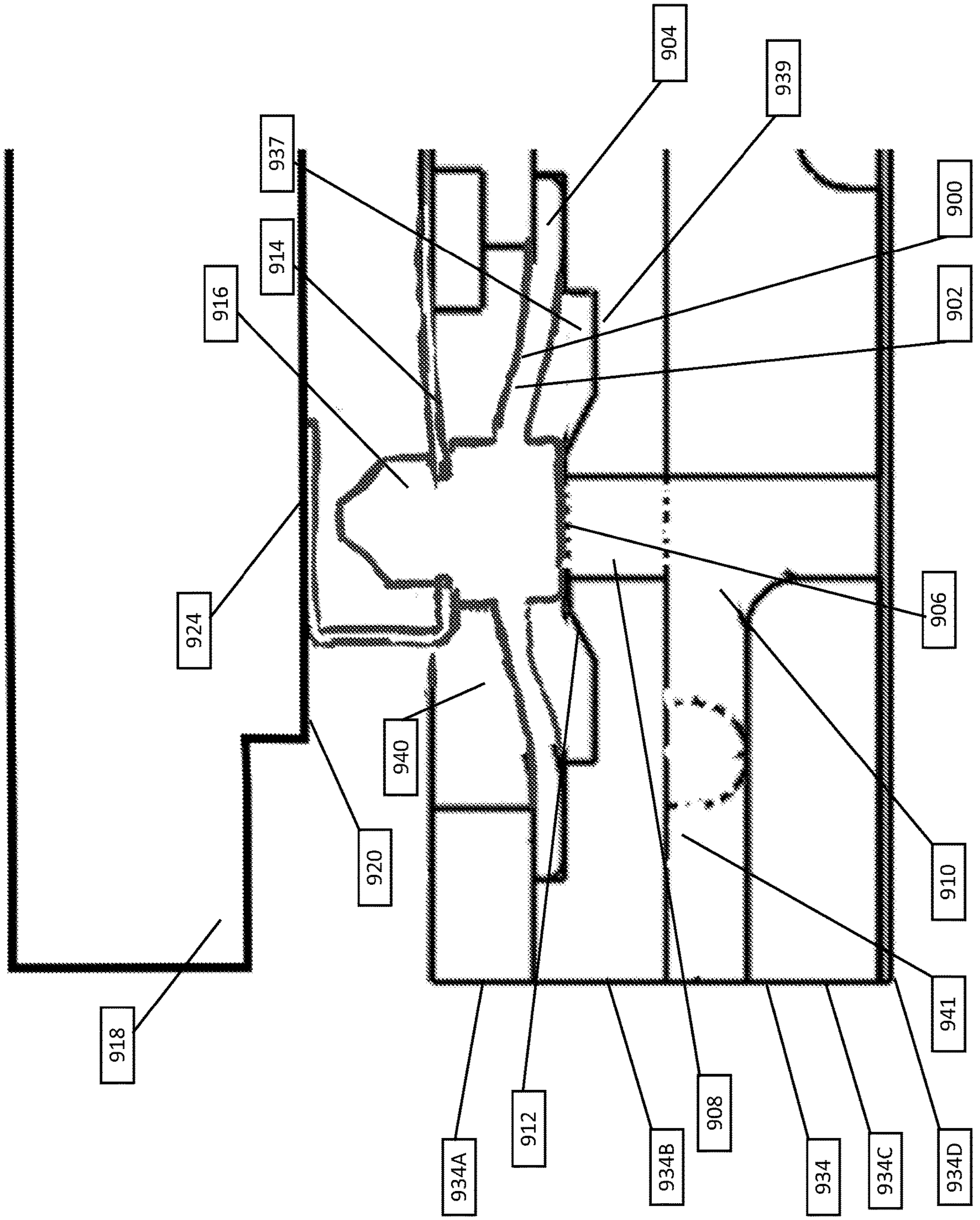

FIG. 136 shows the valve of FIG. 135 in a deflected state.

Figure 137:
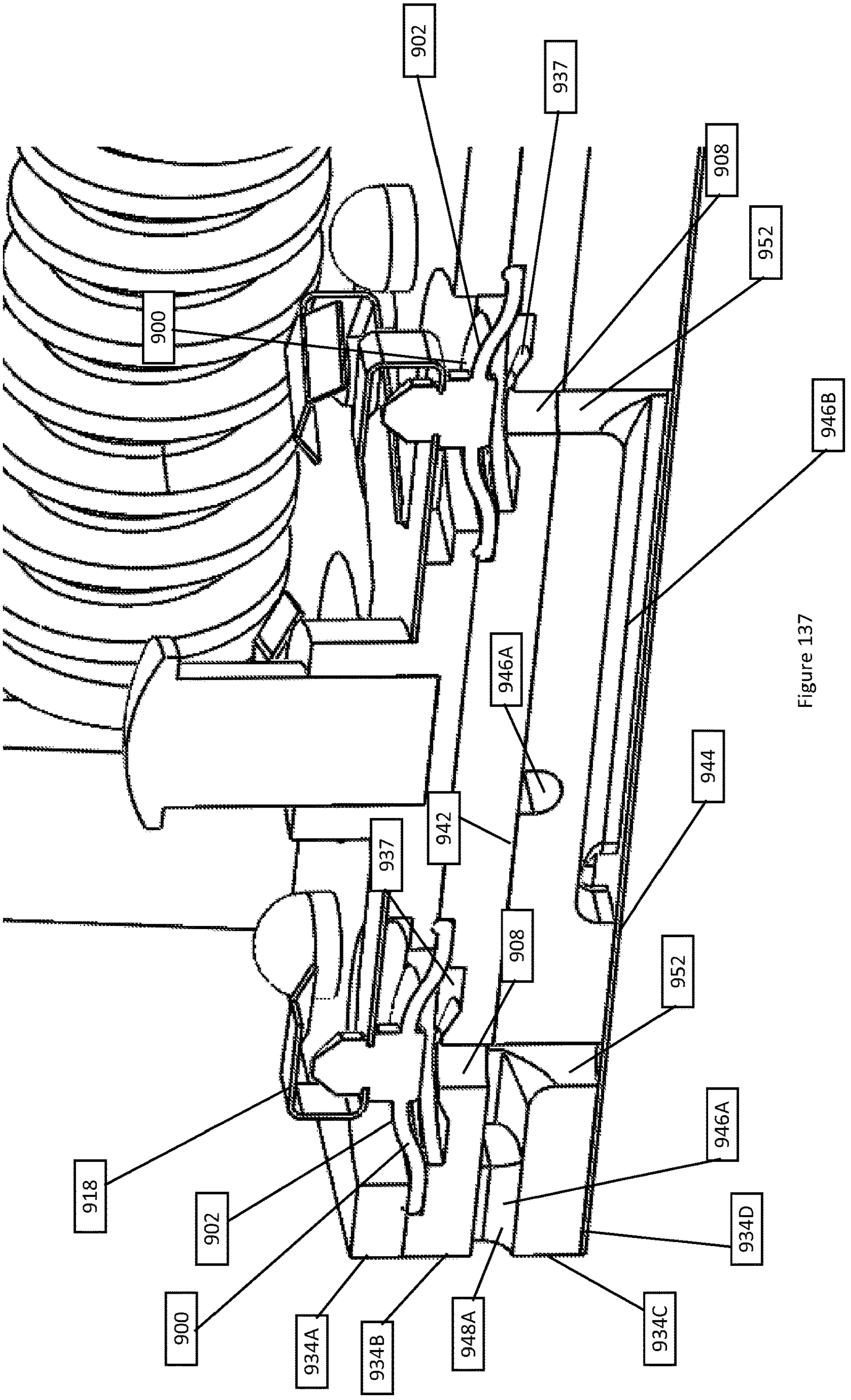

FIG. 137 is a top perspective view of FIG. 131 with the actuator gear removed.

Figure 138:
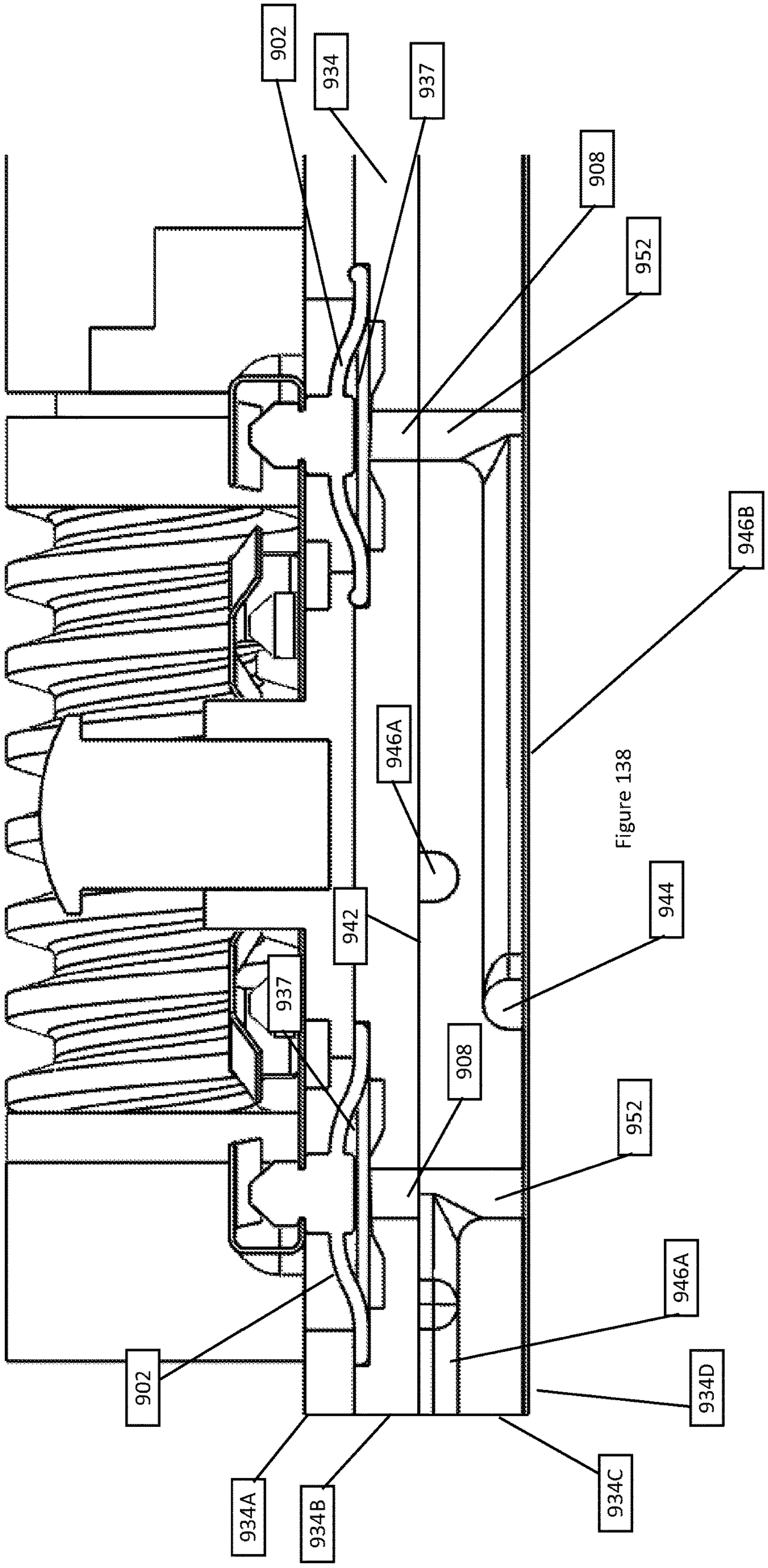

FIG. 138 is a side view of FIG. 137.

Figure 139A:
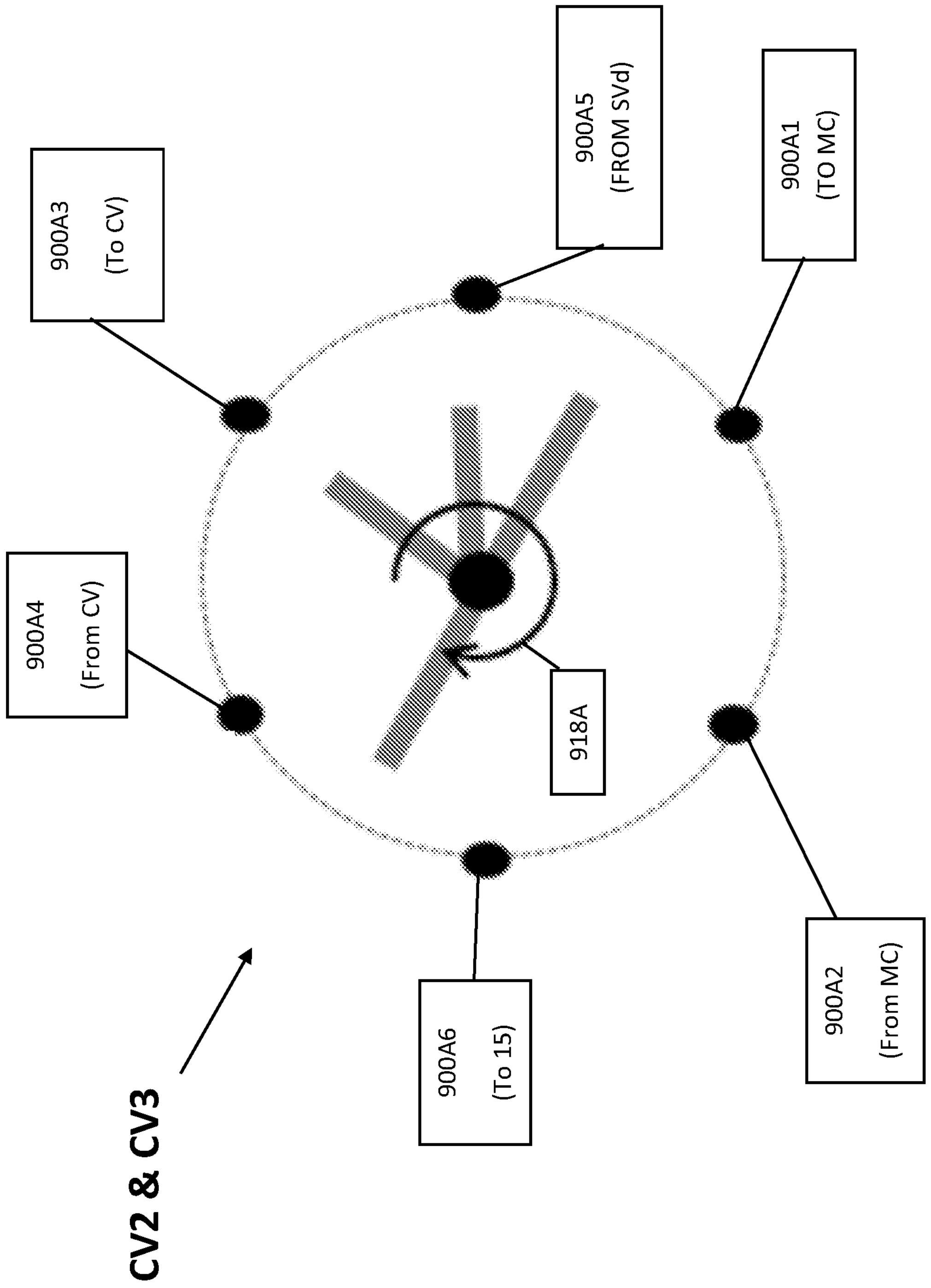

FIG. 139A shows schematically an arrangement of a set of valves and actuator gear useable with the subject invention.

Figure 139B:
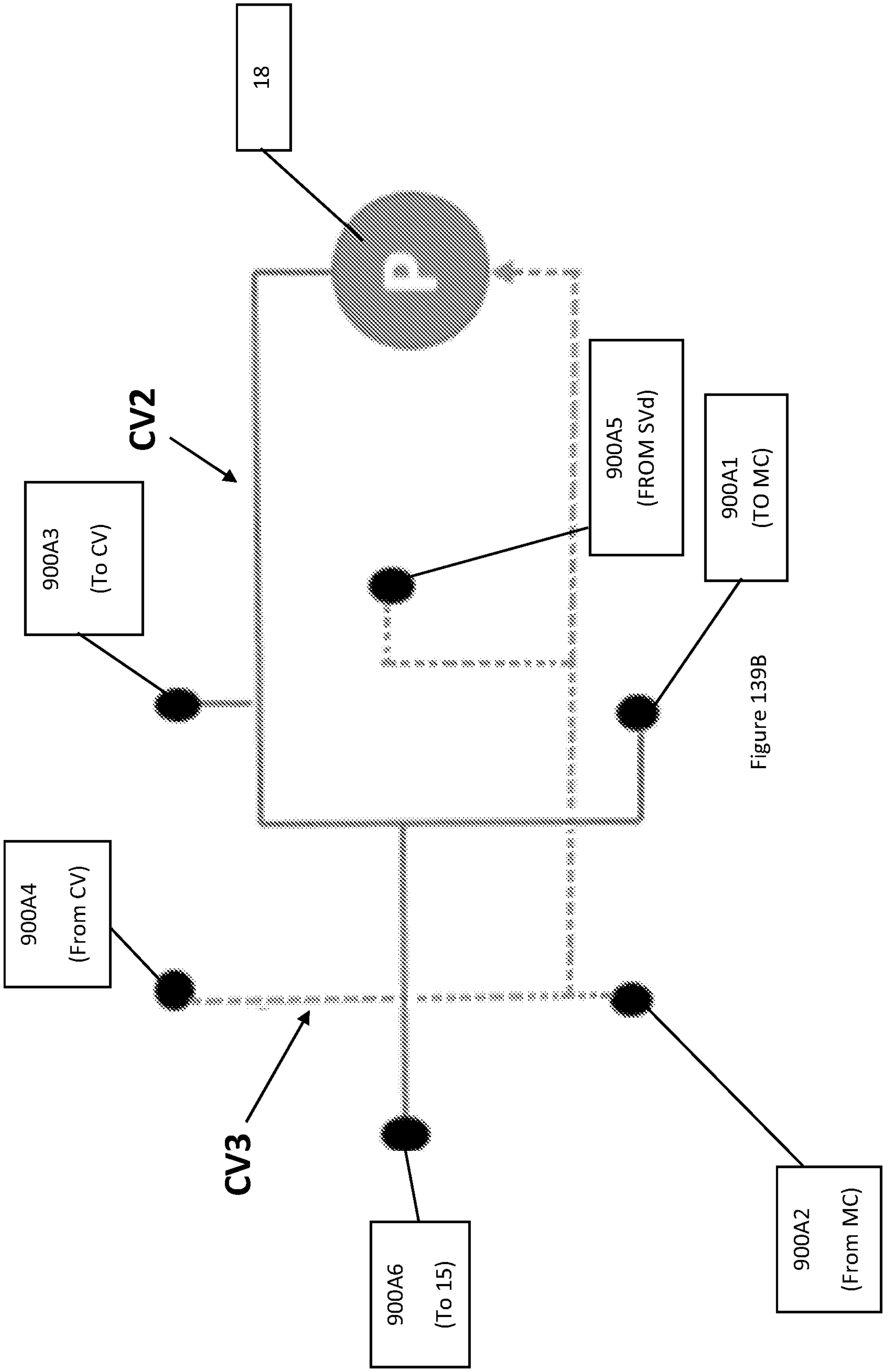

FIG. 139B shows a schematic of the valves of FIG. 139A and features of the drug delivery device to which the valves may be fluidically coupled.

Figure 139C:
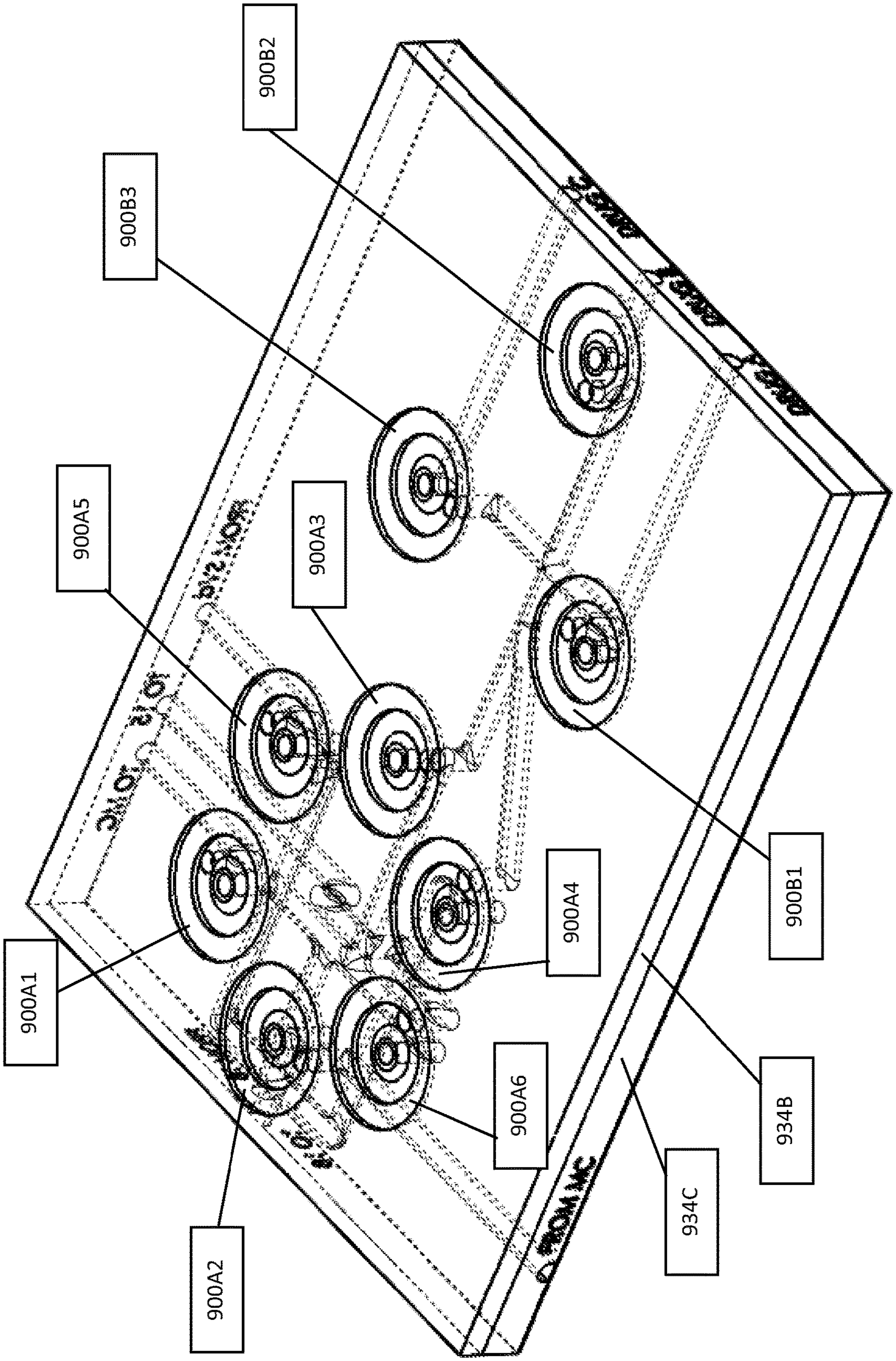
Figure 140A:
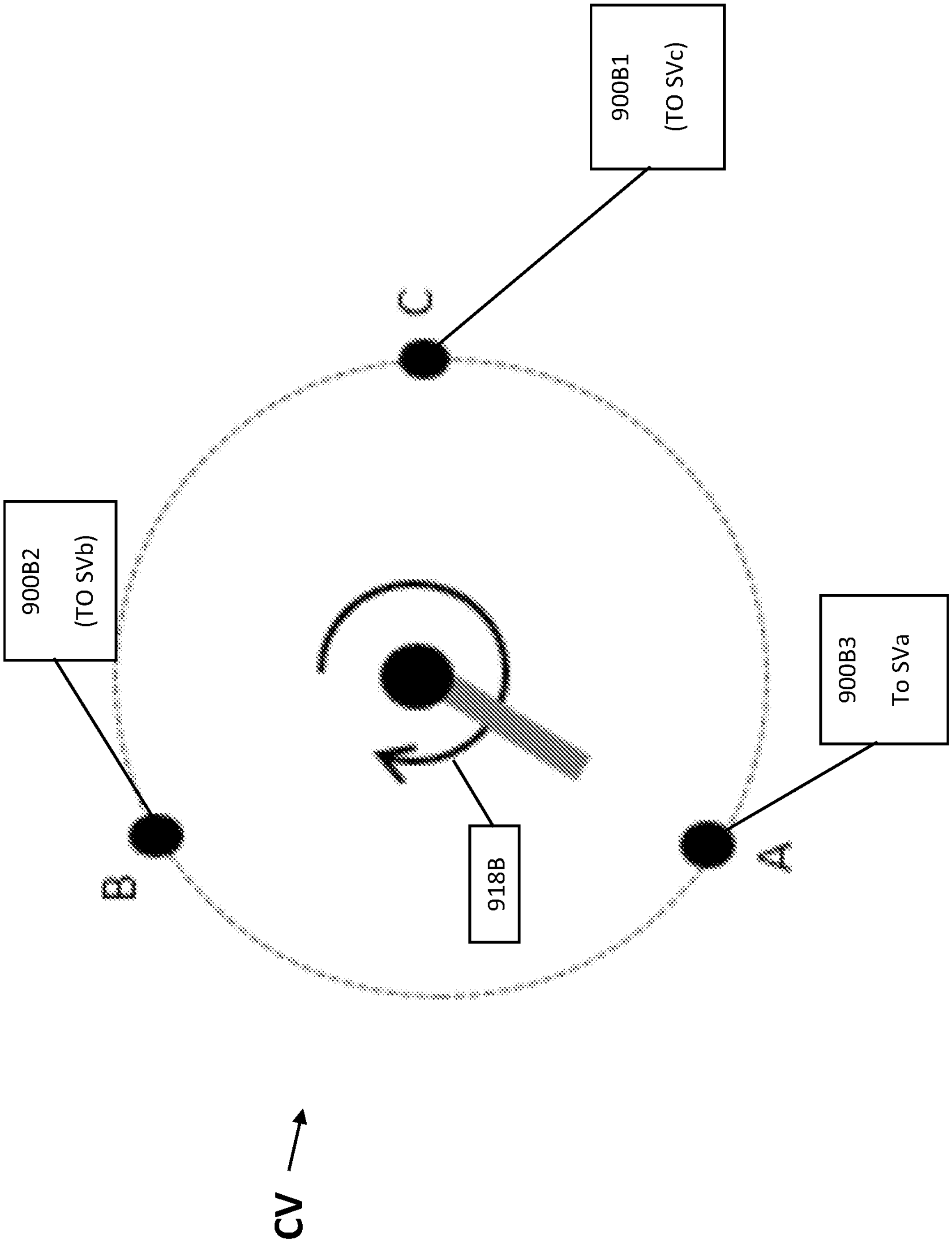

FIG. 139C is a copy of FIG. 124 marked up with placement of the valves shown in FIGS. 139A and 140A.

Figure 139D:
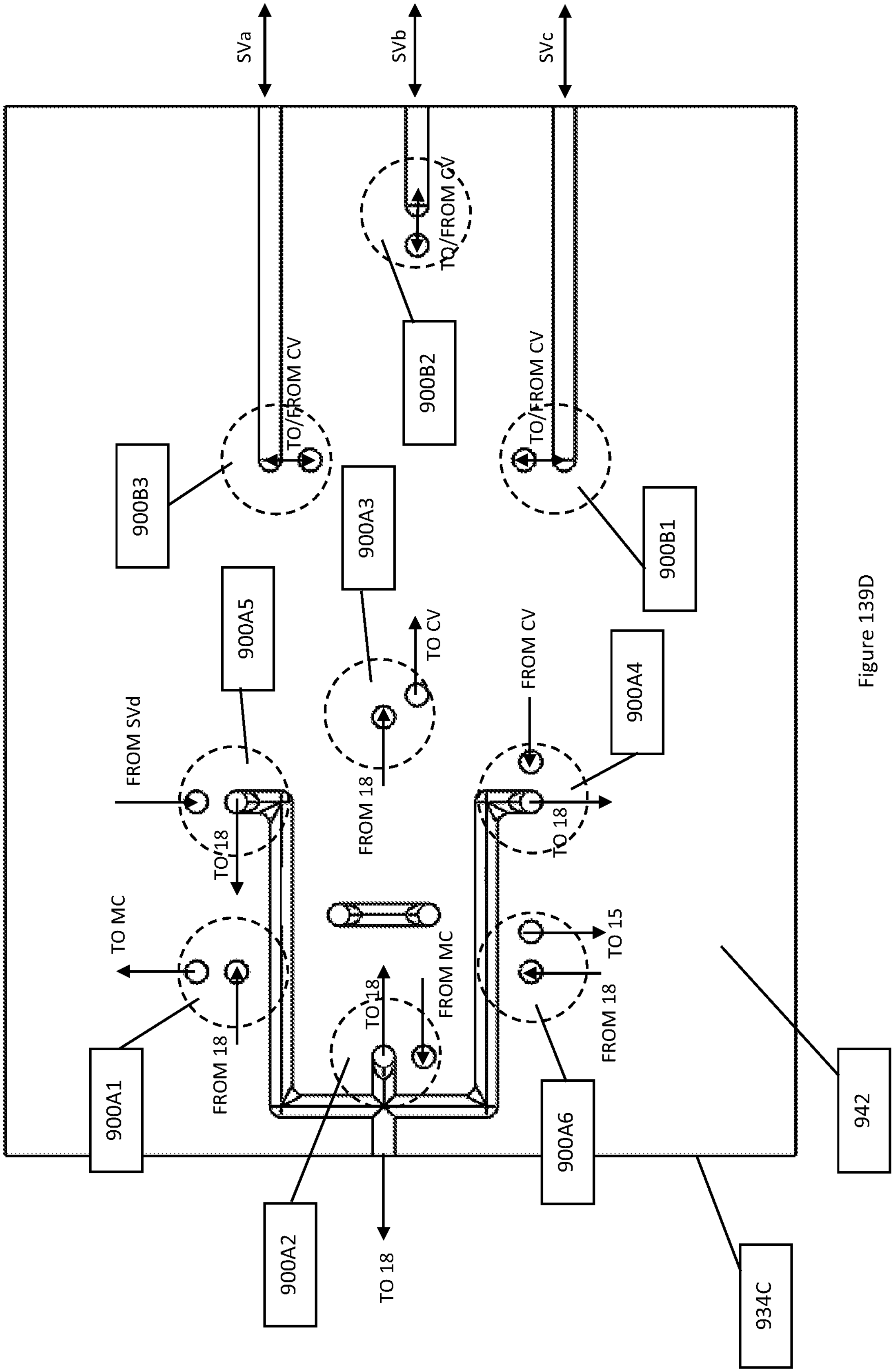
Figure 139E:
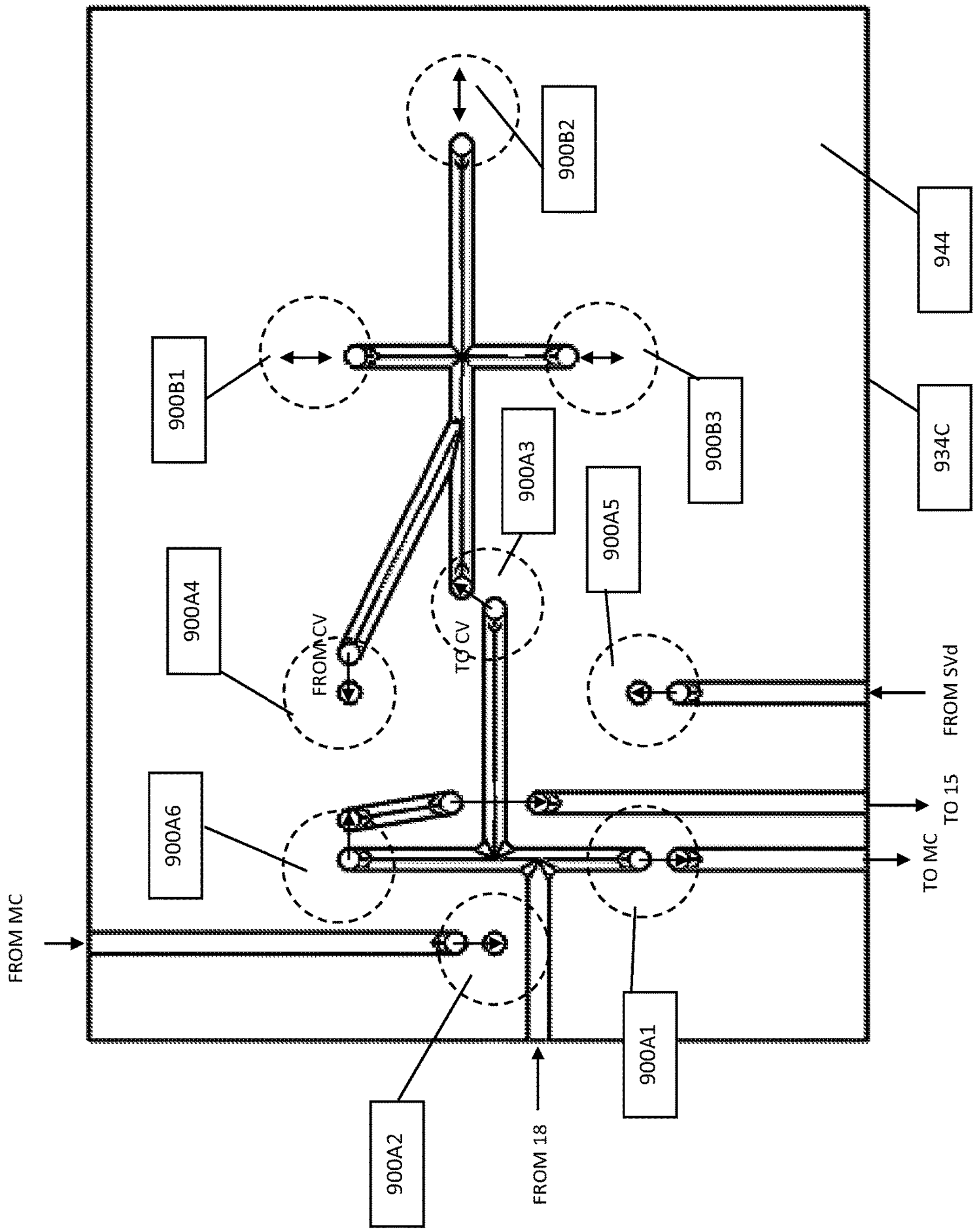

FIGS. 139D and 139E are copies of FIGS. 129 and 130, respectively, marked up to show fluid connections between the valves and features of the drug delivery device to which the valves may be fluidically coupled.

FIG. 140A shows schematically an alternate arrangement of a set of valves and actuator gear useable with the subject invention.

Figure 140B:
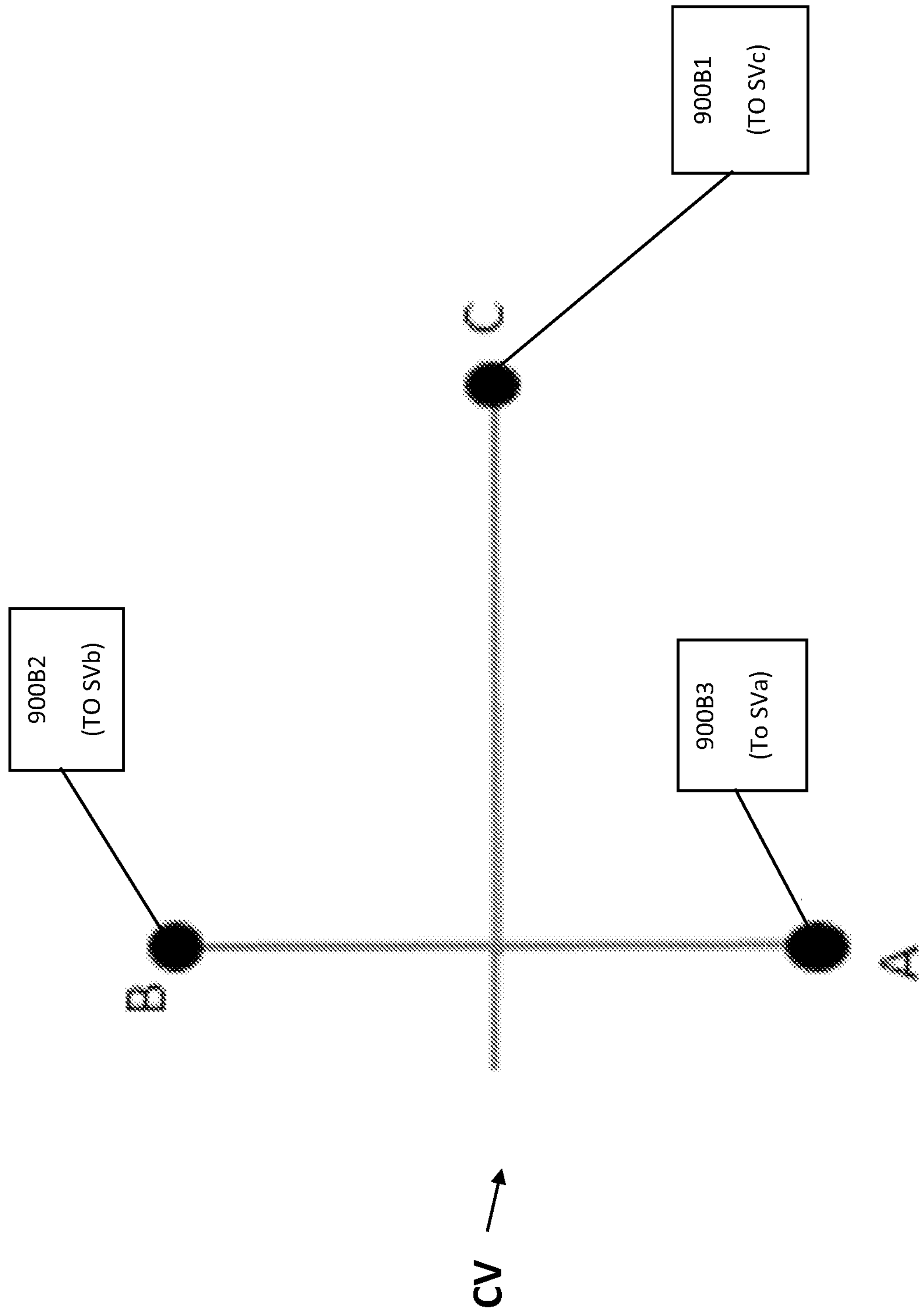

FIG. 140B shows a schematic of the valves of FIG. 140A and features of the drug delivery device to which the valves may be fluidically coupled.

Figure 141:
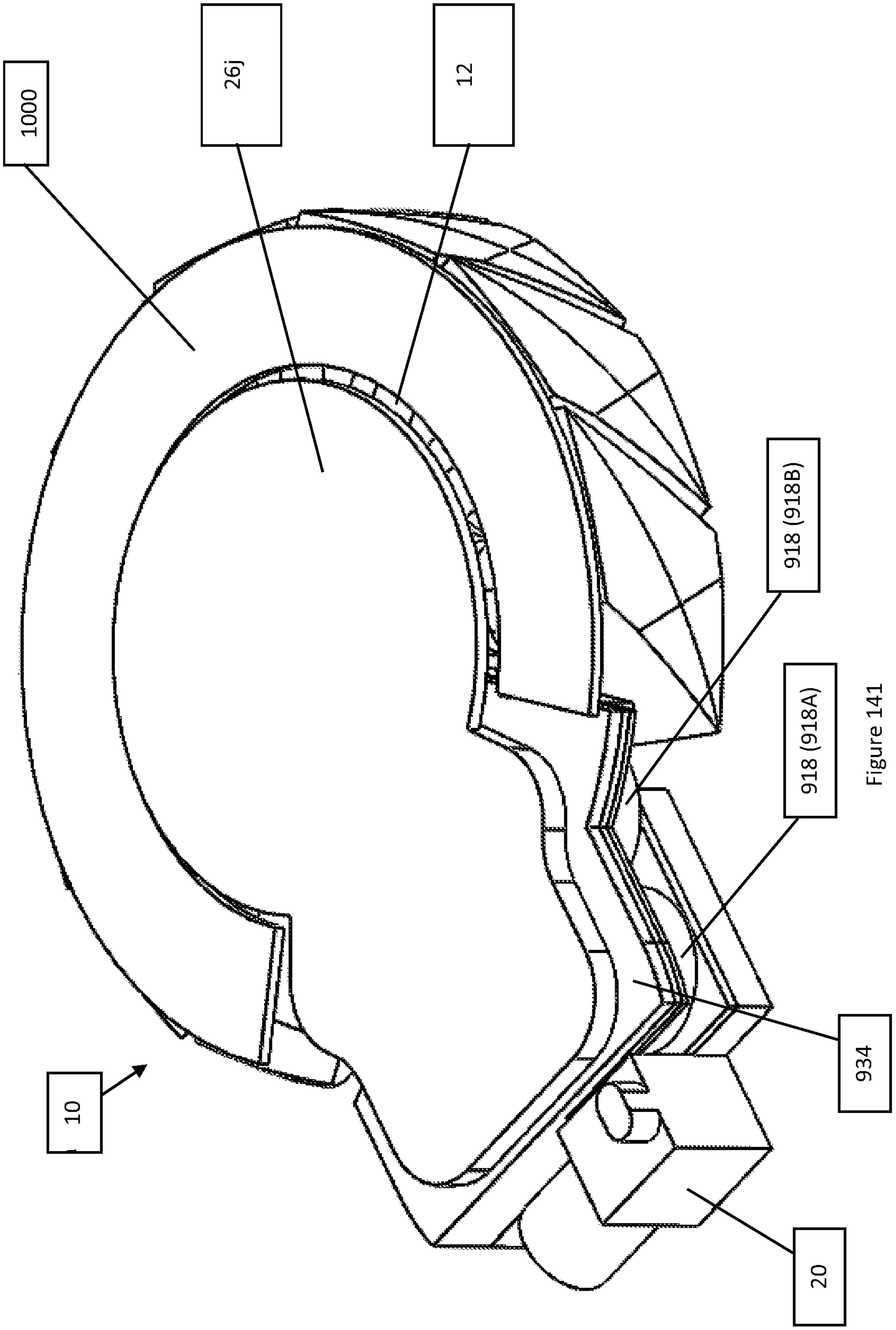

FIG. 141 shows a top perspective view of a drug delivery device in accordance with the subject invention.

Figure 142:
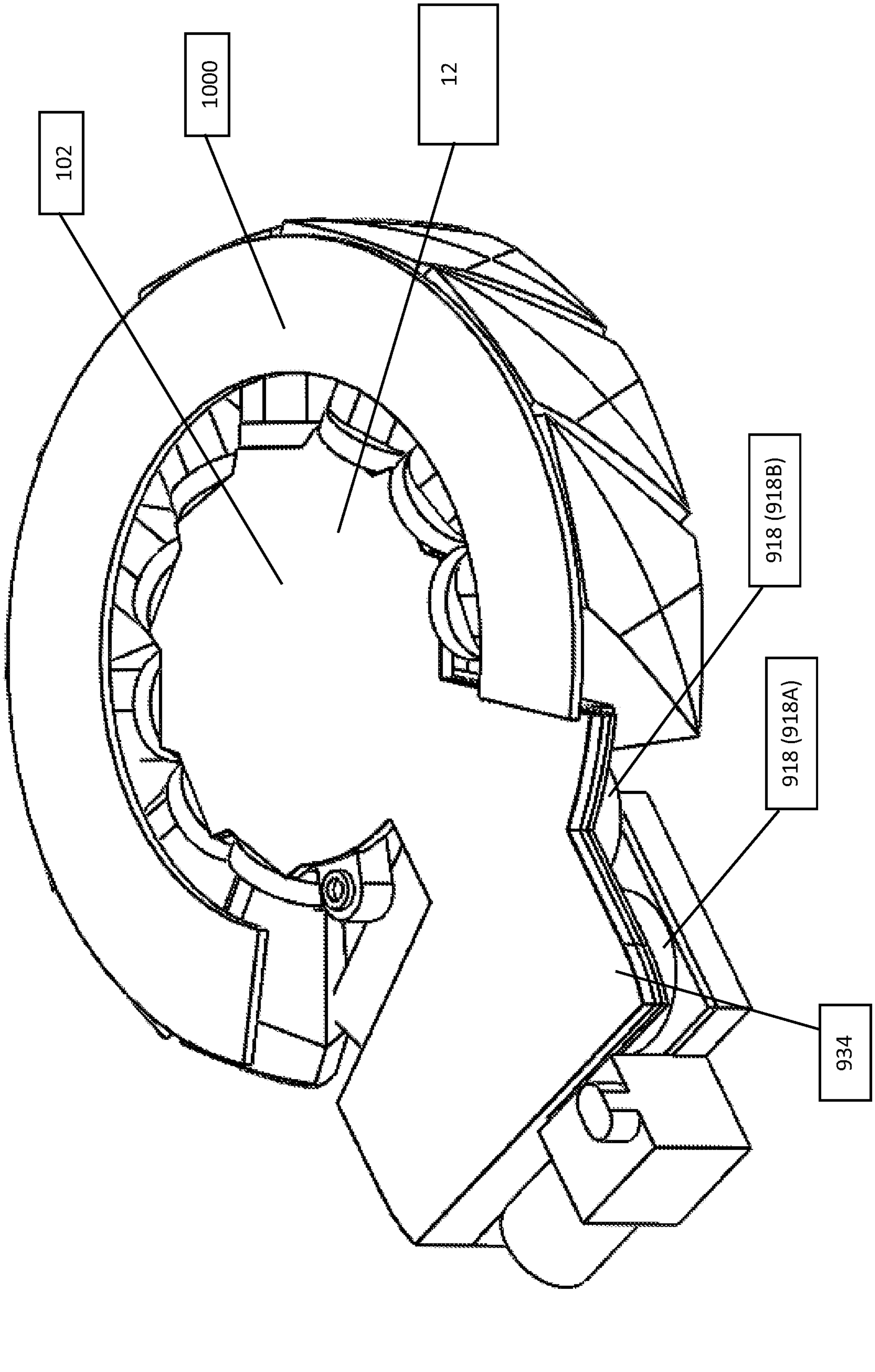

FIG. 142 is a top perspective view of the drug delivery device of FIG. 141 with the reservoir removed.

Figure 143:
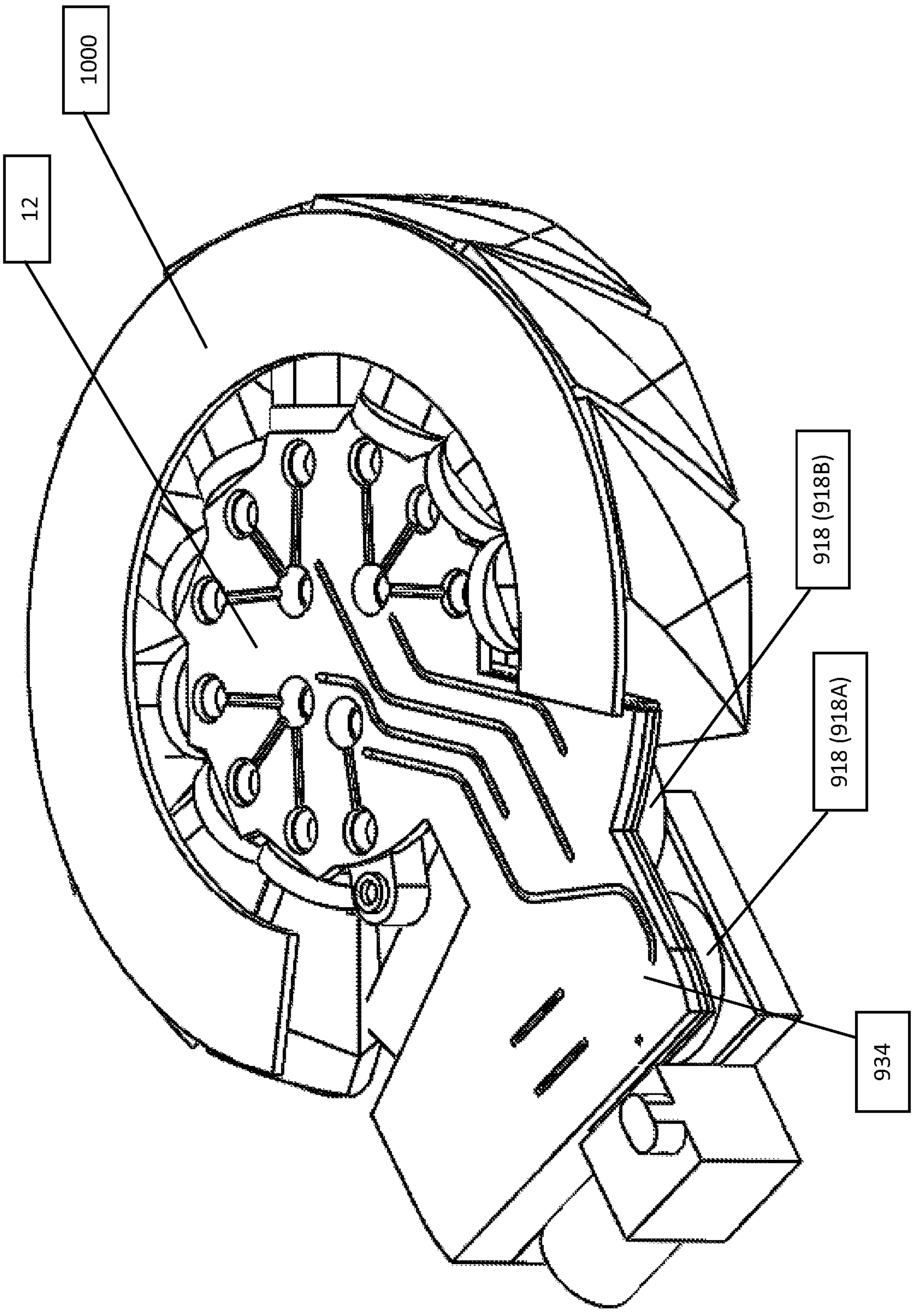

FIG. 143 is a top perspective view of the drug delivery device of FIG. 141 with the reservoir the barrier removed.

Figure 144:
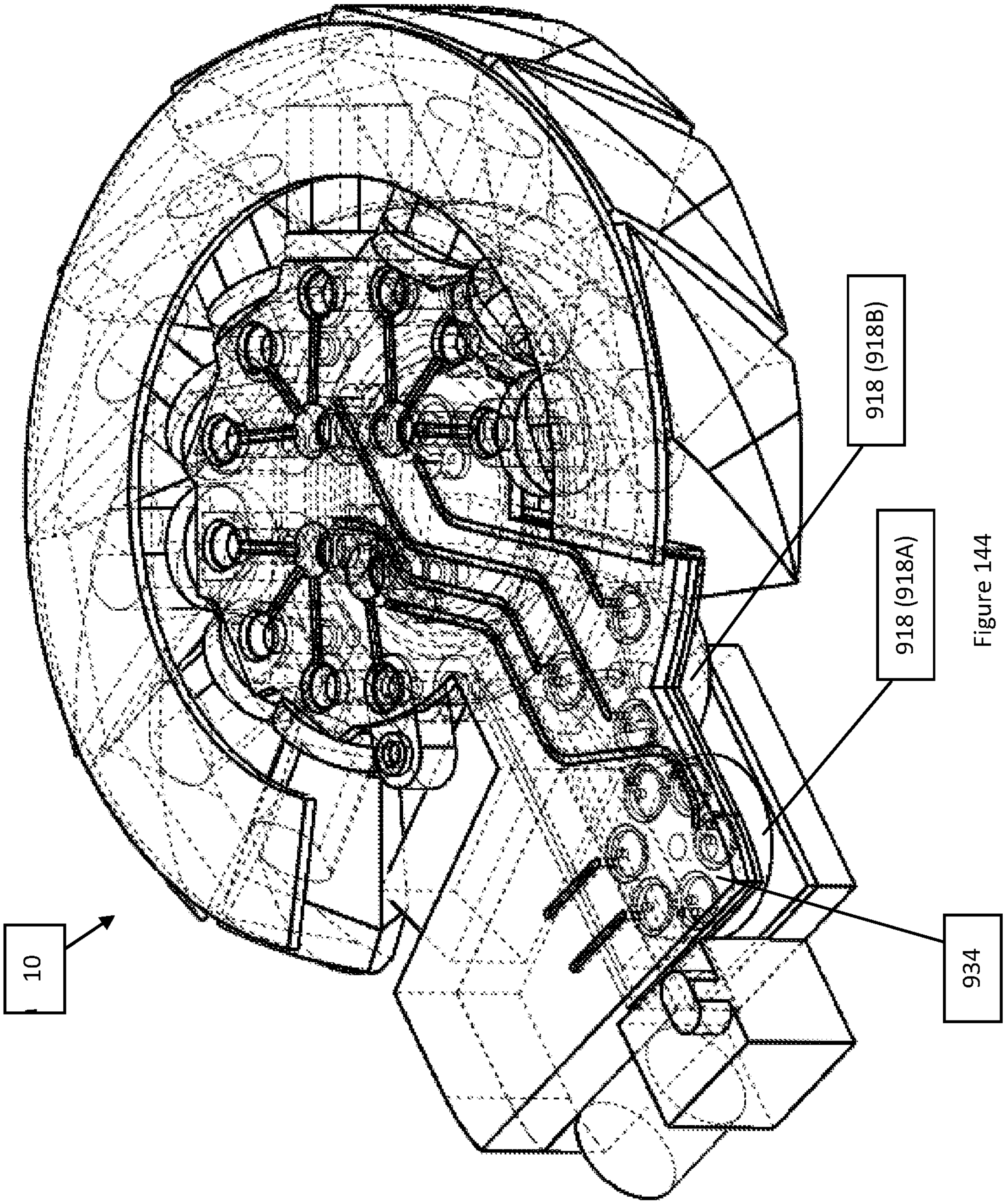

FIG. 144 shows FIG. 143 in transparency to show internal passageways.

Figure 145:
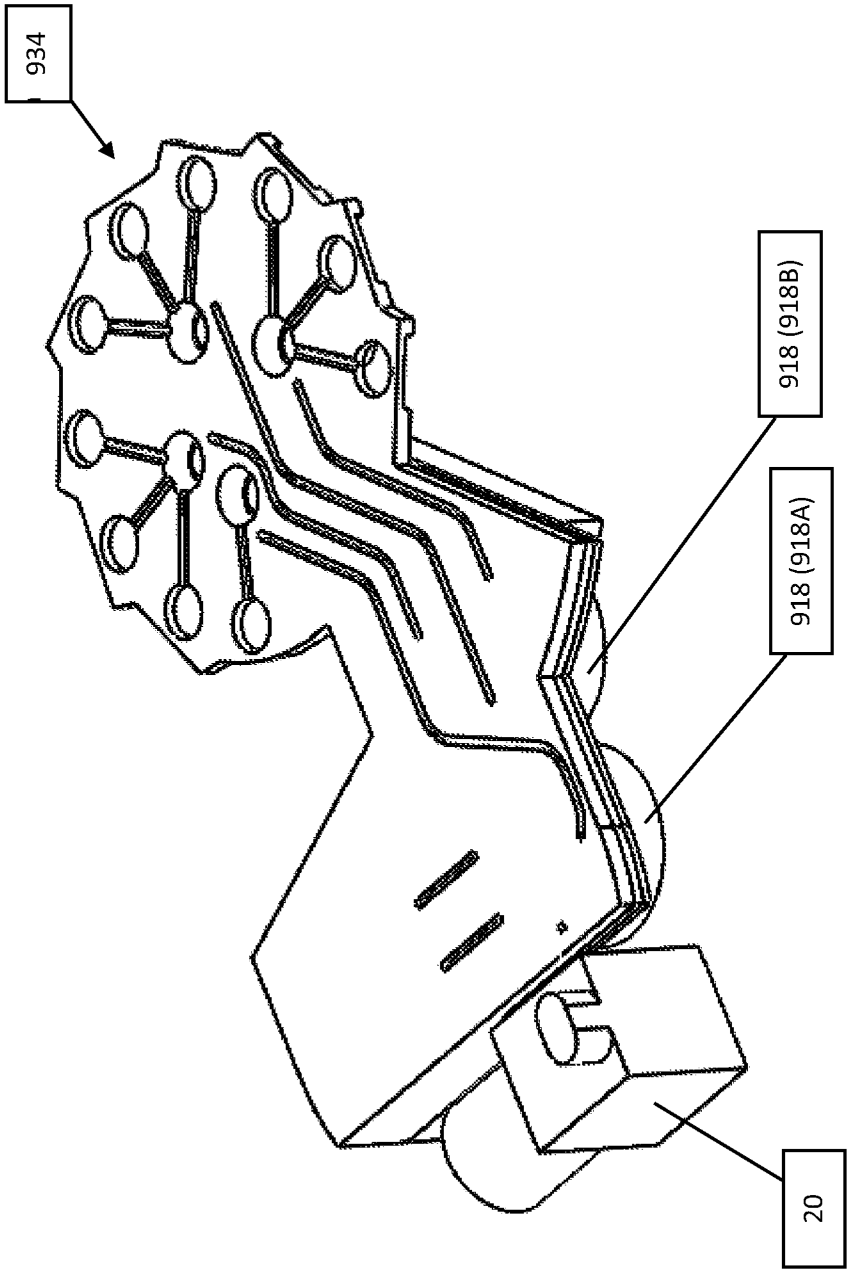

FIG. 145 is a top perspective view of an alternate valve module useable with the subject invention.

Figure 146:
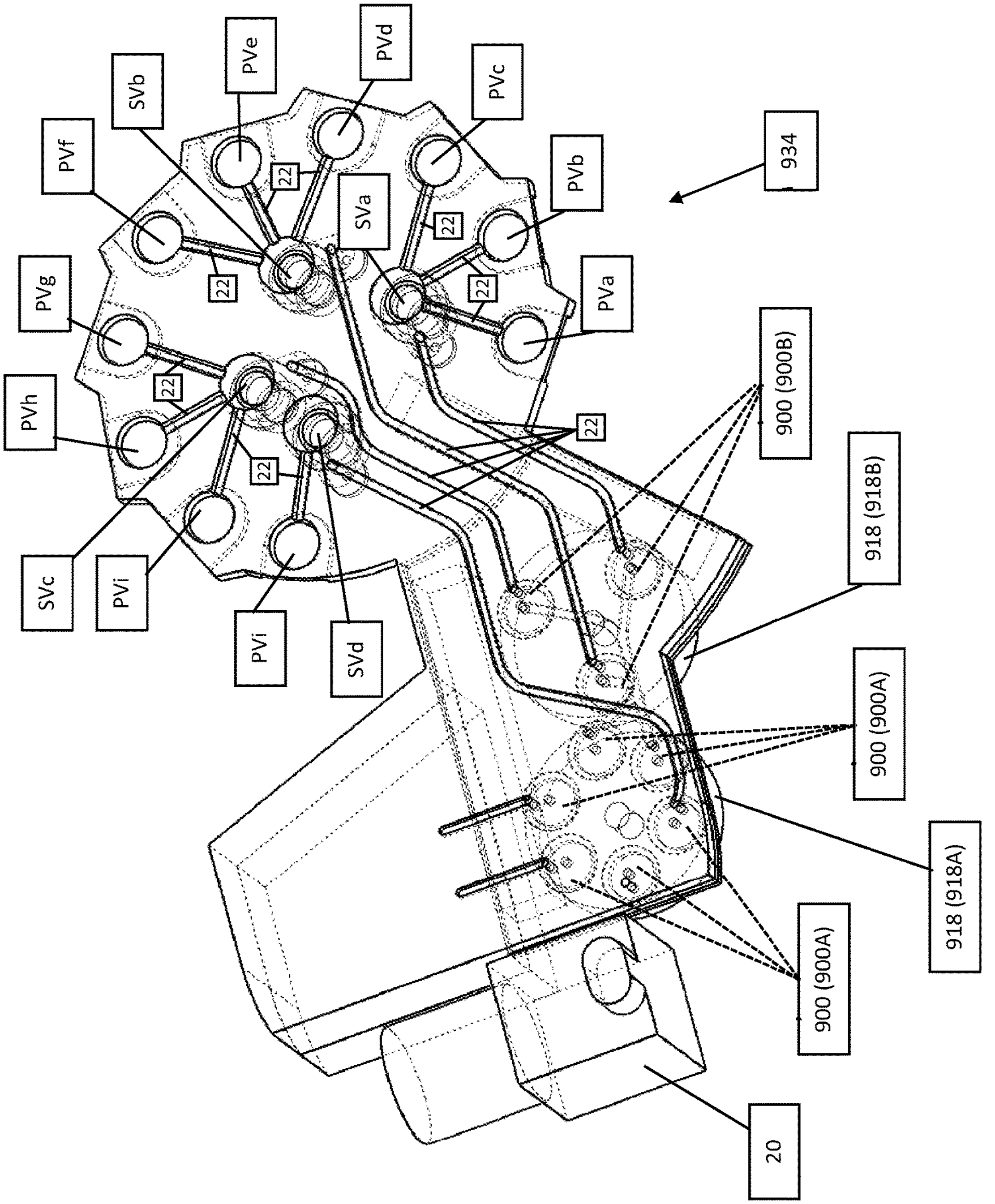

FIG. 146 is an enlarged view of FIG. 145 with certain portions being shown in transparency.

Figure 147:
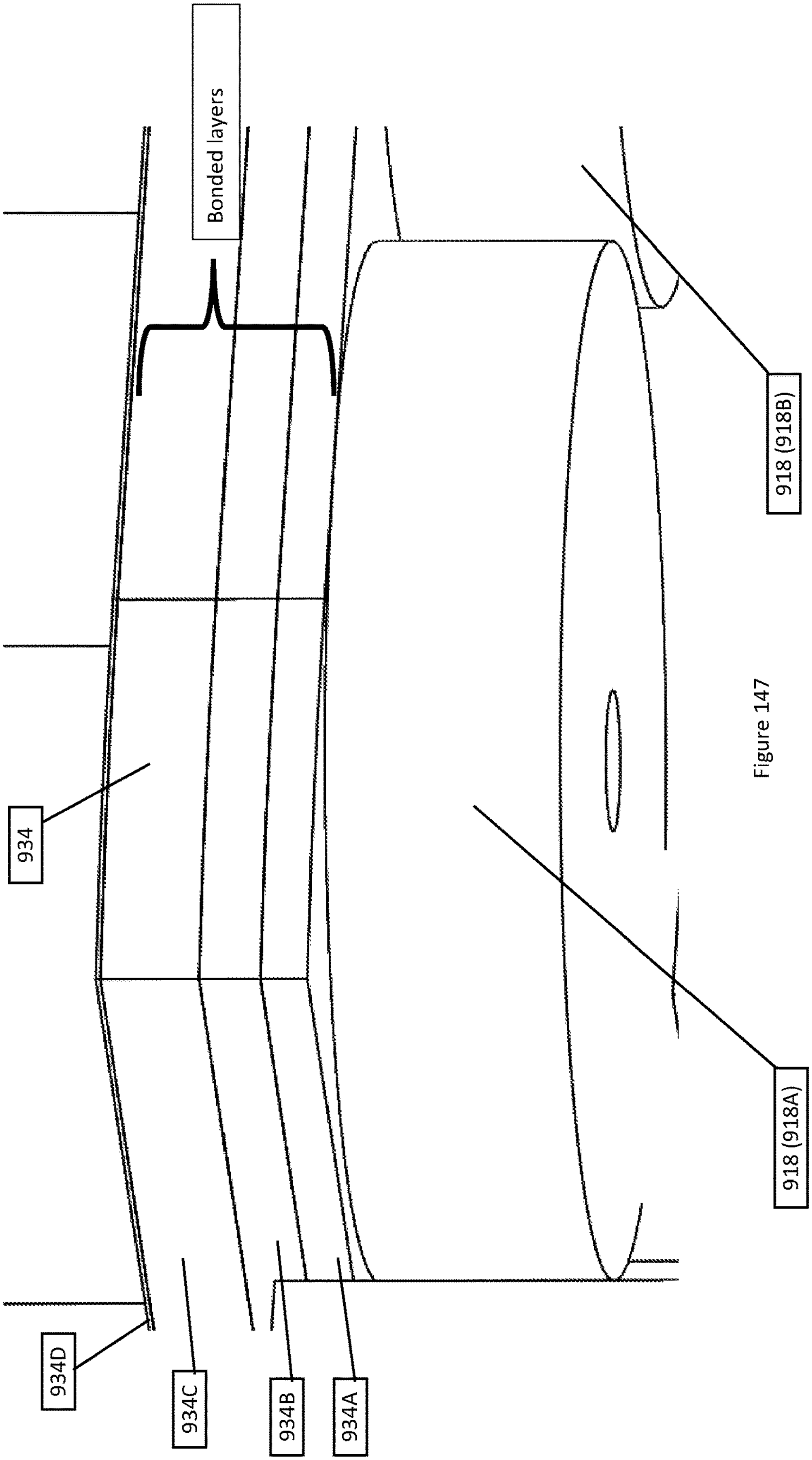

FIG. 147 is a side view showing placement of an actuator gear for the valve module of FIG. 145.

Figure 148A:
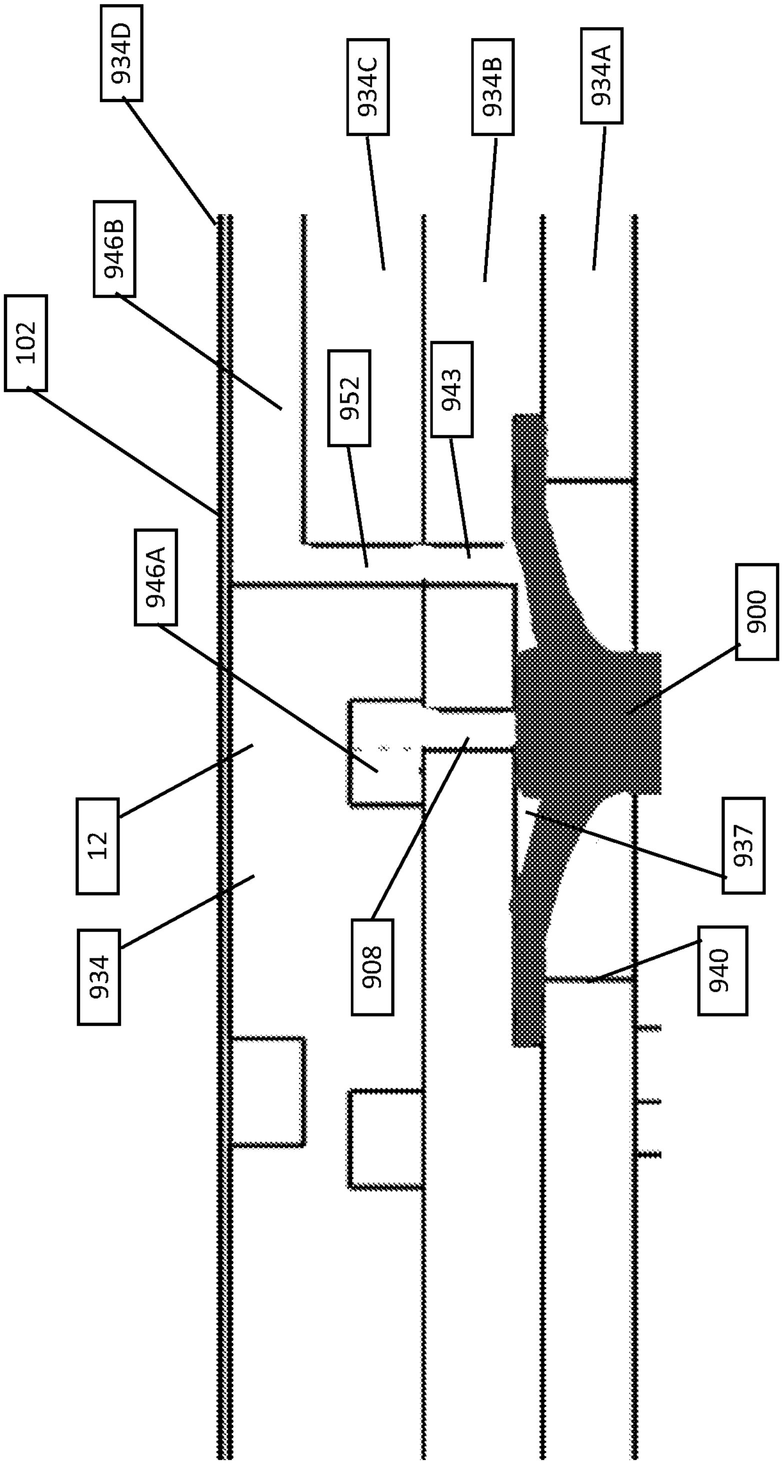
Figure 148B:
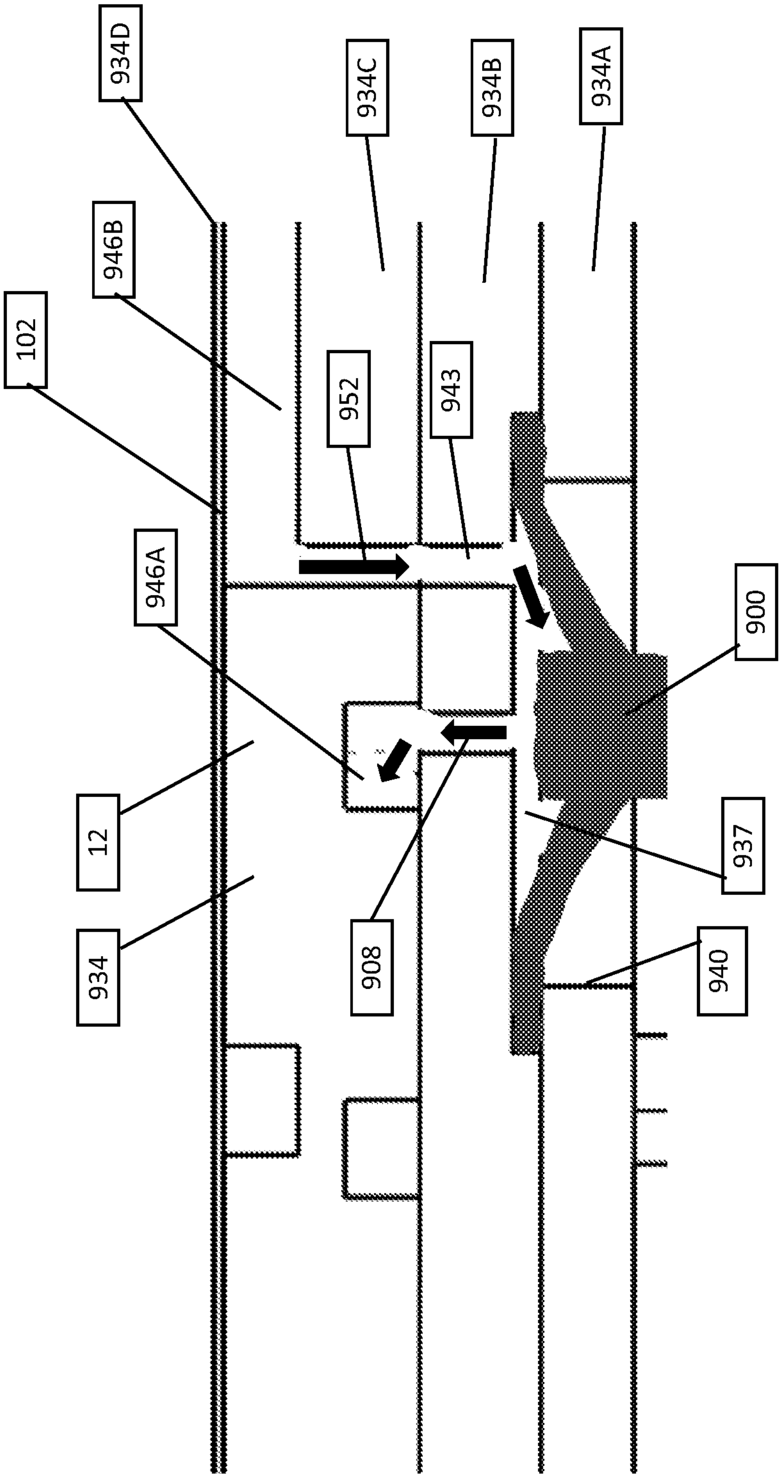

FIGS. 148A-148B show schematically valves configured to deflect in a downward (towards the interior) direction to a deflected state (FIG. 148A) from an unbiased state (FIG. 148B).

Figure 149:
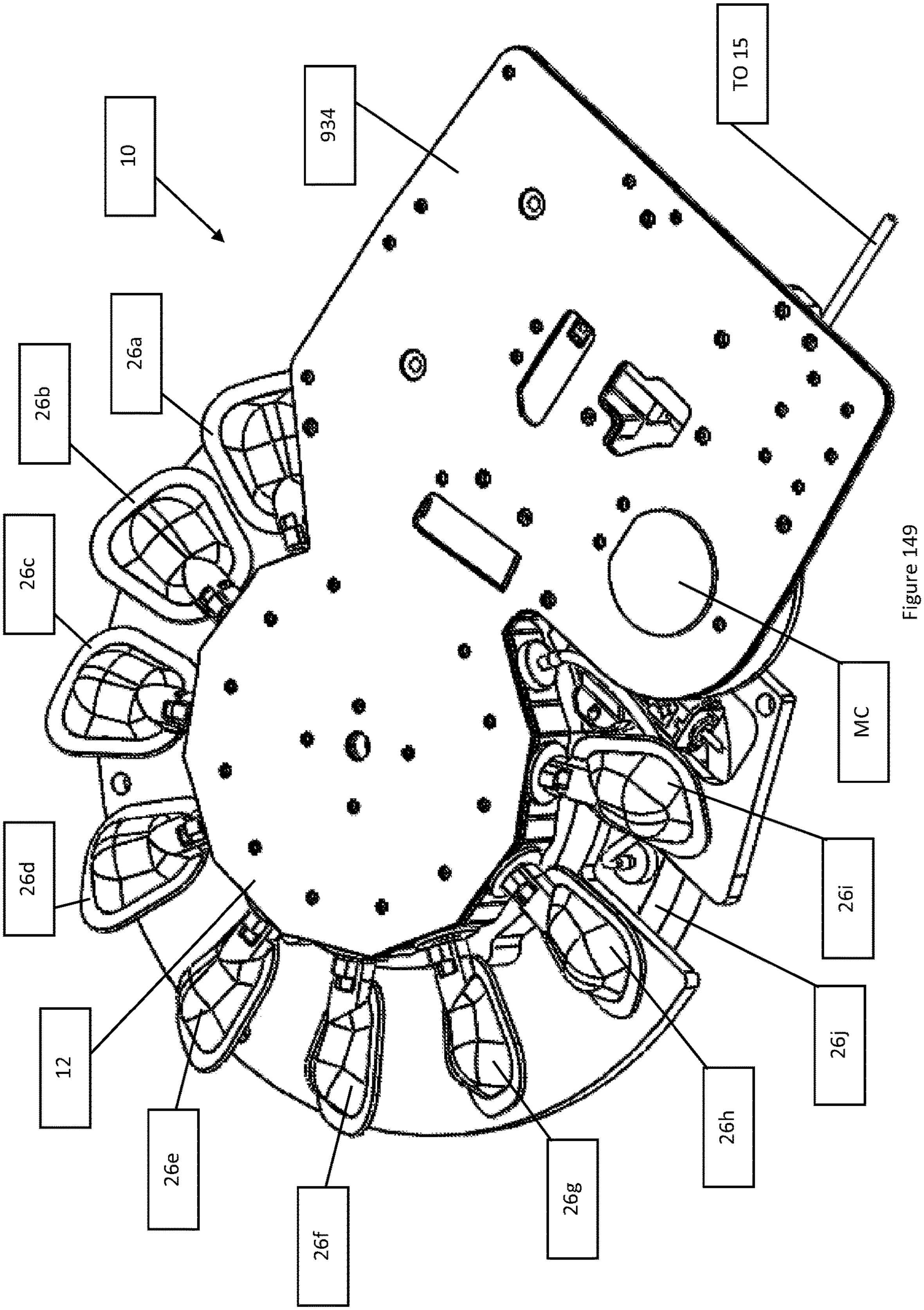

FIG. 149 is a top perspective view of an alternate valve module useable with the subject invention.

Figure 150:
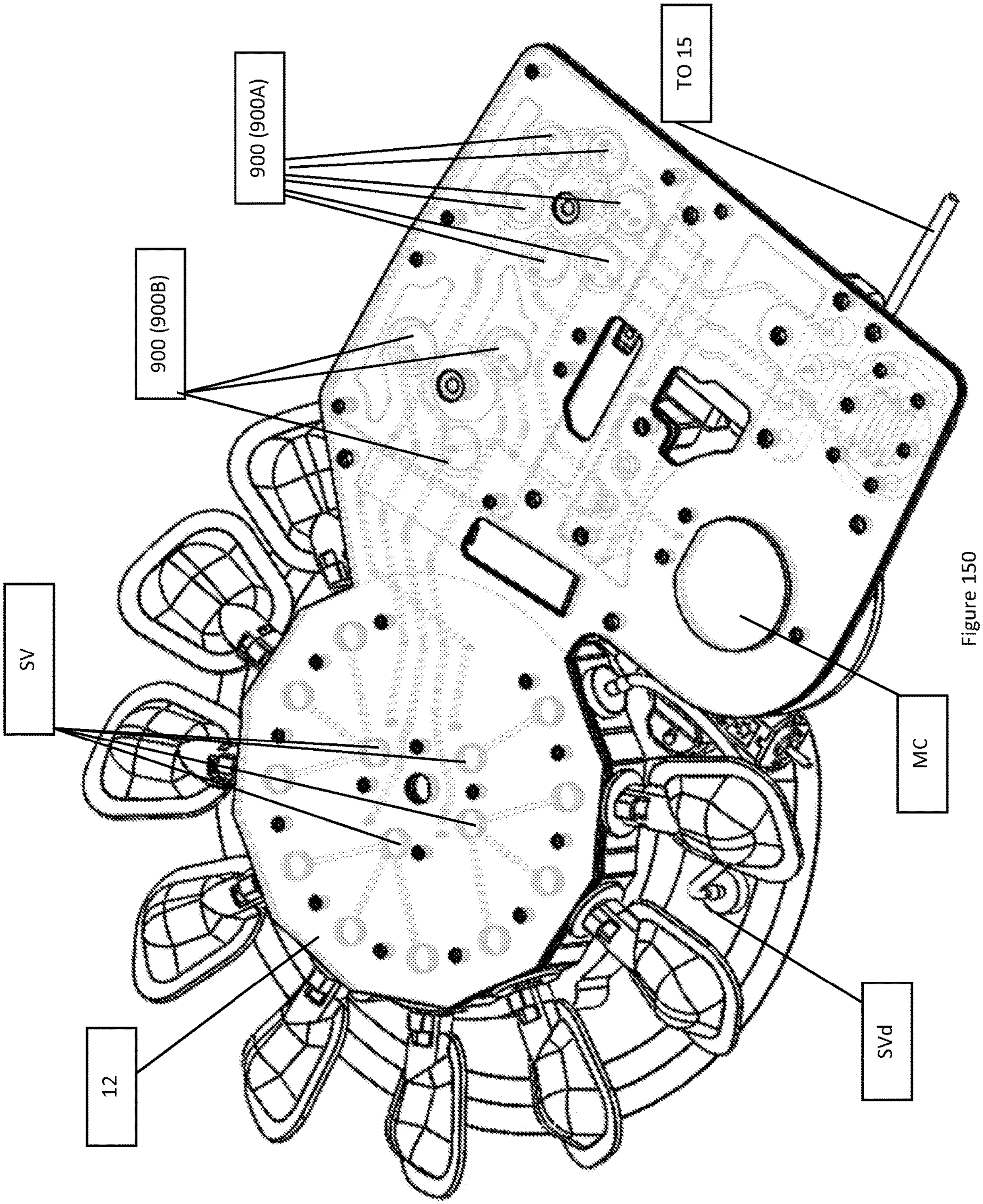

FIG. 150 is a copy of FIG. 149 with certain portions shown in transparency.

Figure 151:
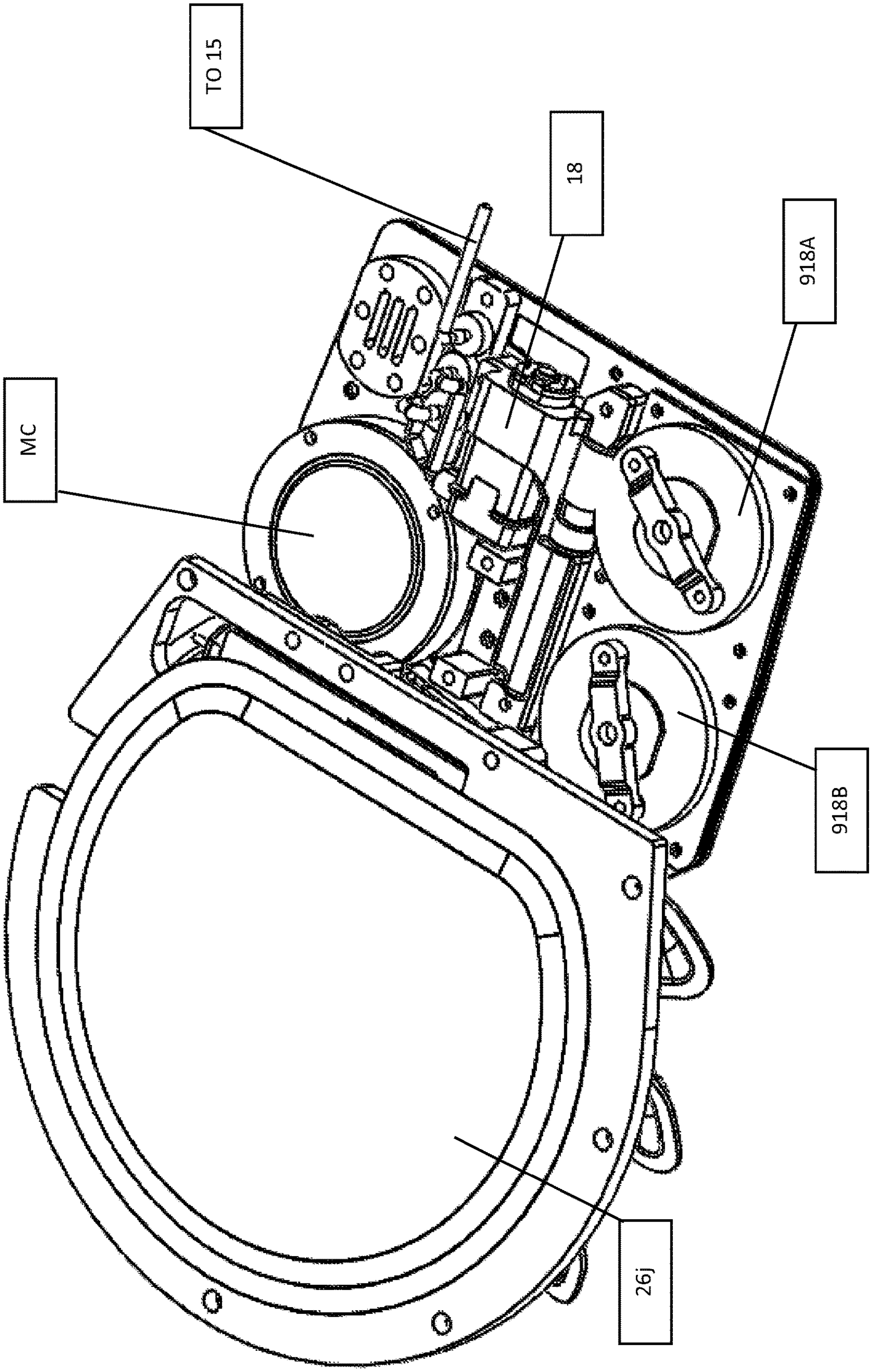

FIG. 151 is a bottom perspective view of the valve module of FIG. 149.

Figure 152:
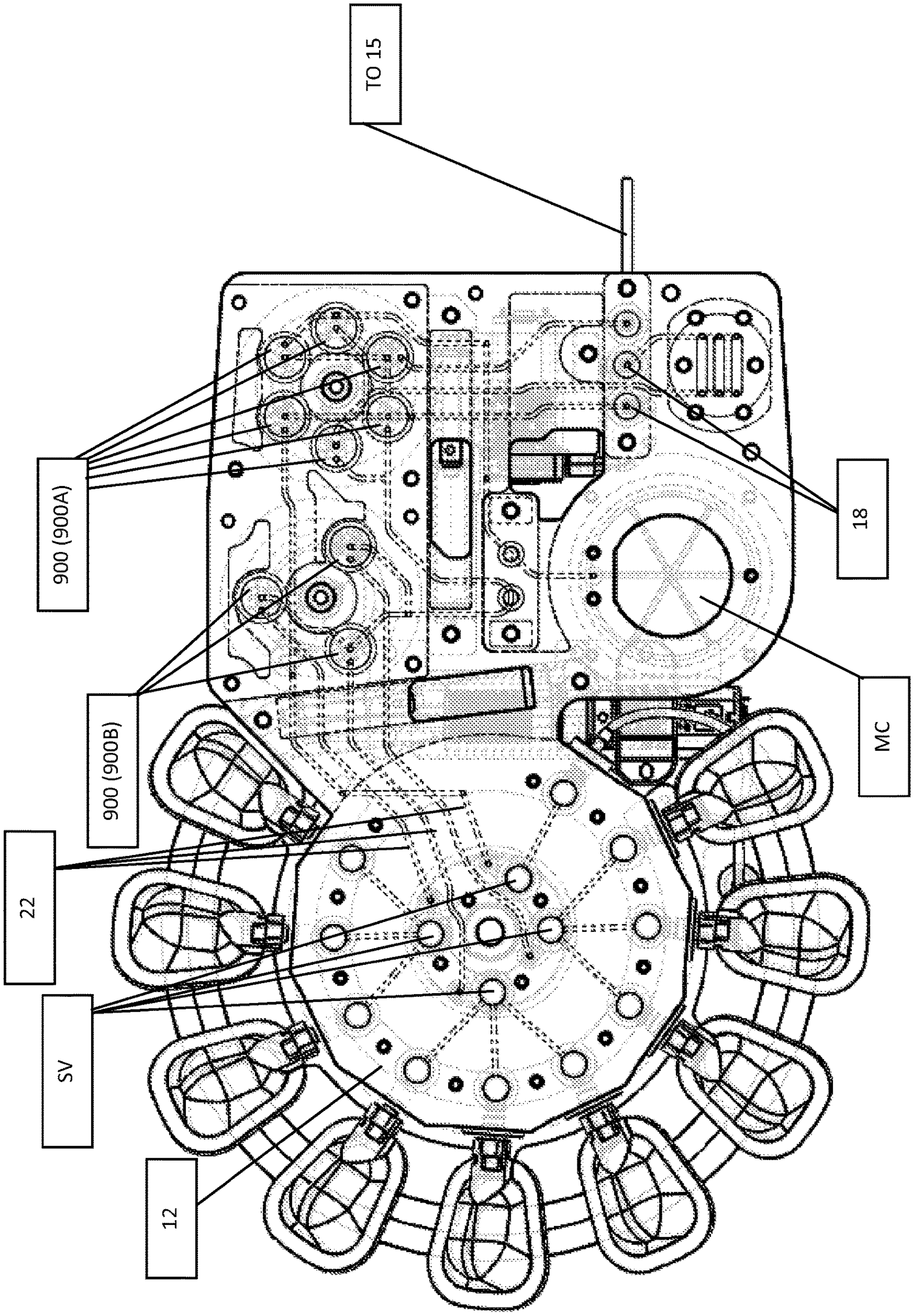

FIG. 152 is a top view of the valve module of FIG. 140 showing internal passageways in transparency.

Figure 153:
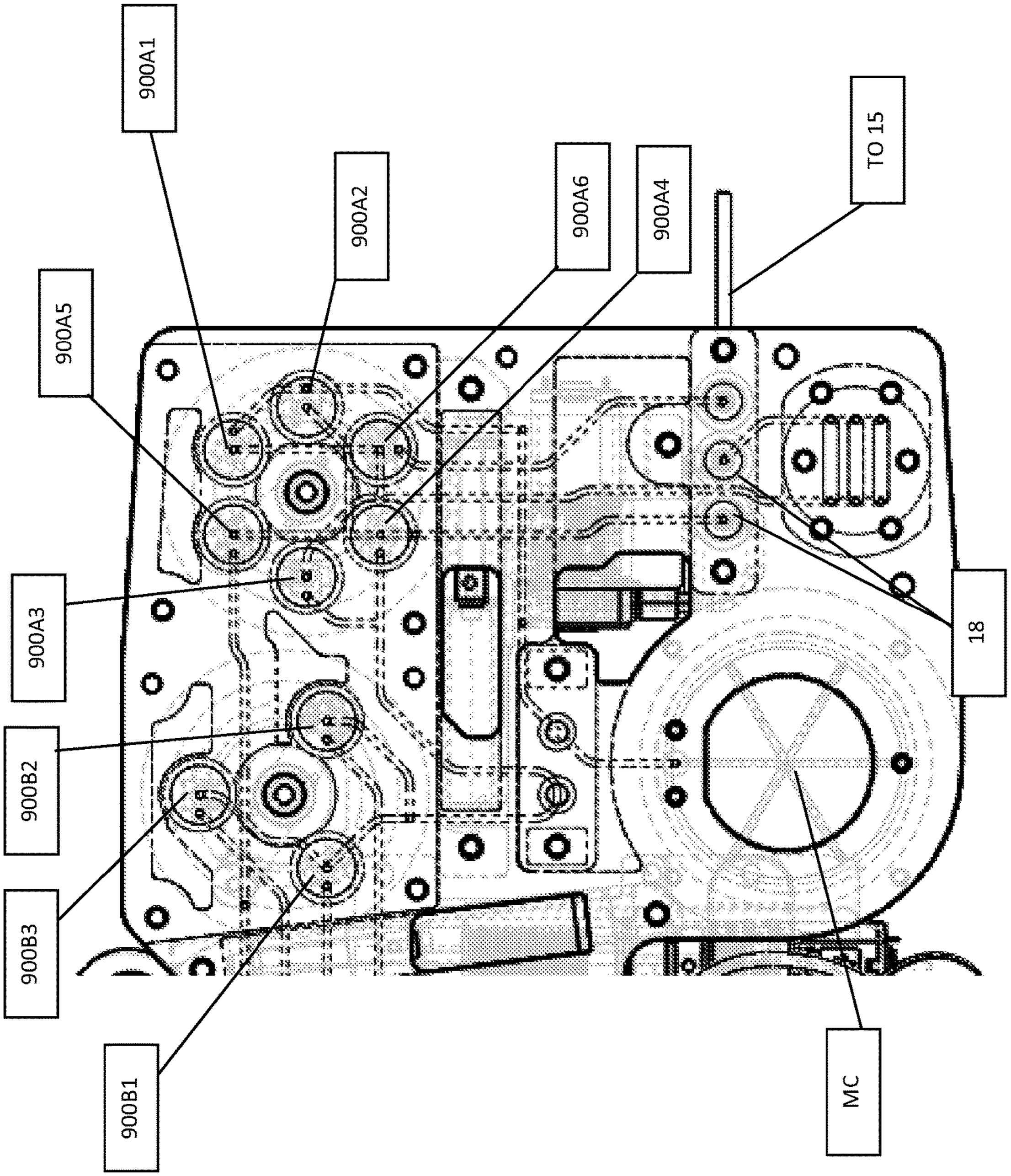

FIG. 153 is an enlarged portion of FIG. 152.

Figure 154:
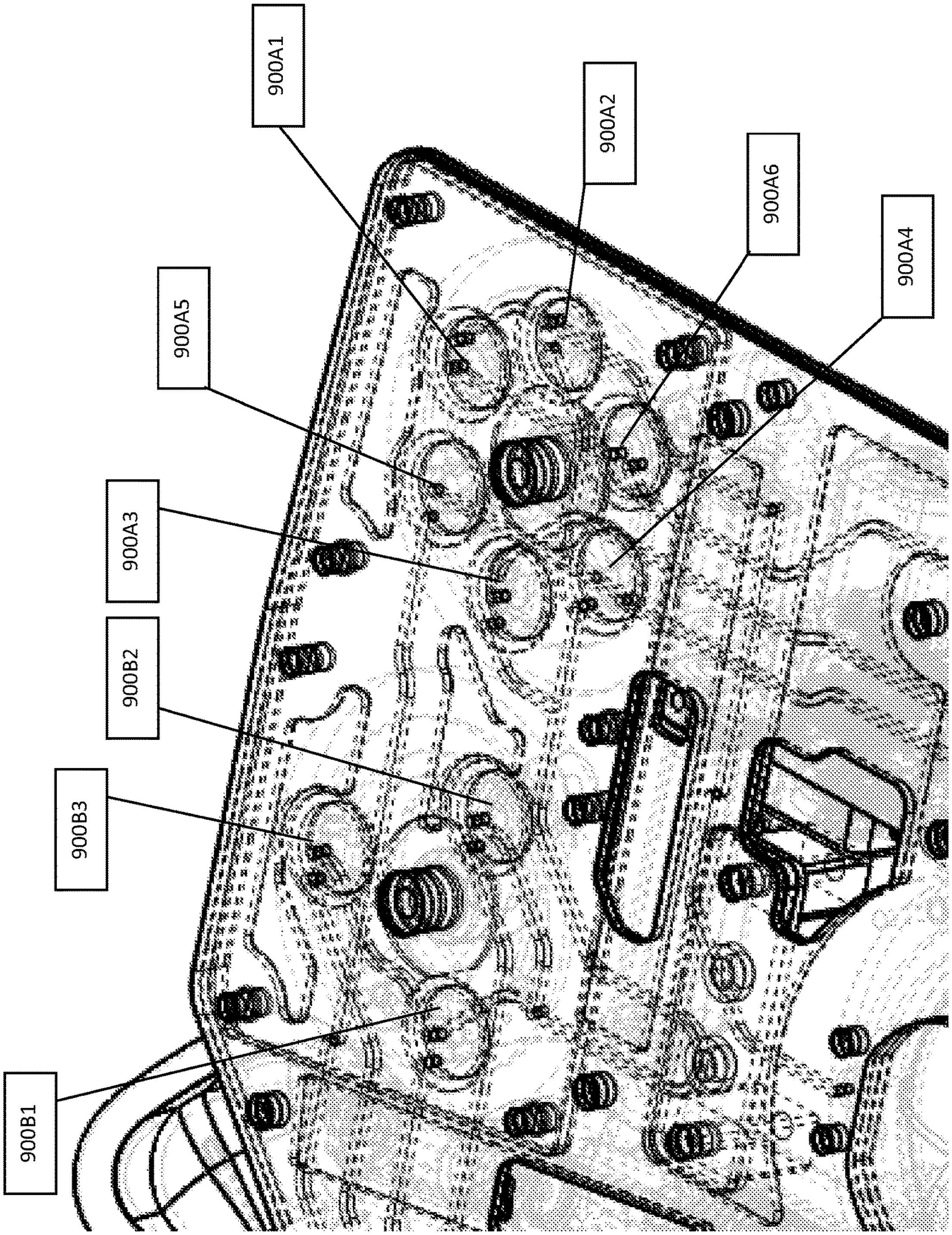

FIG. 154 is a top perspective view of the enlarged portion shown in FIG. 153.

Figure 155:
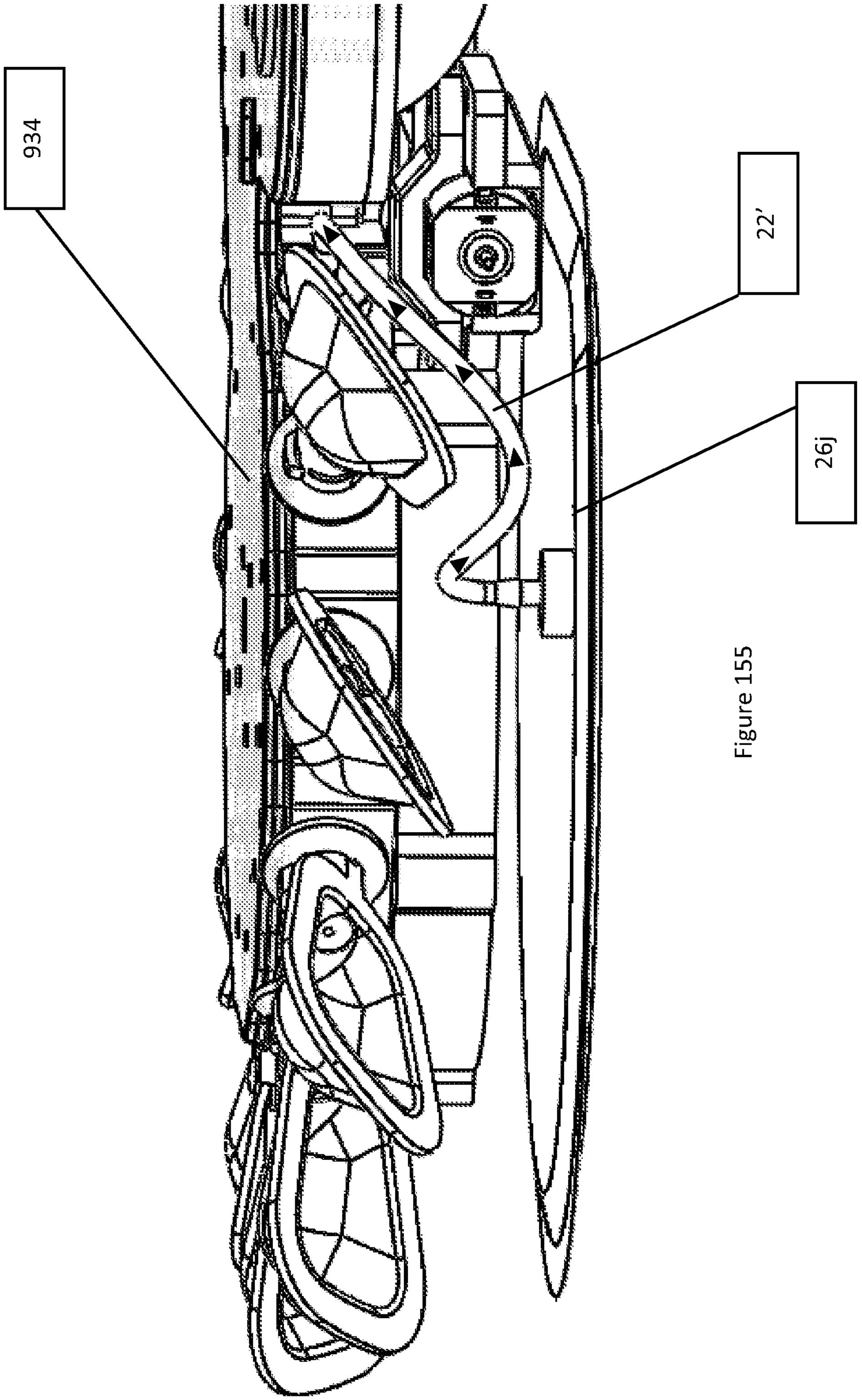

FIG. 155 is a side view of a portion of the valve module of FIG. 149 showing a tube defining one or more of the fluid ducts.

FIGS. 156-167 show exemplary fluid flows of a drug delivery device, under negative pressure or positive pressure, in accordance with the subject invention.

FIGS. 168-172 show exemplary complete flows of a drug delivery device, utilizing negative and positive pressure, in accordance with the subject invention.

FIGS. 173-186 show an alternate embodiment of a drug cartridge useable with a drug delivery device, in accordance with the subject invention.

FIGS. 187-198 show a seal useable with a drug cartridge, in accordance with the subject invention.

FIGS. 199-207 show an actuator for opening the seal shown in FIGS. 187-198, in accordance with the subject invention.

DETAILED DESCRIPTION OF THE INVENTION

In one aspect, the subject invention is directed to methods of preparing a drug cartridge and, separately, a drug delivery device. With reference to the Figures, an exemplary drug delivery device is shown and designated by reference number 10. As will be appreciated by those skilled in the art, various drug delivery devices may be prepared by the method of the subject invention. The configuration and assembly of the components of the drug delivery device may vary and still fall within the scope of the subject invention.

Figure 1:
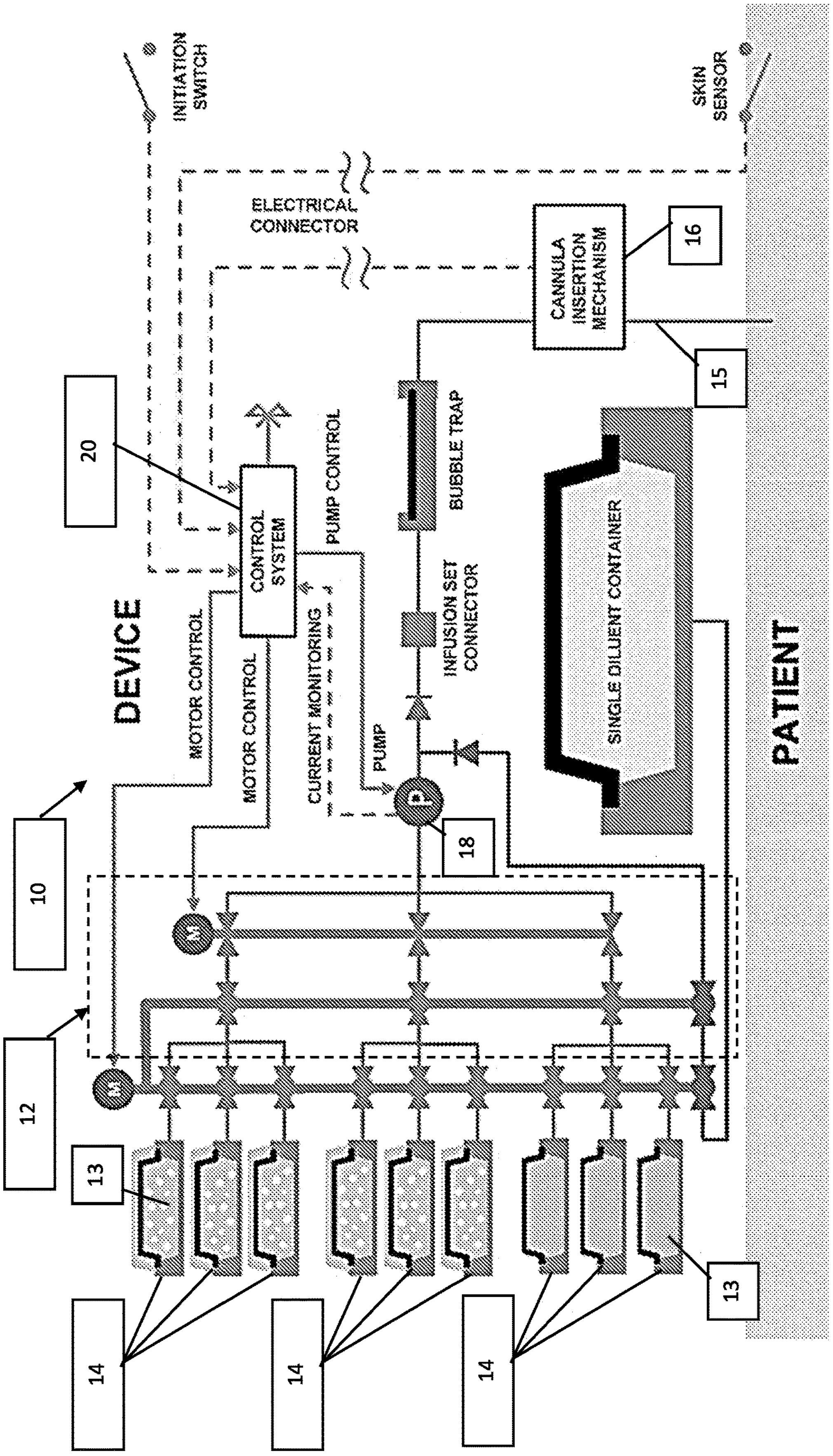
FIG. 1 is a schematic showing architecture, container communication, and functional components of a drug delivery device in accordance with the subject invention.

With reference to FIG. 1, the drug delivery device 10 may include a body 12 to which are attached one or more drug cartridges 14. The drug delivery device 10 is shown as a body-wearable patch-type drug delivery device having a needle support 16, a pump 18, and a control 20. The control 20, which may include a computer processing unit or logic controller, may be configured to control the pump 18 to control flow of drug from, and between, the drug cartridges 14 to a needle 15 for injection into a patient mounted to the needle support 16. The needle 15 may be a standard hypodermic needle or cannula; or may be a soft cannula ensheathed in a rigid sheath. The drug 13 may be caused to flow from one drug cartridge 14 to another, e.g., to deliver a diluent from one drug cartridge 14 to another drug cartridge 14. The pump 18 may be used to extract drug from the drug cartridges 14 and to urge the drug to other drug cartridge(s) 14 and to further urge the drug through defined fluid ducts or pathways to the needle 15 for delivery therefrom into the patient. The pump 18 may be also bi-directionally configured to reverse, causing drug to cycle in and out of the drug cartridge(s) 14, e.g., to facilitate reconstitution. The control 20 may be also configured to cause insertion of the needle 15 into the patient and/or retraction of the needle 15 from the patient in preparing for the drug administration and post drug delivery. Any known configurations for these processes may be utilized. In addition, as shown schematically in FIG. 1, various other components (such as valving, a bubble trap, a motor) may be also provided with the drug delivery device 10. Any source of power, e.g., a stored source of power, such as a battery, may be provided to provide power for operation of the needle 15, the pump 18, the control 20, and valving (as described below). One or motors may be provided to control the pump 18 and the valving. The motor(s) are preferably electrical, such as stepper motors.

Figure 6:
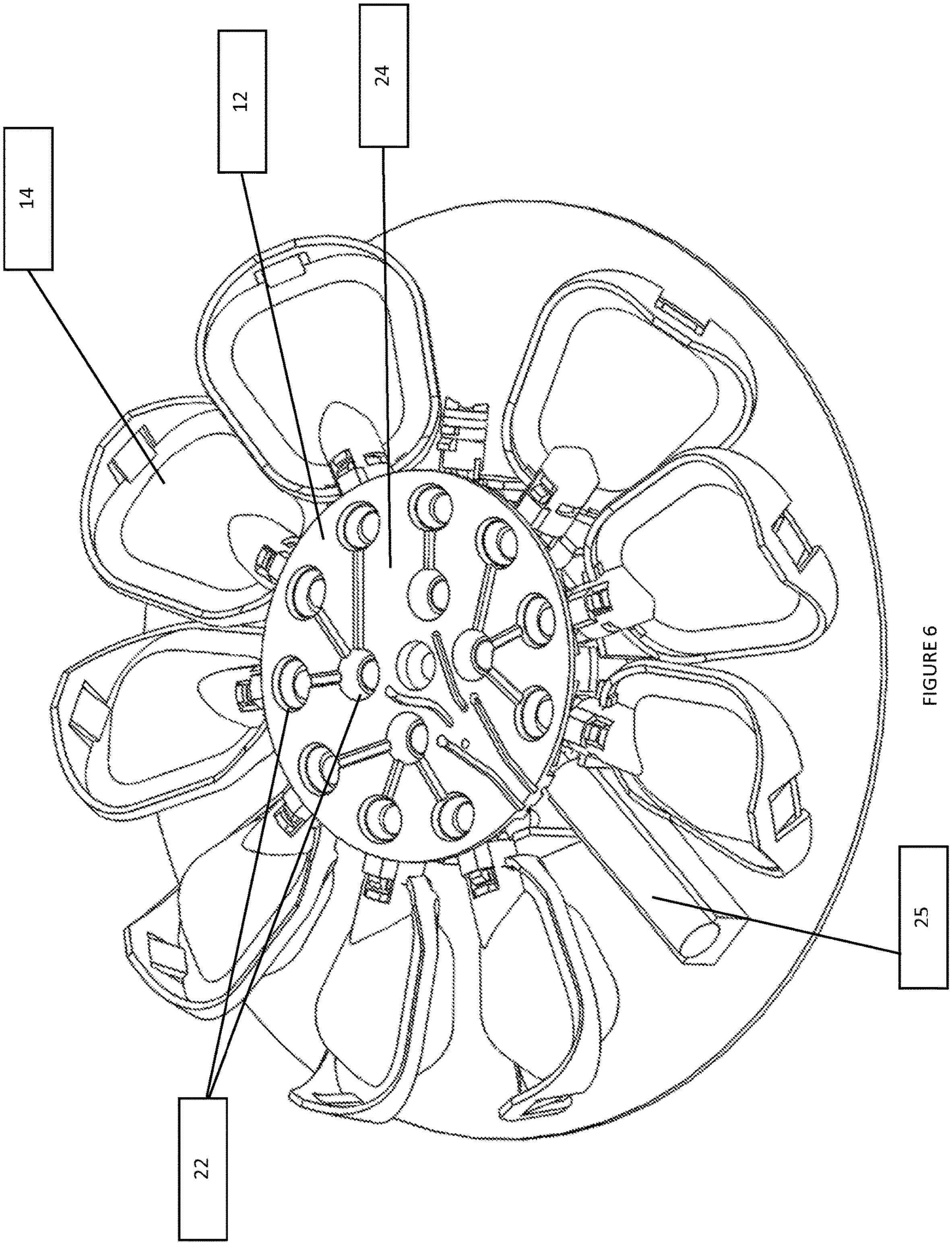
FIG. 6 is an enlarged view of the drug cartridges and body of FIG. 5.
Figures 6A, 6B, 6C, 6D:
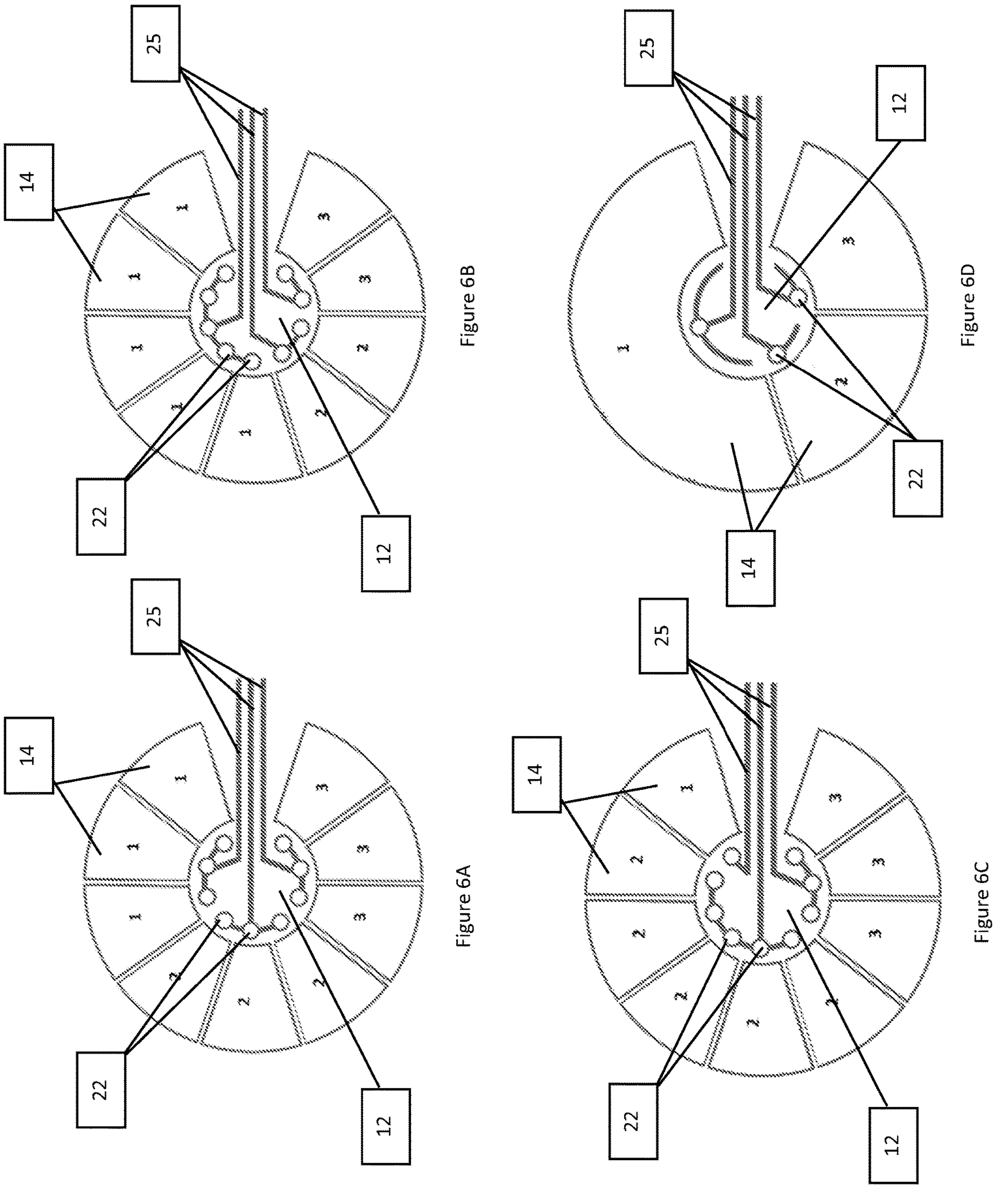
FIG. 6A is a schematic of an assembly configuration, whereby three sets of three drug containers are connected to the body.
FIG. 6B is a schematic of an assembly configuration, whereby one group of five drug containers and two groups of two drug containers are connected to the body.
FIG. 6C is a schematic of an assembly configuration, whereby one group of five drug containers, one group of three drug containers, and a separate single drug container are connected to the body.
FIG. 6D is a schematic of an assembly configuration, whereby multiple drug containers for each group in 6B are replaced by single larger drug containers.

With reference to FIGS. 2-6, the drug cartridges 14 may be mounted to the body 12 in various configurations, including along a periphery of the body 12. The body 12 may be disc shaped, allowing for the drug cartridges 14 to be mounted about the circumference of the body 12. To facilitate flow of the drug, the body 12 may be formed with a plurality of fluid ducts 22 arranged to extend from the drug cartridges 14 to one or more outlet ducts 25. The fluid ducts 22 may be arranged in any manner, including being single passageways from the drug cartridges 14 to the one or more outlet ducts 25. Alternatively, the fluid ducts 22 may be manifolded to combine several of the fluid ducts 22 in various combinations, possibly with all of the fluid ducts 22 ultimately combining as one fluid flow directed to one or more outlet ducts 25. As shown in FIGS. 6A-6D, the drug cartridges 14 may be combined in various combinations. FIG. 6A shows three groupings of the drug cartridges 14 (designated as numbers 1, 2, and 3), each containing three of the drug cartridges 14, and each grouping feeding into one of the outlet ducts 25. This allows for the drug cartridges 14 within a grouping to be mixed (e.g., the drug cartridges 14 within grouping 1 may be varied to allow for different combinations) with the resultant combinations being possibly further mixed downstream of the outlet ducts 25. FIG. 6B shows three groupings, but not evenly weighted, with grouping 1 including five of the drug cartridges 14, and groupings 2 and 3, each including two of the drug cartridges 14. Variations in size of the groupings may be used to control the amounts and concentration of the resulting drug combinations. Variations in size in groupings may be seen in FIG. 6C as well. FIG. 6D shows the use of various sized drug cartridges 14 to correspond to the groupings, with different sized cartridges providing for variation in amounts of individual components and/or in concentration. For example, the drug cartridge 14 of grouping 1 may be formed to extend along a longer arc about the body 12 than either of the drug cartridges 14 corresponding to groupings 2 and 3. As will be appreciated by those skilled in the art, one or more of the groupings may be manifolded together into a common outlet duct 25 (i.e., the outlet ducts 25 may vary in quantity and are not limited to one-to-one correspondence with the groupings of the drug cartridges 14).

Figure 65:
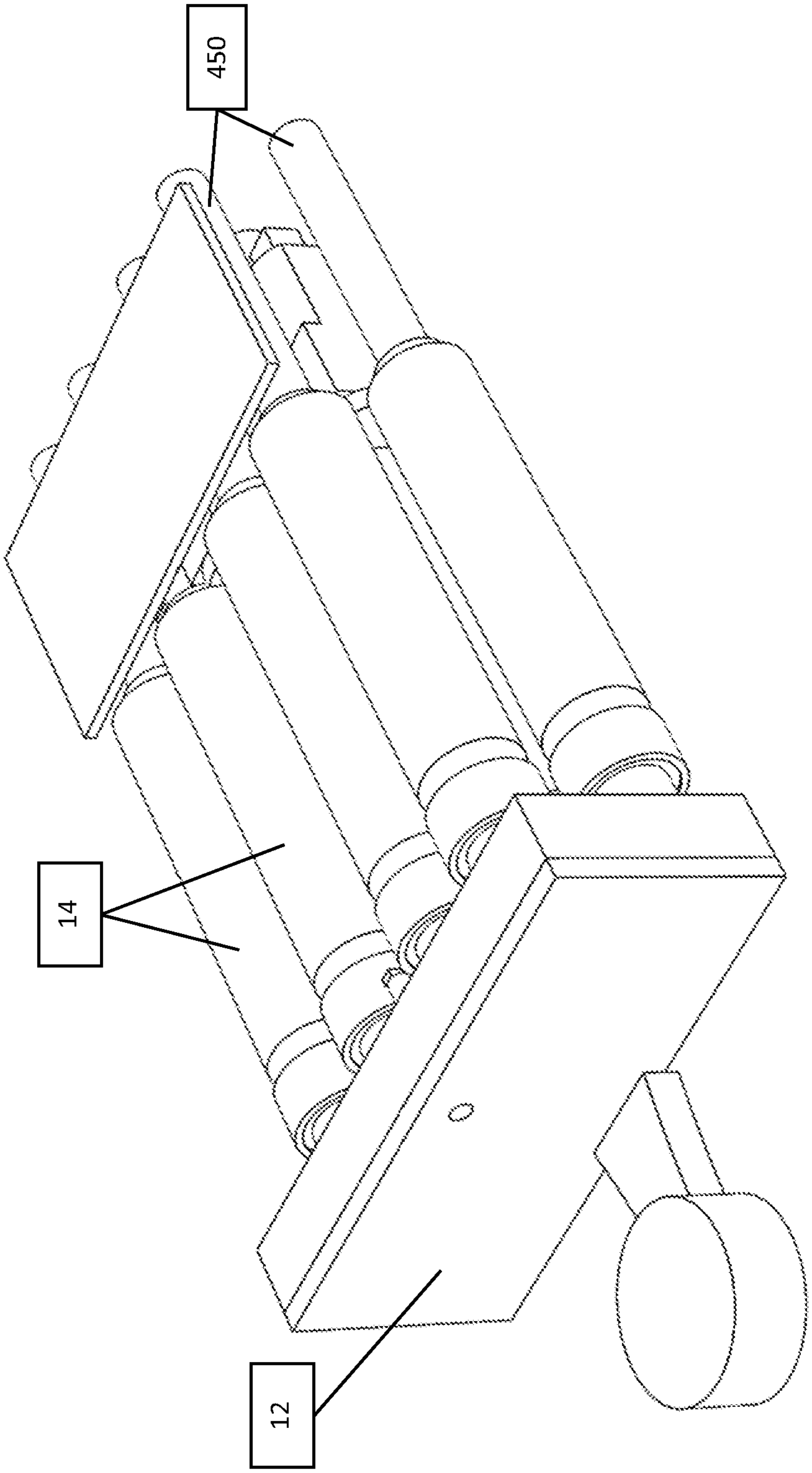
FIG. 65 shows a drug delivery device with barrel-configured drug cartridges, in accordance with the subject invention.
Figure 173:
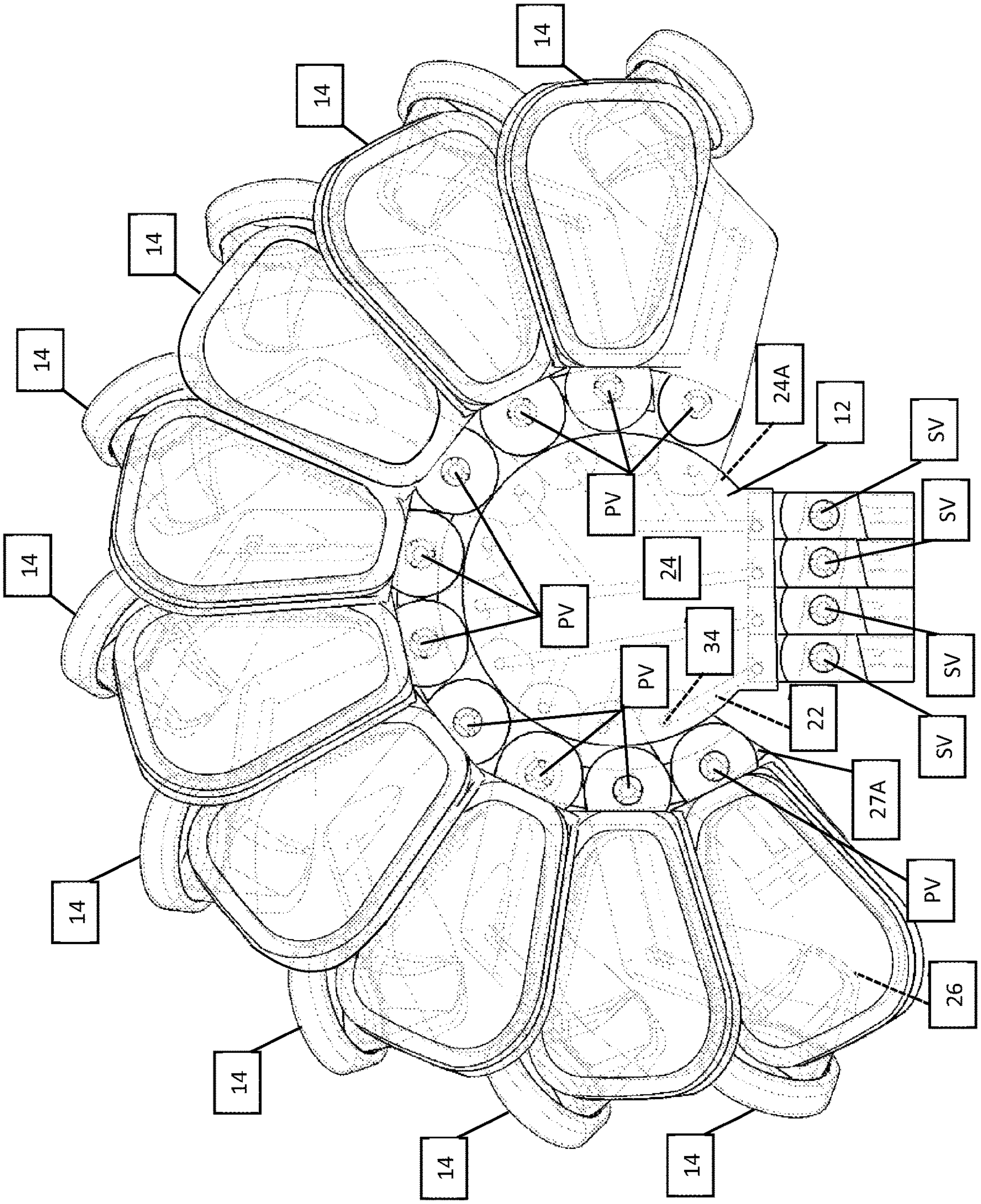
Figure 174:
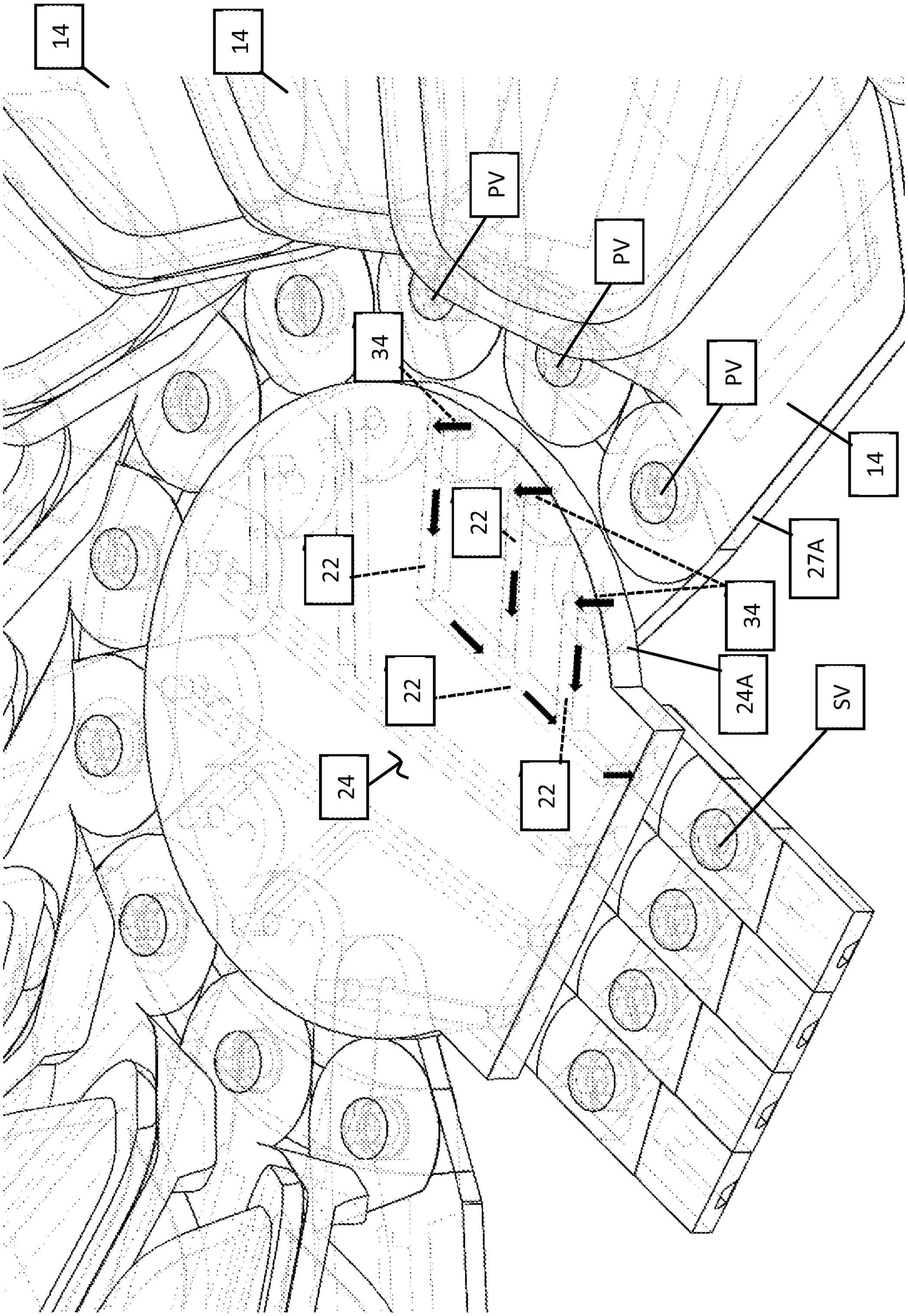
Figure 175:
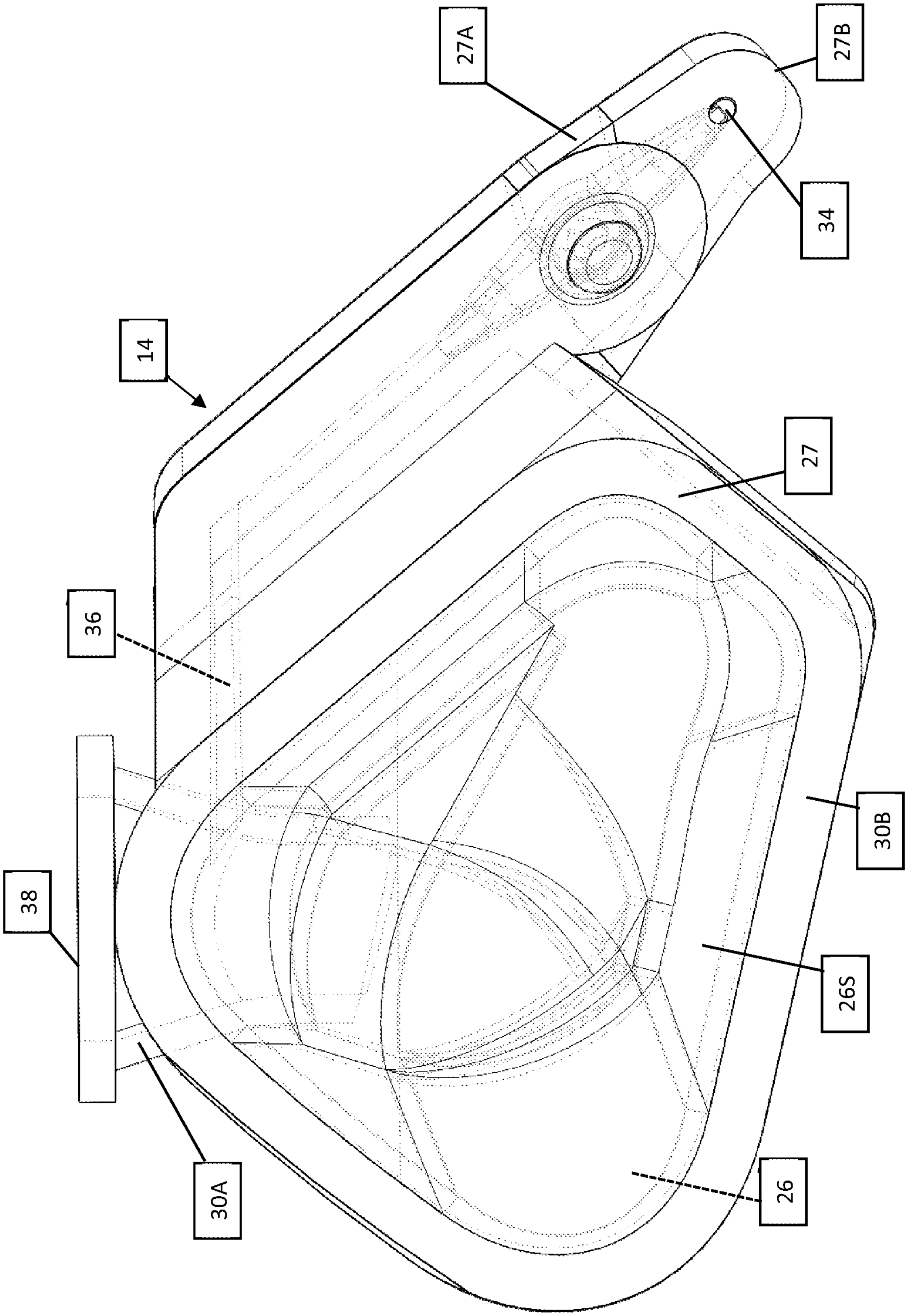
Figure 176:
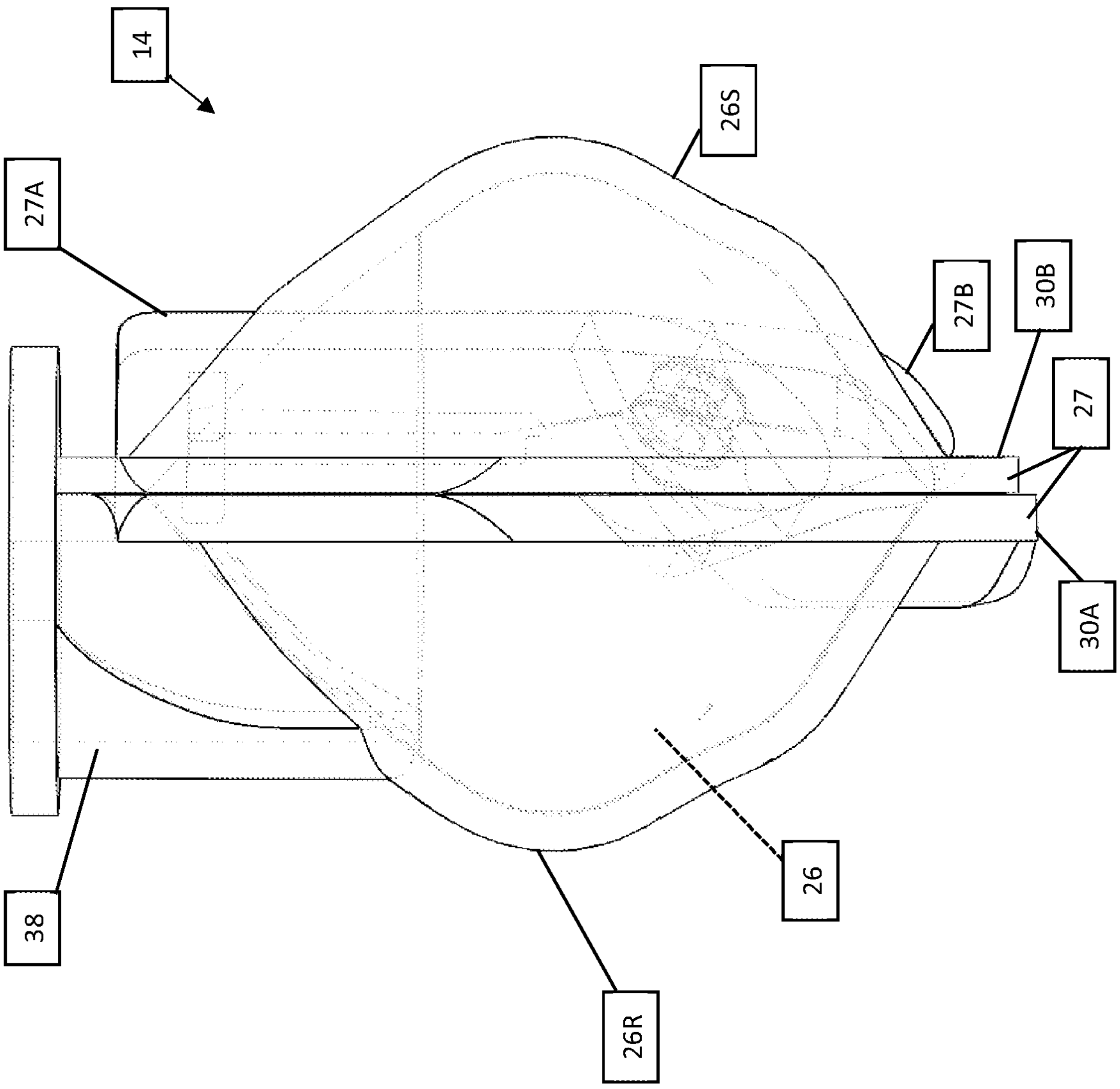
Figure 177:
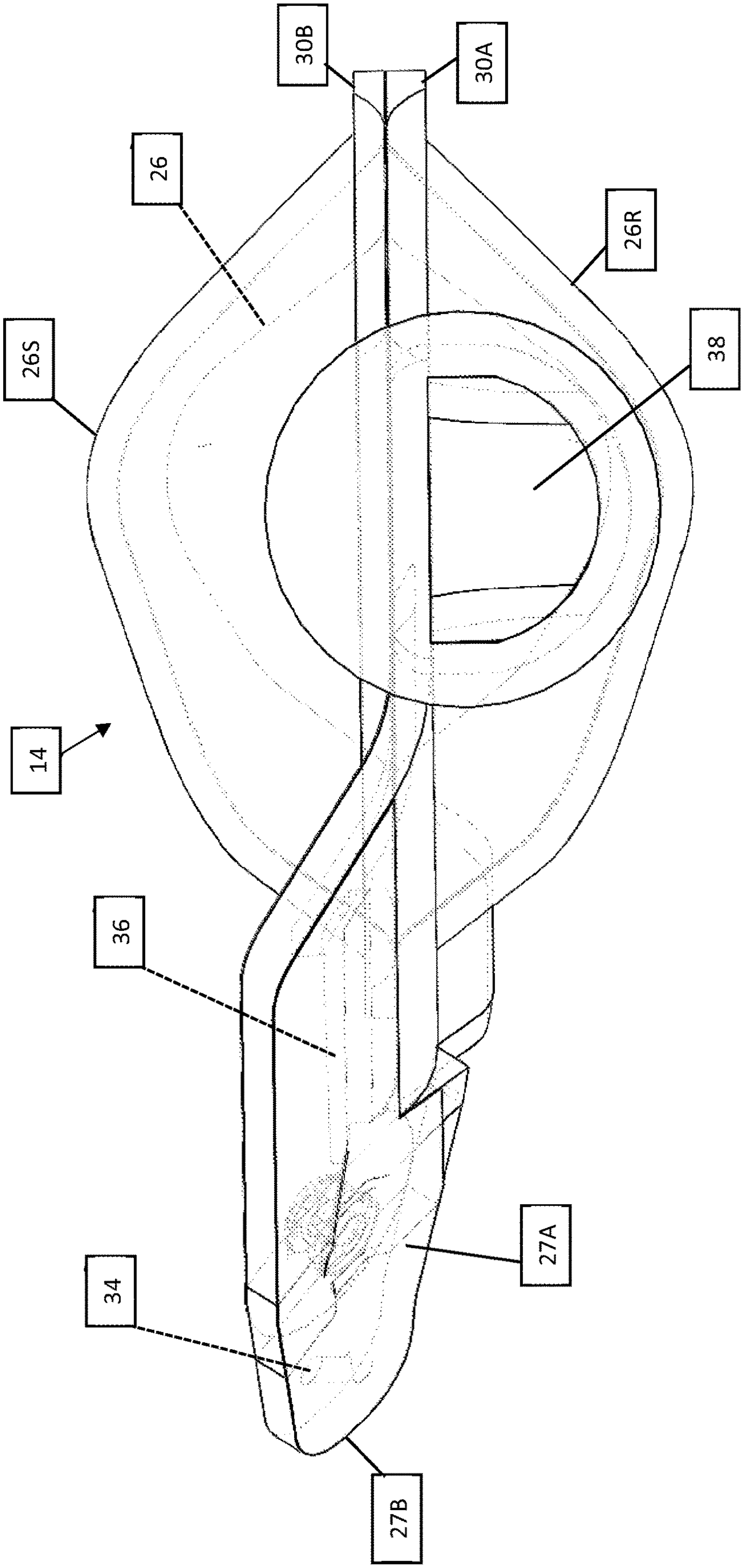

With reference to FIGS. 65-69, the drug cartridges 14 may be mounted to a face of the body 12 so as to extend therefrom in a generally normal direction. In this manner, the drug cartridges 14 may be generally within the footprint of the body 12. With circumference-mounting, as discussed above, the drug cartridges 14 may radiate outwardly from the circumference of the body 12. The drug cartridges 14, arranged about the circumference of the body 12, may be joined to the fluid ducts 22 along the circumferential edge of the body 12 (e.g., as shown in FIG. 6) and/or at points on a face of the body 12 (e.g., as shown in FIGS. 173-174). With face-mounting, as shown in FIG. 65, the drug cartridges 14 may axially extend away from the body 12, e.g., within the footprint thereof. Circumference-mounting may minimize the axial profile of the drug delivery device 10, while, face-mounting may minimize the radial profile of the drug delivery device 10.

The body 12 may be formed in any manner. By way of non-limiting example, the body 12 may be a single monolithic body having the fluid ducts 22 etched, milled, molded, and/or otherwise formed therein. The fluid ducts 22 may be formed along an external surface of the body 12 and/or be recessed within the body 12. The body 12 may be formed of polymeric material.

At least a portion of the fluid ducts 22 may be open to be exposed along a first face 24 of the body 12. This allows for fluid pathways for the drug to be exposed along the first face 24.

Figure 2:
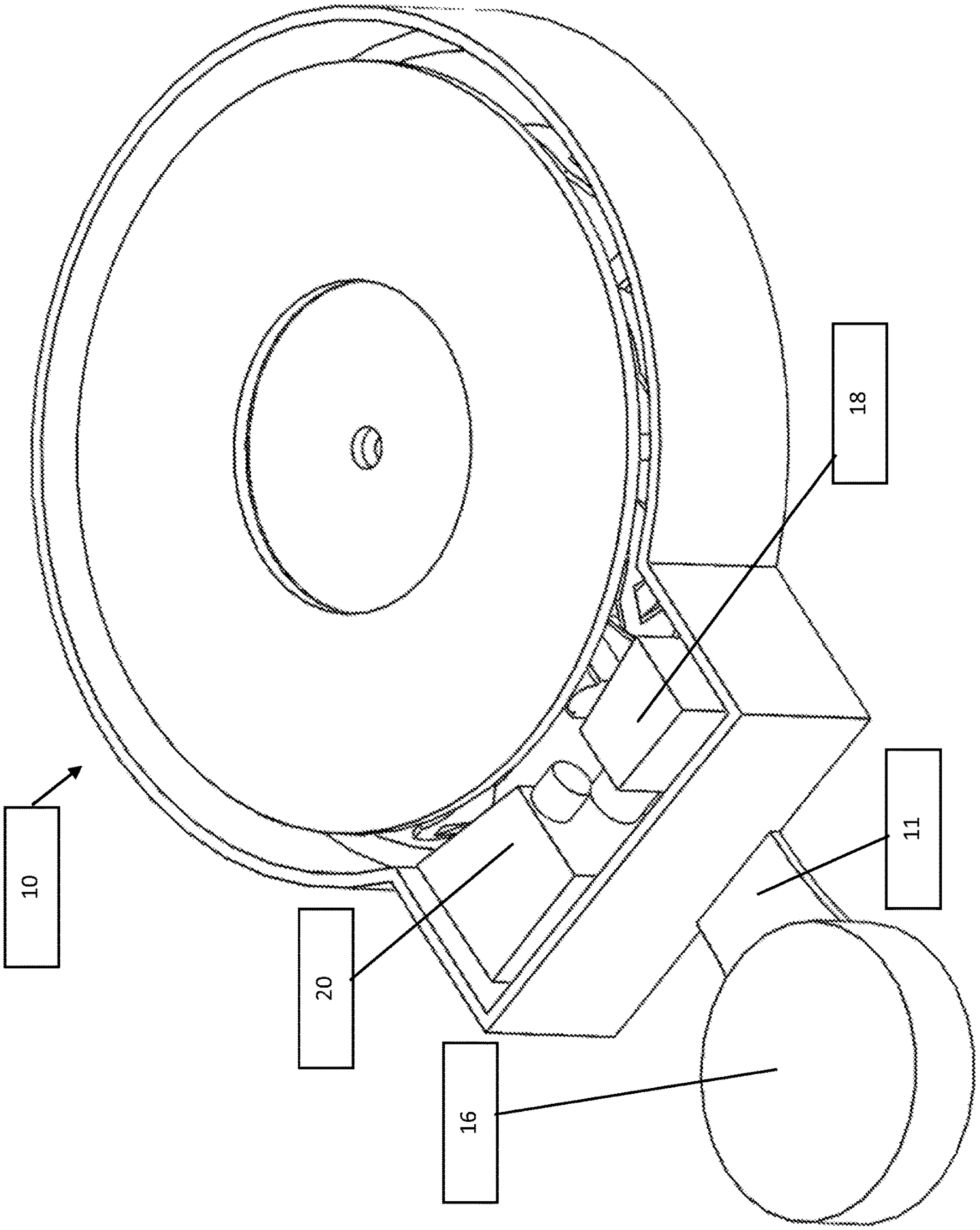
FIG. 2 is an isometric block model of a drug delivery device in accordance, with the subject invention with the top housing removed.
Figure 3:
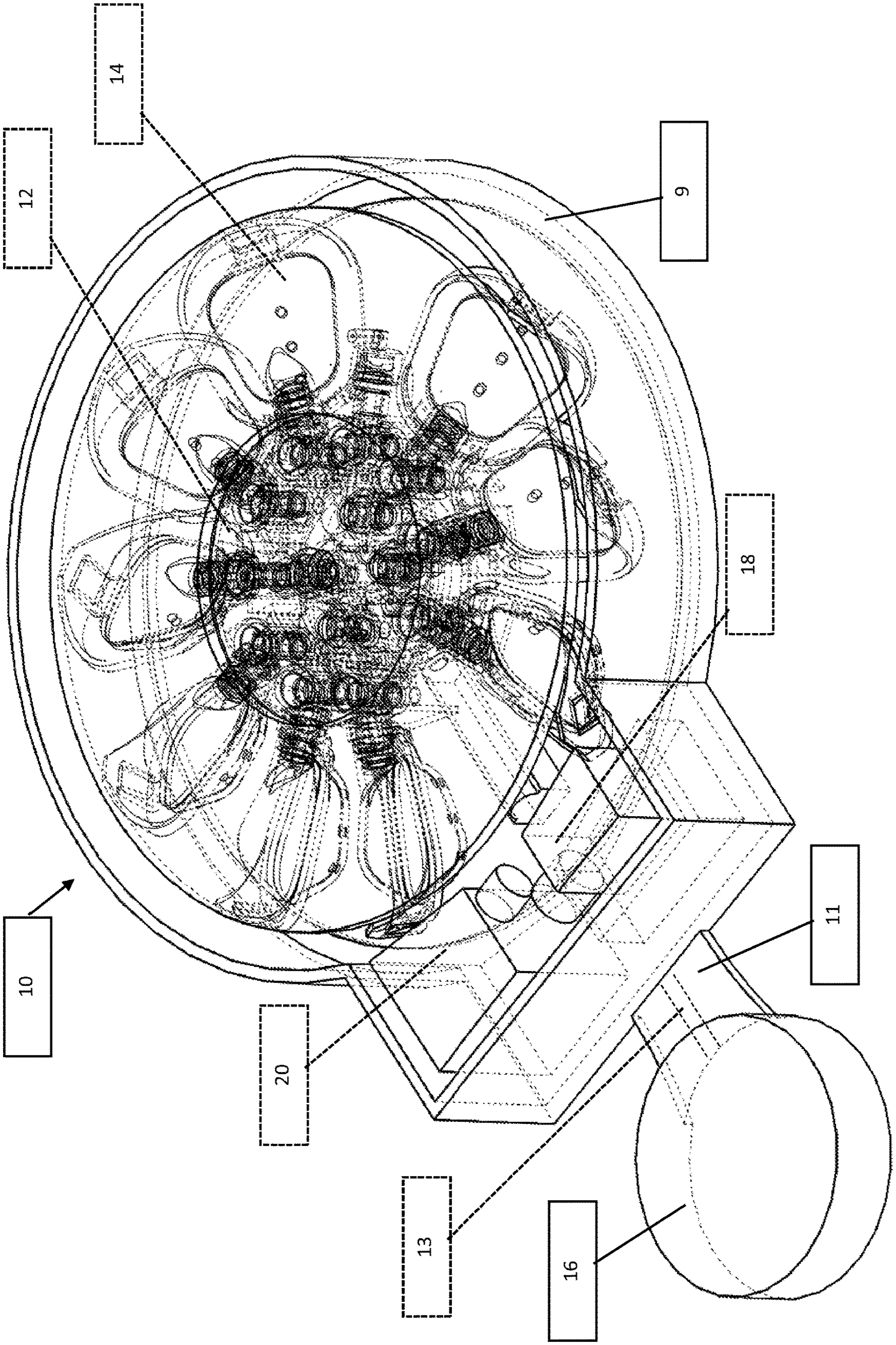
FIG. 3 is an isometric hidden-lines view of the embodiment in FIG. 2, showing the positioning of components within the drug delivery device.
Figure 4:
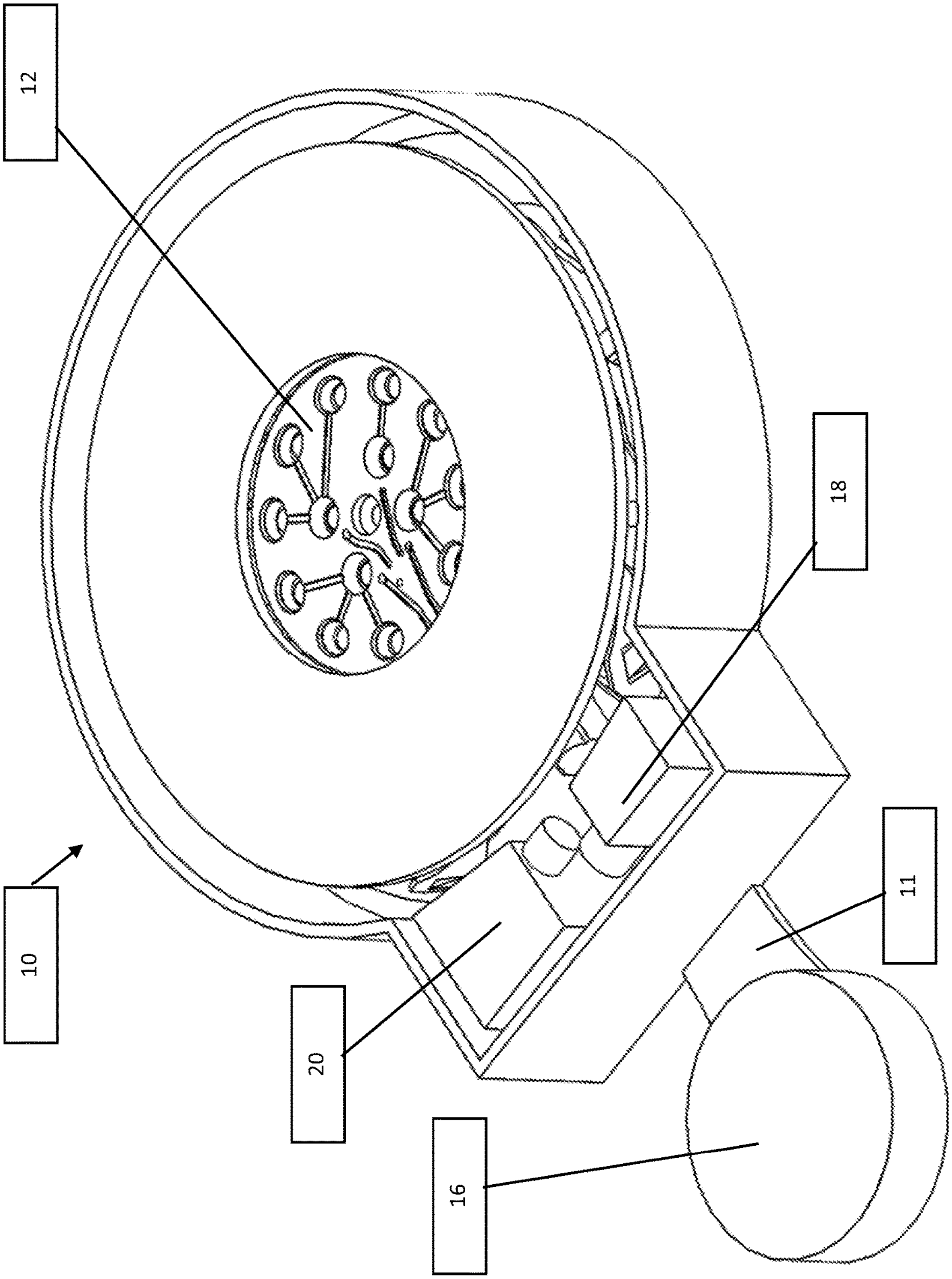
FIG. 4 is an isometric view of the embodiment in FIG. 3 with the barrier removed to show the body.
Figure 5:
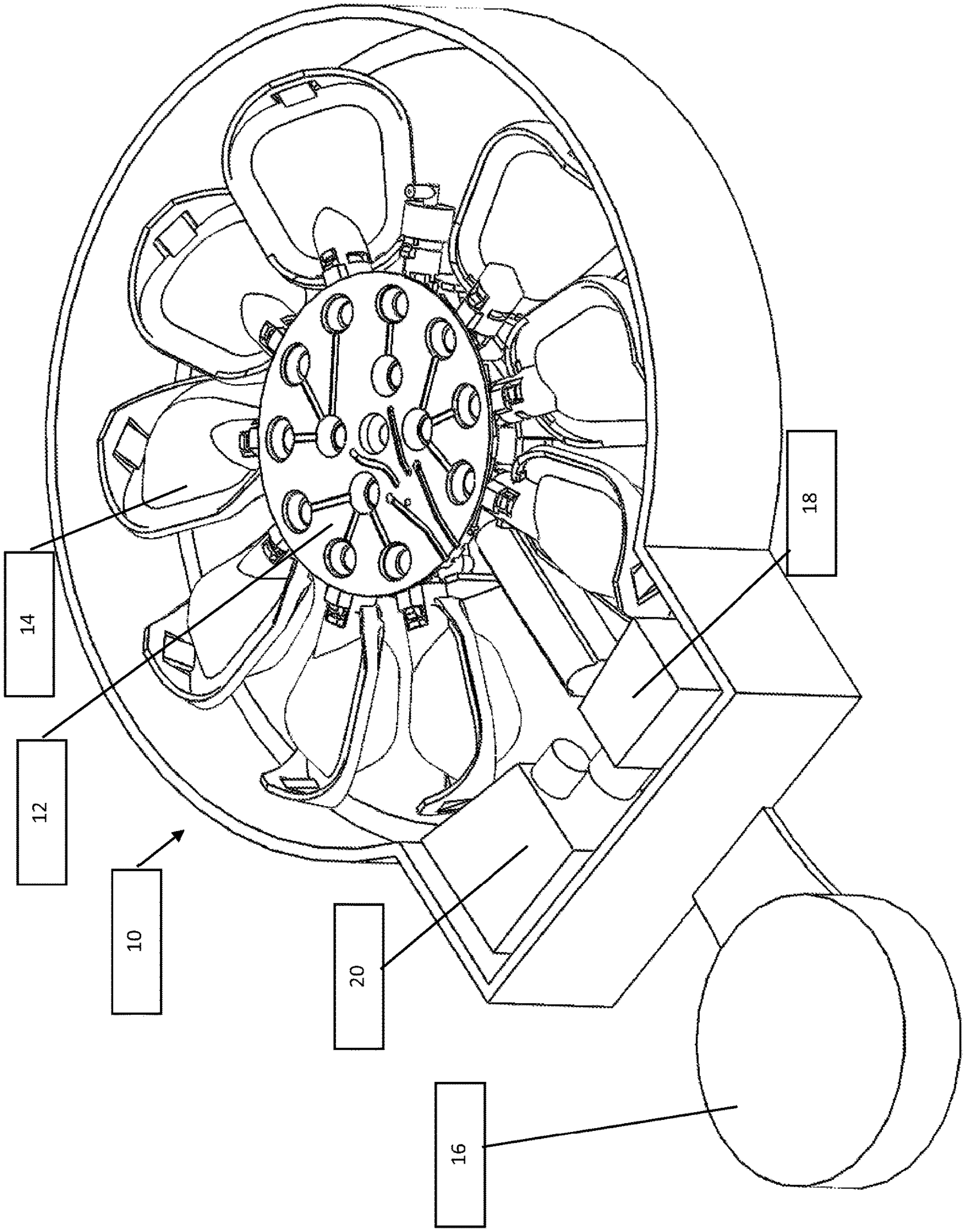
FIG. 5 is an isometric view of the embodiment in FIG. 4 with the diluent pack removed to show the drug cartridges.

As shown in FIGS. 2-4, the body 12 may be connected to the needle support 16 by a flexible tether 11, through which passes at least one fluid passageway 13 formed to convey drug from one or more outlet ducts 25 to the needle 15 for delivery to a patient, the tether 11 may be formed by any flexible materials, such as a polymeric or elastomeric material. In this manner, the body 12 and the needle support 16 may be secured to the body of the patient, with the tether 11 providing a flexible connection therebetween. Preferably, the tether 11 is not directly secured to the patient's body (e.g., the tether 11 is not adhered to the patient's body).

One or more electrical conductors may also pass through the tether 11 to electrically connect the body 12 and the needle support 16. This allows for signal and power transmission between the body 12 and the needle support 16. Alternatively, wireless receivers and/or transmitters may be provided on the body 12 and the needle support 16 to allow for wireless signal transmission therebetween.

Figure 79B:
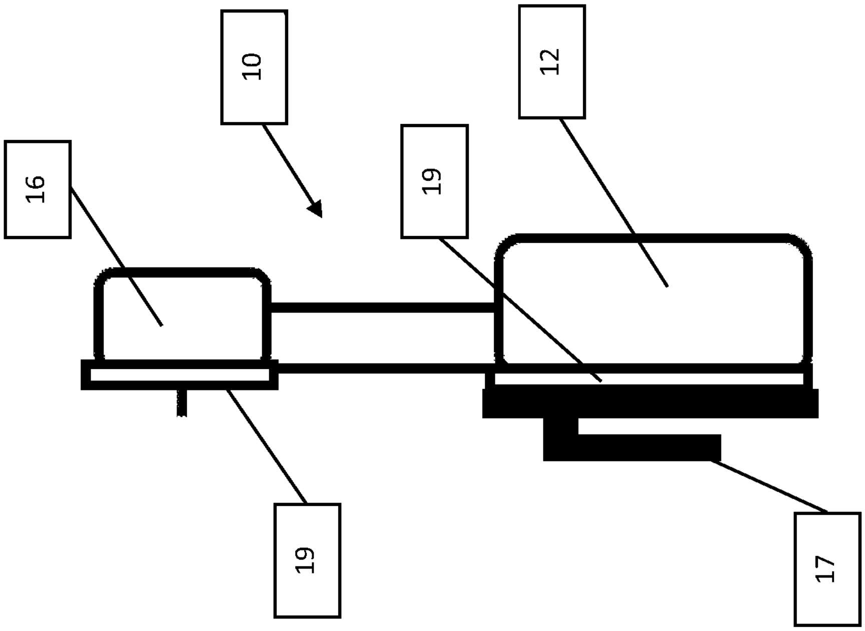
Figure 79A:
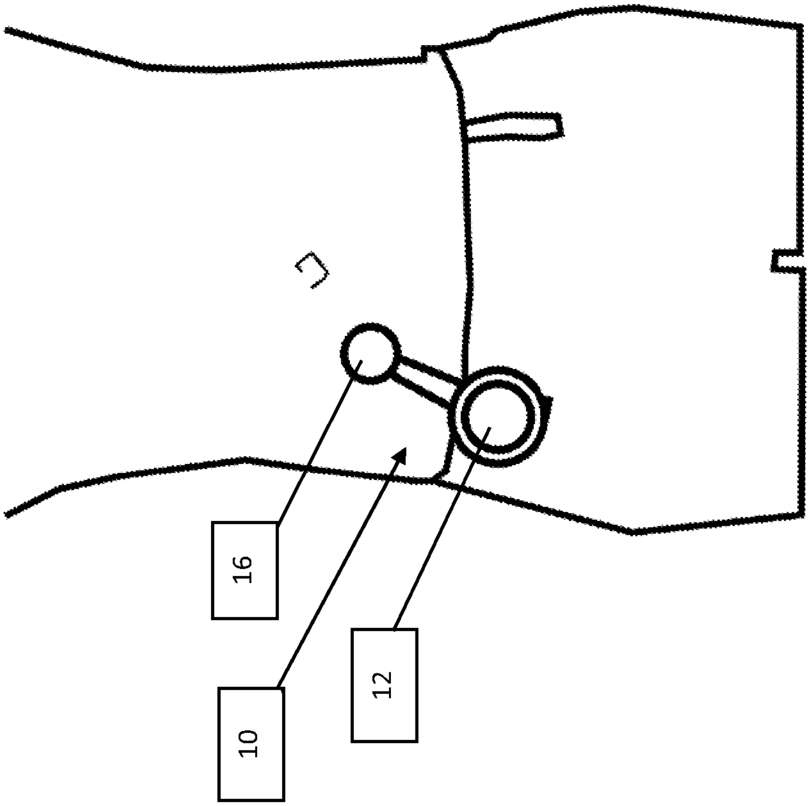
Figure 80B:
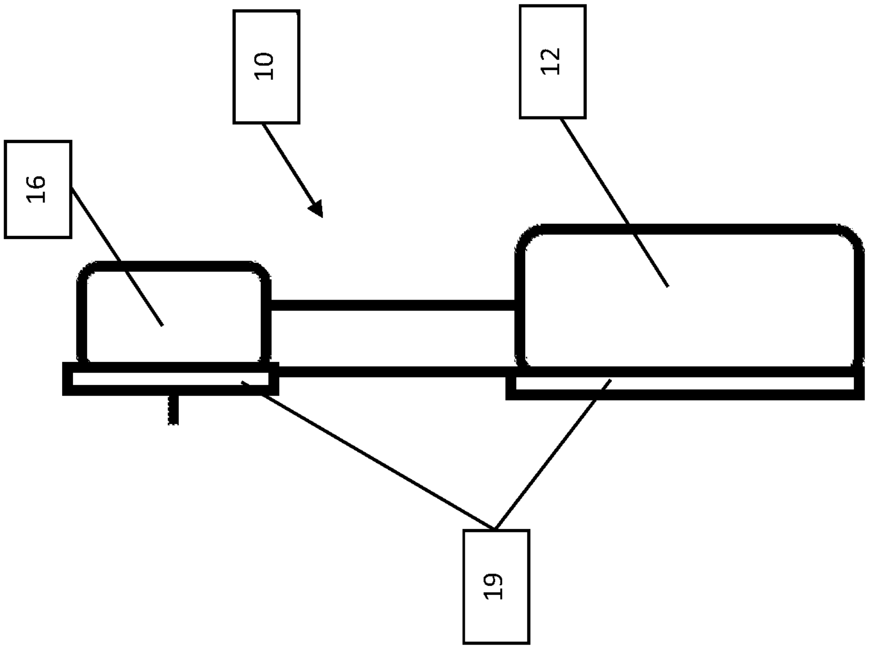
Figure 80A:
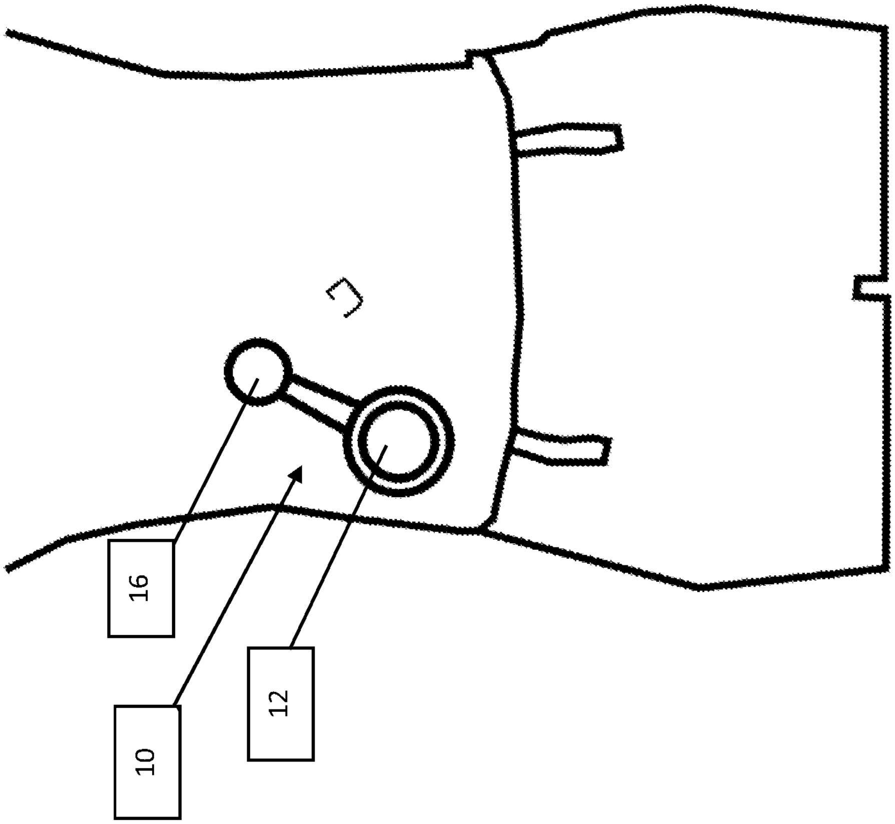
Figure 81B:
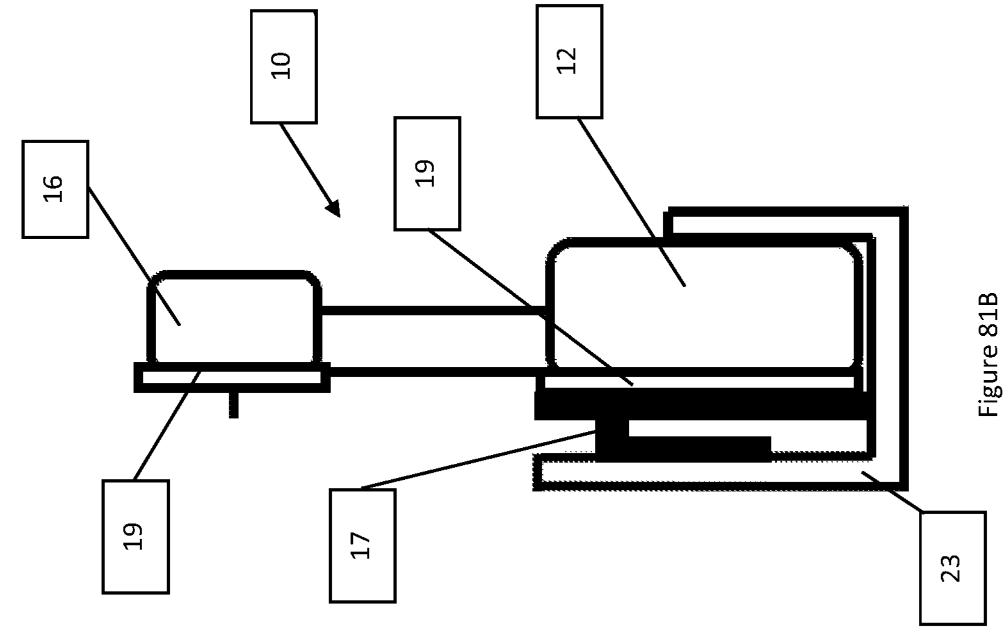
Figure 81A:
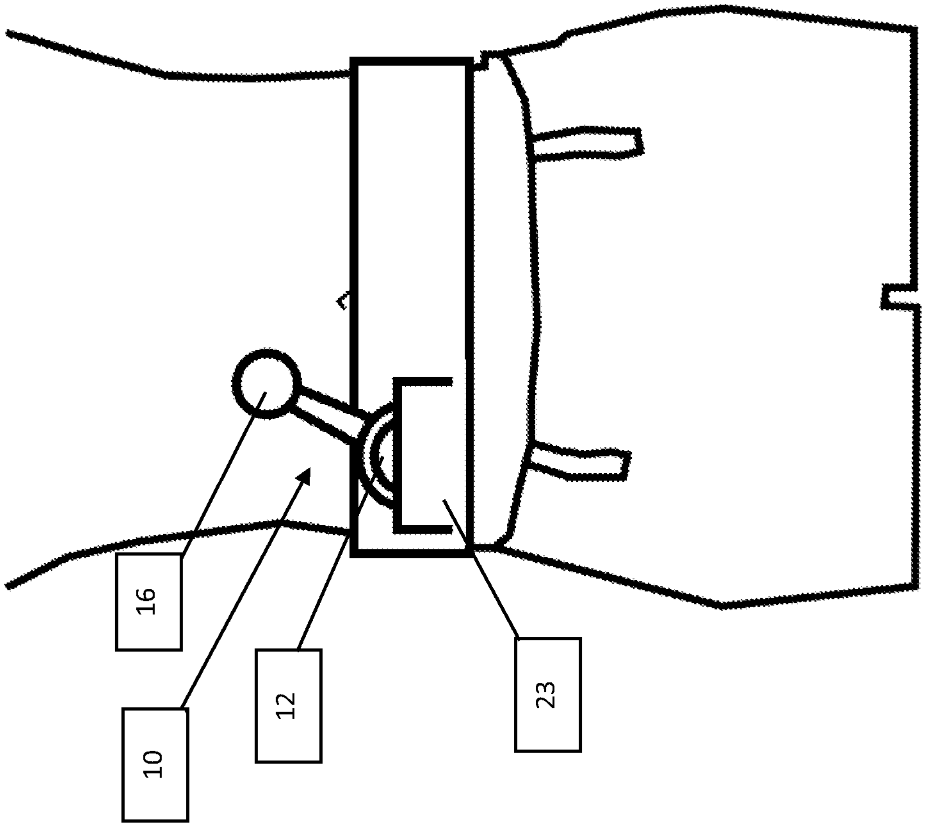

The drug delivery device 10 may be formed multi-bodied, including a body portion corresponding to the body 12 and a separate body portion corresponding to the needle support 16. In addition, the drug delivery device 10 is particularly well-suited for mounting to the physical anatomy of a patient for injection. This allows for on-body injection, particularly allowing for delivery of drug over an extended period-of-time. A patient may conveniently have the drug delivery device 10 mounted on their skin or to a piece of clothing (e.g., clipped to a belt), during injection, allowing for other activities, such as reading, watching entertainment, and so forth. The drug delivery device 10 is preferably for one-time use, being temporarily mounted to the patient's body, as shown in FIGS. 79A-81B. As shown in FIGS. 80A-80B, releasable adhesive 19 may be provided on portions of the drug delivery device 10 corresponding to the body 12 and the needle support 16, such as a pressure-sensitive adhesive, to securely mount the drug delivery device 10 to the patient's body. In addition, or as an alternative, as shown in FIGS. 81A-81B, the drug delivery device 10 may be provided with a belt or strap 21 for securing about a portion of the patient's body, such as the waist, in mounting the drug delivery device 10 to the patient's body. It is preferred that the drug delivery device 10 be securely mounted to minimize inadvertent removal of the needle 15 from the patient during drug delivery. The belt or strap 21 may be provided with a pocket 23 for receiving all or a portion of the drug delivery device 10, such as the portion of the drug delivery device 10 corresponding to the body 12. The needle support 16 may be mounted to the patient with the adhesive 19 with the body 12 portion of the drug delivery device 10 being in the pocket 23 to be supported by the belt or strap 21. Further, as shown in FIGS. 79A-79B, the drug delivery device 10 may be provided with a clip 17 for mounting onto a waistband, or other portion, of a patient's clothing. The needle support 16 may be mounted to the patient with the adhesive 19 with the body 12 being supported by the clip 17. The clip 17 may be secured to the body 12 using any known mode of connection, including fusion, adhesion, and so forth. The clip 17 may be used also in connection with the belt or strap 21, to act as a spacer in the product 23 to better ensure that the body 12 is supported in a stable manner. The clip 17 may be also removable to provide a patient with the option of using it as a clip, or, with removal of the clip 17, using an underlying adhesive 19 in mounting to the body.

As shown in FIG. 3, the drug delivery device 10 may include a housing 9 which encases the body 12. The housing 9 may also contain the pump 18 and the control 20. The one or more outlet ducts 25 may extend through a portion of the housing 9, for example, into communication with the at least one fluid passageway 13 located in the tether 11. A channel may be defined in the housing 9, or tubing or the like may be provided, to define the portions of the one or more outlet ducts 25 extending through the housing 9.

Figure 11:
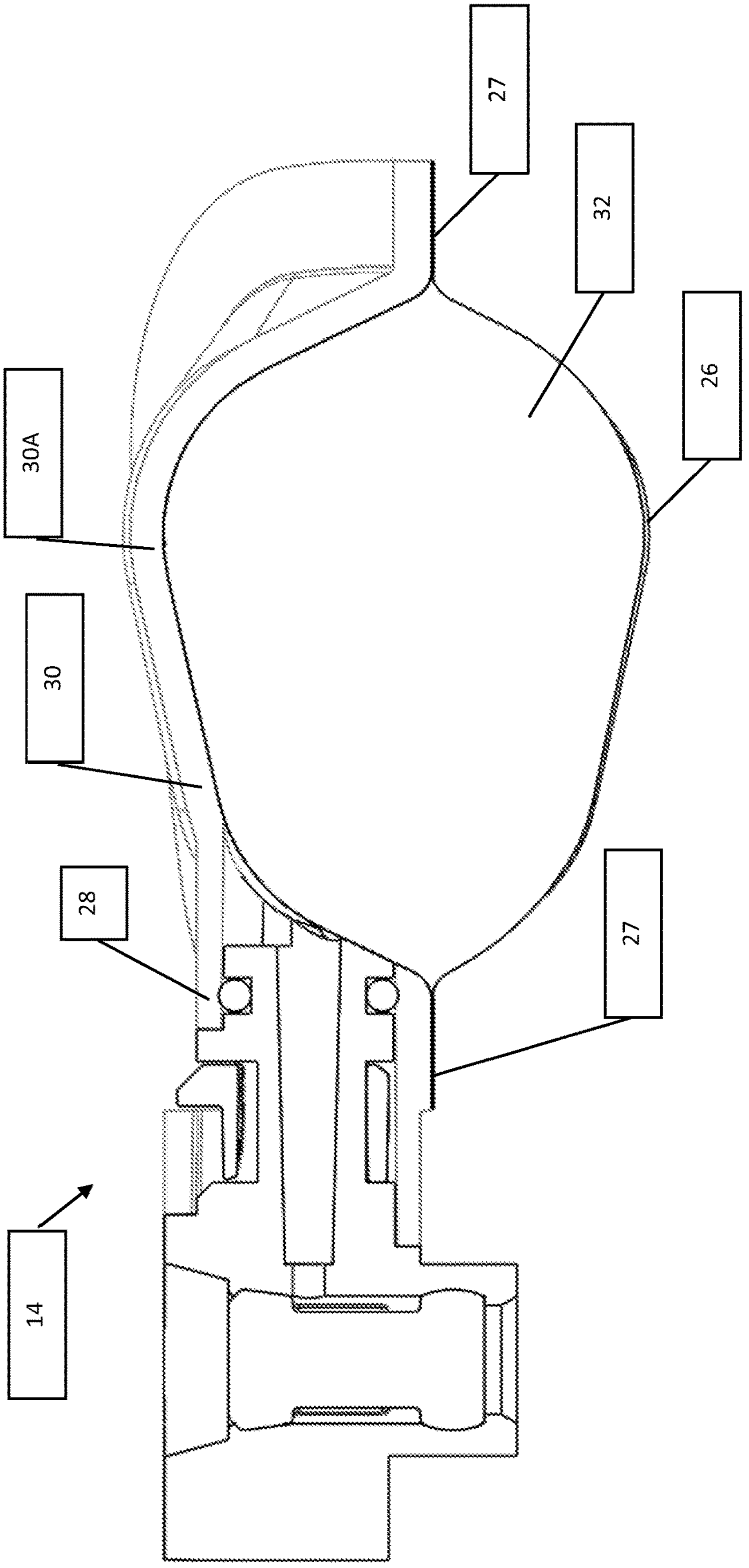
FIG. 11 is a section view of the drug cartridge of FIG. 10, without the lower portion of the rigid shell.
Figure 12:
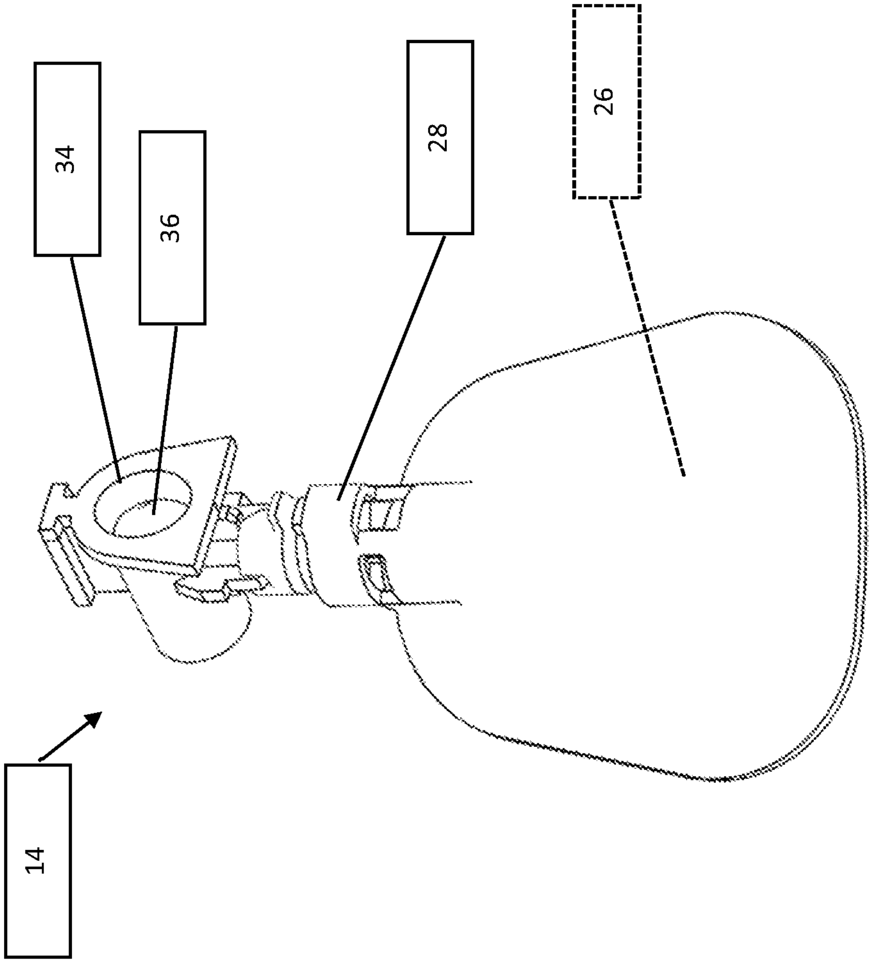
FIG. 12 shows a drug cartridge in a vented state in accordance with the subject invention.

In a further aspect of the subject invention, methods of preparing the drug cartridges 14 are provided. With reference to FIGS. 7-36 and 175-186, the drug cartridges 14 may be provided to be initially separate from the body 12, particularly to allow for pre-filling thereof with drug. As will be appreciated by those skilled in the art, the drug cartridges 14 may be formed in various manners consistent with the disclosure herein. As shown in FIG. 12, the drug cartridges 14 may be each formed to include a reservoir 26 and a cartridge support body 28. The cartridge support body 28 includes a fluid outlet 34 and an internal lumen 36 for conveying drug from the reservoir 26 to the fluid outlet 34.

Figure 8:
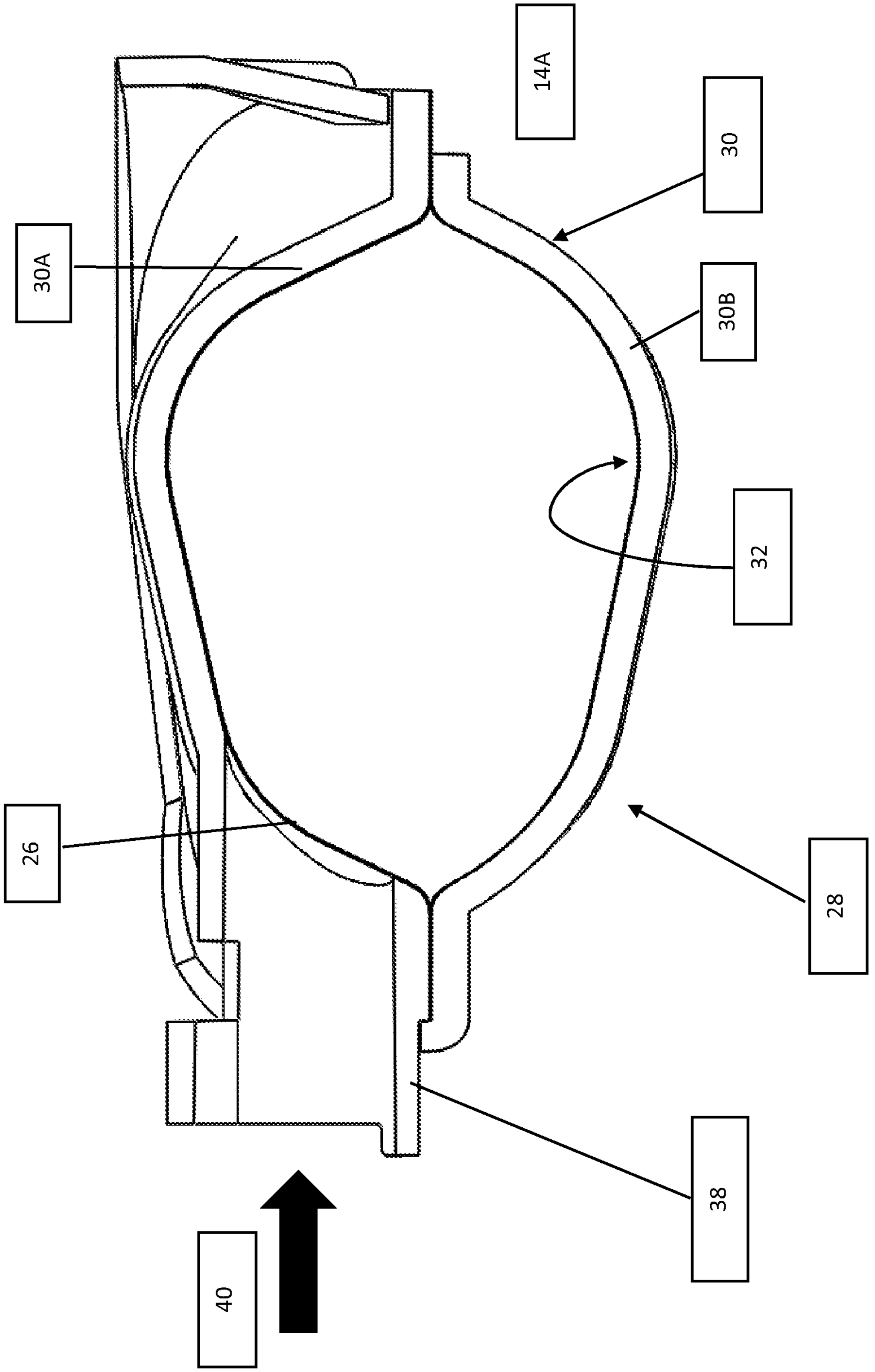
FIG. 8 is a section view of a reservoir section of a drug cartridge in accordance with the subject invention.
Figure 8A:
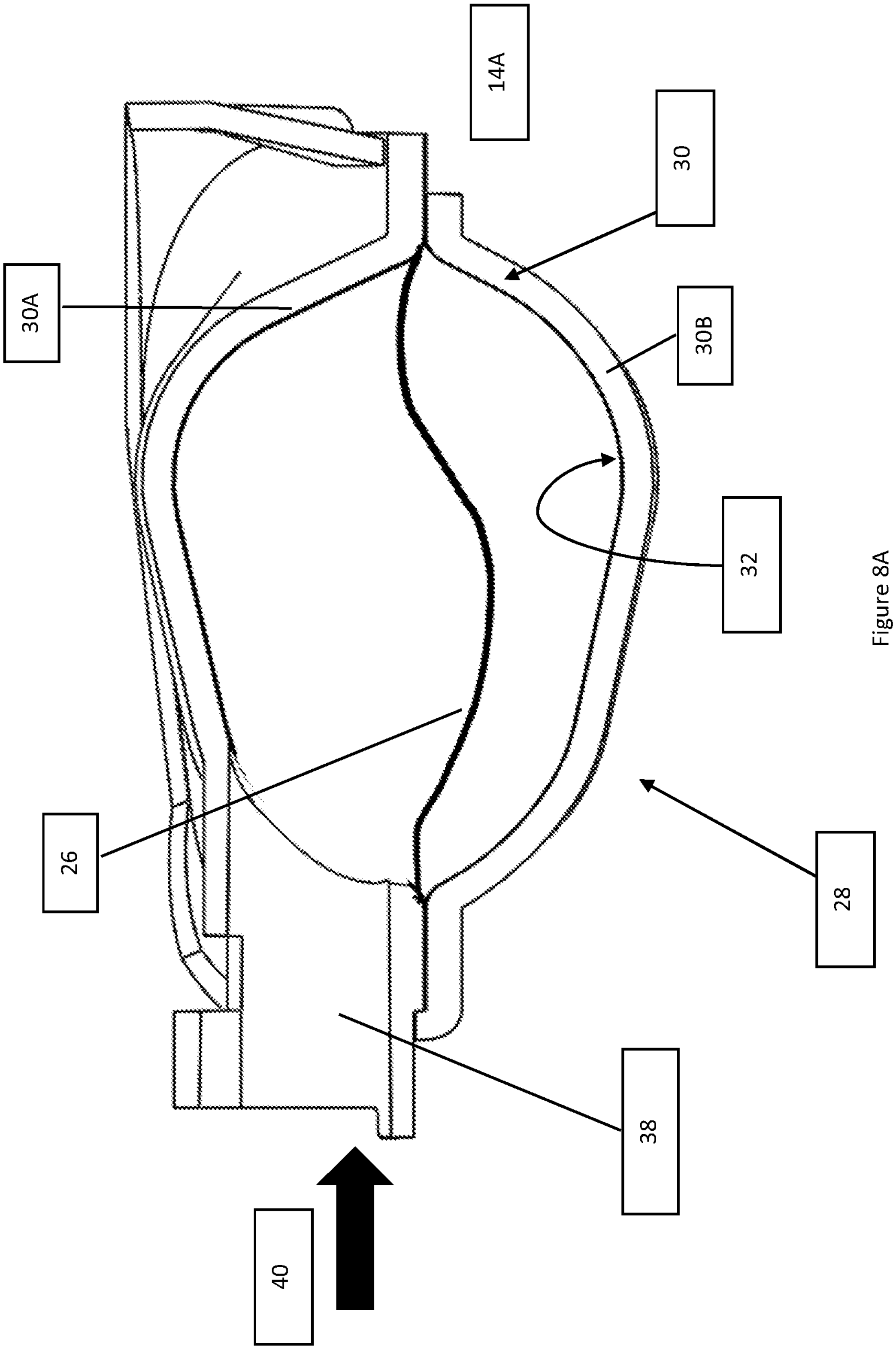
FIG. 8A shows the reservoir component of FIG. 8 with a partially collapsed reservoir.
Figure 10:
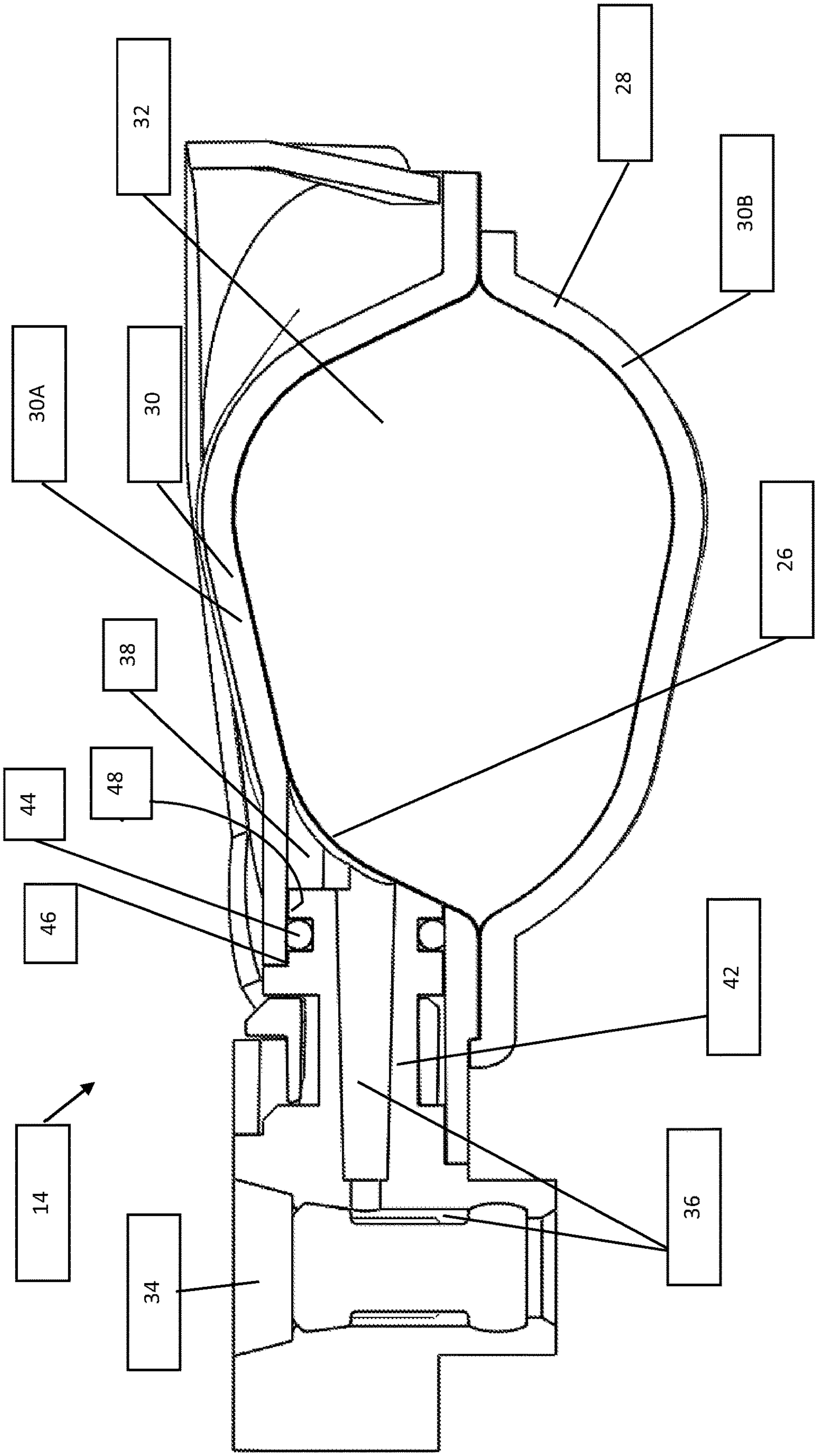
FIG. 10 is a section view of a drug cartridge, illustrating a radially sealed closure, in accordance with the subject invention.
Figure 19:
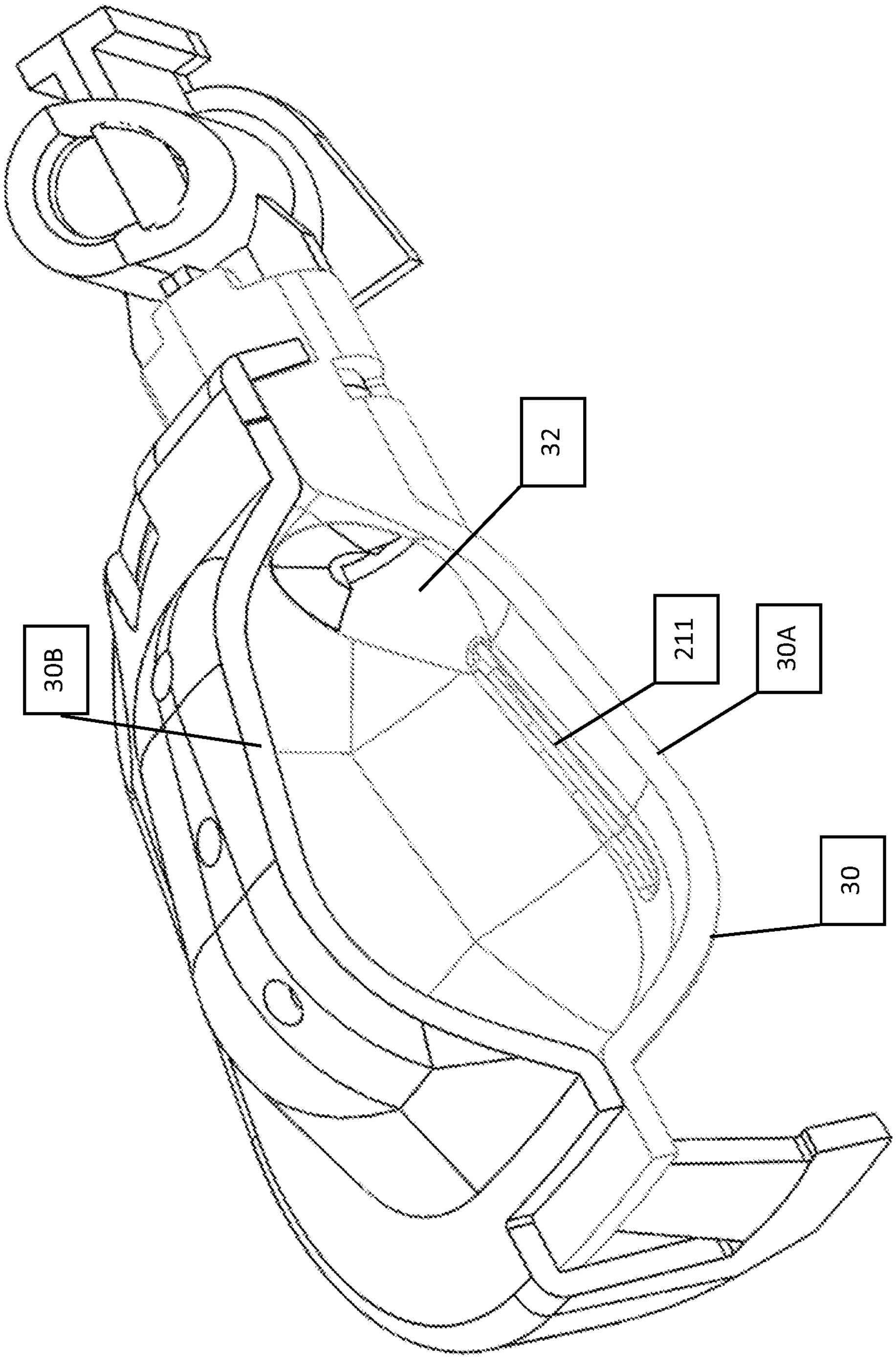
FIG. 19 is a section view of a drug cartridge, illustrating an internal flow channel, in accordance with the subject invention.
Figure 21:
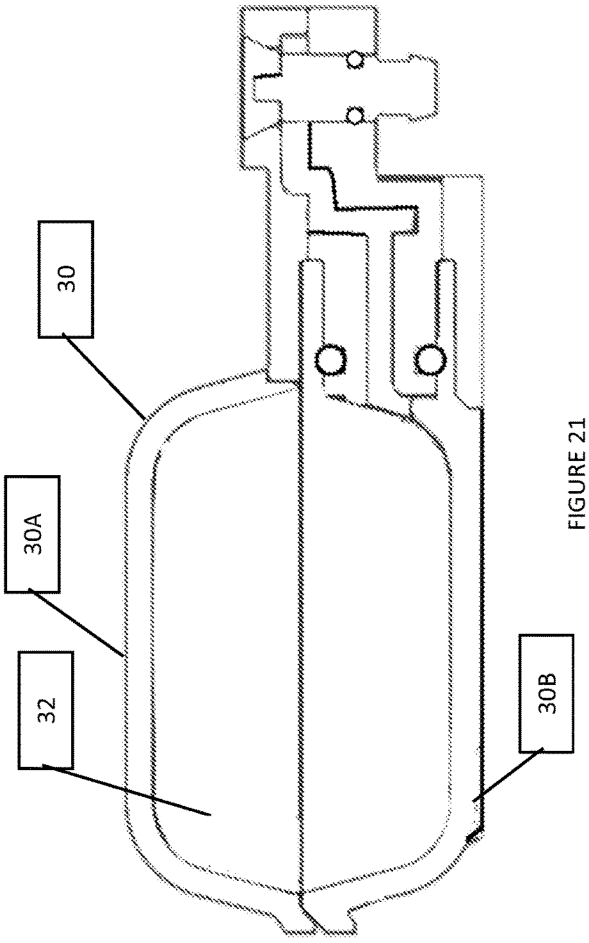
FIG. 21 shows a drug cartridge with a rigid shell that allows for full expansion of the reservoir, in accordance with the subject invention.
Figure 22:
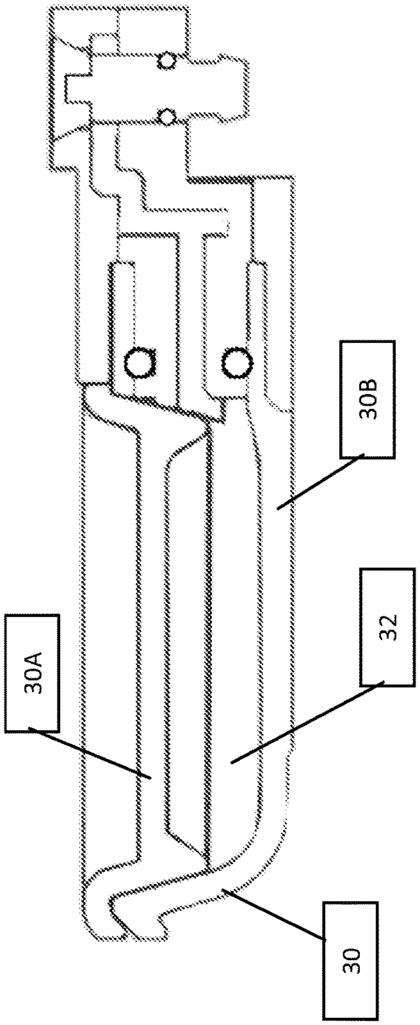
FIG. 22 shows a drug cartridge with a rigid shell that constrains the expansion of the reservoir, in accordance with the subject invention.

To avoid the need for venting of the reservoir during drug delivery, the reservoir 26 may be formed deformable to allow for collapsing during removal of drug. As shown in FIG. 10, the cartridge support body 28 may include a rigid shell 30, which ensconces the reservoir 26. The rigid shell 30 defines an internal volume 32. The rigid shell 30 maintains its shape with the collapsing of the reservoir 26 during use, as shown in FIG. 8A. The rigid shell 30 may be formed from an upper portion 30A joined to a lower portion 30B, e.g., by adhesion, fusion, welding, snap-engaging, heat sealing, and so forth. This two-part arrangement allows for the upper and lower portions 30A, 30B to be placed about the reservoir 26 during assembly. As shown in FIG. 19, one or more channels 211 may be formed on interior portions of the shell 30, e.g., in the upper portion 30A, to provide one or more surface disruptions about the reservoir 26. As shown, for example, in FIG. 29, the channels 211 may be located about the shell 30 and formed as through-holes in the shell 30 to provide venting for the internal volume 32, particularly during expansion and collapse of the reservoir 26 therewithin. The surface disruptions may minimize adhesion of the reservoir 26 to the shell 30 during use, thus, allowing for improved filling and voiding of the reservoir 26. In addition, as shown in FIGS. 21-22, the upper and lower portions 30A, 30B may be formed with concavity or convexity to delimit different size reservoirs.

The reservoir 26 may be elastomeric or a thermoformed membrane, formed as a pouch or joined components (e.g., heat-sealed, laser welded, fused, adhered, and so forth). Compatibility with accommodated drug components and resistance to through-transmission of contaminants are critical for the reservoir 26. As shown in FIG. 11, the reservoir 26 may include a flange 27 which is located between the upper and lower portions 30A, 30B of the rigid shell 30. The lower portion 30B is shown removed in FIG. 11 to best show the flange 27.

In an embodiment, the drug cartridge 14 may be modular to facilitate pre-filling with drug, with the cartridge support body 28 being divided over multiple parts. As shown in FIG. 8, a reservoir section 14A of the drug cartridge 14 may include the reservoir 26, the rigid shell 30, and a filling port 38 defining an open passageway into the reservoir 26. As shown in FIG. 8 by arrow 40, after sterilization of the reservoir section 14A, drug may be introduced through the filling port 38 into the reservoir 26. The drug may be one or more drug components, e.g., a combination of two different drugs, in various physical states. As discussed below, the drug may include solid components which may be reconstituted by the drug delivery device 10 to be ready for use.

Figure 9:
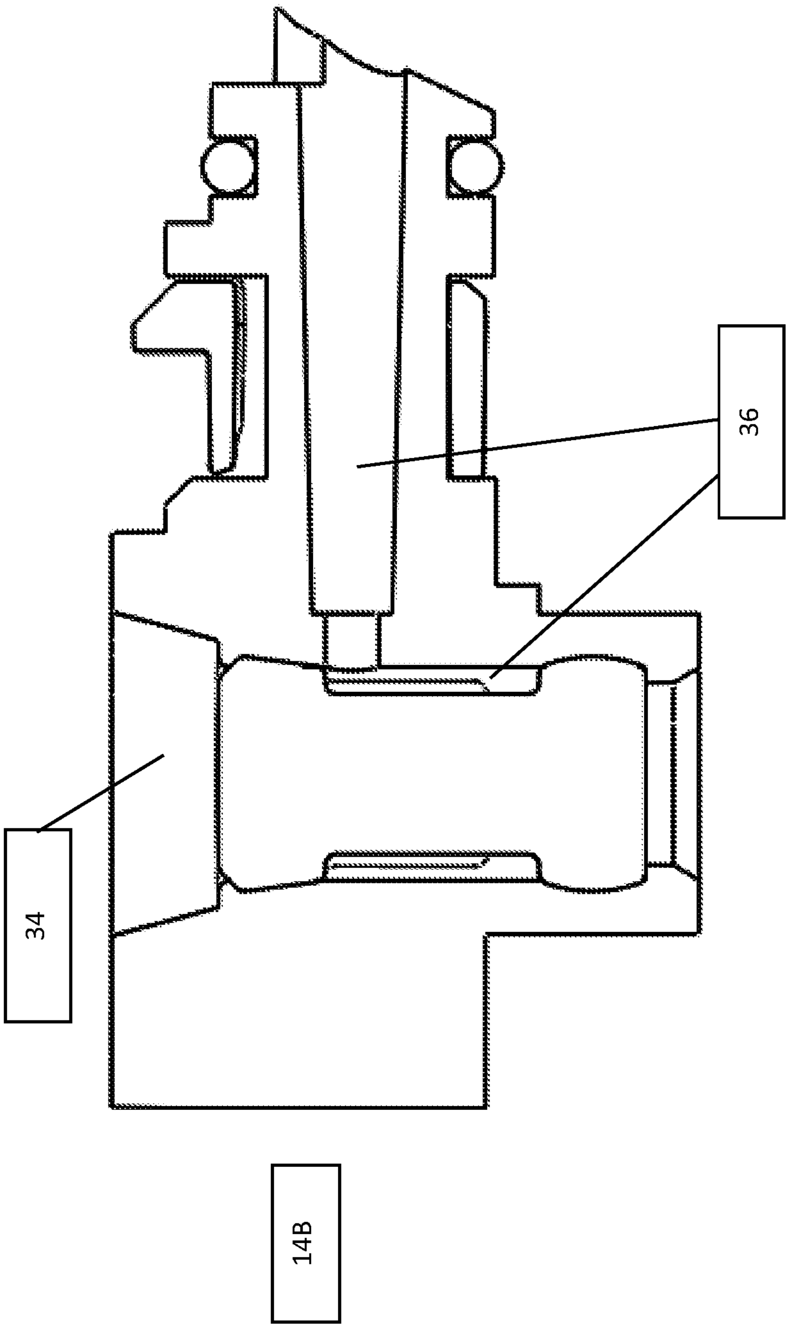
FIG. 9 is a section view of a plug adapter component of a drug cartridge in accordance with the subject invention.

As shown in FIG. 9, a plug adapter 14B of the drug cartridge 14 may be separately provided which is configured to mount to the reservoir component 14A. The plug adapter 14B may include the fluid outlet 34 and the internal lumen 36.

Separate from the filling of the reservoir 26, the internal lumen 36 of the plug adapter 14B may be sterilized with at least one lumen seal being formed on the plug adapter 14B across the sterilized internal lumen 36 to limit ingress of contaminants. The at least one seal may separate the fluid outlet 34 from the sterilized internal lumen 36 or may be located externally of the fluid outlet 34. Details of seal formation are discussed below. As will be recognized by those skilled in the art, the entire internal lumen 36 may not be sealed. For example, a portion of the internal lumen 36 adjacent to the fluid outlet 34, along with the fluid outlet 34, may be outside the seal.

Figure 7:
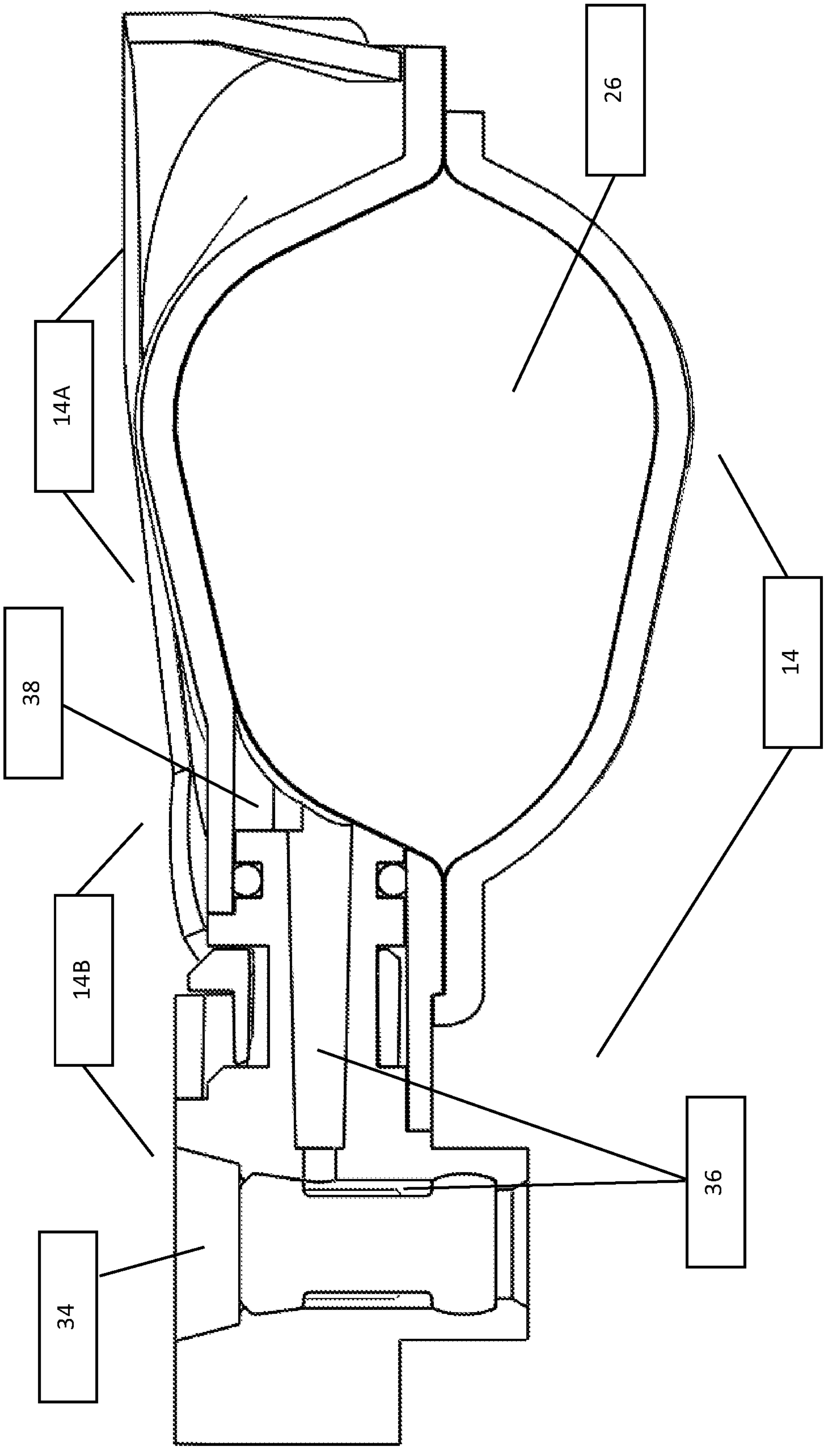
FIG. 7 is a section view of a drug cartridge, including the reservoir section and plug adapter in an assembled state, in accordance with the subject invention.

With the reservoir 26 having been filled, and the internal lumen 36 having been sterilized, the plug adapter 14B may be assembled with the reservoir section 14A to form the drug cartridge 14, as shown in FIGS. 7 and 10. The plug adapter 14B may act to plug the filling port 38. As assembled, a portion of the internal lumen 36 extends through the filling port 38 into communication with the reservoir 26. With this arrangement, a fluid pathway is defined from the reservoir 26 to the fluid outlet 34.

The reservoir section 14A and the plug adapter 14B may be manufactured, placed in sealed packaging, sterilized, and assembled in separate processes. This allows for bulk processing. Once sterilized, the packaged components may be maintained in a clean environment awaiting use, as described herein. The sterilized components, may be handled and assembled in a clean, controlled environment, such as under a clean controlled-environment hood and/or in a clean controlled-environment enclosure or room.

Alternatively, the drug cartridge 14 may be formed as a single component, not requiring the separate reservoir component 14A and plug adapter 14B. As shown in FIGS. 175-178, the upper portion 30A (being shown in a lower position in FIG. 177 it is taken that the upper and lower portions 30A, 30B are first and second portions independent of their gravitational orientation) may be provided with the filling port 38. The flange 27 on the upper portion 30A may be extended to include wing portion 27A. The wing portion 27A is disposed at an angle relative to a plane defined at an interface of the upper and lower portions 30A, 30B. The wing portion 27A also extends outwardly, away from the reservoir 26 to define a free end 27B. The fluid outlet 34 may be defined in the wing portion 27A in proximity to the free end 27B. The internal lumen 36 is provided to extend from the reservoir 26 to the fluid outlet 34 to define a flow path to the fluid outlet 34 from the reservoir 26. As shown in FIG. 173, the wing portion 27A, with the fluid outlet 34 being defined thereon, allows for the drug cartridge 14 to be mounted to a face of the body 12 with the reservoir 26 radiating outwardly from the circumference of the body 12. This allows for a smaller footprint for the drug delivery device 10. The wing portions 27A for the reservoirs 14 may be formed to be tessellated when mounted to the body 12, generally with no gaps therebetween.

With the arrangement of FIGS. 175-186, the filling port 38 and the internal lumen 36 are separately provided. In this manner, the reservoir 26 may be filled through the filling port 38 with the filling port 38 being subsequently sealed, e.g., with an elastomeric plug and/or a crimped cap. To minimize hindrance of the internal lumen 36 during filling, it is preferred that the internal lumen 36 be located in proximity to the filling port 38. This allows for the internal lumen 36 to be located above the majority of the reservoir 26 with the drug cartridge 14 in an upright position for filling, which is preferred for lyophilization.

As described above, the upper portion 30A may be formed to be rigid and to ensconce the reservoir 26. Alternatively, as shown in FIGS. 175-186, the reservoir 26 may be formed integrally with the upper and lower portions 30A, 30B. For example, the flange 27 may be rigid and bound each of the upper and lower portions 30A, 30B. Flexible reservoir walls 26R, 26S may be provided on the upper and lower portions 30A, 30B, respectively, being edge mounted to the flange 27. The flexible reservoir walls 26R, 26S, along with the flange 27, collectively define the reservoir 26. The flexible reservoir walls 26R, 26S may be formed of any elastomeric or thermoformable membrane, such as a film of cyclic olefin copolymer (COC), optionally with a layer of poly-chloro-trifluoro-ethylene (PCTFE). The flexible reservoir walls 26R, 26S are formed to be responsive to the filling of the reservoir 26, as well as, removal of drug therefrom. The flexible reservoir walls 26R, 26S are collapsible with the removal of drug from the reservoir 26 with the reservoir 26 not being vented.

Figure 179:
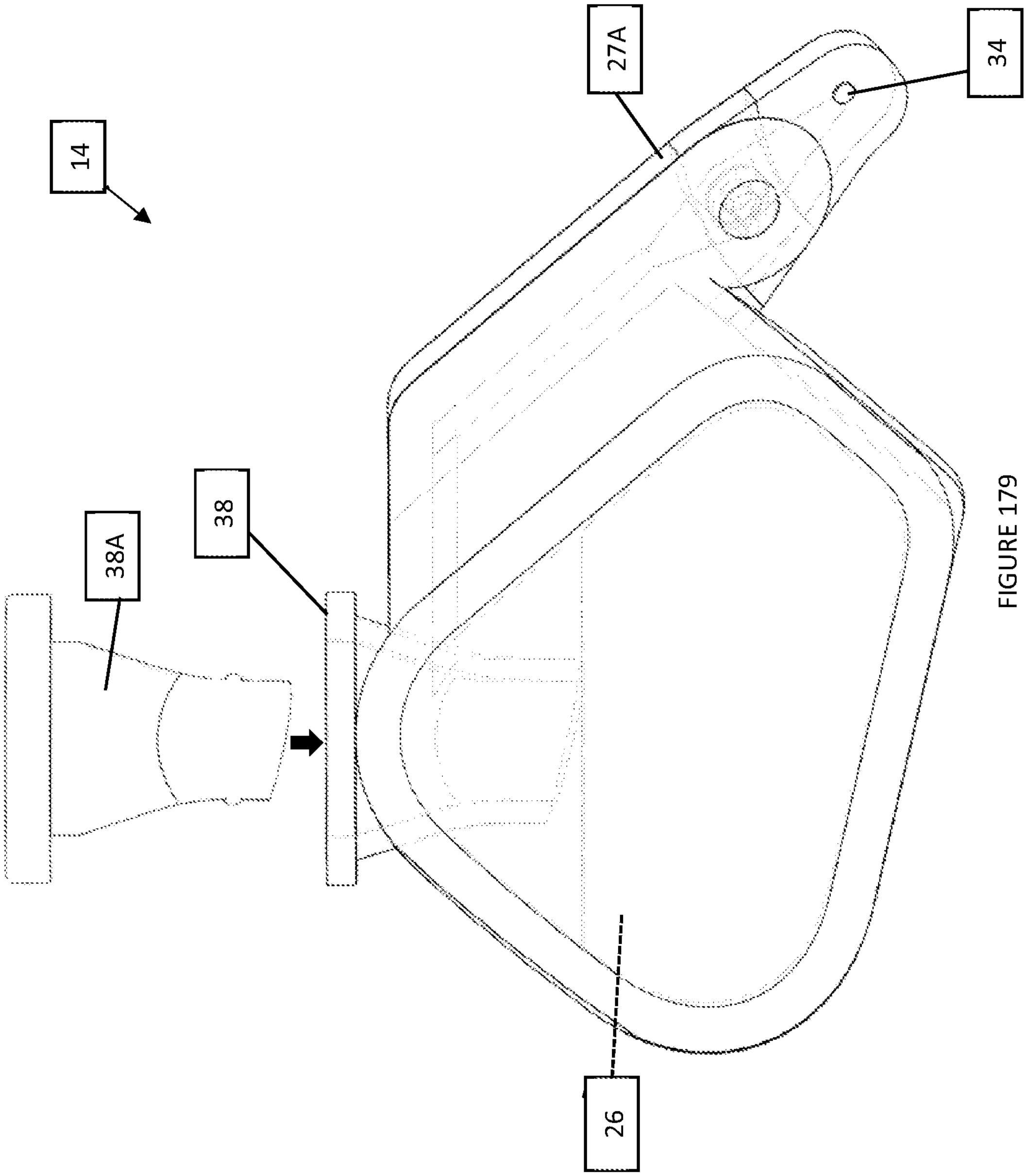

As part of the filling of the reservoir, the drug cartridge 14 may be utilized for lyophilization of drug. Here, drug is initially introduced in a liquid state into the reservoir 26. The plug adapter 14B may include a vent adjustable from an open state to a closed state. Once filled and assembled, the drug cartridge 14, with the vent in an open state, may be subjected to lyophilization conditions (low temperature and vacuum to extract moisture) to cause the drug in the reservoir 26 to lyophilize. Subsequently, the vent on the plug adapter 14B may be adjusted to the closed state. Likewise, as shown in FIG. 179, the filling port 38 may be provided with an adjustable vent plug 38A to facilitate lyophilization of drug in the reservoir 26.

Figure 58:
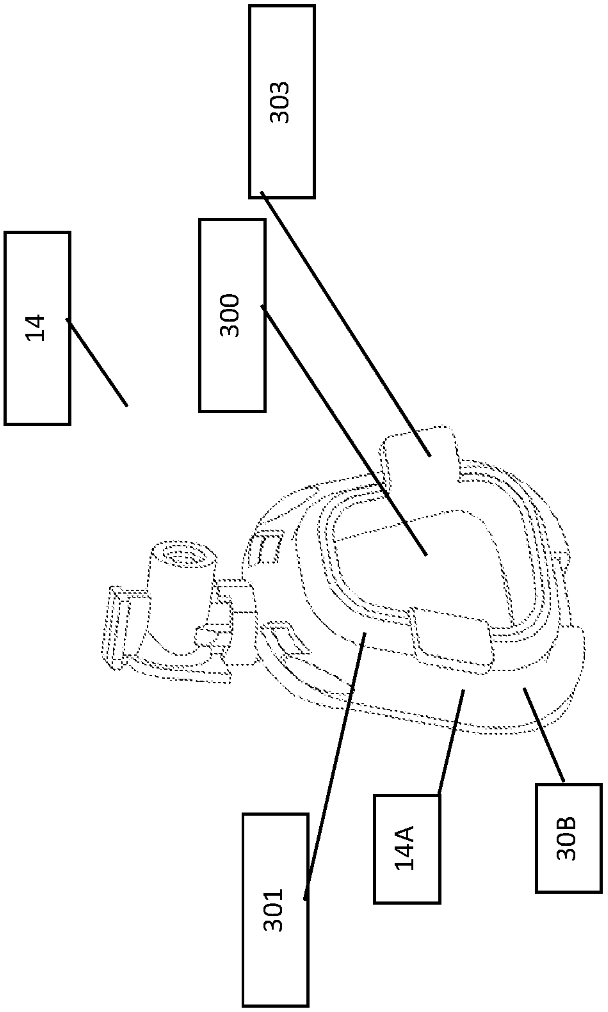
FIG. 58 shows a drug cartridge with a reservoir support useable for dry products, in accordance with the subject invention.
Figure 59:
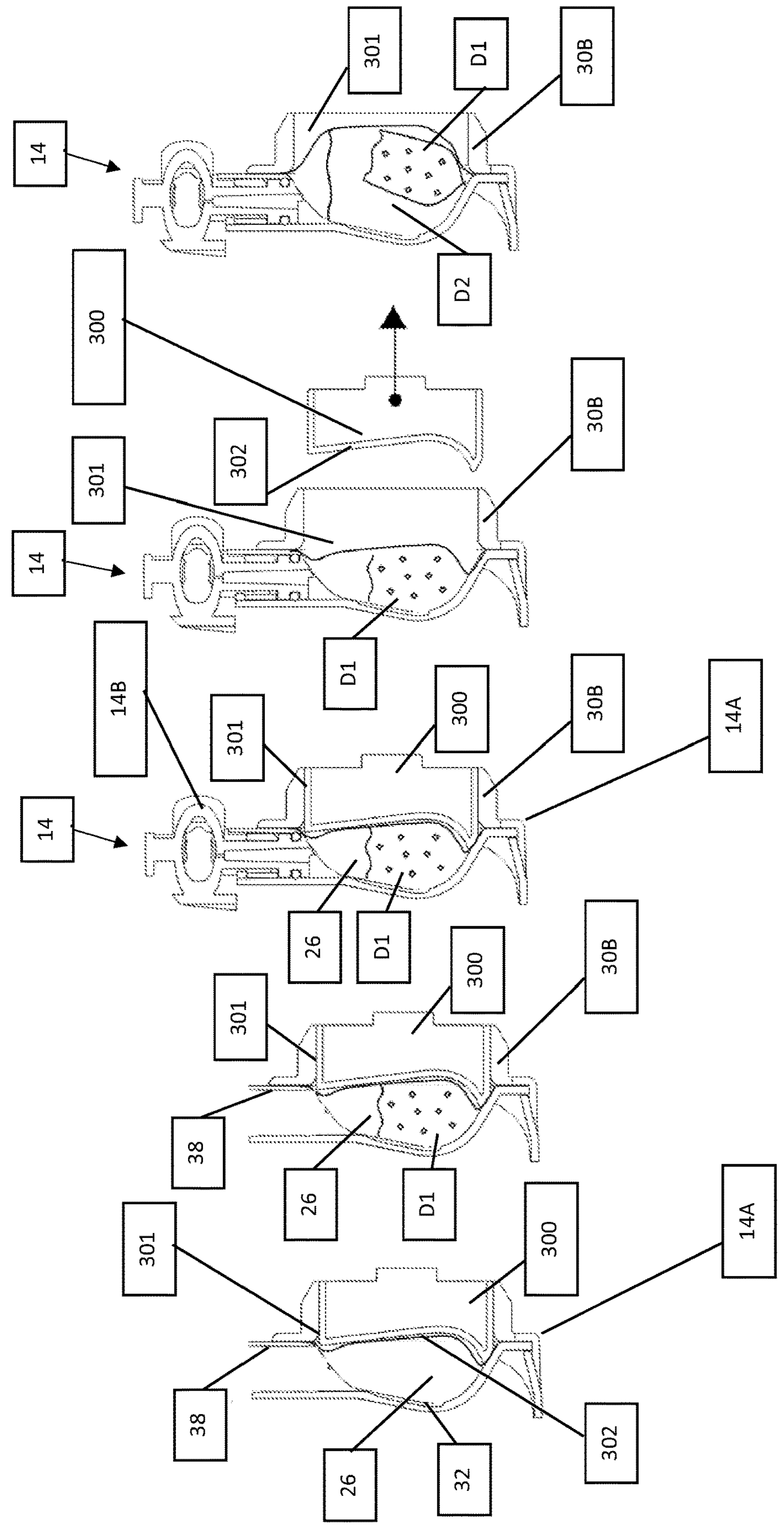
FIG. 59 shows the reservoir support of FIG. 58 in use.

Alternatively, drug in dry form may be initially introduced into the reservoir 26 with subsequent introduction of a diluent to reconstitute the drug into liquid form at the time of use of the drug delivery device. To limit "dead space" in the reservoir 26 during the loading of drug in dry form, a reservoir support 300 may be utilized, as shown in FIGS. 58-64E. By minimizing "dead space," empty volume inside the reservoir 26 is limited. As shown in FIGS. 58-59, the reservoir section 14A, particularly the lower portion 30B of the rigid shell 30, may be formed with an opening 301 formed to receive the reservoir support 300 in the internal volume 32, adjacent to the reservoir 26. The reservoir support 300 includes a front face 302 for limiting the expansion of the reservoir 26. The front face 302 may be contoured to provide the reservoir 26 with a larger volume away from the filling port 38. In this manner, as shown in FIG. 59, with drug in dry form D1 introduced in the reservoir 26, the front face 302 limits the expansion of the reservoir 26. In a filled state, the reservoir 26 may be bulb-shaped. Once the reservoir 26 has been filled with the drug in dry form D1, the plug adapter 14B or the vent plug 38A may be mounted to the reservoir section 14A (upper portion 30A) and then the reservoir support 300 may be removed. Drug in the form of diluent D2 may be then added during reconstitution, with the reservoir 26 expanding. Back pressure may be monitored in loading the drug in the form of diluent D2 to determine the fill level. With minimization of "dead space," pockets of compressible gases are minimized, thus, allowing for pressure readings which are more accurate of actual fill levels. In addition, better control over concentration of the resulting liquid drug may be achieved.

Figure 60:
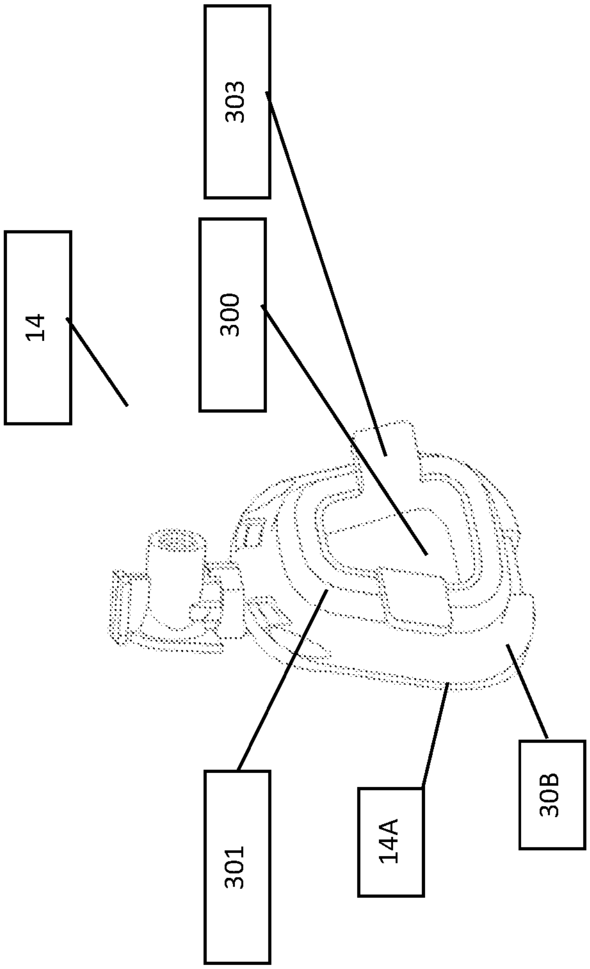
FIG. 60 shows a drug cartridge with an alternate reservoir support useable for dry products, in accordance with the subject invention.
Figure 61:
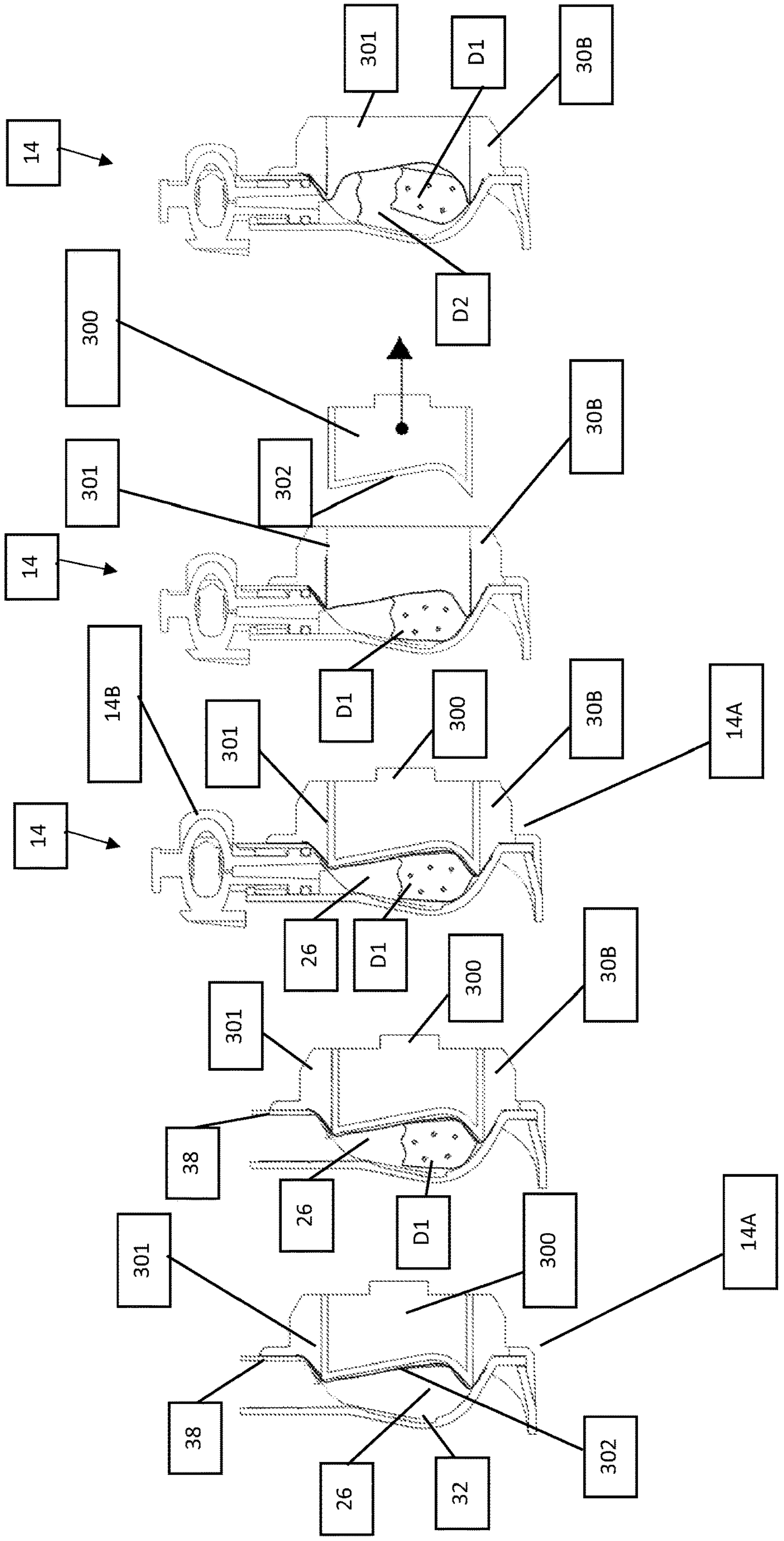
FIG. 61 shows the reservoir support of FIG. 60 in use.

As shown in comparing FIGS. 60 and 61, the reservoir support 300, including the front face 302, may be provided with different configurations corresponding to different volumes of drug. FIG. 61 is directed to a smaller drug volume, requiring less volume in the reservoir 26, than that shown in FIG. 59. As such, the reservoir support 300 is provided with added length to extend deeper into the internal volume 32, positioning the front face 302 to provide greater restriction to the expansion of the reservoir 26 than as shown in FIG. 59.

Figure 62:
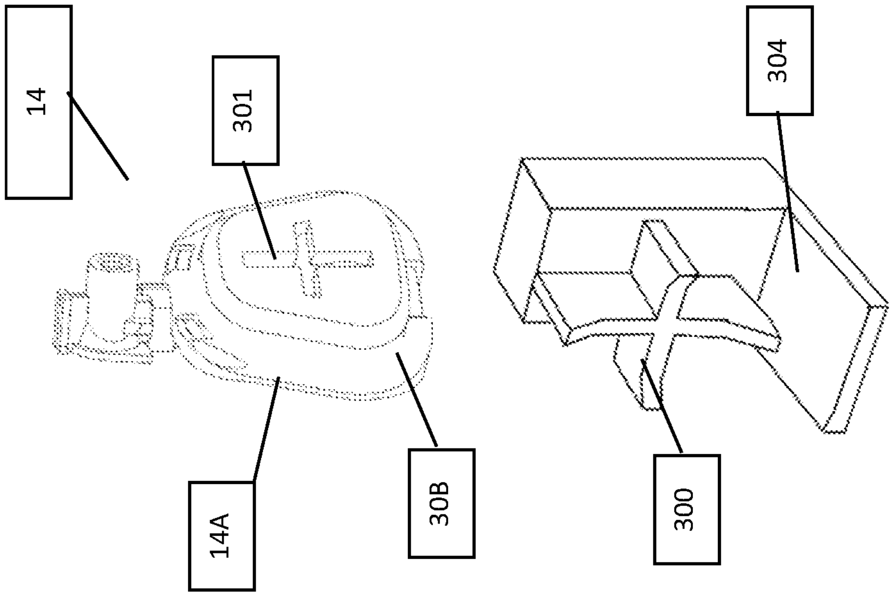
FIG. 62 shows a drug cartridge with a reservoir support fixture, in accordance with the subject invention.
Figure 63:
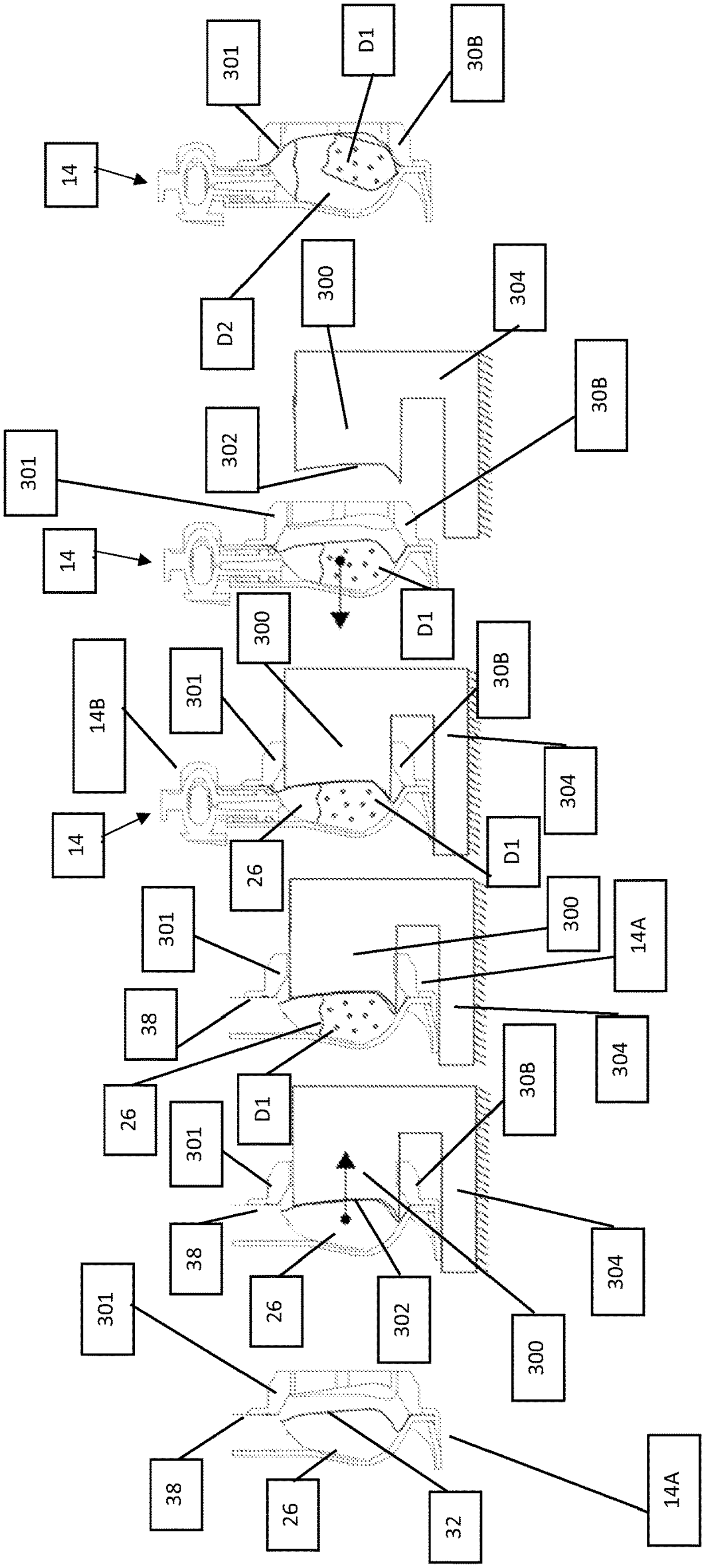
FIG. 63 shows the reservoir support fixture of FIG. 62 in use.

The opening 301 may be formed to closely receive the reservoir support 300 to allow for removable mounting of the reservoir support 300 in the opening (e.g, by friction or interference fit). To facilitate handling of the reservoir support 300, particularly for removal from the opening 301, outwardly extending tabs 303 may be provided, as shown in FIGS. 58 and 60. Alternatively, as shown in FIGS. 62 and 63, the reservoir support 300 may be provided as a separate tool or fixture which is insertable into the opening 301 formed on the rigid shell 30. This allows for the front face 302 to be positioned at various locations within the reservoir 26, depending on the extent of insertion of the reservoir support 300 into the rigid shell 30. The opening 301 may be provided with a cruciform shape, with the profile of the reservoir support 300 matching, to act as a guide therefor. In this configuration, as shown in FIGS. 62-63, the reservoir support 300 may be provided with a support 304.

Figure 64A:
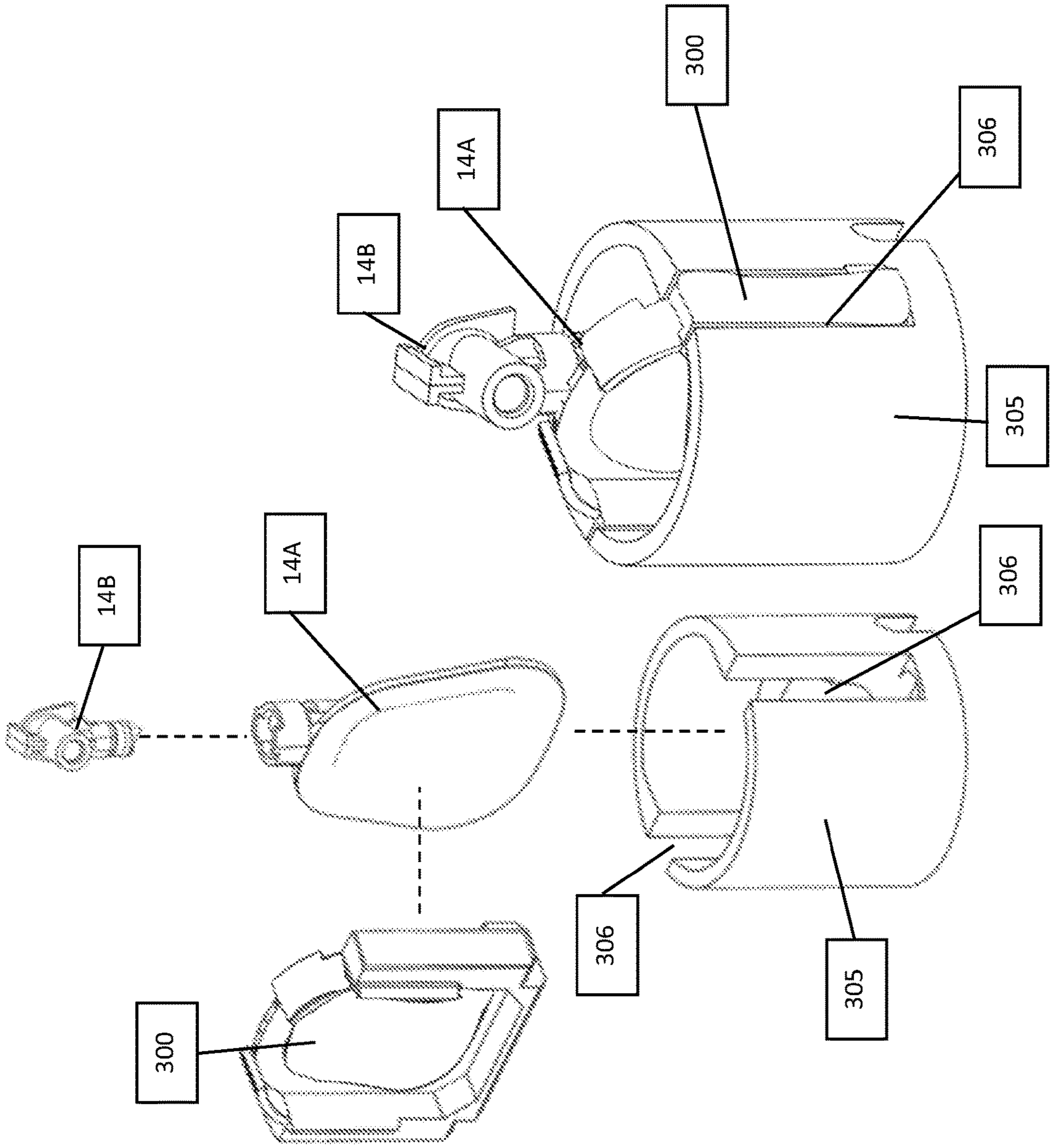
FIG. 64A shows a jig useable with the subject invention.

FIG. 64A shows a cup-shaped jig 305 having slots 306 formed therein for receiving the reservoir section 14A mounted to the reservoir support 300. The slots 306 may be formed to be slightly greater than the edge thickness of the reservoir support 300 for close fit therewithin. The jig 305 may be used to hold the reservoir section 14A/reservoir support 300 combination during any of the filling processes described above in connection with FIG. 59, 61, or 63. In addition, the jig 305 may be internally contoured to match the external surface contours of the reservoir section 14A and the reservoir support 300, in order to maximize contact area. Advantageously, the jig 305 may hold the reservoir section 14A and the reservoir support 300 during lyophilization. By matching the internal contour of the jig 305 with external surface contours of the reservoir section 14A and the reservoir support 300, heat transfer between the components may be maximized. Material for the jig 305 may be selected to have high thermal conductivity to promote heat transfer during lyophilization (e.g., anodized aluminum).

Figure 64B:
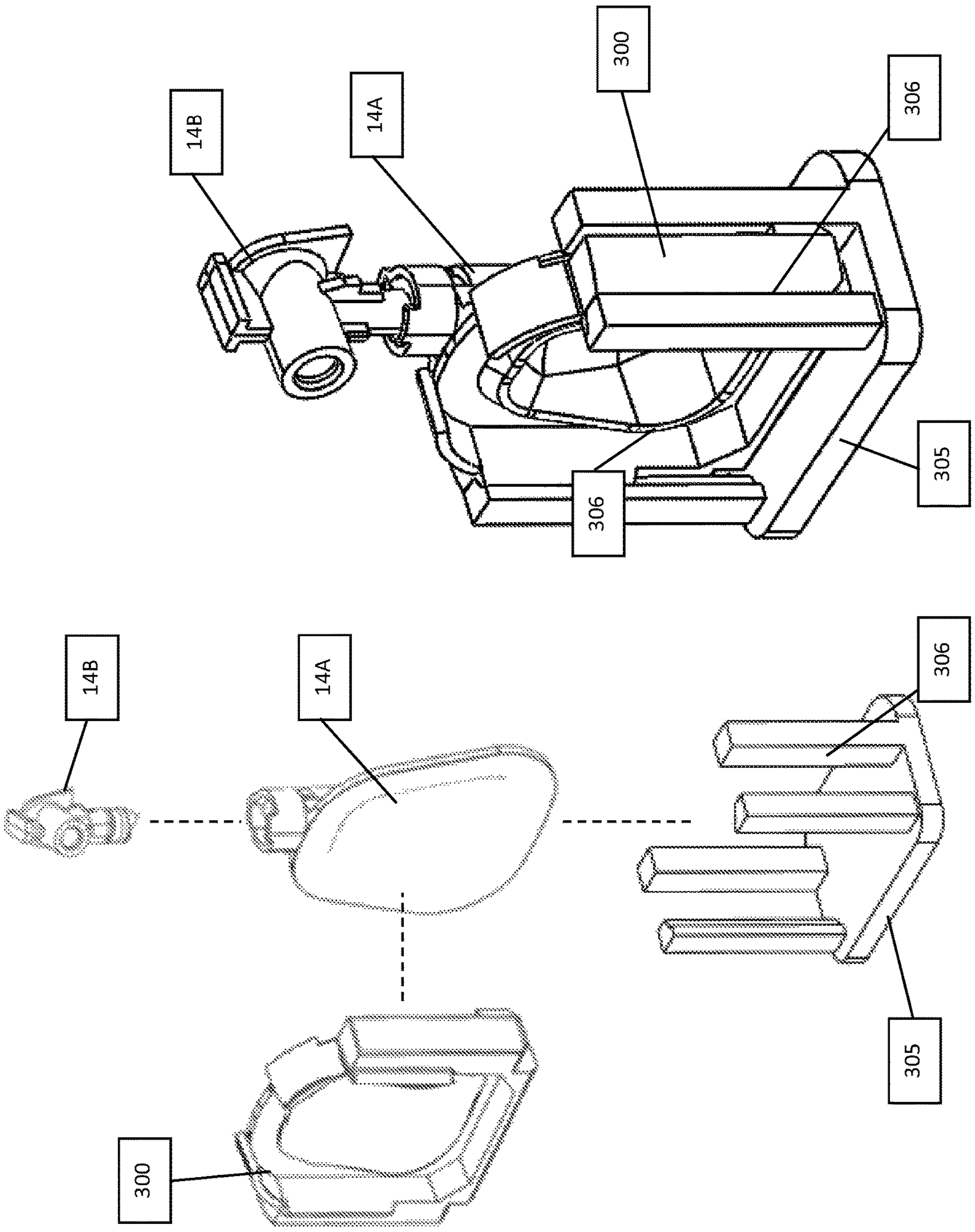
FIG. 64B shows an open jig useable with the subject invention.

An alternative open jig 307 is shown in FIG. 64B, having slots 306 formed therein for receiving the reservoir section 14A mounted to the reservoir support 300. The open jig 307 leaves exposed major portions of the reservoir section 14A to promote heat transfer via radiation and convection during lyophilization. This allows for more uniform heat transfer across the surface of the reservoir section 14A, as compared to the cup-shaped jig 305, which relies on conduction through the matching internal contours of the jig 305, as well as radiation and convection for the upper portion of the reservoir section 14A.

Figure 64C:
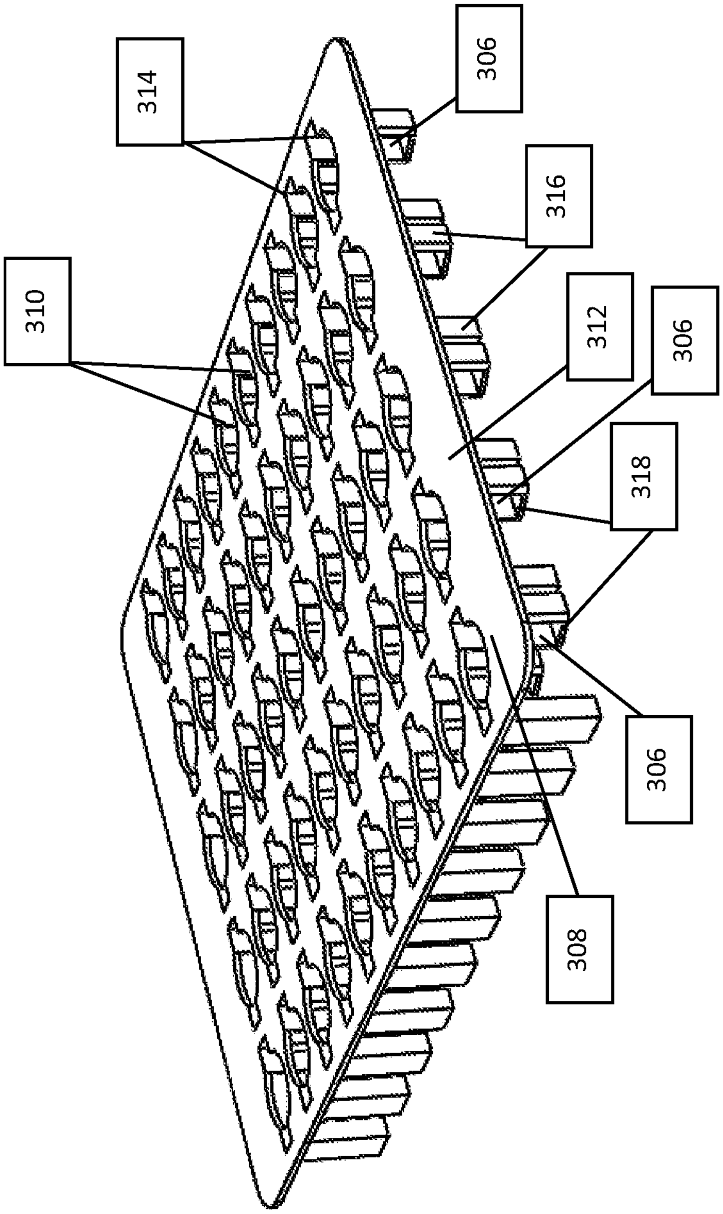
FIG. 64C shows a tray useable with the subject invention.
Figure 64D:
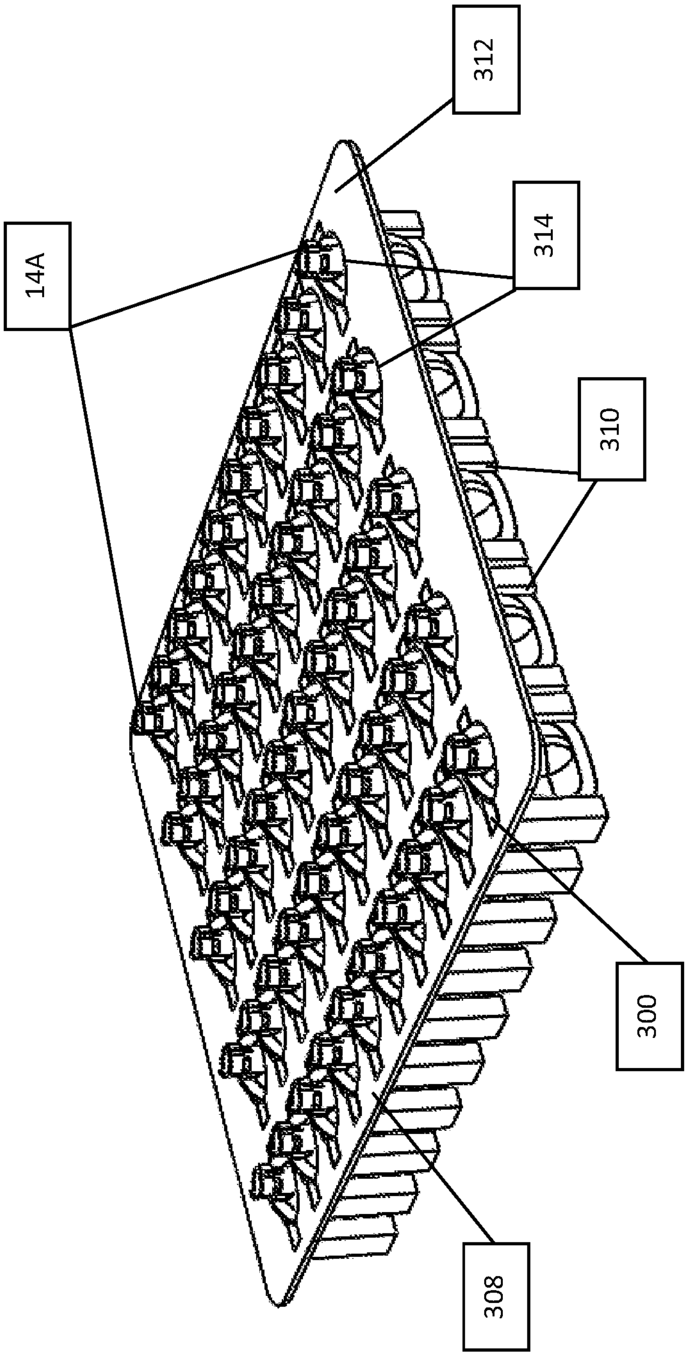
FIG. 64D shows the tray of FIG. 64C loaded with drug cartridges.
Figure 64E:
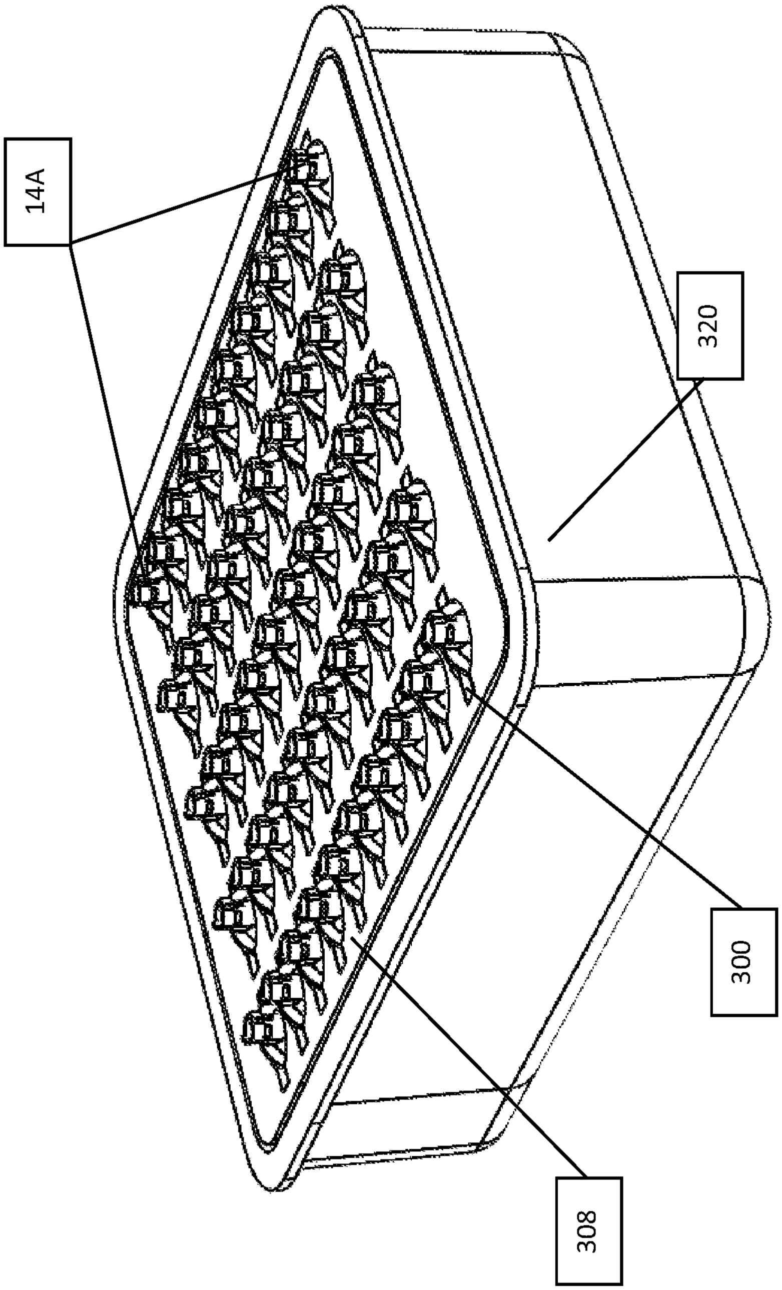
FIG. 64E shows the loaded of FIG. 64D placed in a tub.

Both the jig 305 and the open jig 307 may be placed in a support structure, such as a tray or tub, in various quantities to allow for batch lyophilization and transportation. Alternatively, as shown in FIGS. 64C-64E, a tray 308 may be provided formed with wells 310 each configured to receive the reservoir sections 14A having the reservoir support 300 mounted thereto. The tray 308 includes a support panel 312 with openings 314 for the wells 310. Each of the openings 314 includes a profile to allow the reservoir section 14A, with the reservoir support 300 mounted thereto, to pass through. For example, as shown in FIG. 64C, the openings 314 may each include a profile having an enlarged central area, e.g., generally elliptical area, with laterally extending wings, e.g., rectangular wings. Each of the wells 310 includes a pair of legs 316 depending downwardly from the support panel 312. The legs 316 are each internally open to define the slots 306 for receiving the reservoir sections 14A. A bottom 318 is provided for each of the legs 316 to restrict downward movement of the reservoir sections 14A within the slots 306.

As shown in FIG. 64D, the tray 308 permits a plurality of the assembled reservoir sections 14A/reservoir supports 300 to be accommodated in the wells 310. The wells 310 may be arranged in various arrays to permit efficient packing. As shown in FIG. 64E, the tray 308, once loaded, may be placed in a tub 320 for subsequent processing and transportation. The support panel 312 preferably has portions extending beyond the wells 310 which allow for the support panel 312 to be edge supported by the tub 320. Preferably, the legs 316 are out of contact with the tub 320 with the tray 308 placed in the tub 320 (i.e., spacing is present between the legs 316 and sidewalls of the tub 320). In addition, preferably, the tub 320 is provided with sufficient depth to avoid contact between the tub 320 and the reservoir sections 14A with the tray 308 placed in the tub 320 (i.e., spacing is present between the bottoms 318 and a base of the tub 320). The tray 308 may be formed from a polymeric material and formed by molding.

As will be understood by those skilled in the art, the plug adapter 14B may be replaced with the vent plug 38A in each of the embodiments of FIGS. 58-64E.

The drug cartridge 14, as being pre-filled, acts as a drug container during transportation and storage, prior to use. The materials of the drug cartridge 14 must be compatible with the corresponding drug. In addition, the drug cartridge 14 must be provided with sufficiently robust sealing to withstand ingress of contaminants over the duration of the expected time to use.

Figure 13:
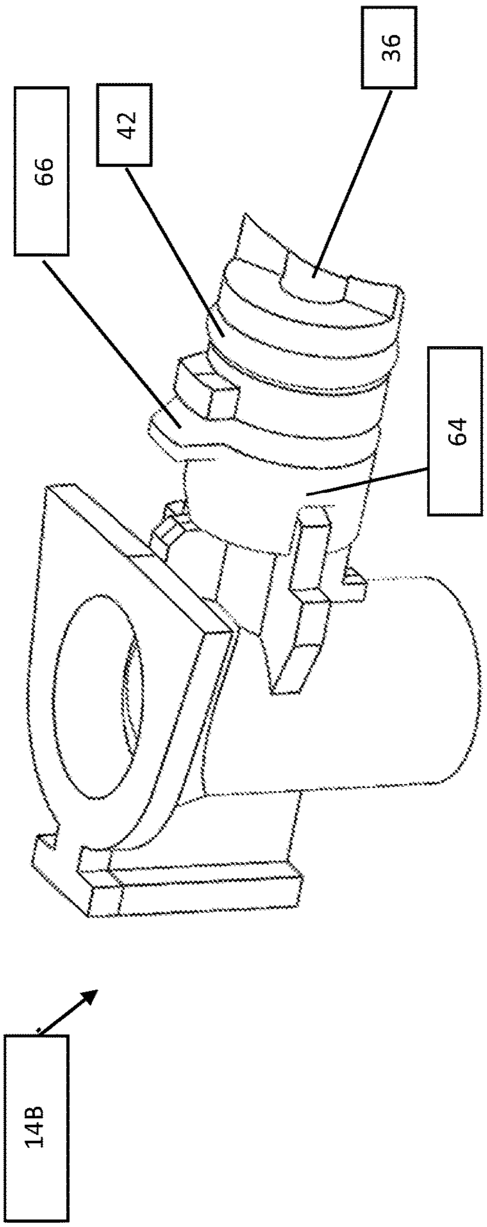
FIG. 13 is a detailed view of a plug adapter useable for radial sealing in accordance with the subject invention.
Figure 14:
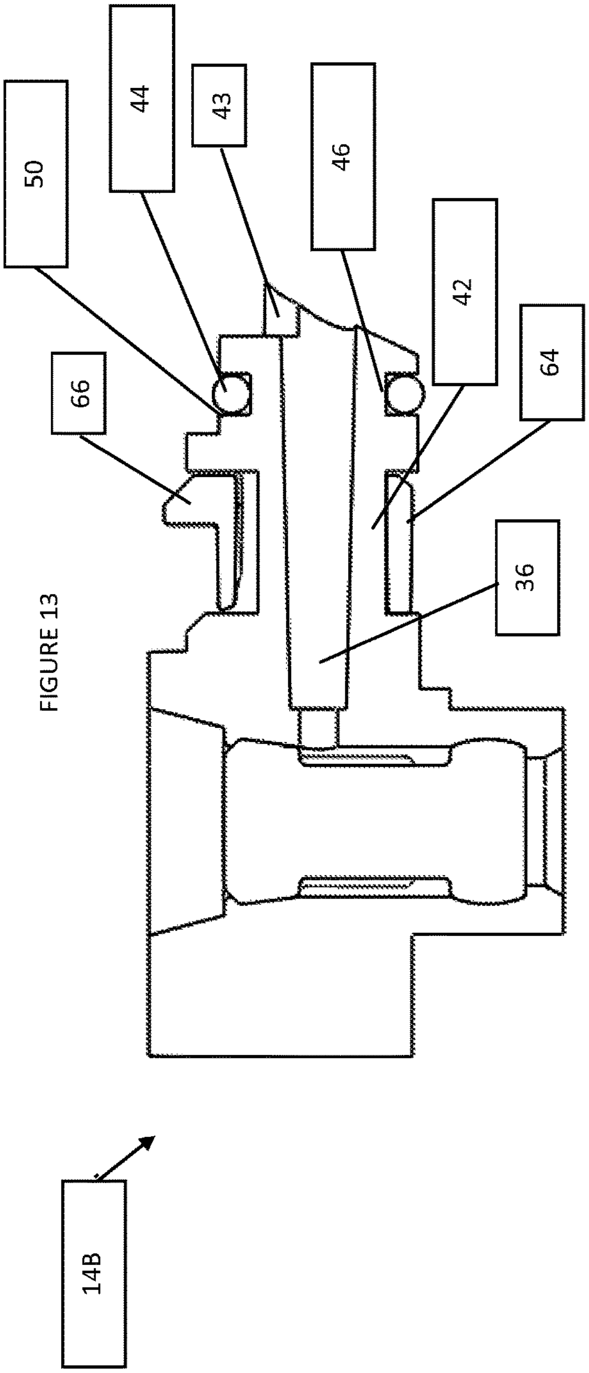
FIG. 14 is a section view of the plug adapter of FIG. 13.
Figure 15:
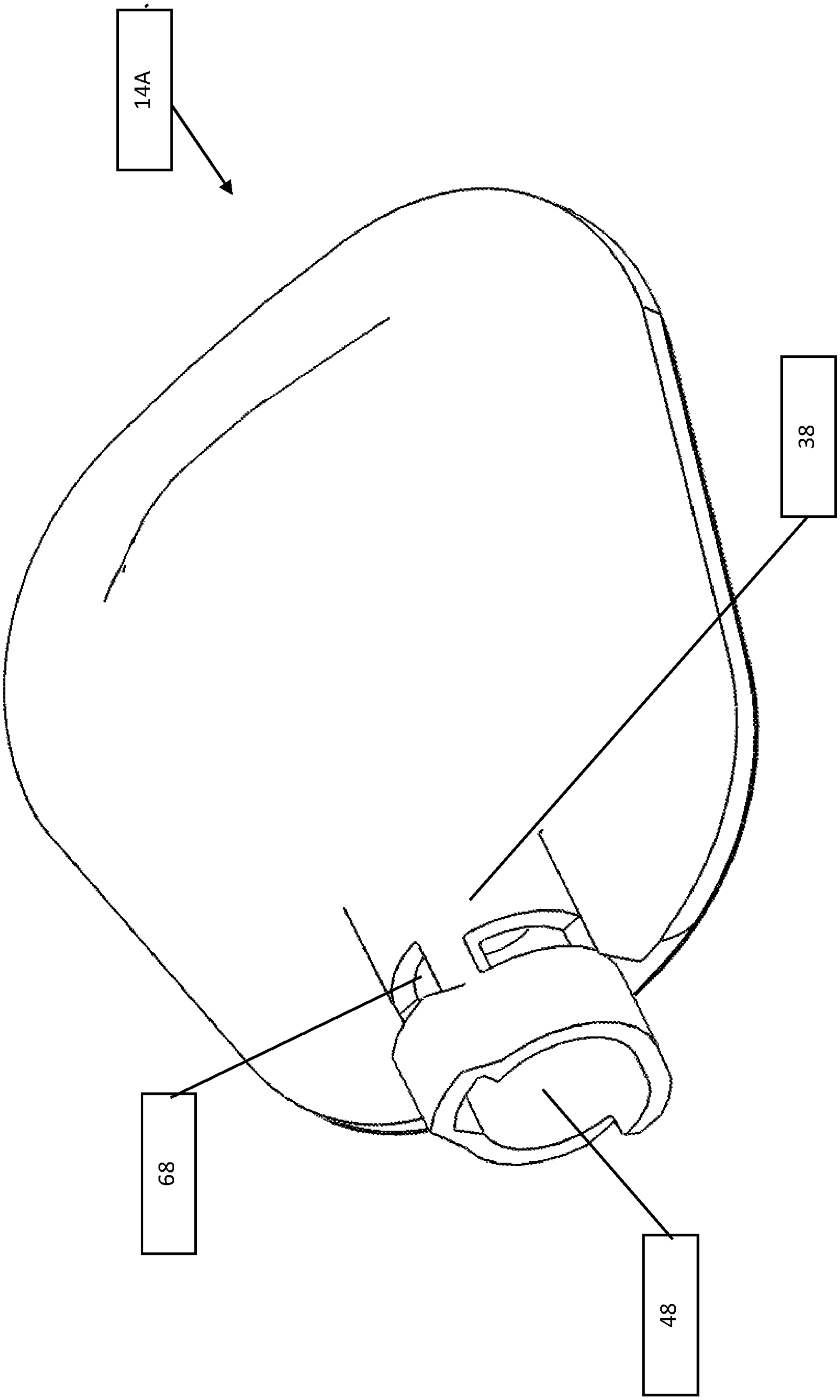
FIG. 15 is an isometric view of a reservoir section useable for radial sealing in accordance with the subject invention.
Figure 24:
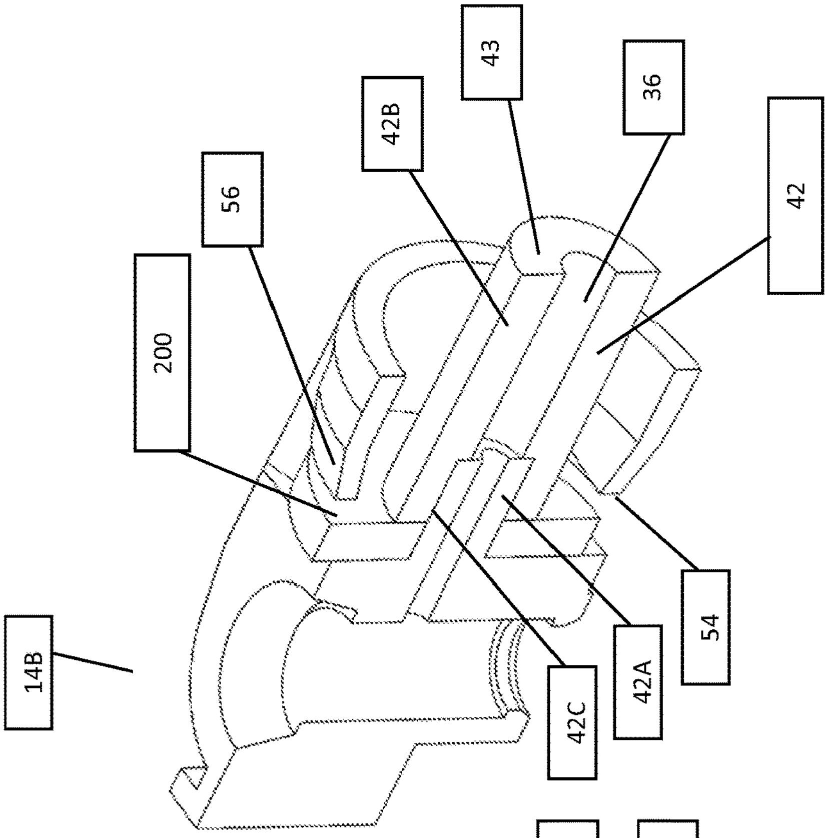
FIG. 24 shows a section view of the plug adapter of FIG. 23, with a seal in place.
Figure 23:
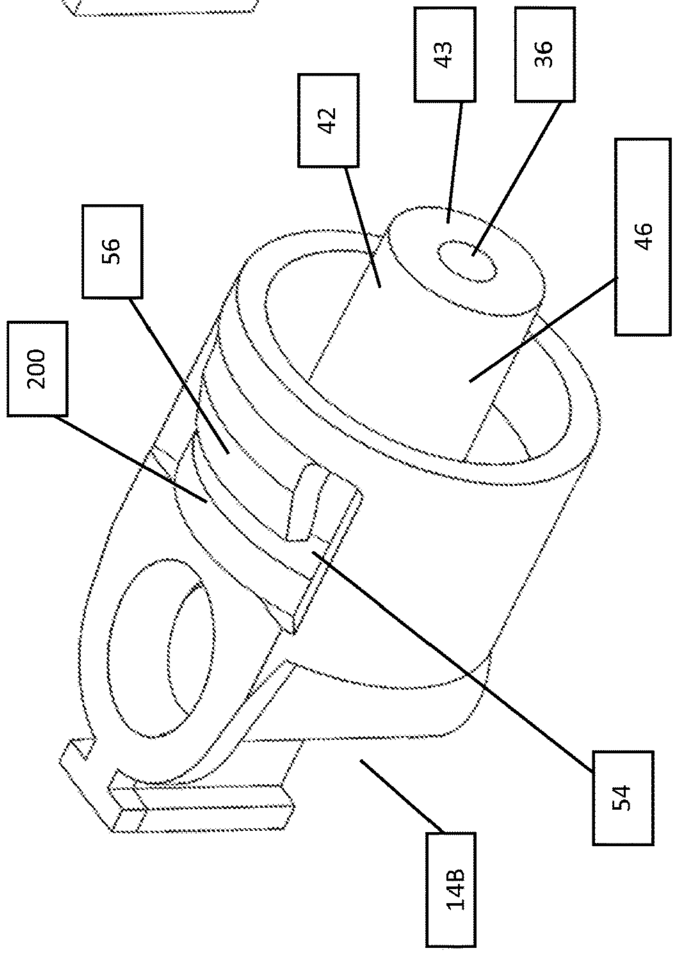
FIG. 23 shows a plug adapter useable with the subject invention which utilizes a face seal and inwardly directed detents.
Figure 25:
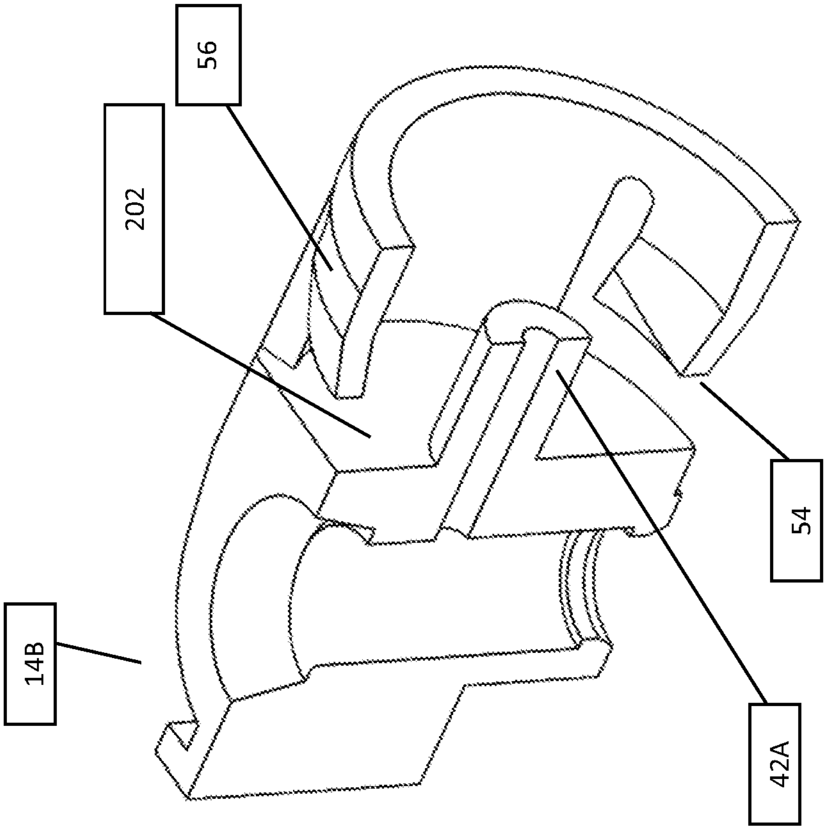
FIG. 25 shows a section view of the plug adapter of FIG. 23, without a seal in place.
Figure 27:
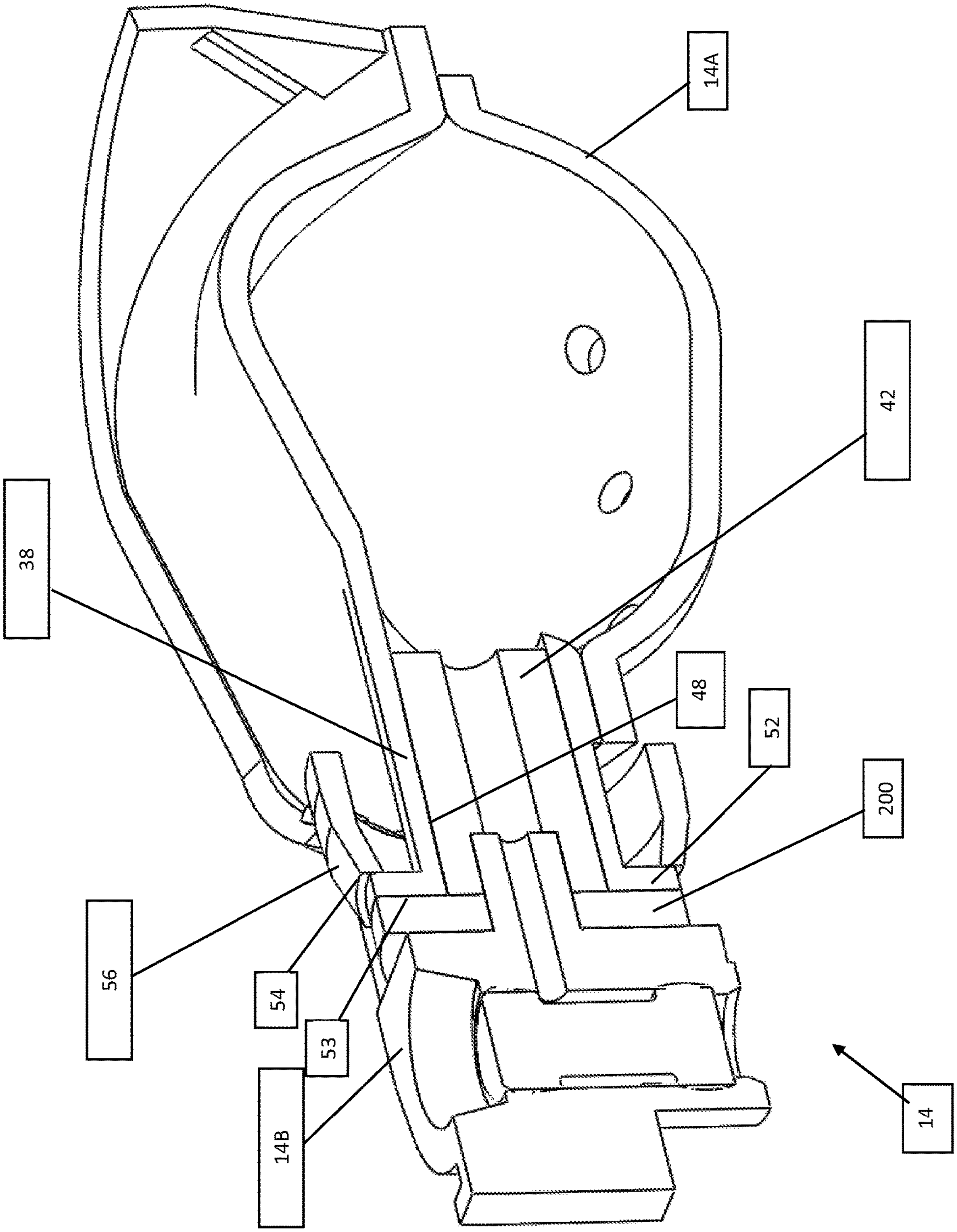
FIG. 27 is a section view of a drug cartridge that utilizes the face seal reservoir of FIG. 26 and the plug adapter of FIG. 23.
Figure 28:
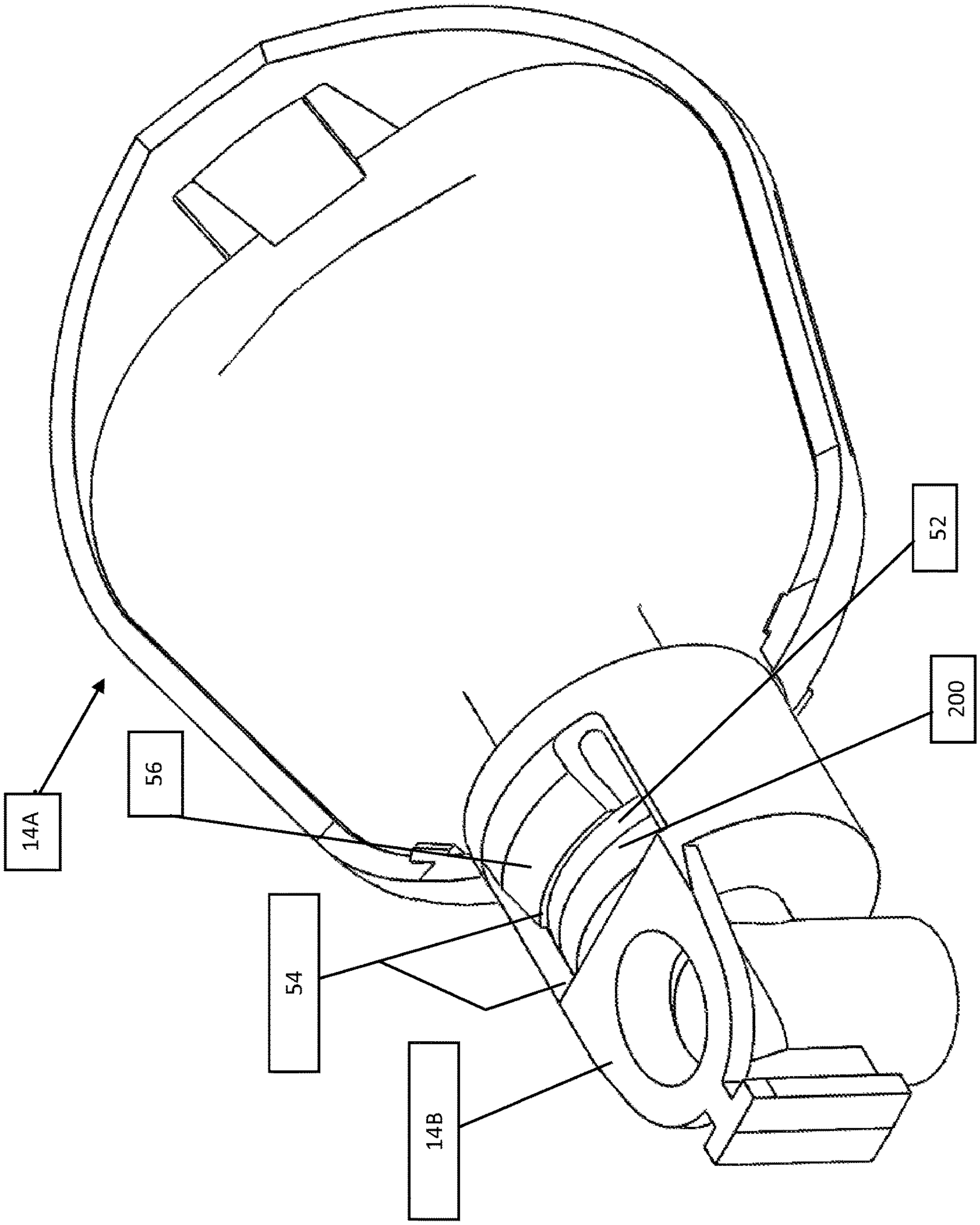
FIG. 28 is an isometric view of the drug cartridge of FIG. 27.

The plug adapter 14B may be formed to assemble with the reservoir section 14A in forming the drug cartridge 14 in various manners. As shown in FIGS. 13 and 14, a portion of the internal lumen 36 may be defined in an elongated neck 42, defined in the plug adapter 14B, which terminates at neck end 43. The neck 42 is formed to be telescopingly received in the filling port 38. One or more seals 44 may be provided between an external surface 46 of the neck 42 and an internal surface 48 of the fluid port 38. The seals 44 (e.g., O-rings) are preferably secured to the external surface 46, e.g., by being seated in sealing channels 50. Alternatively, as shown in FIGS. 23-25, the external surface 46 of the neck 42 may be formed smooth, optionally tapered, e.g., convergently towards neck end 43. As shown in FIG. 27, this allows the neck 42 to create a face seal with the internal surface 48 of the fluid port 38 through tight face-to-face interengagement therebetween.

Figure 26:
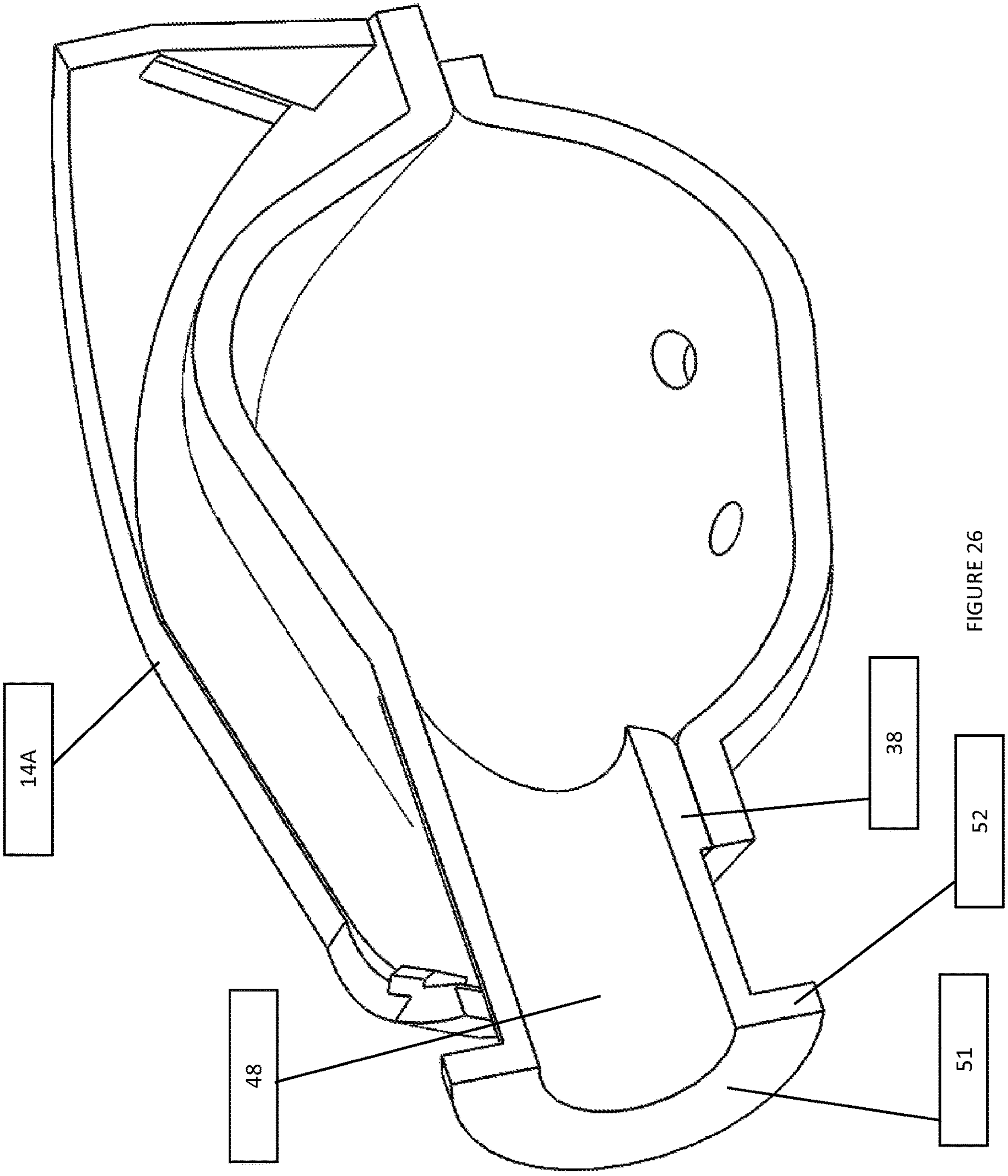
FIG. 26 shows a reservoir that may be assembled to the face seal plug adapter of FIG. 23.
Figure 29:
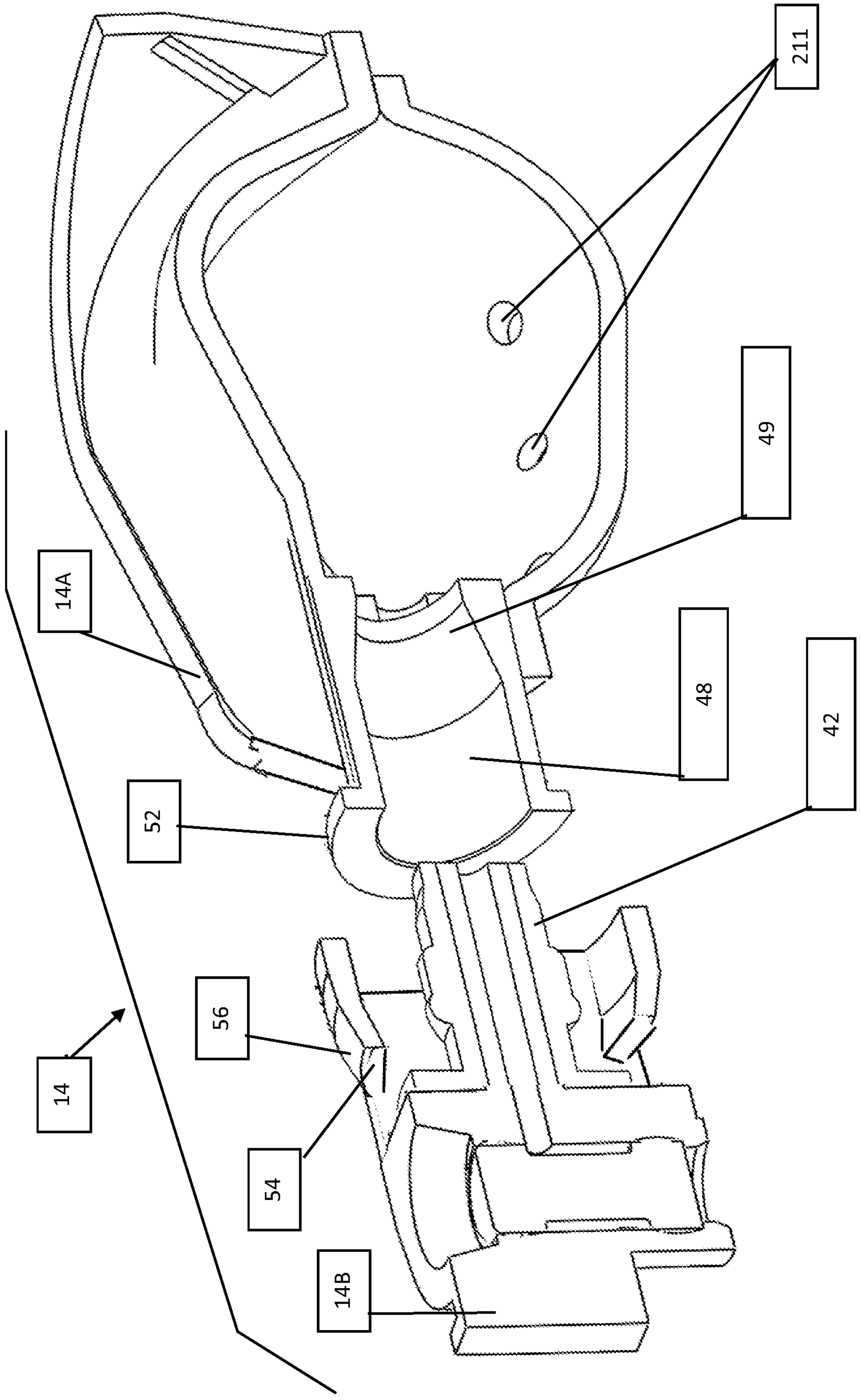
FIG. 29 is a section view of a drug cartridge that utilizes the face seal reservoir and plug adapter, with the plug adapter having venting passageways along the neck, and the reservoir having a tapered neck.
Figure 30:
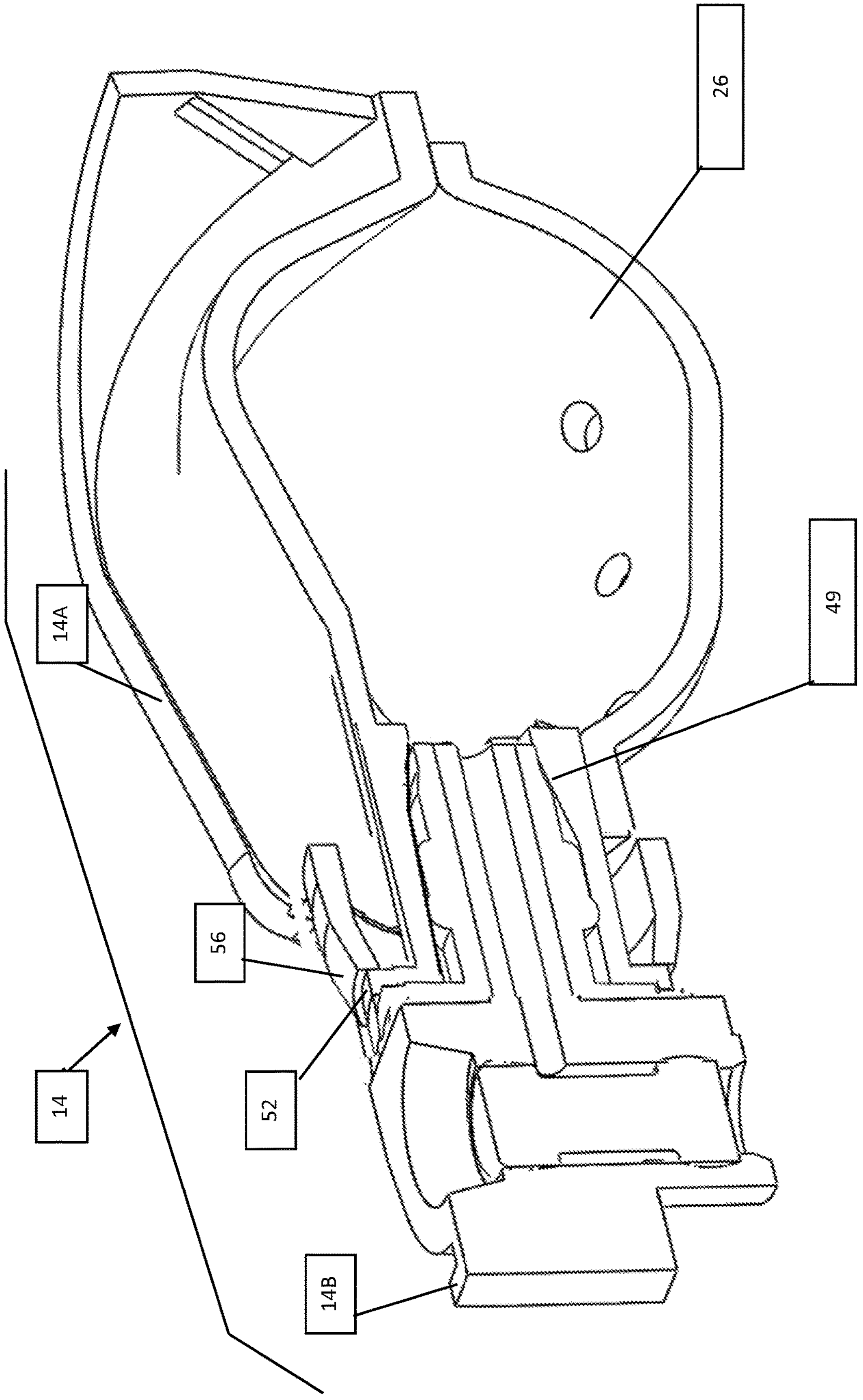
FIG. 30 is a section view of the drug cartridge of FIG. 29 in the sealed position.

Cooperating locking members may be provided between the reservoir section 14A and the plug adapter 14B to allow for locking therebetween upon assembly. As shown in FIG. 26, the filling port 38 may terminate at a locking rib 52 formed to snap engage a locking channel 54 formed in the plug adapter 14B, as shown in FIGS. 29 and 30. An inwardly directed detent 56 may be provided along the locking channel 54 to limit reverse movement of the filling port 38 away from the plug adapter 14B.

To enhance the integrity of the connection, as shown in FIGS. 23-28, a flexible seal 200 may be disposed in the locking channel 54 to pressingly engage the locking rib 52 with the plug adapter 14B being mounted to the reservoir section 14A. The locking rib 52 may be flange-shaped. Preferably, there is face-to-face engagement between an outer surface 51 of the locking rib 52 and the flexible seal 200.

It is preferred that the flexible seal 200 be formed of a resilient material suitable for sealing, such as an elastomeric material, a foam, a thermoplastic, a metal, and so forth. With the plug adapter 14B being formed from a thermoplastic material, the flexible seal 200 must be assembled to achieve two-material construction. To facilitate assembly, the neck 42 may be formed as a two-piece component with a base stem 42A to which is mounted sleeve 42B. Portions of the internal lumen 36 passes through both the base stem 42A and the sleeve 42B. The seal 200 may be annular shaped to be inserted into the locking channel 54, circumscribing the base stem 42A, and placed against external face 202. The sleeve 42B may then be mounted to the base stem 42A so as to overlap an inner portion of the seal 200. The sleeve 42B may be provided with a mounting channel 42C formed to telescopingly receive the base stem 42A. The sleeve 42B may be fixed to the base stem 42A using any known technique, including, but not limited to, adhesion, fusion, friction fit, interference fit, shrink fit, and so forth.

As shown in FIGS. 82A-84B, the sleeve 42B may be tapered along with the filling port 38 to provide a shape-mating fit therebetween. In addition, or alternatively, the base stem 42A and the sleeve 42B may be varied to define a portion of the internal lumen 36, particularly the first lumen portion 36A. As shown in FIGS. 86-89, the sleeve 42B may be formed to overlap an end of the base stem 42A, with the base stem 42A partially encircling the first lumen portion 36A. This allows for at least one change in direction to be defined in the internal lumen 36, particularly adjacent to the reservoir 26. Advantageously, one or more changes leading into the reservoir 26 limits the momentum of any liquid being introduced into the reservoir for reconstitution, as discussed below, thereby minimizing foaming and splashing. In particular, a third lumen portion 36C may be defined transverse to the first lumen portion 36A, defining a change in direction in the internal lumen 36. In addition, a fourth lumen portion 36D may be defined communicating the third lumen portion 36C and the reservoir 26, transversely disposed to the third lumen portion 36C, to provide a secondary change in direction in the internal lumen 36.

Figure 18:
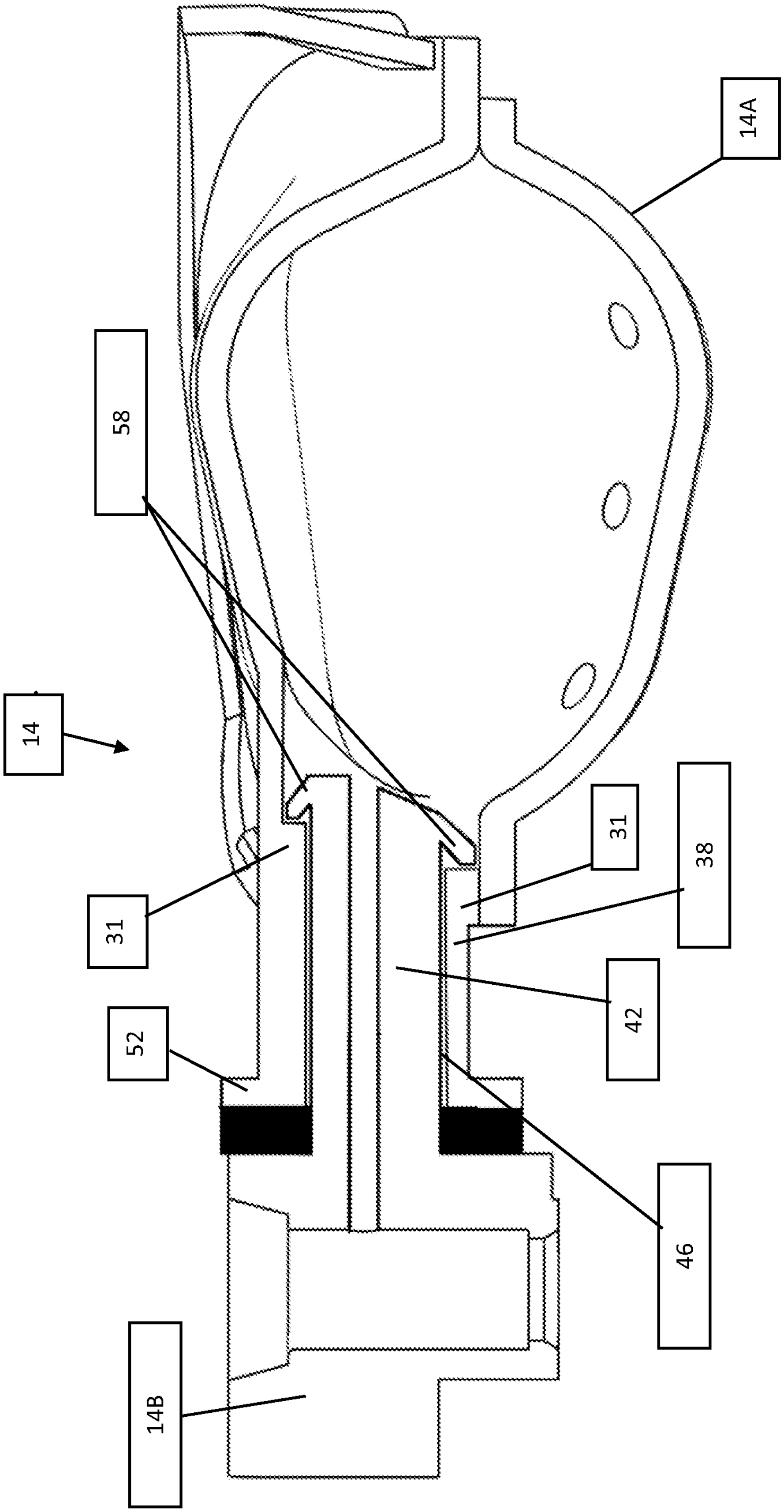
FIG. 18 is a section view of a drug cartridge, illustrating a face seal with internal retention features, in accordance with the subject invention.

Alternatively, as shown in FIG. 18, the locking rib 52 may be formed to extend radially inwardly of the filling port 38 with a locking collar 58 extending outwardly from the external surface 46 of the neck 42 formed to snap engage against inward shoulders defined by inward portions 31 of the locking rib 52. This arrangement likewise resists separation of the filling port 38 from the plug adapter 14B.

Further, as shown in FIGS. 13-16, a locking ring 64 may be provided about the neck 42 having locking tab 66 formed to snap engage a locking opening 68 formed in the reservoir section 14A. Seals may be provided as needed. Also, the external face 202 of the plug adapter 14B may act as a stop to define proper positioning between the reservoir component 14A and the plug adapter 14B. As will be appreciated by those skilled in the art, other locking arrangements may be utilized.

In addition, or alternatively, a ferrule 63 may be used to maintain the plug adapter 14B mounted to the reservoir section 14A, as shown in FIGS. 82-89B. The sleeve 42B may be provided with a locking flange 33, and the plug adapter 14B may include a stop flange 201, on which the external face 202 is located. The ferrule 63 may be formed of material capable of being crimped, including a metal or polymer sufficient malleable to be crimped (with or without heat or other external factors). As shown in FIGS. 82A-83B and 87A-88B, the ferrule 63 may initially be provided as a blank having a tubular body with sufficient diameter, and length, to encompass, the stop flange 201, the locking flange 33, and the locking rib 52. As shown in FIGS. 84A-86 and 89A-89B, with crimping, the ferrule 63 is conformed to tightly engage the stop flange 201, the locking flange 33, and the locking rib 52, with the stop flange 201 and the locking rib 52 pressing inwardly against the locking flange 33, to create a mechanical lock therebetween. Preferably, the ferrule 63 is formed with sufficient length to be bent to cover face portions of the stop flange 201 and the locking rib 52. As will be appreciated by those skilled in the art, the ferrule 63 may be formed as a sleeve, which is heat-shrinkable or weldable or adherable, to tightly conform to the stop flange 201, the locking flange 33, and the locking rib 52. The ferrule 63 should have sufficient stability, once affixed, to avoid creep, to avoid unwanted loosening.

As shown in FIGS. 32A-32E, as a further alternative, the plug adapter 14B may be latched to the reservoir section 14A to form a connection therebetween. Here, the locking rib 52 may be configured as a flange about the internal surface 48 of the filling port 38. Upstanding walls 57 may be provided on opposing sides of the outer surface 51 of the locking rib 52 to provide a yoke shape. Locking recesses 54A may be formed in the upstanding walls 57 formed to snap fittingly receive locking detents 52A defined on opposing surfaces of the plug adapter 14B. The upstanding walls 57 should be provided with some flexibility to allow outward deflection in permitting the locking detents 52A to be inserted into the locking recesses 54A. To enhance the integrity of the seal between the plug adapter 14B and the reservoir section 14A, the flexible seal 200 may be provided in the form of a gasket configured to rest on the outer surface 51 with a central opening providing access therethrough to the interior of the filling port 38.

It is noted that the interengagement between the locking detents 52A and the locking recesses 54A may be used to assemble the plug adapter 14B and the reservoir section 14A together with subsequent joining of elements, for example, having portions of the upstanding walls 57 joined to the plug adapter 14B using one or more of adhesion, fusion, and welding. In addition, or alternatively, the locking detents 52A may be joined to the locking recesses 54A using one or more of the aforementioned techniques.

Figure 32A:
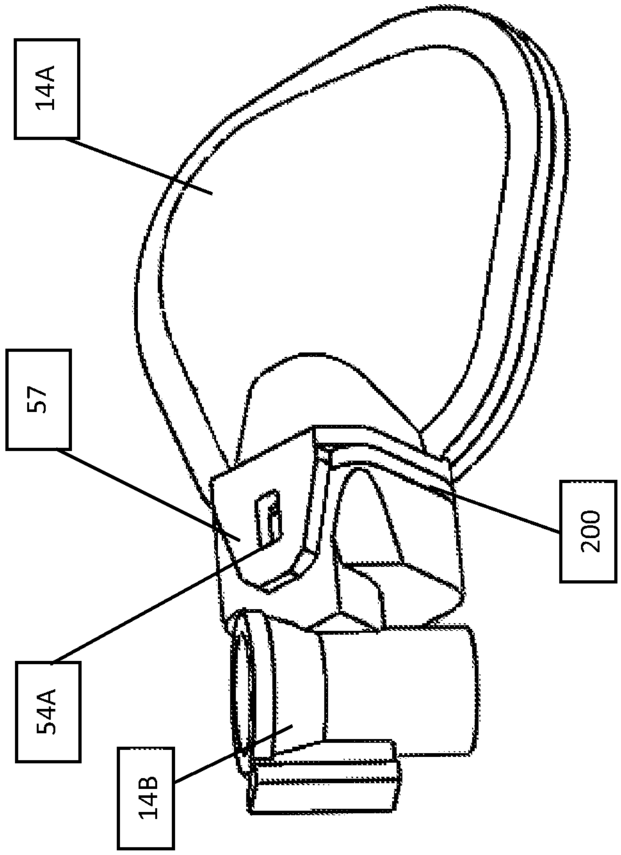
FIG. 32A is an isometric view of a drug cartridge that utilizes a latching arrangement between the plug adapter and the reservoir section.
Figure 32B:
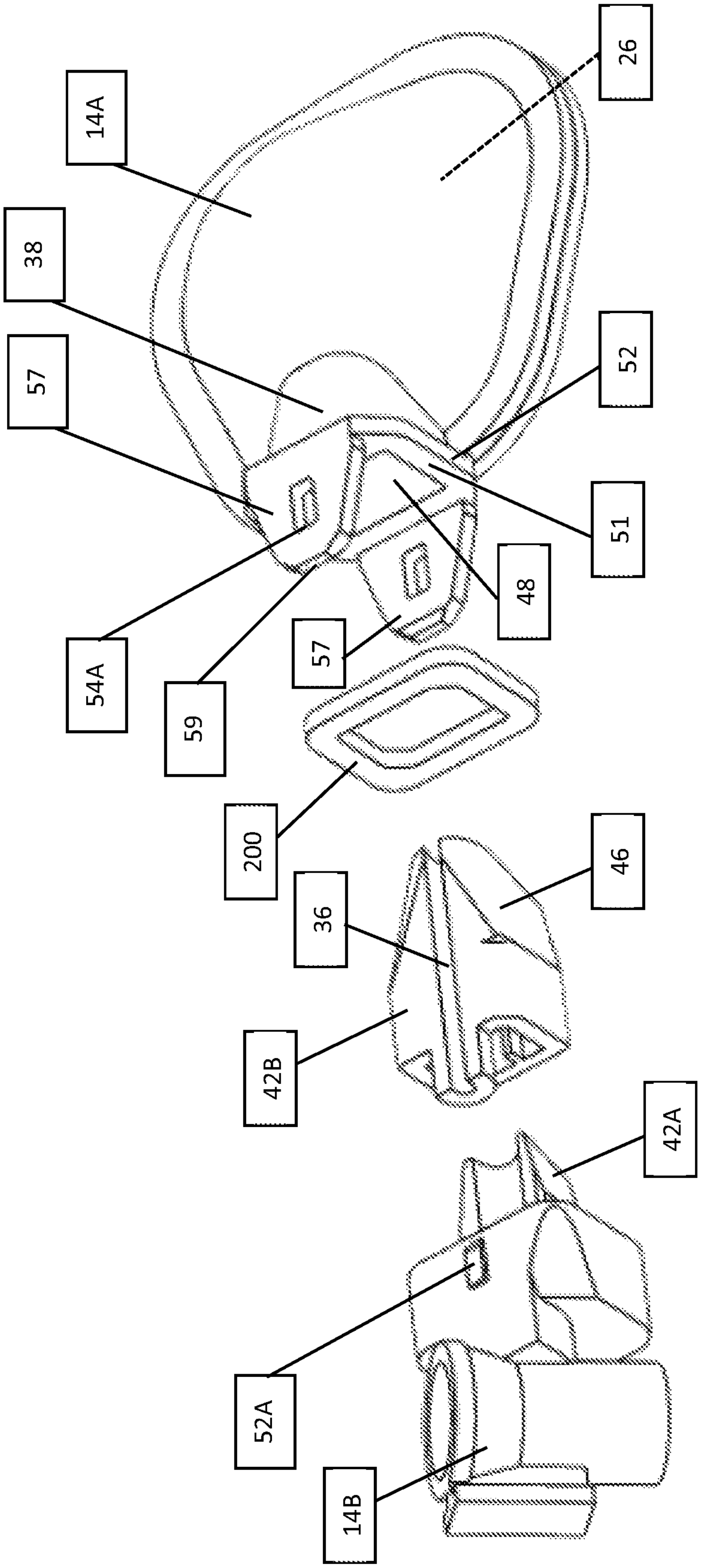
FIG. 32B is an exploded isometric view of the drug cartridge of FIG. 32A.
Figure 32C:
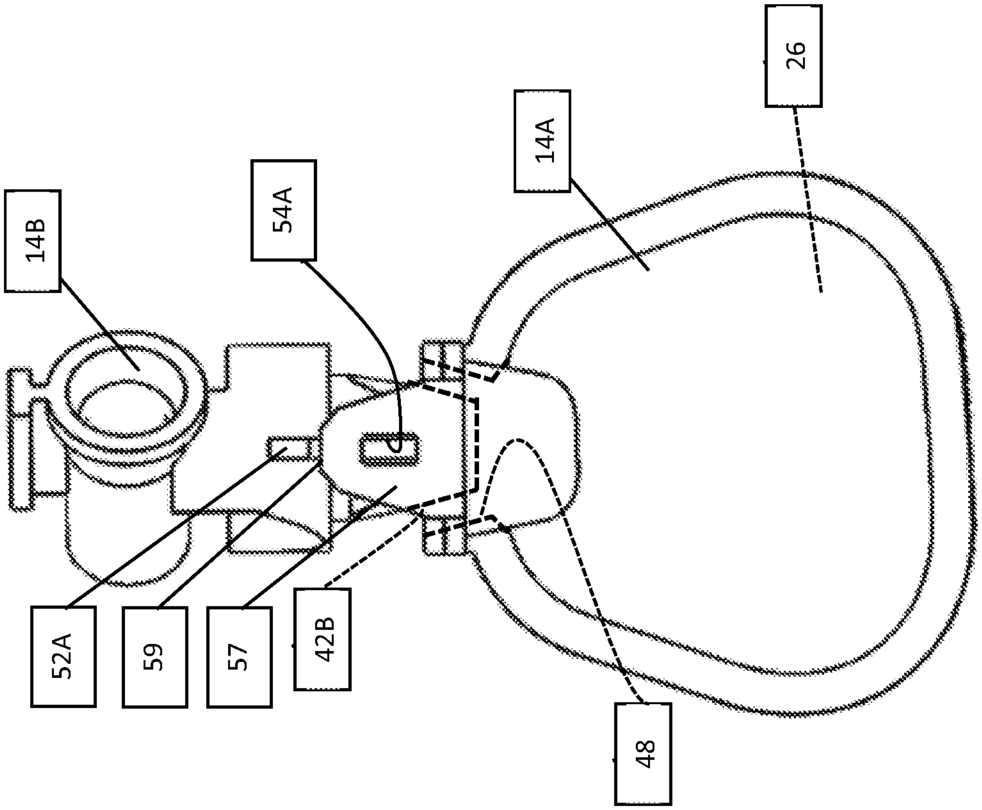
FIG. 32C shows the plug adapter of FIG. 32A in the vented position.
Figure 32D:
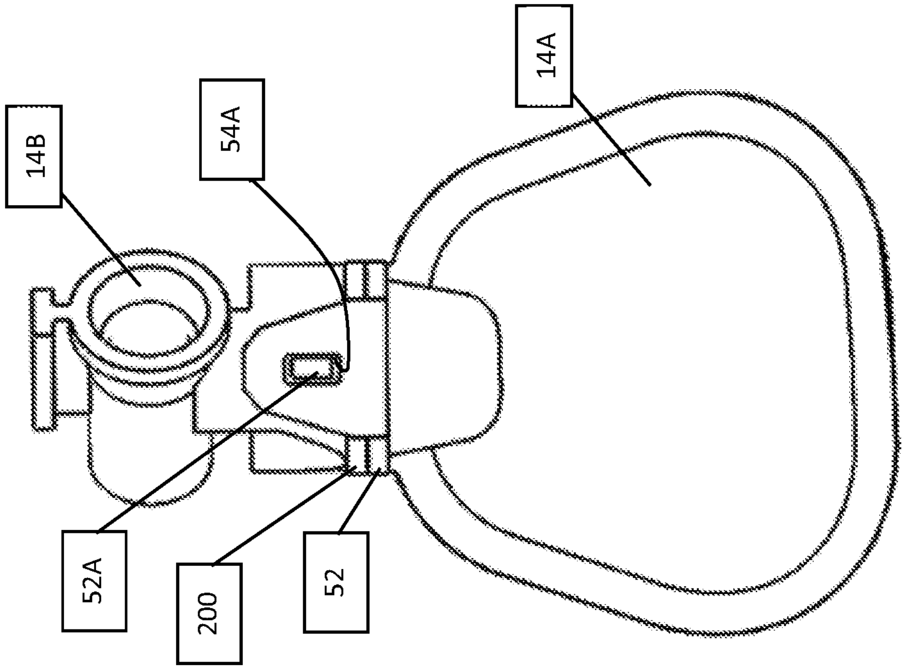
FIG. 32D is shows the plug adapter of FIG. 32A in the sealed position.
Figure 32E:
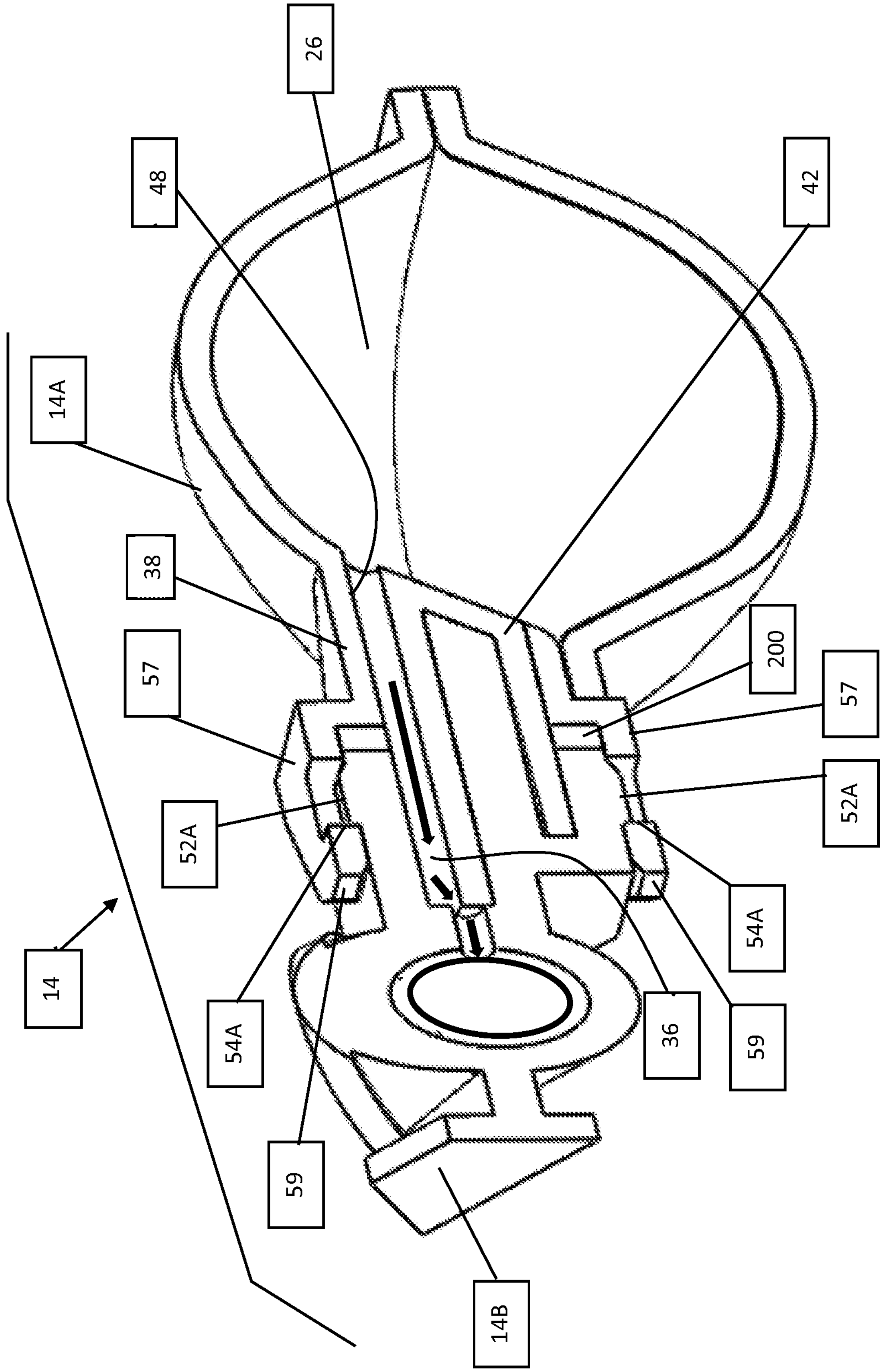
FIG. 32E is a section view of the drug cartridge of FIG. 32D with the plug adapter in the sealed position.

As shown in FIG. 32B, the plug adapter 14B may be provided with a two-piece construction, as discussed above, with the sleeve 42B being mounted to the base stem 42A to form the neck. In addition, the sleeve 42B may have a polygonal profile with one or more faces being tapered. The filling port 38 may have a similarly formed cross-section, converging in a direction towards the reservoir 26 to provide a shape-mating fit with the sleeve 42B. With this configuration, as shown in FIG. 32C, the plug adapter 14B may be partially inserted into the filling port 38 to allow venting of the reservoir 26. To maintain plug adapter 14B in the venting state, leading edges 59 of the upstanding walls 57 may be located to act as a stop against the locking detents 52A. The leading edges 59 are located to space the sleeve 42B from the internal surface 48 of the filling port 38. As shown in FIG. 32D, with the locking detents 52A being urged past the leading edges 59 and into snap fitting engagement with the locking recesses 54A, the sleeve 42B is urged into sealing contact with the internal surface 48. FIG. 32E shows in cross-section the plug adapter 14 in the sealed state.

To configure the drug cartridge 14 with an adjustable vent, for example, for lyophilization as described above, as shown in FIGS. 20A-20C, at least one venting passageway 72 may be defined at the mouth 62 of the filling port 38. The venting passageways 72 may be defined as recessed channels in the internal surface 48 of the filling port 38 with one or more venting protrusions 60 separating the venting passageways 72. The venting protrusions 60 are preferably discontinuous about the inner periphery of the mouth 62. As shown in FIG. 20B, to allow for venting, the neck 42 is inserted into the filling port 38 to no further than the length of the venting protrusions 60 to maintain the one or more seals 44 above the ends of the venting passageways 72. This allows for an open vent state with the venting passageways 72 being in open communication with the reservoir 26. The vent may be adjusted to a closed state, as shown in FIG. 20C, with further insertion of the neck 42 into the filling port 38 so that the one or more seals 44 are located between the venting passageways 72 and the reservoir 26 to close off communication therebetween.

Figure 16:
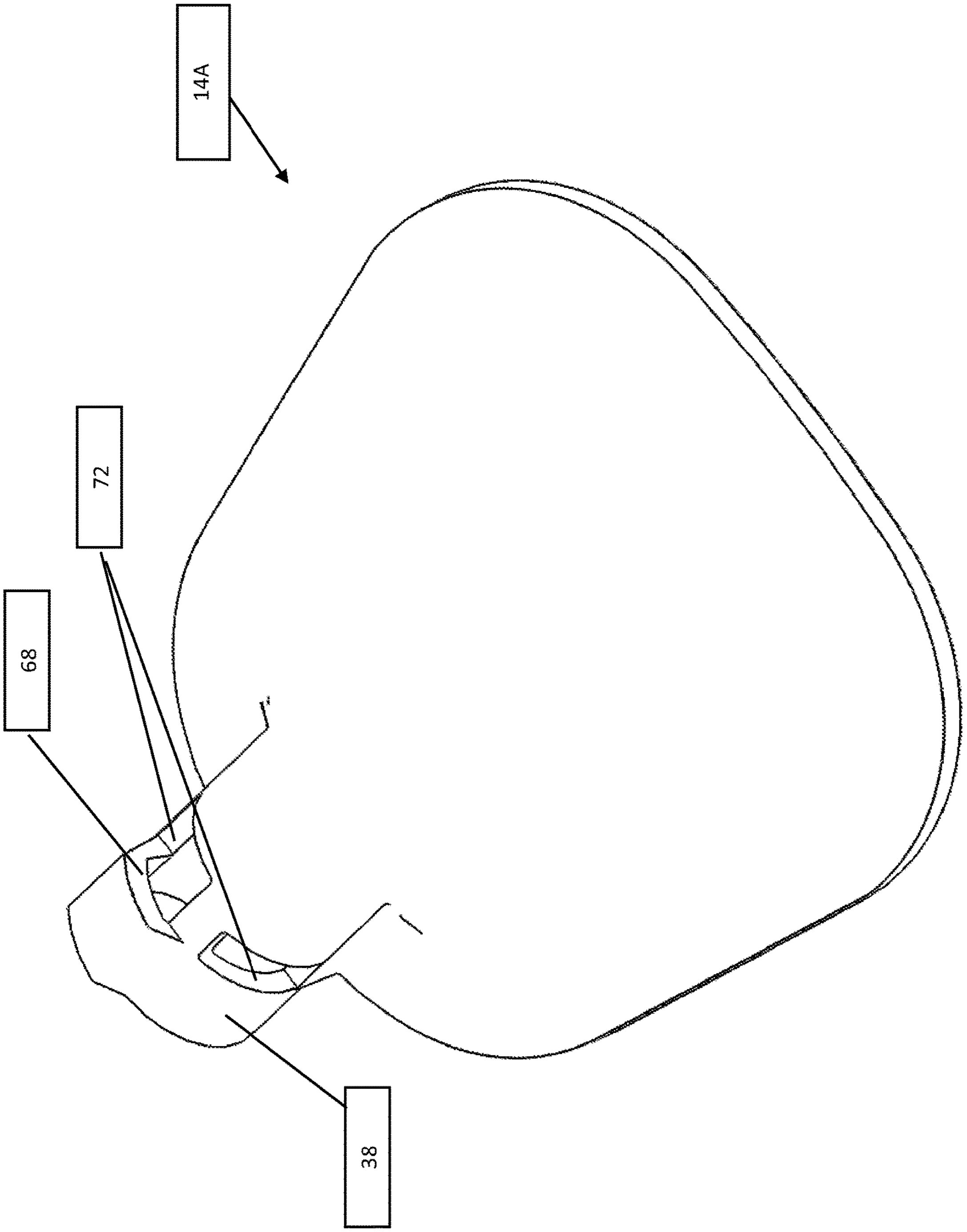
FIG. 16 is an alternate view of the reservoir section of FIG. 15 to illustrate retaining features for a radially sealed closure.
Figures 17A, 17B, 17C:
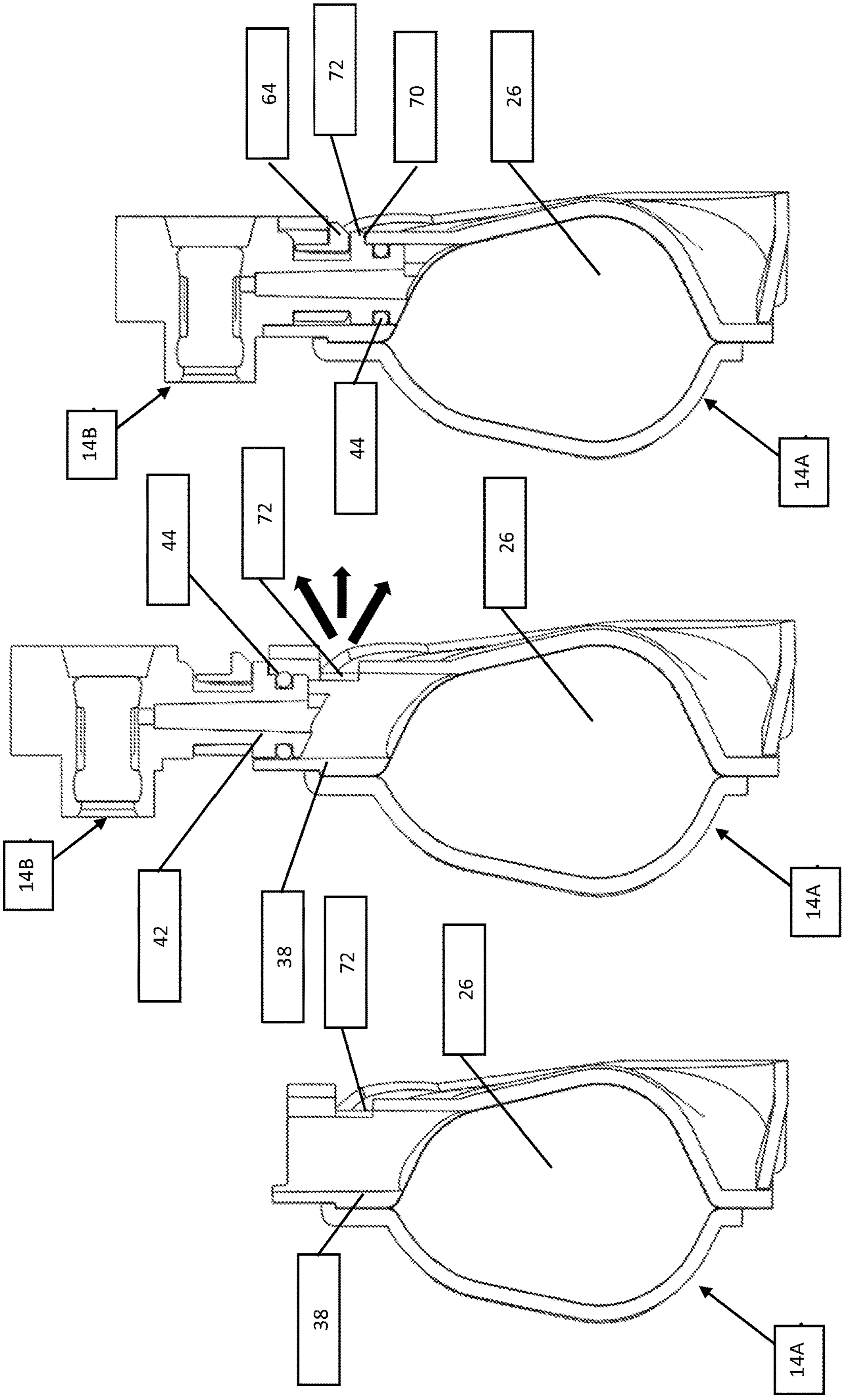
FIG. 17A shows a reservoir section, oriented for filling, in accordance with the subject invention.
FIG. 17B shows the reservoir section of FIG. 17A with a plug adapter in a vented position.
FIG. 17C shows the plug adapter fully seated with the reservoir section of FIG. 17A.
Figure 20C:
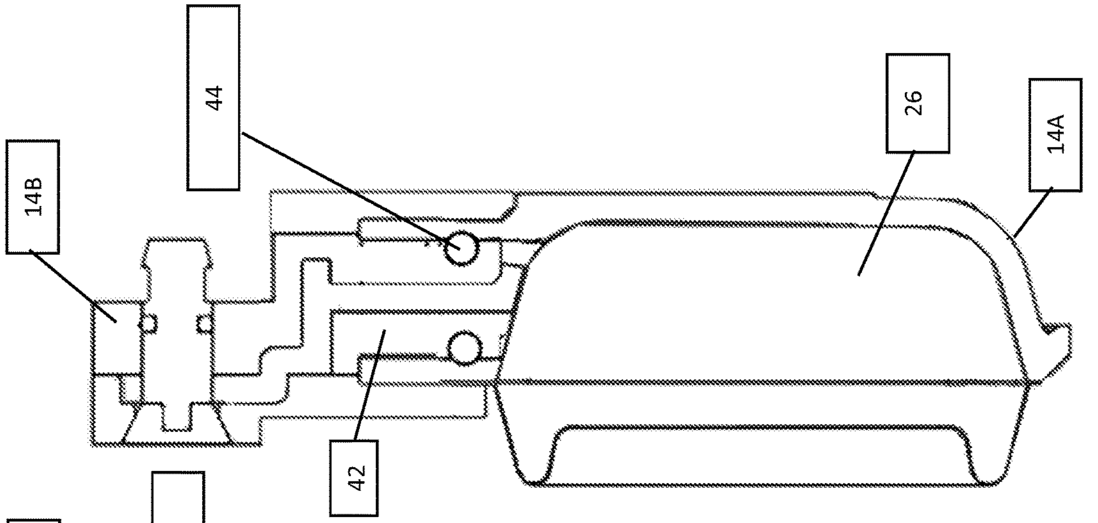
FIG. 20C shows the plug adapter fully seated with the reservoir section of FIG. 20A.
Figure 20B:
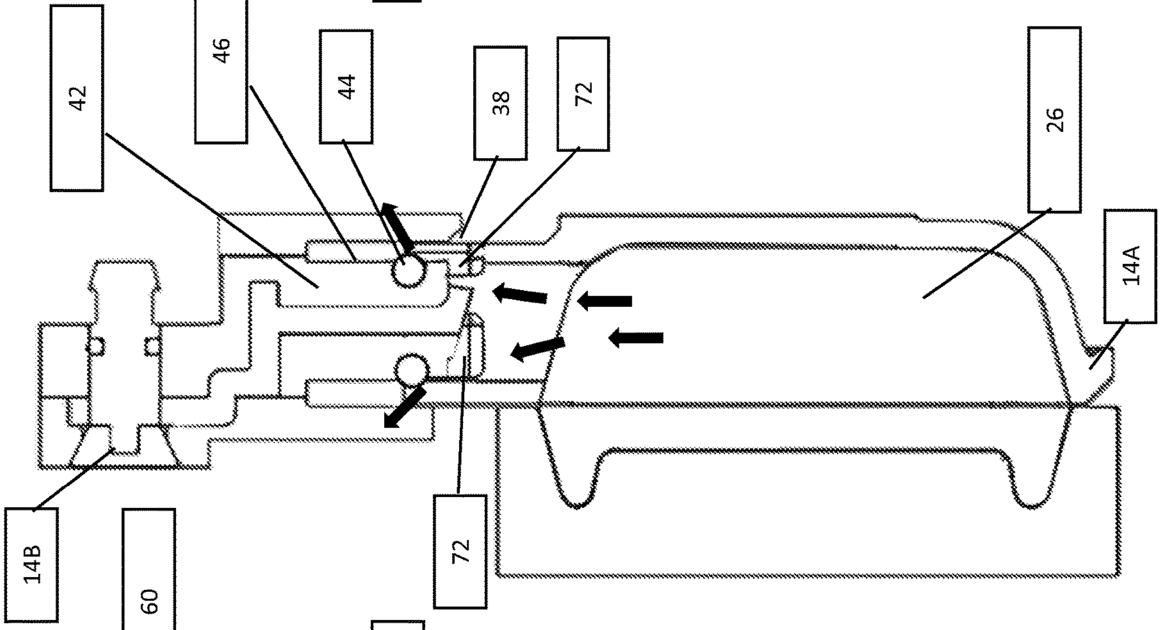
FIG. 20B shows the reservoir section of FIG. 20A with a plug adapter in a vented position.
Figure 20A:
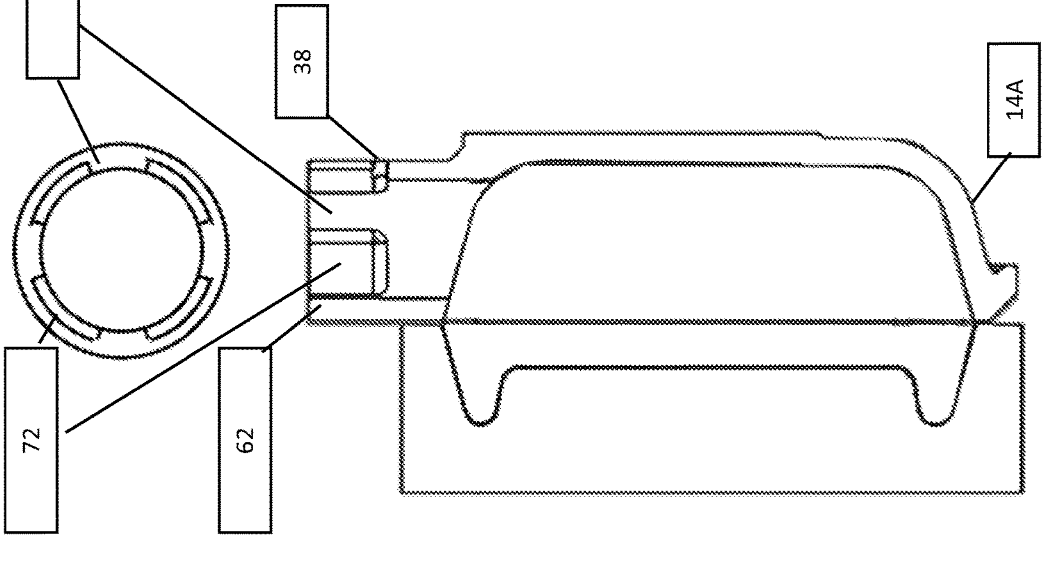
FIG. 20A shows an open reservoir section, oriented for filling, in accordance with the subject invention.

With the embodiment of FIGS. 20A-20C, vented gases by-pass portions of the plug adapter 14 to escape. Alternatively, as shown in FIG. 16, the venting passageways 72 may be formed as through-holes through the filling port 38. This provides unrestricted venting directly to external atmosphere. As shown in FIGS. 17A-17C, venting is achieved in the same manner as described above with the open vent state shown in FIG. 17B and the closed vent state shown in FIG. 17C, with the one or more seals 44 being adjusted in the same fashion.

Figure 31A:
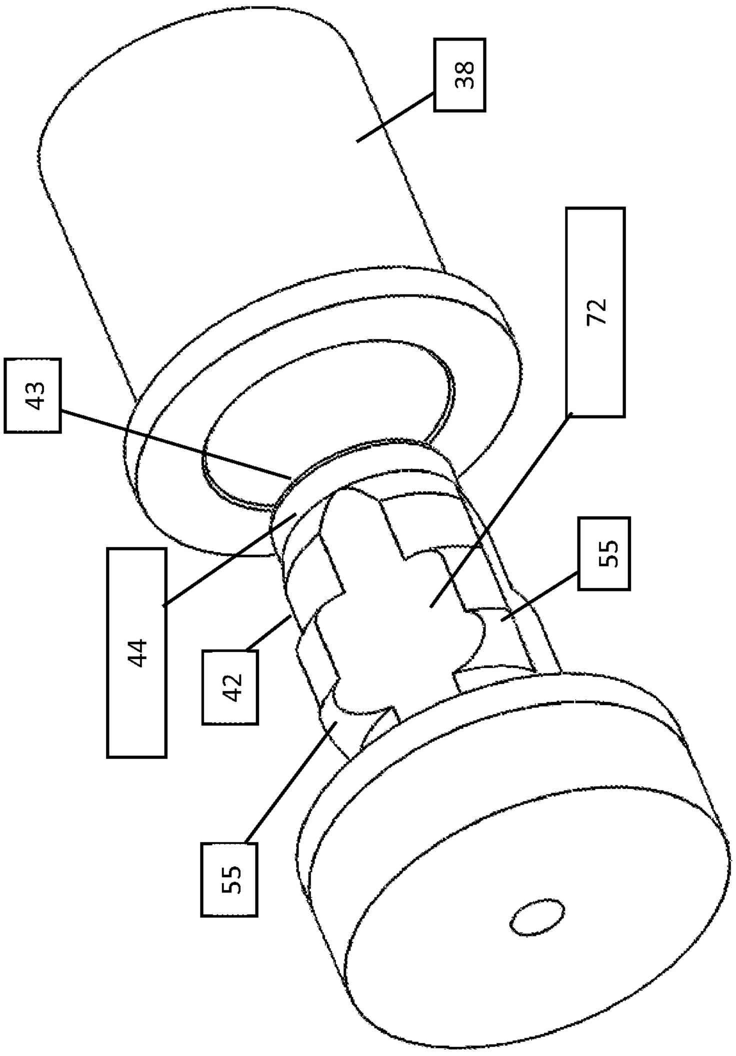
FIG. 31A is an isometric view of the sealing elements of the drug cartridge of FIG. 29.
Figure 31B:
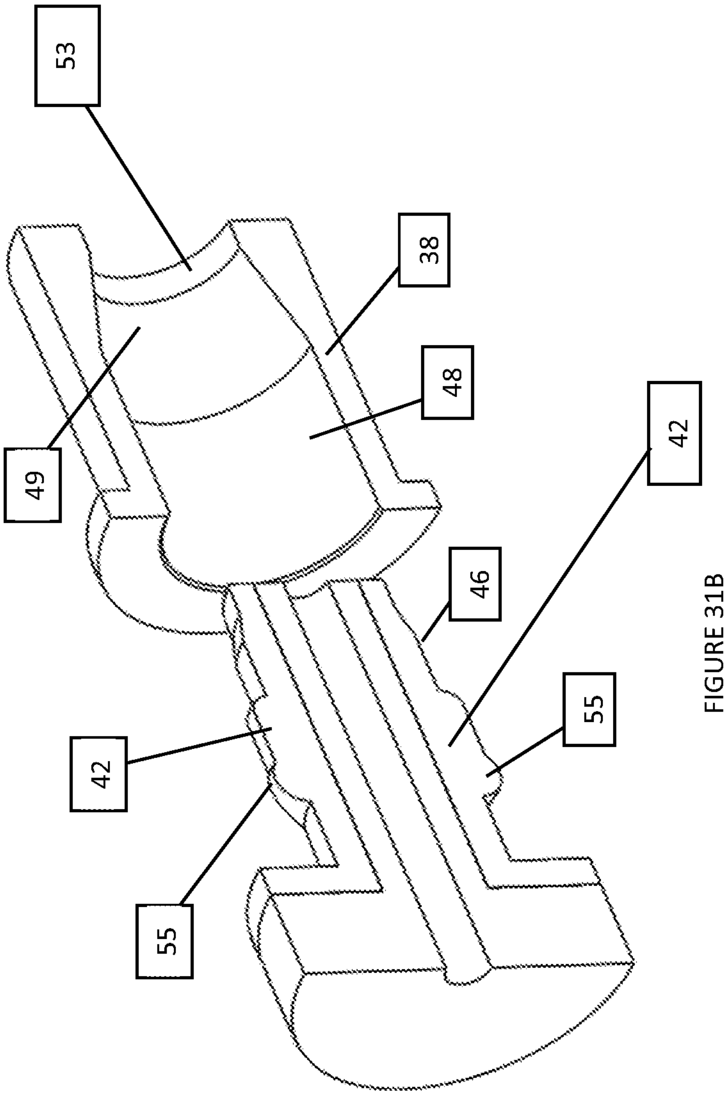
FIG. 31B is a section view of the sealing elements of FIG. 31A.
Figures 33A, 33B, 33C, 33D:
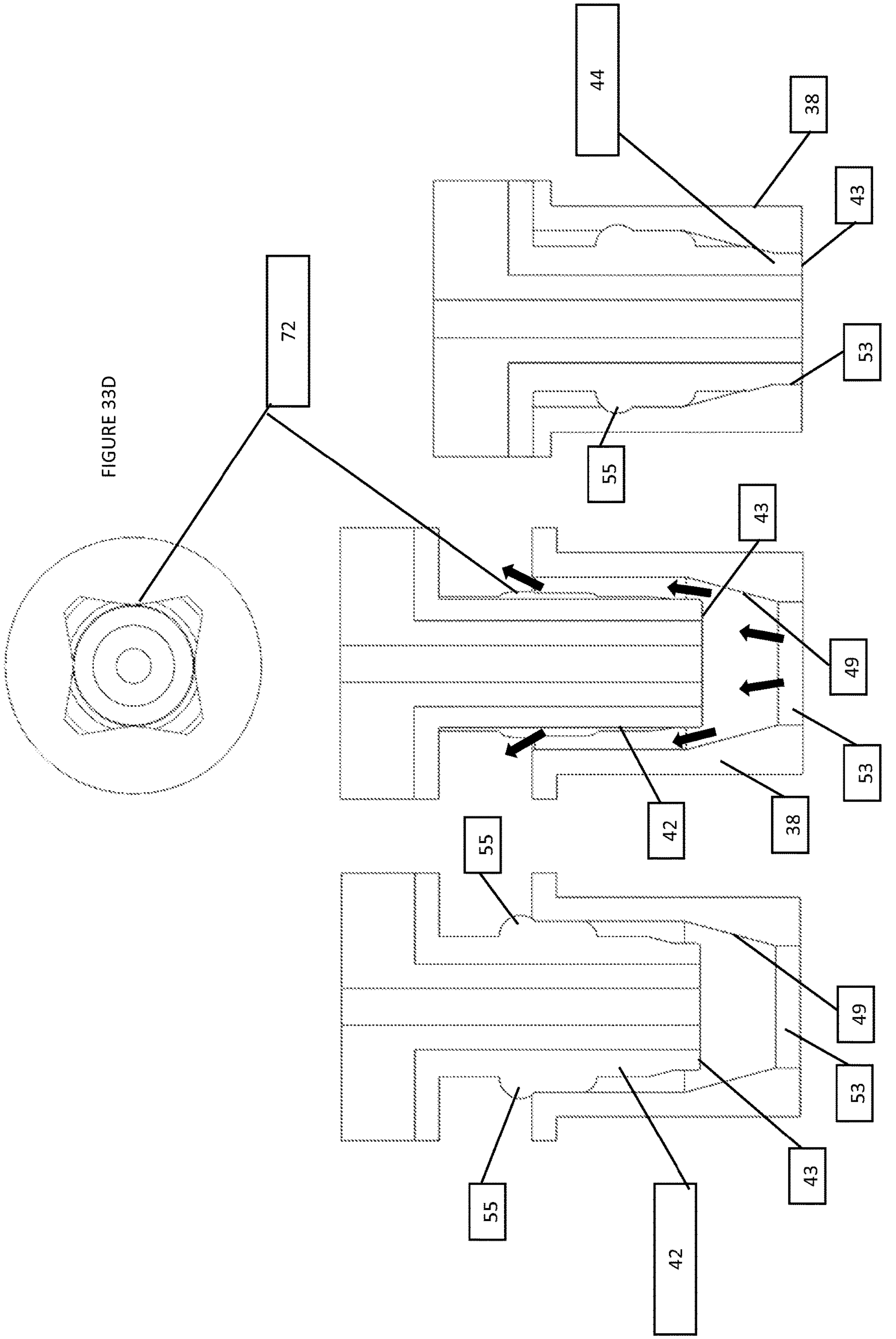
FIG. 33A shows the sealing elements of FIG. 31A in the vented position. The cut plane is positioned such that the protruding beads are visible.
FIG. 33B shows the sealing elements of FIG. 31A in the vented position for lyophilization.
FIG. 33C shows the sealing elements of FIG. 31A in the sealed position.

In addition, as shown in FIGS. 31A-31B, the internal surface 48 of the filling port 38 may include a tapered section 49, adjacent the reservoir 26, which is convergently tapered in a direction towards the reservoir 26 to define a reduced-diameter opening 53. A plurality of protruding beads 55 may be formed on the external surface 46 of the neck 42 with the venting passageways 72 being defined therebetween. The protruding beads 55 are configured to pressingly engage the filling port 38. The at least one seal 44 is located on the external surface 46 of the neck 42 between the protruding beads 55 and the neck end 43. As shown in FIGS. 33A-33B, to achieve the open vent state, the neck 42 is inserted into the filling port 38 with the neck end 43 being out of contact with the tapered section 49. As shown in FIG. 33C, further insertion of the neck 42 into the filling port 38 causes the vent to close with the neck end 43 being received in the opening 53 and with the at least one of the seals 44 coming into sealing engagement with the tapered section 49 of the internal surface 48 to close off communication between the venting passageways 72 and the reservoir 26.

Figure 180:
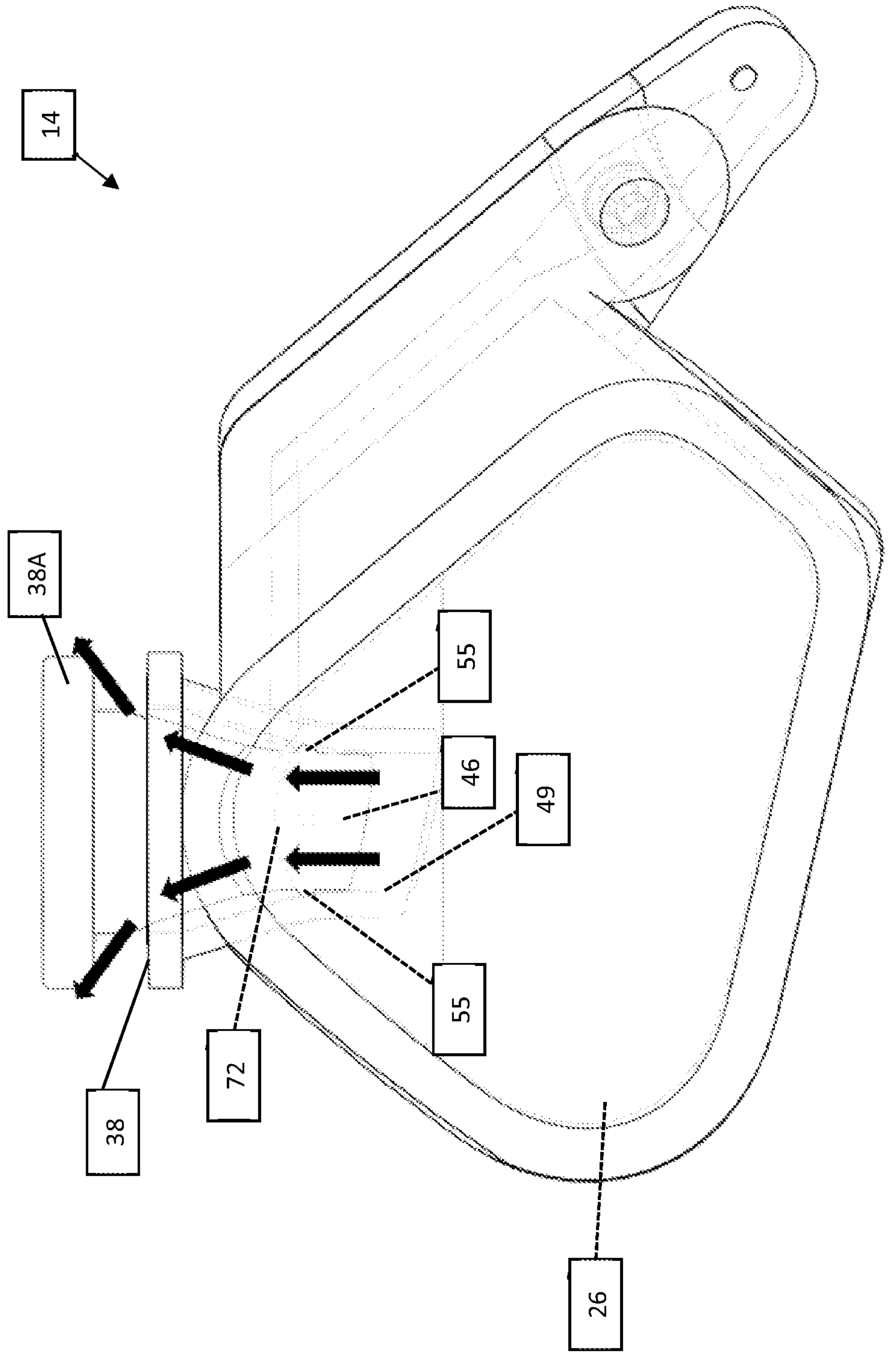
Figure 181:
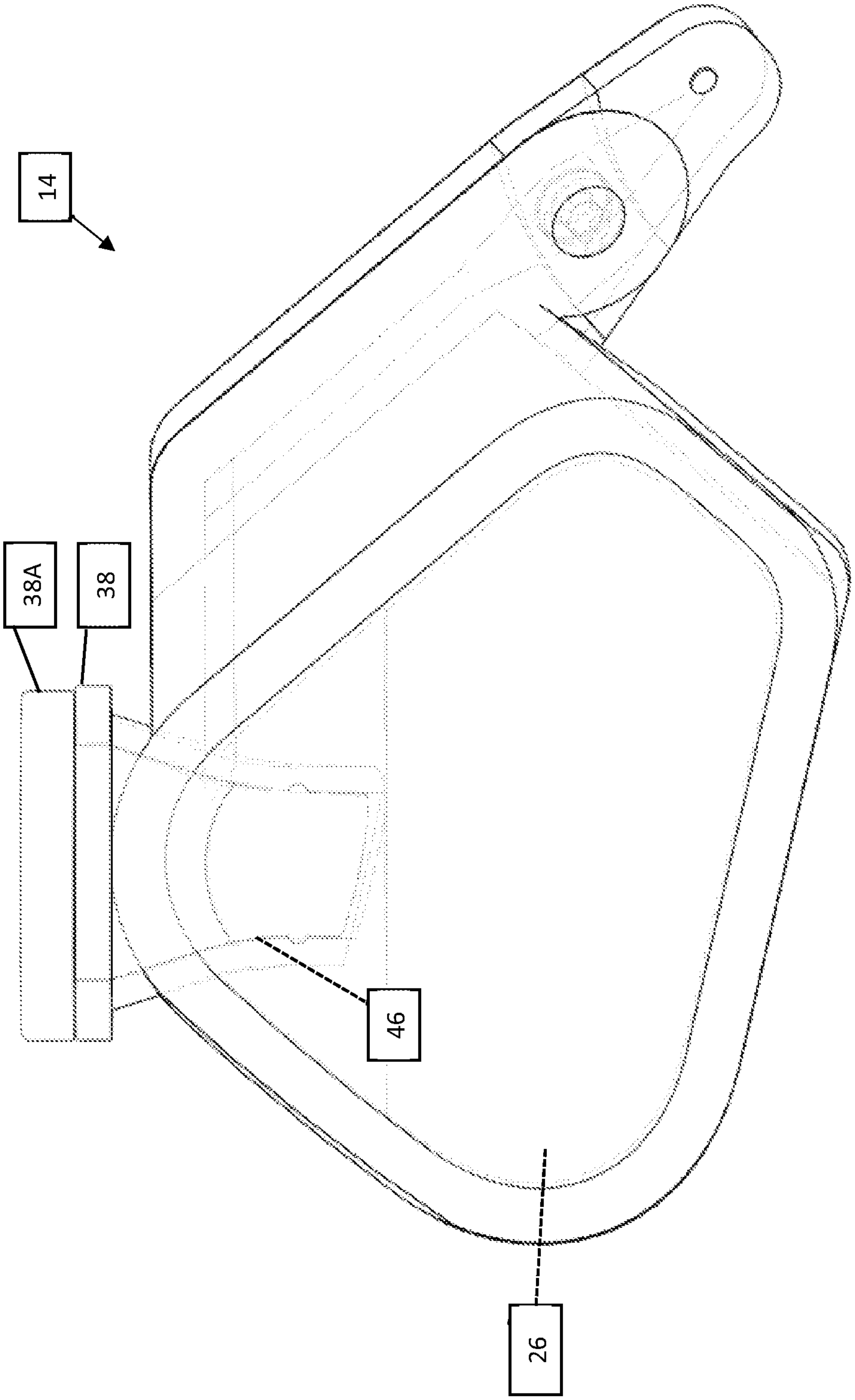
Figure 182:
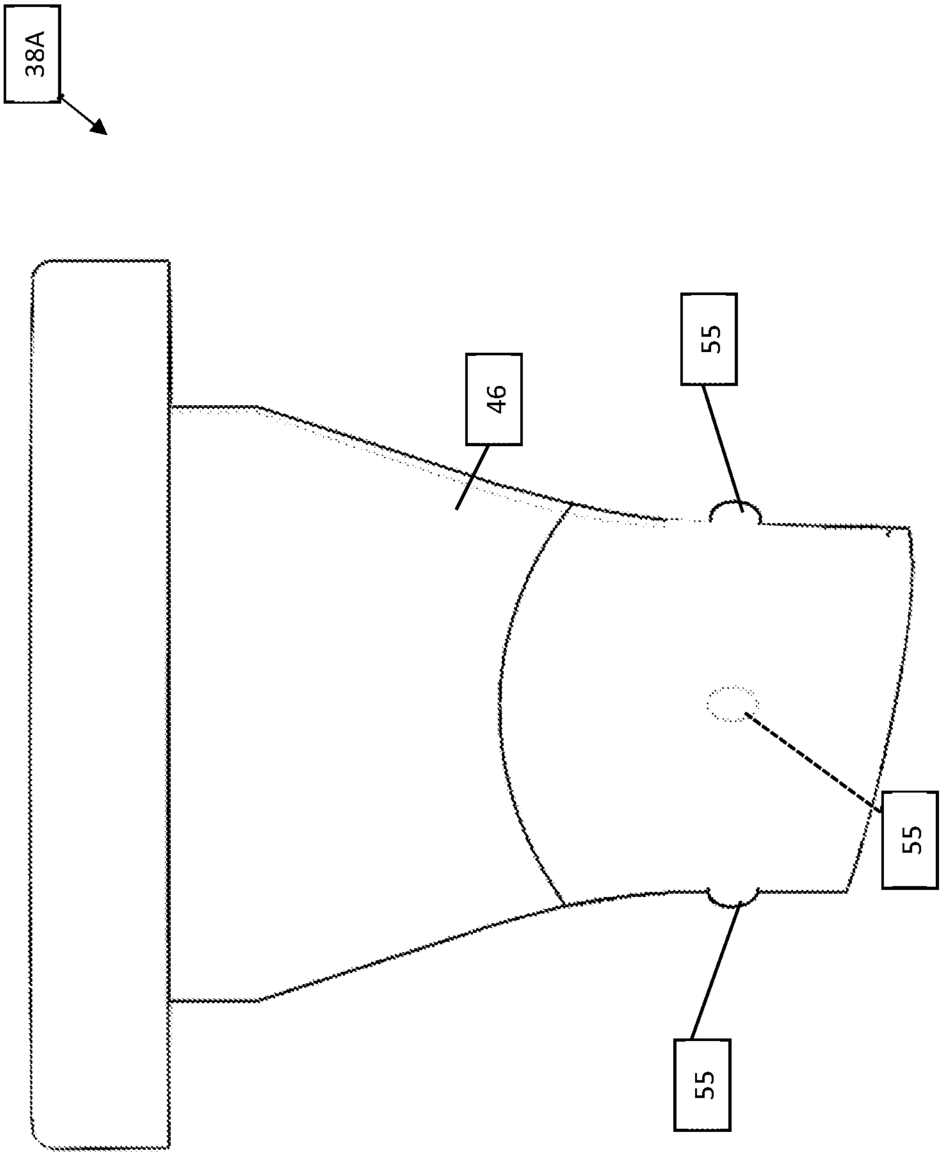
Figure 183:
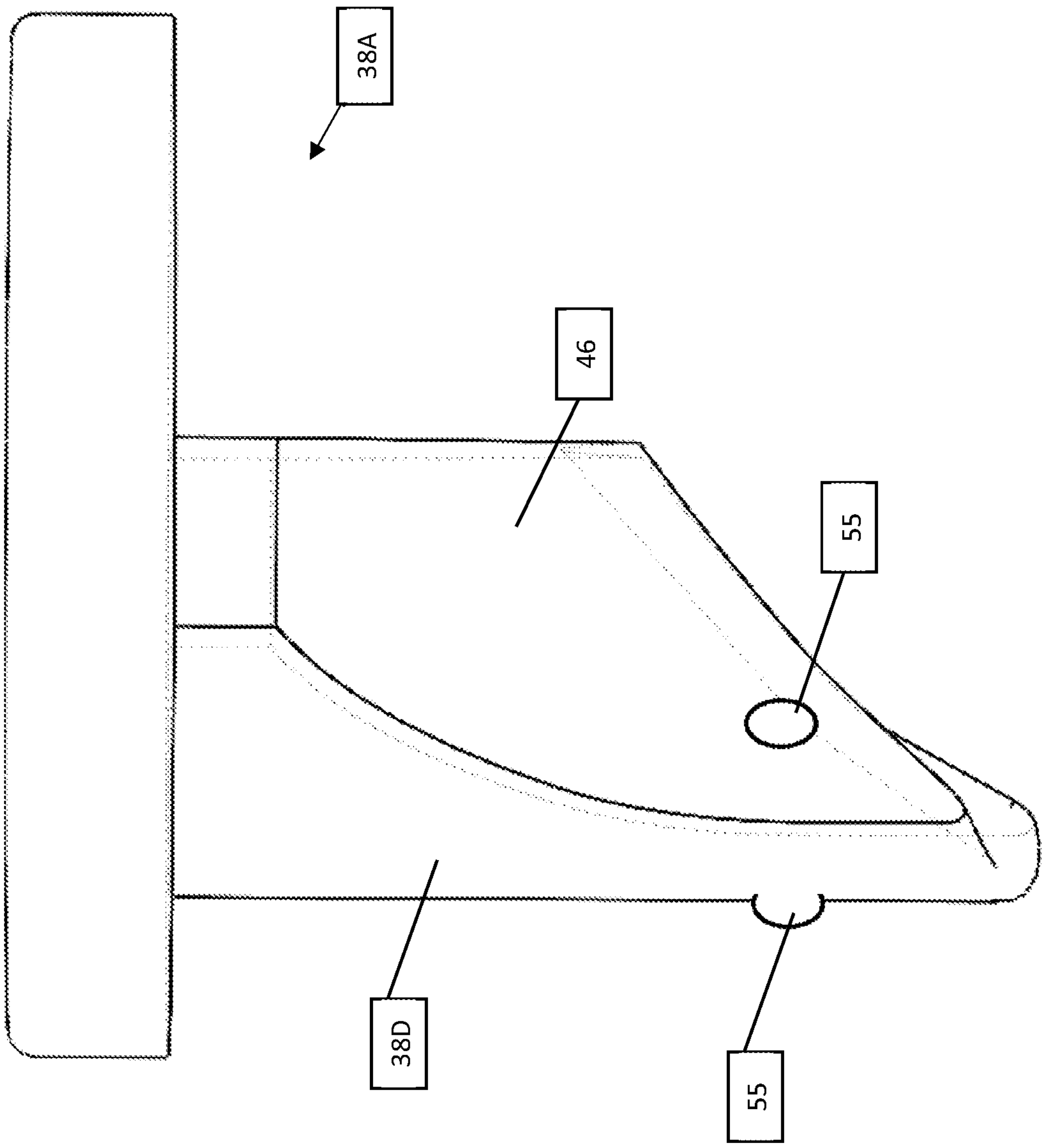
Figure 184:
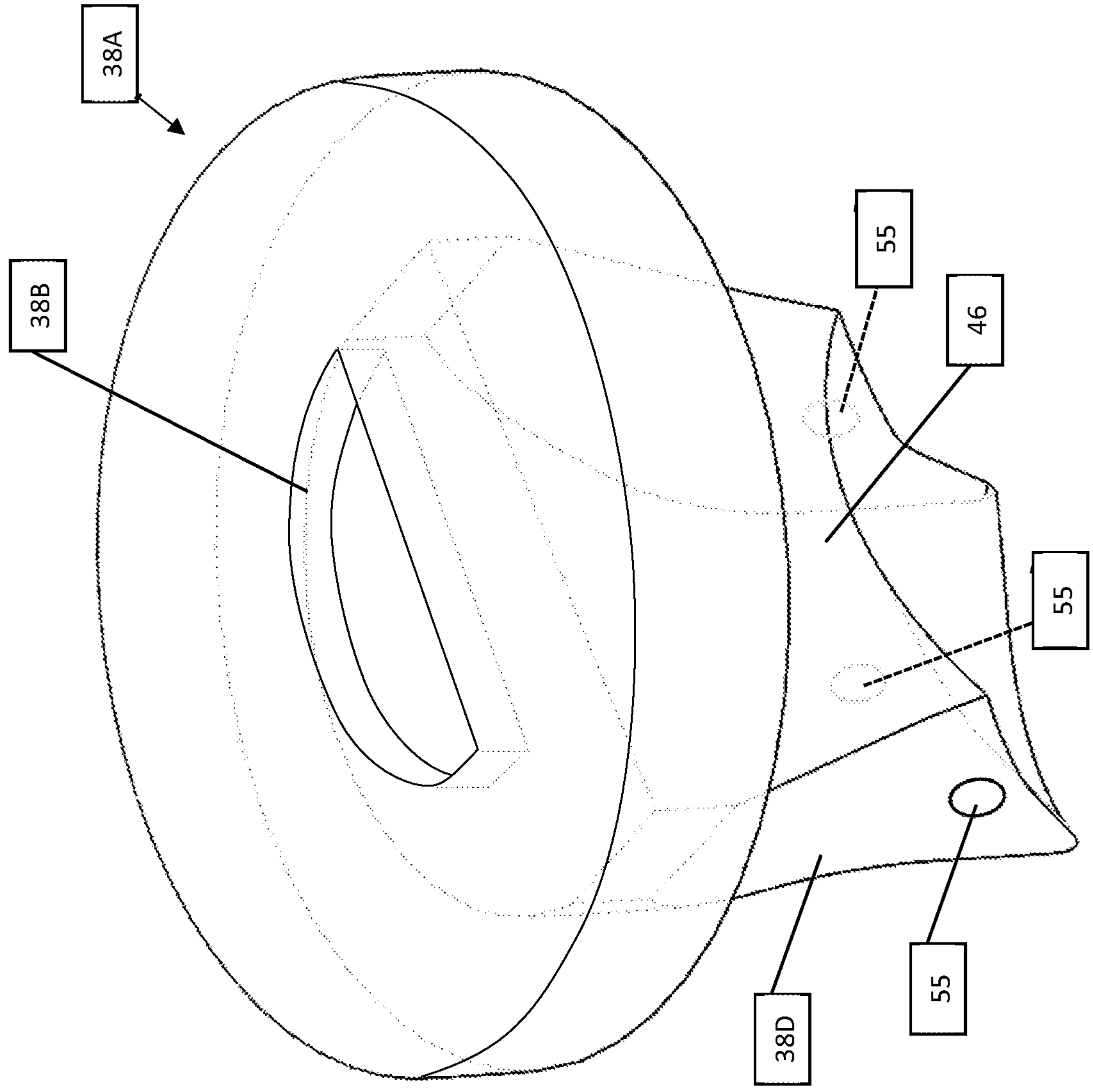
Figure 185:
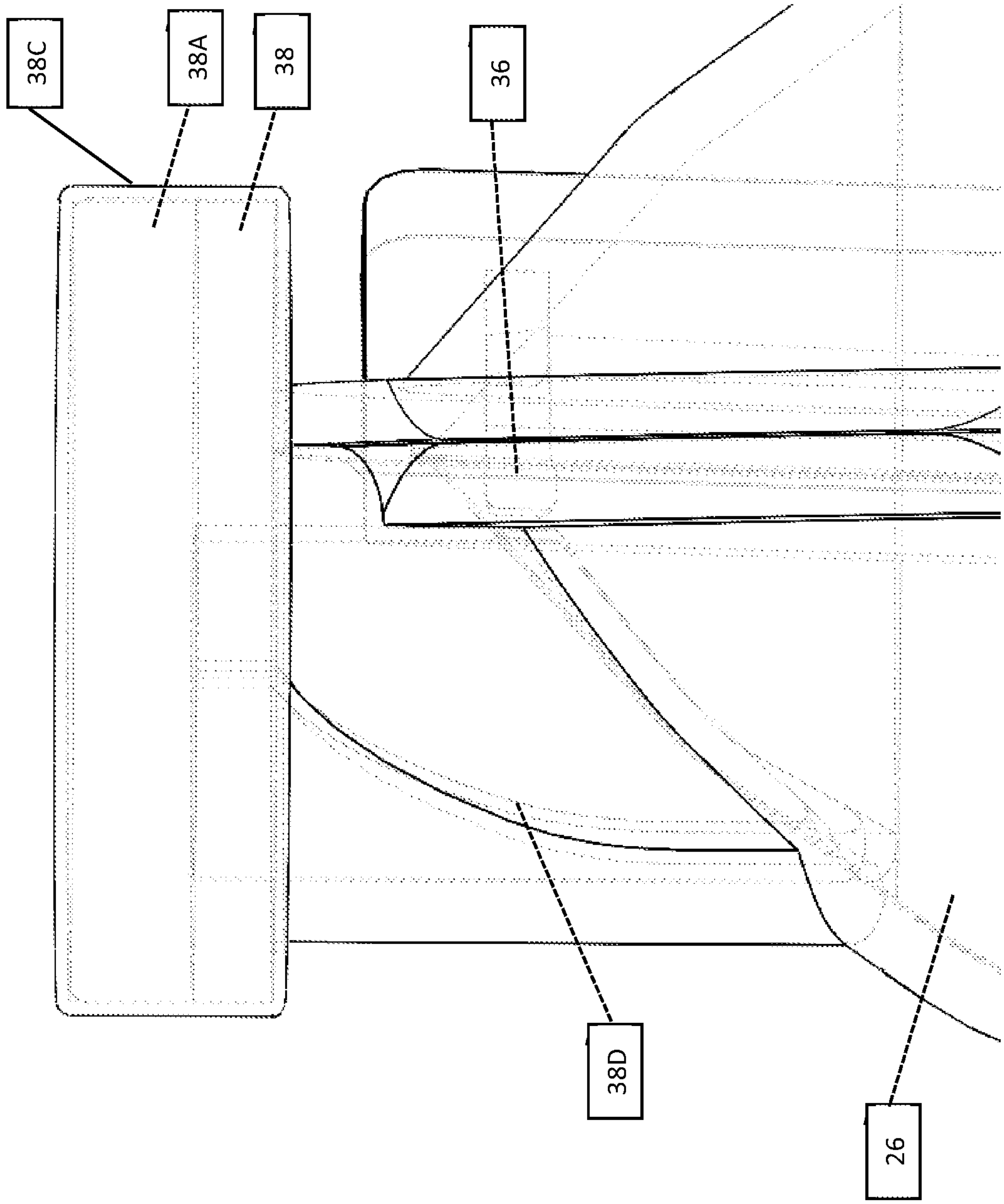
Figure 186:
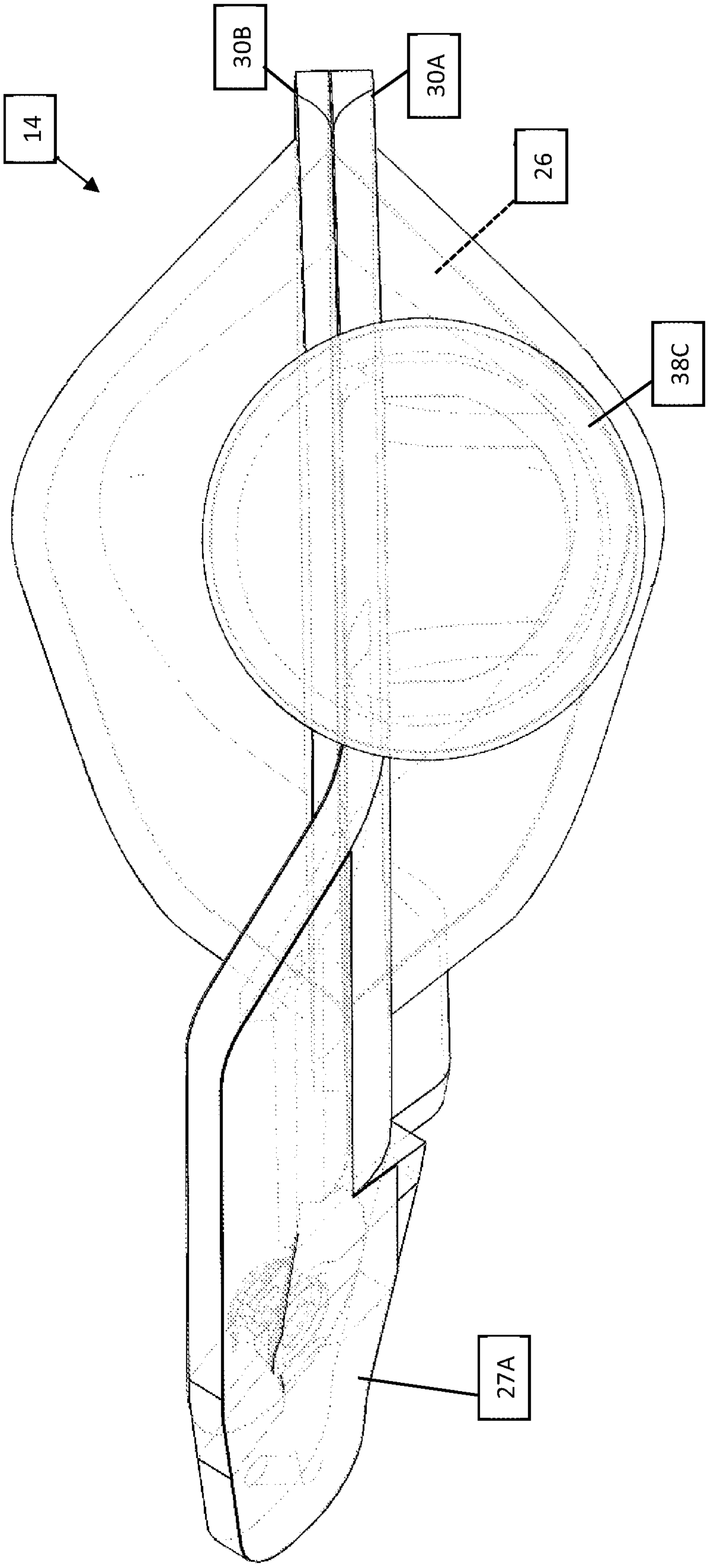
Figure 187:
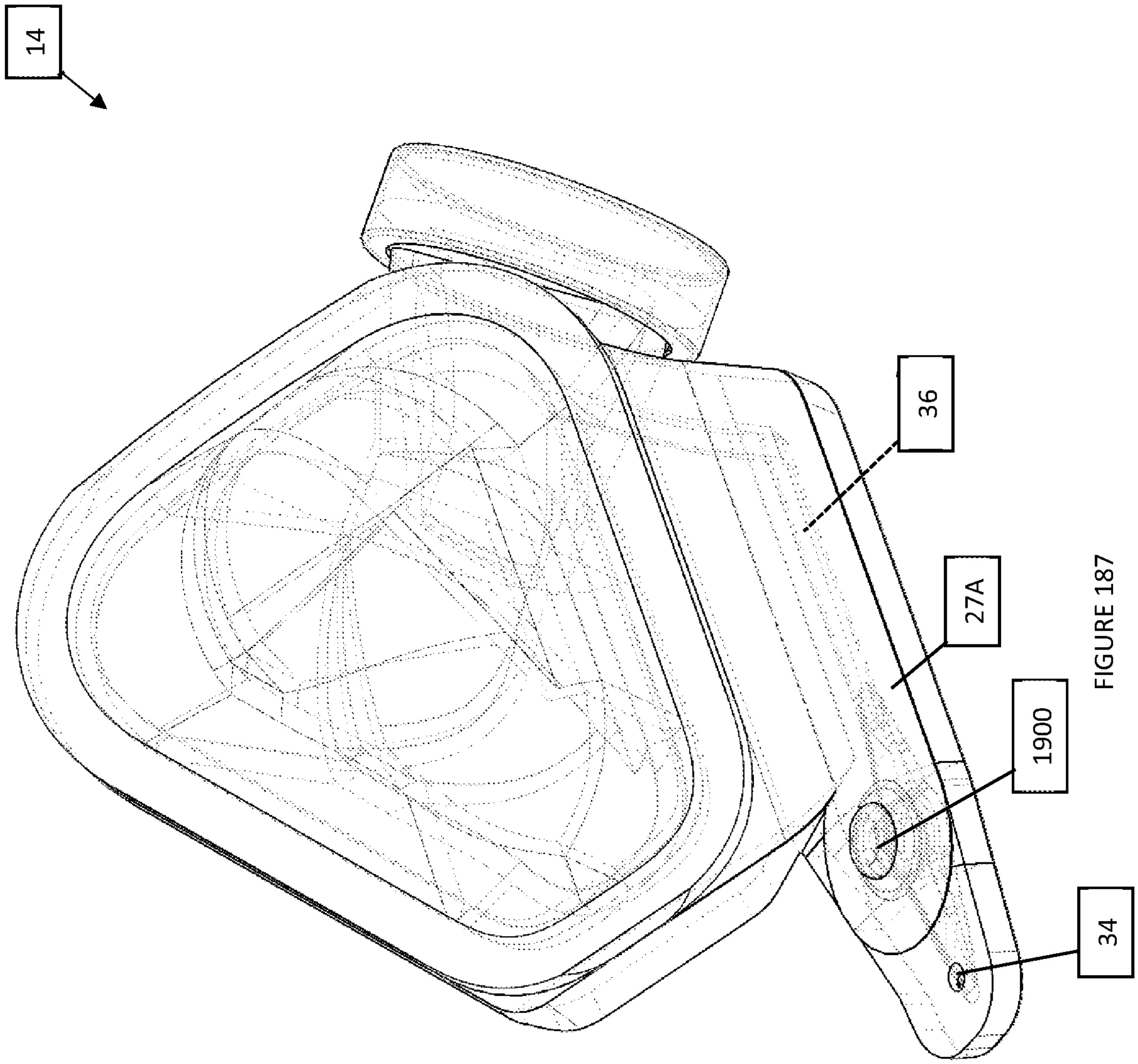
Figure 188:
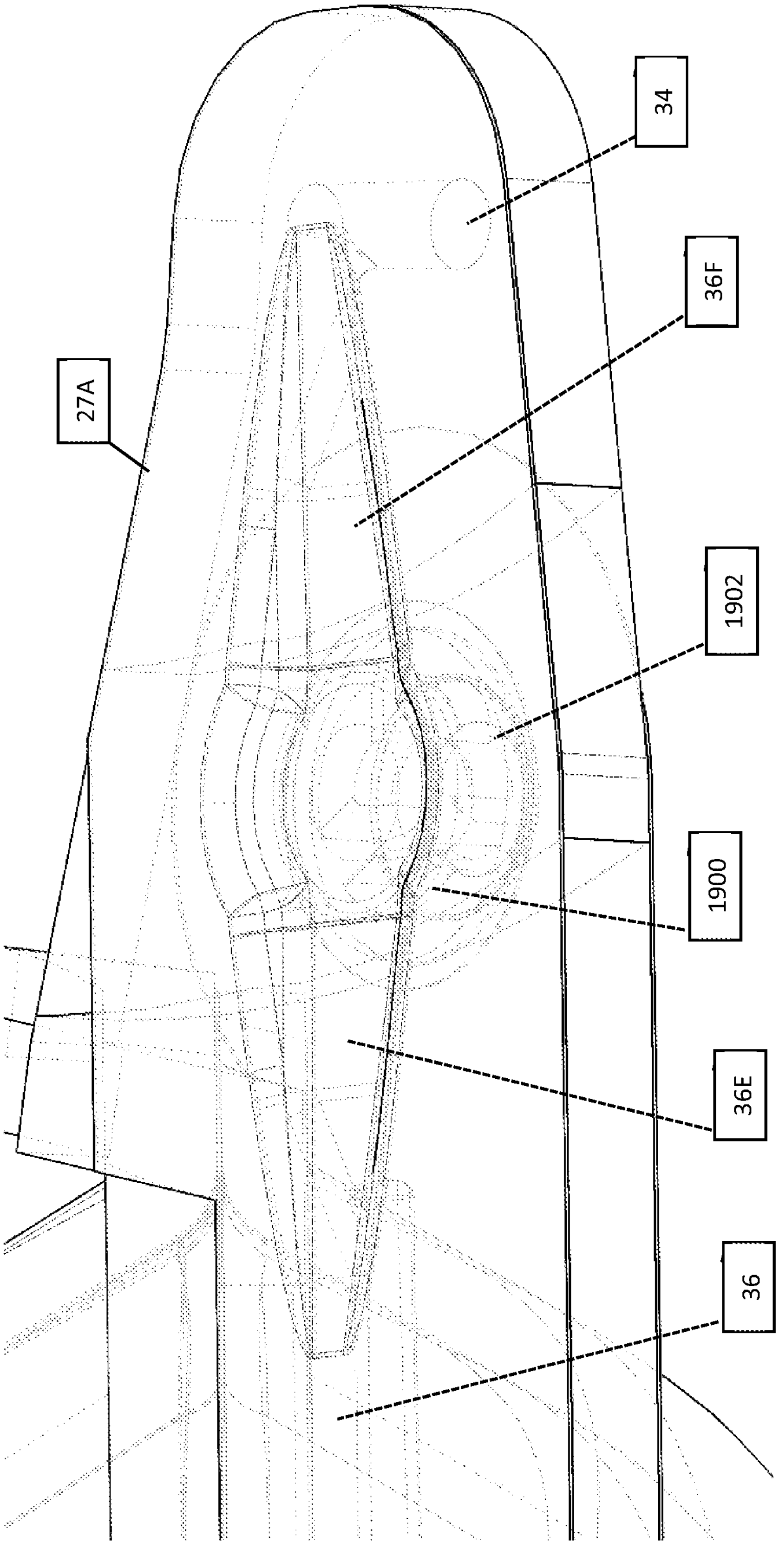
Figure 189:
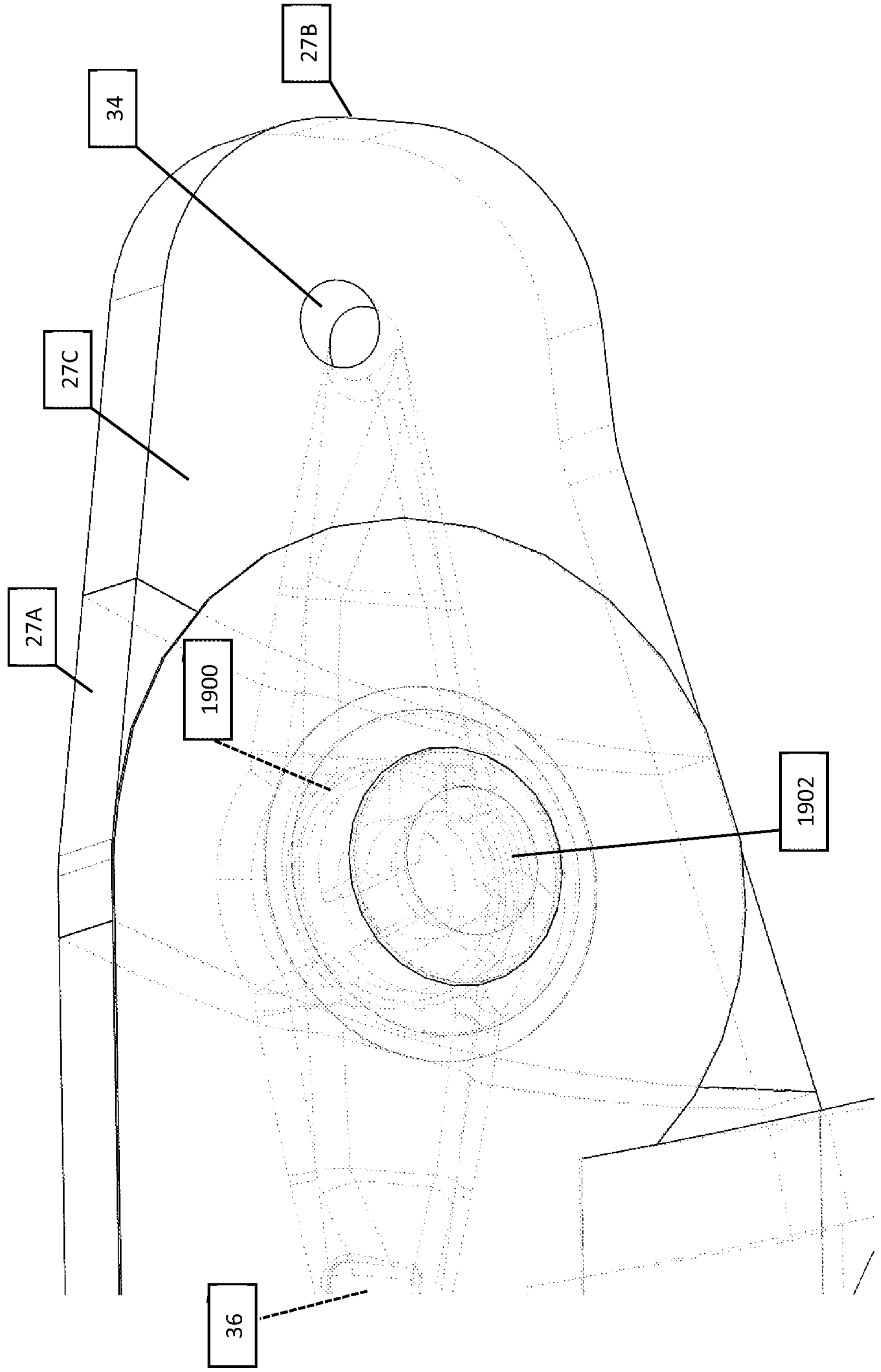

Alternatively, as shown in FIGS. 182-184, the vent plug 38A may be provided with the protruding beads 55 on the external surface 46 thereof. The vent plug 38A may include a hollow 38B on an upper surface thereof, which is engageable by a pick-and-place machine or other tool for insertion into the filling port 38. To prepare the drug cartridge 14, drug is introduced into the reservoir 26, after sterilization, through the filling port 38. Thereafter, as shown in FIG. 180, the vent plug 38A (after sterilization) may be partially inserted into the filling port 38 into an open, venting state with the venting passageways 72 being defined between the external surface 46 of the vent plug 38A and the filling port 38. Preferably, to achieve the venting state, the vent plug 38A is inserted into the filling port 38 to have the protruding beads 55 come into contact with the tapered section 49, with portions of the external surface 46 located about the protruding beads 55 being spaced from the filling port 38. The protruding beads 55 resiliently engage the filling port 38 to provide a holding force for the vent plug 38A in the venting state. The drug cartridge 14 may then be subjected to lyophilization conditions (low temperature and vacuum to extract moisture) to cause the drug in the reservoir 26 to lyophilize. During lyophilization, the vent plug 38A acts to retain the drug in the reservoir 26 while allowing venting about the vent plug 38A. Once lyophilization is completed, the vent plug 38A may be further inserted into the filling port 38 into a closed state, as shown in FIG. 181, with the external surface 46 generally coming into face-to-face contact with the filling port 38 to form a tight seal therewith. A crimped cap 38C may be provided to secure the vent plug 38A to the filling port 38, as shown in FIG. 185.

The vent plug 38A may be formed of an elastomeric material which is sterilizable. It is preferred that the vent plug 38A be oversized relative to the filling port 38 and sufficiently resilient to compress when urged to the closed state.

To best ensure stability of the vent plug 38A within the filling port 38, it is preferred that the filling port 38 be provided with a generally D-shaped cross-section (FIG. 177) with vent stem 38D of the vent plug 38D having a matching D-shaped cross-section formed to shape mate with the D-shaped filling port 38. With the vent plug 38A inserted into the filling port 38, the interengagement of the curved portion of the vent stem 38D with the curved portion of the filling port 38 provides multi-axial stability to the vent plug 38A relative to the filling port 38. In addition, the inner surface 38E of the vent stem 38D, as being on the inside of the curved profile of the vent stem 38D, may also define a venting passageway 72 with the vent plug 38A in the open, venting state.

It is noted that the internal lumen 36 may be shown open in certain figures in connection with the venting feature. The internal lumen 36 may be sealed, particularly in a portion of the plug adapter 14B not shown, and, thus, cannot provide venting.

Figure 34A:
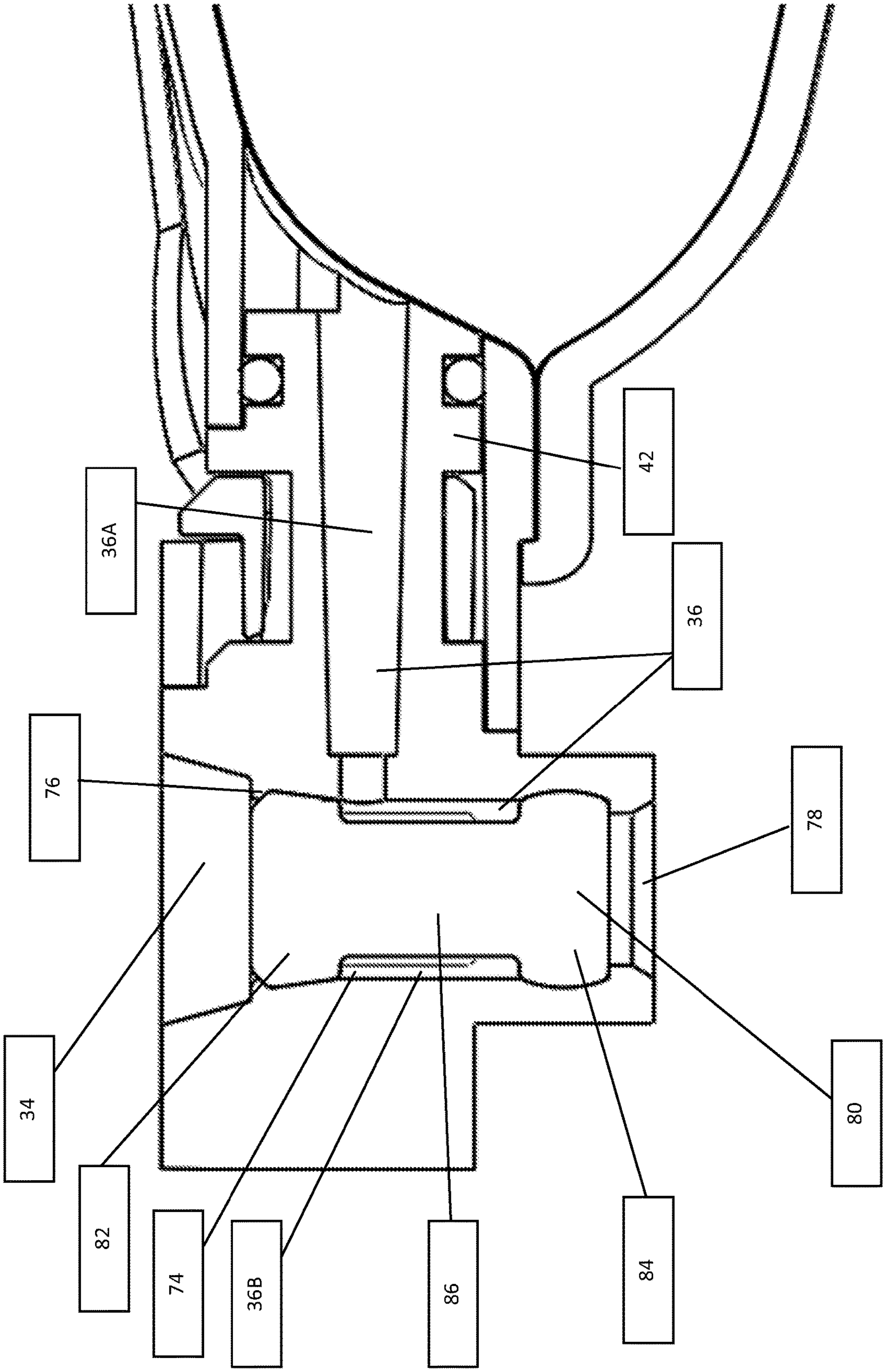
FIG. 34A is a section view of a plug adapter in the sealed position, in accordance with the subject invention.
Figure 35A:
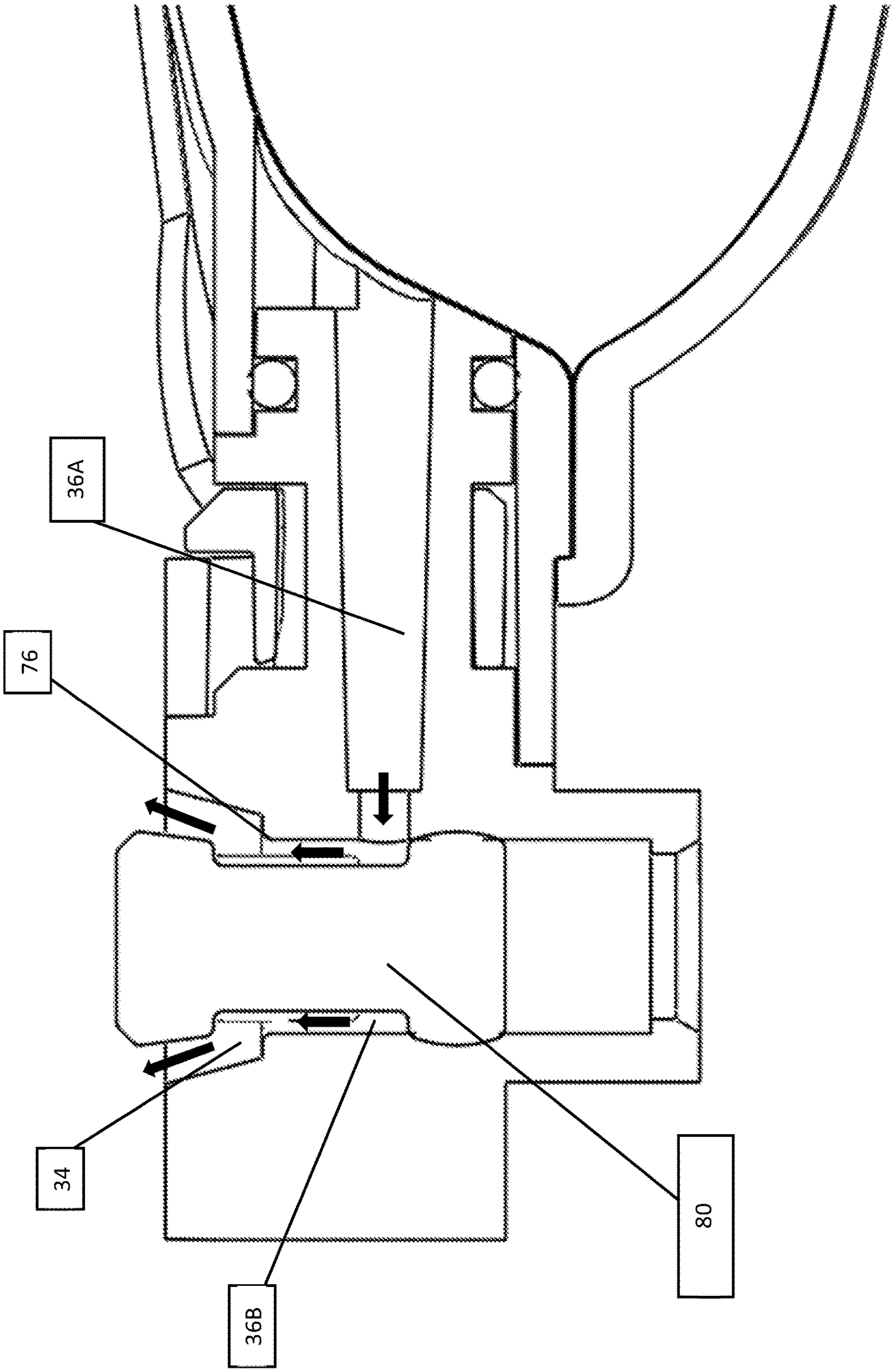
FIG. 35A is a section view of the plug adapter of FIG. 34, in the opened position.

The internal lumen 36 may be sterilized using any technique. The seal may be formed also using any technique. By way of non-limiting example, as shown in FIG. 34A, the internal lumen 36 may be provided with a first lumen portion 36A which extends from the reservoir 26, e.g., through the neck 42. A second lumen portion 36B may be disposed transversely to the first lumen portion 36A. At a first end 74, the second lumen portion 36B terminates at a valve seat 76 located at an interface of the fluid outlet 34 and the inner lumen 36. A second end 78 of the second lumen portion 36B may be open. A valve 80 may be located in the second lumen portion 36B. The valve 80 may be spool shaped having first and second enlarged lands 82, 84 connected by an elongated core 86. To form the seal, the first land 82 is seated in the valve seat 76. Thus, portions of the internal lumen 36 inside of the first land 82 are sealed from contaminants. To cause un-sealing, as shown in FIG. 35A, the valve 80 may be shifted within the second lumen portion 36B to separate from the valve seat 76.

The second end 78 of the second lumen portion 36B may be formed closed, or sealed with a plug or other element. The second end 78 may be provided open to allow for a control element to extend into the second lumen portion 36B to engage the valve 80 in causing shifting thereof. With the second end 78 being open, the second land 84 is positioned between the second end 78 and the first lumen portion 36A to seal the internal lumen 36. In this manner, sterility may be maintained particularly along the first lumen portion 36A and portions of the second lumen portion 36B leading towards the fluid outlet 34. The valve 80 is formed such that the second land 84 remains continuously between the first lumen portion 36A and second end 78 during shifting of the valve 80.

The valve 80 may include elastomeric and/or non-elastomeric materials. The valve 80 requires sufficient internal resilience to maintain the formed seal. In addition, as discussed below, the valve 80 may be exposed to ultraviolet radiation, x-ray radiation, pulsed light or electron-beam treatment. Appropriate material selection is required.

As will be appreciated by those skilled in the art, the valve 80 provides a seal which is inside of the internal lumen 36, thus leaving open the fluid outlet 34 exposed. With this arrangement, sterility of the internal lumen 36 to the reservoir 26, and the reservoir 26, is maintained. Further sterilization, however, will be required, e.g., of the fluid outlet 34, for actual use.

Figure 34B:
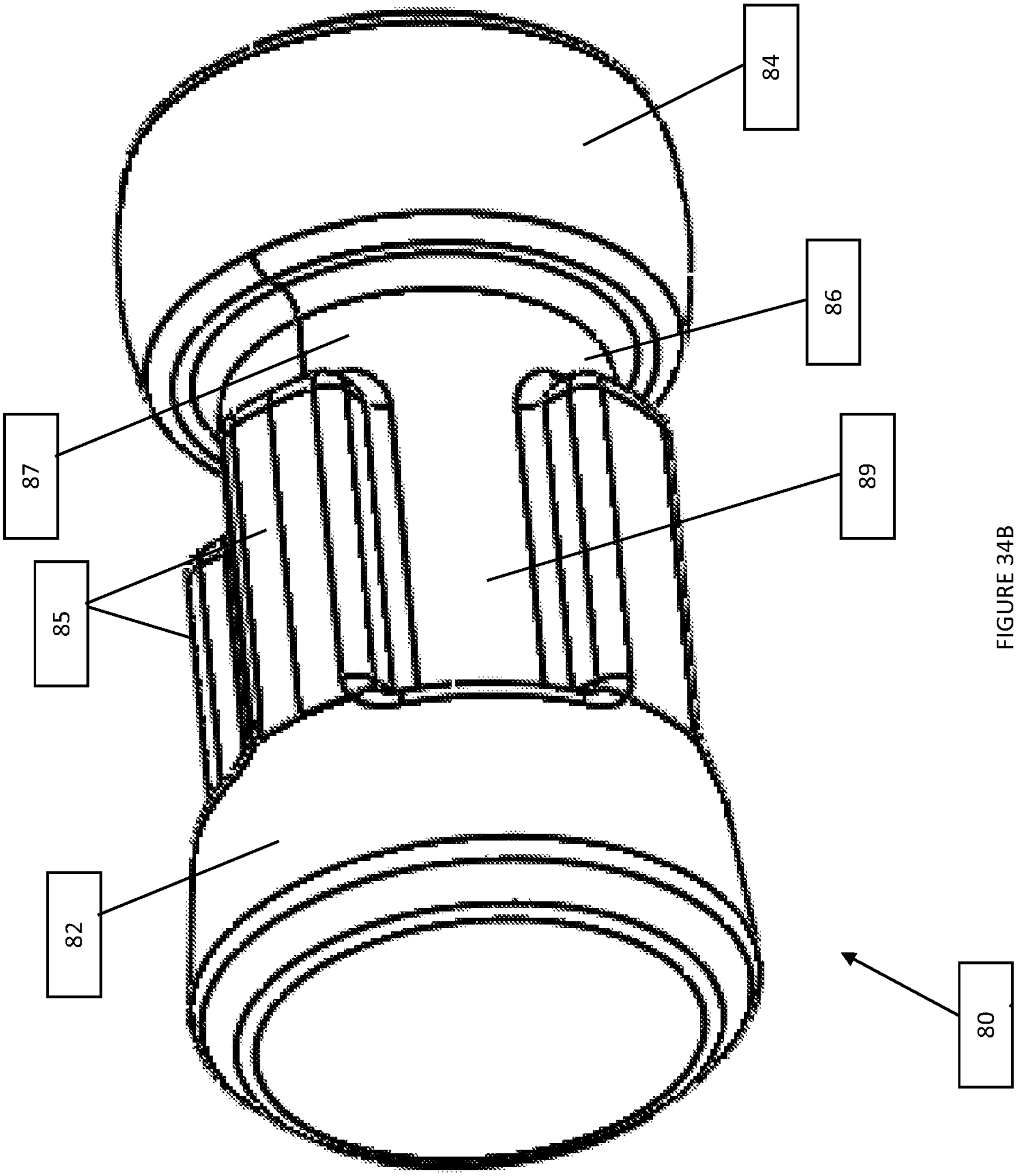
FIG. 34B is a perspective view of a valve useable with the plug adapter, in accordance with the subject invention.
Figure 34C:
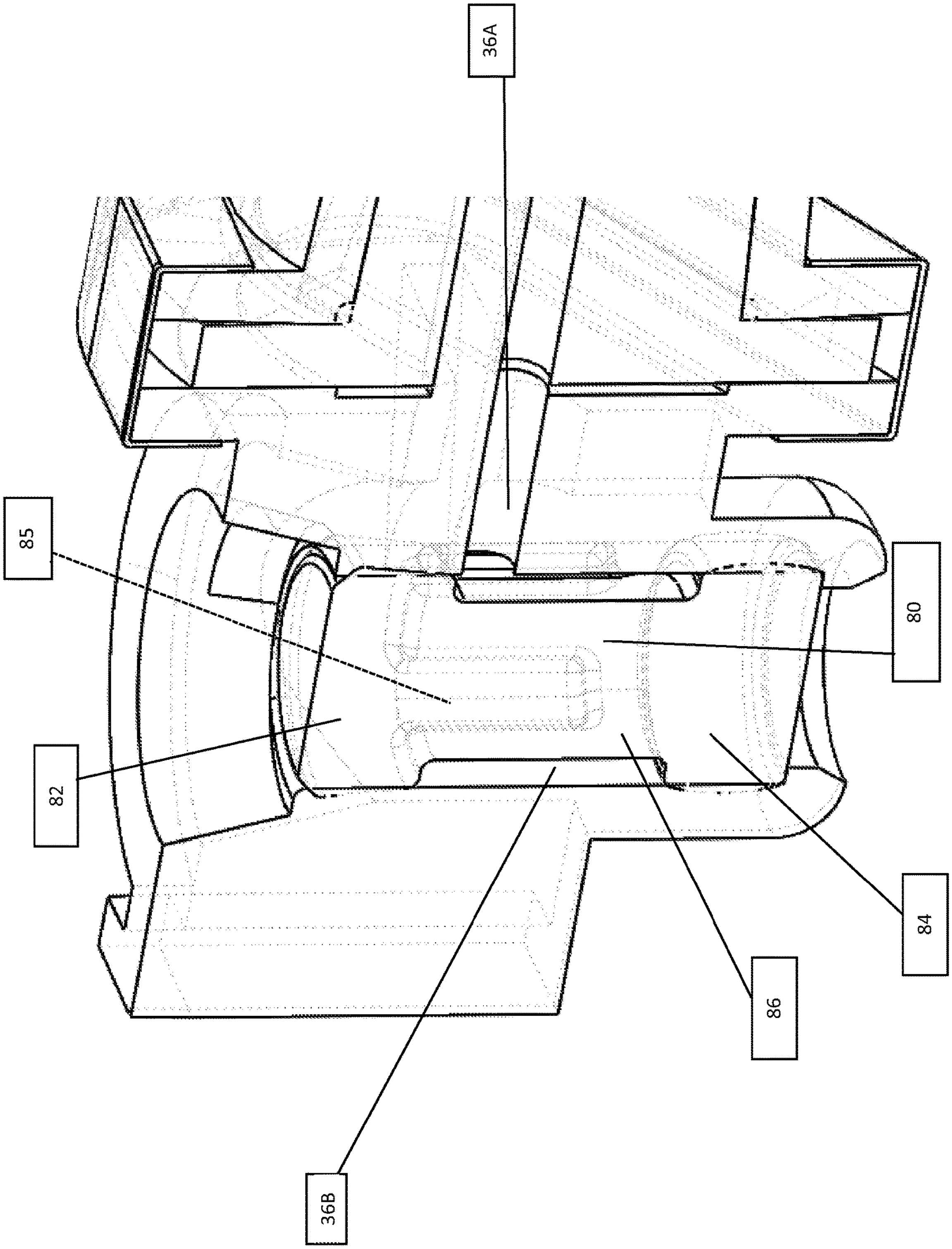
FIG. 34C is a section view of a plug adapter using the valve of FIG. 34A, in the sealed position.
Figure 35B:
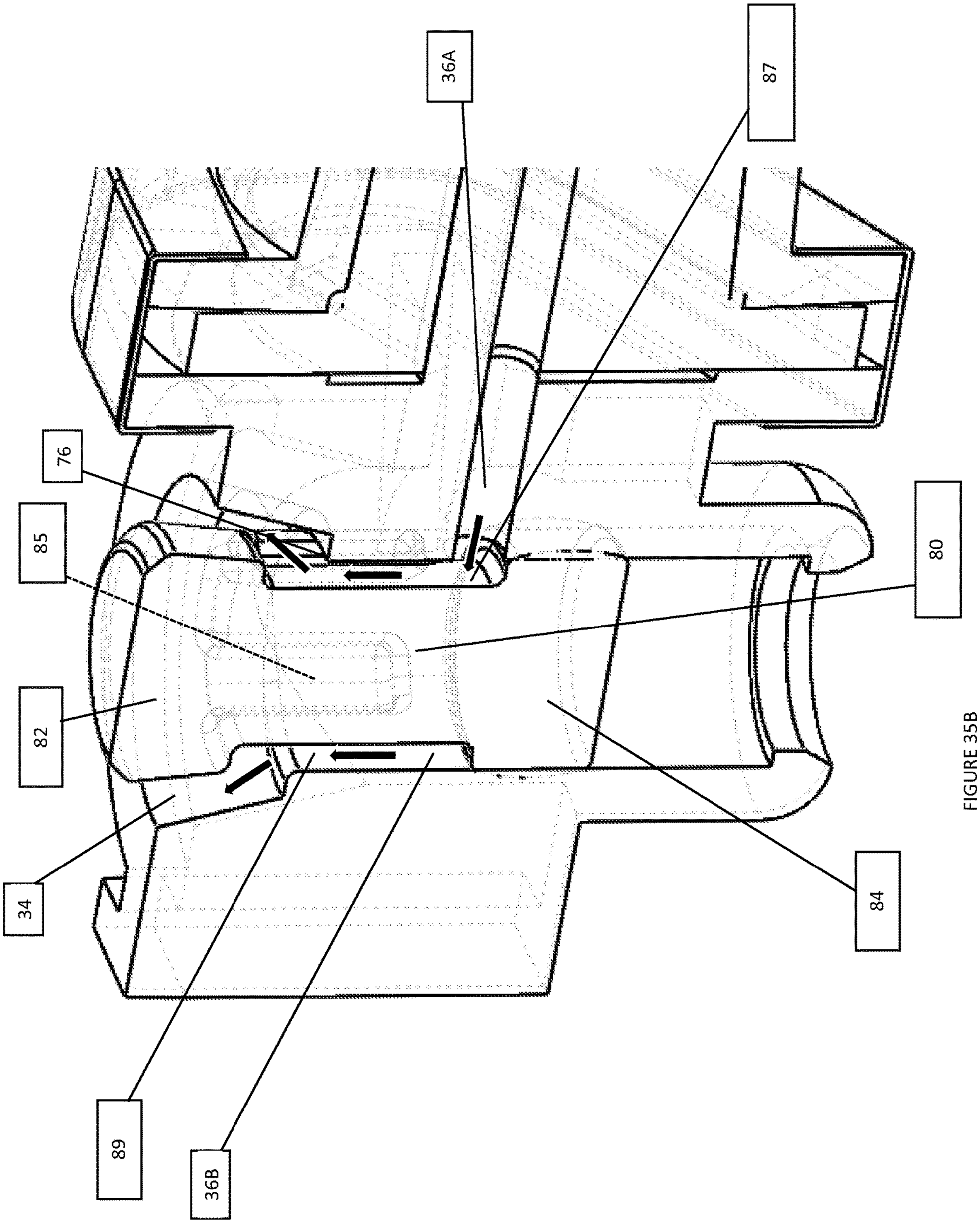
FIG. 35B is a section view of a plug adapter using the valve of FIG. 34A, in the opened position.

As shown in FIGS. 34B and 34C, the valve 80 may include a plurality of spaced-apart positioning ribs 85 extending longitudinally along the elongated core 86 from the first land 82. Preferably, the positioning ribs 85 are spaced from the second land 84 to define an open ring 87 between the positioning ribs 85 and the second land 84, about the elongated core 86. The positioning ribs 85 collectively define an outer diameter which is larger than the diameter of the valve seat 76. Thus, as shown in FIG. 35B, the positioning ribs 85 engage the valve seat 76 to center the valve 80 within the valve seat 76, and provide stability to the valve 80 in the un-sealed position. Channels 89 are defined between the positioning ribs 85 to allow flow therethrough with the valve 90 being un-sealed (with the positioning ribs 85 engaging the valve seat 76). Preferably, the positioning ribs 85 are parallel to define the channels 89 are parallel.

Figure 178:
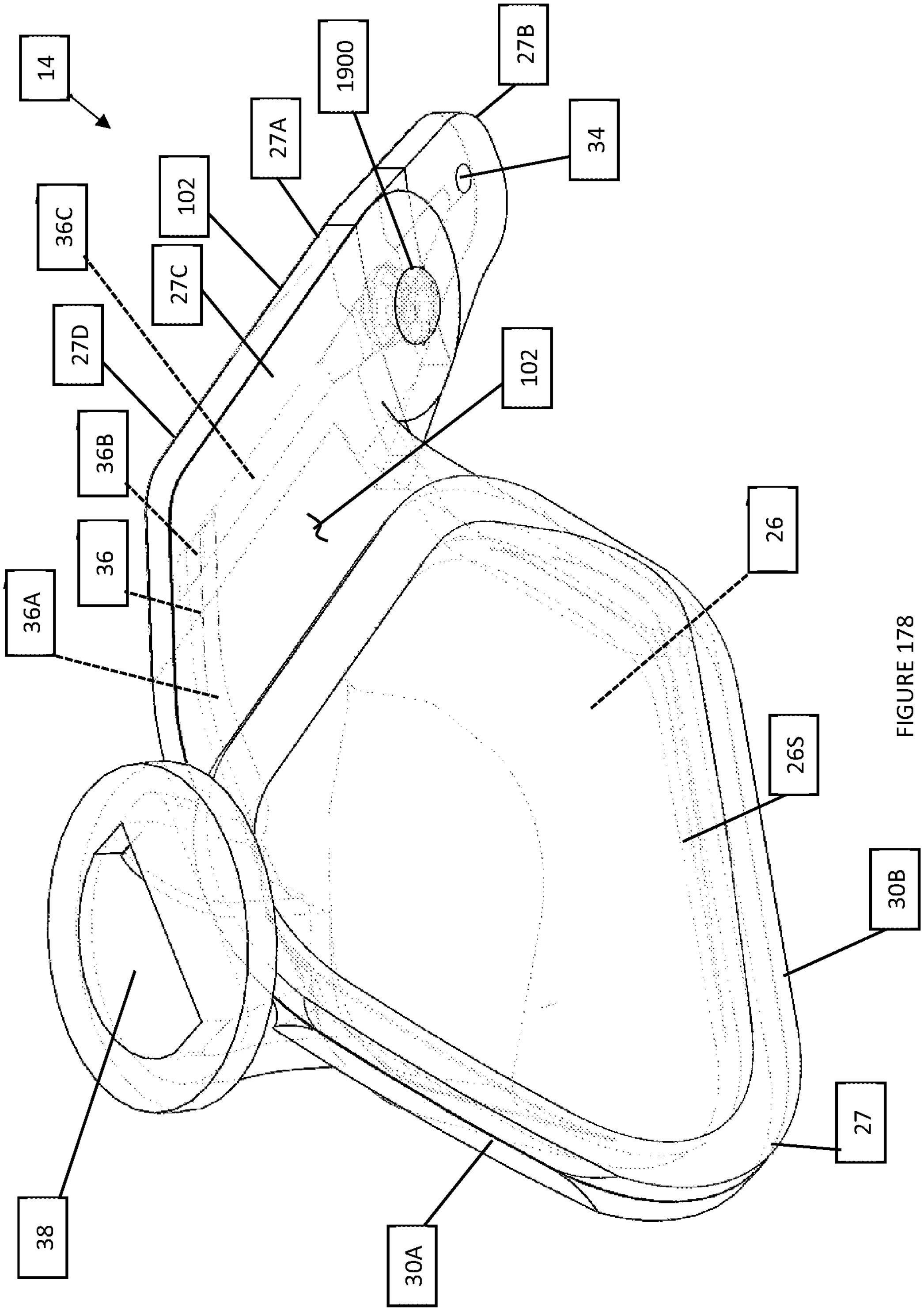

As shown in FIG. 178, the internal lumen 36 may be formed in similar manner described above in connection with the fluid ducts 22. In particular, the first lumen portion 36A may be formed along a first face 27C of the wing portion 27A to be exposed for sterilization. The second lumen portion 36B may provide a change in direction with the third lumen portion 36C formed along a second face 27D of the wing portion 27A. The first and third lumen portions 36A, 36C, as being open trenches, allow for sterilization including the second lumen portion 36B. A barrier 102 (discussed infra) may be provided on each of the first face 27C and the second face 27D to seal the first lumen portion 36A and the third lumen portion 36C. Alternatively, the flexible reservoir walls 26R, 26S may be extended through the flange 27 on opposing sides of the wing portion 27A to provide the barriers 102 seal the first and third lumen portions 36C. As will be understood by those skilled in the art, the internal lumen 36 may be provided in various configurations with different portions being exposed or recessed along the wing portion 27A. Within these configurations, exposed portions of the internal lumen 36 are covered to provide closed flow paths.

Figure 190:
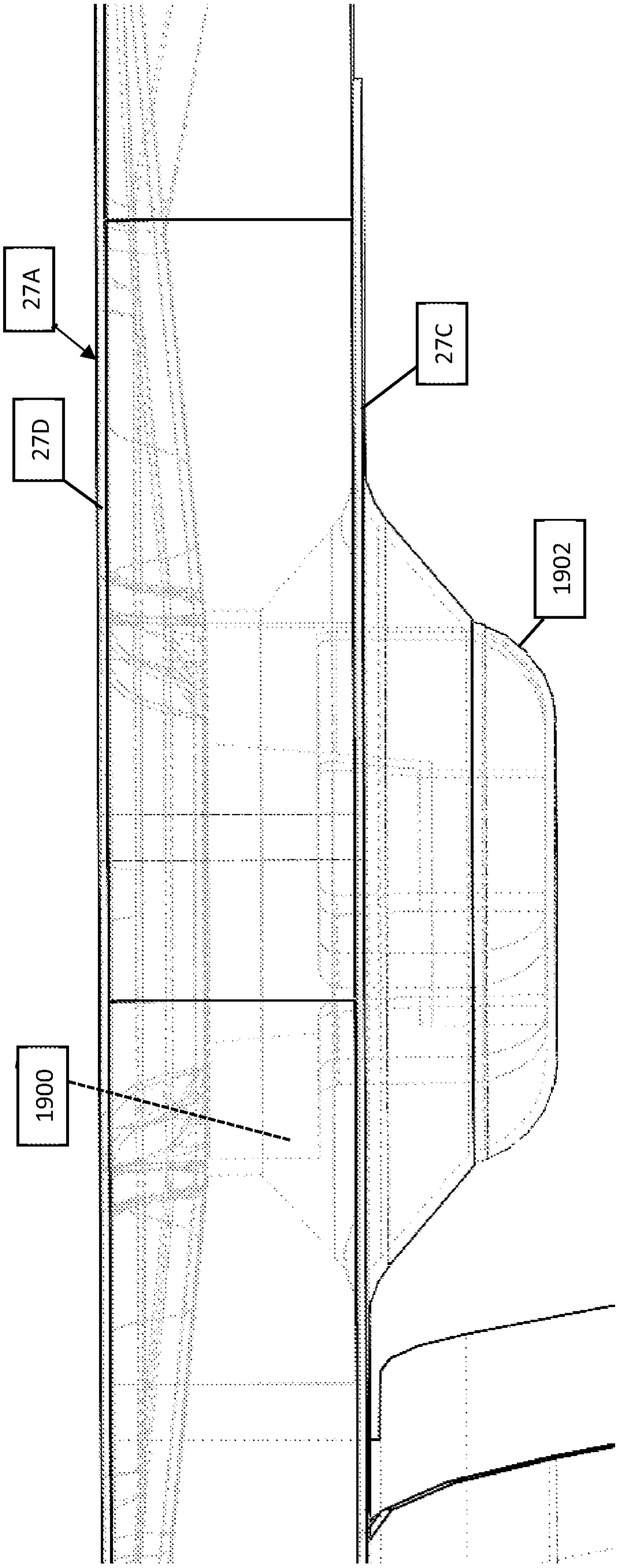
Figure 191:
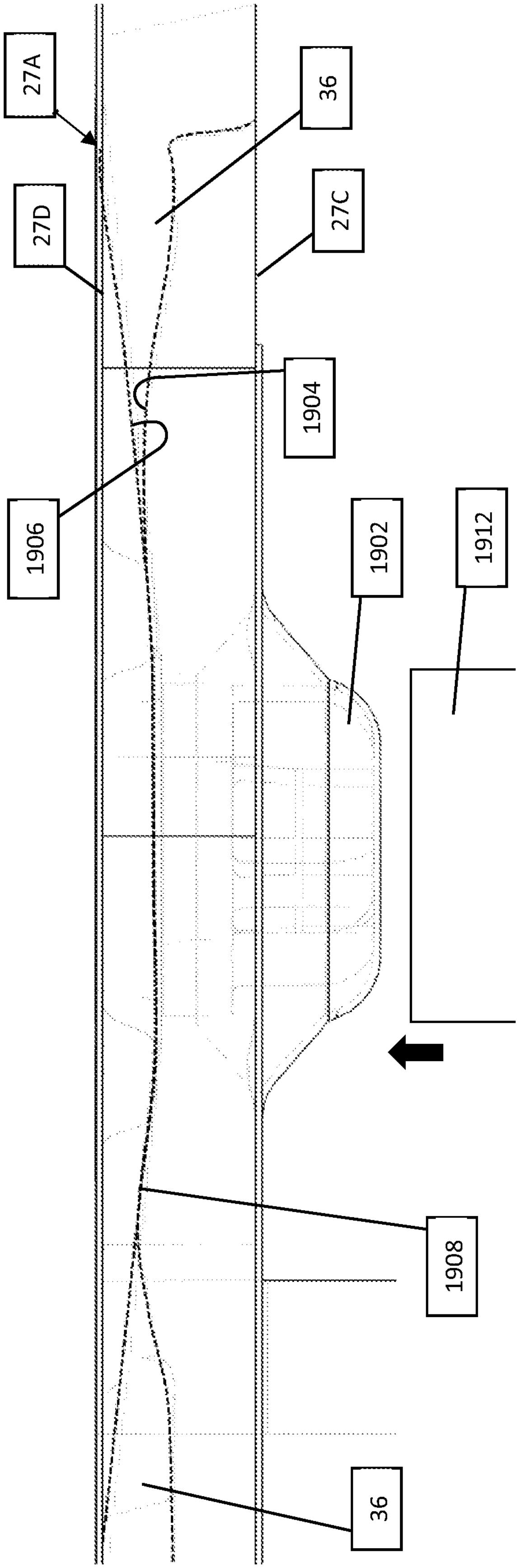
Figure 192:
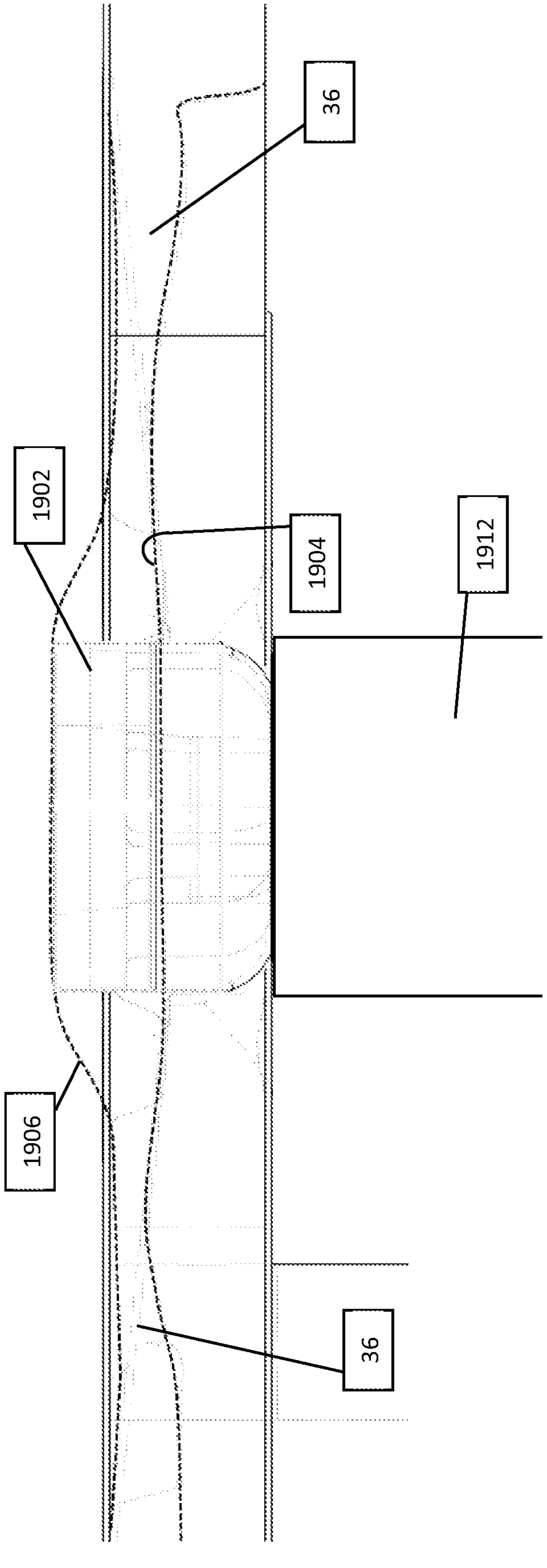
Figure 193:
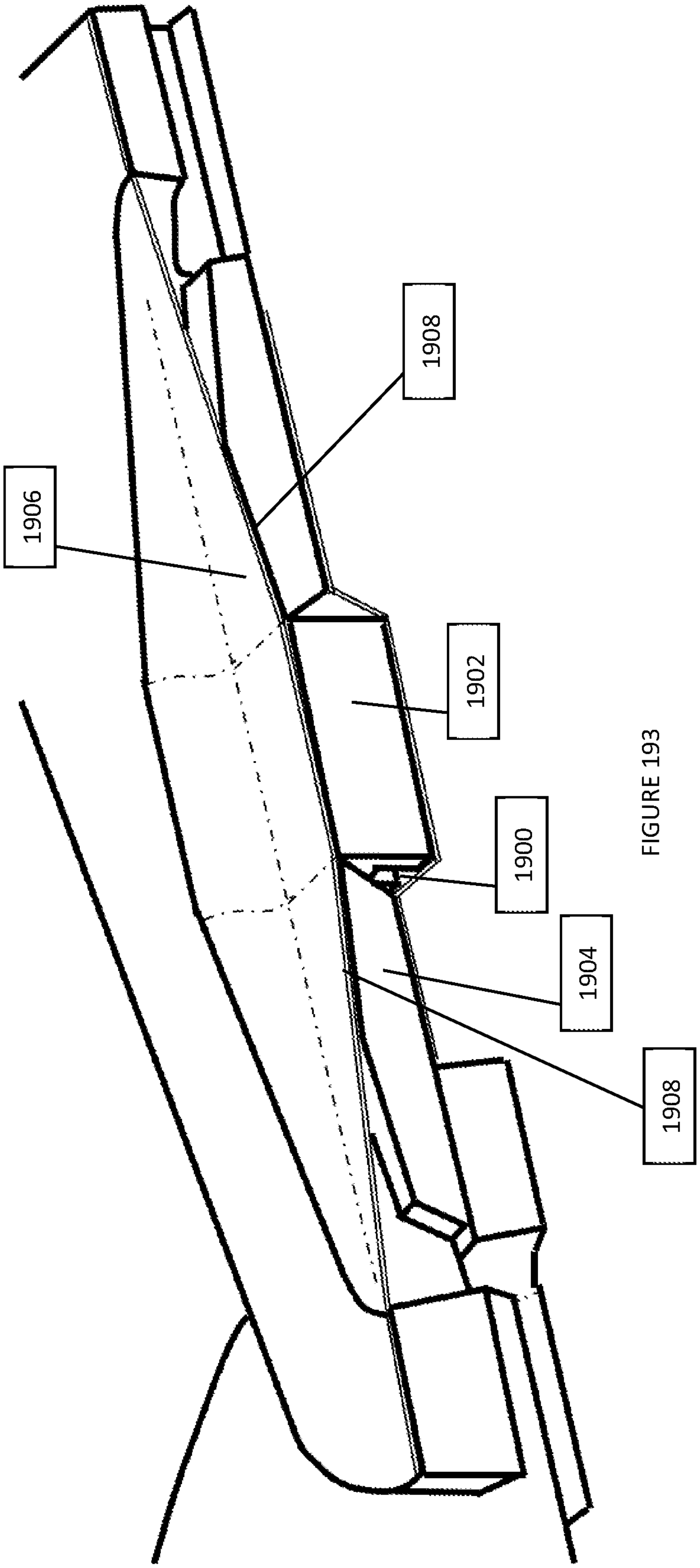
Figure 194:
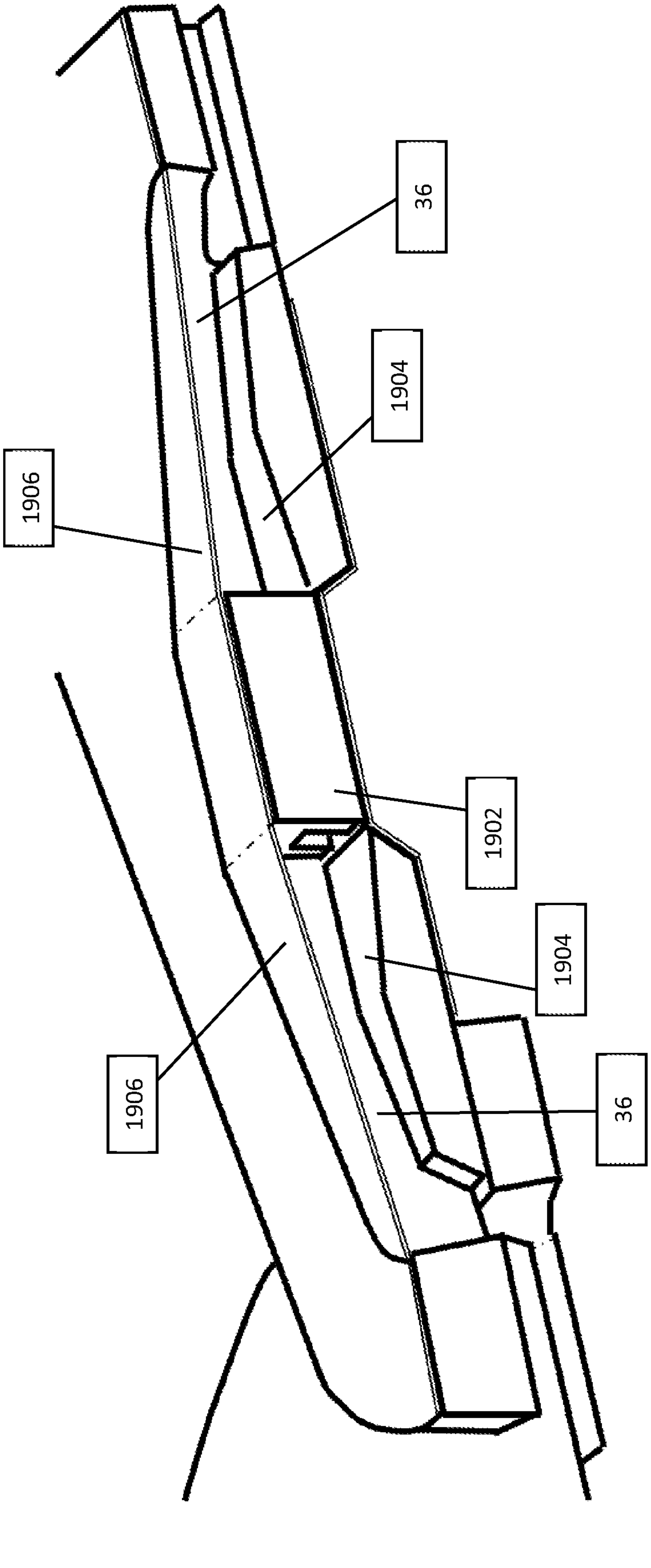
Figure 195:
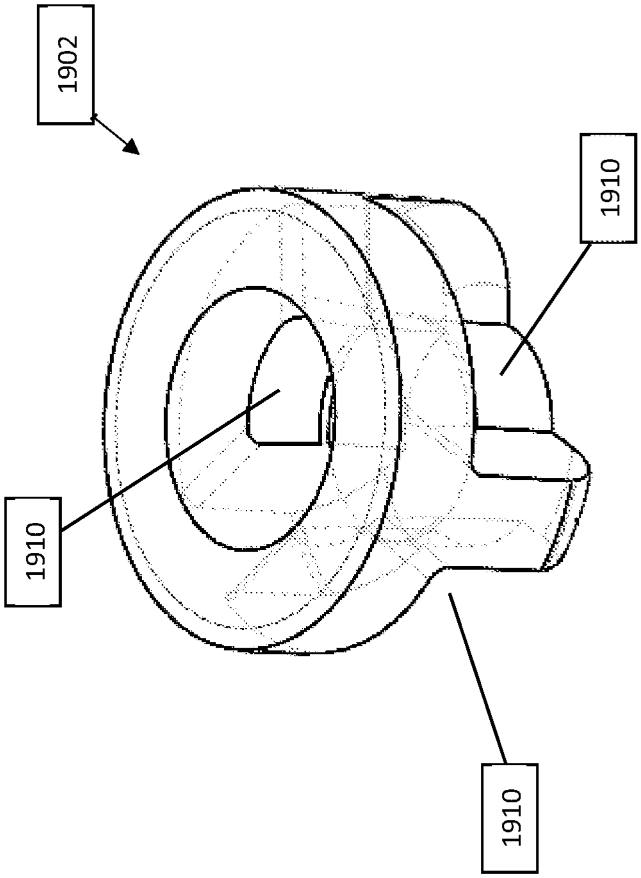
Figure 196:
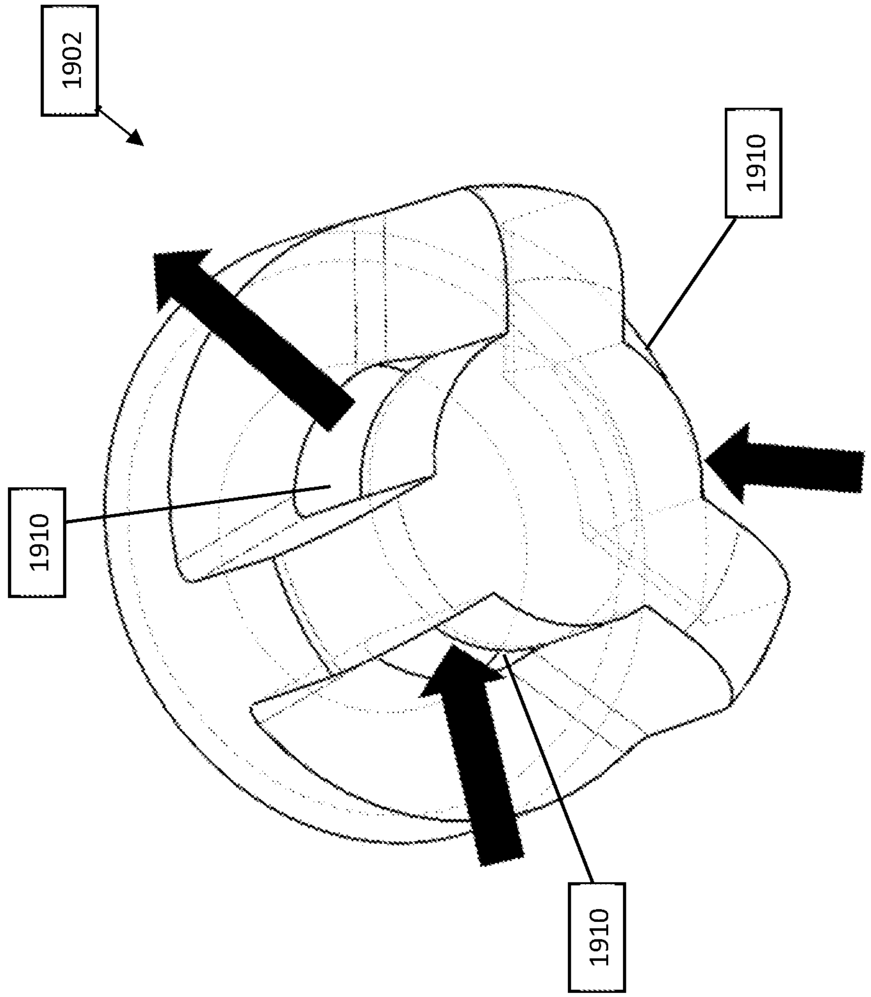
Figure 197:
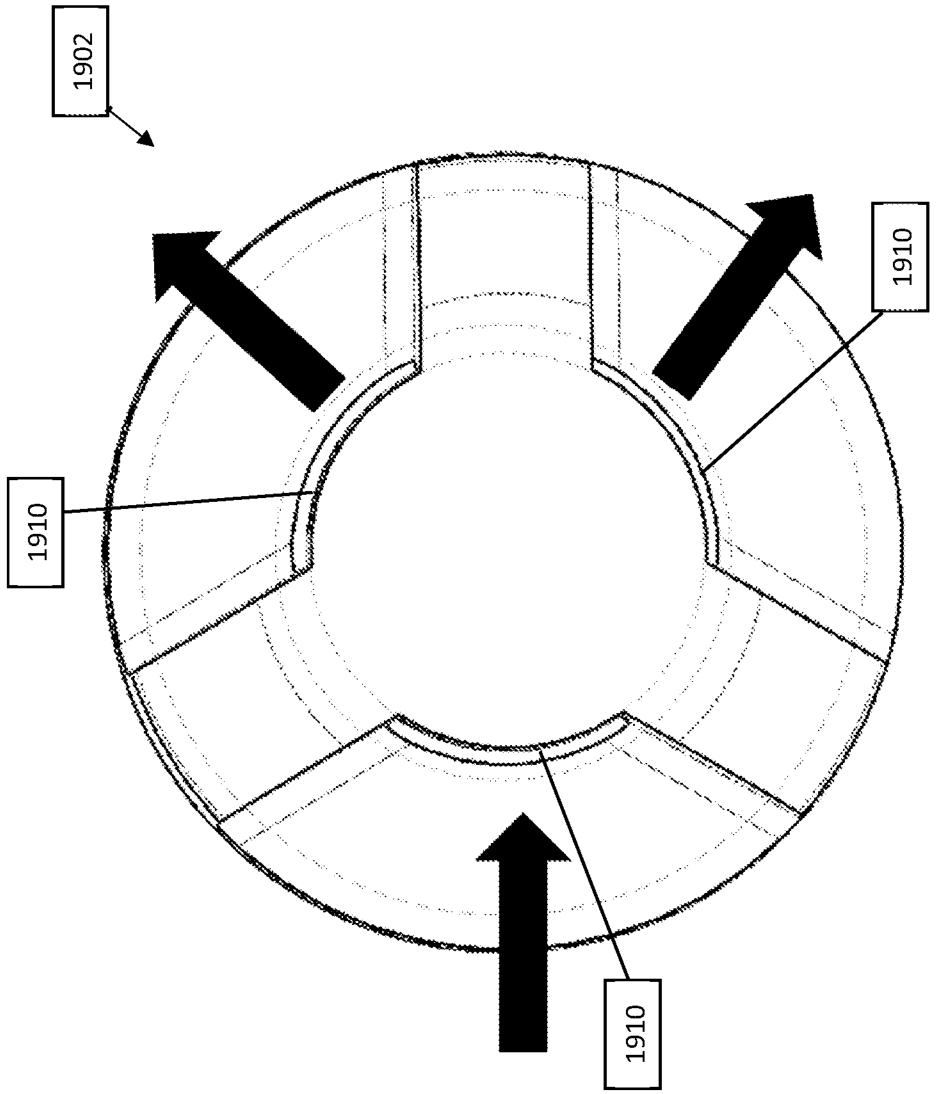
Figure 198:
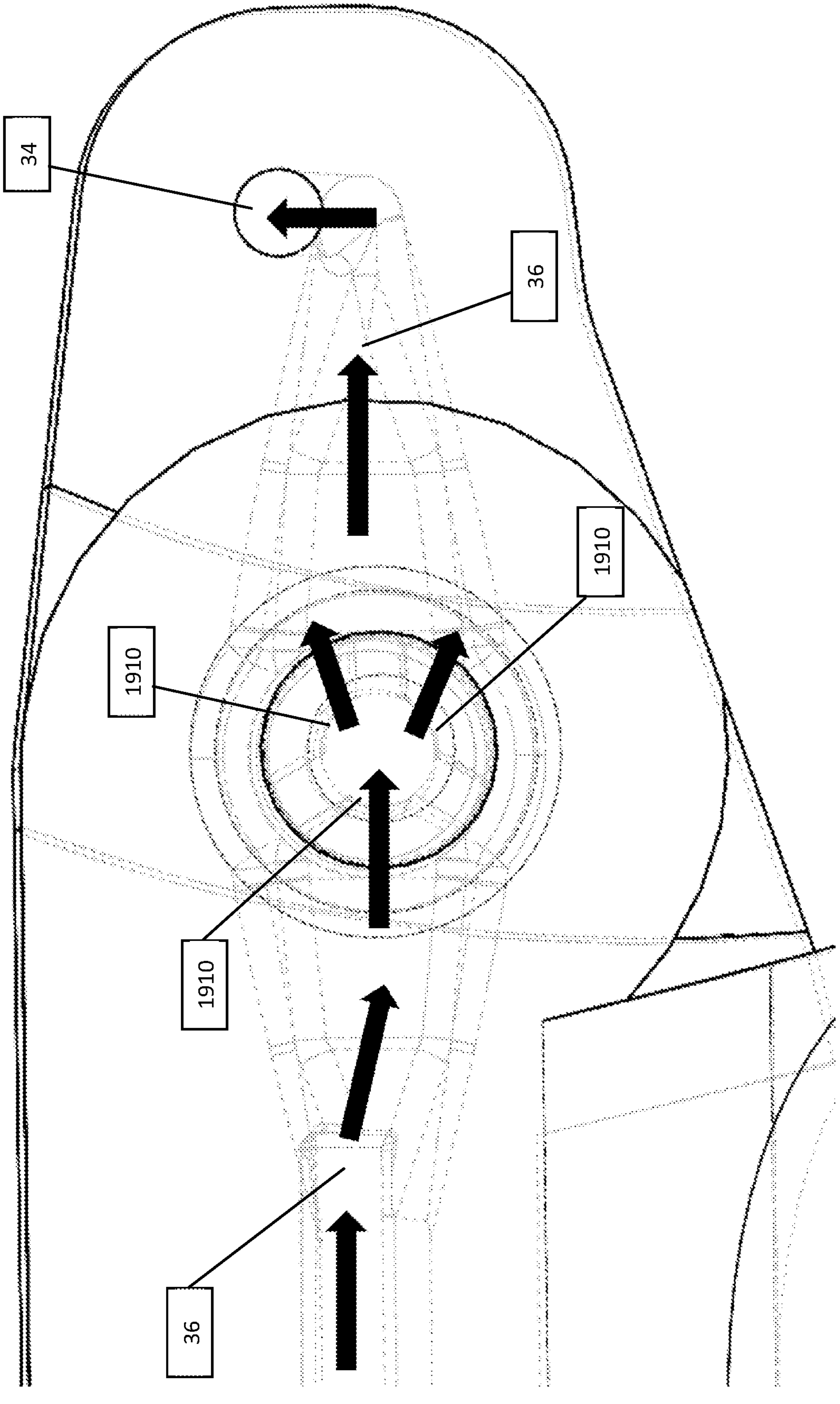

As an alternative to the valve 80, a seal may be provided along the internal lumen 36 upstream from the fluid outlet 34. As shown in FIGS. 187-198, a well 1900 may be formed in the wing portion 27A along the internal lumen 36. A shiftable seal element 1902 is provided seated in the well 1900. The well 1900 is formed along the internal lumen 36 so as to cause an interruption therein in the fluid path to the fluid outlet 34. As shown in FIG. 190, the shiftable seal element 1902 is in a closed state, protruding from the first face 27C of the wing portion 27A. As shown in FIGS. 191 and 193, with the shiftable seal element 1902 in the closed state, a sealing surface 1904, located about the well 1900, is joined with a sealing sheet 1906 spanning across the well 1900 to define at least one seal 1908 along the internal lumen 36 impervious to fluid or liquid flow. The sealing sheet 1906 also is secured to the shiftable seal element 1902 so that the pressing of the shiftable seal element 1902 into the well 1900 to an open state results in delamination of the sealing sheet 1906 from the sealing surface 1904, undoing of the seal 1908, and the opening of the internal lumen 36 across the well 1900. As shown in FIGS. 195-197, the shiftable seal element 1902 includes open passageways 1910 which come into alignment with the internal lumen 36 with the shiftable well 1902 being in the open state. The open passageways 1910 are provided at multiple radial locations to ensure flow through the shiftable seal element 1902, regardless of its radial orientation within the well 1900. As shown in FIG. 198, with the shiftable seal element 1902 in the open state, the internal lumen 36 is open with an unobstructed flow path to the fluid outlet 34.

As will be appreciated by those skilled in the art, any means of pressing may be utilized to press the shiftable seal elements 1902 into the open state, including manual or automated pressing. For example, as shown in FIGS. 191-192, a driven actuator 1912 may be utilized which applies pressure to the shiftable sealing element 1902 to cause displacement thereof.

Portions of the internal lumen 36 adjacent to the well 1900 may be enlarged. In particular, the internal lumen 36 may have a divergent portion 36E leading into the well 1900 and a convergent portion 36F leading out of the well 1900. The sealing surface 1904 may be located within the divergent portion 36E and the convergent portion 36F. In addition, the sealing surface 1904 may be raised about the well 1900 with the shiftable seal element 1902 being seated within the sealing surface 1904 in the closed state.

The sealing sheet 1906 may be any material which may be sufficiently secured to the sealing surface 1904 to form the seal 1908 and then be non-destructively separated from the sealing surface 1904. The sealing sheet 1906 forms a portion of the internal lumen 36 in the open state, requiring structural integrity post-delamination. By way of non-limiting example, the sealing sheet 1906 may be a thermoformable film with the sealing surface being thermoplastic (e.g., cyclic olefin copolymer). The sealing sheet 1906 may be an extension of one of the barriers 102, including being an extension of one of the flexible reservoir walls 26R, 26S. For example, the flexible reservoir wall 26R may be extended through the flange 27 to cover open portions of the internal lumen 36 and to act as the sealing sheet 1906.

Like the valve 80, the sealing sheet 1906 provides a seal which is inside of the internal lumen 36 and spaced from the fluid outlet 34, thus leaving the fluid outlet 34 exposed. With this arrangement, sterility of the internal lumen 36 to the reservoir 26, and the reservoir 26, is maintained. Further sterilization, however, will be required of the fluid outlet 34, for actual use.

The cross-section of the fluid outlet 34 and/or the internal lumen 36 (e.g., the second lumen portion 36B) may be varied to minimize volume loss and to minimize the diameter thereof. For example, as shown in FIG. 82A, the fluid outlet 34 may be formed with a non-circular cross-section, e.g., an oval cross-section. In addition, one or more sides of the cross-section may be truncated. With the second lumen portion 36B having a non-circular cross-section, the valve 80 may be formed to conform to the cross-section of the second lumen portion 36B.

Figure 67A:
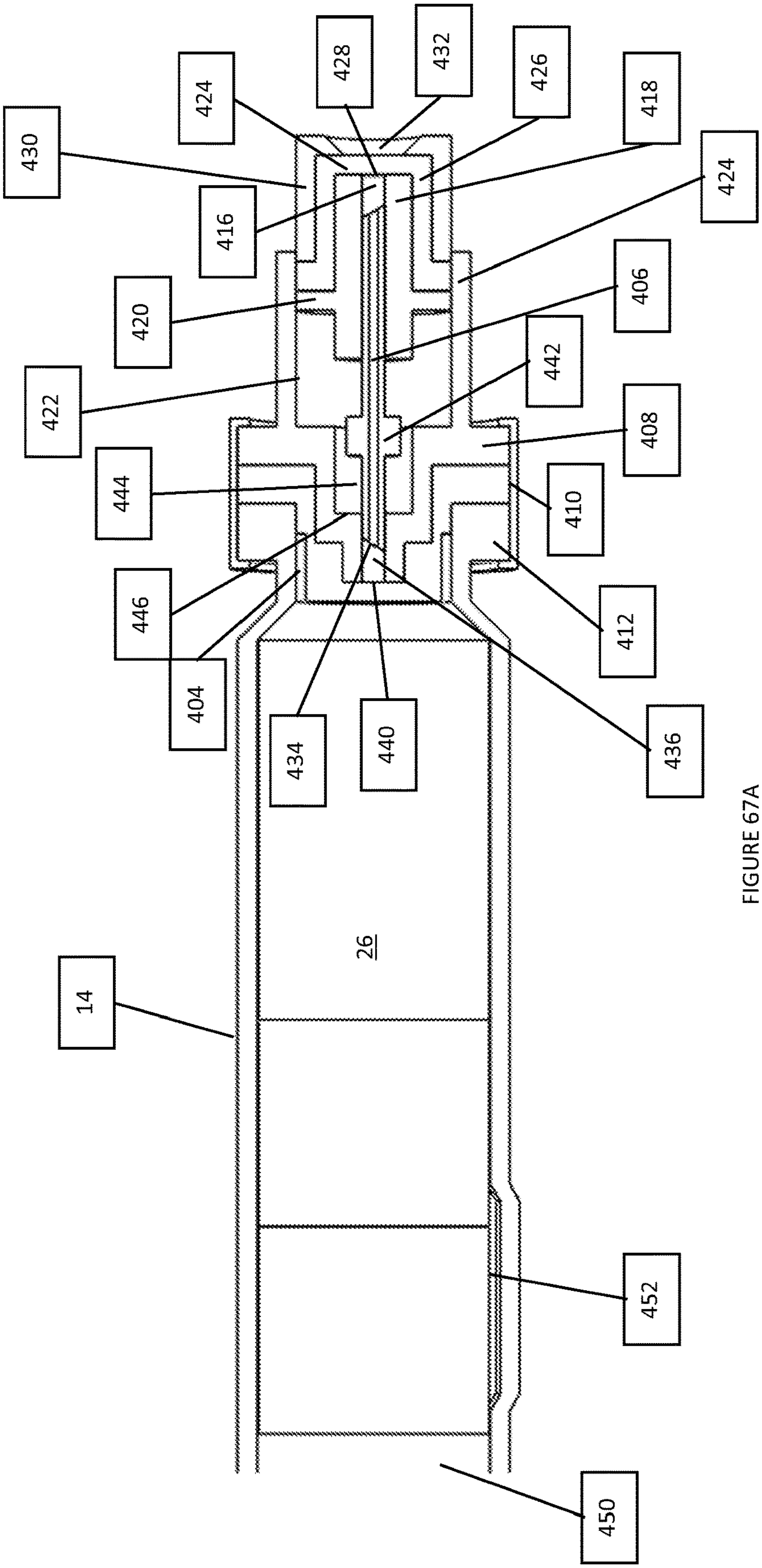
FIG. 67A shows a barrel-configured drug cartridge, in a sealed state, in accordance with the subject invention.
Figure 67B:
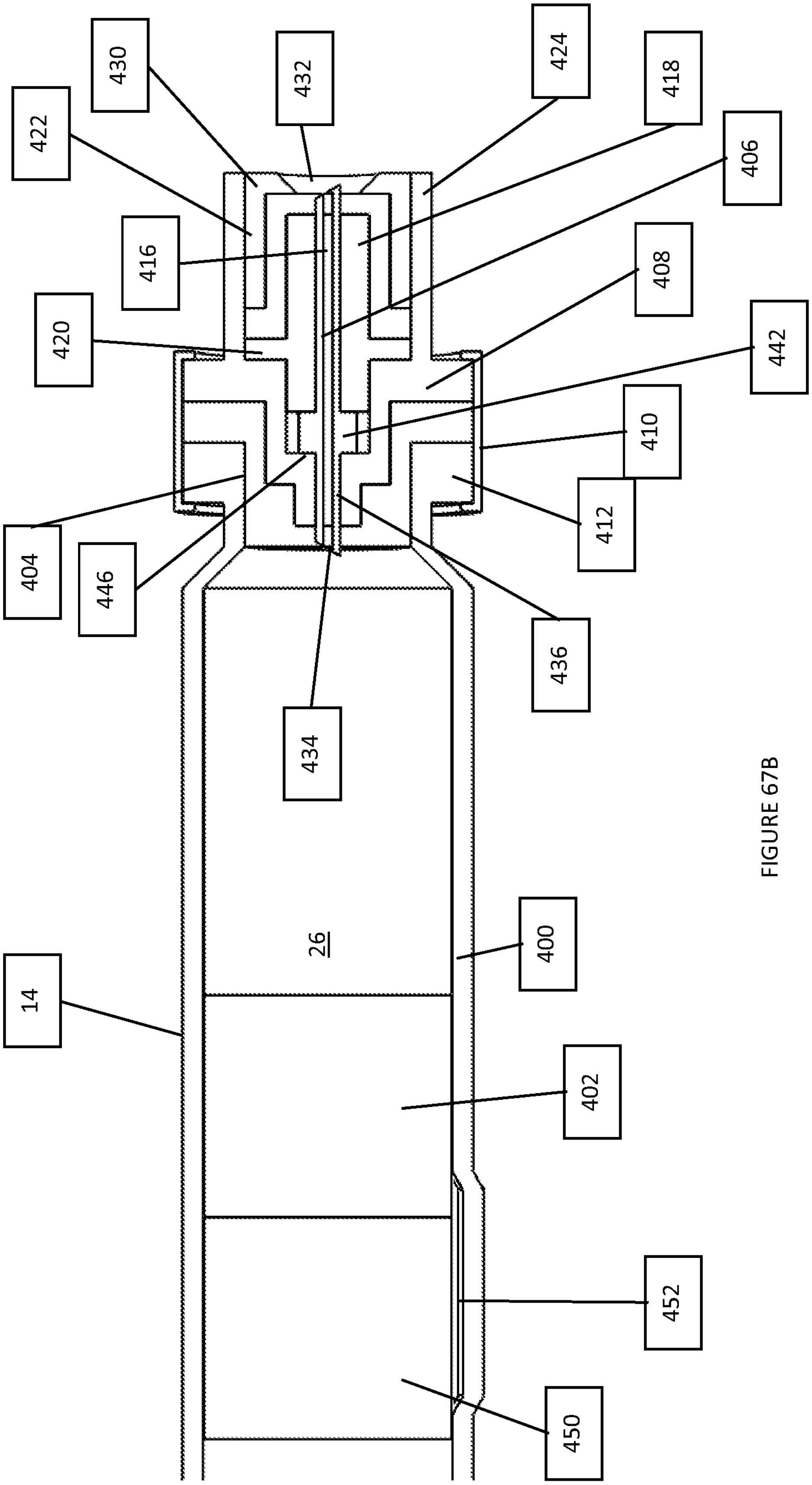
FIG. 67B shows the drug cartridge of FIG. 67A in an actuated state.
Figure 68:
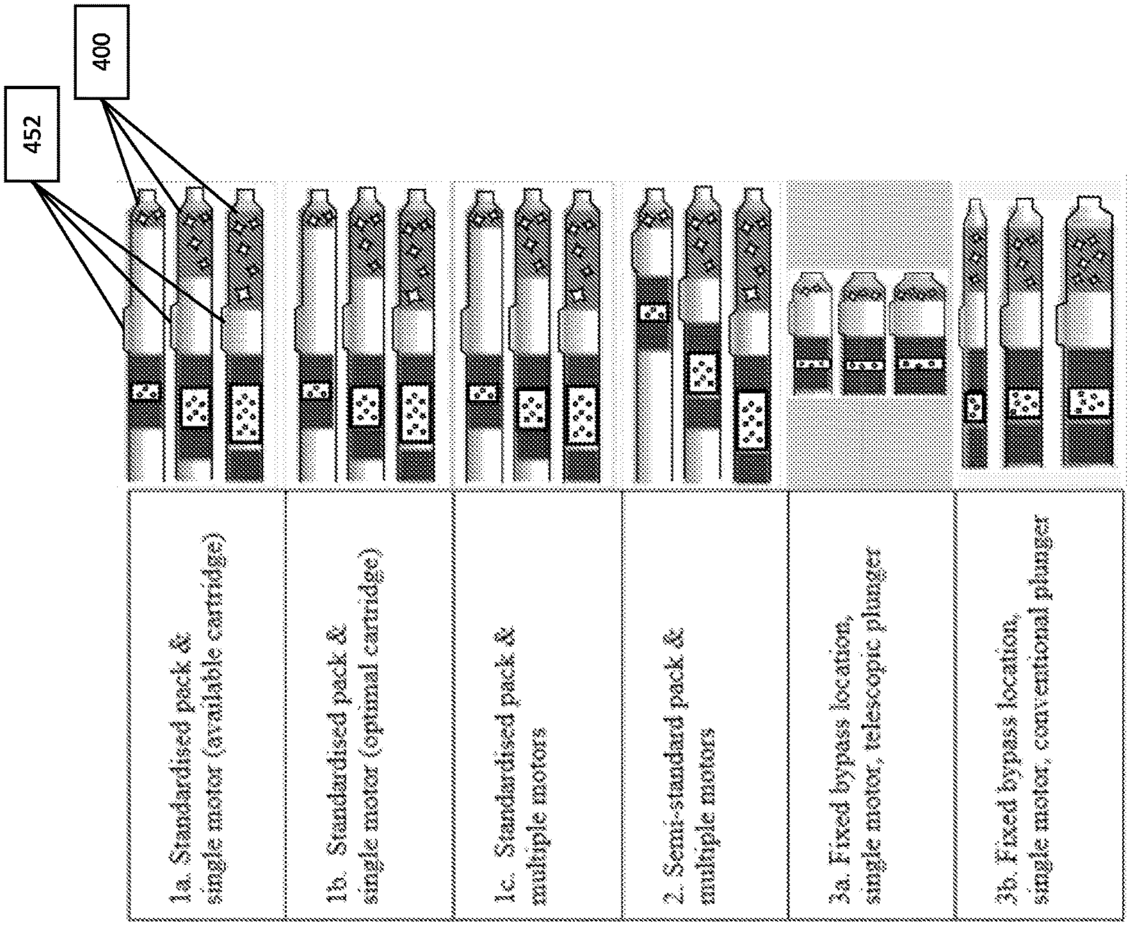
FIG. 68 illustrates various configurations of barrel-configured drug cartridges with by-pass channels.
Figure 69:
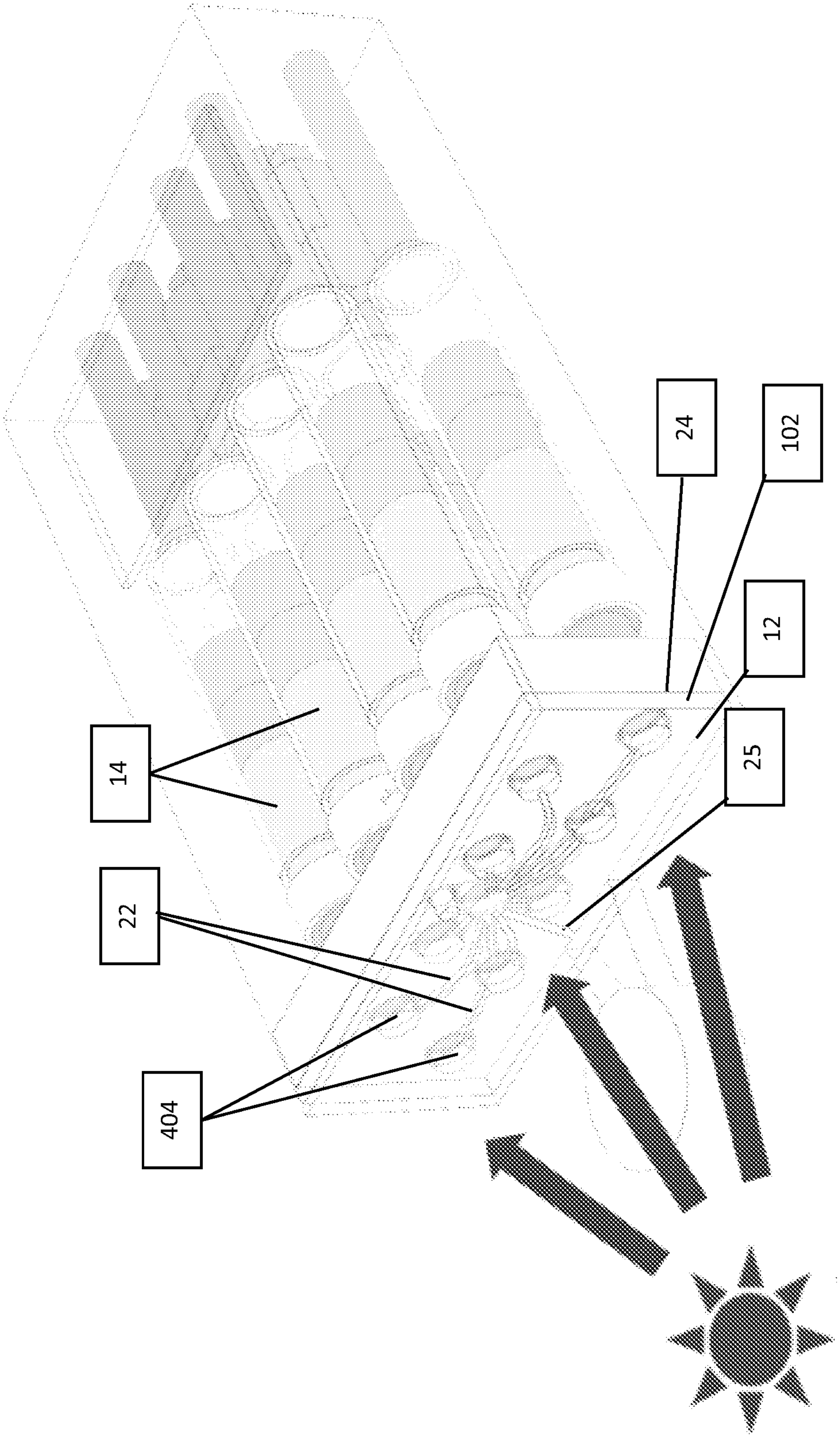
FIG. 69 shows sterilization of a portion of the drug delivery device of FIG. 65.

As shown in FIGS. 65-72, as an alternative to the configuration of drug cartridge 14 described above, the drug cartridges 14 may be configured to include a barrel 400 with a piston 402 configured to slide along therewithin in fluid-tight contact, in some manner as a syringe. Here, the reservoir 26 is defined by the barrel 400 distally of the piston 402 so that distal advancement of the piston 402 causes the reservoir 26 to contract and drug to be expelled therefrom via an outlet 404. As shown in FIG. 69, the outlets 404 may be in communication with the fluid ducts 22, formed in the body 12, leading to one or more of the outlet ducts 25. The fluid ducts 22 may be arranged in parallel between the outlets 404 and/or in series, so that flow passes through one or more of the outlets 404 in being conveyed to the one or more of the outlet ducts 25.

Figure 66:
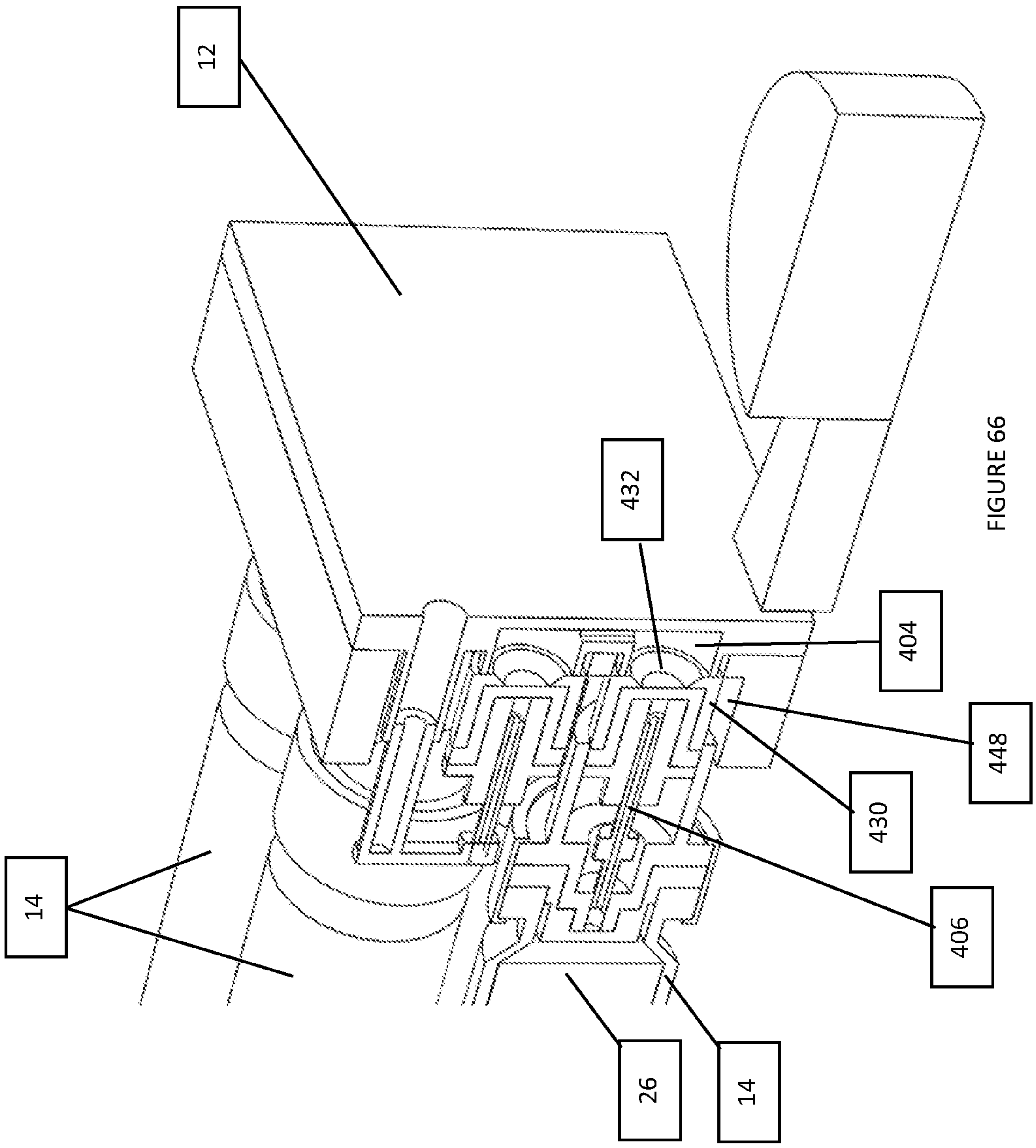
FIG. 66 is a section view of the drug delivery device of FIG. 65.

The outlets 404 may be each sealed to maintain sterility of the reservoir 26 prior to use. With reference to FIGS. 66, 67A, and 67B, for each of the barrels 400, a delivery cannula 406 may be provided, movably disposed within a hub 408 retained by collar 410 to neck 412 of the barrel 400. As shown in FIG. 67A, in a pre-use state, a distal end 414 of the delivery cannula 406 may be seated within open channel 416 of fixing member 418. The fixing member 418 acts to retain the distal end 414 of the delivery cannula 406 in a fixed location. The fixing member 418 may include a radially protruding guide collar 420 formed to slide along an internal surface 422 of guide ring 424, formed on the hub 408 to distally protrude from the collar 410. The guide collar 420 may also act to hold the fixing member 418 in fixed location relative to the guide ring 424.

A distal seal 426 may be provided to span across, and thereby seal, a distal end 428 of the open channel 416. The distal seal 426 may be formed to be cup-shaped with a portion of the fixing member 418 being telescoped therein. The distal seal 426 may include an outer flange 428 in sliding contact with the internal surface 422 of the guide ring 424. A cup-shaped pressing member 430 may be mounted over the distal seal 426 with a needle opening 432 axially aligned with the distal end 414 of the delivery cannula 406. The pressing member 430 is formed to slide within the guide ring 424.

In addition, as shown in FIG. 67A, in the pre-use state, a proximal end 434 of the delivery cannula 406 may be seated with hub channel 436. A proximal seal 438 may be provided to span across, and thereby seal, a proximal end 440 of the hub channel 436.

The fixing member 418 may be formed of an elastomeric material and the open channel 416 may be formed to snugly receive the distal end 414 of the delivery cannula 406. This arrangement will provide for holding force for maintaining the delivery cannula 406 in the position shown in FIG. 67A. It is particularly desired to maintain spacing between the distal end 414 of the delivery cannula 406 and the distal seal 426, and to maintain spacing between the proximal end 434 of the delivery cannula 406 and the proximal seal 438, prior to use. A positioning ring 442 may be provided about the delivery cannula 406, which is spaced from the hub 408 in the pre-use state. The hub 408 may be formed with a hollow 444 distally of the hub channel 436, to accommodate the positioning ring 442. A stop shoulder 446 may be formed about the hub channel 436 at a proximal end of the hollow 444.

The distal seal 426 and the proximal seal 438 may be each formed of an elastomeric material which is pierceable and provides for anti-microbial sealing.

To prepare for use, force is applied to cause the pressing member 430 to move proximally relative to the barrel 400. This results in proximal displacement of the fixing member 418 relative to the hub 408, with proximal movement of the delivery cannula 406 relative to the hub 408, as shown in FIG. 67B. With sufficient proximal displacement, the proximal end 434 of the delivery cannula 406 breaches the proximal seal and comes into communication with the reservoir 26. In addition, the positioning ring 442 comes into contact with the stop shoulder 446 to restrict further proximal movement of the delivery cannula 406. With the delivery cannula 406 being held by the stop shoulder 446, and with further proximal displacement of the fixing member 418 relative to the barrel 400 under force of movement by the pressing member 430, the distal end 414 of the delivery cannula 406 is caused to breach the distal seal 426 to extend through the needle opening 432. This allows for communication with one or more of the fluid ducts 22 via the outlet 404.

With reference to FIG. 66, the pressing members 430 may be seated in recesses 448 formed in the body 12 so as to be non-movably fixed relative to the body 12. The barrels 400 may be caused to be displaced distally relative to the body 12, thus, causing the pressing members 430 to move proximally relative to the barrels 400, as discussed above. This allows for flow paths to be created between the reservoirs 26 of the barrels and the fluid ducts 22.

As shown in FIG. 65, the drug delivery device 10 may also include plungers 450, each aligned with one of the barrels 400, to extend thereinto and cause distal displacement of the respective piston 402. The barrels 400 are open-ended (at the proximal ends) to allow the plungers 450 to enter into the barrels 400 in engaging the pistons 402. It is noted that, with the barrels 400 be sealed as described above, and with the reservoirs 26 containing drug in incompressible form (solid or liquid), the distally-directed pressing of the pistons 402, by the plungers 450, shall result in distal displacement of the barrels 400. With sufficient distal displacement, the proximal movement of the pressing members 430 relative to the barrels 400, as described above, may be achieved.

With the drug cartridges 14 being configured to include the barrels 400, any barrel configuration may be utilized. For example, as shown in FIGS. 67A, 67B, and 68, one or more of the barrels 400 may be provided with by-pass channels 452. As will be recognized by those skilled in the art, the by-pass channels 452 allow for two- or more part mixing within the barrels 400. The piston 402 of a barrel 400 may be initially located to separate the reservoir 26 into two parts, each containing a separate component (liquid-liquid or liquid-dry combinations). With distal advancement of the piston 402, the components may be brought together with mixing and/or reconstitution transpiring. FIG. 68 shows schematically different possible arrangements for multi-component mixing or reconstitution.

In addition, as shown in FIGS. 70-72 and 74-78, the barrels 400 may be disposed about the circumference of the body 12. With reference to FIGS. 74-78, one of the plungers 450 may be utilized which is rotatable relative to the body 12 to come into selective alignment with the barrels 400. The plunger 450 may be bi-directionally rotatable, allowing for rapid alignment with the barrels 400 in sequence, as needed. In addition, the barrels 400 may contain two or more drug components, separated by moveable pistons 402, each formed to sealingly slide along the inside of one of the barrels 400. For example, within one or more of the barrels 400, a first drug component 456 may be provided, separated by the piston 402, from a second drug component 457. Configurations for barrels/movable pistons to allow for reconstitution and/or mixing are known in the art. For example, as is known in the art, the by-pass channel 452 may be provided in each of the barrels 400 which allows first and second drug components 456, 457 to mix upon sufficient displacement of the piston 402. The second drug component 457 may be in liquid form, and incompressible, thus transmitting force of movement from the plunger 450 to the piston 402, through the second drug component 457. The barrels 400 may be open-ended to accept the plunger 450 with the outlets 404 of the barrels 400 being directed radially outwardly from the body 12. Secondary pistons 461 may be provided to seal the second drug components 457 within the barrels 400. For each of the barrels 400, the plunger 450 may be caused to pressingly engage the secondary piston 461 in causing displacement thereof, resulting in displacement of the piston 402, with force of movement being transmitted through the second drug component. With sufficient displacement of the piston 402, the piston 402 overlaps with the by-pass channel 452, thereby creating a fluid pathway across the piston 402 between the first and second drug components 456, 457. With further displacement of the secondary piston 461, the second drug component 457 is urged through the by-pass channel 452 to mix with the first drug component 456. Further displacement causes the secondary piston 461 to come into engagement with the piston 402. With even further displacement, the secondary piston 461 and the piston 402 are collectively displaced causing the mixed first and second drug components 456, 457 to be expelled from the outlet 404, as shown in FIGS. 75-78.

Figure 70:
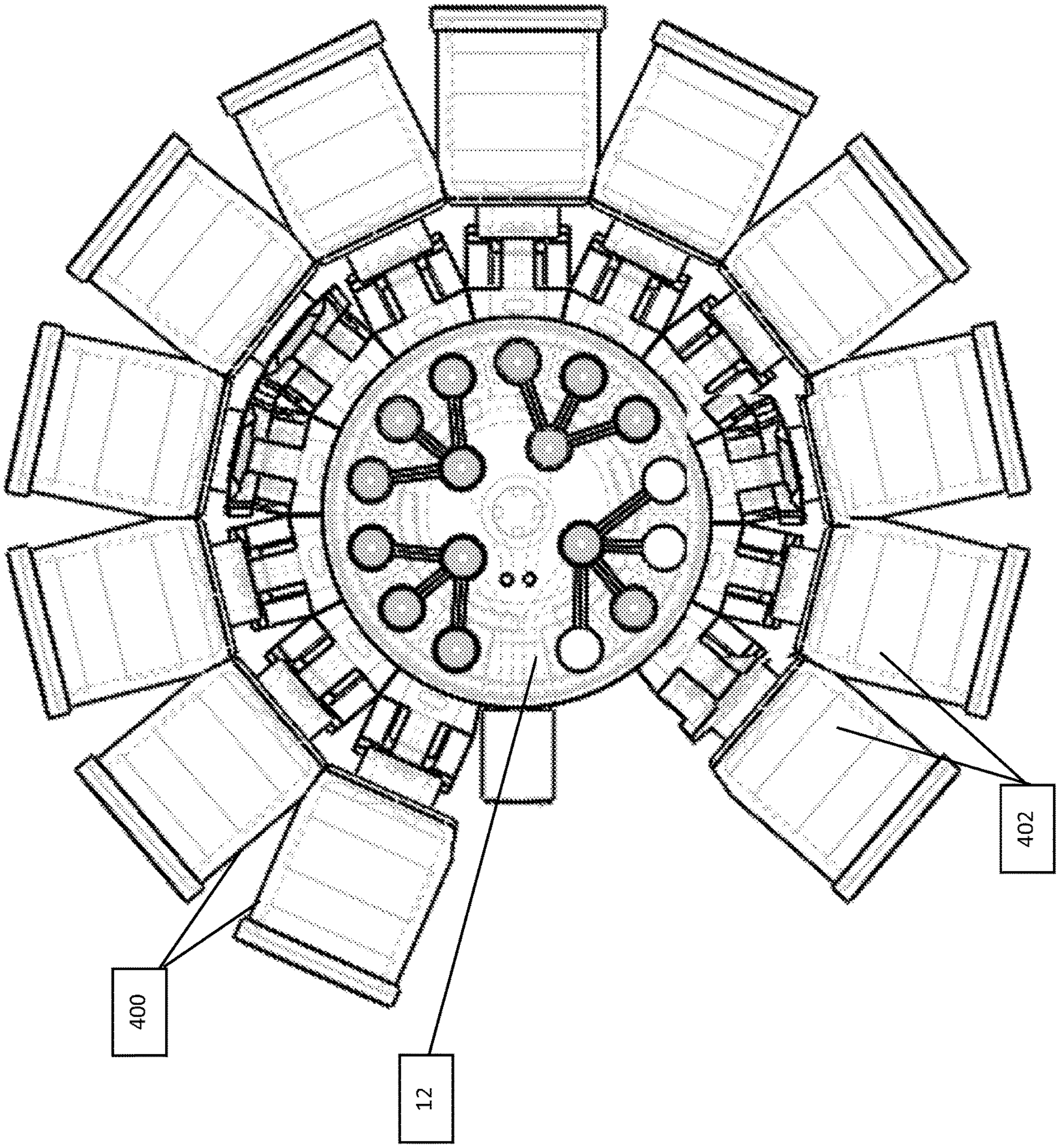
FIG. 70 shows a drug delivery device with an alternate barrel-configured drug cartridge, in accordance with the subject invention.
Figure 71:
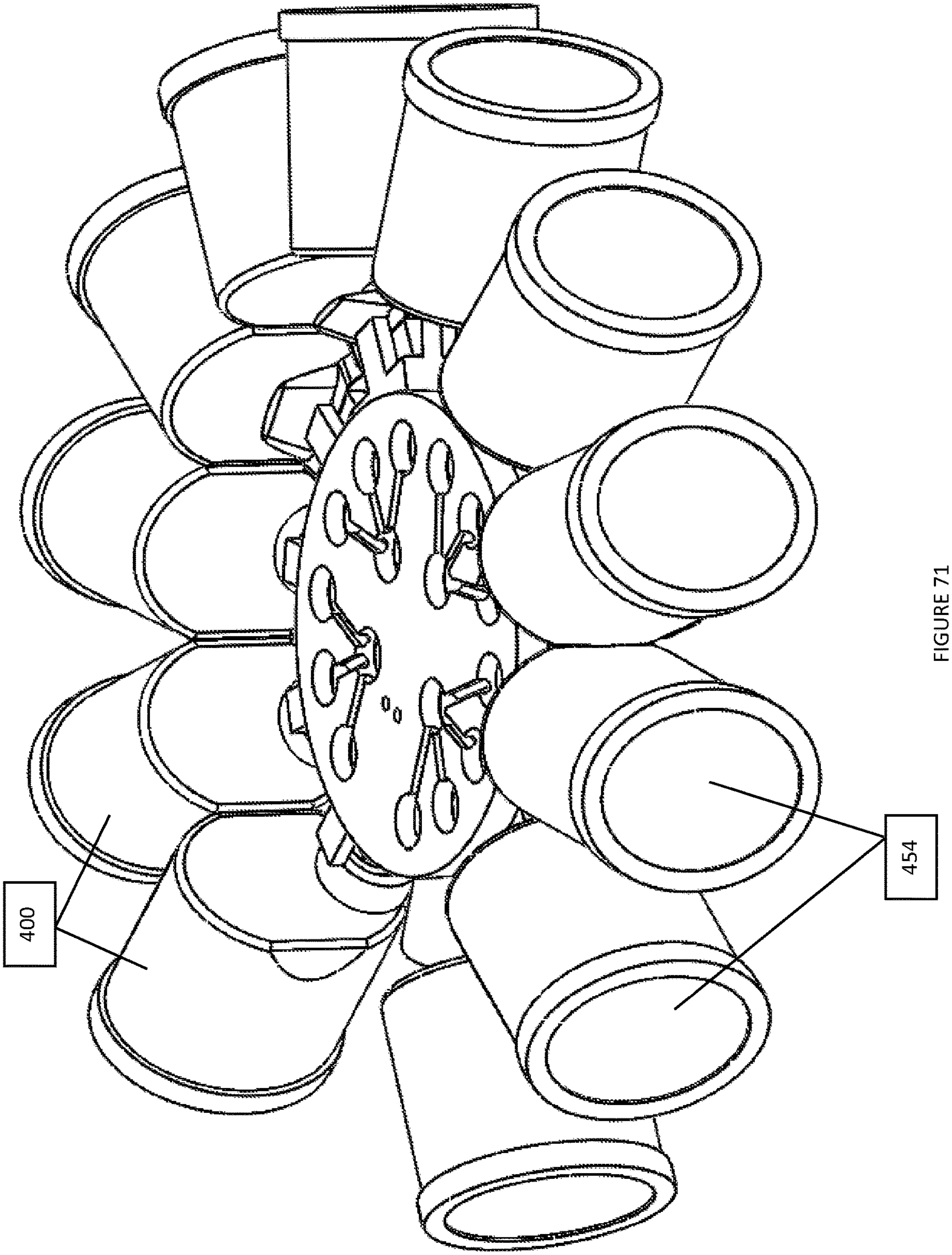
FIG. 71 is an isometric view of the drug delivery device of FIG. 70.
Figure 72:
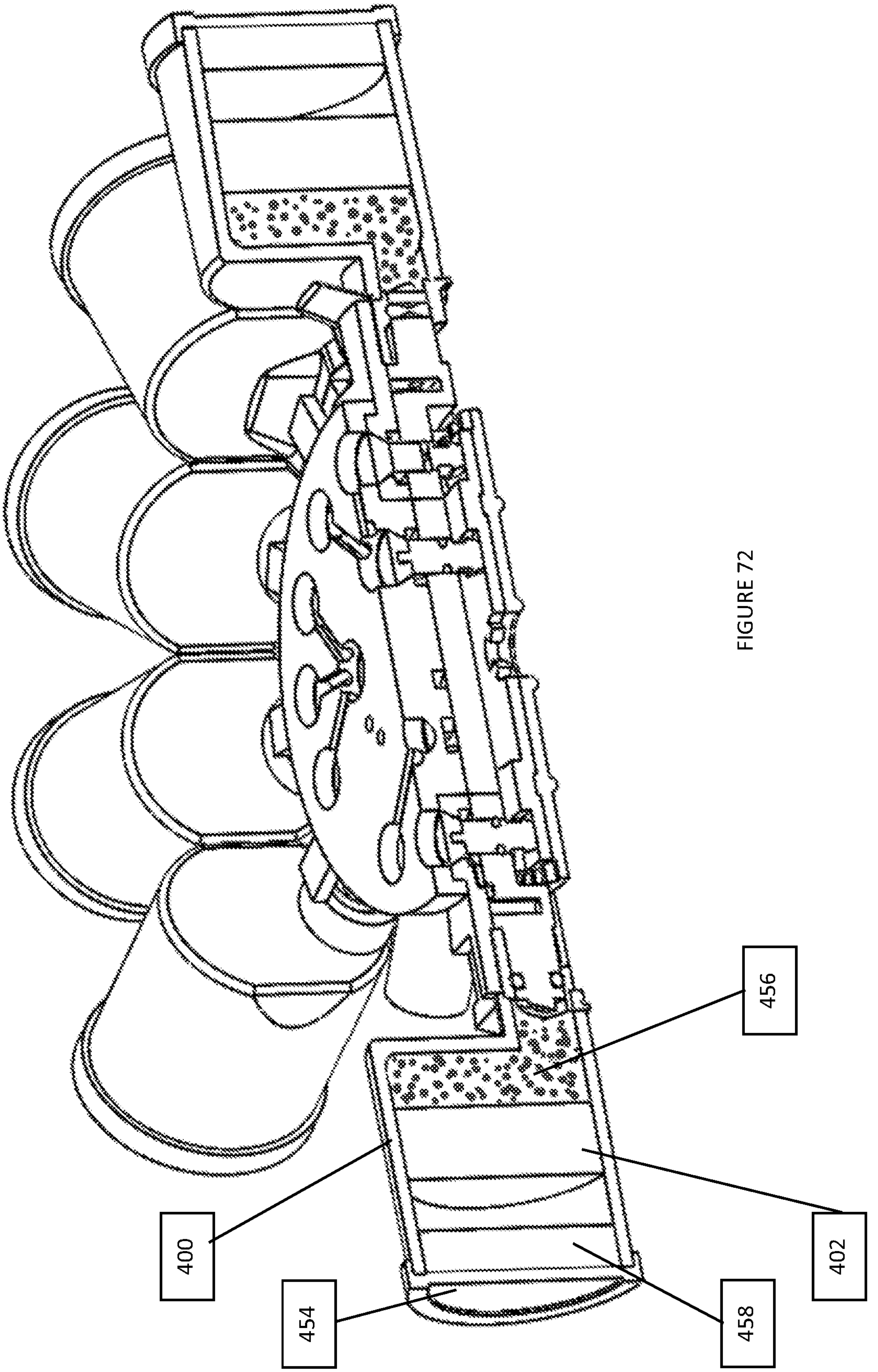
FIG. 72 is a section view of the drug delivery device of FIG. 70.

In addition, as shown in FIGS. 70-72, the barrels 400 may be configured to accommodate the first drug component 456, which may be in a dry state or a liquid state, and mixed with at least one further liquid component, introduced into the barrels 400 via the body 12. In this manner, the drug component 456 may be reconstituted and/or mixed with one or more other drug components provided from outside the respective barrels 400. Pistons 402 may be used to delineate a reduced volume within each of the barrels 400, for the first drug component 456, prior to use. This allows for a limited-volume pocket to be defined to house the first drug components 456 in a compacted state. With diluent or other liquid being pumped into the barrels 400, the pistons 402 may be displaced (e.g., radially outwardly), thus increasing the volume inside the barrels 400 about the first drug components 456, in reconstituting the first drug components 456 and/or forming a mixture therewith. Once prepared, the resulting reconstituted drug or drug mixture may be withdrawn from the barrels 400 via the body 12, e.g., by negative pressure generated by the pump 18. The barrels 400 in this configuration may be closed-ended, e.g., with rear seals 454 sealing the proximal ends thereof to define a sterile envelope for the interior of each of the barrels 400. The rear seals 454 may be vented to allow for pressure equilibration with displacement of the pistons 402. For example, the rear seals 454 may each include a micro-filtration element (e.g., 0.2 micron filtration element) to provide sterile venting, whereby air may be expelled from the barrels 400 with ingress of microbes thereinto being inhibited. In addition, one or more spacers 458 may be provided rearwardly of the pistons 402 to limit travel thereof. The spacers 458 may be used to control the permissible displacement of the pistons 402, thereby controlling the permissible resulting volumes for drug component 456 and any introduced other component(s). This allows for control over the volume and concentration of any resulting reconstituted drug or mixture. The spacers 458 may be porous or have openings to allow for free movement of air therethrough with displacement of the pistons 402.

Various arrangements, in addition to the valve 80 and the sealing sheet 1906, may be utilized to form the seal on the drug cartridge 14, e.g., forming a seal on the plug adapter 14B across the sterilized internal lumen 36. These arrangements provide for a seal which will require further sterilization, like the arrangement utilizing the valve 80 or the sealing sheet 1906. This category of seals shall be referenced as the "non-sterile connection seal arrangements." In addition, seal arrangements may be provided which provide for sterile connection to the body 12 of the drug delivery device 10, thus eliminating the need for later sterilization of the drug cartridge 14, including the fluid outlet 34. This category of seals shall be referenced as the "sterile connection seal arrangements." It is noted that certain arrangements may provide for the seal to be located within the internal lumen 36 and certain arrangements provide for the seal to be located external of the fluid outlet 34.

Figure 36A:
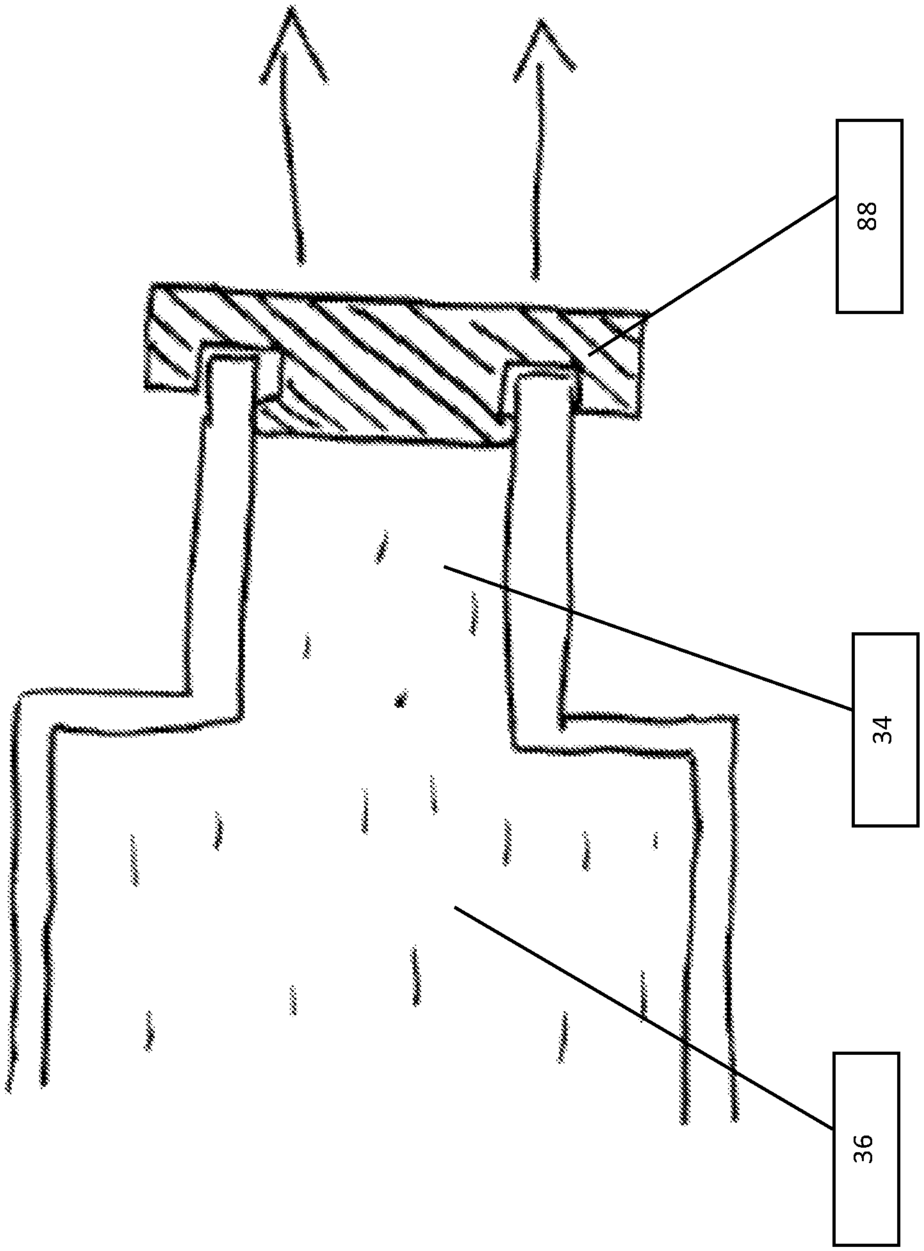
FIG. 36A shows a method of accessing a drug cartridge by translating a plug, in accordance with the subject invention.
Figure 36B:
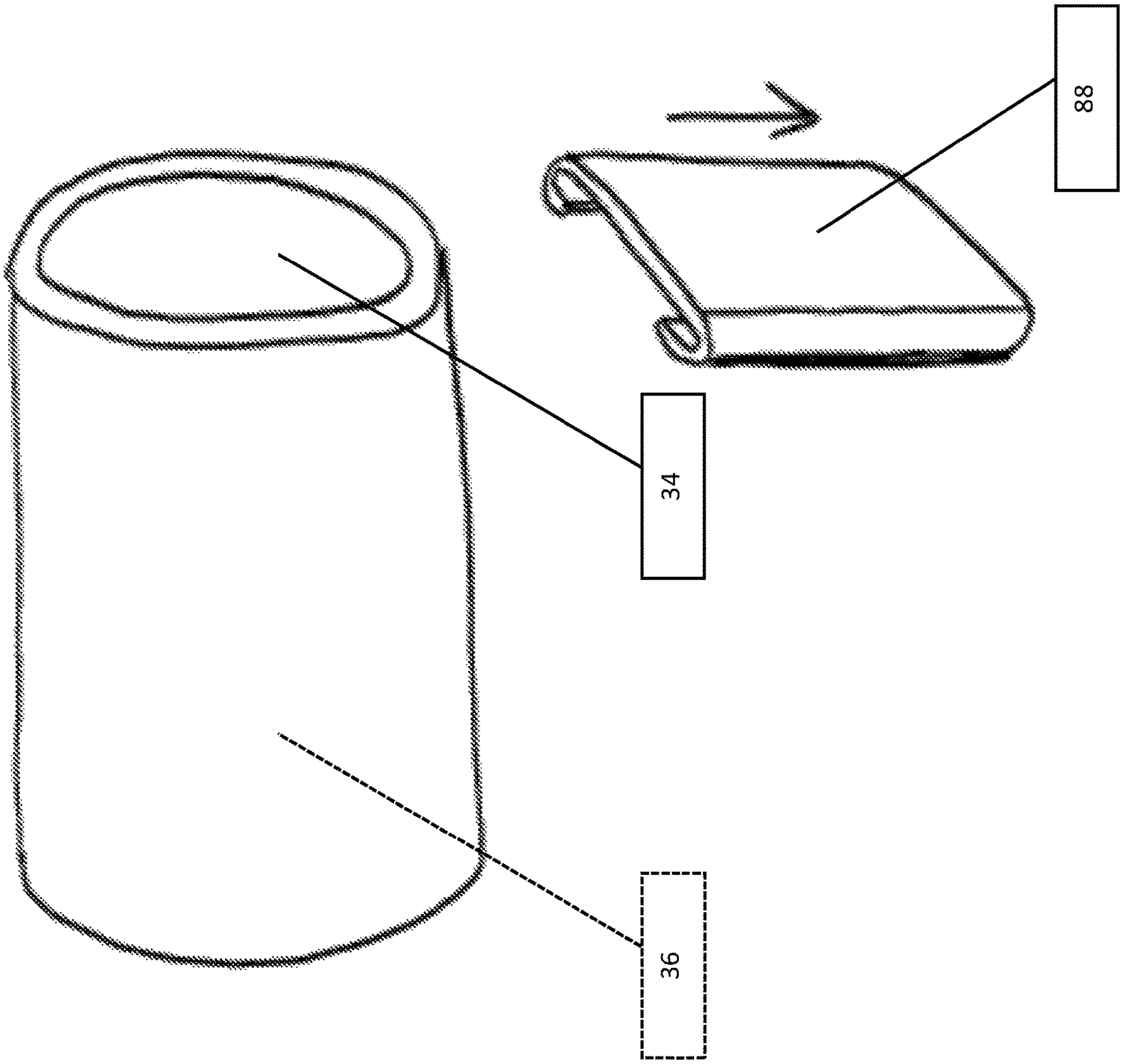
FIG. 36B shows a method of accessing a drug cartridge by sliding a seal away from an outlet, in accordance with the subject invention.
Figure 36C:
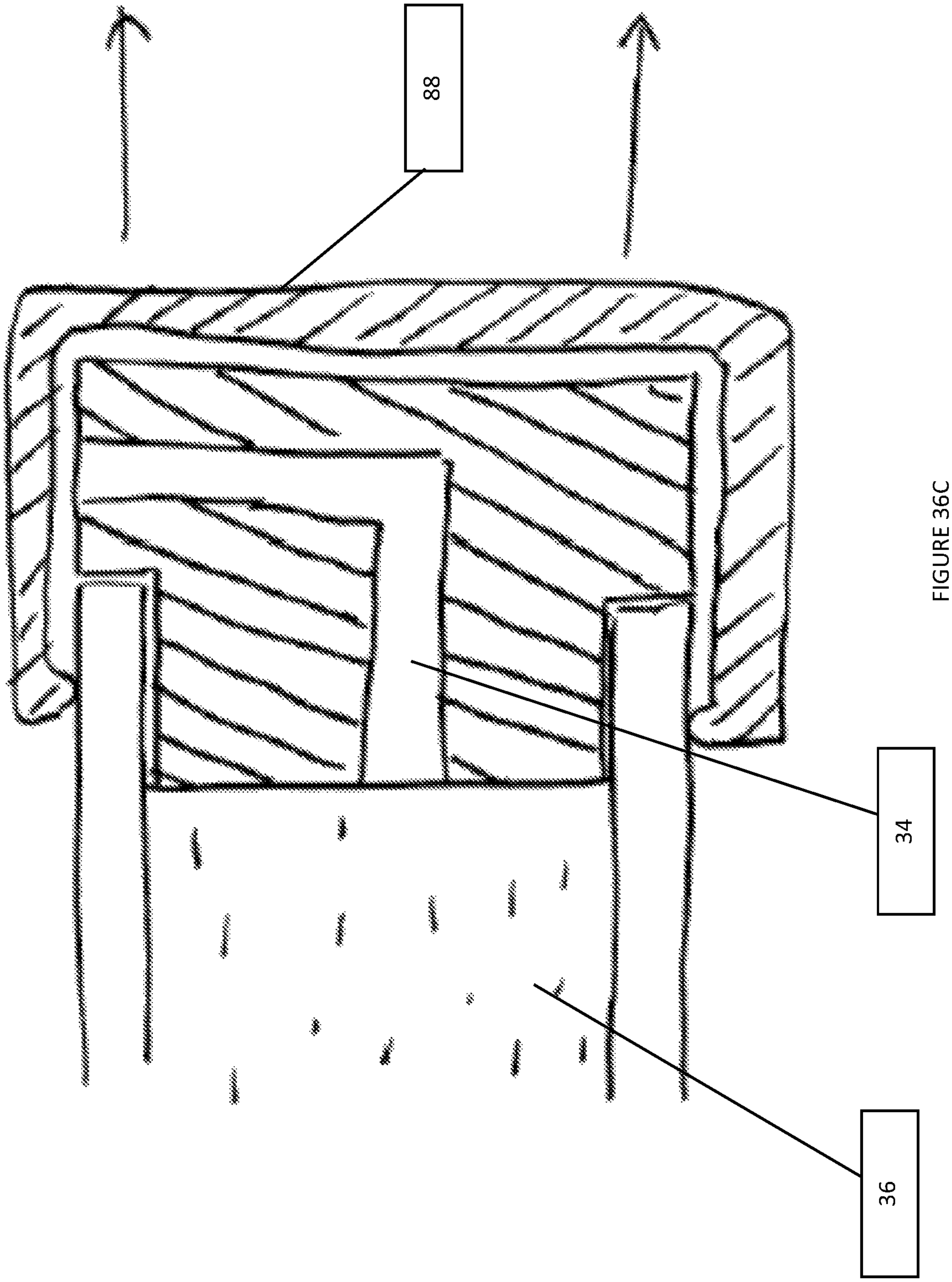
FIG. 36C shows a method of accessing a drug cartridge by translating a lid, in accordance with the subject invention.
Figure 36D:
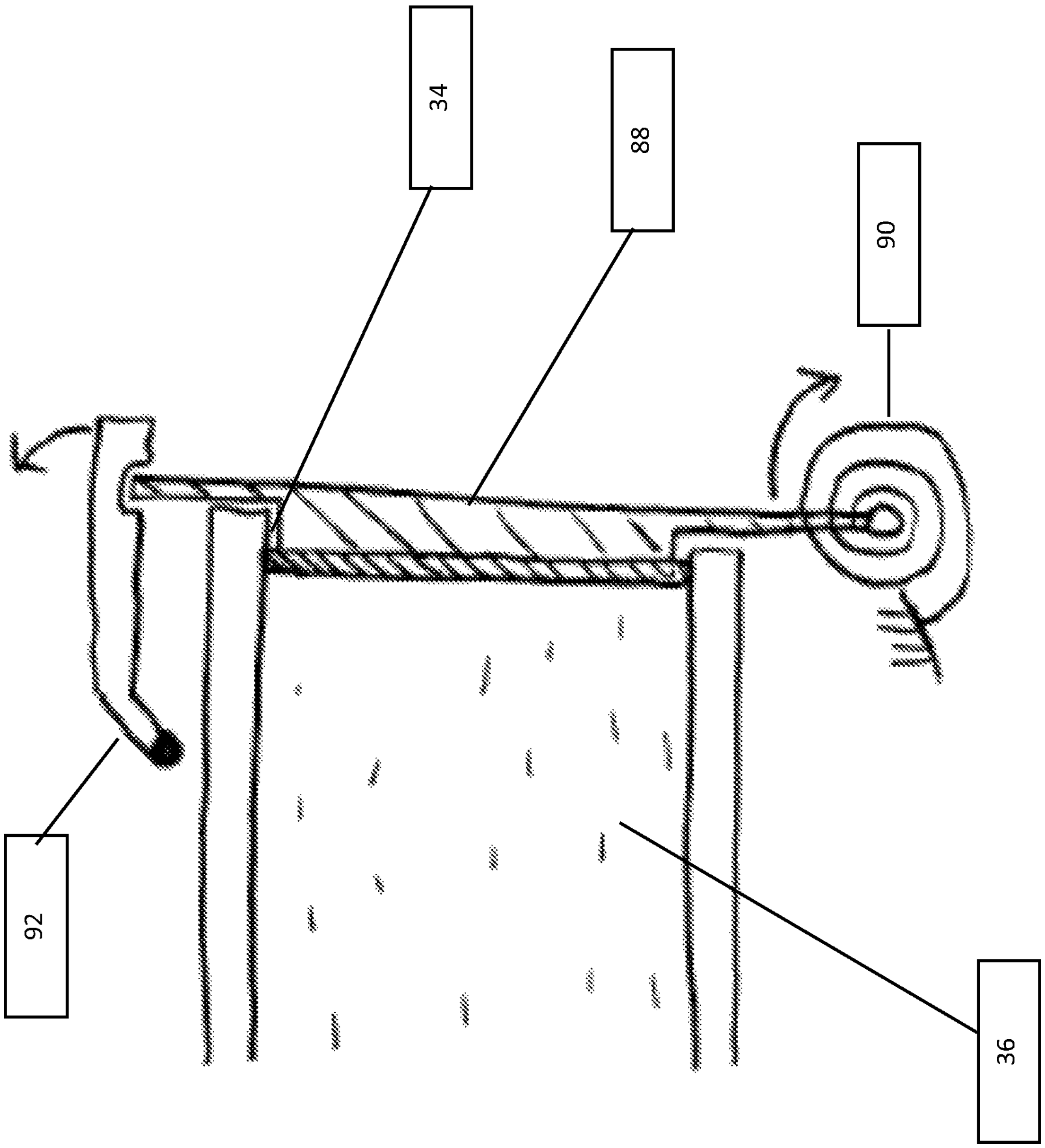
FIG. 36D shows a method of accessing a drug cartridge by opening a latch, in accordance with the subject invention.
Figure 36E:
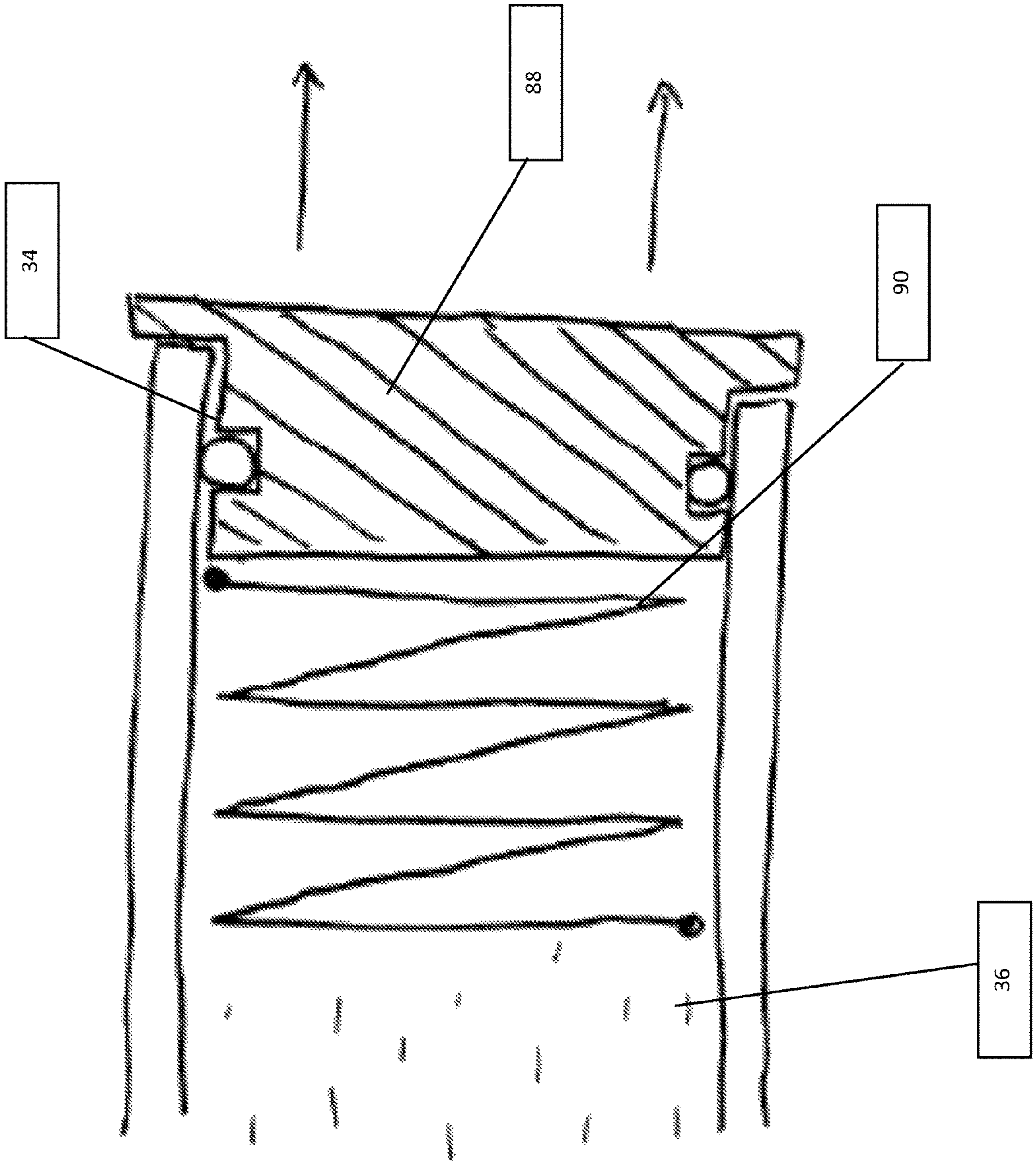
FIG. 36E shows a method of accessing a drug cartridge by translating a plug using an internal spring, in accordance with the subject invention.

FIGS. 36A-38B show different non-sterile connection seal arrangements useable with the subject invention as alternatives to the valve 80 or the delivery cannula 406. With reference to FIGS. 36A-36E, a removable cap or plug 88 may be provided, which may be formed to resiliently engage a portion of the fluid outlet 34 and/or the internal lumen 36 (FIGS. 36A and 36E). As shown in FIGS. 36B-36D, the cap or plug 88 may be removably mounted to portions of the plug adapter 14B about the fluid outlet 34 and/or the inner lumen 36. As shown in FIGS. 36D and 36E, a spring or other biasing mechanism 90 may be provided to assist in removal of the cap or plug 88. A latch 92 may be provided to resist the biasing force of the spring 90 in maintaining the cap or plug 88 in place until proper time for removal.

Figure 37A:
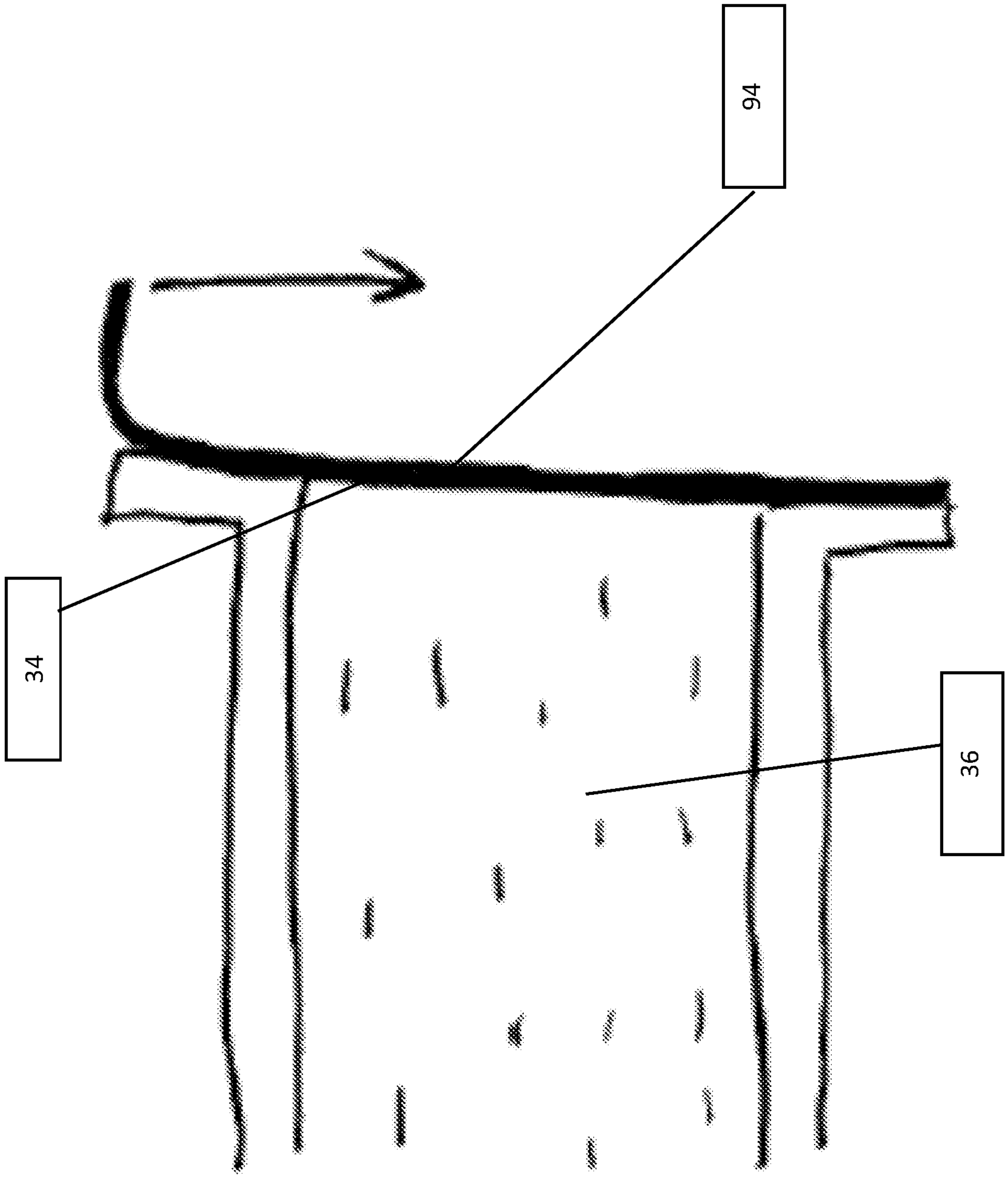
FIG. 37A shows a method of accessing a drug cartridge by peeling a film, in accordance with the subject invention.
Figure 37B:
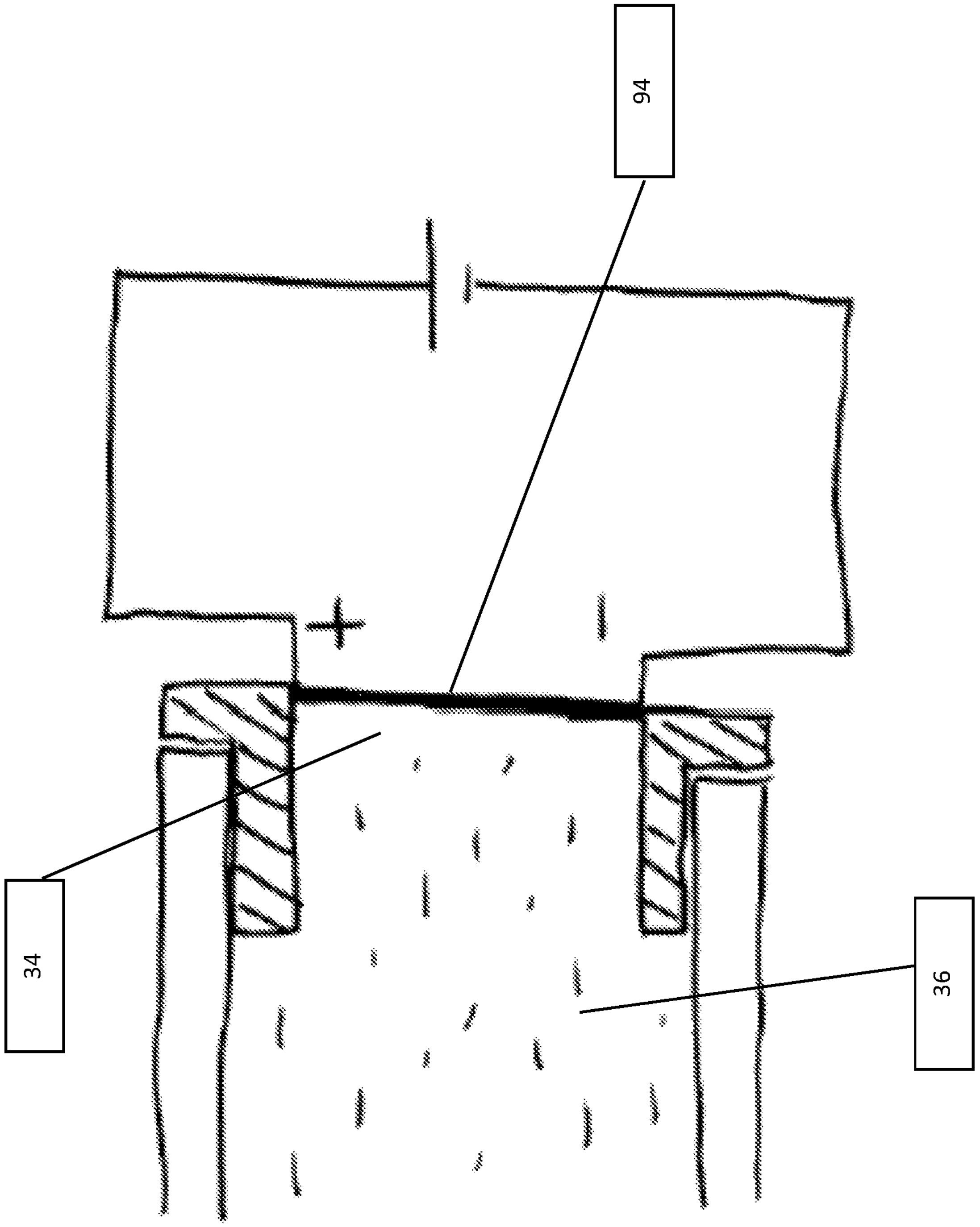
FIG. 37B shows a method of accessing a drug cartridge by rupturing a film with an electromotive force, in accordance with the subject invention.
Figure 37C:
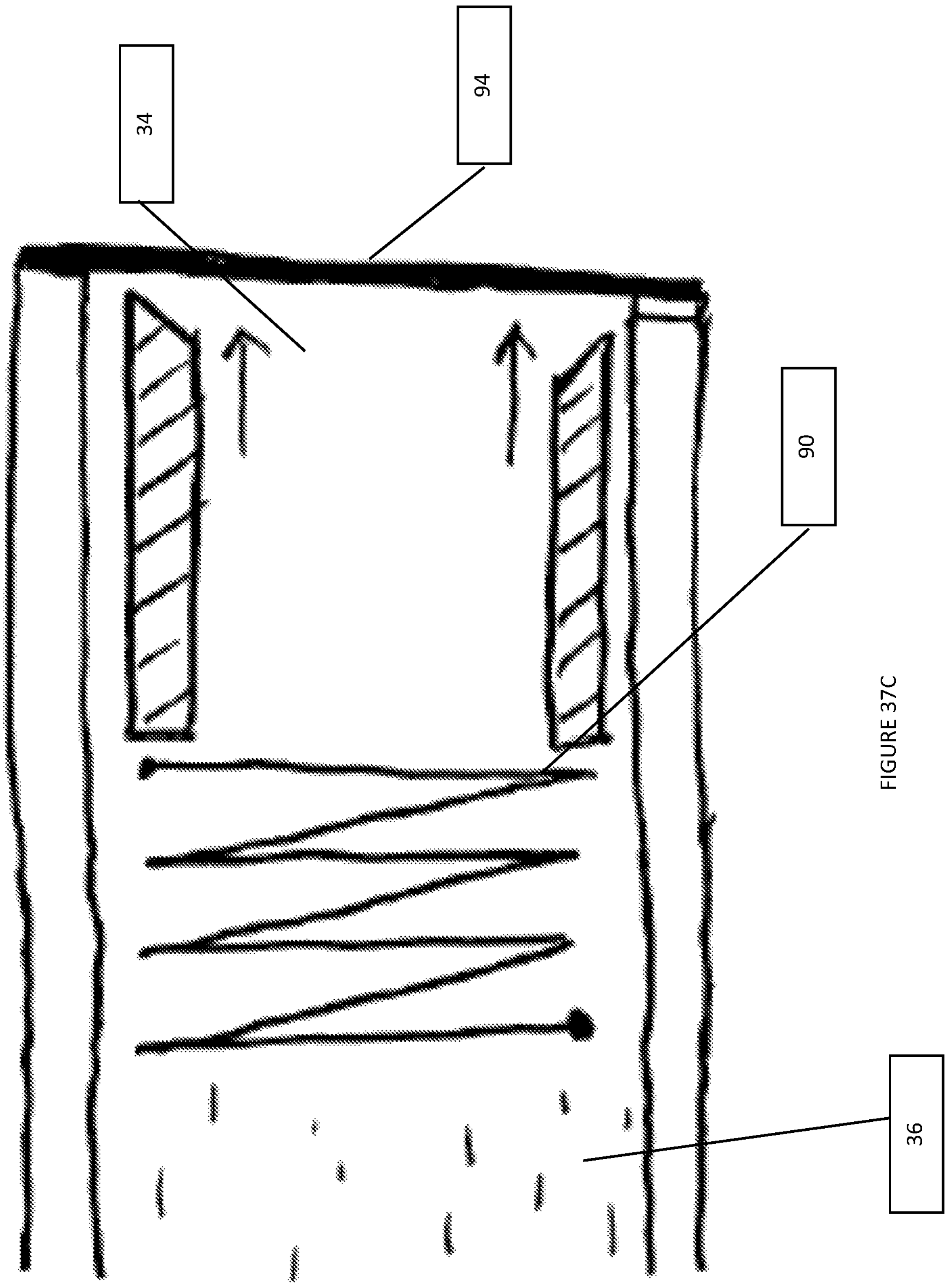
FIG. 37C shows a method of accessing a drug cartridge by rupturing a film using spring force, in accordance with the subject invention.
Figure 37D:
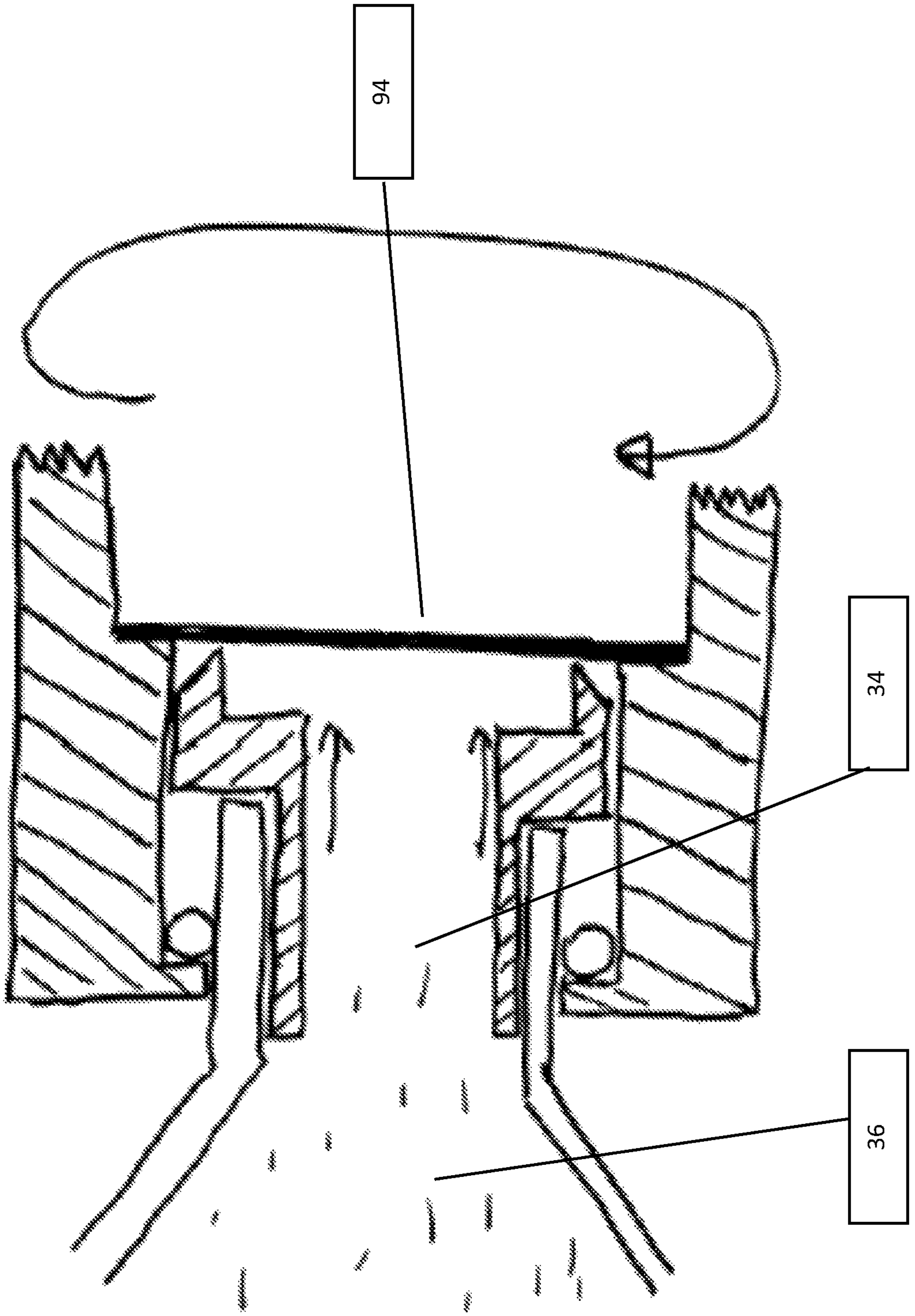
FIG. 37D shows a method of accessing a drug cartridge by cutting a film using rotational movement, in accordance with the subject invention.

Alternatively, as shown in FIGS. 37A-37D, a film 94 may be applied across portions of the plug adapter 14B to cover, and seal, the fluid outlet 34 and the internal lumen 36. As shown in FIG. 37A, the film 94 may be peelable. As shown in FIGS. 37B-37D, the film 94 may be rupturable, possibly using electromotive force (FIG. 37B), spring force (FIG. 37C), and/or mechanical force (FIG. 37D).

Figure 38A:
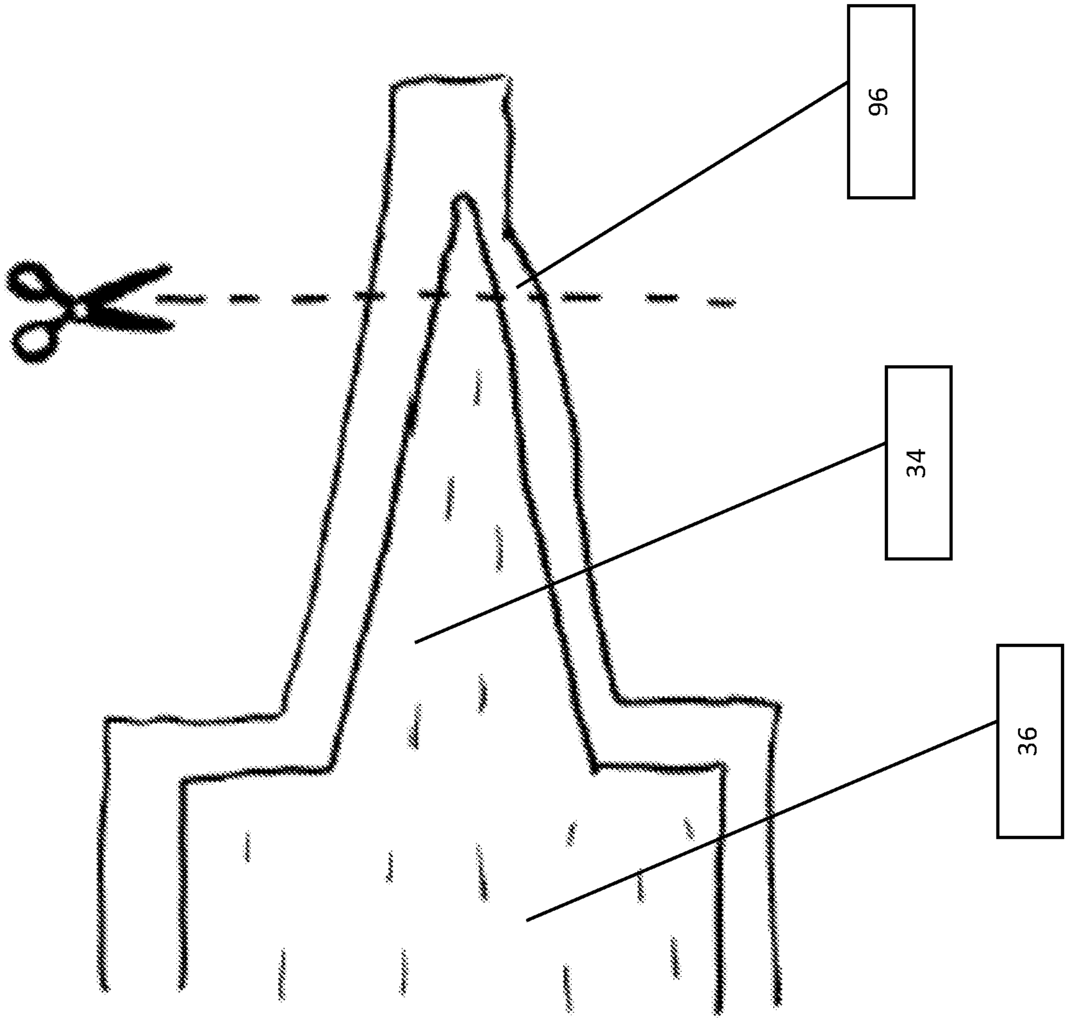
FIG. 38A shows a method of accessing a drug cartridge by cutting along a score line, in accordance with the subject invention.
Figure 38B:
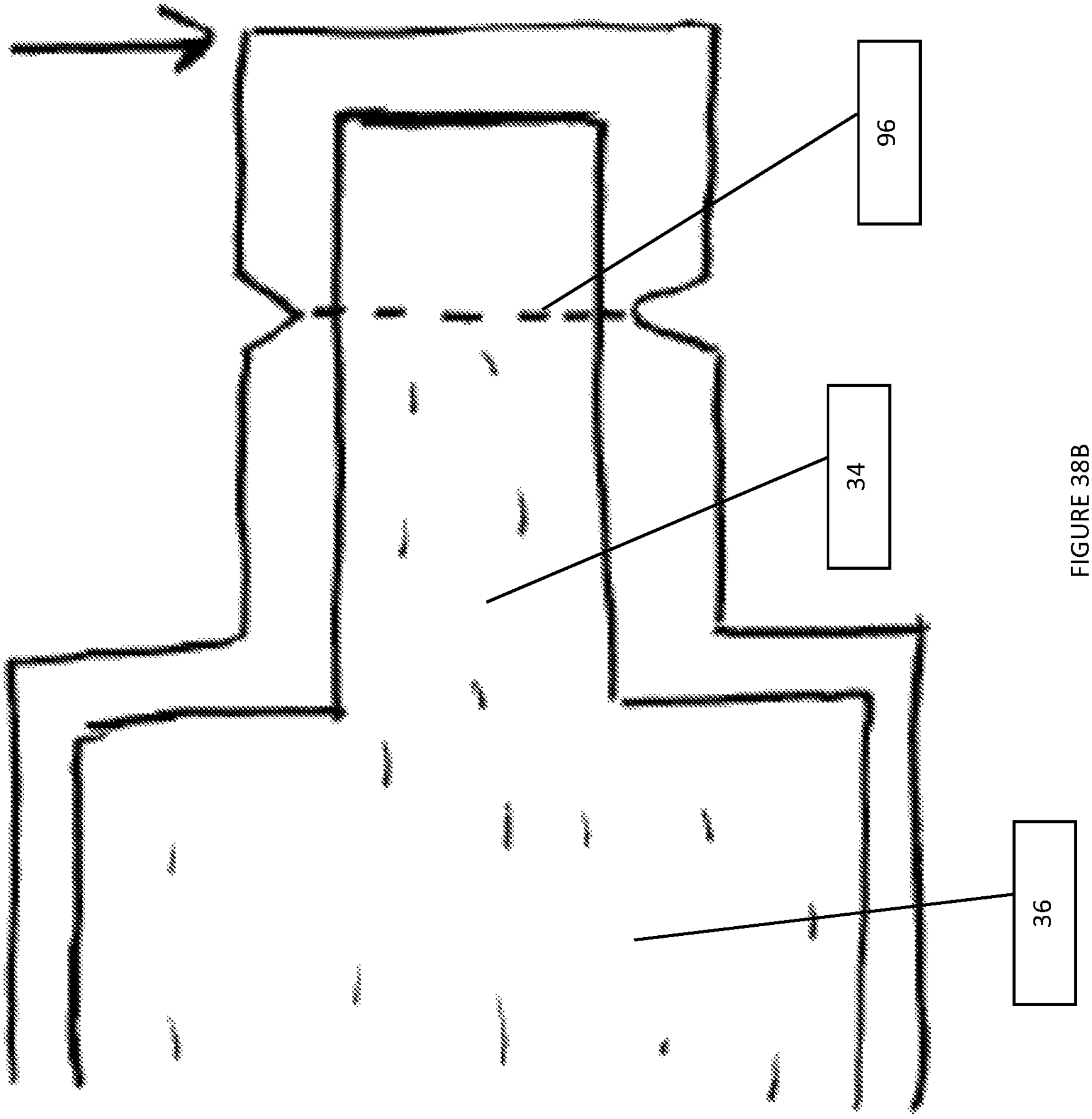
FIG. 38B shows a method of accessing a drug cartridge by shearing along a score line, in accordance with the subject invention.

Further, as shown in FIGS. 38A-38B, portions of the plug adaptor 14B may be heat sealed or otherwise joined to form a continuous seal across the fluid outlet 34 and the internal lumen 36. As shown in FIG. 38A, this seal may be cut or otherwise disrupted to open the seal and expose the fluid outlet 34. As an alternative, as shown in FIG. 38B, one or more score lines 96 may be provided to define line(s) of weakness allowing for removable of a portion of the seal to expose the fluid outlet 34.

Figure 39A:
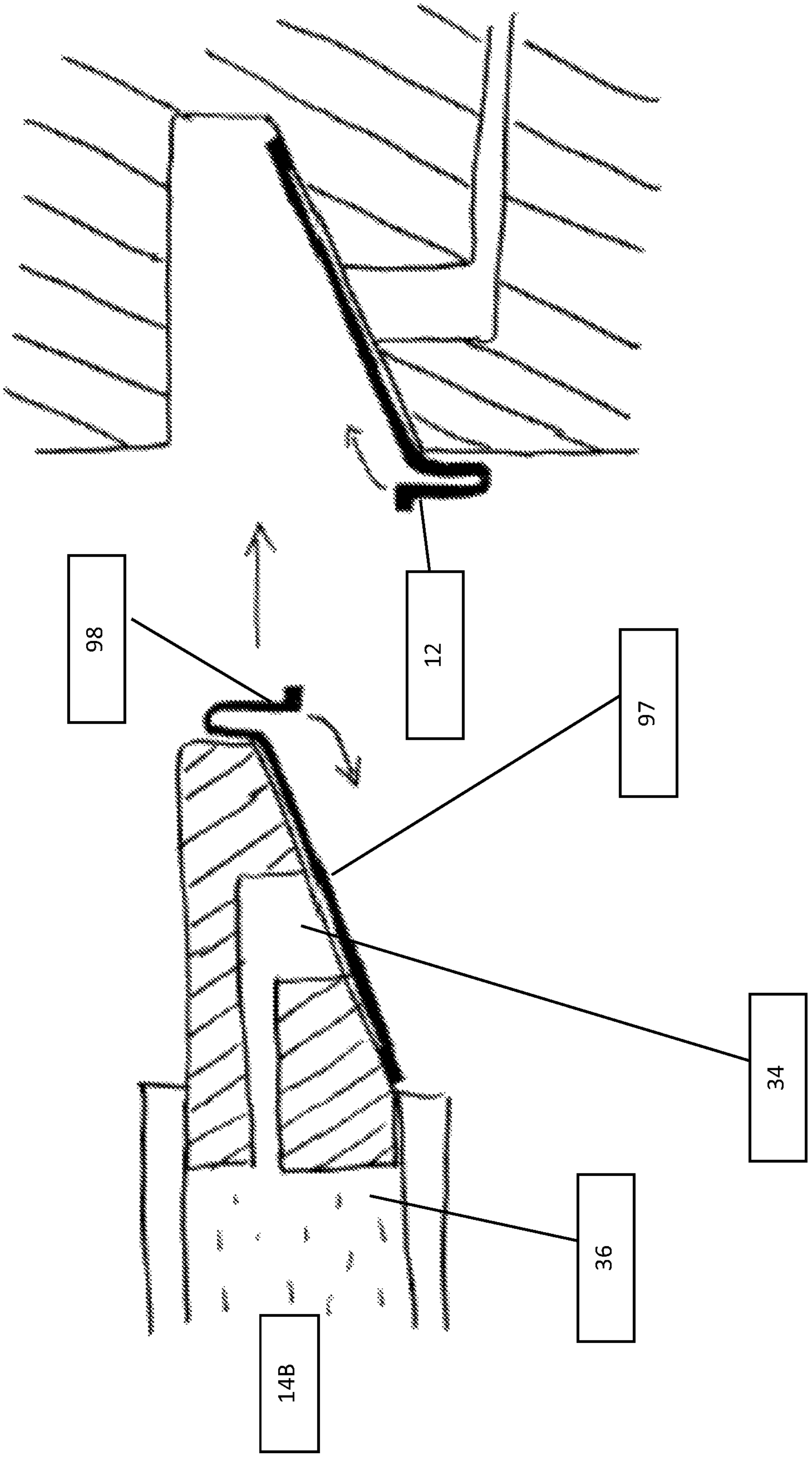
FIG. 39A shows a method of accessing a drug cartridge by engaging two edges of film covering the fluid path, in accordance with the subject invention. In this illustration, the film is mounted to flat surfaces.
Figure 39B:
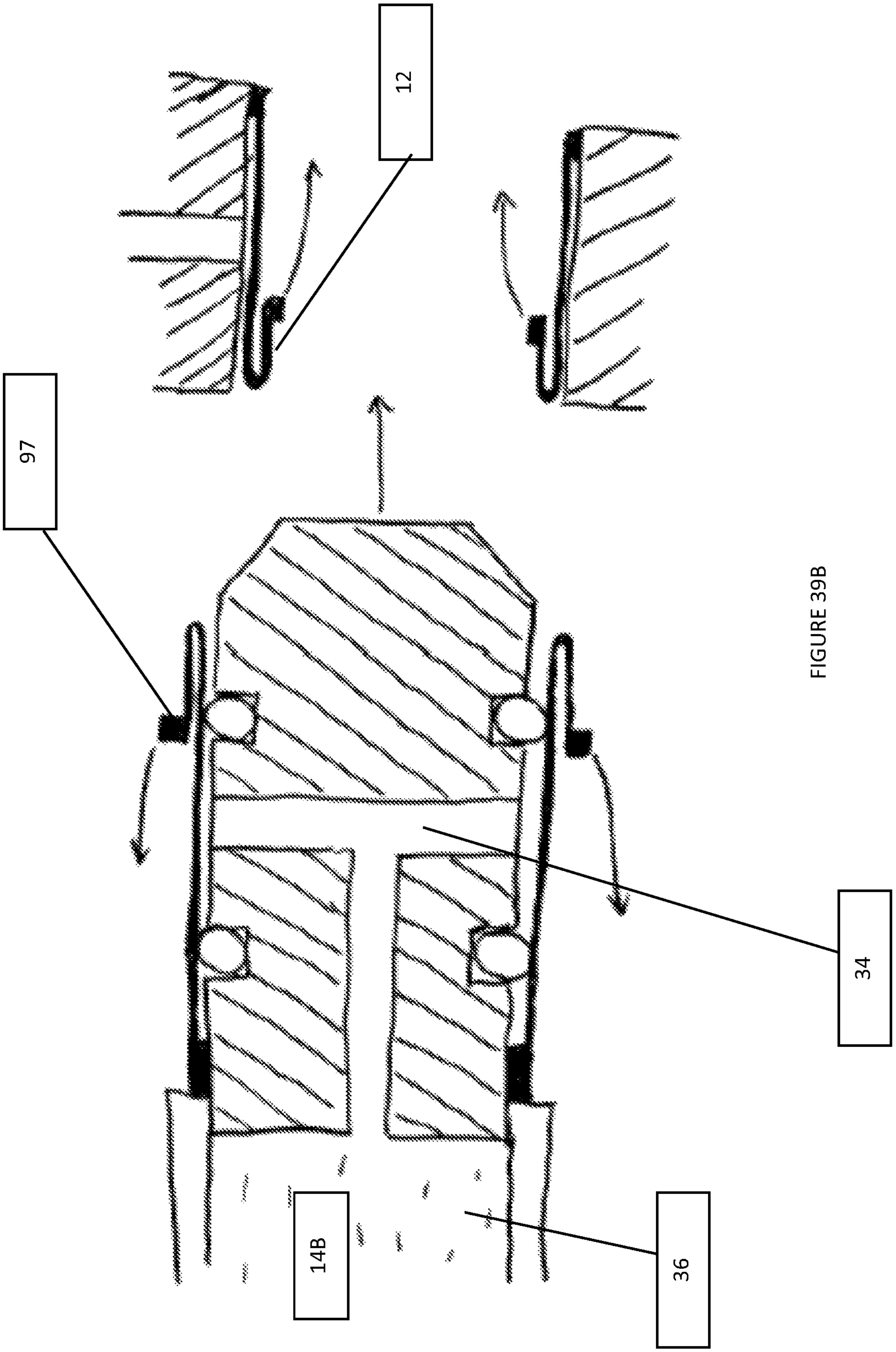
FIG. 39B shows a method of accessing a drug cartridge by engaging two edges of film covering the fluid path, in accordance with the subject invention. In this illustration, the film is mounted to cylindrical surfaces.
Figure 39C:
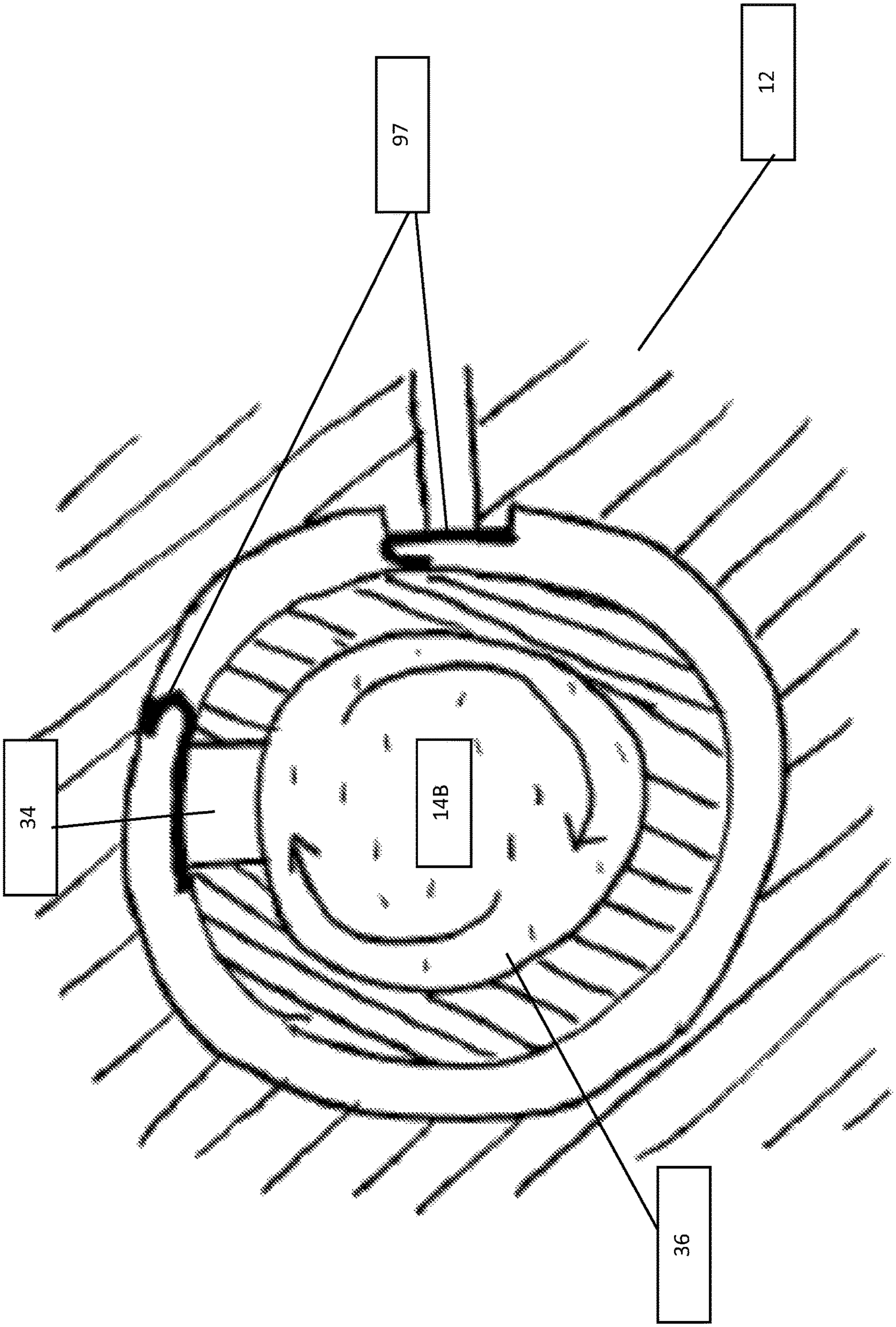
FIG. 39C shows a method of accessing a drug cartridge by peeling film via relative rotation of an internal component, in accordance with the subject invention.
Figure 39D:
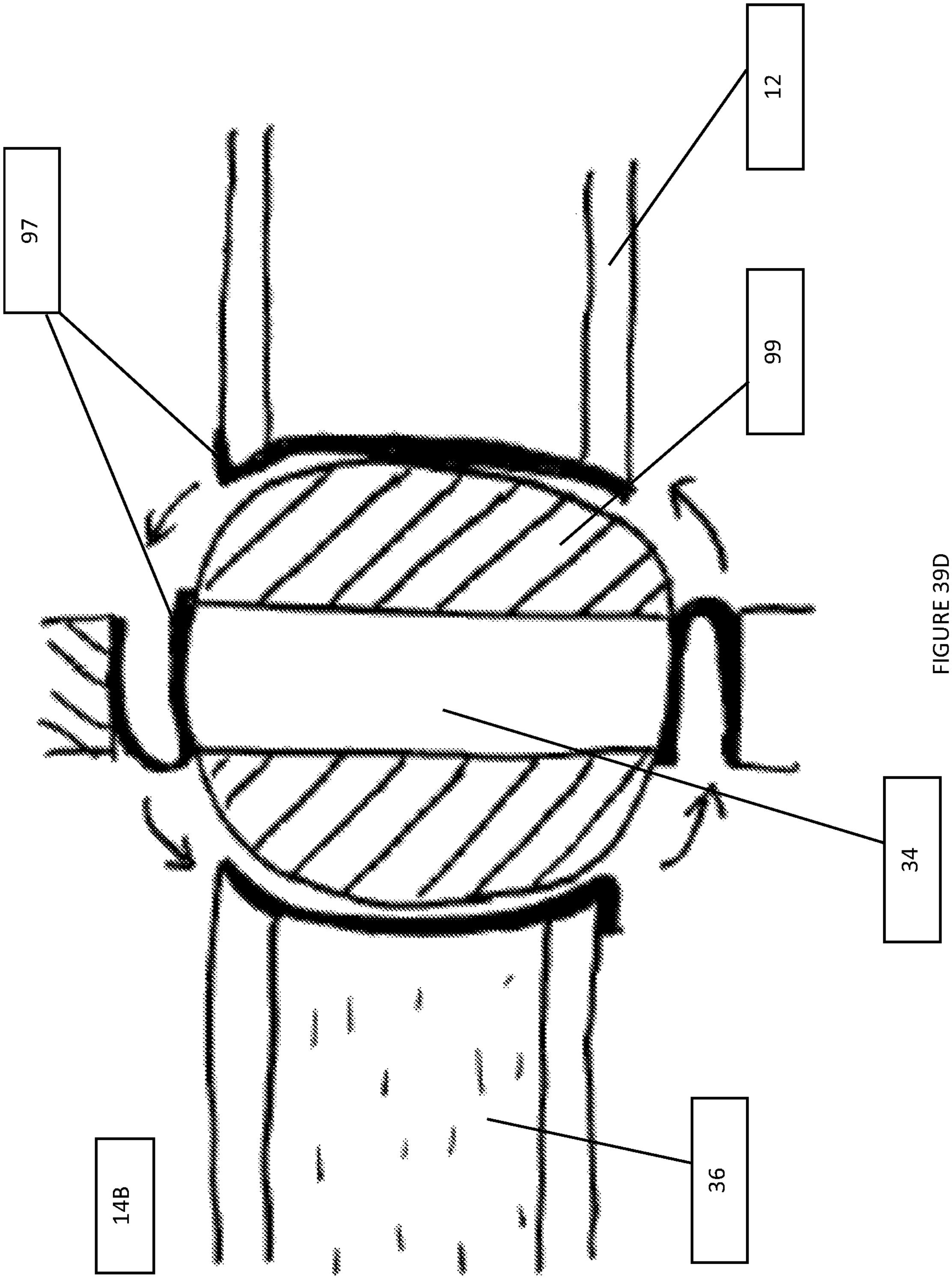
FIG. 39D shows a method of accessing a drug cartridge by peeling film via ball-valve type element, in accordance with the subject invention.

FIGS. 39A-41D show different sterile connection seal arrangements useable with the subject invention. For example, as shown in FIGS. 39A-39D, "rolling diaphragm" arrangements may be utilized where a sterile barrier 97 is provided on the plug adaptor 14B with an outward extending edge 98. The sterile barrier 97 seals the internal lumen 36. With attachment of the plug adaptor 14B to the body 12, the outward extending edge 98 may catch a portion of the body 12 and be rolled backward to expose the internal lumen 36. As shown in FIGS. 39A-39C, the plug adapter 14B and the body 12 may be formed with different cooperating surfaces to facilitate removal of the sterile barrier 97, including matching tapered surfaces (FIG. 39A) and matching cylindrical surfaces (FIG. 39B, removal with insertion; FIG. 39C, removal with rotation after insertion). FIG. 39D shows the use of a ball-valve type element 99 to connect the internal lumen 36 to the body 12, where adjustment of the ball-valve type element 99 causes removal of the sterile barriers 97 and allows for communication between the internal lumen 36 and the body 12.

Figures 2, 40A:
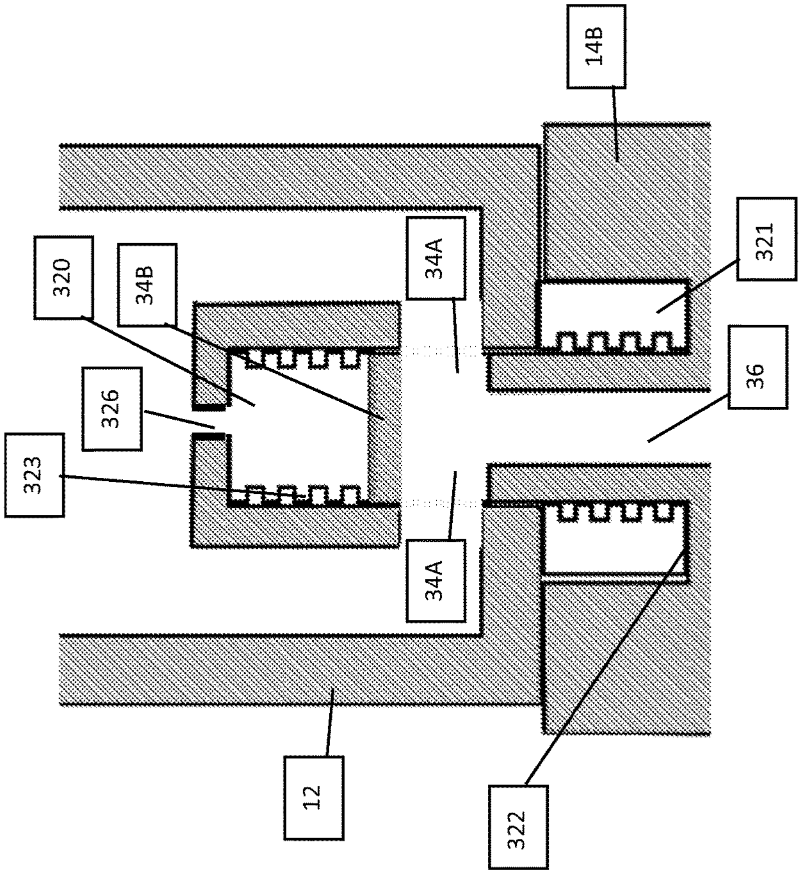
Figures 1, 40A:
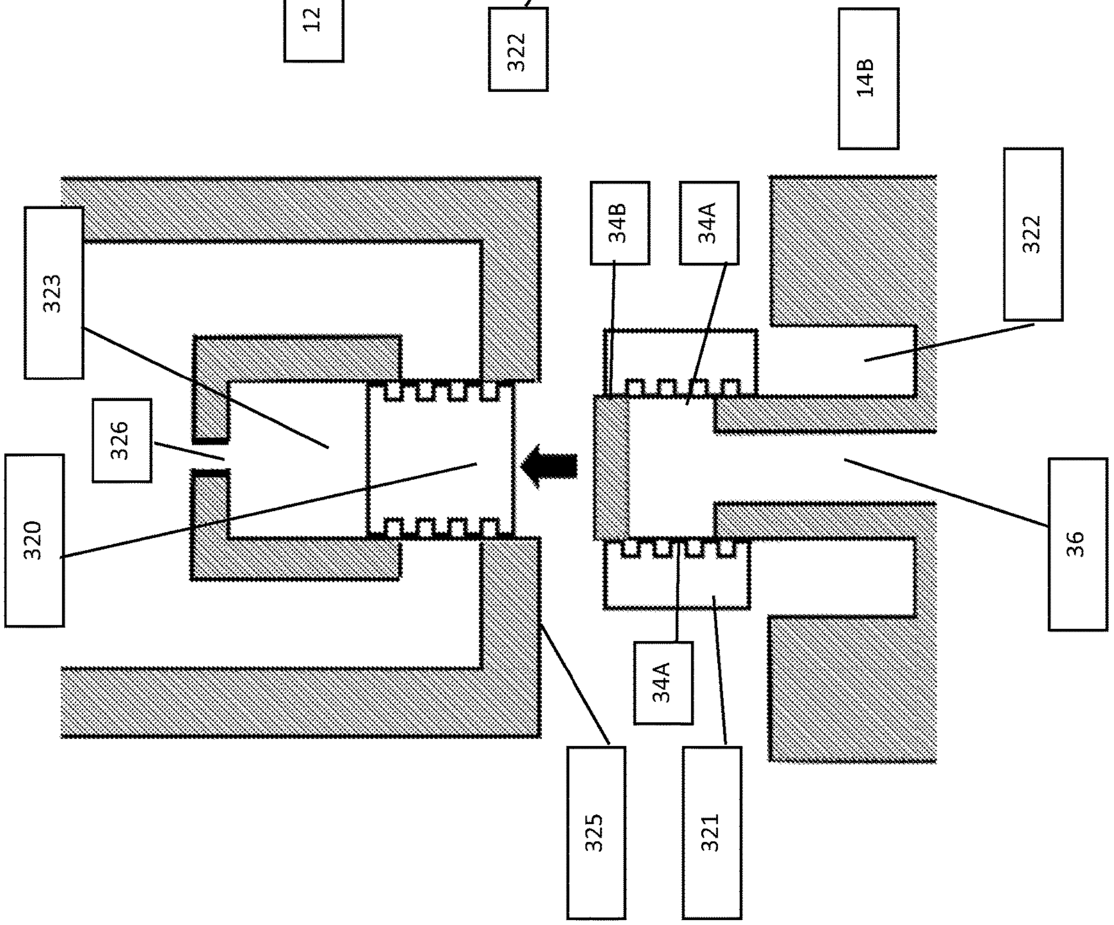
Figure 40B:
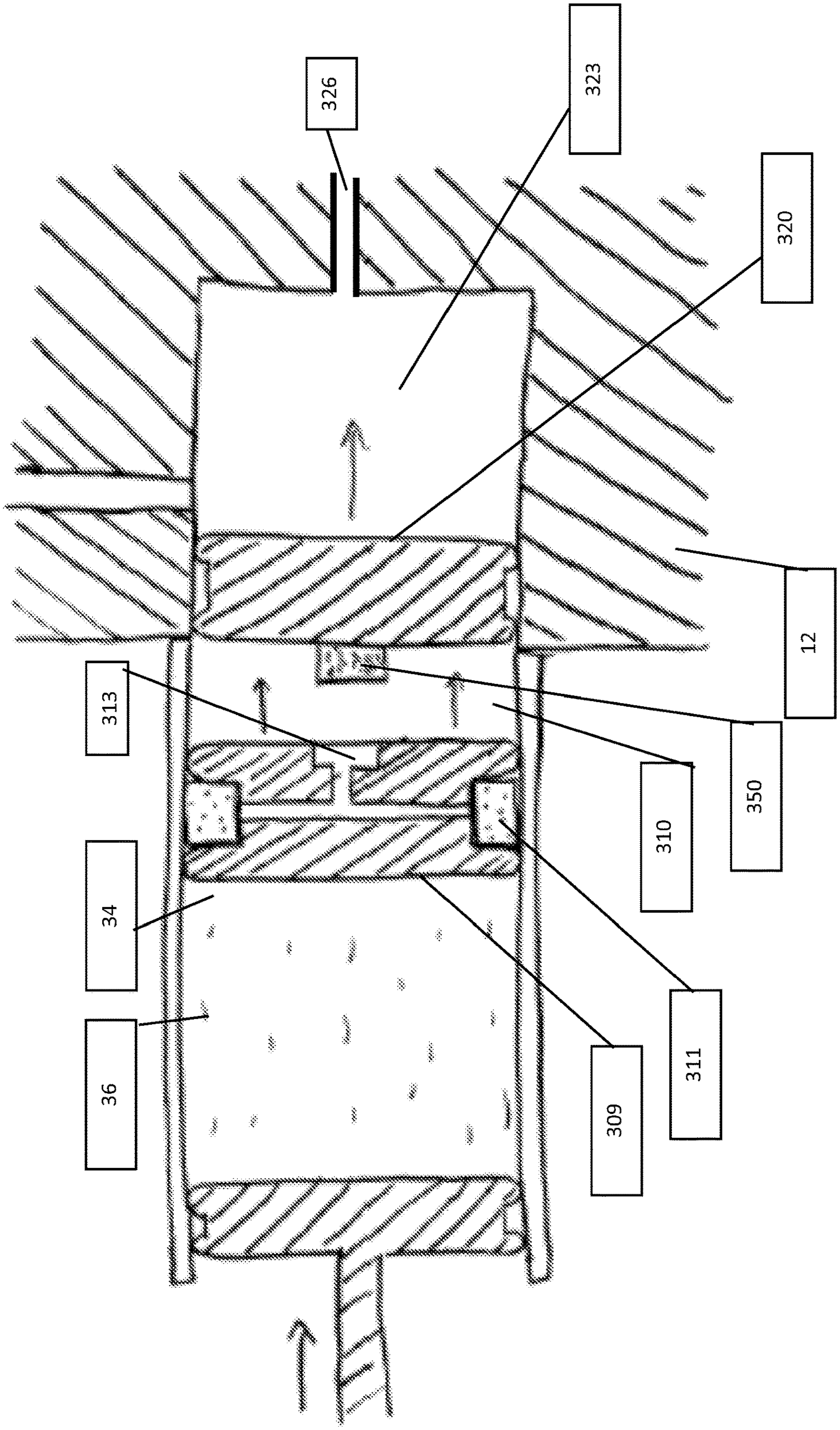
FIG. 40B shows a method of decontaminating the fluid path using a disinfectant reservoir and a slidable piston, in accordance with the subject invention.
Figure 40C:
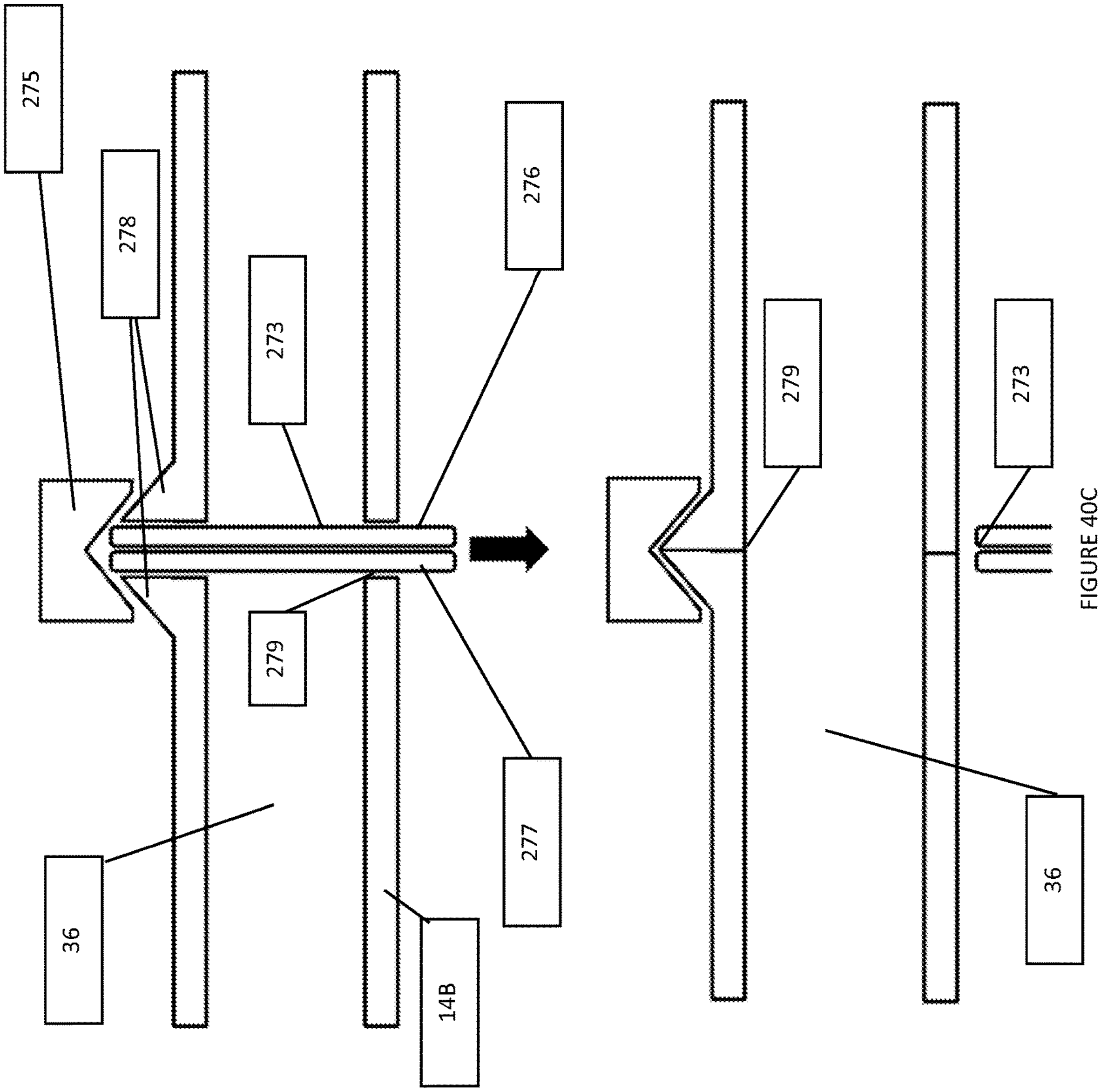
FIG. 40C shows a method for accessing a drug cartridge using removable lateral seals and a clamping mechanism, in accordance with the subject invention.

FIGS. 40A-40C show different shifting seal arrangements where adjustment of seals allows for flow of drug. For example, in FIG. 40A, plug seal 320 may be provided in a first channel 323 in the body 12. A second channel 322 may be formed in the plug adapter 14B about the internal lumen 36. The fluid outlet 34 may be formed with side ports 34A and a closed end 34B. An annular ring seal 321 is initially located about the fluid outlet 34 to seal the side ports 34A. As shown in FIG. 40A-1, with insertion of the fluid outlet 34 into the body 12, the plug seal 320 is caused to shift in the first channel 323 and the ring seal 321 is caused to shift into the second channel 322. Thus, as shown in FIG. 40A-2, the side ports 34A are exposed to allow communication between the internal lumen 36 and the body 12. One or more vent openings 326 may be provided in the first channel 323 to allow for air to escape with the shifting of the plug seal 320 into the first channel 323.

With reference to FIG. 40B, the plug seal 320 may be provided in the first channel 323 with a disinfectant reservoir 350. A slidable piston 309 may be provided in the fluid outlet 34 having an annular wiper 311. Disinfectant channels 313 are formed in the piston 309 to convey disinfectant to the wiper 311. To form a connection between the internal lumen 36 and the body 12, pressure is applied to the liquid drug (which is generally incompressible), resulting in forward movement of the piston 309. Disinfectant emitted from the disinfectant reservoir 350 is conveyed to the wiper 311, via the disinfectant channels 313, so that the inner surface of the fluid outlet 34 is sterilized with movement of the piston 309. With sufficient movement, the piston 309 engages the plug seal 323, causing movement into the first channel 323. With further sufficient movement, the piston 309 by-passes at least one fluid duct in the body, allowing for open communication with the internal lumen 36. The first channel 323 may be vented by one or more of the vent openings 326.

With reference to FIG. 40C, a lateral seal 273 may be provided, formed by multiple film layers 276, 277, to have a certain level of stiffness. The lateral seal 273 may be located through a slit 279 to span the fluid outlet 34 and/or the internal lumen 36 to provide a seal thereof. Flanges 278 may be formed about portions of the slit 279 with a clamping element 275 acting on the flanges 278 to maintain the slit 279 in close, seal contact with the lateral seal 273, which is retained in place. To allow open communication with the internal lumen 36, the lateral seal 273 is removable through the slit 279 with the slit 279 self-sealing. Sufficient resiliency must be provided in the materials about the slit 279 to allow for proper sealing against the lateral seal 273 and subsequent self-sealing.

Figure 41A:
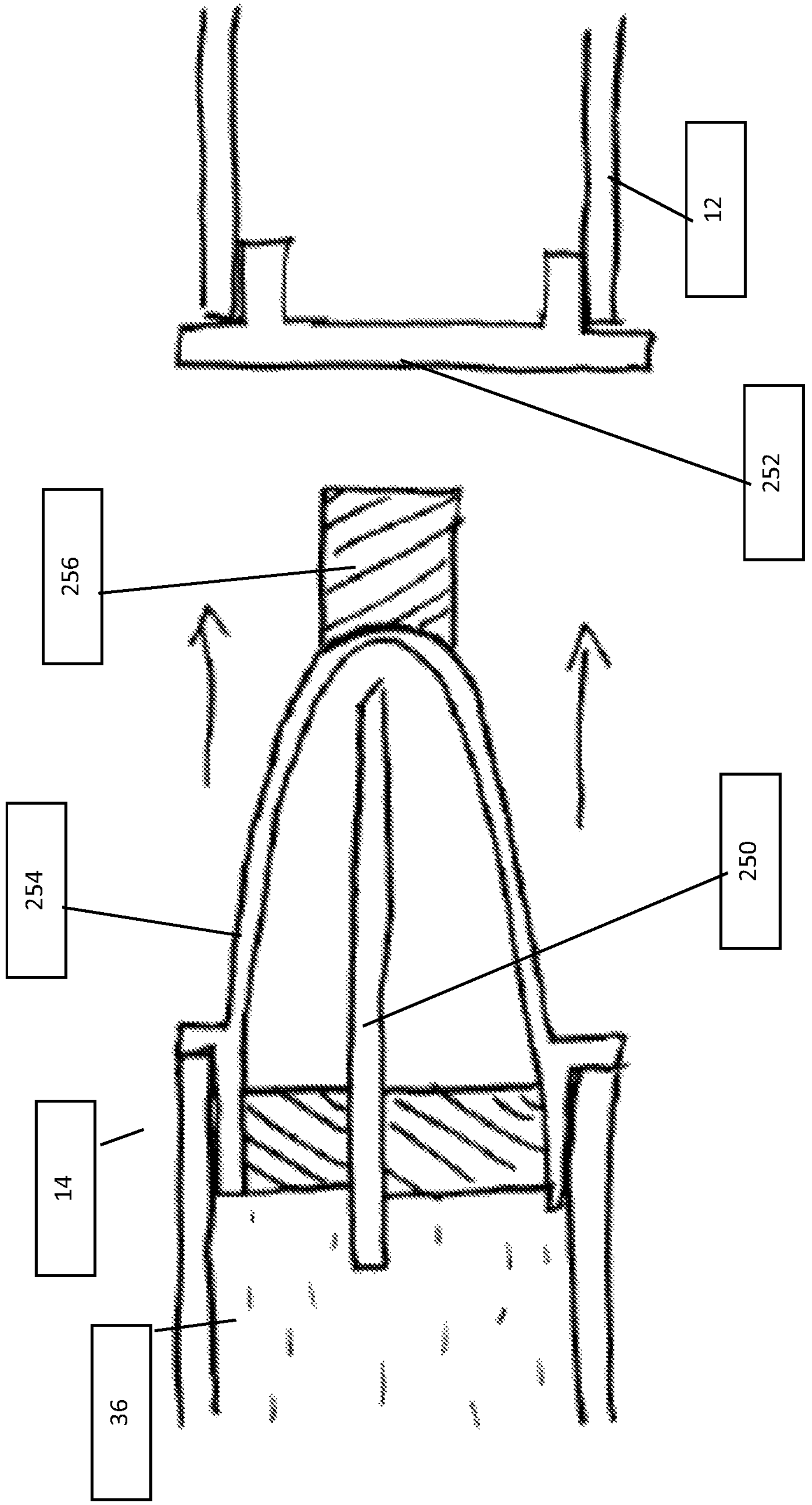
FIG. 41A shows a method of decontaminating the fluid path using a disinfectant reservoir which is pierced by a cannula, in accordance with the subject invention.
Figure 41B:
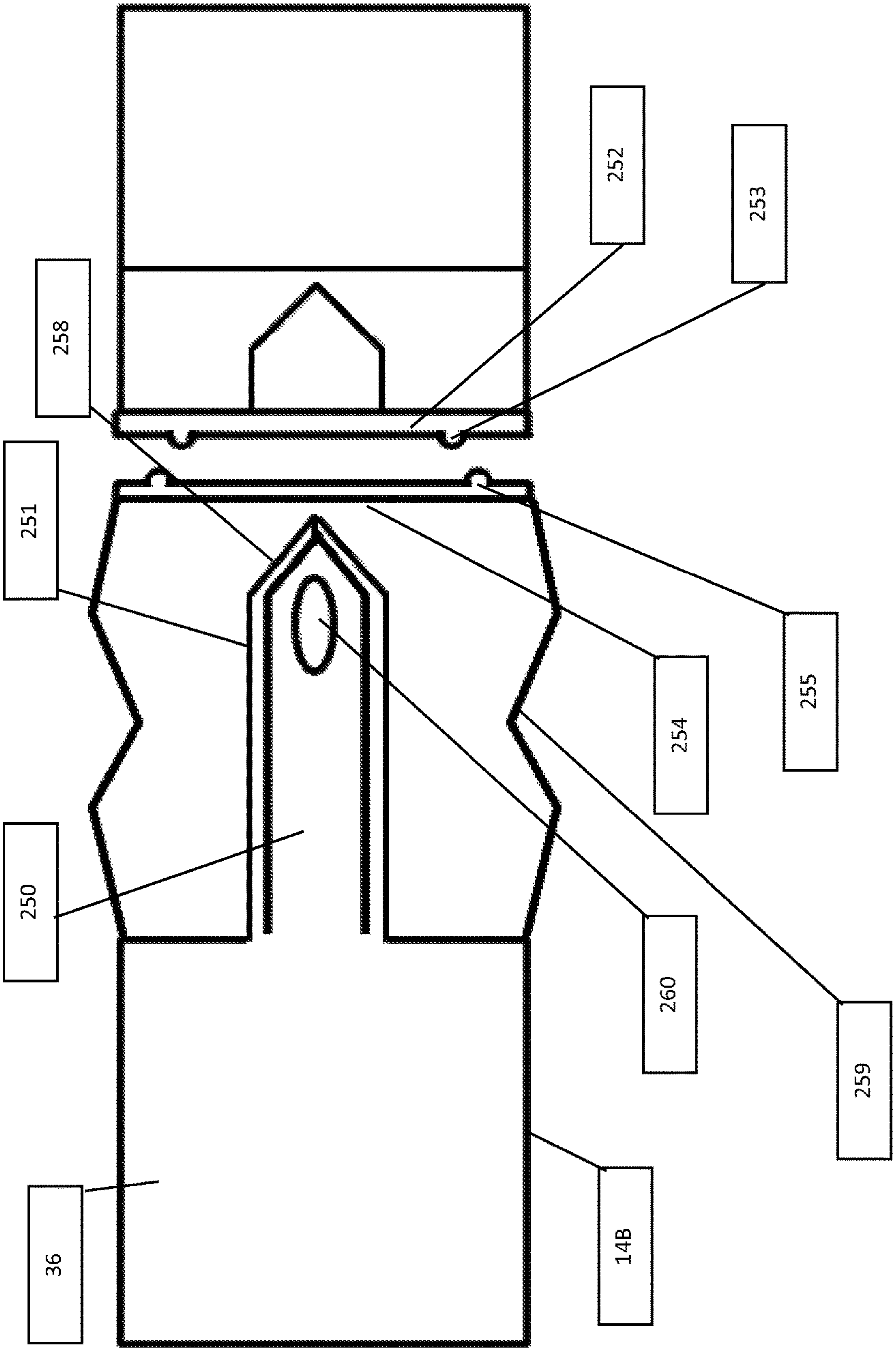
FIG. 41B shows a method for accessing a drug cartridge using a single-tip sheathed needle and septum, in accordance with the subject invention.
Figure 41C:
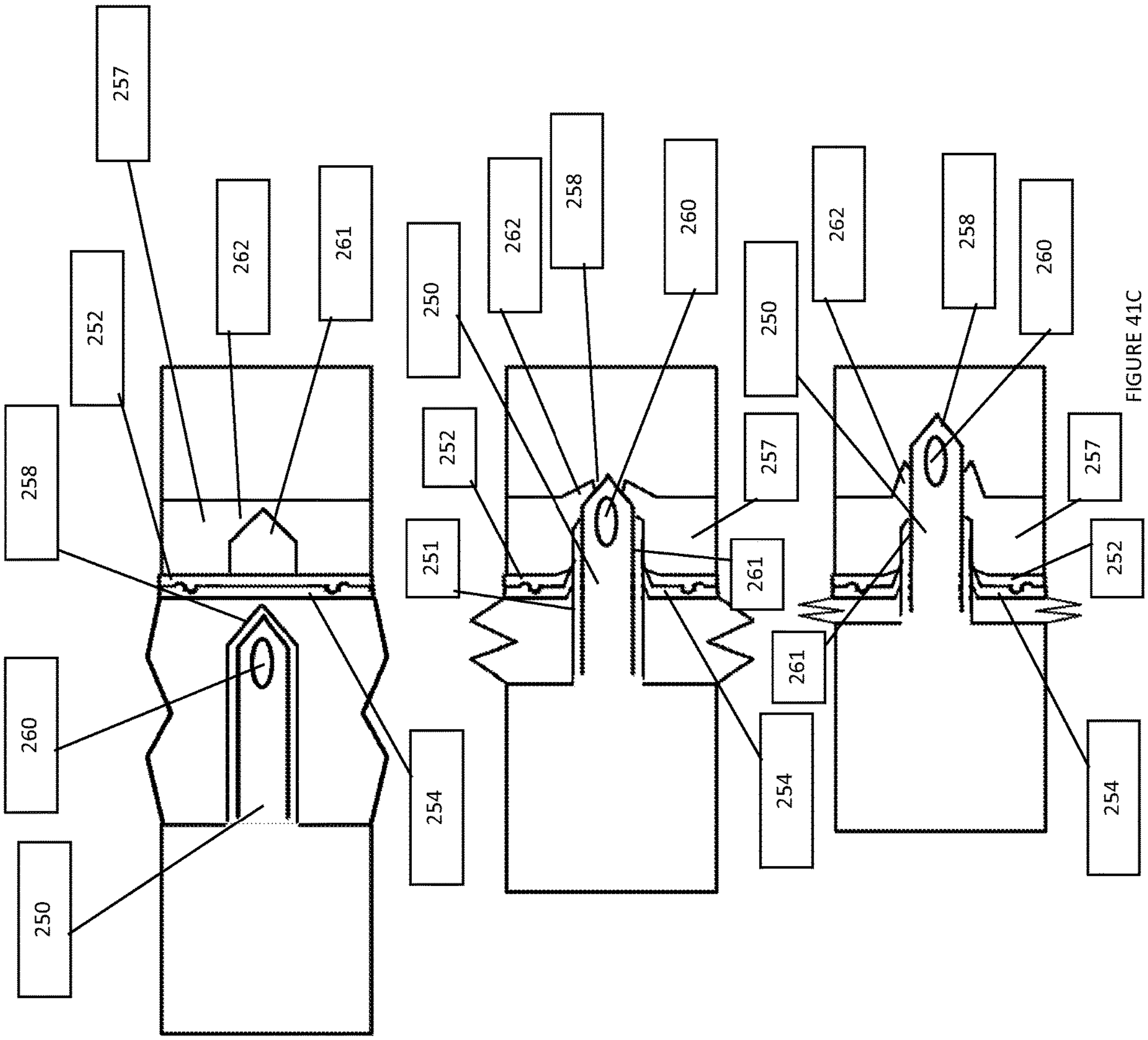
FIG. 41C shows the system of FIG. 41B in use.
Figure 41D:
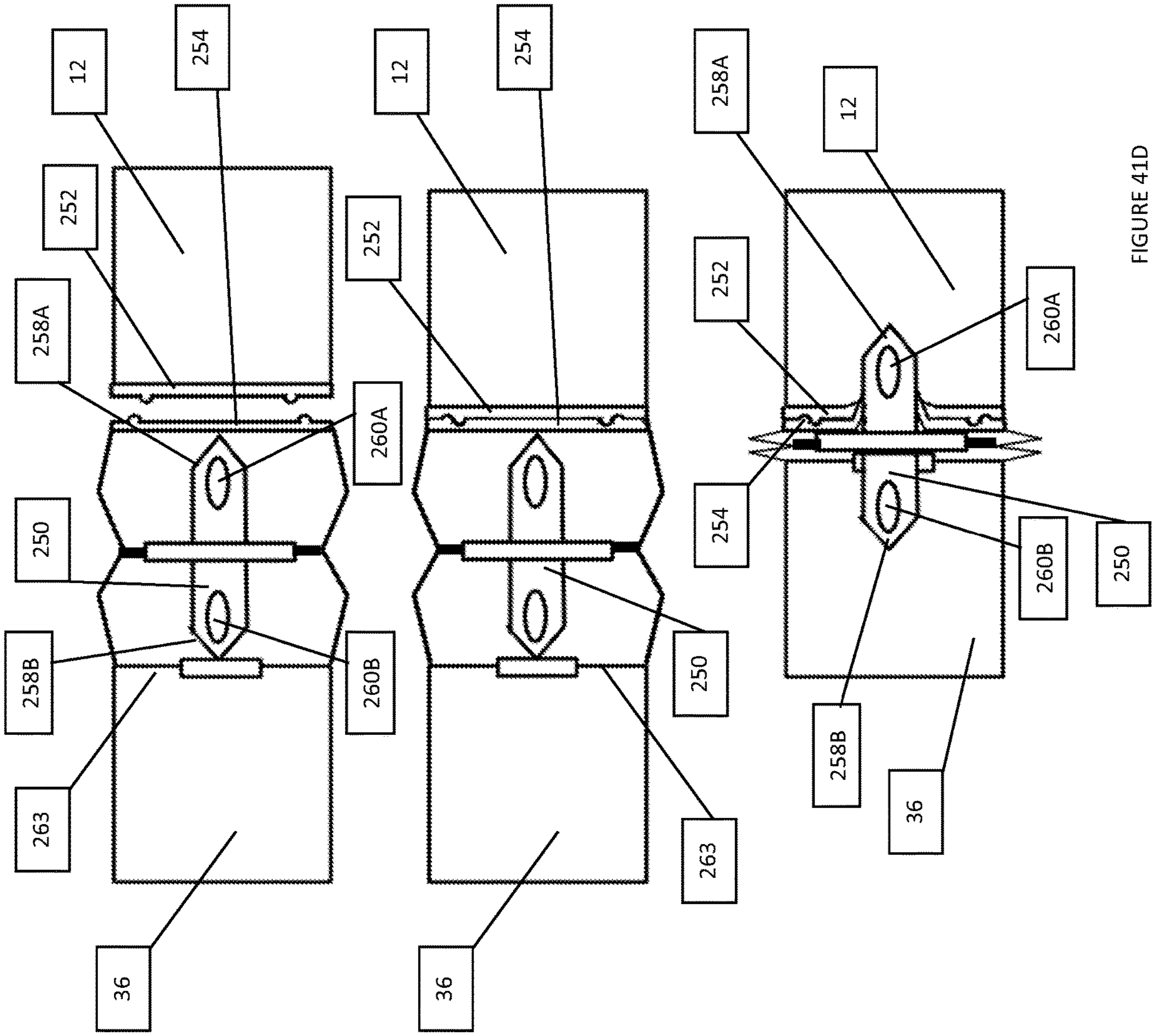
FIG. 41D shows a method for accessing a drug cartridge using a dual-tip sheathed needle and septa, in accordance with the subject invention.
Figure 41E:
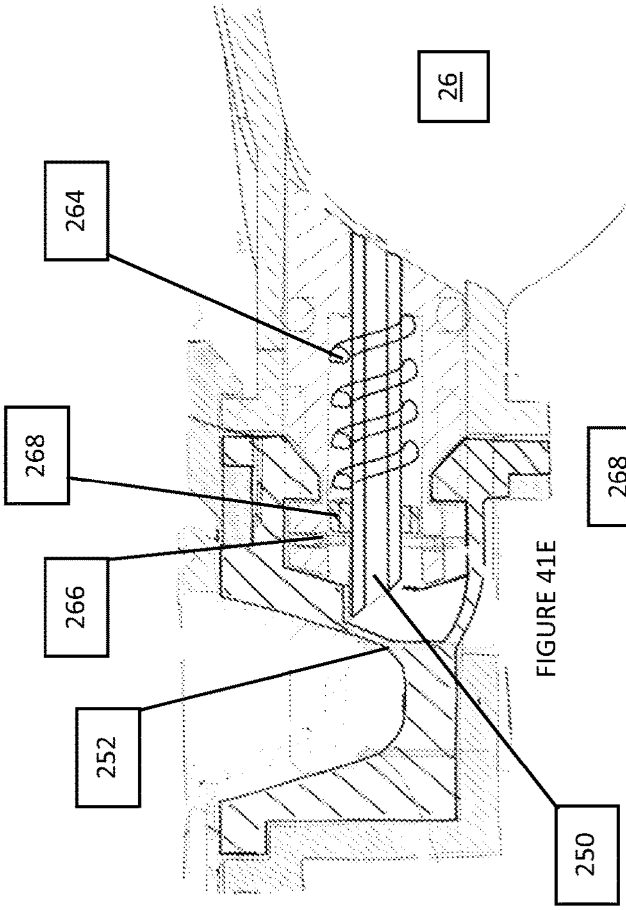
FIG. 41E shows a method for accessing a drug cartridge using a spring-loaded needle, in the pre-loaded state, within the drug cartridge outlet, in accordance with the subject invention.
Figure 41F:
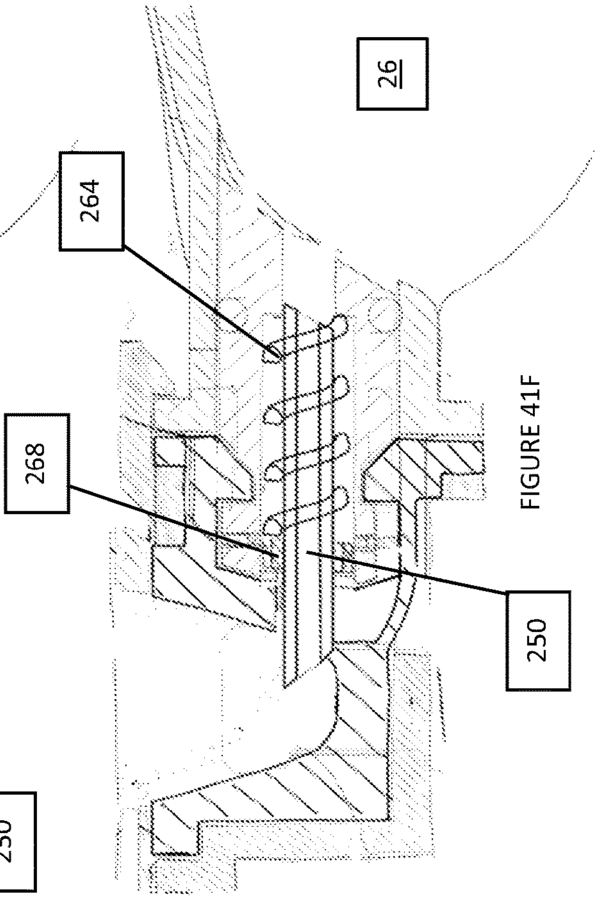
FIG. 41F shows a method for accessing a drug cartridge using a spring-loaded needle, in the extended state, within the drug cartridge outlet, in accordance with the subject invention.
Figure 42:
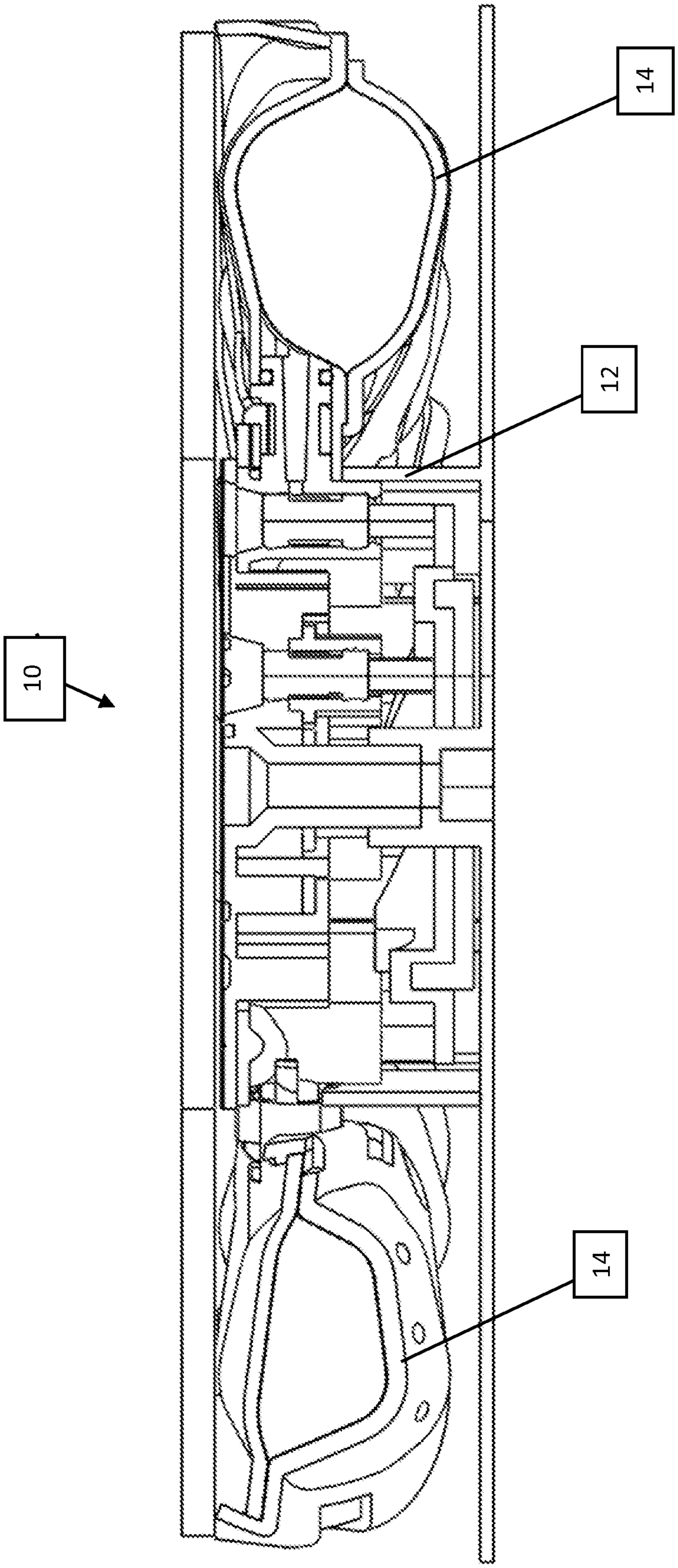
FIG. 42 is a section view of a drug delivery device, illustrating a useable fluid path, in accordance with the subject invention.
Figure 43:
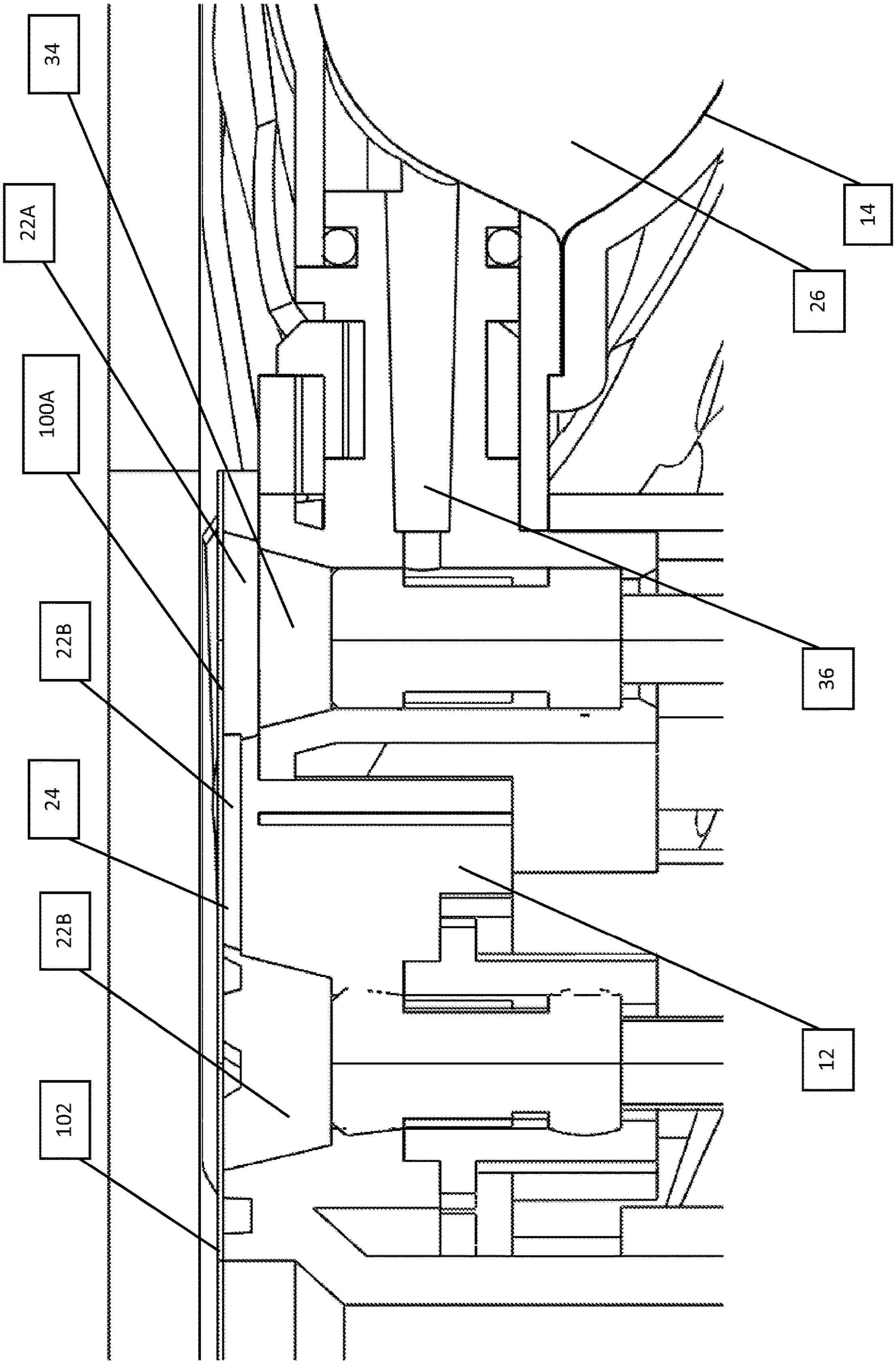
FIG. 43 is a detailed view of a section of FIG. 42.
Figure 44:
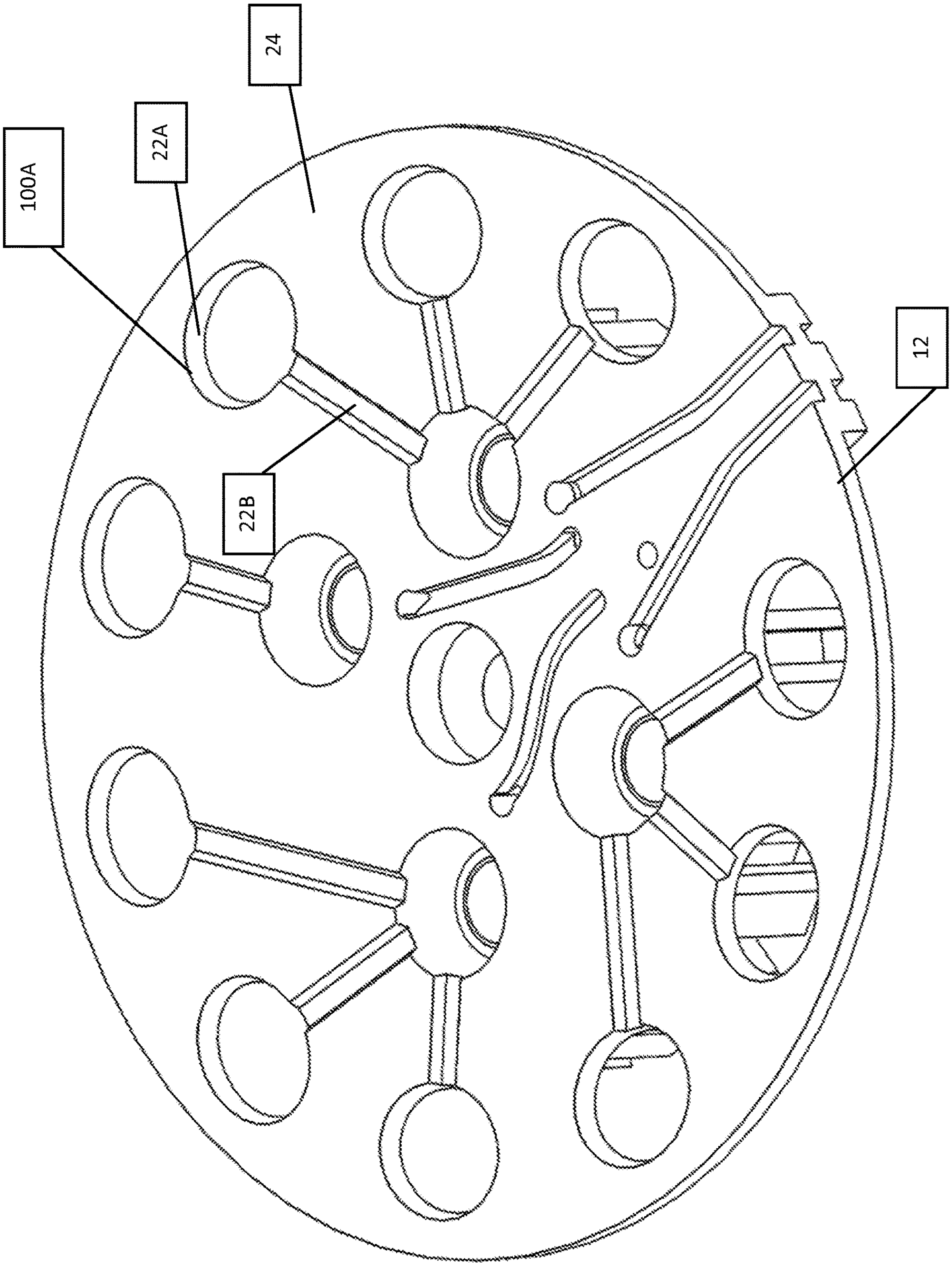
FIG. 44 is an isometric view of a body useable with the subject invention.
Figure 45:
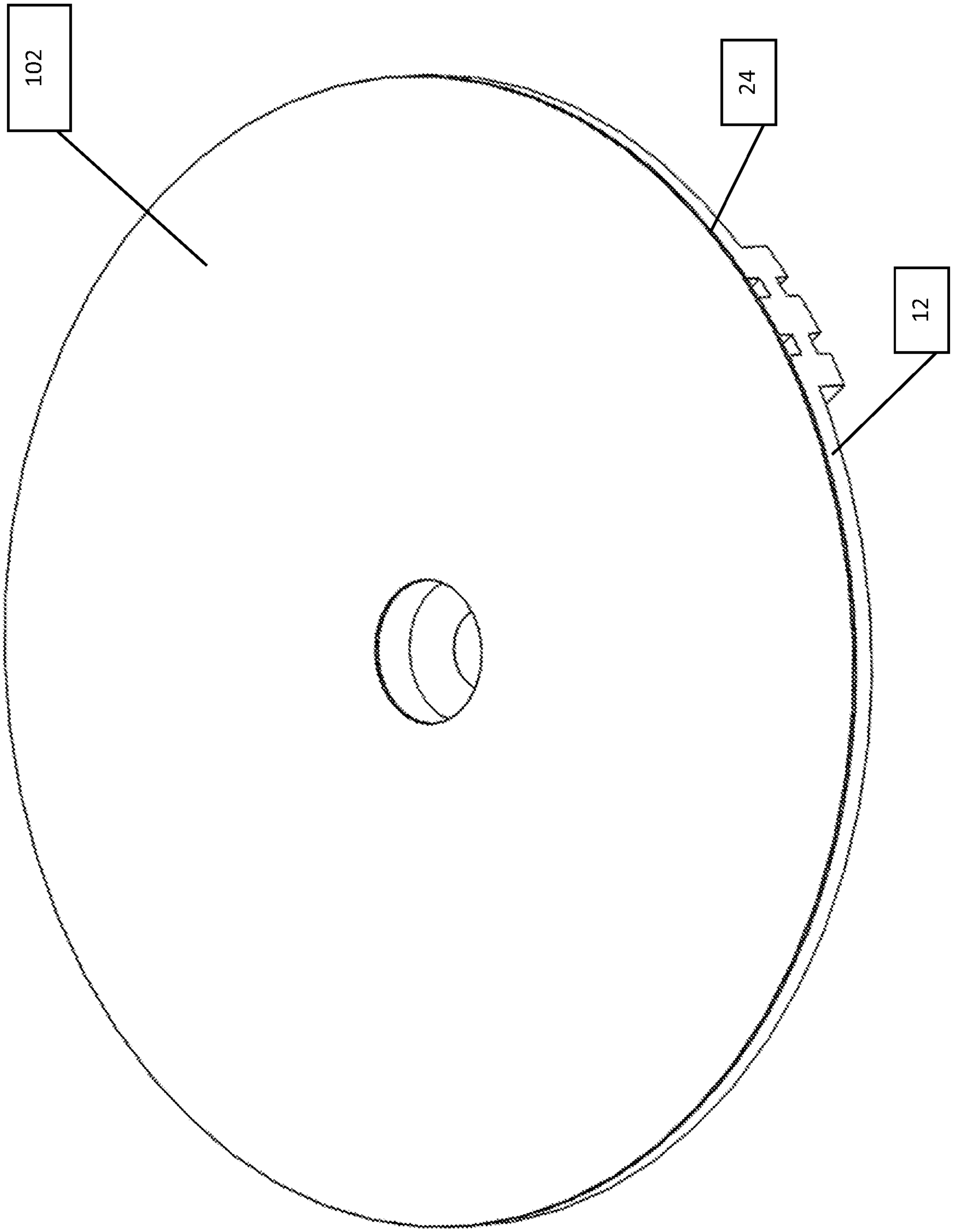
FIG. 45 shows the body of FIG. 44 with a barrier.

With reference to FIGS. 41A-41F, a cannula 250 may be provided with the internal lumen 36 configured for piercing through a septum 252 located on the body 12. The cannula 250 may be supported by a bulkhead or plug located within the fluid outlet 34. As shown in FIG. 41A, the cannula 250 may be encased in a sealed septum 254 with a disinfectant wiper 256 located on an exterior thereof. The cannula 250 is maintained in a sterile condition within the sealed septum 254. In use, the cannula 250 is caused to pierce the sealed septum 254, pass through the wiper 256 and pierce the septum 252. This allows for open communication between the internal lumen 36 and the body 12. FIGS. 41B and 41C show the cannula 250 encased in sheath 251 (e.g., an elastomeric sheath) and having a closed end 258 with side ports 260. Here, with the cannula 250 piercing the septum 252, open communication is provided through the side ports 260. As shown in FIG. 41B, a collapsible wall 259 (e.g., having bellows or pleats) may be provided about the cannula 250 sealed off by the septum 254. The wall 259 may be formed to collapse with the septum 254 pressing against the septum 252. With sufficient advancement, the cannula 250 pierces the septum 254. With piercing the septum 252, the cannula 250 is caused to advance through the septum 254, with the sheath 251 being restricted due to engagement with the septum 254. This allows for the cannula 250 to be exposed with further advancement through the septum 252 to allow communication between the internal lumen 36 and the body 12 via the side ports 260. Cooperating annular ribs 253, 255 may be formed on the septa 252, 254 which are concentrically aligned with the septa 252, 254 being in pressing engagement. The annular ribs 253, 255 co-act to maintain alignment between the septa 252, 254. FIG. 41C shows that a pierceable backing 257 may be provided behind the septum 252 to provide rigidity and support to the septum 252. A central open passage 261 may be provided in the backing 257 which leads to a thinned web 262 aligned to be pierced by the cannula 250. As shown in FIGS. 41E and 41F, a spring 264 may be provided for advancing the cannula 250. A locking ring 266 may be utilized to retain the cannula 250 in an initial state, as shown in FIG. 41E. The locking ring 266 may be displaced or disrupted to allow the spring 264 to advance the cannula 250 in piercing the septum 252. A seal collar 268 may be provided about the cannula 250 to advance therewith, to provide a seal about the cannula 250.

FIG. 41D provides the cannula 250 as double-ended with two closed ends 258A, 258B and two sets of side ports 260A, 260B. Here, a secondary septum 263 is provided located interiorly of the cannula 250. The cannula 250 may be partially embedded into the secondary septum 263 to be held in place. In use, the cannula 250 pierces both the septum 252, the sealed septum 254, and the secondary septum 263 to allow for open communication between the internal lumen 36 and the body 12 via the two sets of side ports 260A, 260B.

In any of the embodiments of FIGS. 41A-41F, any of the septum 252, 254, and/or the secondary septum 263 may include biocidal materials to promote sterility, including, but not limited to, antimicrobial silver.

With the reservoir section 14A of drug cartridge 14 sterilized, then aseptically filled and sealed by the plug adaptor 14B, the drug cartridge 14 may be stored and transported as needed. External portions of the drug cartridge 14, including the fluid outlet 34, may be open to atmosphere during storage and assembly to the body of the device, thus not being sterile.

As shown in FIGS. 42-56, the drug cartridge 14 may be mounted to the body 12 in any manner. For example, portions of the plug adaptor 14B and the body 12 may be joined by laser welding, adhesive, fusion, and so forth. The drug cartridge 14 is assembled to the body 12 to have the fluid outlet 34 be aligned with a first fluid duct 22A to define a continuous flow path for the drug from the reservoir 26. The first fluid duct 22A extends from the fluid outlet 34 to a first opening 100A formed in the first face 24 of the body 12. A secondary fluid duct 22B may extend from the first opening 100A to be in communication with the first fluid duct 22A. The secondary fluid duct 22B continues the flow path from the fluid outlet 34. The secondary fluid duct 22B is open along the first face 24. As shown in FIGS. 173-174, the drug cartridge 14 may be mounted to a second face 24A of the body 12 with the first fluid duct 22A extending from the fluid outlet 24 and through the thickness of the body 12 to the secondary fluid duct 22A.

A barrier 102 may be provided across the first face 24 to at least cover the first opening 100A. The barrier 102 closes the open side of the first opening 100A to contain the flow path within the fluid duct 22A and the first opening 100A. The barrier 102 is also selected to allow for passage therethrough of ultraviolet radiation, x-ray radiation, pulsed light or electron-beam, depending on the decontamination process selected. The barrier 102 may be, but not is required to be, transparent to the respective emission. The barrier 102 may be transmissive to the respective transmission to be effective, without requiring 100% of the respective emission to pass through.

The ultraviolet radiation, x-ray radiation, pulsed light or electron-beam may emanate from one or more sources which are stationary or mounted on moving fixtures. The body 12 may be stationary or moving when exposed to the ultraviolet radiation, x-ray radiation, the pulsed light or the electron-beam. The body 12 must be situated relative to the source(s) of the ultraviolet radiation, x-ray radiation, the pulsed light or the electron-beam to ensure sufficient exposure for the required level of decontamination. By way of non-limiting example, the one or more sources of ultraviolet radiation, x-ray radiation, pulsed light or electron-beam may be located inside a tunnel above a moving belt carrying the body 12. The rate of movement of the belt may be manipulated to control the rate of exposure of the body 12. In addition, multiple sources of ultraviolet radiation, x-ray radiation, pulsed light or electron-beam may be utilized in the tunnel which are spaced apart along a radius about the moving belt to provide semi- or hemi-spherical coverage of the body 12. Alternatively, the one or more sources of ultraviolet radiation, x-ray radiation, pulsed light or electron-beam may be mounted on rigid fixtures, movable arms, or the like, to provide coverage to the body 12, which may be stationary. Relative movement between the body 12 and the source(s) of ultraviolet radiation, x-ray radiation, pulsed light or electron-beam may be provided, with one or both elements moving. All elements may be also statically set in fixed, stationary positions with no relative movement therebetween.

Figure 57:
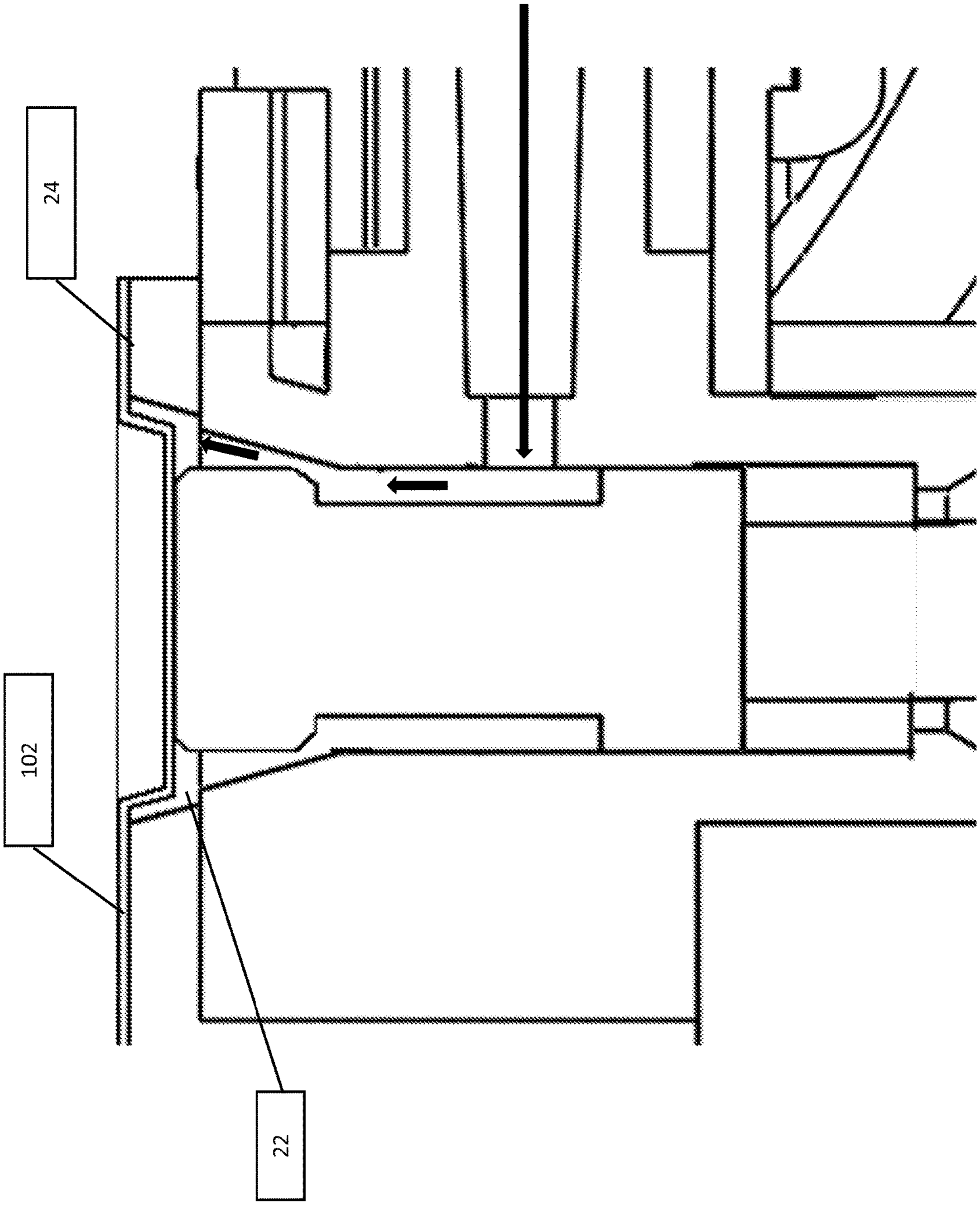
FIG. 57 is a detailed view of a section of FIG. 56.

The barrier 102 may be a single- or multi-ply polymeric film which includes one or more of: fluoropolymer; fluoropolymer copolymer; polyimide; polymethylepentine; silicone; cyclic olefin copolymer; and, cyclic olefin polymer. Alternatively, the barrier 102 may be molded, extruded, laminated and/or thermoformed from one or more of the listed materials. In addition, as shown in FIG. 57, the barrier 102 may be conformed to the topography of the first face 24 including extending into one or more of the fluid ducts 22. This reduces open volume therein.

The barrier 102 may be fixed to the first face 24 in any manner, including, but not limited to, heat sealing, adhesion, fusion, and so forth.

Figure 46:
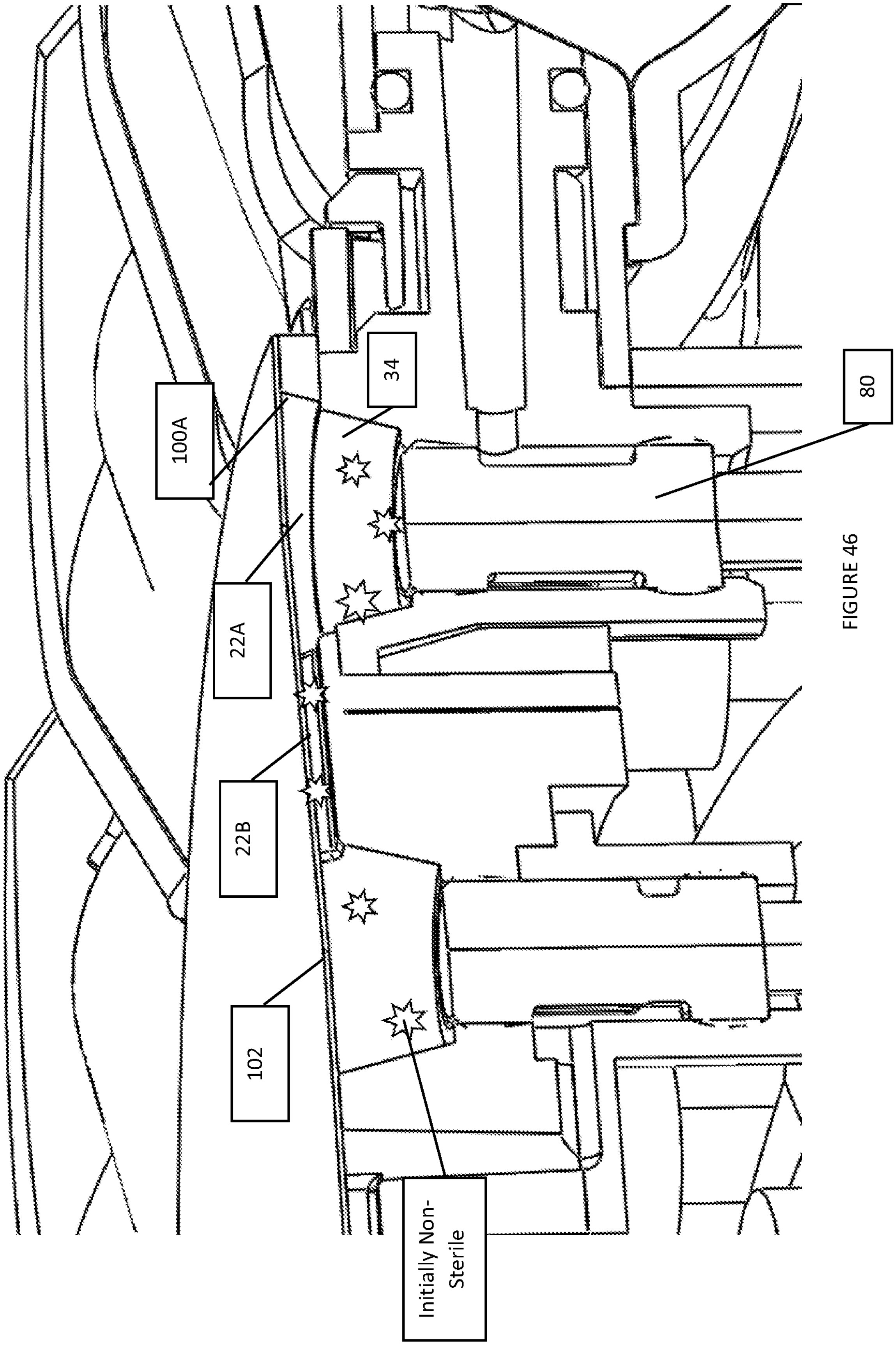
FIG. 46 is a section view showing potential non-sterile regions of a drug delivery device that require sterilization.
Figure 47:
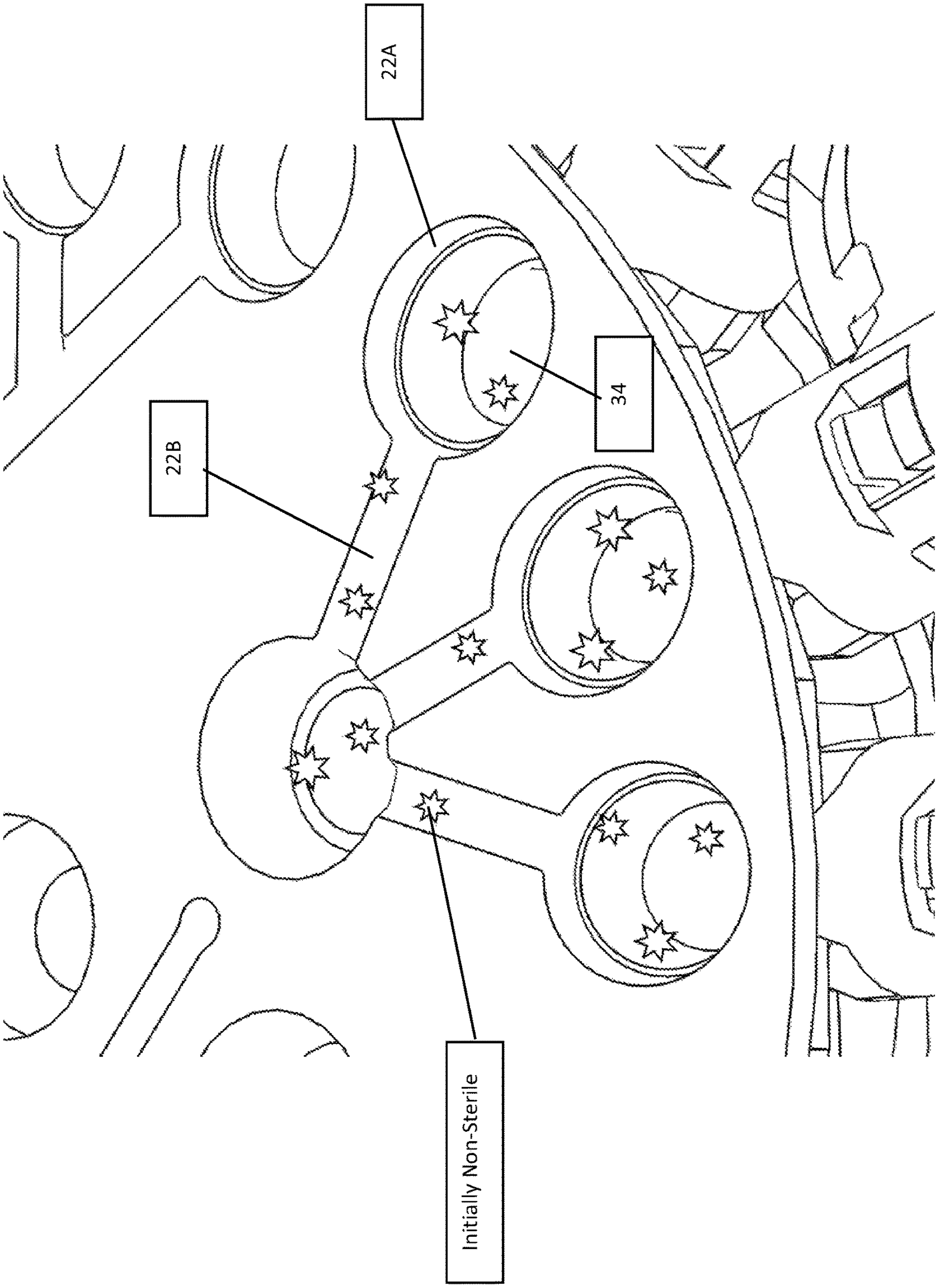
FIG. 47 is an isometric view showing potential non-sterile regions of a drug delivery device that require sterilization.

As shown in FIGS. 46 and 47, with the drug cartridges 14 being secured to the body 12, certain portions of the fluid path may be non-sterile, such non-sterile portions shown representatively by stars. This may occur where the drug cartridges 14 have non-sterile connection seal arrangements, such as with the use of valve 80. Thus, portions of the fluid outlet 34 may be non-sterile. Likewise, portions of the body 12 may be non-sterile, such as the first fluid duct 22A, the second fluid duct 22B, and the opening 100A.

The barrier 102 allows for decontamination, including sterilization, of the flow path along the first face 24. In this manner, the drug cartridge 14 may be separately prepared and assembled to the body 12, with the fluid ducts 22 and the fluid outlet 34 being decontaminated. As shown in FIGS. 48-52 and 69, with the fluid ducts 22 being open along the first face 24 and exposing the fluid outlet 34, the first face 24 may be exposed to ultraviolet radiation, x-ray radiation, pulsed light or an electron beam so that the ultraviolet radiation, x-ray radiation, pulsed light or electron-beam may pass through the barrier 102, to decontaminate exposed surfaces of the fluid ducts 22A, 22B and the fluid outlet 34. A sterile path may be provided, allowing for opening of the seal (FIGS. 55-56) to permit liquid flow. Negative pressure may be applied to the fluid ducts 22 to draw drug from the reservoirs 26 of the drug cartridges 14 simultaneously or in series (in various combinations). In addition, diluent may be pumped through the fluid ducts 22, as needed, to reconstitute dry drug components in one or more of the drug cartridges 14, with subsequent withdrawal of reconstituted liquid drug utilizing negative pressure.

Figure 48:
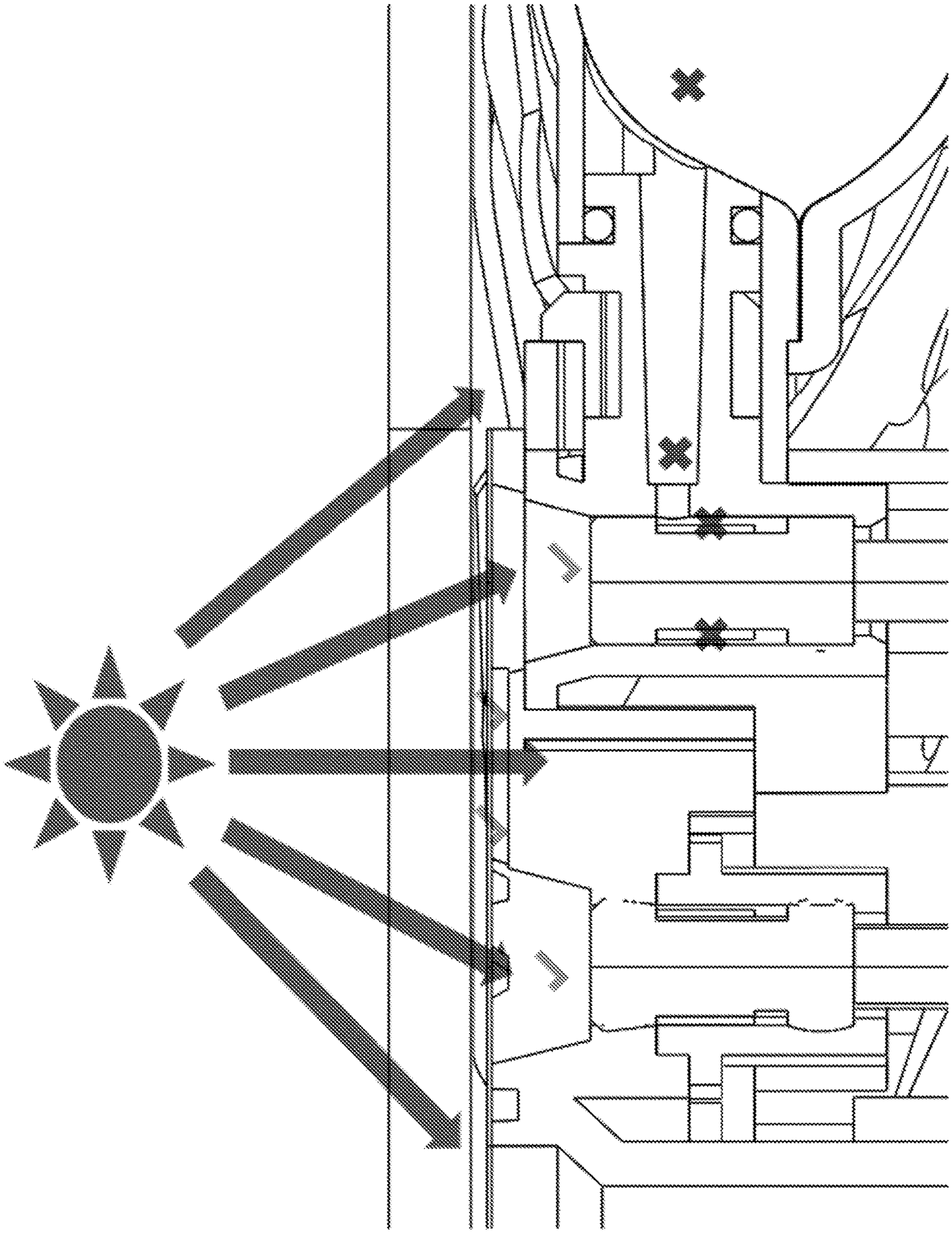
FIG. 48 is a section view showing regions of a drug delivery device which should be sterilized via ultraviolet radiation, pulsed light or electron-beam, and which should not.
Figure 49:
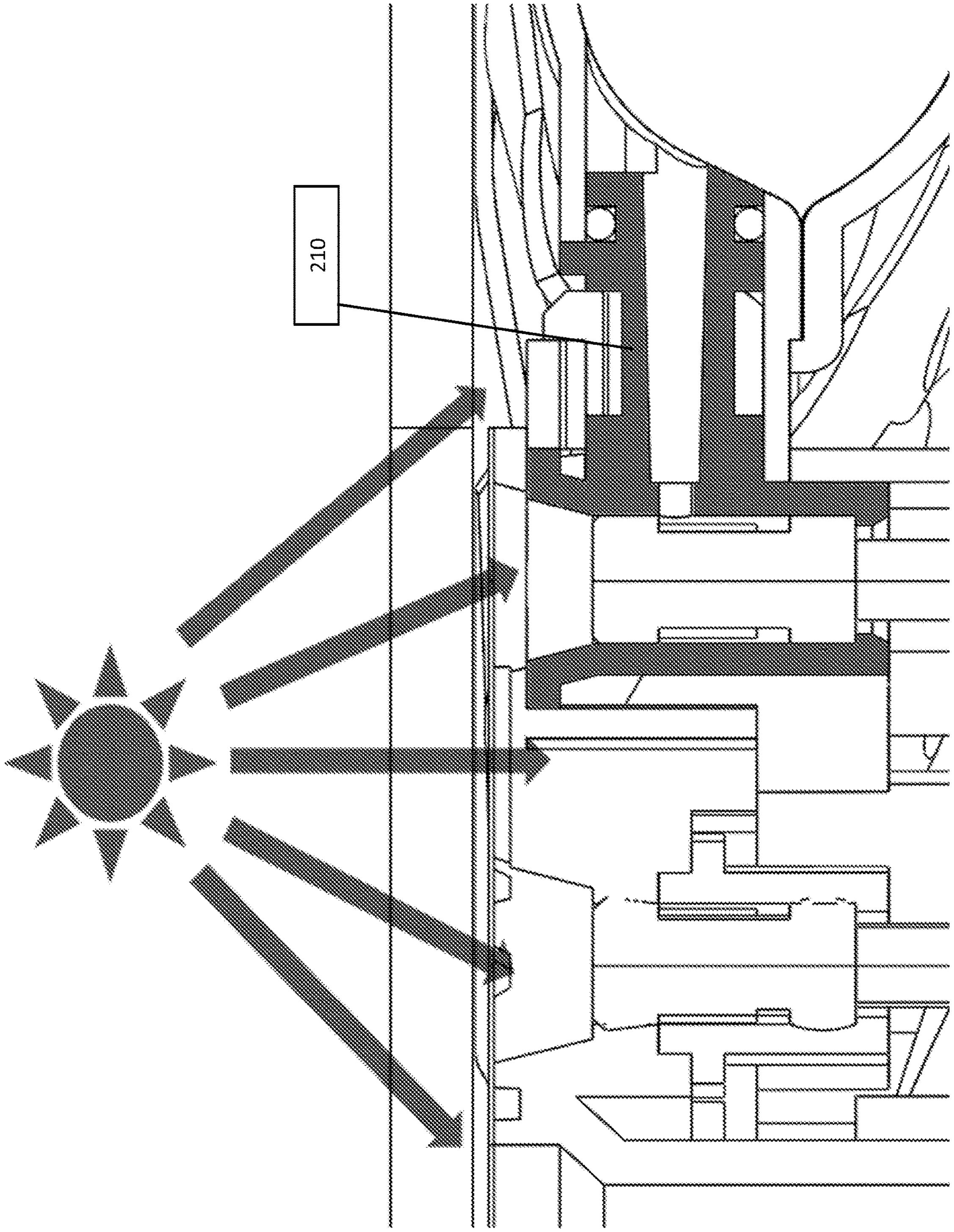
FIGS. 49-49C show locations where additives may be utilized in a drug delivery device to block penetration of ultraviolet radiation or pulsed light.
Figure 50:
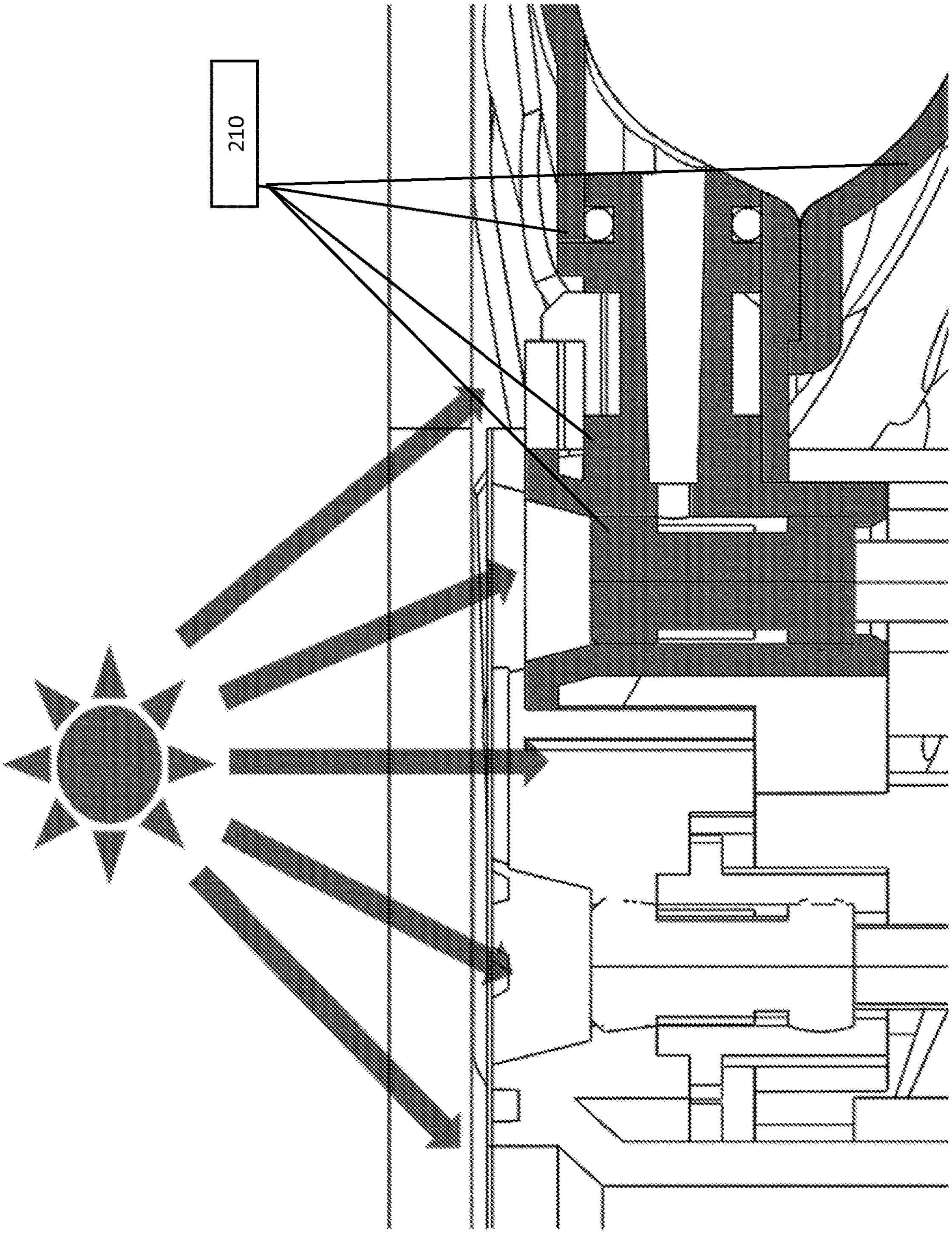
FIG. 50 shows additional locations, beyond the locations shown in FIG. 49, where additives may be utilized to block penetration of ultraviolet radiation or pulsed light.
Figure 51:
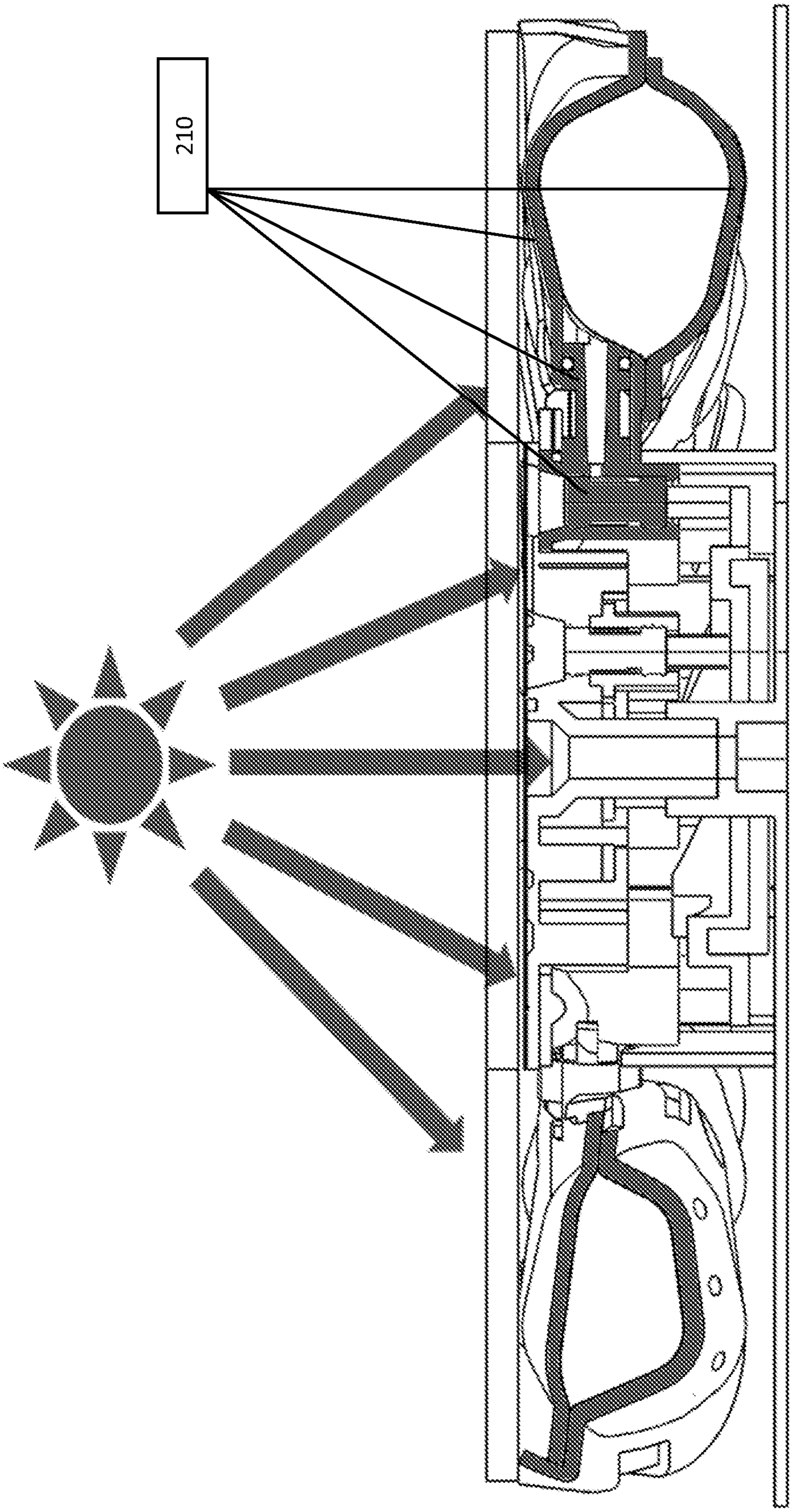
FIG. 51 is a full section view of a drug delivery device, illustrating the blocking components shown in FIG. 50.
Figure 52:
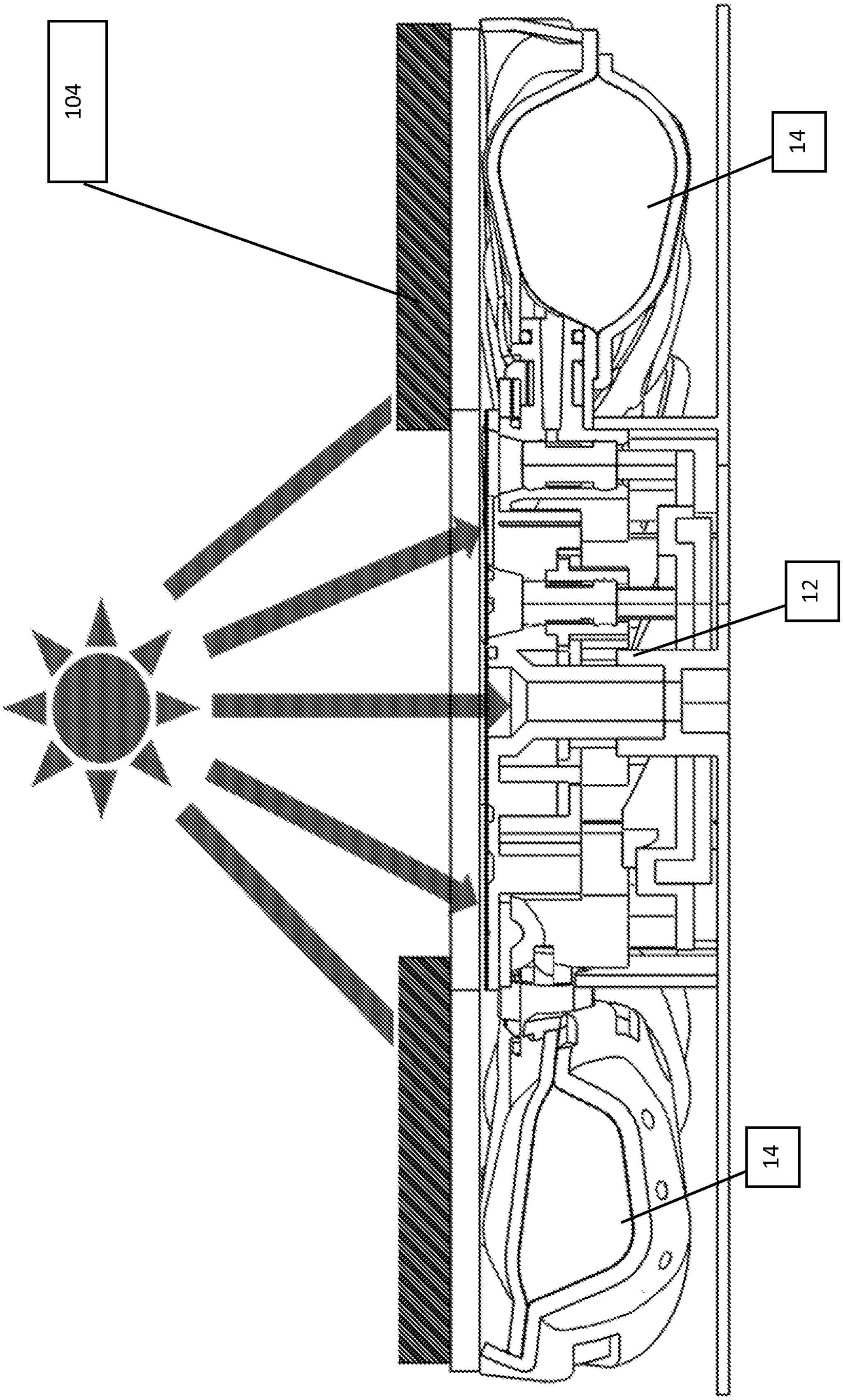
FIG. 52 is a section view of a drug delivery device, showing a shield to block ultraviolet radiation, pulsed light or electron-beam radiation.
Figure 52A:
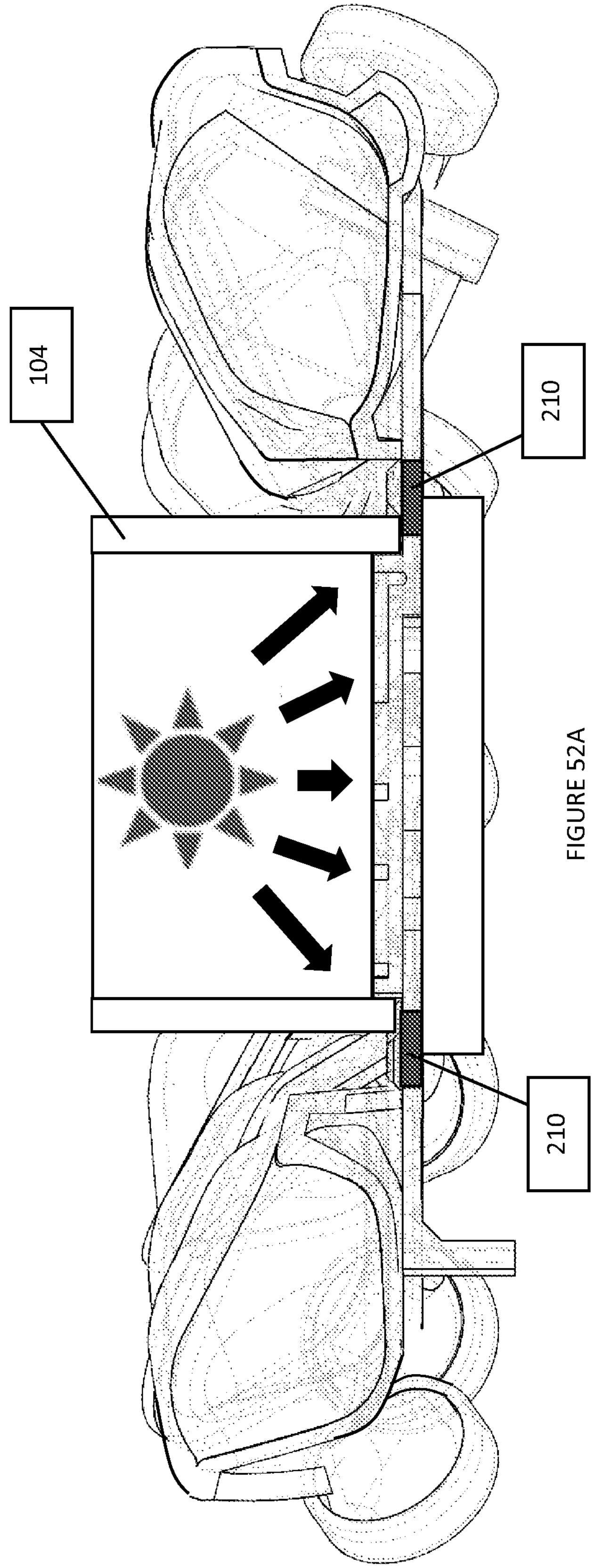
FIG. 52A is a section view of a drug delivery device, which shows an alternative shield for blocking ultraviolet radiation, pulsed light or electron-beam radiation.
Figure 52B:
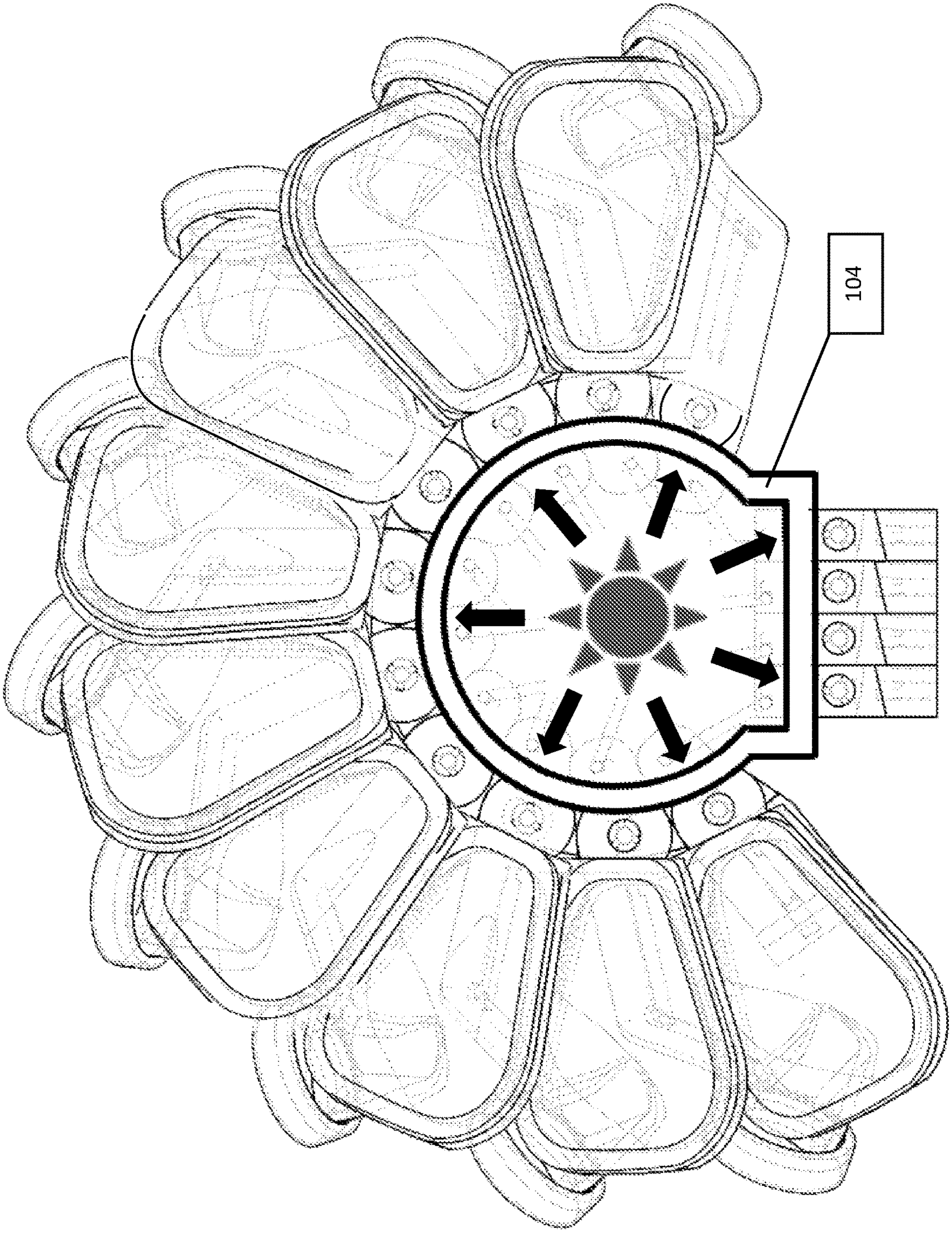
FIG. 52B is a top view of the shield shown in FIG. 52A.
Figure 53:
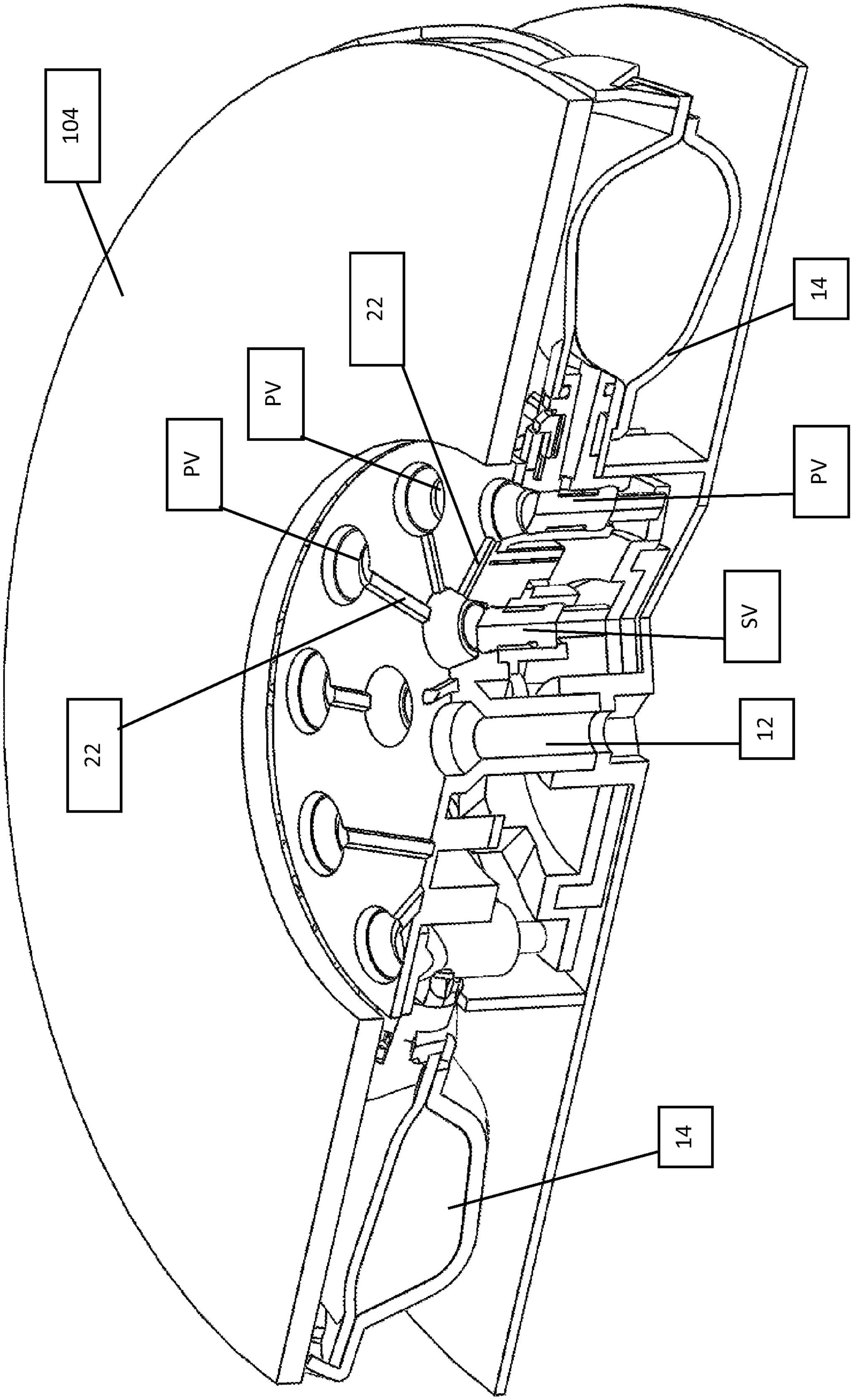
FIG. 53 is a section view of a drug delivery device, which shows a fluid path and valving configuration, in accordance with the subject invention.

As shown representatively in FIG. 48 with "x" markings, it is preferred to have certain portions of the drug cartridge 14 protected from ultraviolet radiation, x-ray radiation, pulsed light or electron-beam exposure. These areas may be sensitive to such exposure, resulting in harm to the contained drug components. As shown in FIGS. 52-53, to protect the sensitive areas of the drug cartridges 14, including the reservoirs 26, from deleterious effects due to exposure to ultraviolet radiation, x-ray radiation, pulsed light or electron-beam, one or more shields 104 may be provided which block ultraviolet radiation, x-ray radiation, pulsed light or electron-beam, depending which is being used. The shields 104 may be planar (as shown in FIG. 52) or tubular (as shown in FIGS. 52A-52B). The sensitive areas may include biocidal materials to promote sterility, including, but not limited to, antimicrobial silver. In addition, or alternatively, where ultraviolet radiation and/or x-ray radiation is utilized, ultraviolet-blocking and/or x-ray-blocking additives may be added to shaded portions 210 of the drug cartridge 14, as shown in FIGS. 49-51. The ultraviolet-blocking and/or x-ray-blocking additives may be any known additive which effectively blocks passage of ultraviolet radiation or x-ray radiation, including, but not limited to, inorganic materials, such as oxides (e.g., TiO2 and ZnO), and organic materials, such as amine light stabilizers (such as that sold under the tradename HALS_Chimassorb 2020), UV absorbers (such as those sold under the tradenames Tinuvin 326 and Uvinul 3034, by BASF), and carbon black. The ultraviolet-blocking and/or x-ray-blocking additives may be used on pulsed light, depending on constituent electromagnetic radiations included therein.

Figure 54:
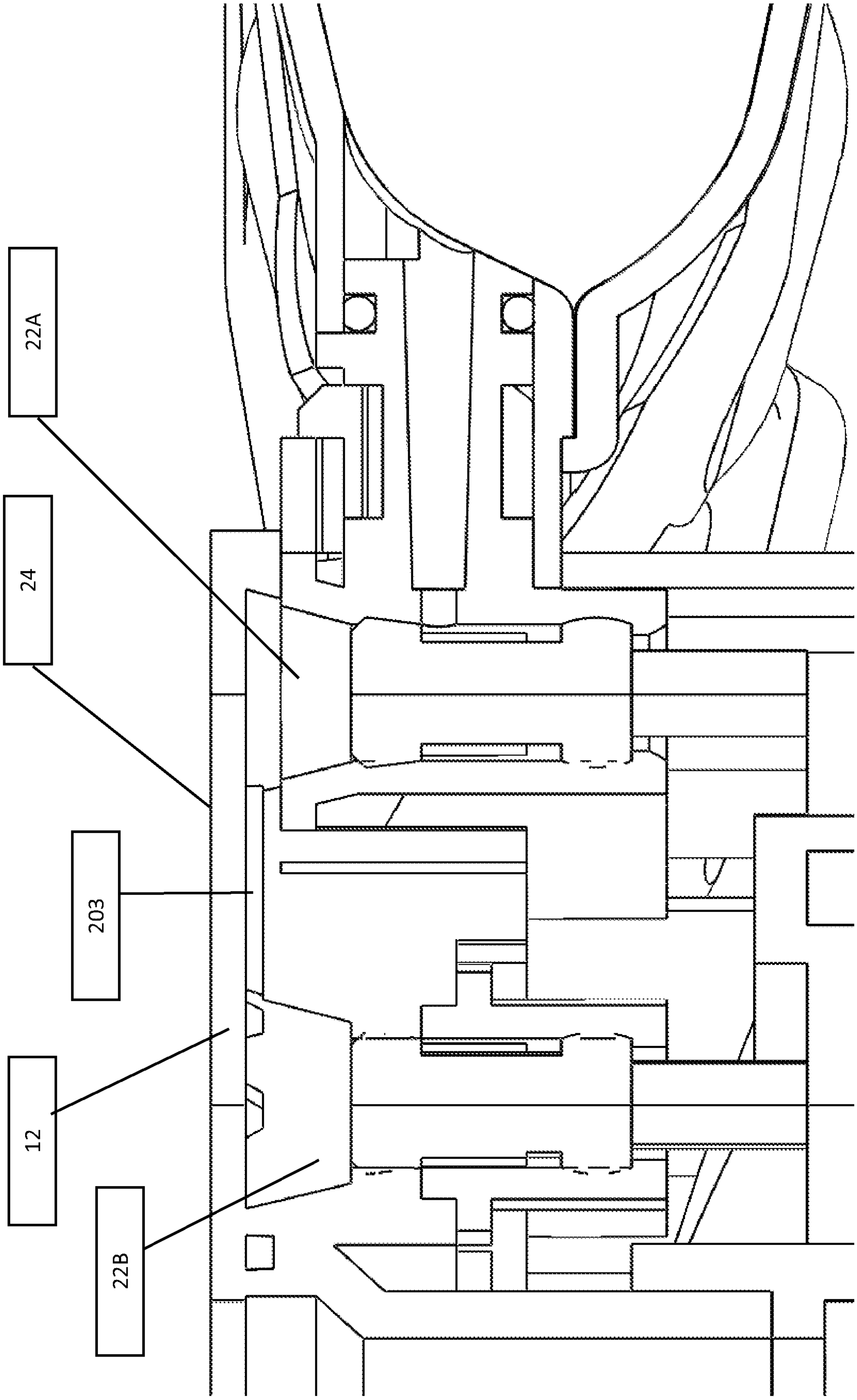
FIG. 54 is a detailed view of a section of FIG. 53, focusing on the body of the device.
Figure 55:
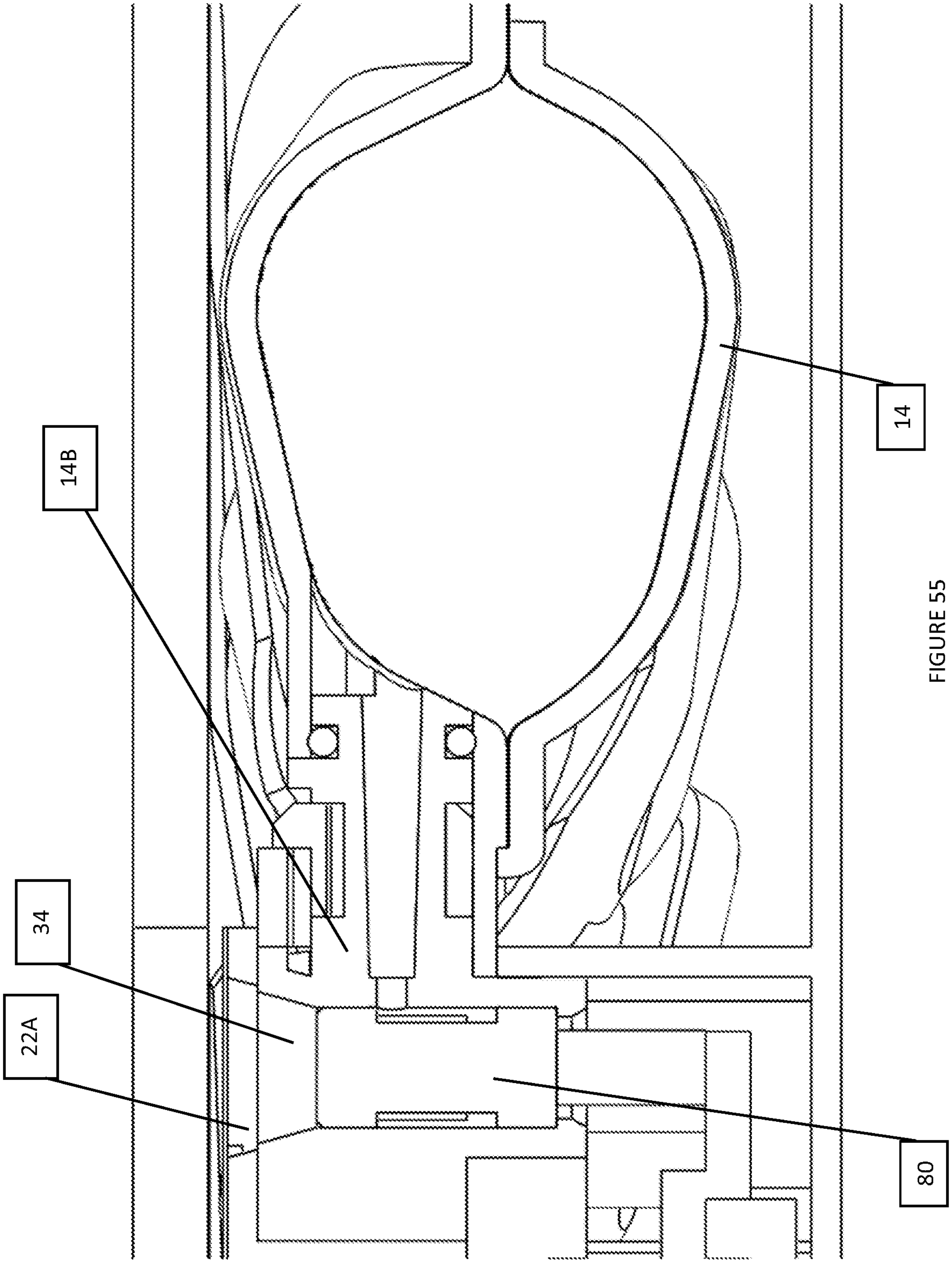
FIG. 55 shows a drug cartridge mounted to a body of a drug delivery device, having a valve in a closed state, in accordance with the subject invention.
Figure 56:
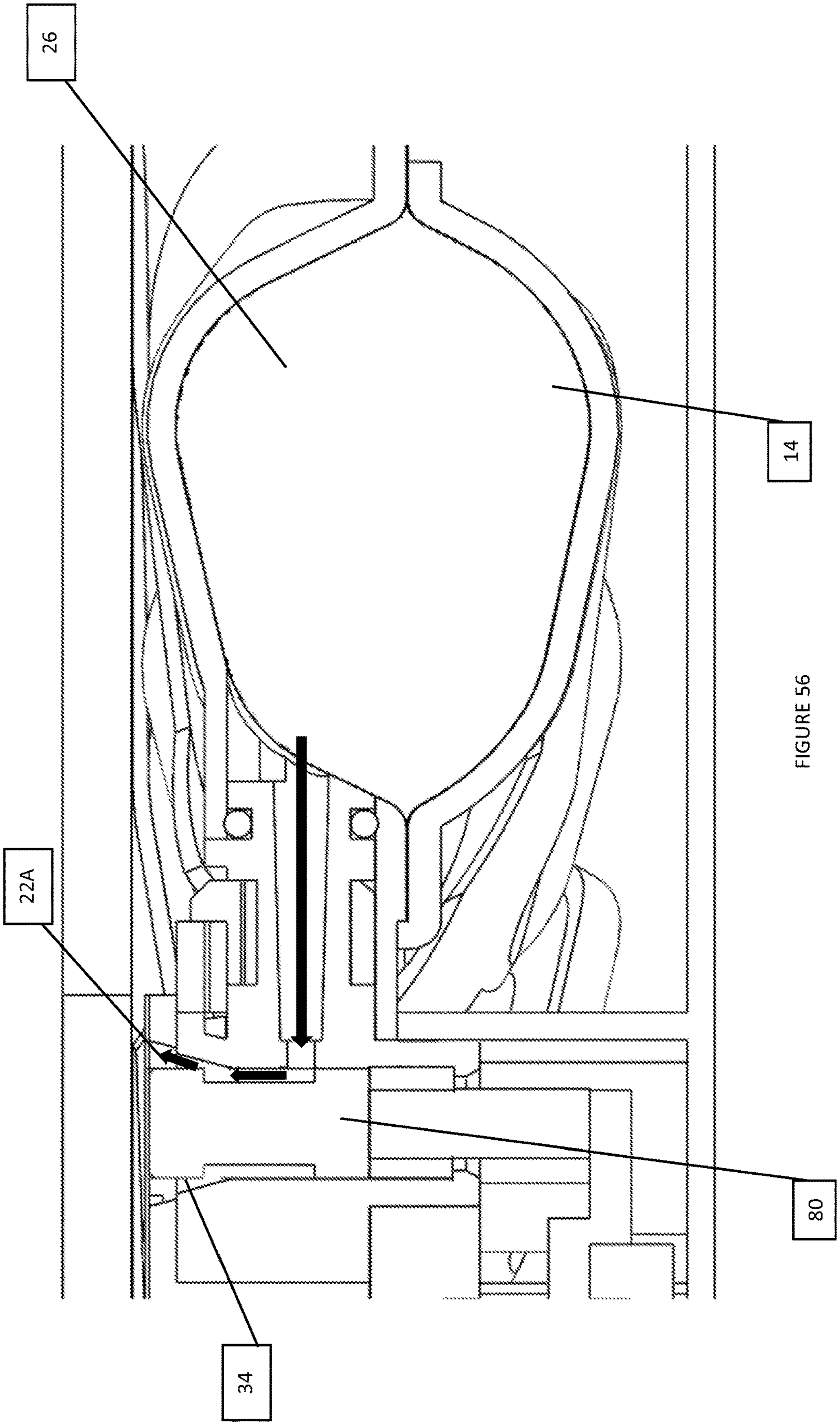
FIG. 56 shows the drug cartridge of FIG. 55, with the valve in an open state, defining a flow path.

As shown above, surfaces needing decontamination are exposed and generally facing the source of ultraviolet radiation, x-ray radiation, pulsed light or electron-beam radiation. With passage through the barrier 102, these surfaces are unobstructed to receive radiation. It is noted that ultraviolet radiation, x-ray radiation, pulsed light and electron-beam radiation have effectiveness to a certain depth of material. Thus, as shown in FIG. 54, one or more of ducts 22 may be provided as encased in the body 12 as encased duct 203. Any encased ducts 203 should be in sufficient proximity to the first face 24 to be properly decontaminated with exposure to ultraviolet radiation, x-ray radiation, pulsed light or electron-beam radiation. As shown in FIG. 54, with the use of encased ducts 203, the barrier 102 may not be omitted or applied to only where the ducts 22 are exposed.

Figure 49A:
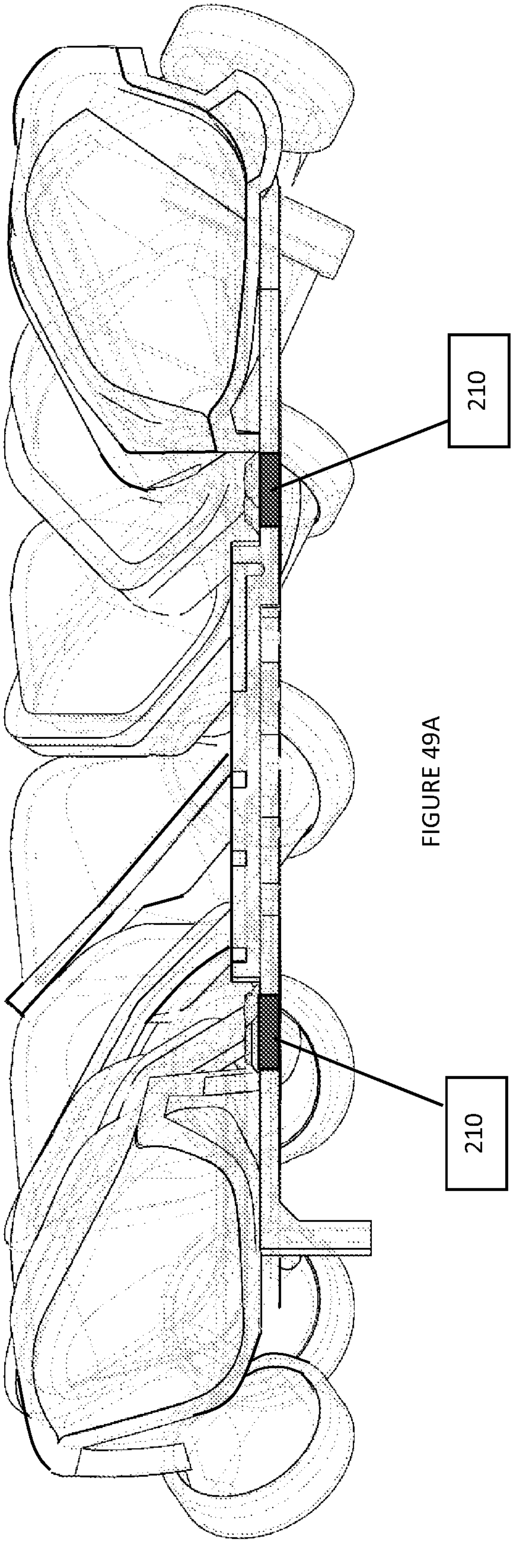
Figure 49B:
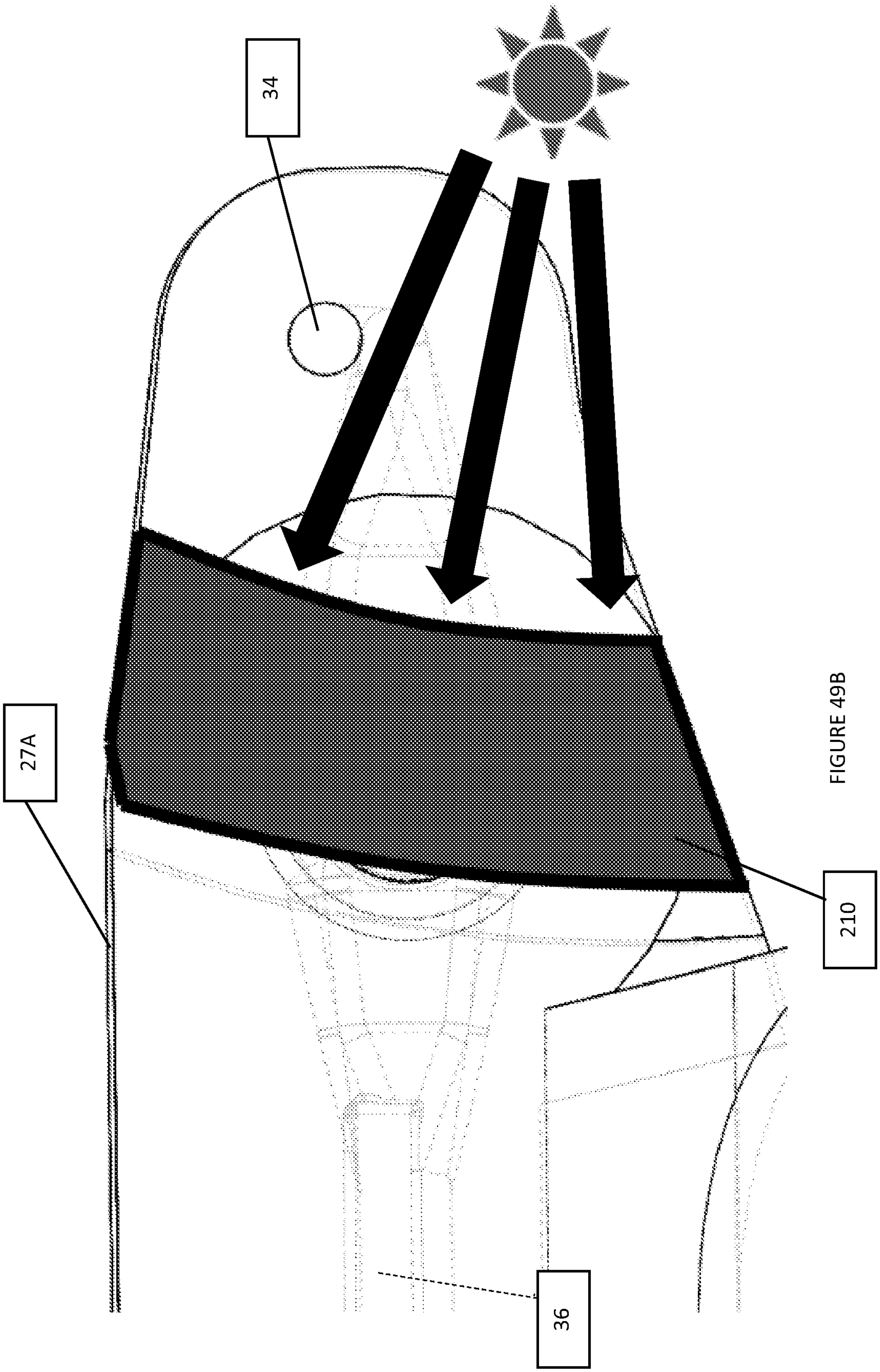
Figure 49C:
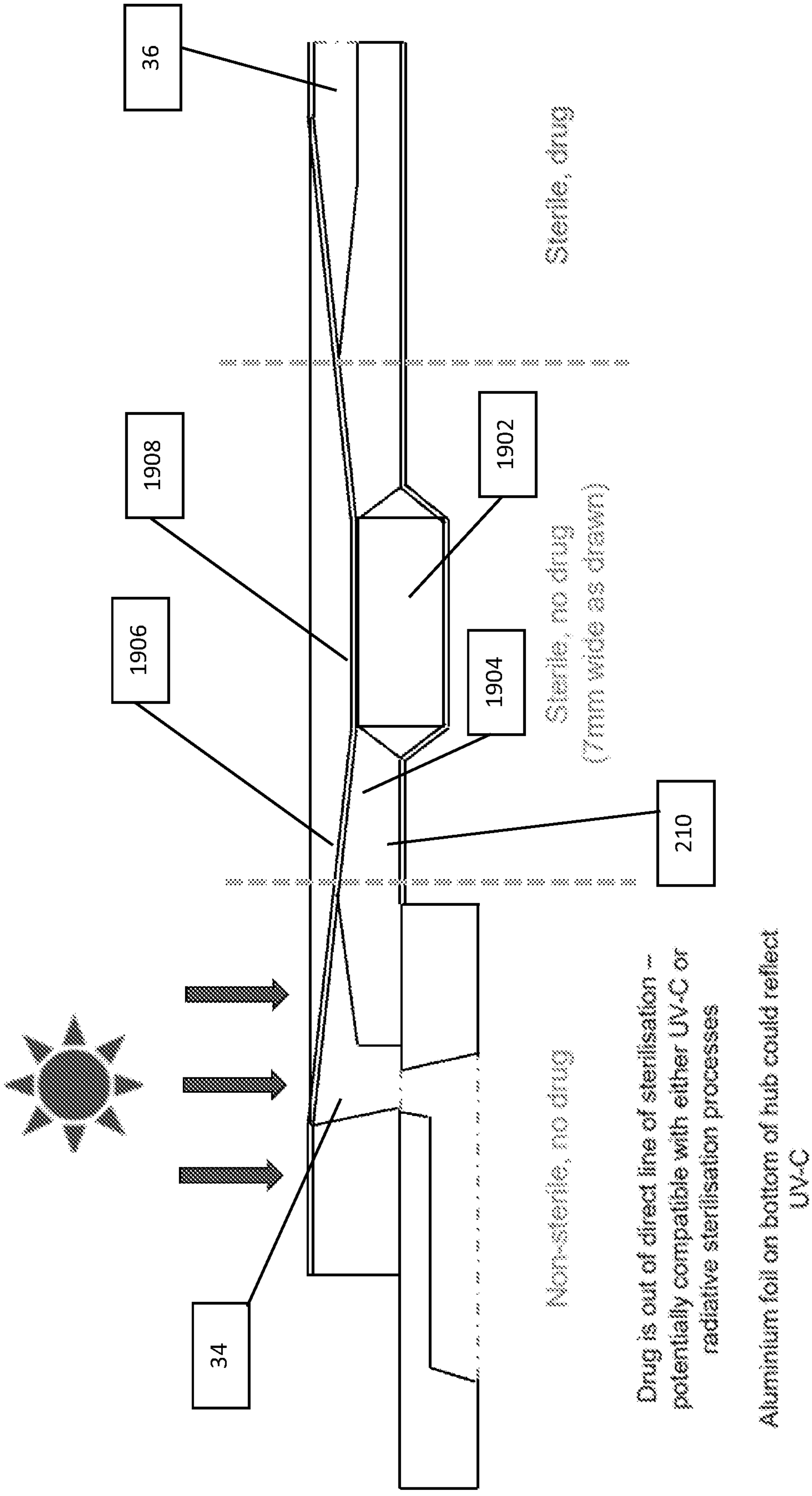

With the drug cartridge 14 being provided with the wing portion 27A, ultraviolet-blocking and/or x-ray blocking additives may be provided across the wing portion 27A to cross the well 1900, the additives being located between the fluid outlet 34 and portions of the internal lumen 36 upstream from the seal 1908, as shown by the shaded portions 210 in FIGS. 49A-49C. In this manner, the fluid outlet may be sterilized without deleterious effects on any drug contained within the internal lumen 36. Moreover, as shown in FIG. 52A, the shield 104, in tubular form, may be shaped to overlap the shaded portions 210, thus providing UV/x-ray blocking in both radial and vertical directions.

Figure 73A:
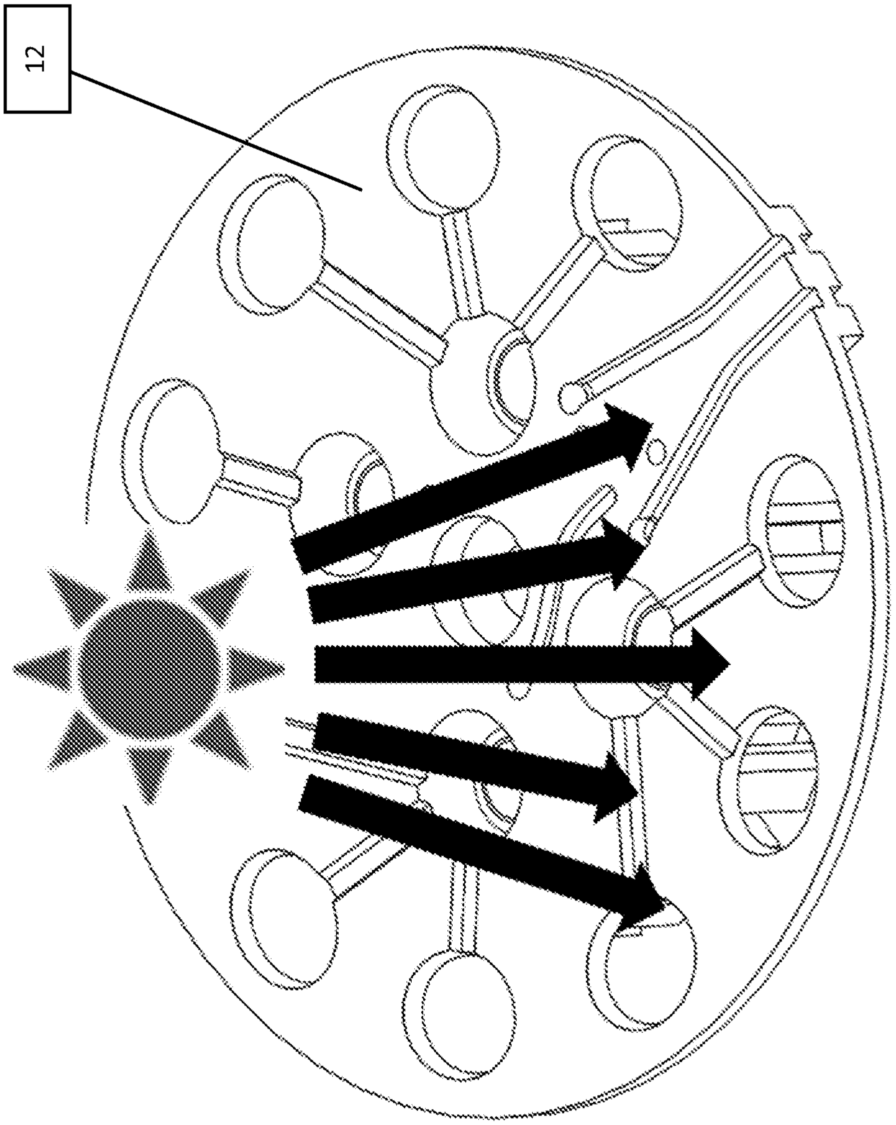
FIG. 73A shows schematically the location on a body of the drug delivery device for ultraviolet radiation exposure.
Figure 73B:
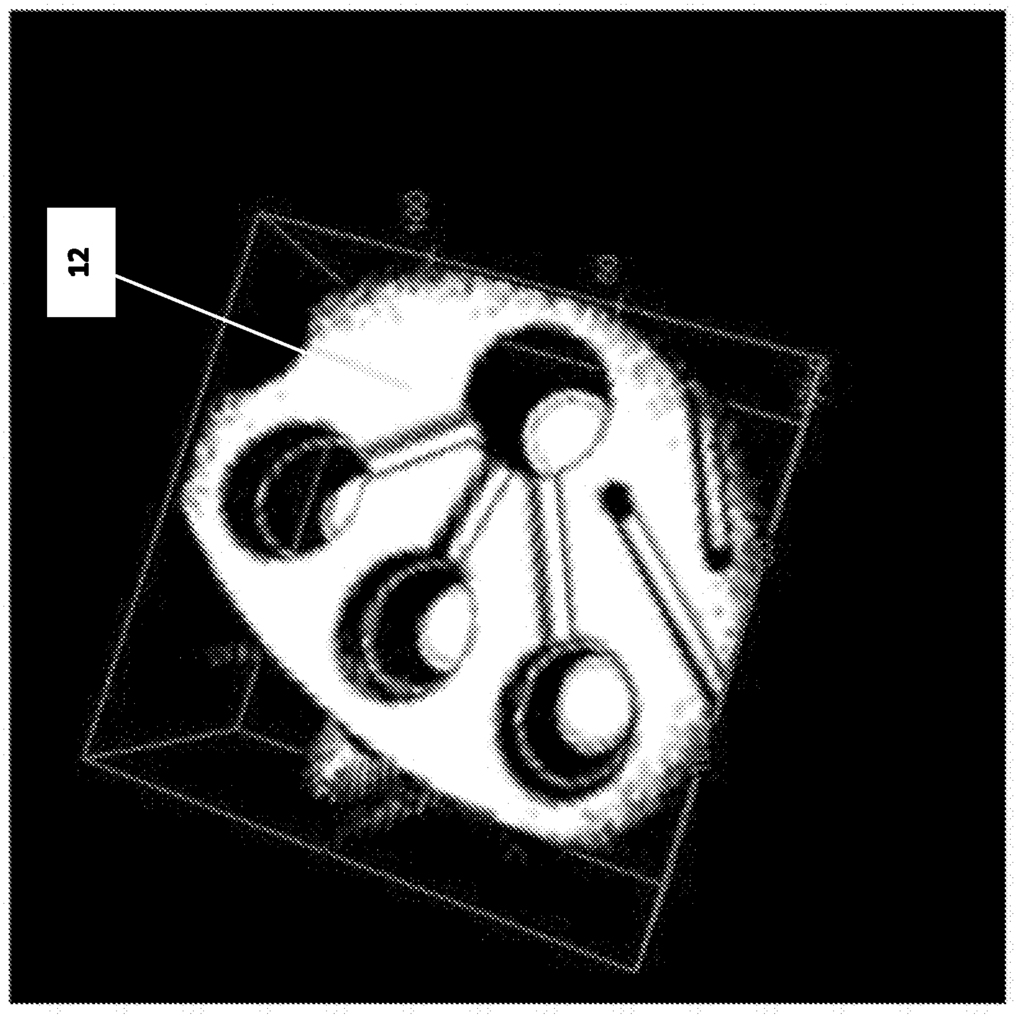
FIG. 73B shows the UV threshold dose achieved after three seconds of ultraviolet radiation exposure.
Figure 73C:
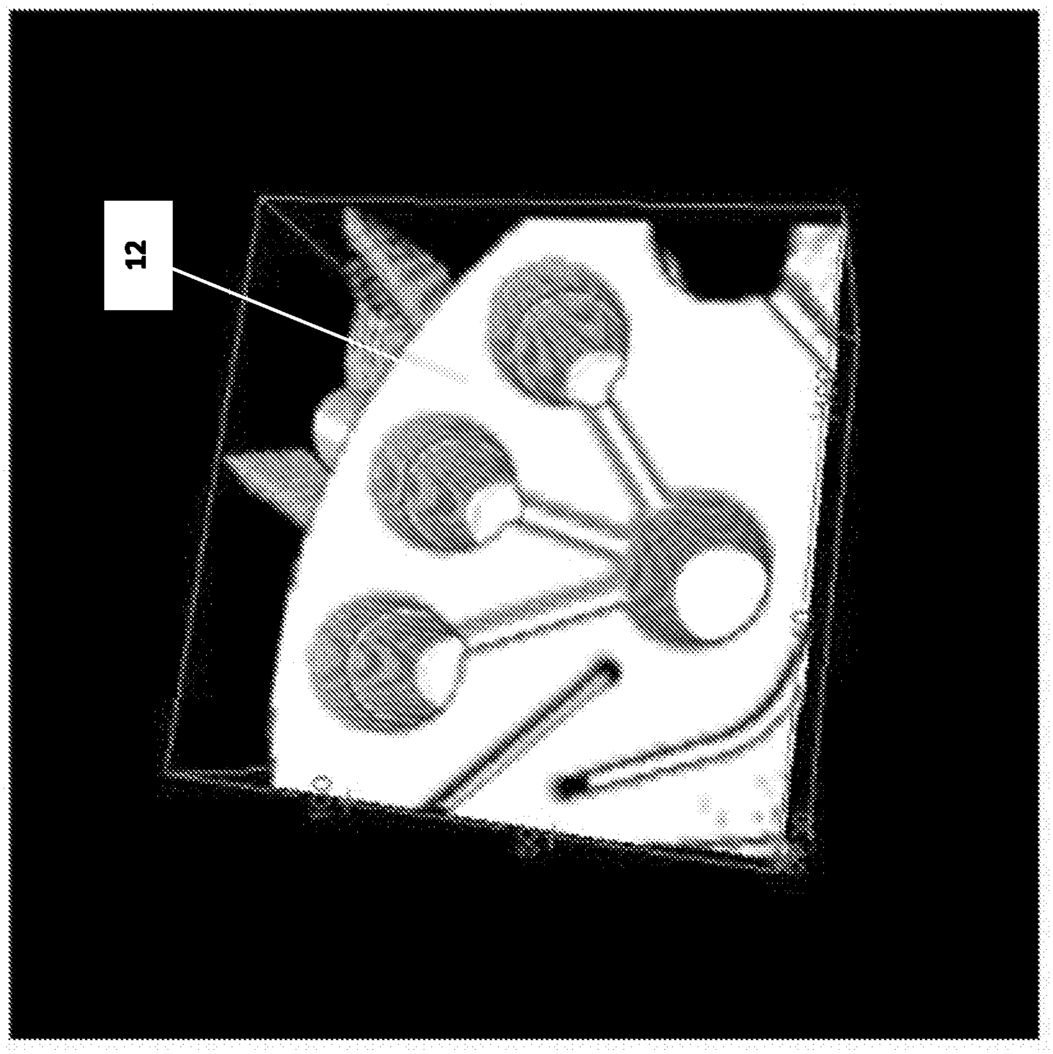
Figure 74:
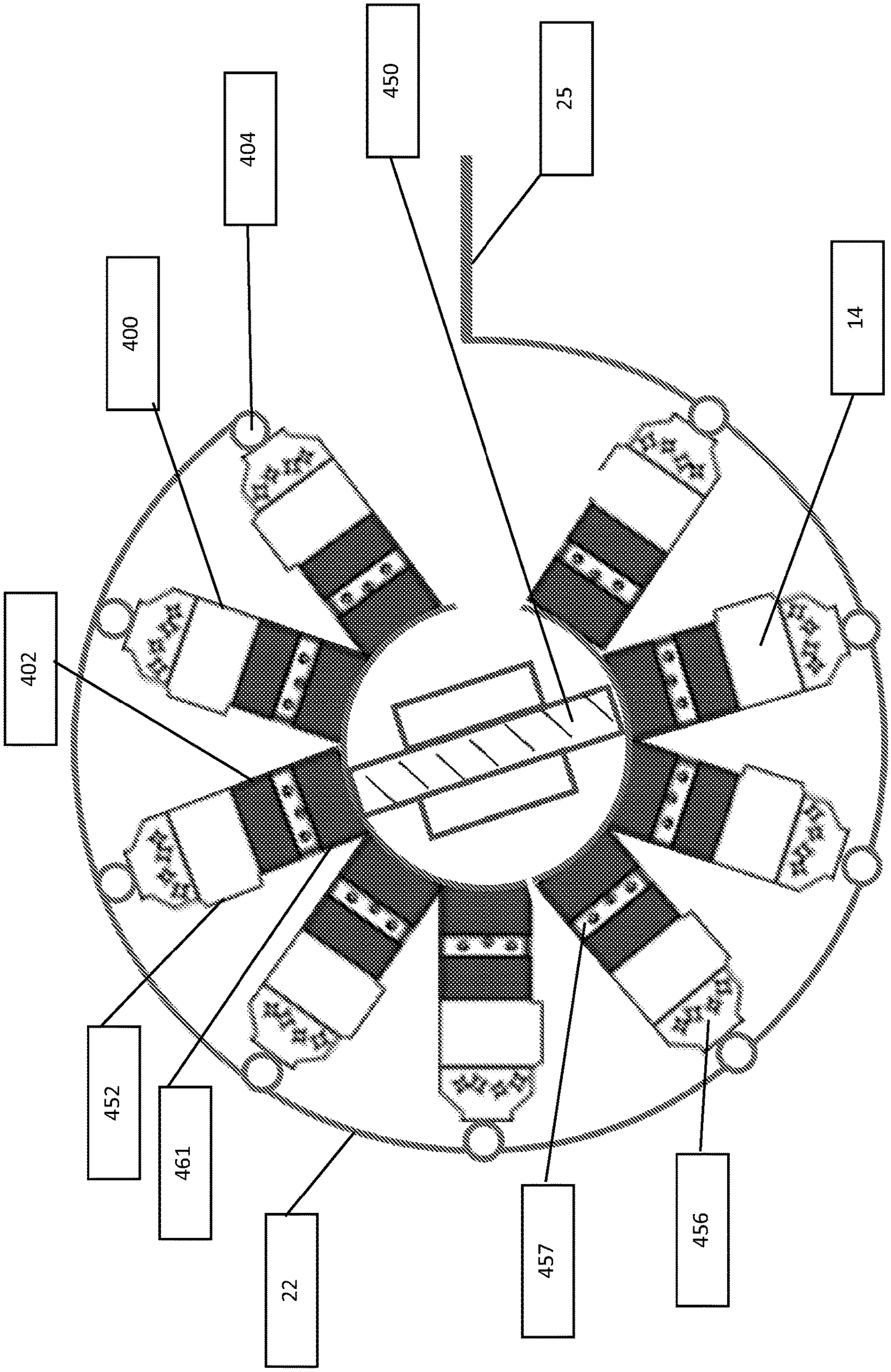
Figure 75:
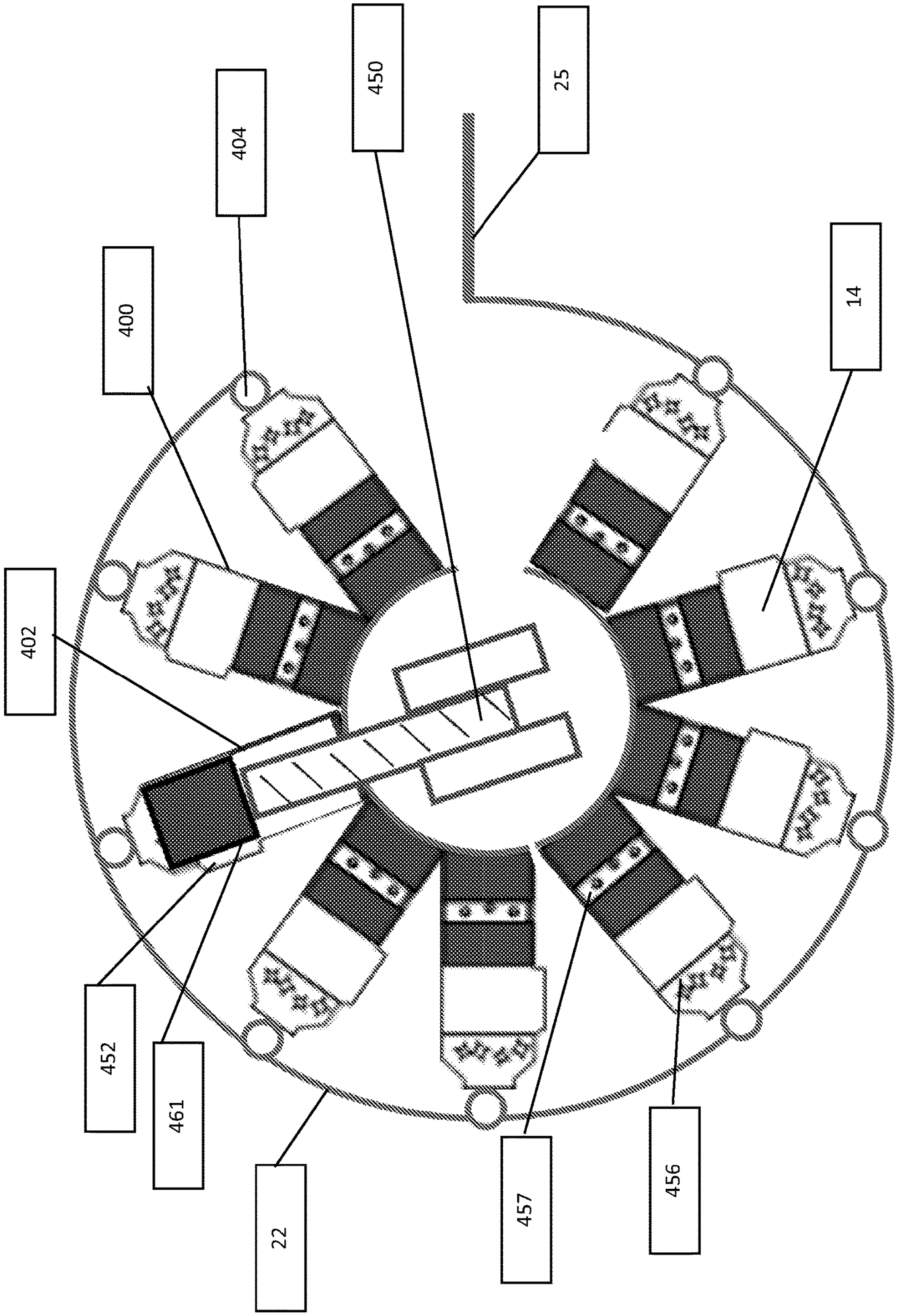
Figure 76:
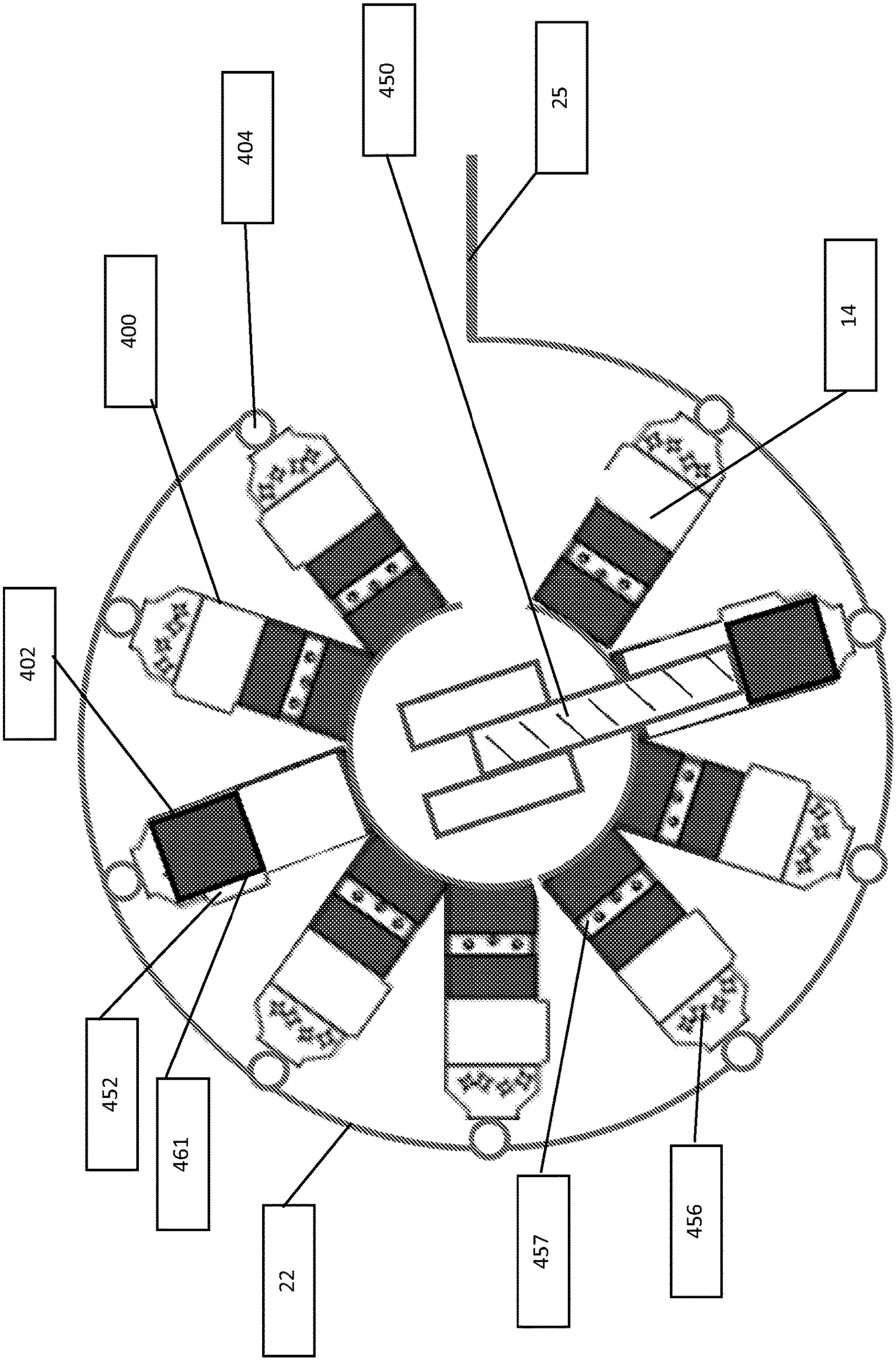
Figure 77:
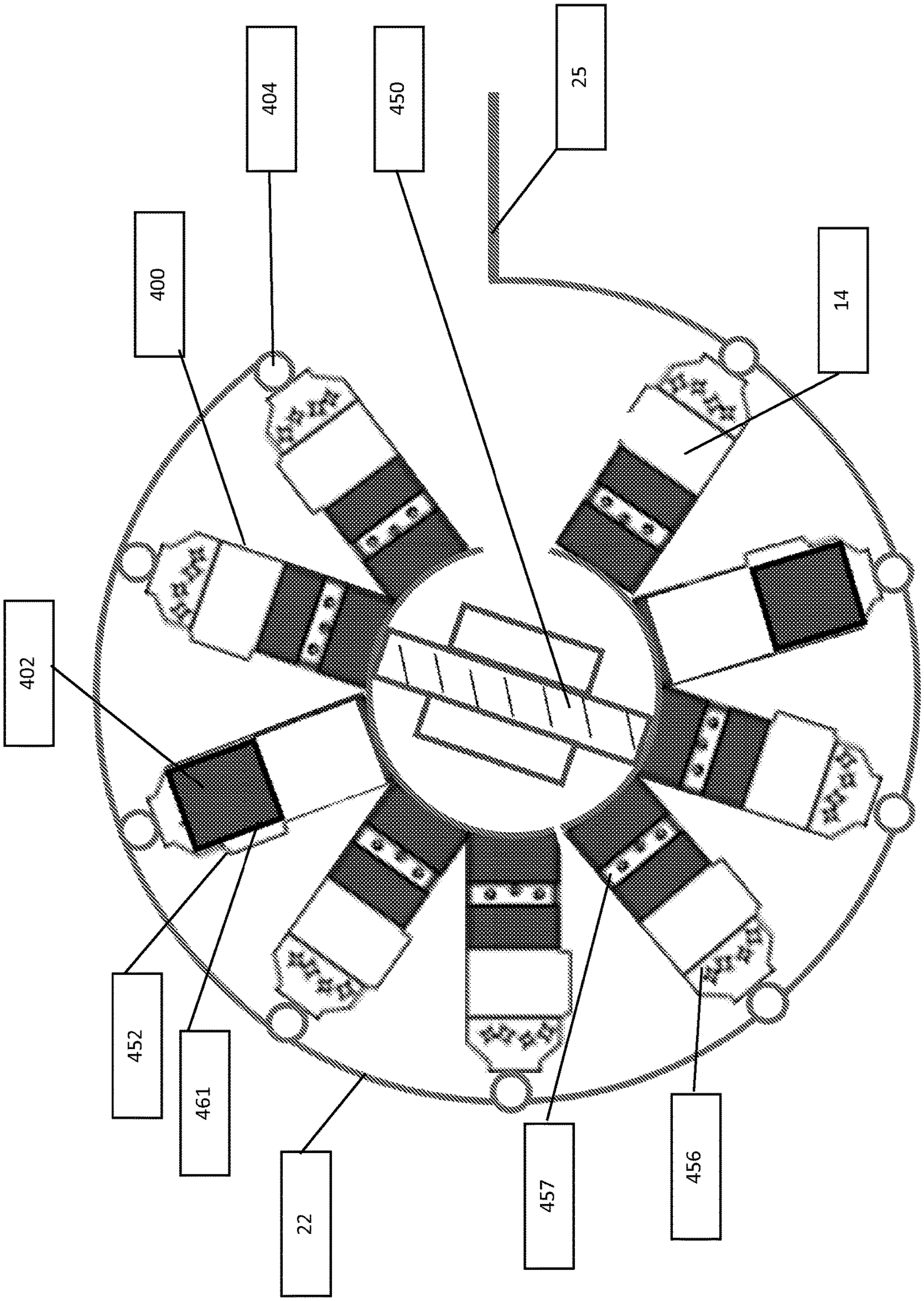
Figure 78:
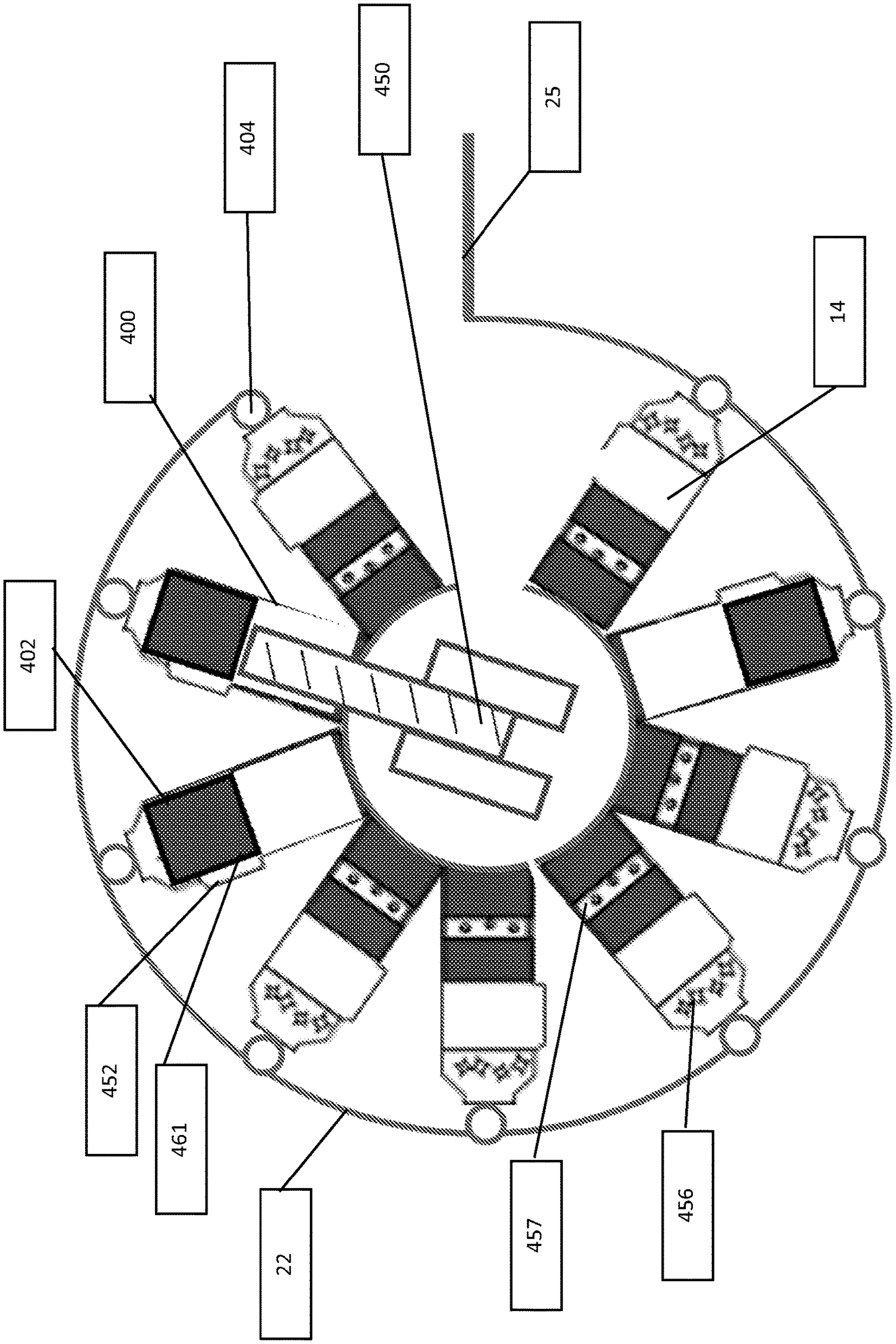

FIG. 73A shows a body 12 which may be decontaminated using ultraviolet radiation. FIGS. 73B-73C show the amount of ultraviolet radiation received on surfaces of the body 12 after certain time intervals. In FIGS. 73B-73C, black surfaces indicate ultraviolet radiation readings of less than 10 mJ/cm$^2$, which may be considered a threshold dose. White surfaces indicate ultraviolet radiation reading of at least 10 mJ/cm$^2$, i.e., of at least the threshold dose. FIG. 73B is an image captured of the body 12 having been exposed to ultraviolet radiation for 3 seconds, while FIG. 73C is an image captured of the body 12 having been exposed to ultraviolet radiation for 30 seconds. As can be seen in FIG. 73C, good distribution of ultraviolet radiation is achievable, even with differently directed surfaces. FIG. 73C shows that the body 12 may be sterilized with exposure to ultraviolet radiation. The same is expected with x-ray radiation, pulsed light and electron-beam radiation.

As will be appreciated by those skilled in the art, additional sterilization techniques, such as heat and gas sterilization (e.g., EtO ethylene oxide), may be used to supplement the application of ultraviolet radiation, x-ray radiation, pulsed light and/or electron-beam radiation. In addition, these sterilization techniques may be used in lieu of ultraviolet radiation, x-ray radiation, pulsed light and/or electron-beam radiation, e.g., where the barrier 102 is not provided or is not transmissive to such radiation. It is also possible to use decontamination techniques utilizing ultraviolet radiation, x-ray radiation, pulsed light and/or electron-beam radiation in varying combinations.

As will be appreciated by those skilled in the art, the decontamination methods described herein may be used with various drug delivery devices, including those having contained drug reservoirs (i.e., not separately provided). In addition, the decontamination methods may be used to sterilize related fluid path(s) prior to filling of drug to sterilize the related fluid path. The subject invention allows for the covering of open fluid ducts in the body of a drug delivery device which are covered by a barrier, and which may be decontaminated by exposure to ultraviolet radiation, x-ray radiation, pulsed light or electron-beam which passes through the barrier.

The drug delivery device 10 may be provided with various fluidic arrangements which permit delivery of drug from the reservoirs 26 of the drug cartridges 14. In addition, the fluidics may be configured to facilitate reconstitution and/or mixing, e.g., by allowing for introduction of a diluent, or other liquid component, into one or more of the reservoirs 26. For example, in one configuration, at least one of the drug cartridges 14 may be provided with the diluent, and the pump 20 may be configured to be bi-directional. This allows for drawing the diluent from the drug cartridge(s) 14 holding the diluent, pumping the diluent into at least one target drug cartridge 14 to allow for reconstitution and/or mixing, and, subsequently, drawing the resulting liquid drug from the target drug cartridge(s) 14 for conveyance to the needle 15 for delivery to the patient.

Figure 90:
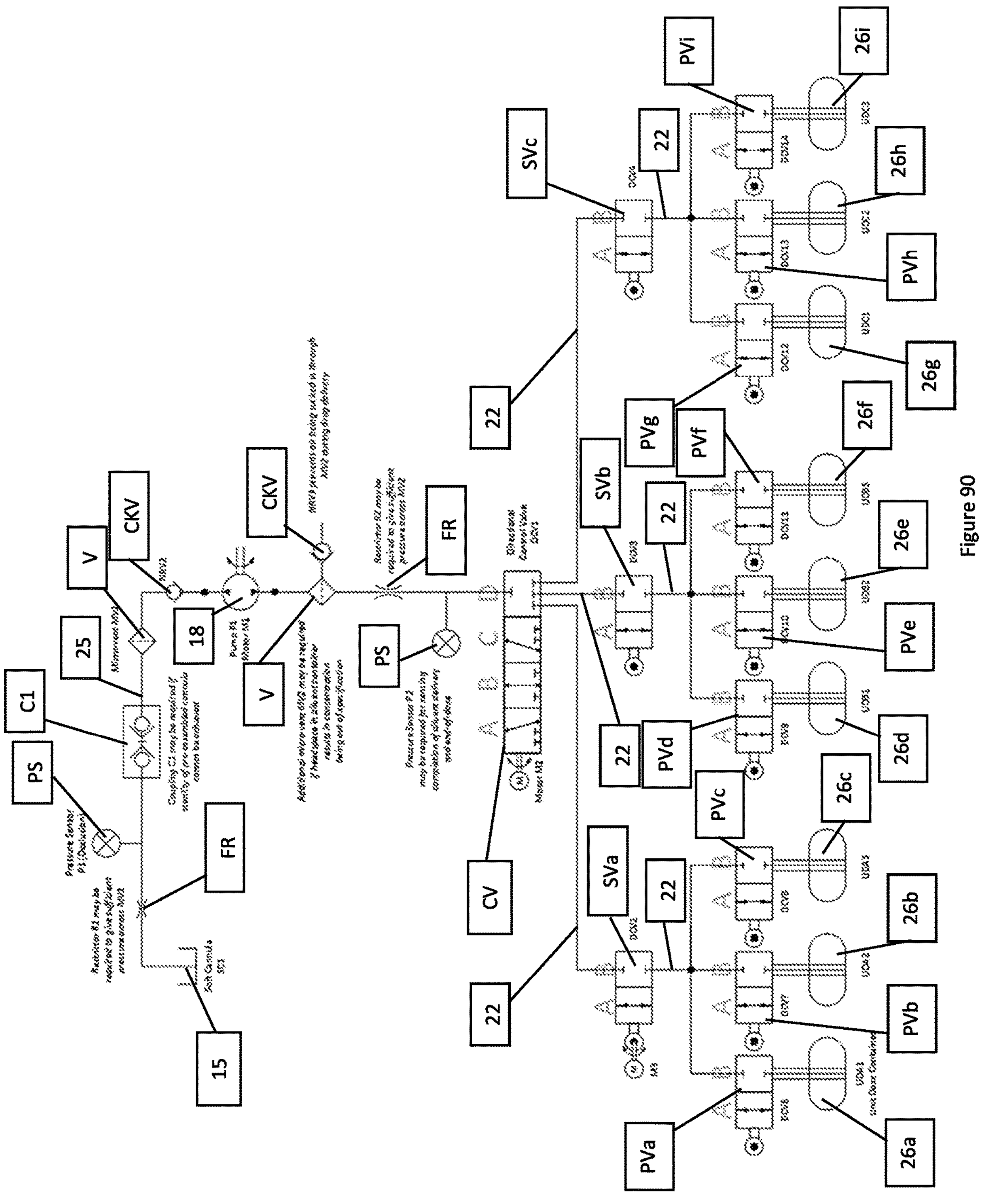
Figure 91:
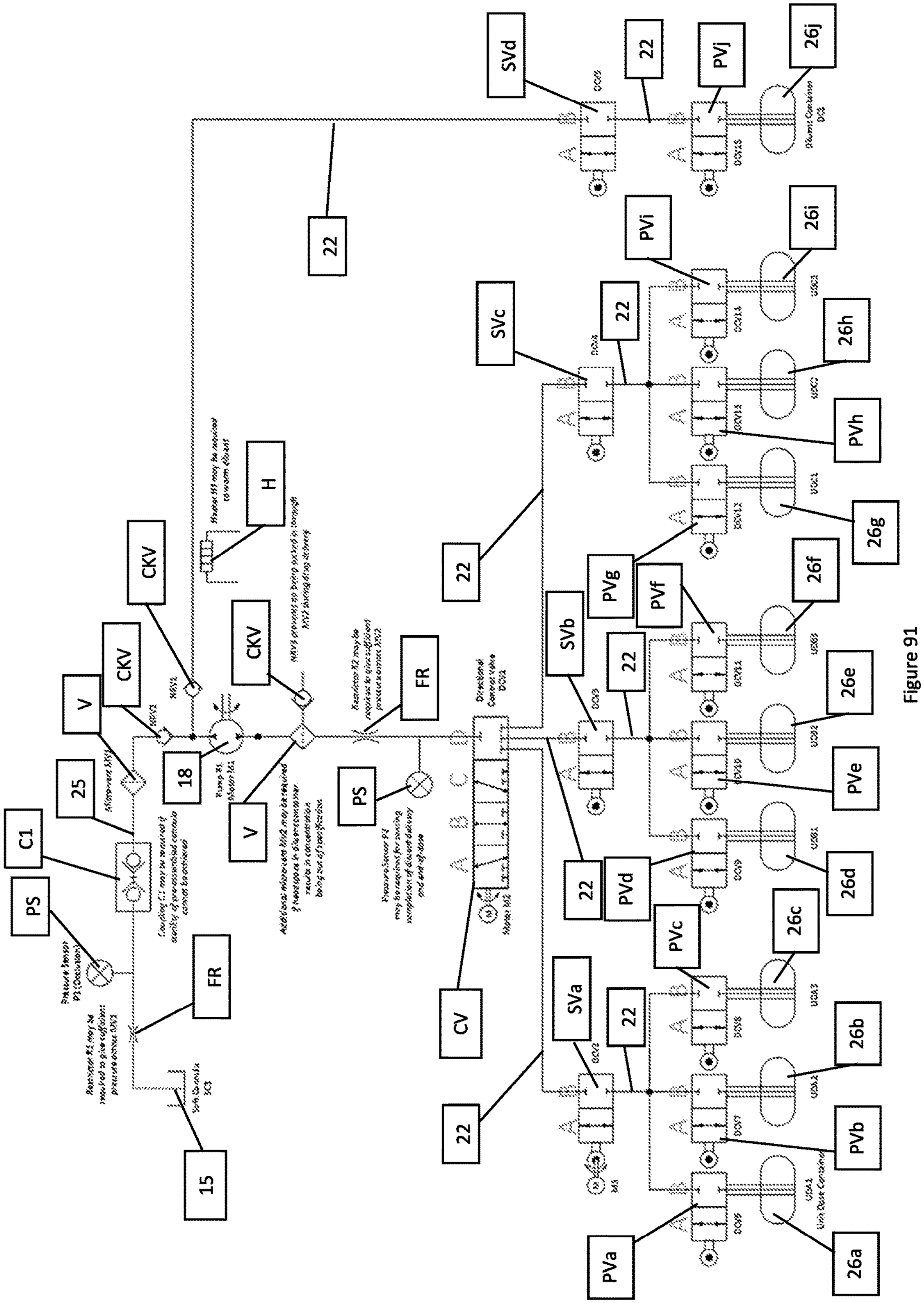

FIGS. 90-94 are schematics showing various fluidic arrangements useable with the drug delivery device 10. With reference to FIG. 90, a fluidic arrangement is shown for conveying drug from a plurality of reservoirs 26 (shown as reservoirs 26*a*-26*i*) to the needle 15. Valving may be provided to allow for selective control from which of the reservoirs 26 is taken drug. This allows for different combinations of drug to be withdrawn in series and/or parallel from the drug cartridges 26 to provide combinatorial drug treatment. Further, the drug may be provided in different forms (e.g., dry, liquid) in different drug cartridges 26, the different forms being combinable. For example, dry drug may be reconstituted and then combined with a liquid drug. In addition, the same drug may be withdrawn from the reservoirs 26, allowing for large volume dosing of a single drug.

As shown schematically in broken lines, each of the reservoirs 26 may be located on a drug cartridge 14. As described above, the valve 80, the sealing sheet 1906, or other seal, including those described above, may be provided on the cartridge 14 to selectively provide access to the drug contained therein. It is possible for the valve 80, the sealing sheet 1906, or other seal to be located on the body 12, functioning to selectively seal the corresponding reservoir 26. The valves 80, the sealing sheets 1906, or other seals sealing the reservoirs 26 may be considered as primary valves PV (shown as primary valves PVa-PVi) configured to selectively permit flow to or from the reservoirs 26. The primary valves PV may be two-position valves or seals (positions A, B) providing selectively an open or closed state. The reservoirs 26, or subsets thereof, may be manifolded to common fluid ducts 22, which in turn may be regulated by secondary valves SV (shown as secondary valves SVa-SVc). The secondary valves SV may be two-position valves (positions A, B), providing selectively an open or closed state, to permit or block flow therethrough. The secondary valves SV allow for flow to, or from, desired subset(s) of the reservoirs 26. FIG. 53 shows a possible arrangement of the primary valves PV and the secondary valves SV. The secondary valves SV may be configured as the valves 80 or the sealing sheets 1906 described above.

Further, fluid ducts 22 may be provided from the secondary valves SV to the pump 18 in defining a fluidic path therebetween. At least one control valve CV may be provided between the secondary valves SV and the pump 18 to allow for selective communication with particular groups of the reservoirs 26. The control valve CV may be multi-positionable, e.g., having a quantity of open positions equal to the number of the secondary valves SV plus an additional closed position (for example, in FIG. 90, the control valve CV has four positions (positions A, B, C, D) with three open positions (corresponding to each of the three control valves CVa-CVc) and one closed position).

In use, the primary valves PV, the secondary valves SV, and the control valve CV may be adjusted to selectively define open fluid paths between the reservoirs 26 and the pump 18. For example, to define an open flow path from the pump 18 to the reservoir 26*i:* 1. the control valve CV may be adjusted to position A; 2. the secondary valve SVc may be adjusted to position A; and, 3. the primary valve PVi may be adjusted to position A. This allows for drug to be withdrawn from the reservoir 26*i* by the pump 18. Once the reservoir 26*i* is voided, the primary valve PVi may be closed by adjusting to position B, and, a next reservoir may be opened, such as the reservoir 26*h*, with the primary valve PVh being adjusted to position A. It is preferred that the primary valves PV and secondary valves SV be in closed state where no flow is intended therethrough. This allows for maximum negative pressure (suction) to be applied by the pump 18 to the target reservoir 26.

The flow path may include vents V, check valves CKV (e.g., one-way check valves), and flow restrictors FR (e.g., Venturi tubes) to allow for venting and smoother flow along any of the fluid ducts 22 and/or the outlet duct(s) 25. The check valves CKV, particularly, as one-way check valves, inhibit back flow from an unsterilized region or from external of the drug delivery device 10, best maintaining sterility of active flow paths. To further protect sterility of the active flow paths, one or more couplings C1 may be provided with at least two of the check valves CKV in series, but in opposing orientations, to restrict back flow in both directions across the coupling C1. Pressure sensors PS may be provided to monitor flow pressures along different portions of flow paths.

The pump 18 may be motor driven, particularly driven by an electric motor (e.g., DC powered electric motor), which may be contained in the housing 9. The pump 18 may be a positive-displacement pump or a peristaltic pump. It is preferred that the pump 18 be bi-directional. With respect to FIG. 90, the fluid path is configured with the pump 18 drawing drug from the reservoirs 26. The pump 18 is, thus, situated, to have a discharge (pressure side) situated towards the needle 15 and inlet (suction side) situated towards the reservoirs 26. As further described below, the pump 18 may be utilized to mix and/or reconstitute drug by causing both flow to and from the reservoirs 26. The pump 18, here, would be bi-directional to allow for reverse action to switch pressure and suction sides of the pump 18. To facilitate this functionality, it is preferred that the pump 18 be configured to allow for bi-directional operation, which is achievable by positive displacement and peristaltic pumps.

The primary valves PV, the secondary valves SV, and the control valve CV may be adjusted by any known means, such as activable solenoids, valve actuators, and so forth. With reference to FIGS. 95-97B, a displaceable actuator plate 500 may be provided defining one or more ramped cam surfaces 502 positioned to displace the primary valves PV, secondary valves SV, and/or the control valve CV with the displacement of the actuator plate 500. As a non-limiting example, the actuator plate 500 may be provided as a liftable disc relative to the body 12, with the ramped cam surfaces 502 being defined along limited arcs of the actuator plate 500, and the primary valves PV and the secondary valves SV may be each configured as the valve 80. As shown in FIGS. 34-35B, the valves 80 may be opened with upward displacement. As shown in FIGS. 95-96B, a plurality of control elements 504 may project upwardly from the actuator plate 500, located to axially align with the primary valves PV and the secondary valves SV.

The actuator plate 500 may be non-rotatably mounted to a gear plate 510 (FIG. 96B). As shown in FIG. 96C, the gear plate 510 may include an opening 511 to allow for mounting to the body 12, with the gear plate 510 being rotatable. A series of gear teeth 512 may be provided along the periphery of the gear plate 510. The gear teeth 512 may be meshingly engaged by one or more drive gears or pinions (not shown), which are motor driven, to cause rotation of the gear plate 510. The same motor used to power the pump 18 may be used to drive the gear plate 510. The motor may include one or more drive shafts, and may include clutches to selectively engage driven elements, such as the pump 18 or the pinion for driving the actuator plate 500. It is also preferred that the motor be reversible to allow for bi-directional movement of the actuator plate 500.

The gear plate 510 includes a plurality of secondary ramped cam surfaces 503. As shown in FIG. 96A, the ramped cam surfaces 502 are formed hollow to allow for insertion therein of the secondary ramped cam surfaces 503. This allows for the actuator plate 500 to rest upon the gear plate 510. With the control elements 504 being received in the internal lumen 36 (e.g., in the second lumen portion 36B), the actuator plate 500 is restricted from rotating relative to the body 12. As shown in FIG. 96B, with rotation of the gear plate 510, the secondary ramped cam surfaces 503 rotate relative to the ramped cam surfaces 502, resulting in a lifting of the actuator plate 500 (compare FIGS. 96D and 96E, and FIGS. 97A and 97B). The lifting of the actuator plate 500 causes the control elements 504 to upwardly displace the valves 80. Upward displacement of the primary valves PV and the secondary valves SV results in the respective valves being separated from the corresponding valve seats 76, as shown in FIGS. 97A and 97B. As shown in FIG. 98, a biasing means 508 (e.g., spring) may be provided to urge the respective valve PV, SV to the open state. This may assist in causing the respective valve PV, SV to open. The biasing means 508 may be a coil spring, defining an open passageway through which the control element 504 may pass.

Figure 199:
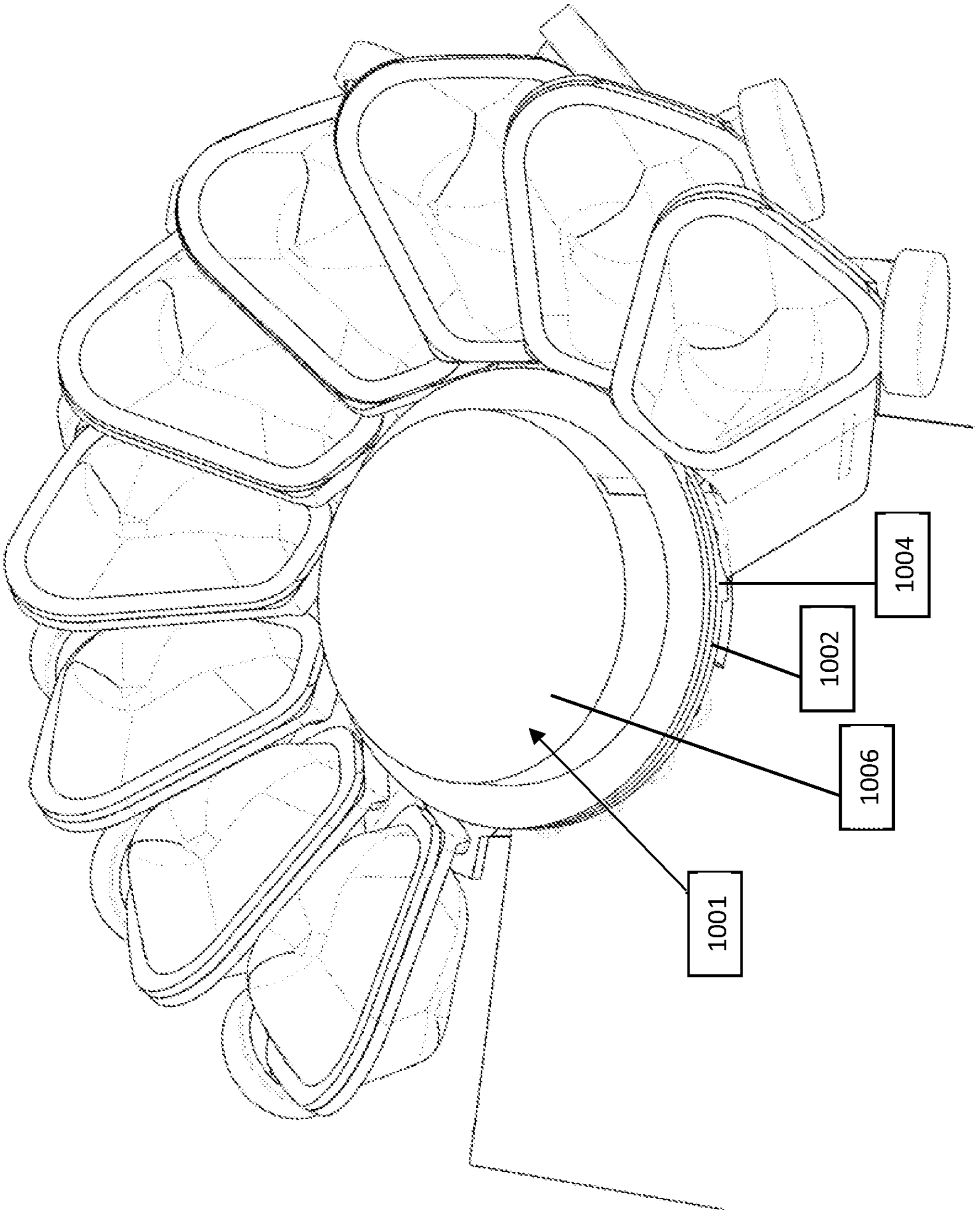
Figure 200:
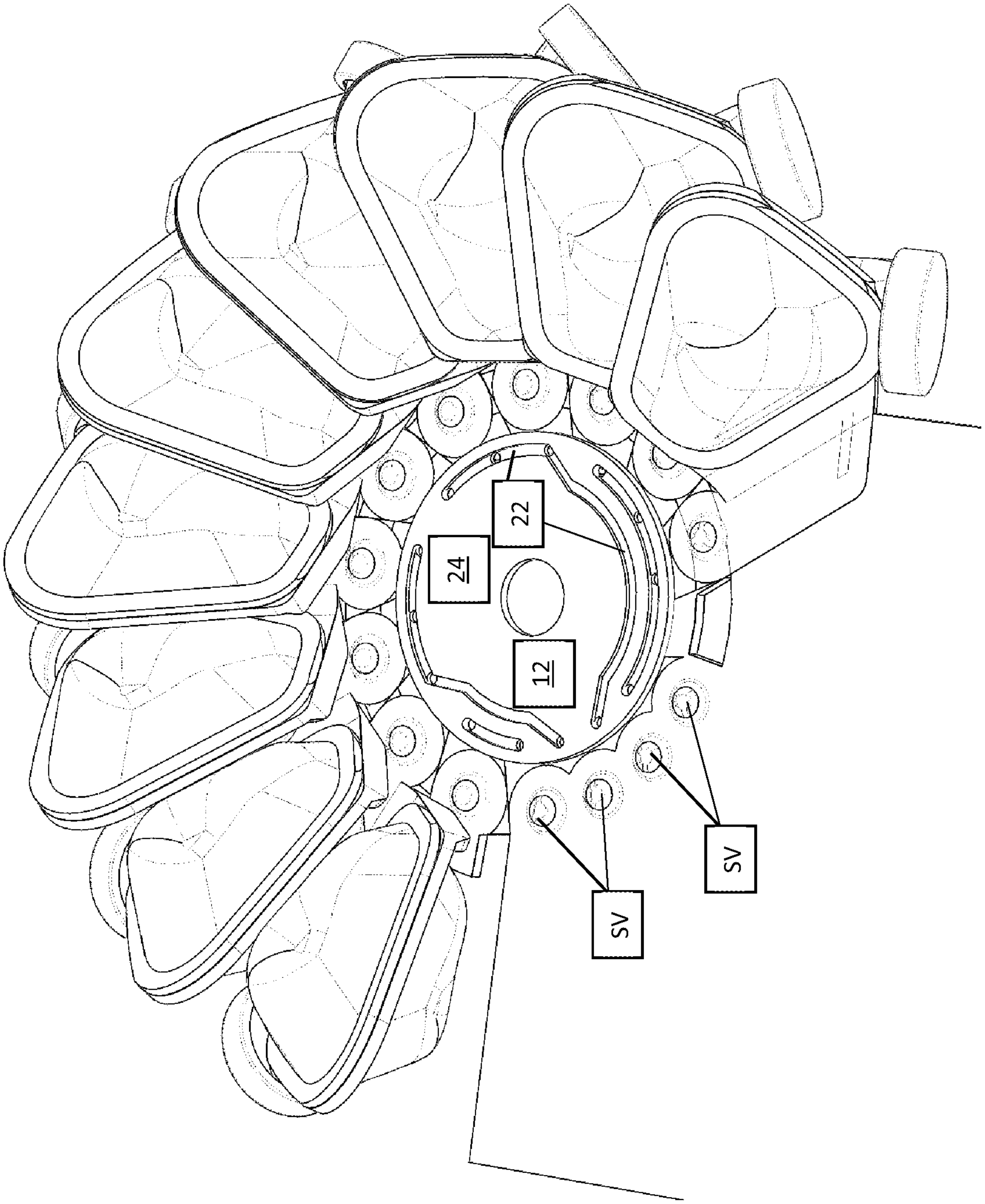
Figure 201:
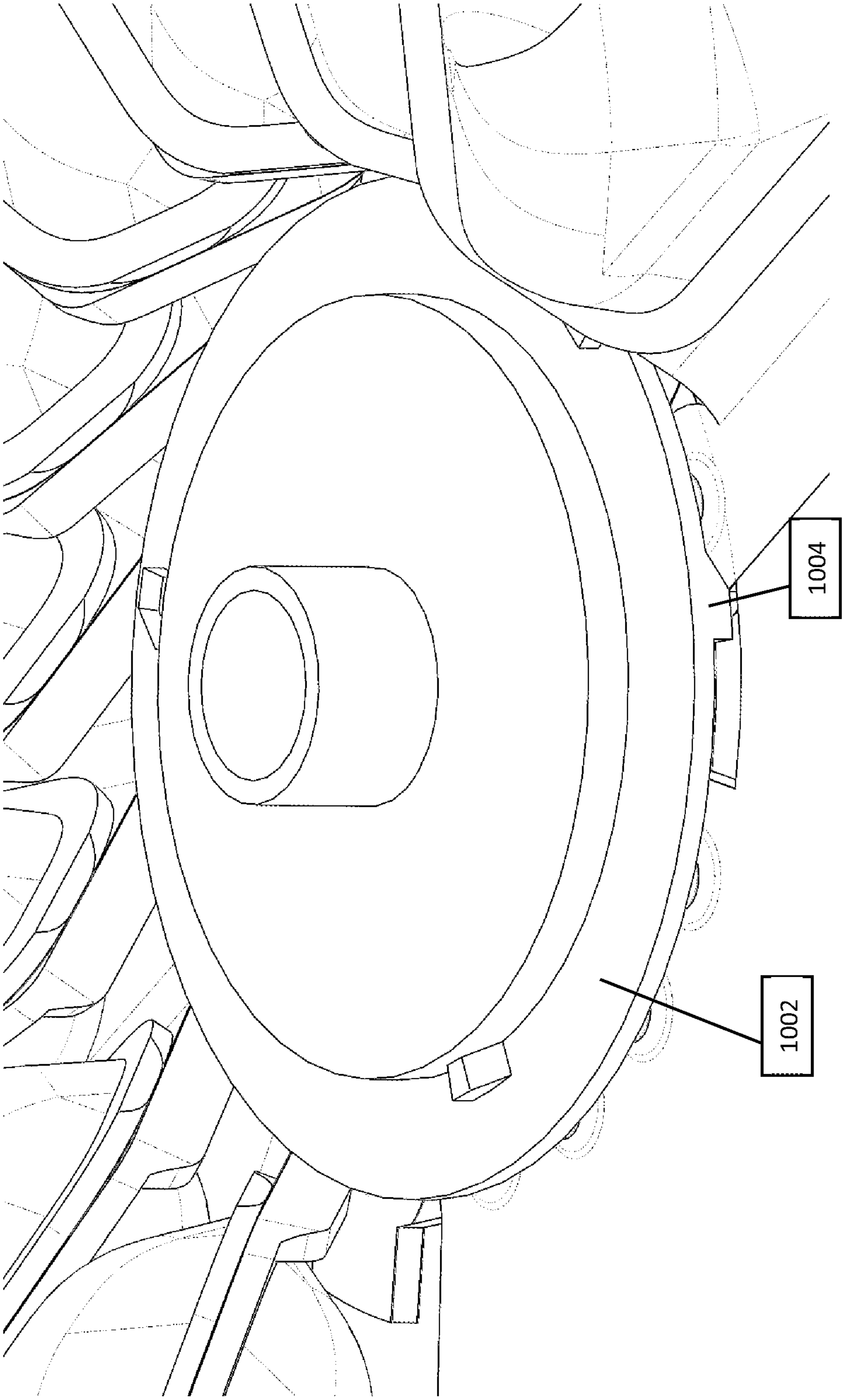
Figure 202:
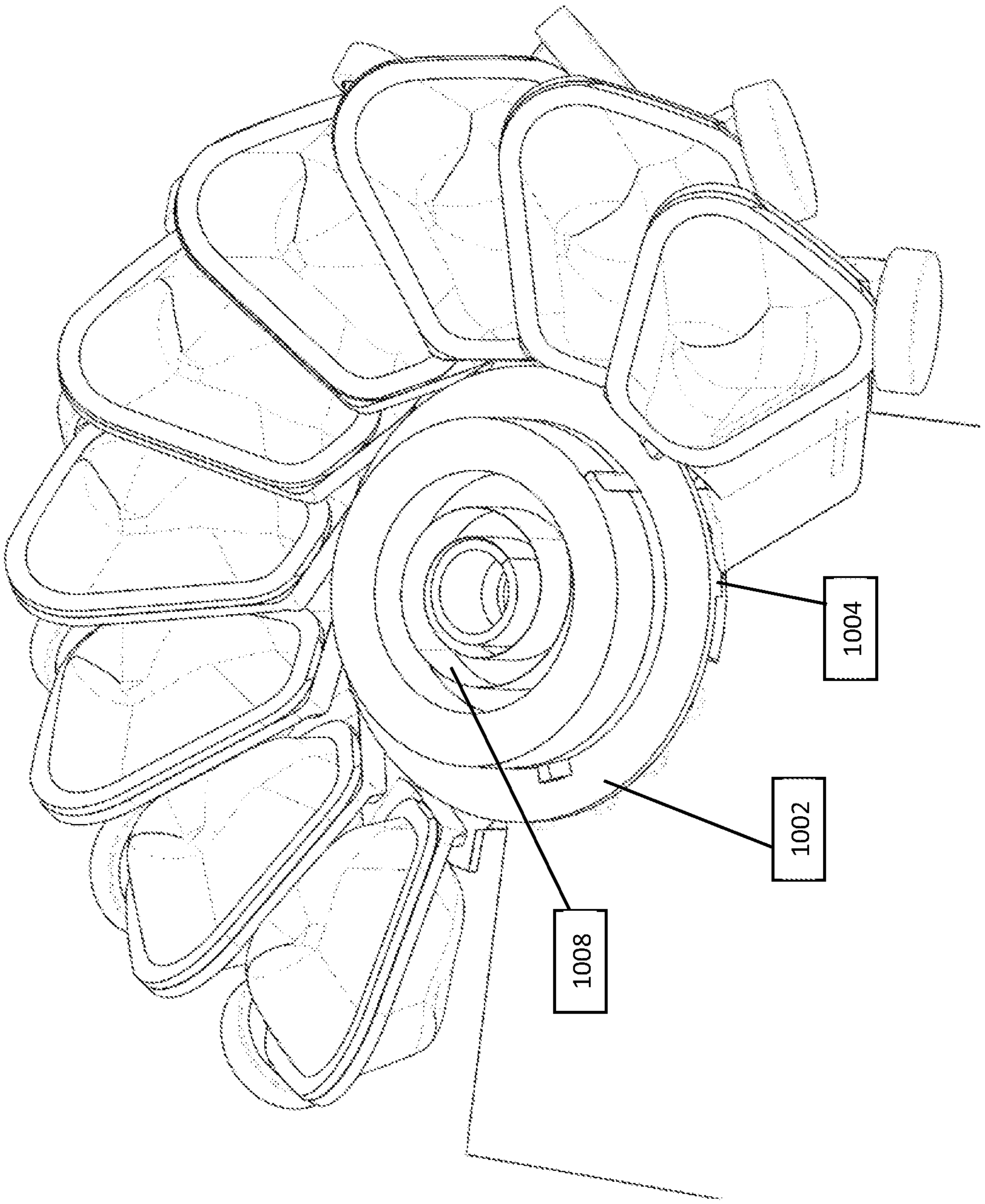
Figure 203:
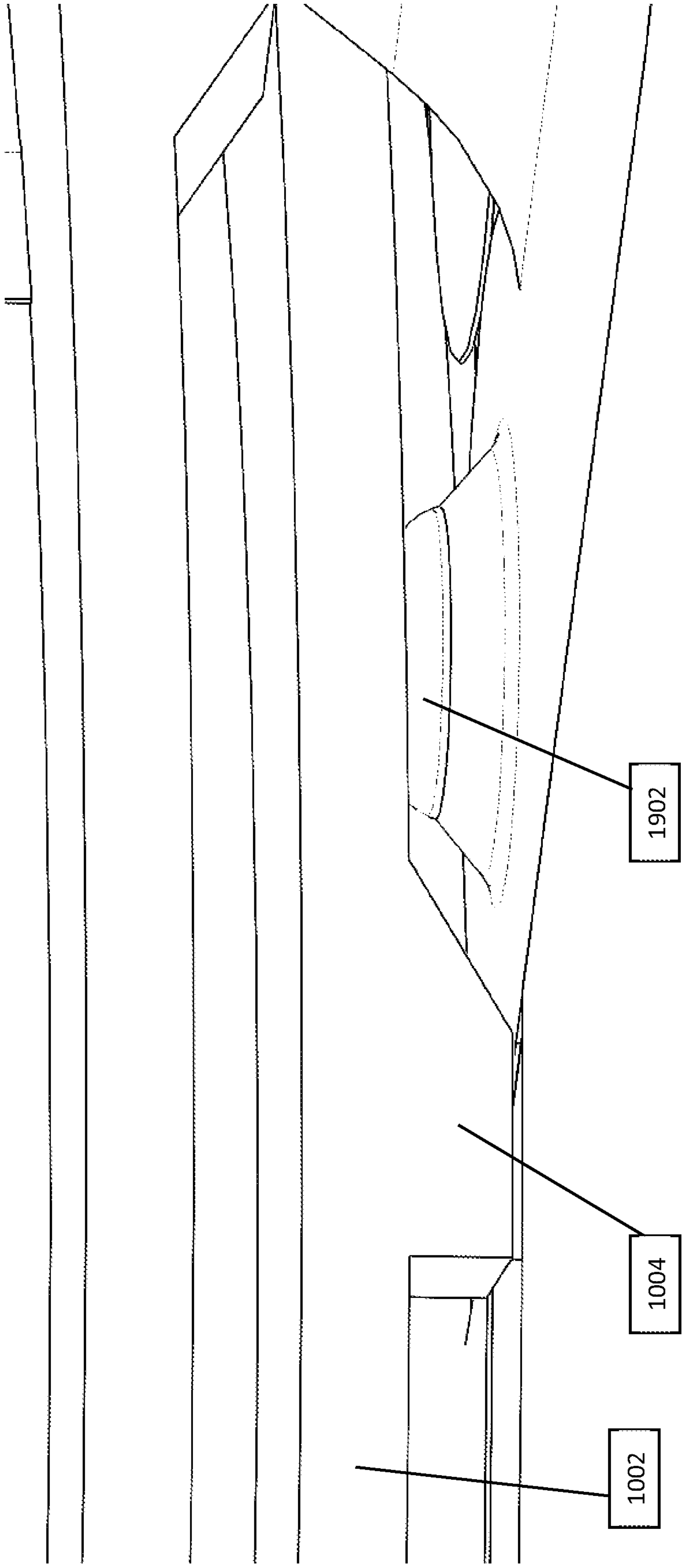
Figure 204:
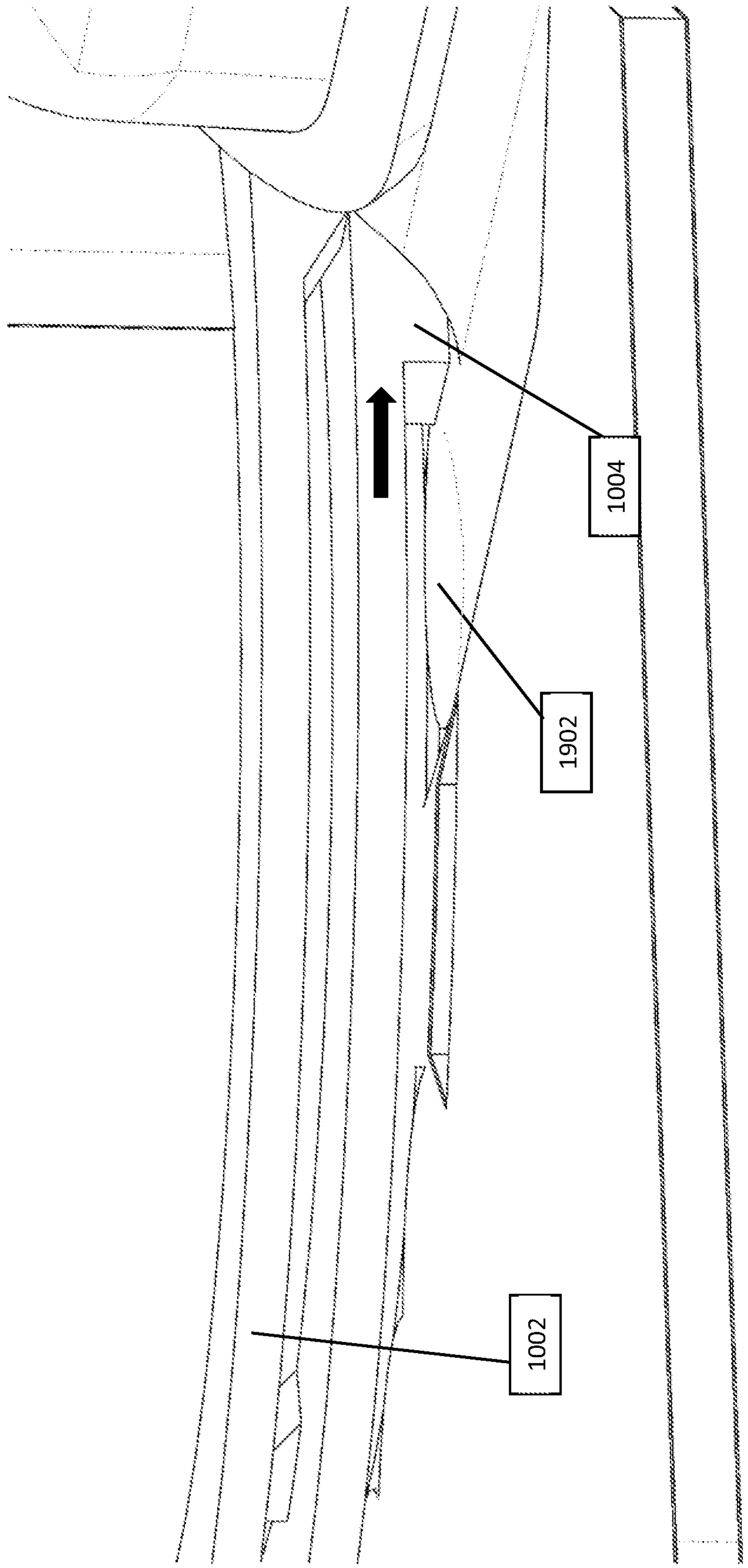
Figure 205:
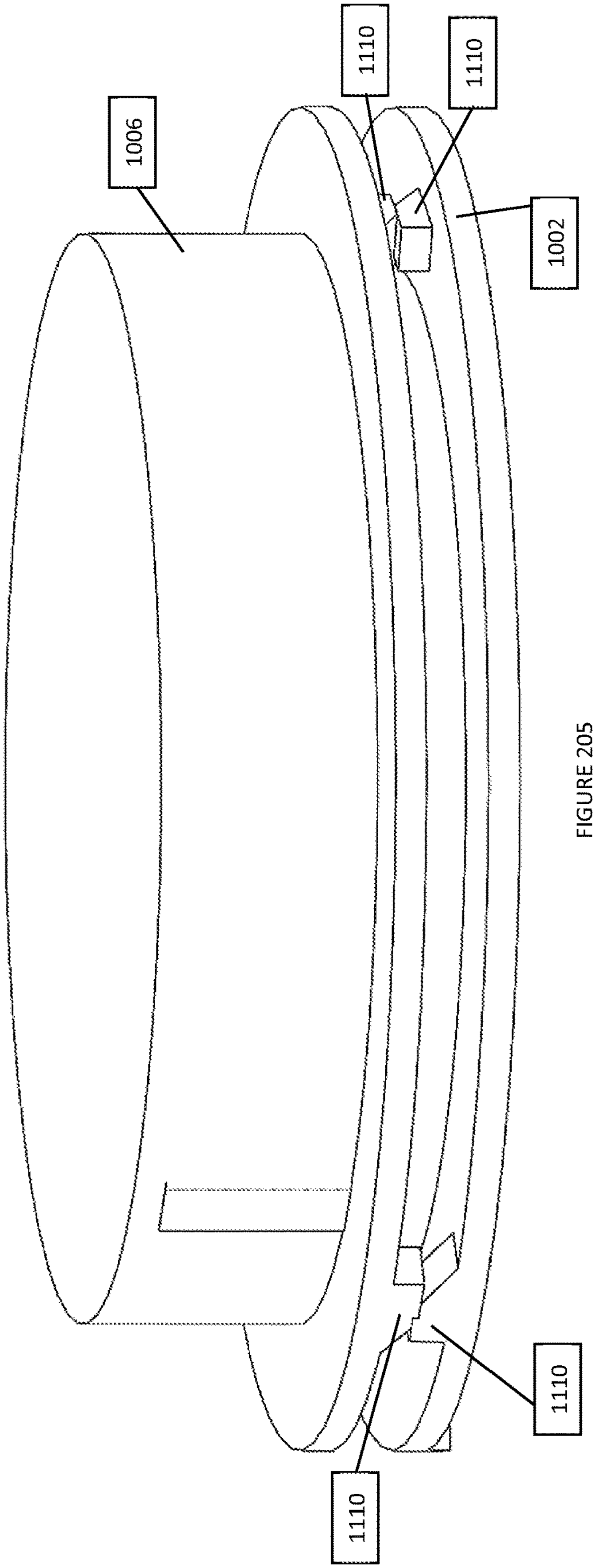
Figure 206:
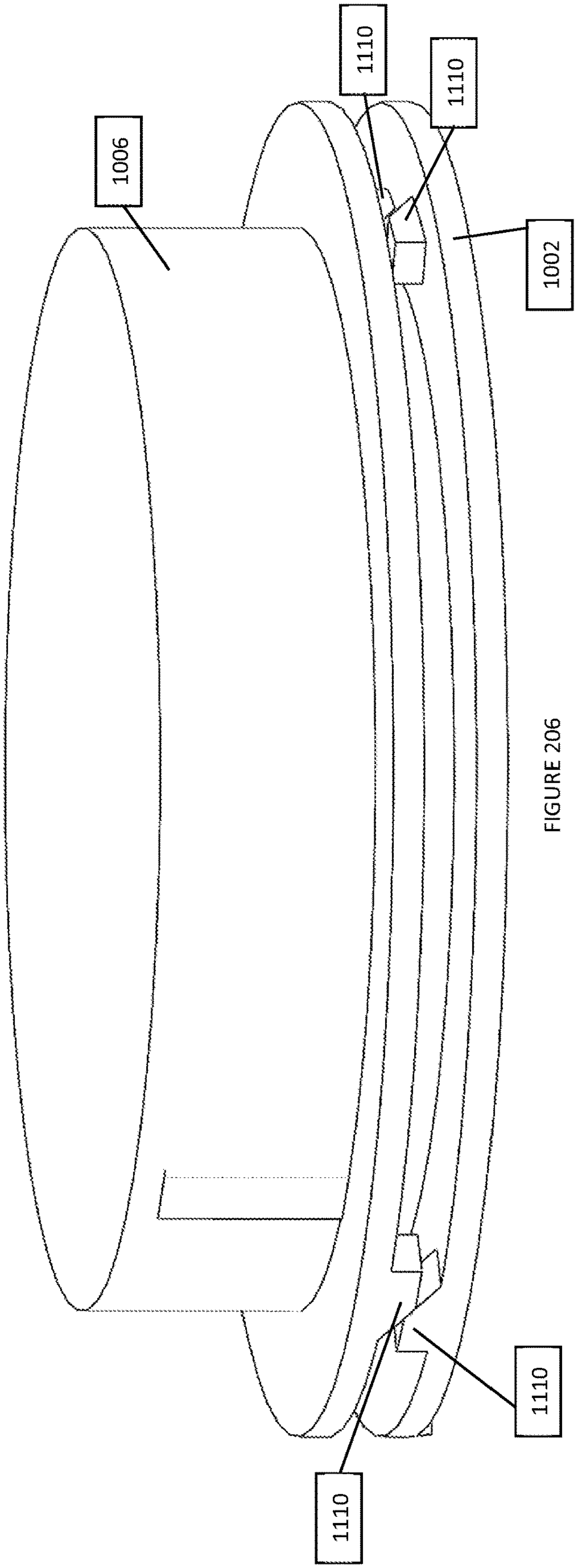
Figure 207:
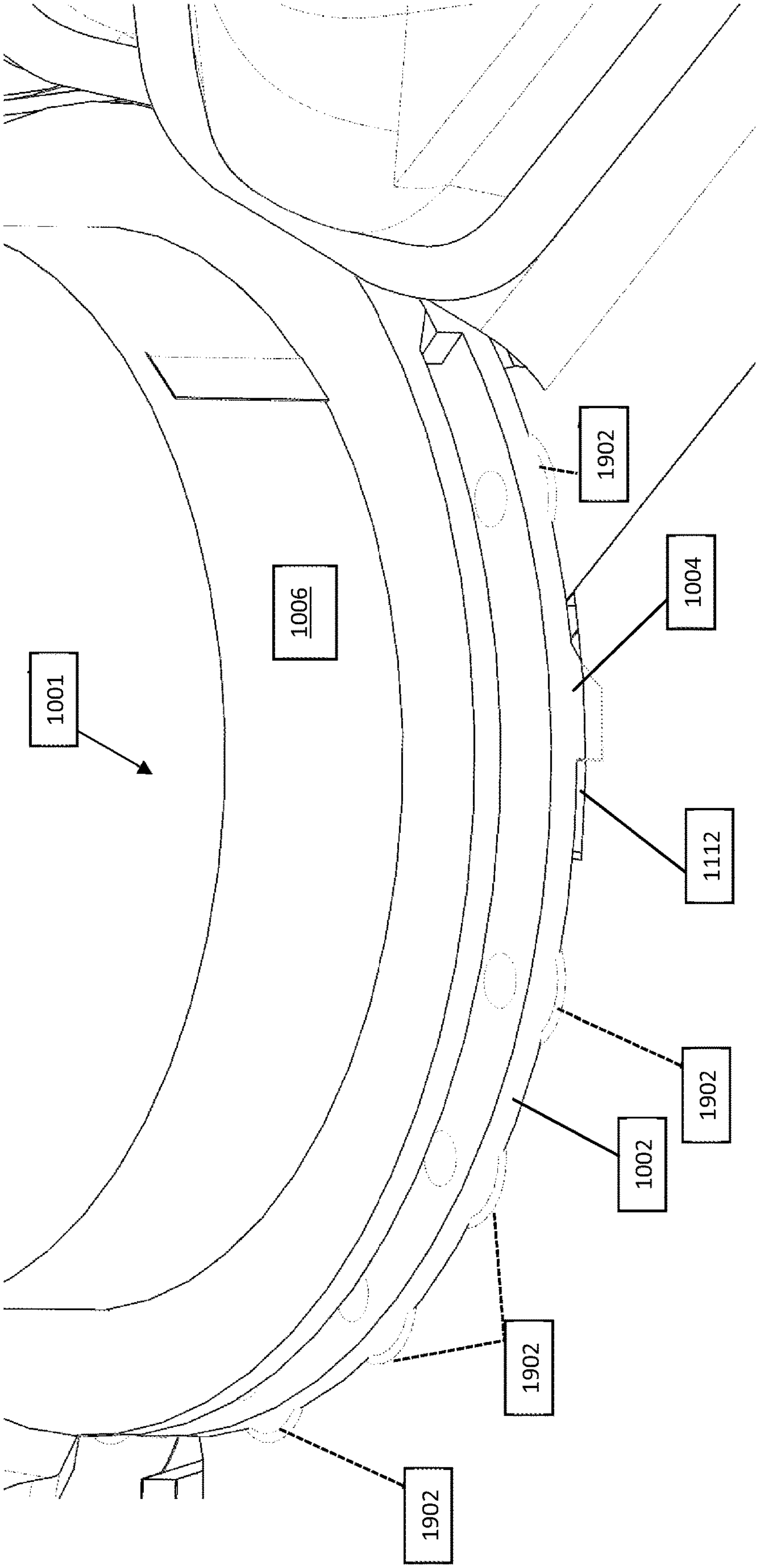

With reference to FIG. 199, an actuator 1001 is shown for opening the sealing sheets 1906 used as any of the primary valves PV and the secondary valves SV. As shown in FIG. 200, the wells 1900 may be arranged in a circle, at the same radius, about the body 12. This allows for sequential opening of the shiftable sealing elements 1902 which are all protruding upwardly relative to the first face 24 of the body 12. The actuator 1001 includes an actuator plate 1002 having a downwardly depending detent 1004. The actuator 1001 includes a housing 1006 fixed to the body 12 with the actuator plate 1002 being rotatable thereabout. A source of rotation 1008, which may be spring driven (e.g., a clock or torsion spring), motor driven, and so forth, is provided between the housing 1006 and the actuator plate 1002 to rotate the actuator plate 1002. The source of rotation 1008 may be maintained in a fixed, pre-use state using any known arrangement. The source of rotation 1008 also may be triggered to rotate using any known arrangement, e.g., manual release, electrical release, frangible release, and so forth. The detent 1004 is located to coincide with the radius along which the wells 1900 are aligned. In addition, the actuator plate 1002 is restricted against movement away from the wells 1900. With rotation of the actuator plate 1002, as shown in FIGS. 203-204, the detent 1004 is caused to traverse each of the shiftable sealing elements 1902 in sequence causing each to be pressed into the respective well 1900 resulting in delamination of the corresponding sealing sheet 1906. To best ensure that the shiftable sealing elements 1902 do not inadvertently return to the closed state, it is preferred that the actuator plate 1002 be held in a down position, flush with the first face 24. This can be achieved by applying pressure to the actuator plate 1002. In addition, the rotational force of the source of rotation 1008 may be utilized by providing cooperating ramped elements 1110 on the housing 1006 and the actuator plate 1002 to convert rotational force into downward normal force (FIG. 206). Alternatively, the housing 1006 may be caused to ride up on the actuator plate 1002 (the ramped elements 1110 being stacked) with the drive plate 1006 being in pressing engagement against the actuator plate 1002 (FIG. 205). To allow the actuator plate 1002 to be maximally pressed in face-to-face engagement with the first face 24, a recess 1112 may be formed in the first face 24 into which the detent 1004 nests after adjusting all of the shiftable sealing elements 1902 (FIG. 207). Advantageously, one full rotation of the actuator plate 1002 may be used to adjust all of the shiftable sealing elements 1902.

As shown in FIGS. 91-94, the drug delivery device 10 may be configured for mixing and/or reconstitution of drugs. With respect to FIG. 91, one of the reservoirs 26 may be provided as a diluent reservoir 26*j* for containing a drug as a diluent. A primary valve PVj may be provided to regulate flow in or out of the diluent reservoir 26*j*. A secondary valve SCd may be also, optionally, provided to regulate flow in or out of the diluent reservoir 26*j*. The primary valve PVj and the secondary valve SVd may be each provided as valves having two positions (positions A, B), selectively providing open or closed states, to permit or block flow therethrough.

With the pump 18 being bi-directional, the pump 18 may be configured with suction directed to the fluid duct 22 communicating with the reservoir 26*j*. With the secondary valve SCd and the primary valve PVj both in the open state (position A), negative pressure from the pump 18 reaches the reservoir 26*j* to draw the diluent therefrom. The diluent may be urged (under positive pressure) to one or more target reservoirs 26, using the valving as described above. For example, the target reservoir(s) 26 may contain drug in a dry or semi-liquid (slurry) state. The diluent may reconstitute this drug to a fully liquid state suitable for injection into a patient. Alternatively, the diluent may be a component for a two- or more part mixture, mixing with the drug of the target reservoir(s) 26. Once the diluent has been delivered to the target reservoir(s) 26, the pump 18 may be reversed to draw the mixed/reconstituted drug for delivery through the needle 15. One or more of the pressure sensors PS may be used to measure pressure in the flow of the diluent. With the filling of the reservoir(s) 26 with the diluent, the pressure therein will increase. By measuring pressure, fill volume and/or concentration may be monitored. For example, with a threshold pressure being detected, a target reservoir 26 may be shut off from further delivery of the diluent.

One or more heaters H (e.g., resistive heater) may be located along the flow path of the diluent to raise the temperature thereof. Heating of the diluent may assist in mixing and/or reconstitution.

To assist with the mixing or reconstituting, the drug delivery device 10 may be agitated after delivery of the diluent to the target reservoir(s) 26. This may be done manually. Alternatively, as shown in FIGS. 99-100, the drug delivery device 10 may be placed on a vibrating plate 600 or a rotating or oscillating turntable 602. In addition, or alternatively, the drug delivery device 10 may be provided with one or more on-board agitating mechanisms, such as: accelerometer 604 (FIG. 101) which may cause reciprocal movement of the drug delivery device 10; a piezoelectric actuator 606 (FIG. 102) which may cause vibration in the drug delivery device 10; and, a magnetic stirrer 608 (FIG. 103) located in the reservoir(s) 26 which may be caused to move, such as rotationally, by adjacent moving magnets 610, which may be provided on the drug delivery device 10, and/or provided separately (e.g., the magnets 610 may be provided on a rotating disk mounted to the body 12).

It is also noted that the reservoir 26*j* for the diluent may be configured as one of the drug cartridges 14, described above. As will be appreciated by those skilled in the art, the reservoir 26*j* may be configured in various modes. For example, as shown in FIG. 104, the reservoir 26*j* may be provided as a low-profile, collapsible reservoir formed generally within the profile of the body 12. In this manner, the reservoir 26*j* may be provided below the drug cartridges 14. With increasing the area covered by the reservoir 26*j*, the height may be kept to a minimum.

Figure 92:
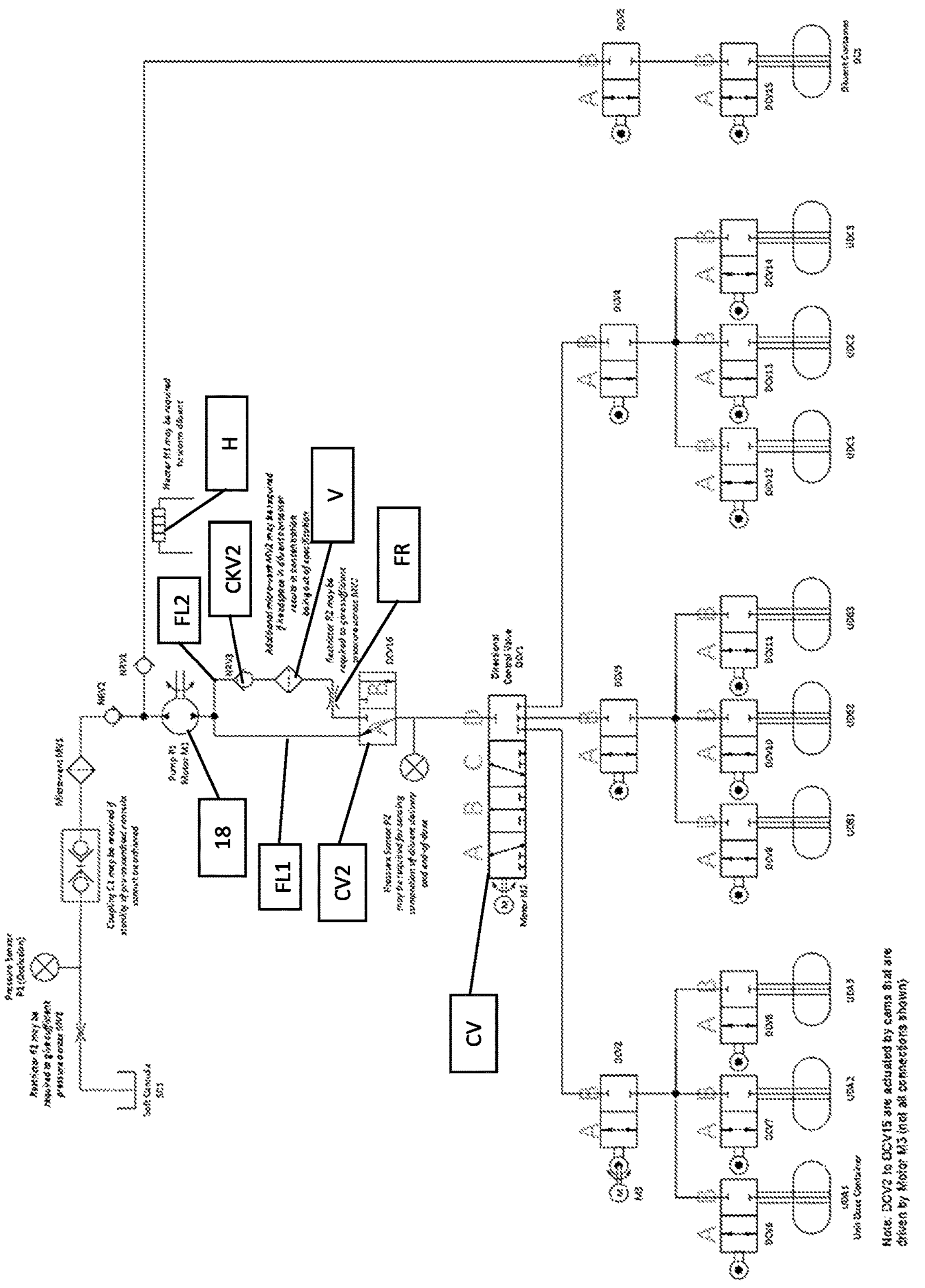

Other fluidic arrangements for the drug delivery device 10 are possible. FIG. 92 shows a modified version of FIG. 91 where parallel flow lines FL1, FL2 are provided from the pump 18, controlled by second control valve CV2. The second control valve CV2 may be a two-position valve (positions A, B) allowing for selective open flow the parallel flow lines FL1, FL2. The flow line FL1 is an uninterrupted flow passage between the pump 18 and the second control valve CV2. The flow line FL2 is configured for one-way flow, by a check valve CKV2, from the pump 18 towards the control valve CV. In addition, a vent V and/or flow restrictor FR may be provided along the flow line FL2. The flow line FL2 may be used for delivery of diluent to the target reservoir(s) 26, and the flow line FL1 may be used for withdrawal of the mixed or reconstituted drug from the target reservoir(s) 26.

Figure 93:
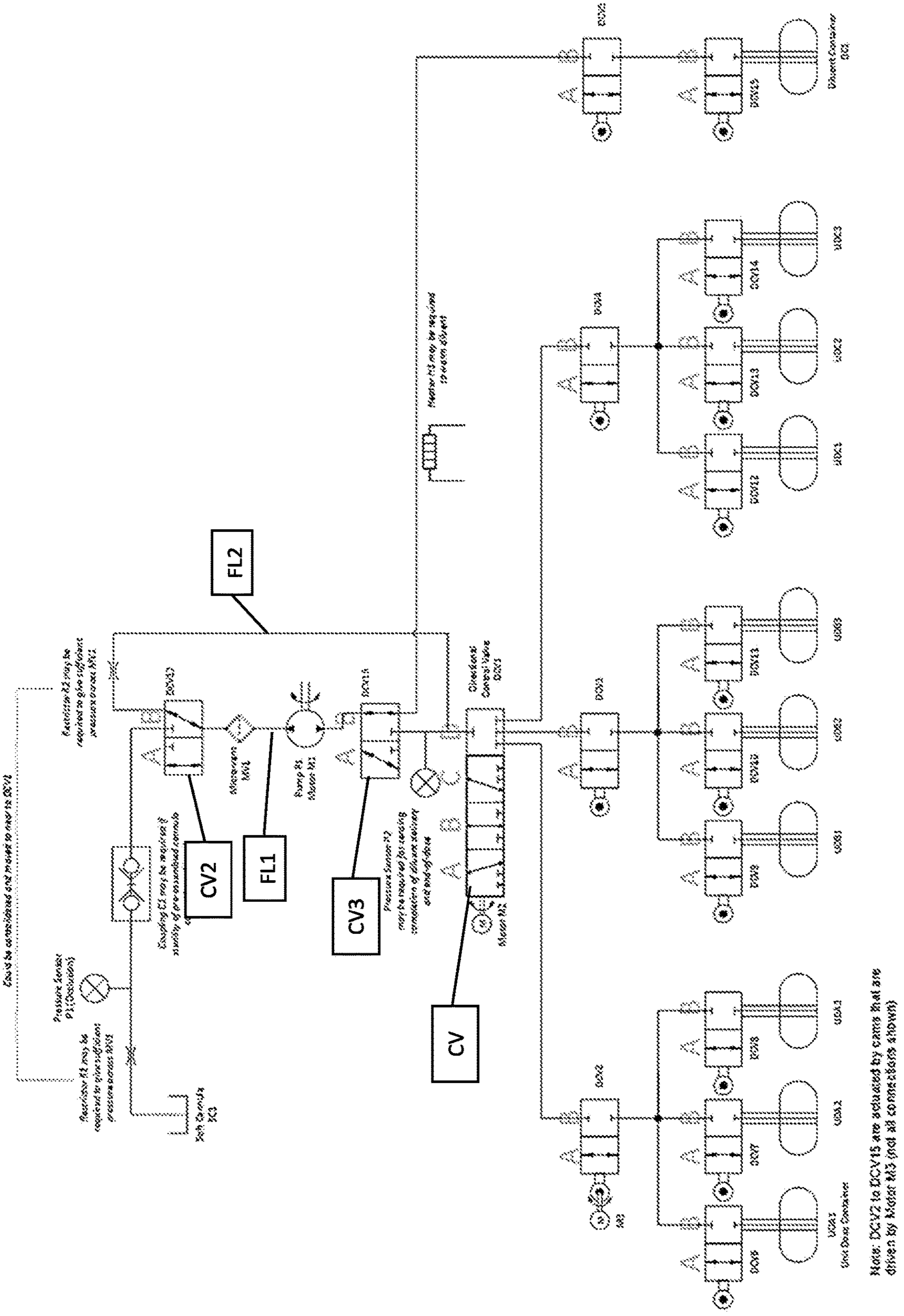

Further, as shown in FIG. 93, the flow line FL2 may be provided to extend across the pump 18. A third control valve CV3 may be provided to regulate flow between the pump 18, the diluent reservoir 26*j*, and the target reservoir(s) 26. The third control valve CV3 may be a two-position valve (positions A, B) to selectively allow flow between the pump 18 and the diluent reservoir 26*j*, and, between the pump 18 and the target reservoir(s) 26.

Figure 94A:
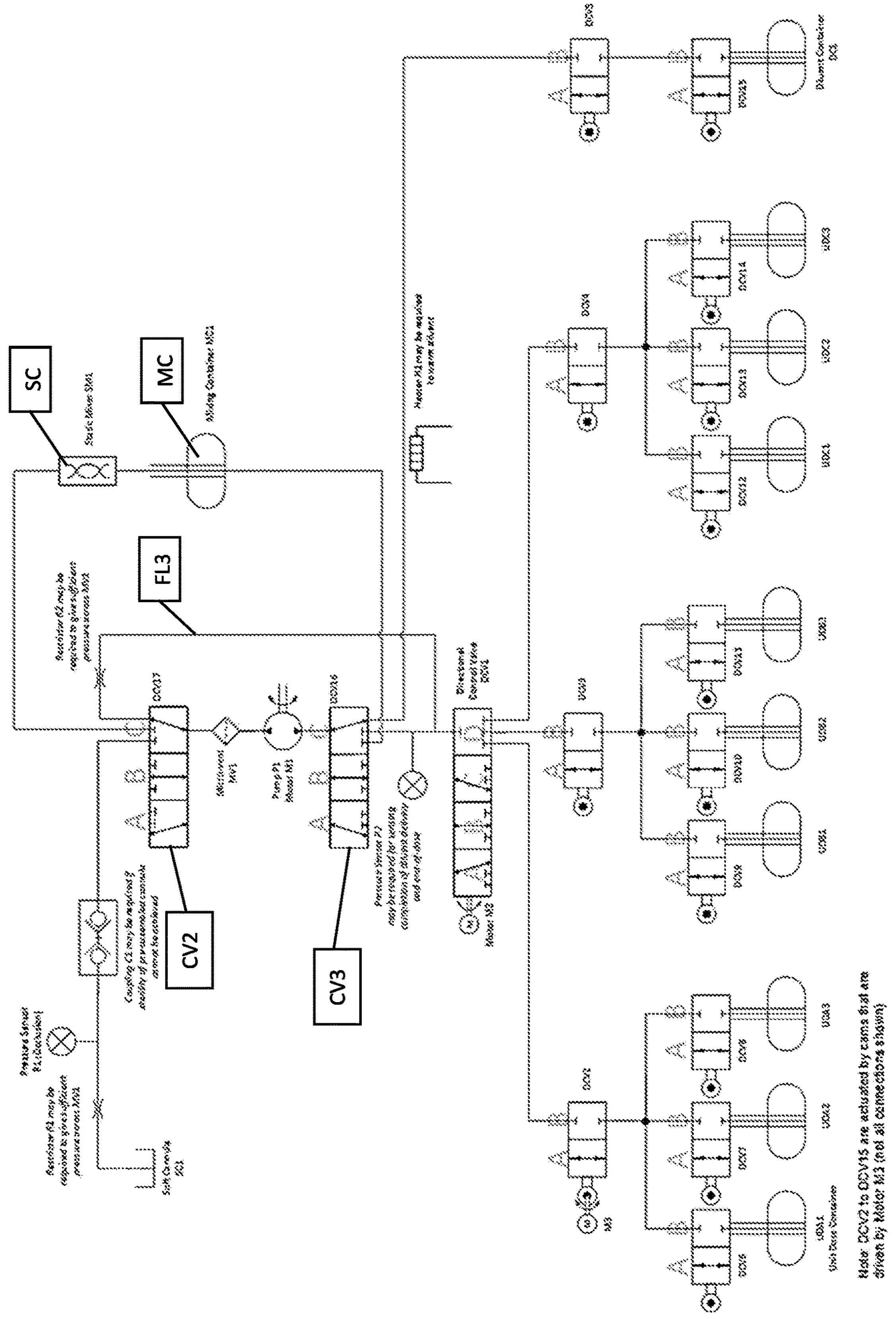

As shown in FIG. 94A, the flow line FL2 may be provided with a mixing container MC. This allows for drug to be drawn from the reservoir(s) 26 and re-pumped thereto, e.g., to assist in reconstitution. One or more static mixers SC may be provided along the flow line FL2. A third flow line FL3 may be provided to extend across the unidirectional pump 18 to provide communication to the target reservoir(s) 26. With the addition of the third flow line FL3, the second and third control valves CV2, CV3 may be configured each as three-position valves for selective communication with each of the flow lines (positions A, B, C).

Figure 94B:
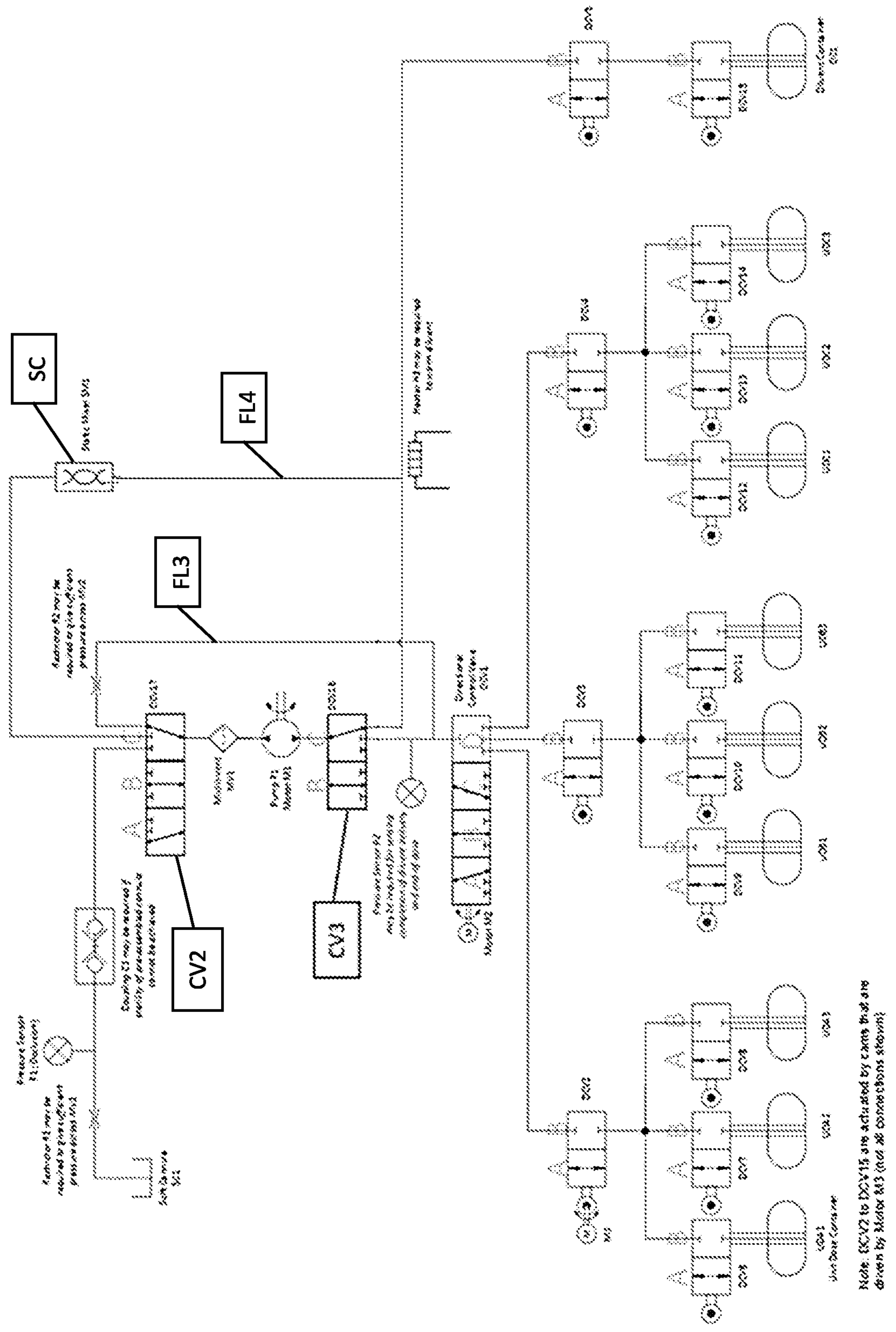

The fluidics of the drug delivery device 10 may be arranged to allow for reconstitution of drug in one or more target reservoir(s) 26 utilizing cycling of the mixture. For example, the arrangement of FIG. 94B may be utilized to withdraw a mixture of the diluent and drug from a target reservoir 26 with the mixture being urged to the diluent reservoir 26*j*, where the mixture may be withdrawn and re-introduced into the target reservoir 14. As shown in FIG. 94B, the flow line FL4 may be provided to extend across the unidirectional pump 18 to provide communication with the diluent reservoir 26*j*. In this case, the control valve CV2 may be a two-position valve. This same cycling may be achieved with the arrangement of FIG. 94A, but with the mixture being directed to the mixing container MC for temporary containment during cycling.

Figure 105A:
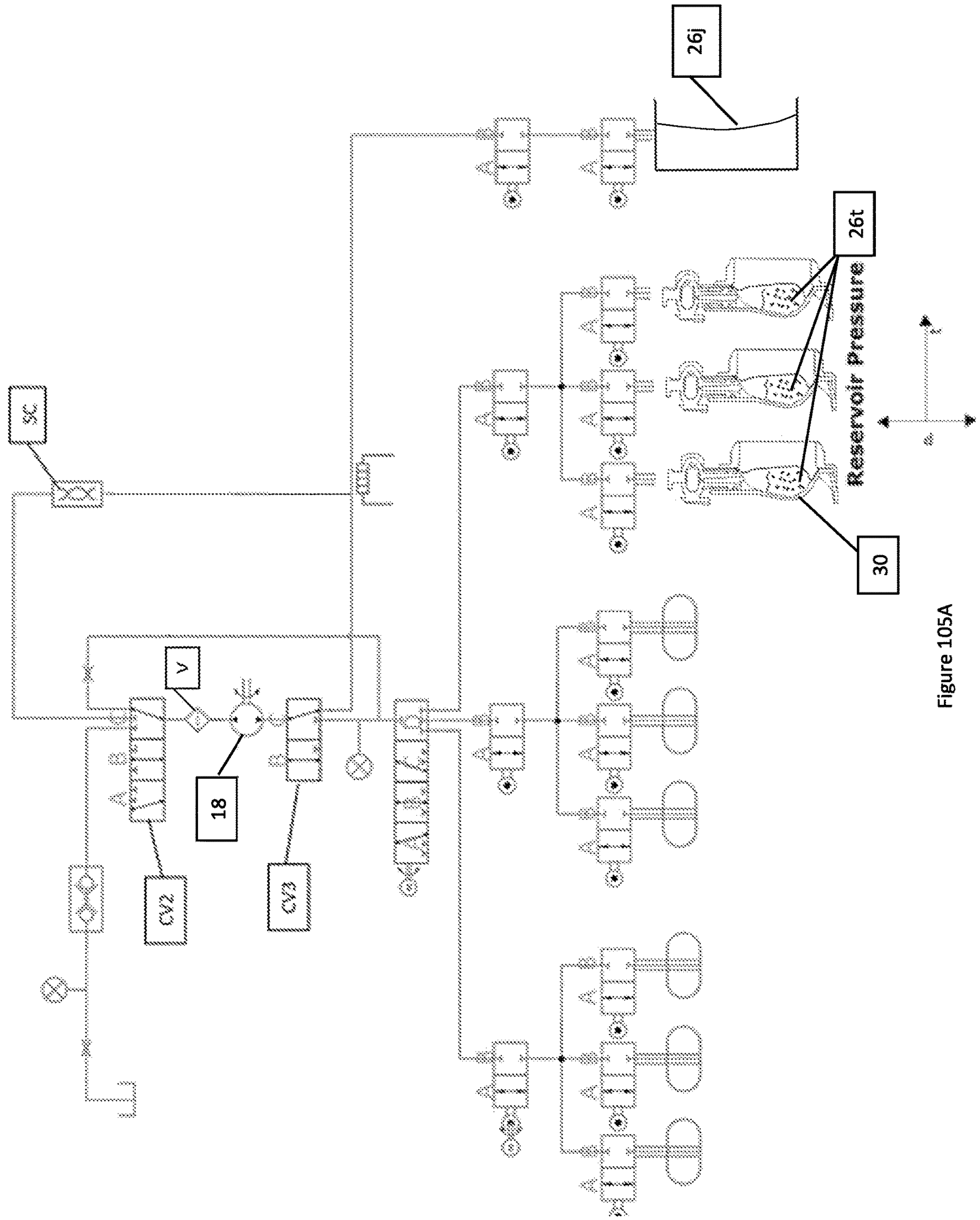

As shown in FIGS. 105A-112, the cycling of the mixture has been found to improve the reconstitution process. For example, as shown in FIG. 105A, in a first state, diluent is contained within the diluent reservoir 26*j* and drug intended for reconstitution is contained within target reservoir 26*t*. With the pump 18 in an off state, as shown in FIG. 105A, the target reservoir 26*t* is at a constant initial pressure. As shown in FIG. 105B, the pump 18 is activated to withdraw the diluent from the diluent reservoir 26*j* and to urge the diluent into the target reservoir 26*t*, resulting in increasing elevated pressure therein. Pressure in the target reservoir 26*t* may be monitored with the pumping of the diluent being stopped upon a predetermined pressure being detected. Subsequently, as shown in FIG. 105C, the pump 18 is reversed to withdraw the mixture of diluent and drug (which may be an intermediate mixture) from the target reservoir 26*t* and to urge the intermediate mixture to the diluent reservoir 26*j*, causing a negative pressure within the target reservoir 26*t*. As shown in FIG. 105C, some of the drug may not have fully mixed with the diluent, thus leaving some drug in the target reservoir 26*t*. Advantageously, as the target reservoir 26*t* is voided under suction of the pump 18, the target reservoir 26*t* collapses. Collapsed portions of the target reservoir 26*t* may come into pressing engagement with the residual drug. Pressure from the collapsed portions of the target reservoir 26*t* may cause the residual drug to spread across the target reservoir 26*t*. This provides for a "de-clumping" effect, increasing the surface of the residual drug with permeation of the diluent therethroughout. With re-introduction of the intermediate mixture, as shown in FIG. 105D (with the pump 18 being again reversed), the intermediate mixture may better mix with the spread residual drug, enhancing the ability thereof to reconstitute.

Figure 105B:
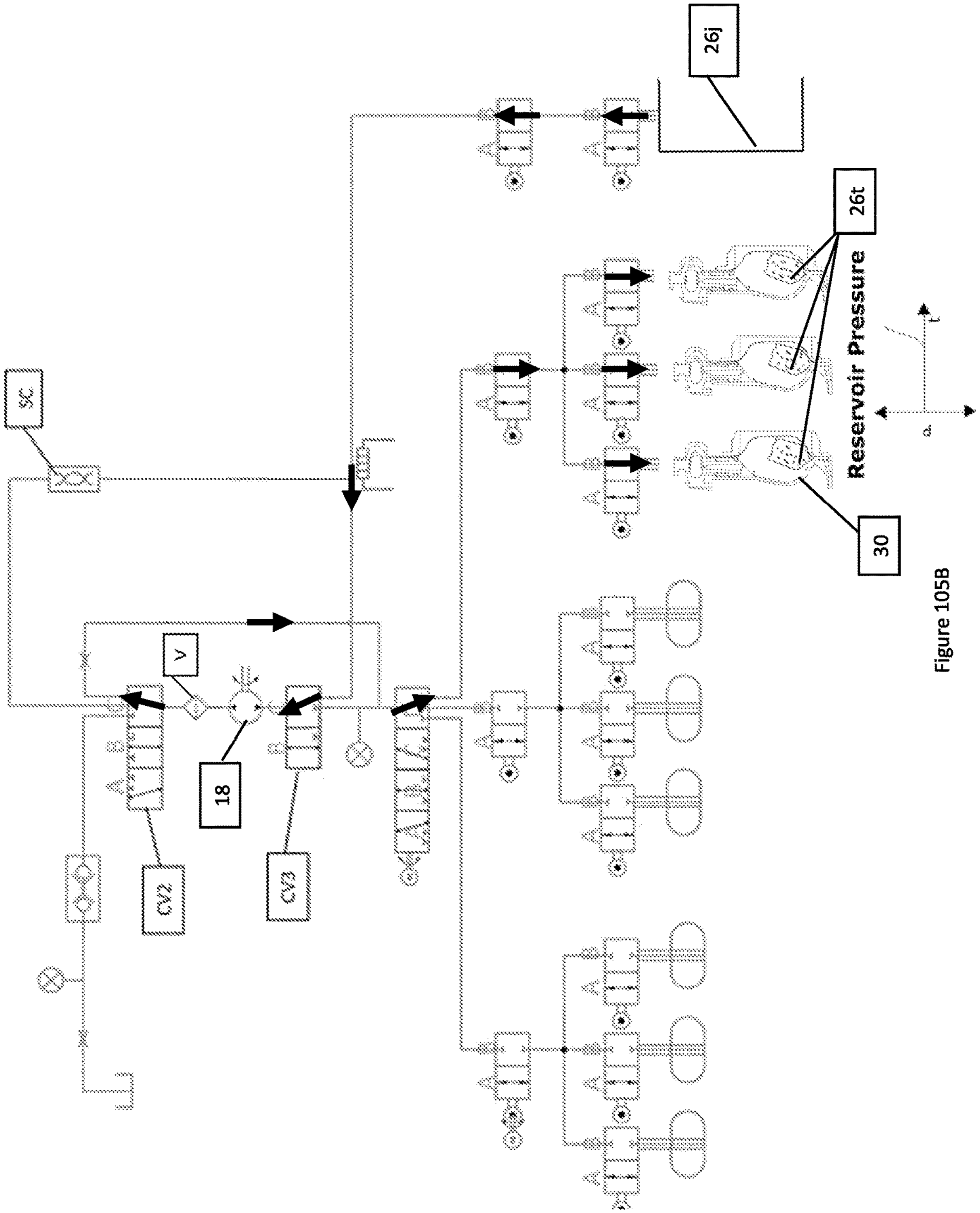
Figure 105C:
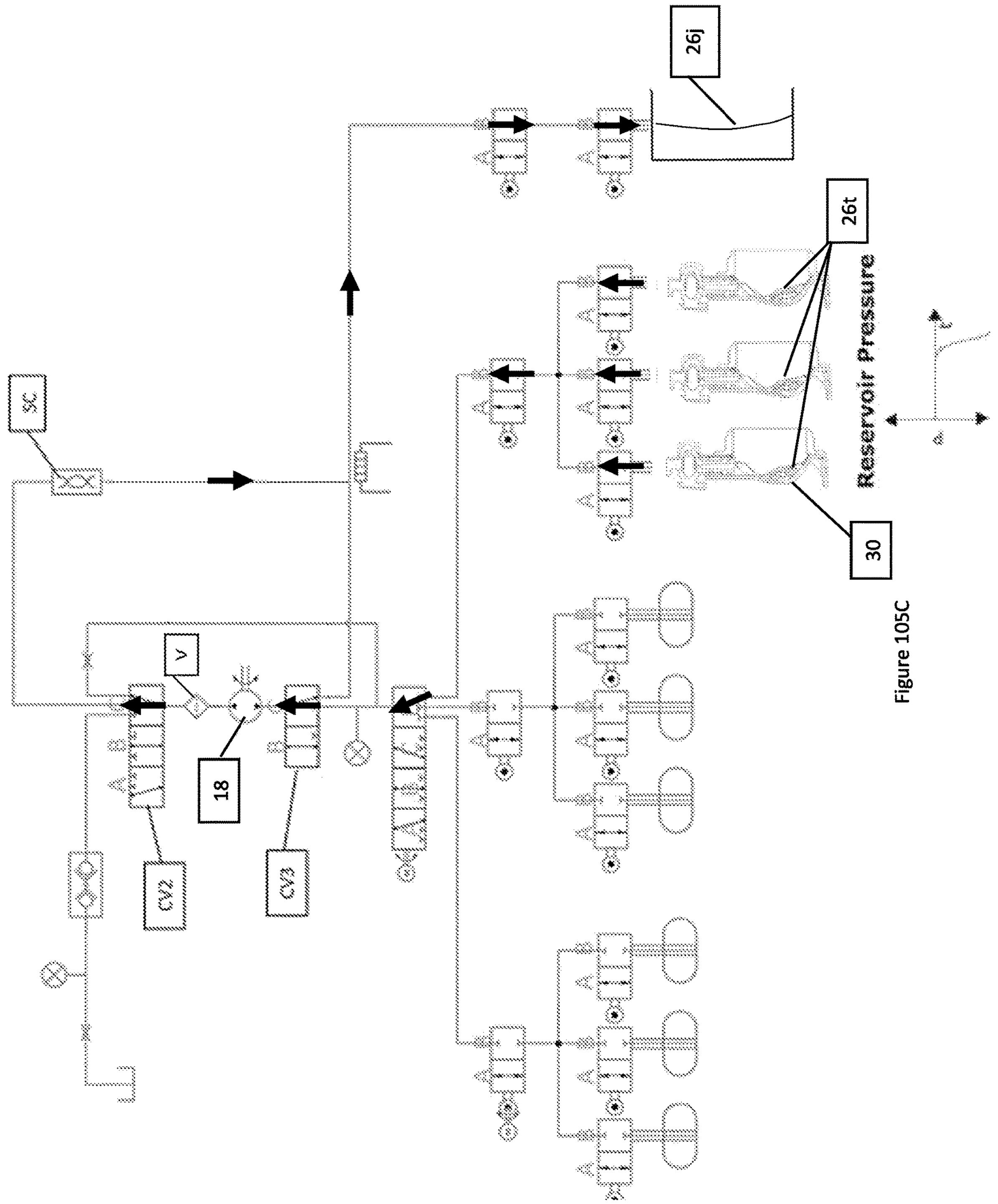
Figure 105D:
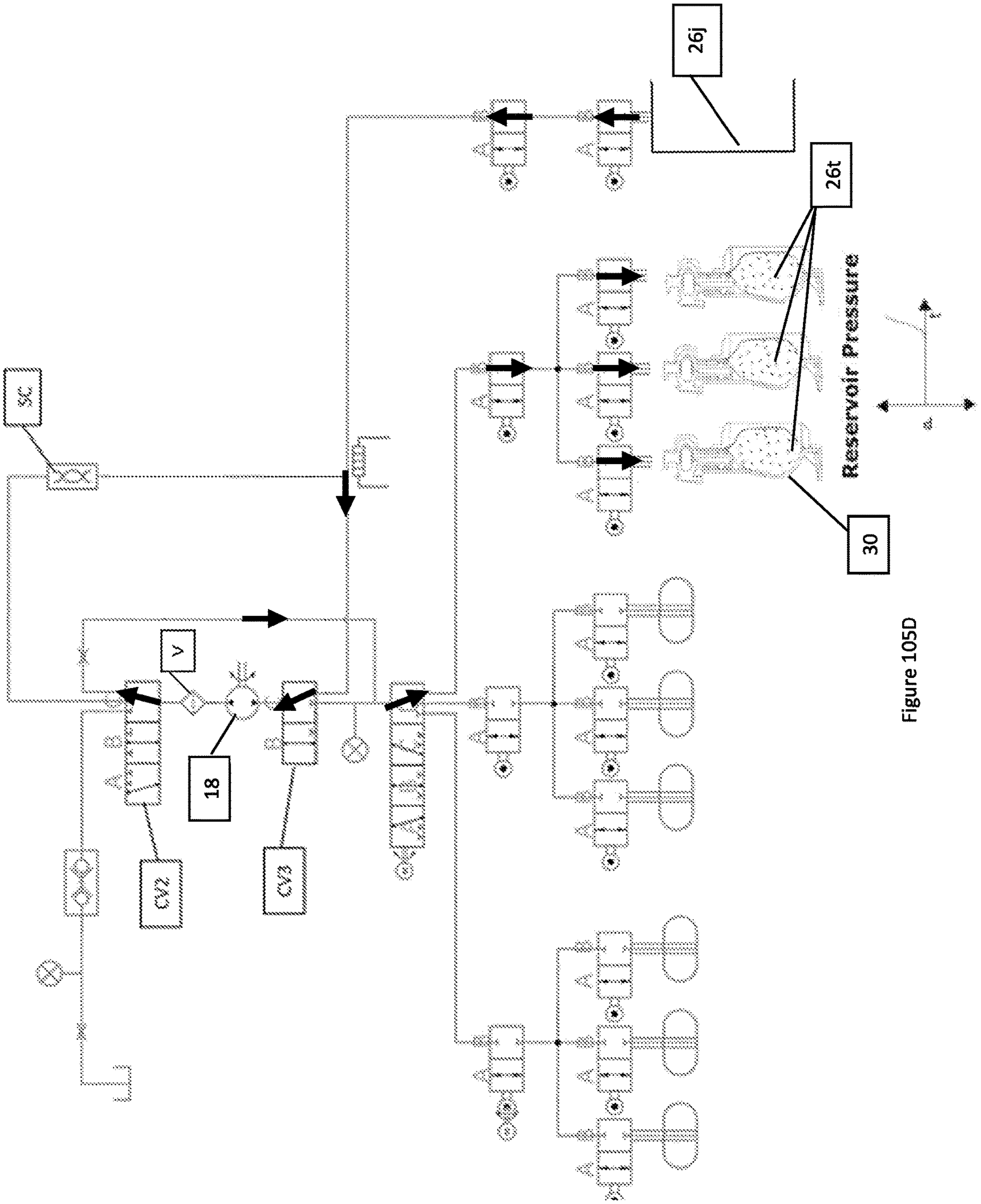
Figure 106A:
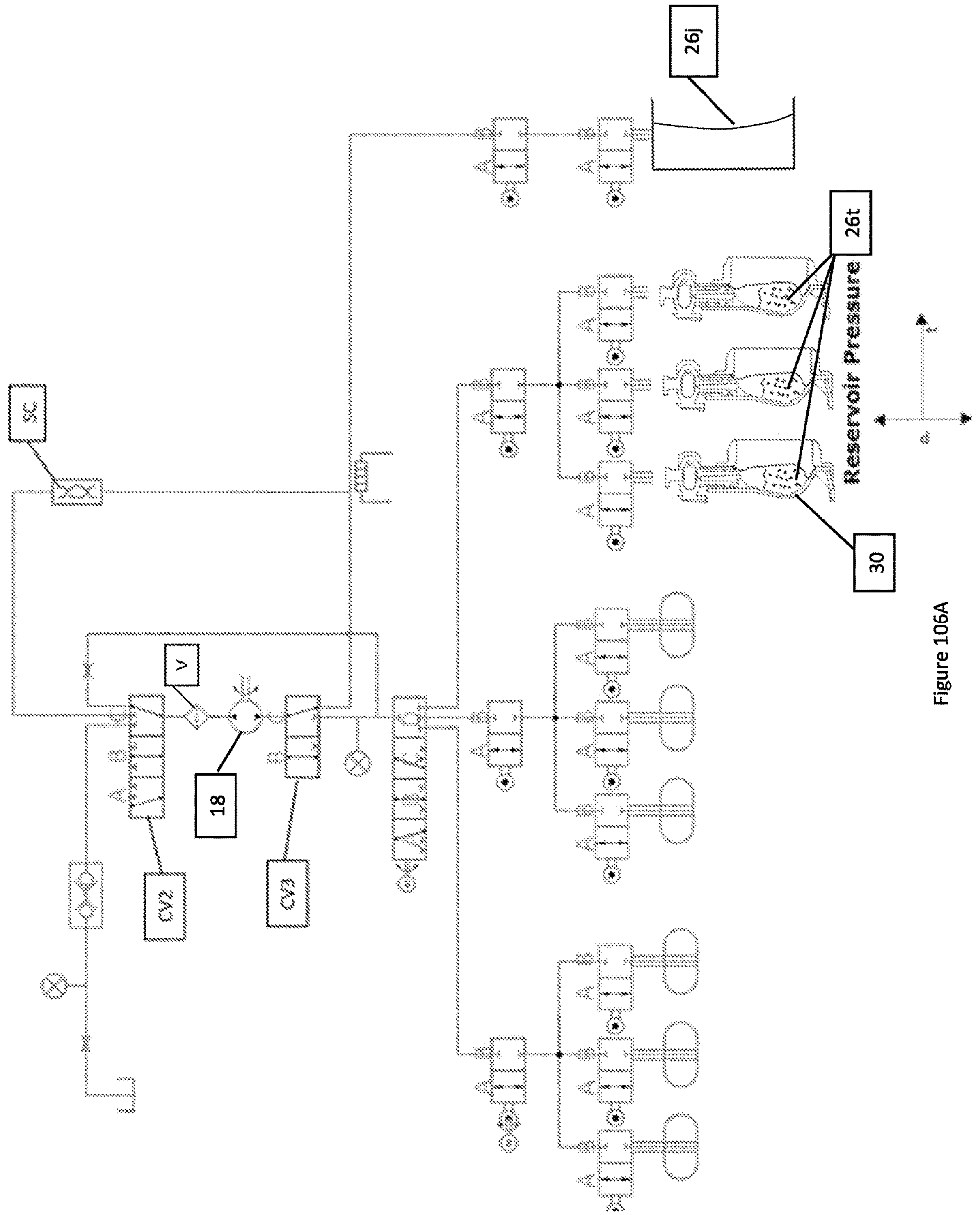
Figure 106B:
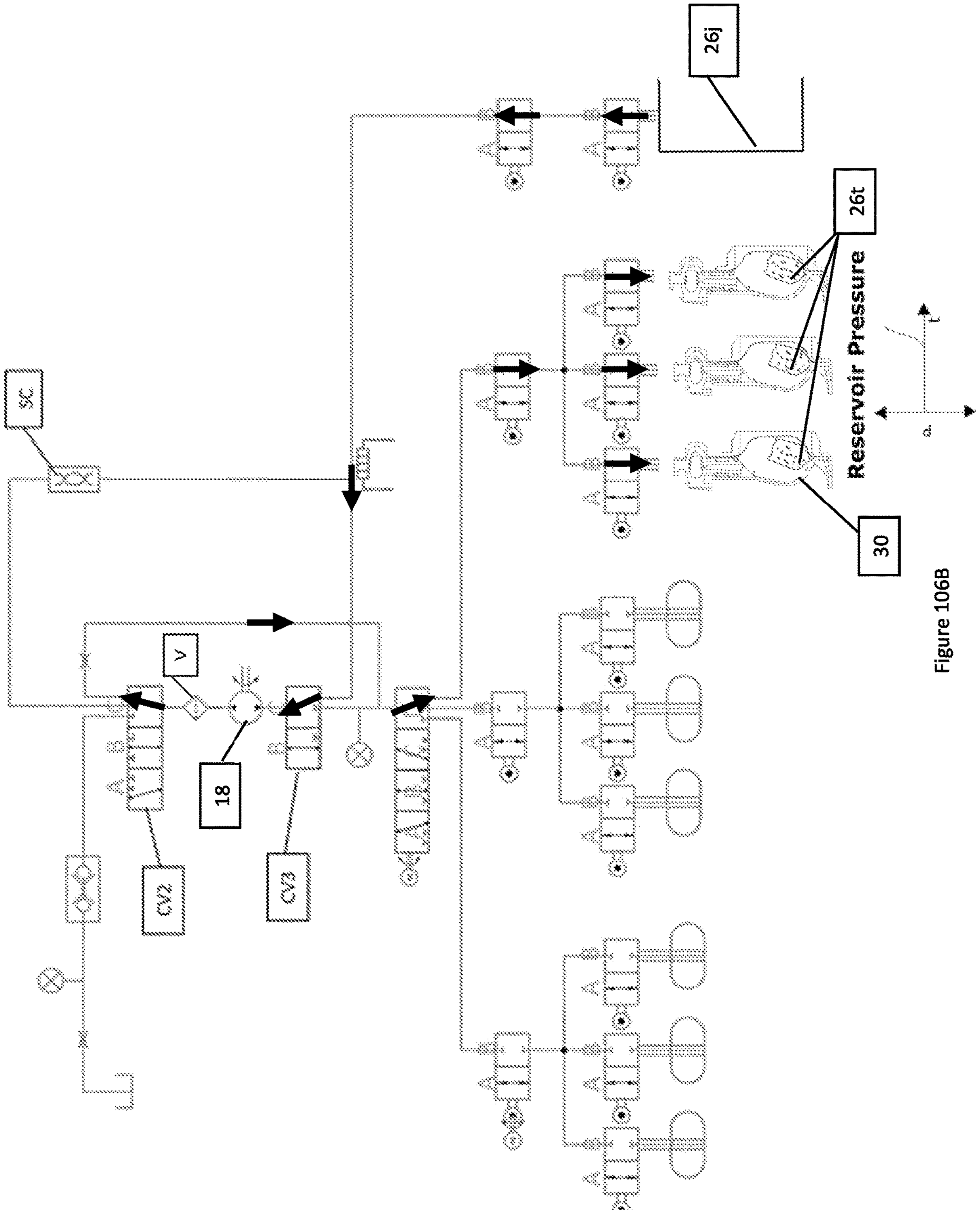
Figure 106C:
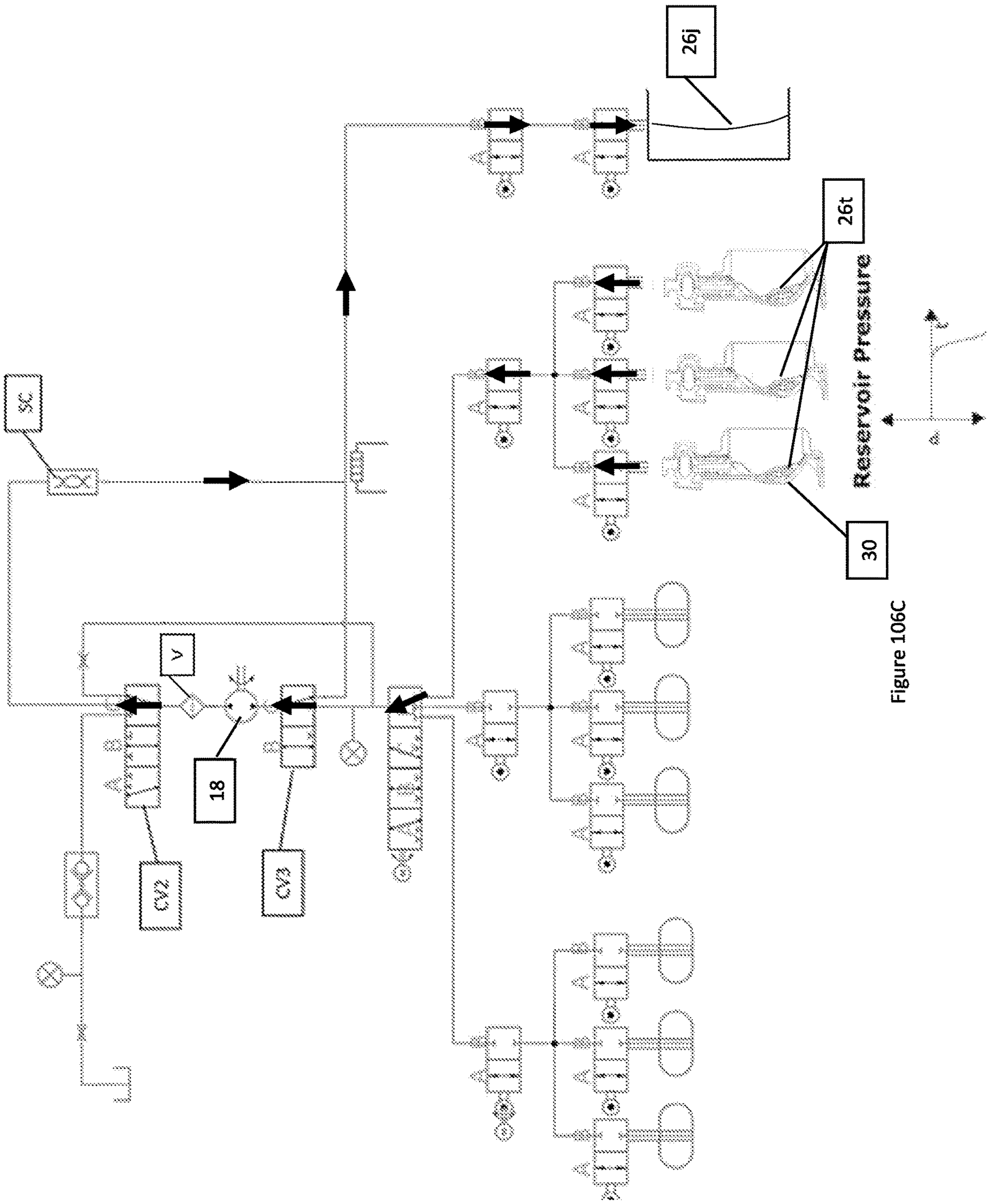
Figure 106D:
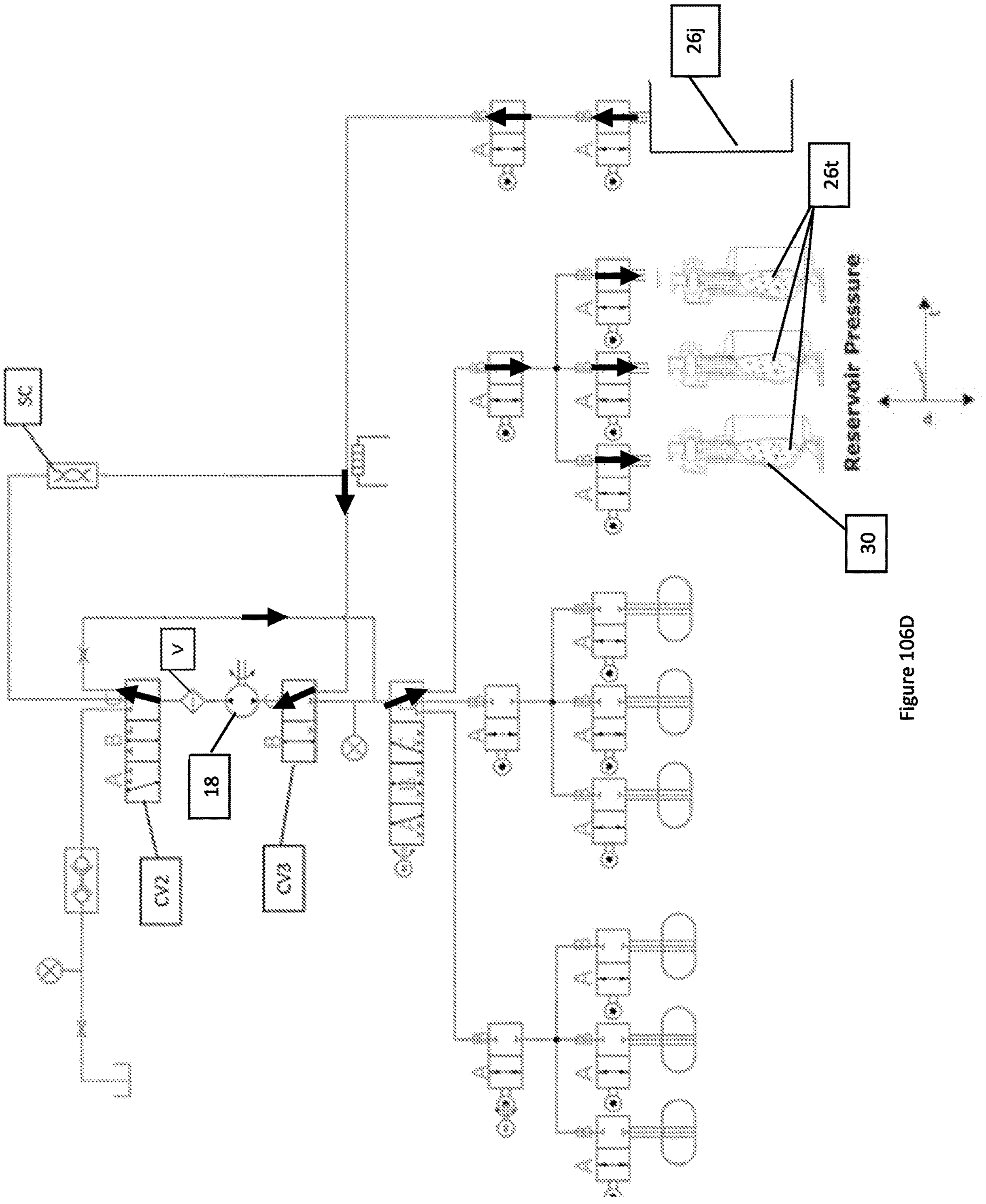
Figure 106E:
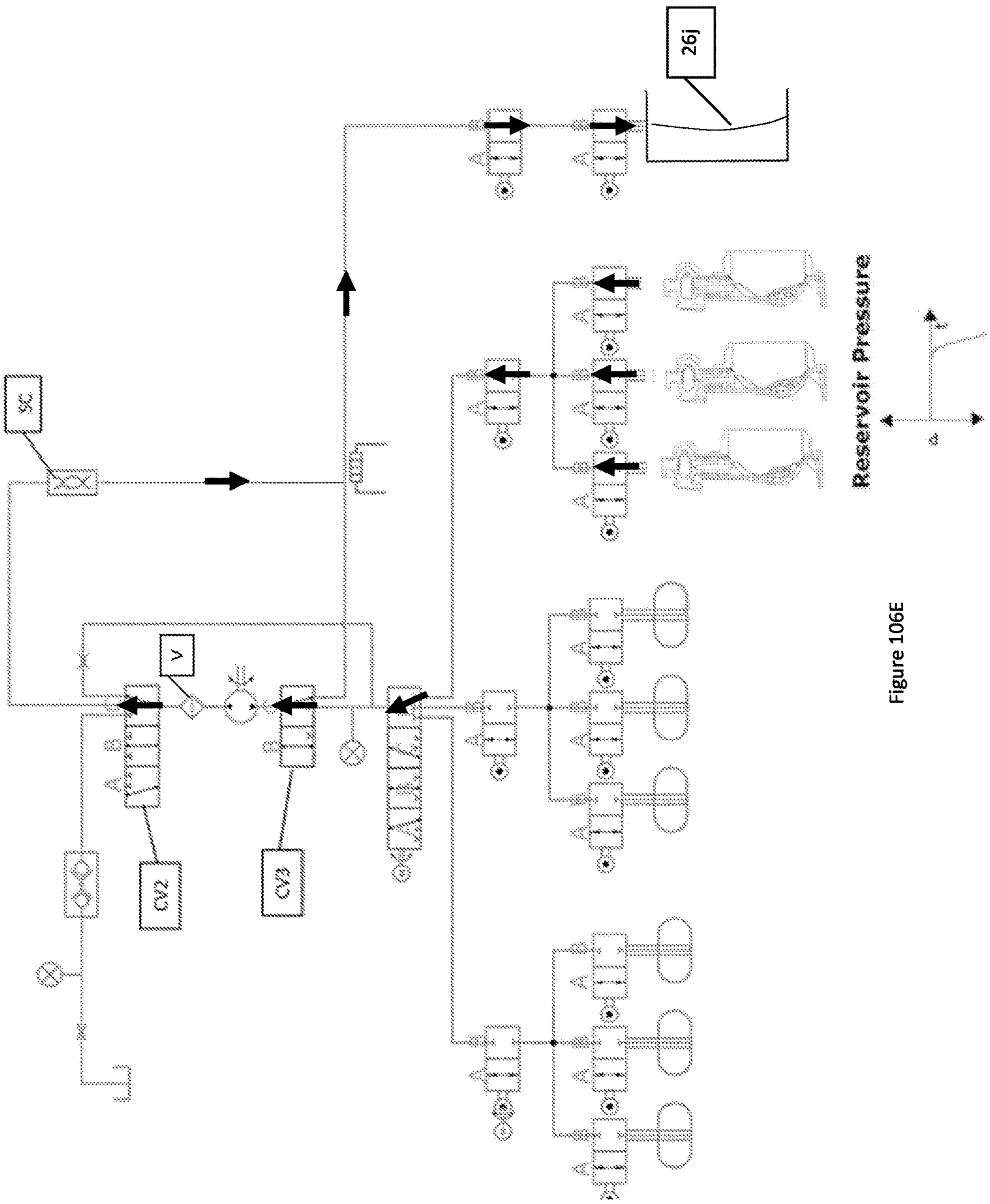
Figure 106F:
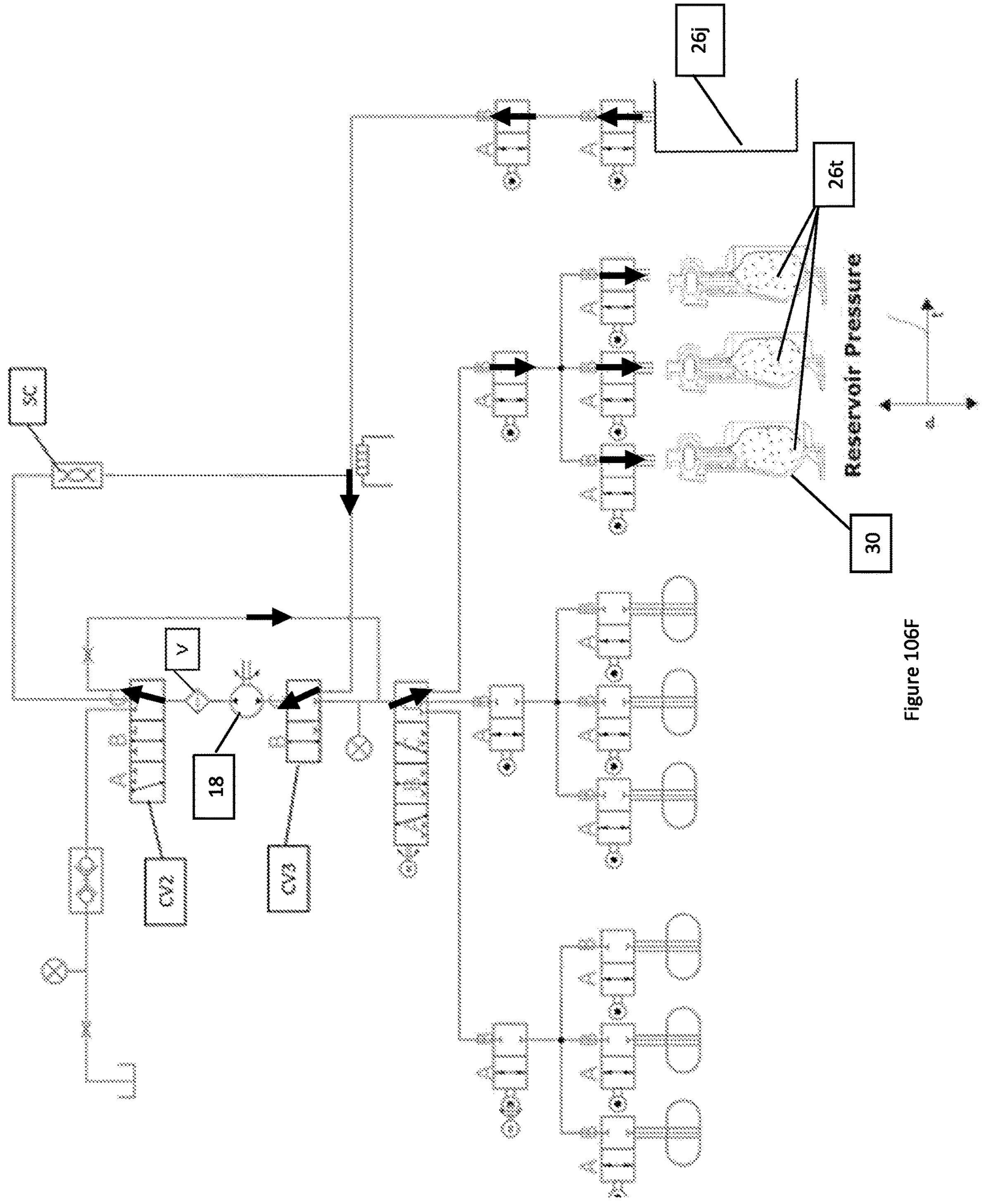

As will be appreciated by those skilled in the art, additional cycles may be utilized beyond the step of FIG. 105D with additional back-and-forth transmission of the intermediate mixture between the diluent reservoir 26*j* and the target reservoir 26*t*. In addition, as shown in FIGS. 106A-106F, subsequent cycles may only introduce a portion of the intermediate mixture. As shown in FIGS. 106A-106C, the same initial steps may be used as shown in FIGS. 105A-105C. As shown in FIG. 106D, a portion of the intermediate mixture is introduced back into the target reservoir 26*t*, with subsequent full voiding of the target reservoir (FIG. 106E) and full introduction of the intermediate mixture into the target reservoir 26*t* (FIG. 106F). Partial cycling may also improve the wettability of the drug, thus, also enhancing reconstitution thereof. With a final mixture being achieved, the final mixture may be withdrawn from the target reservoir 26*t* and directed to the needle 15 for delivery to the patient.

It is noted that the fluidics of FIGS. 105A-106F may be based on that discussed above in connection with FIG. 94B.

In addition, the reservoir support 300 may be utilized to limit expansion of the target reservoir(s) 26*t*. This provides a physical stop delimiting a fill level. Pressure measurement may be utilized, but may not be necessary with use of the reservoir support 300.

Figure 107A:
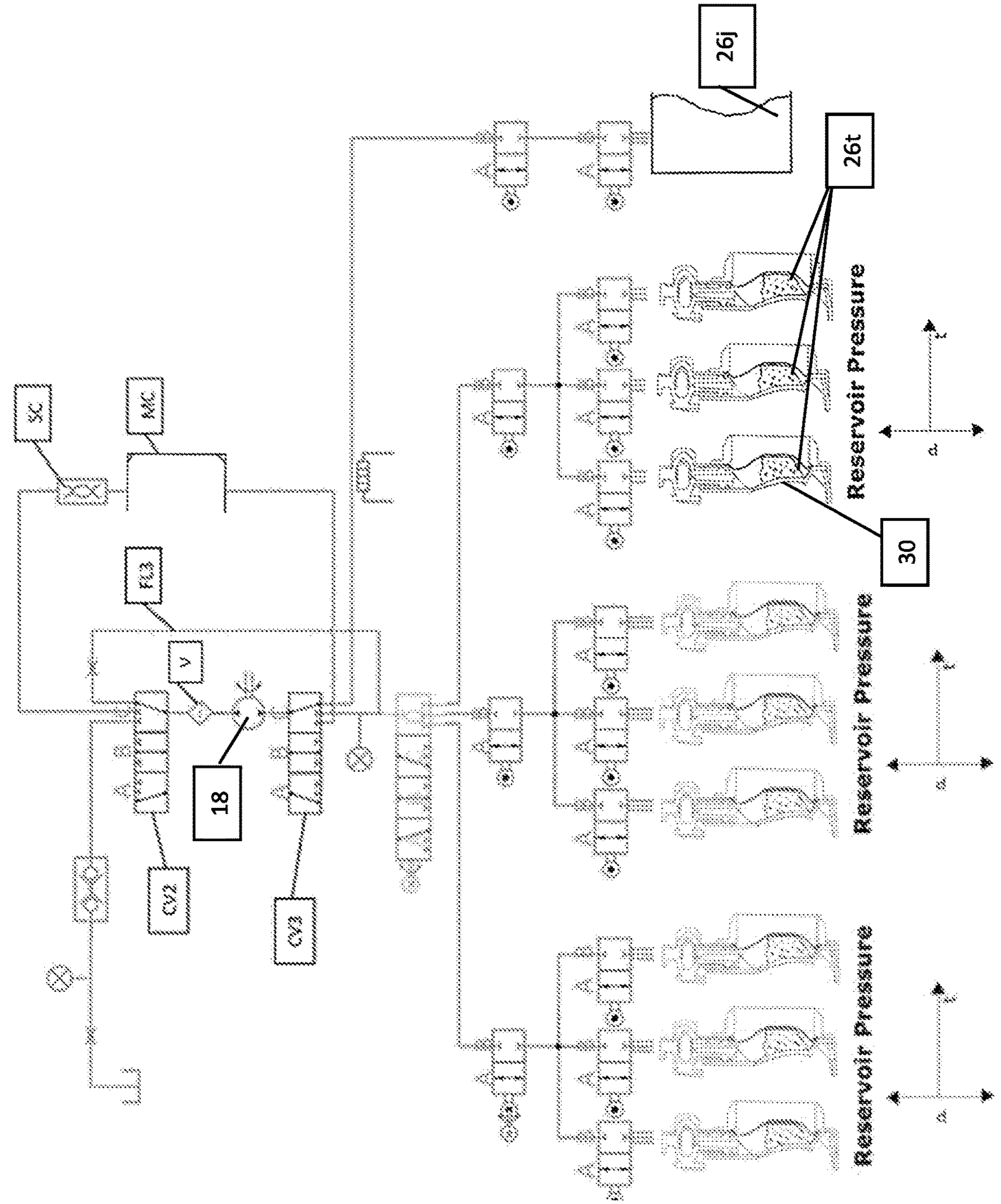
Figure 107B:
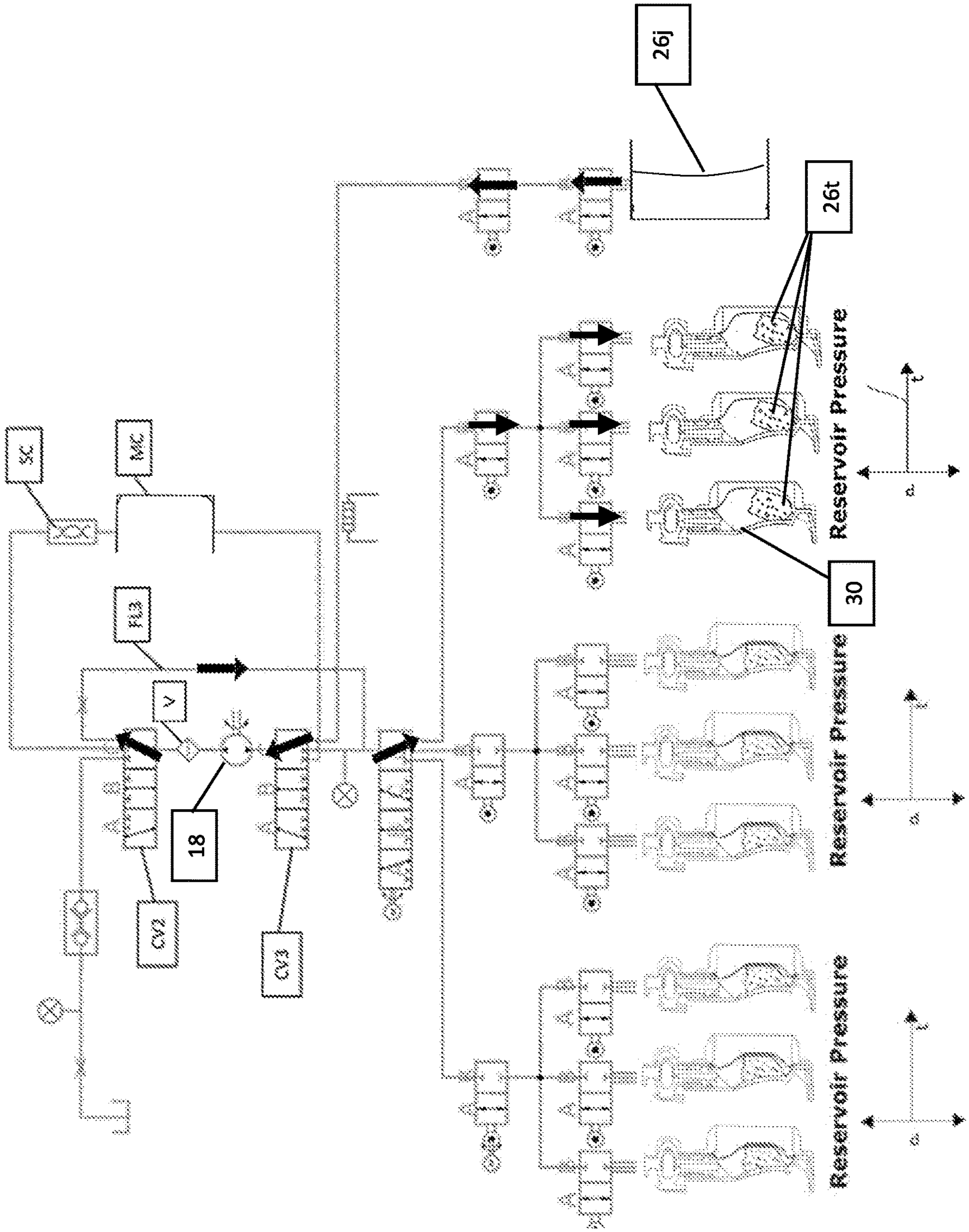
Figure 107C:
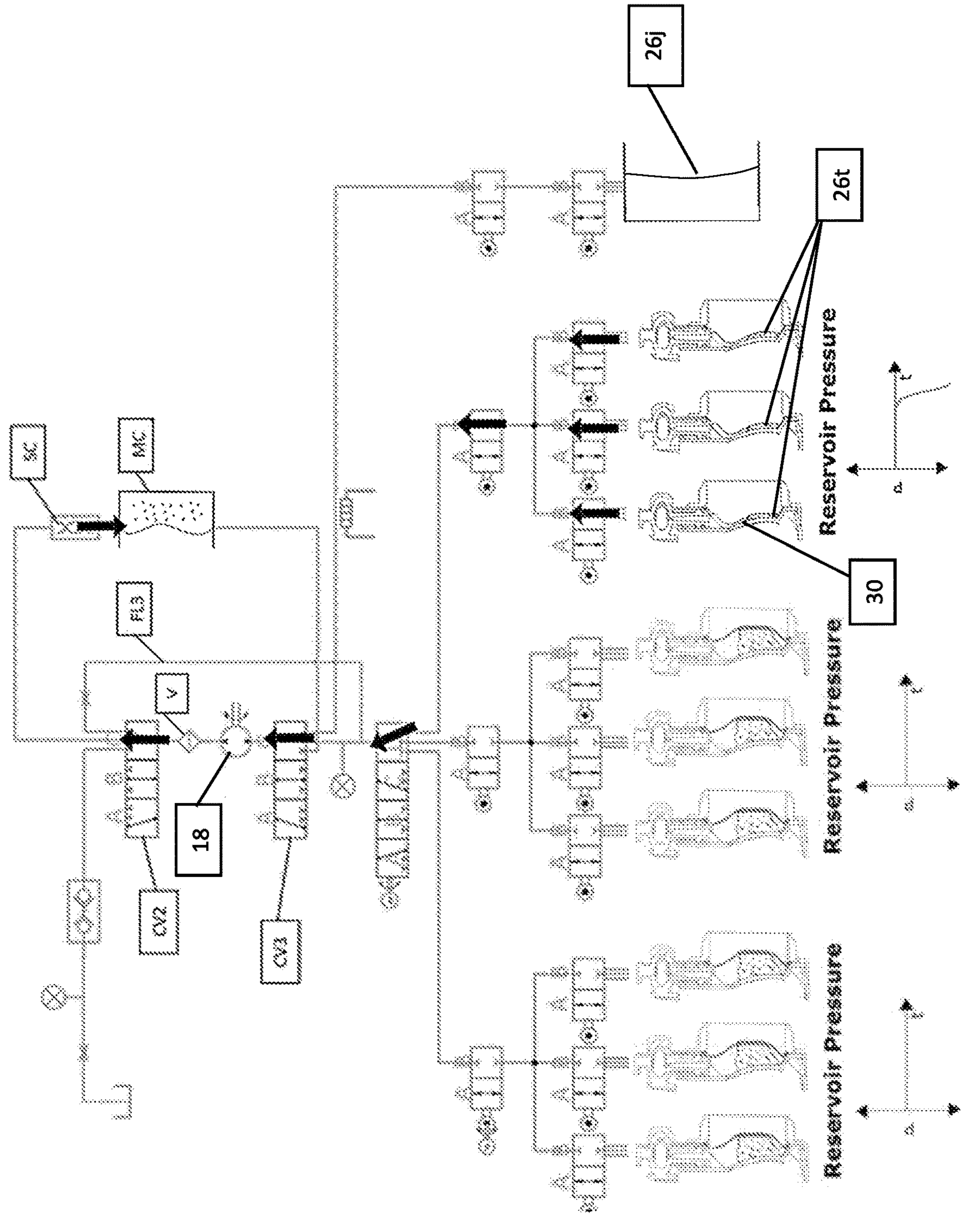
Figure 107D:
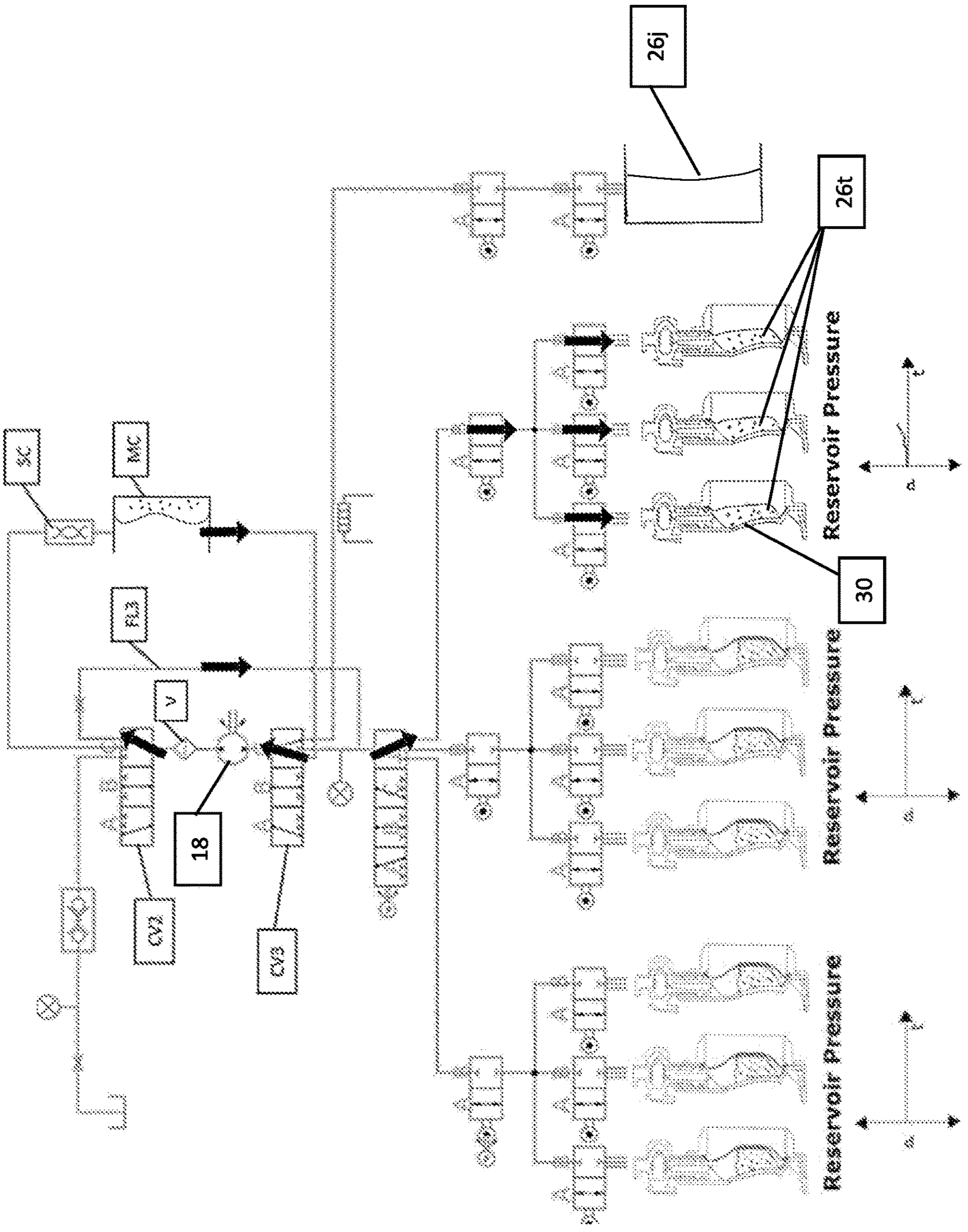
Figure 107E:
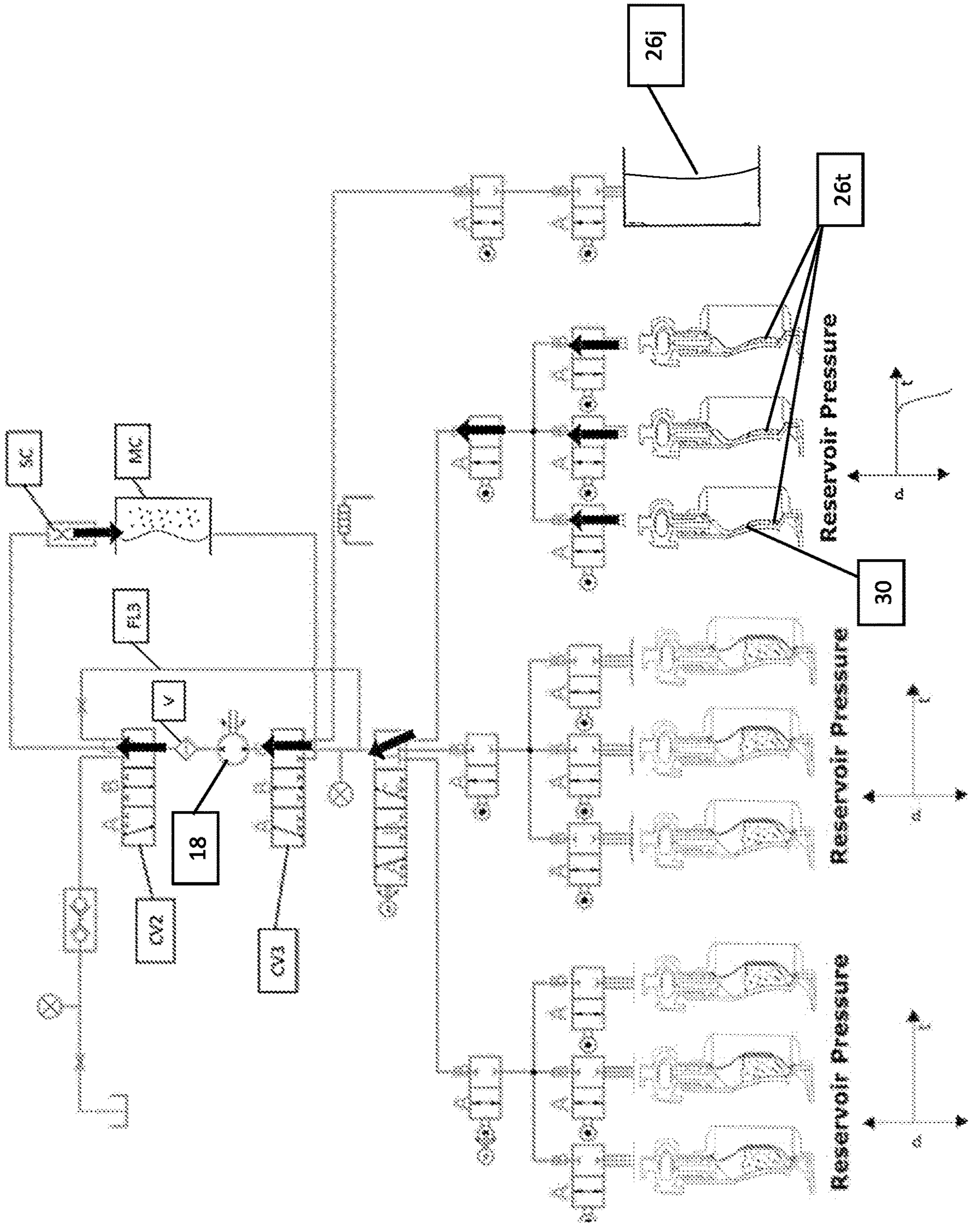
Figure 107F:
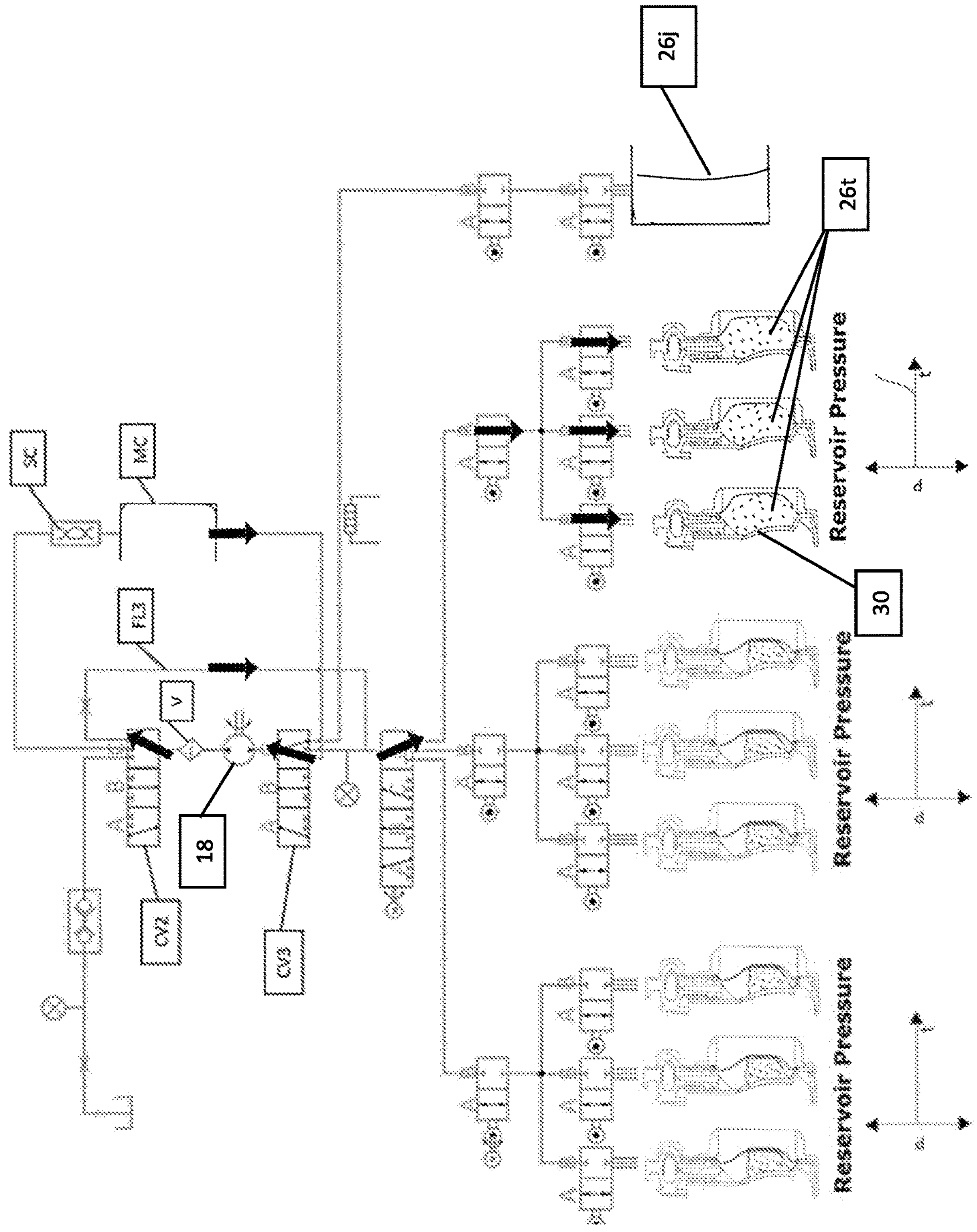
Figure 107G:
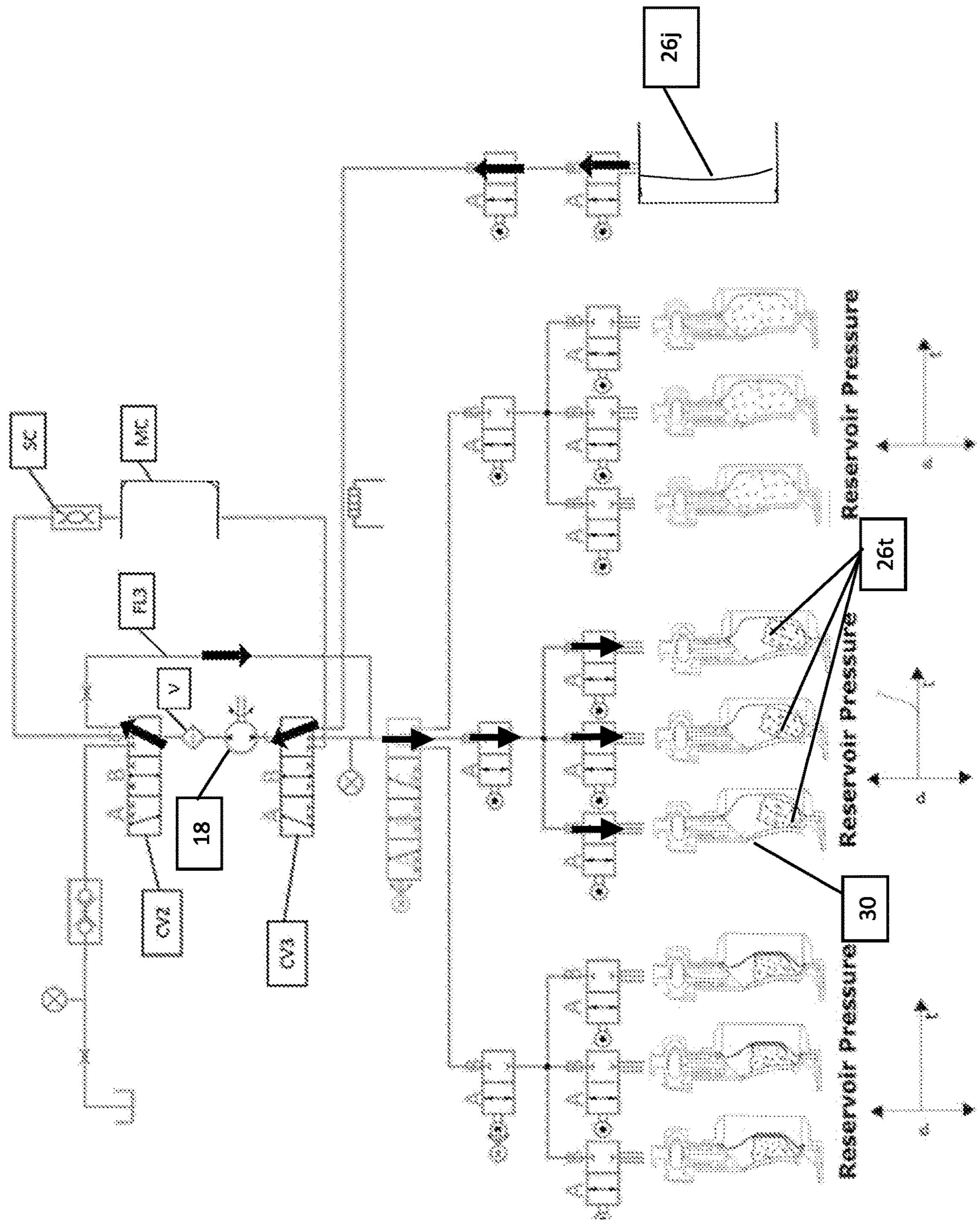
Figure 107H:
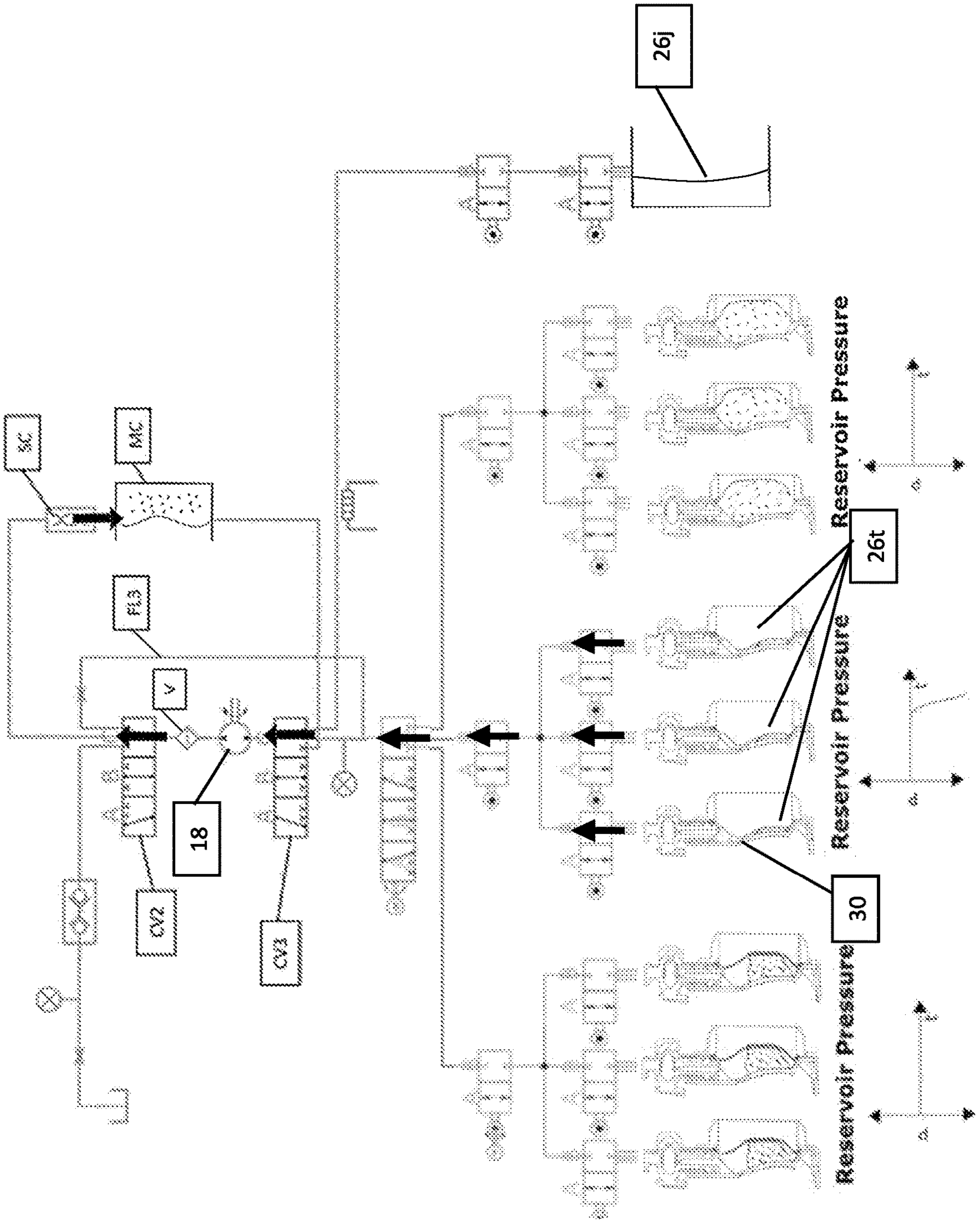
Figure 107I:
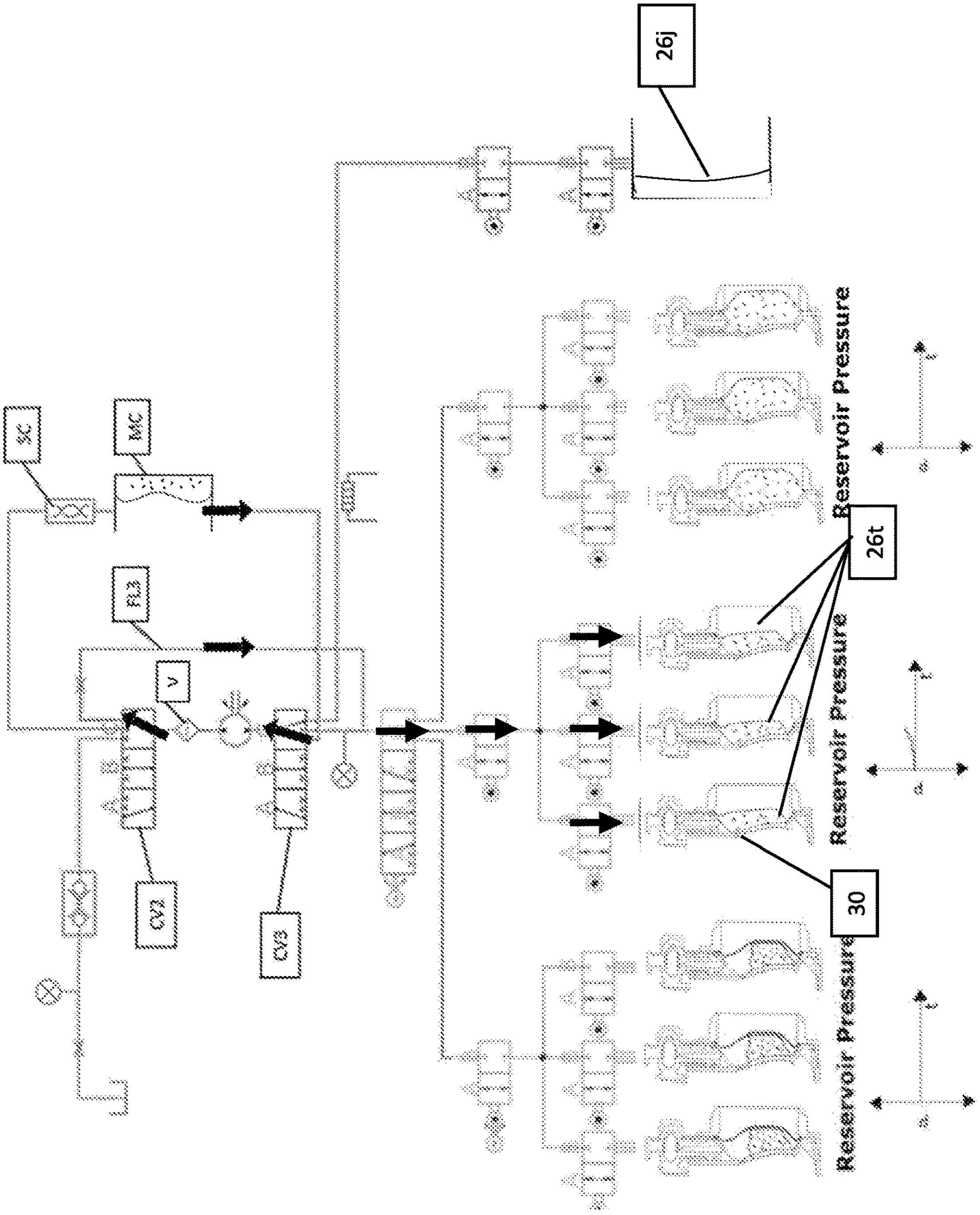
Figure 107J:
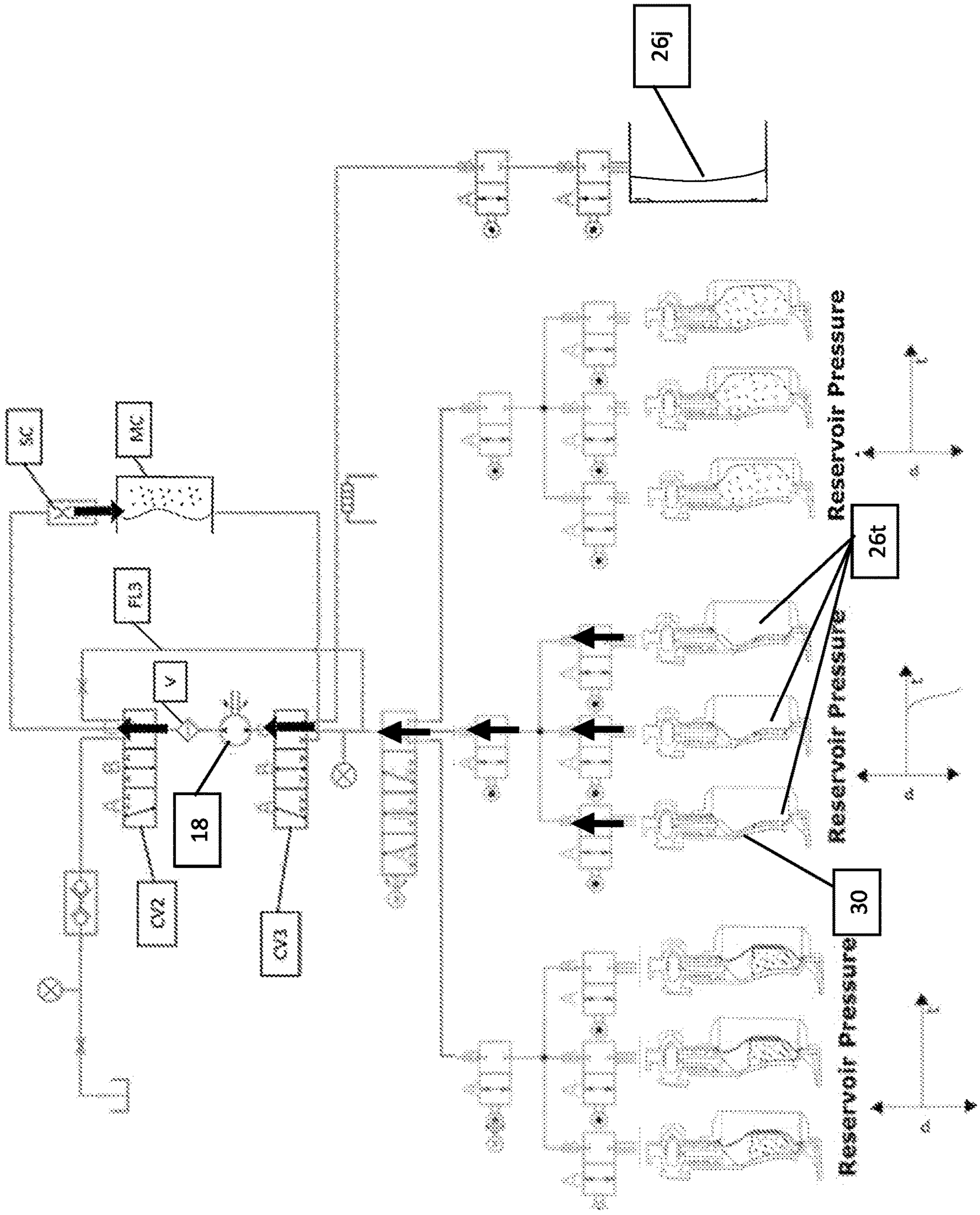
Figure 107K:
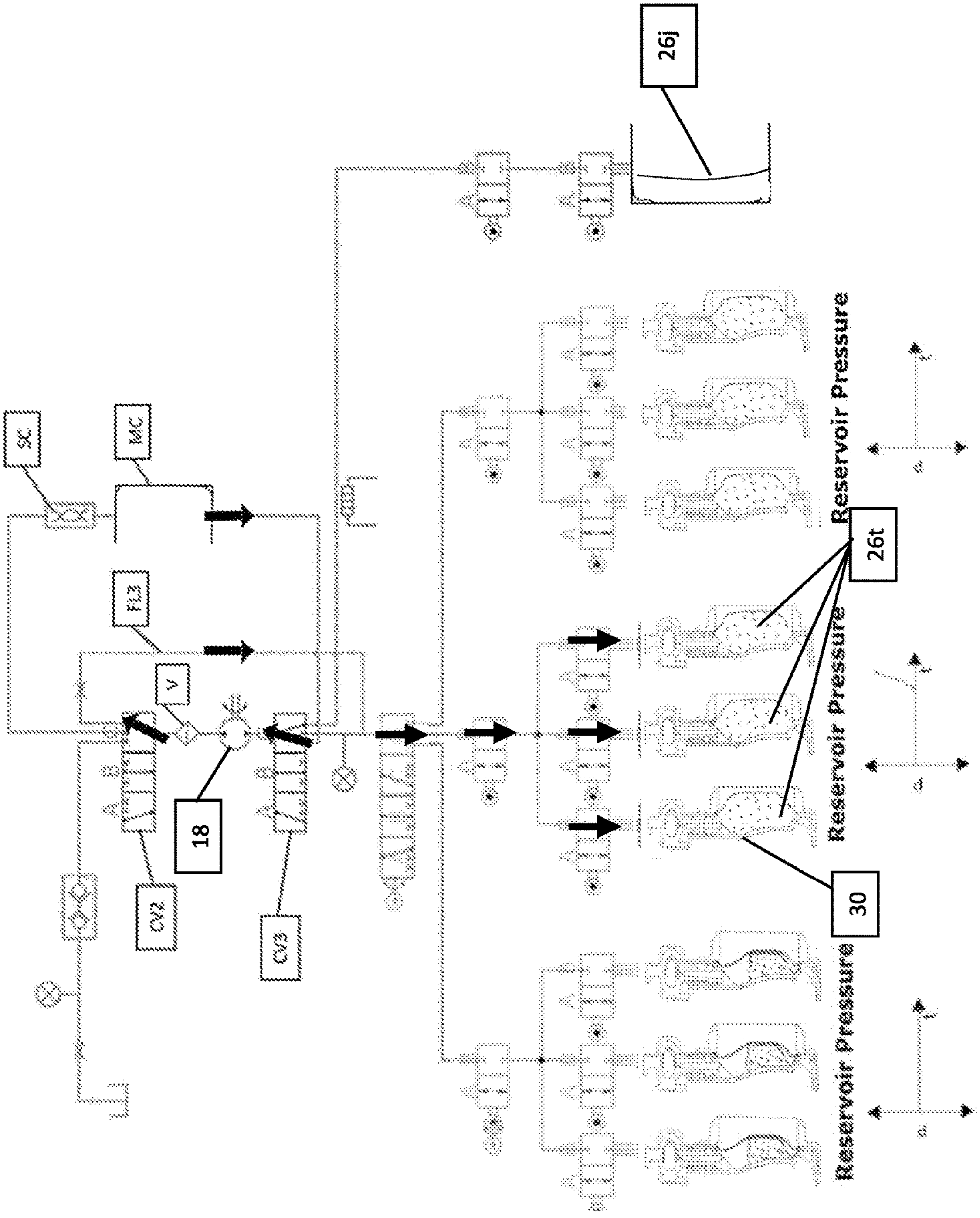
Figure 107L:
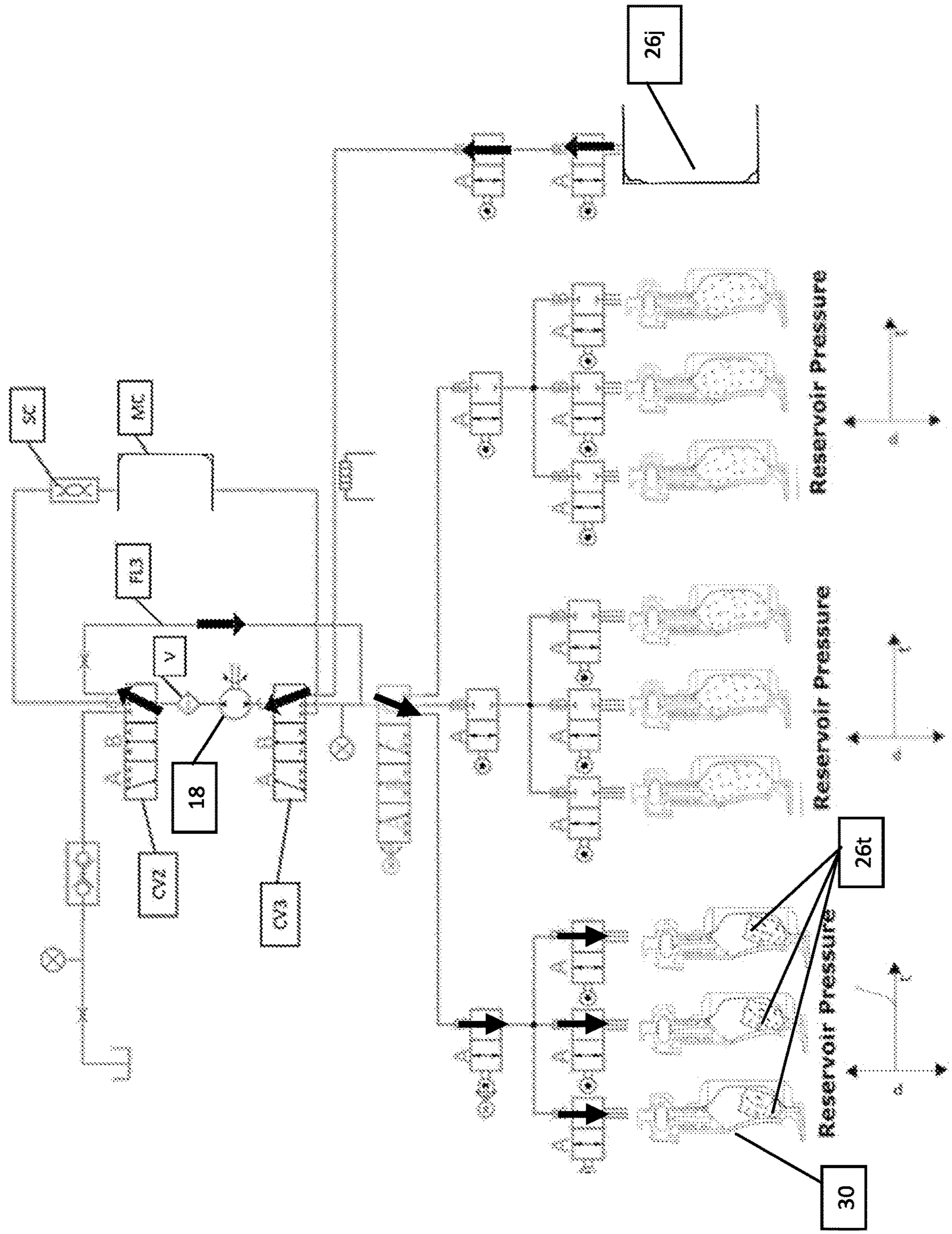
Figure 107M:
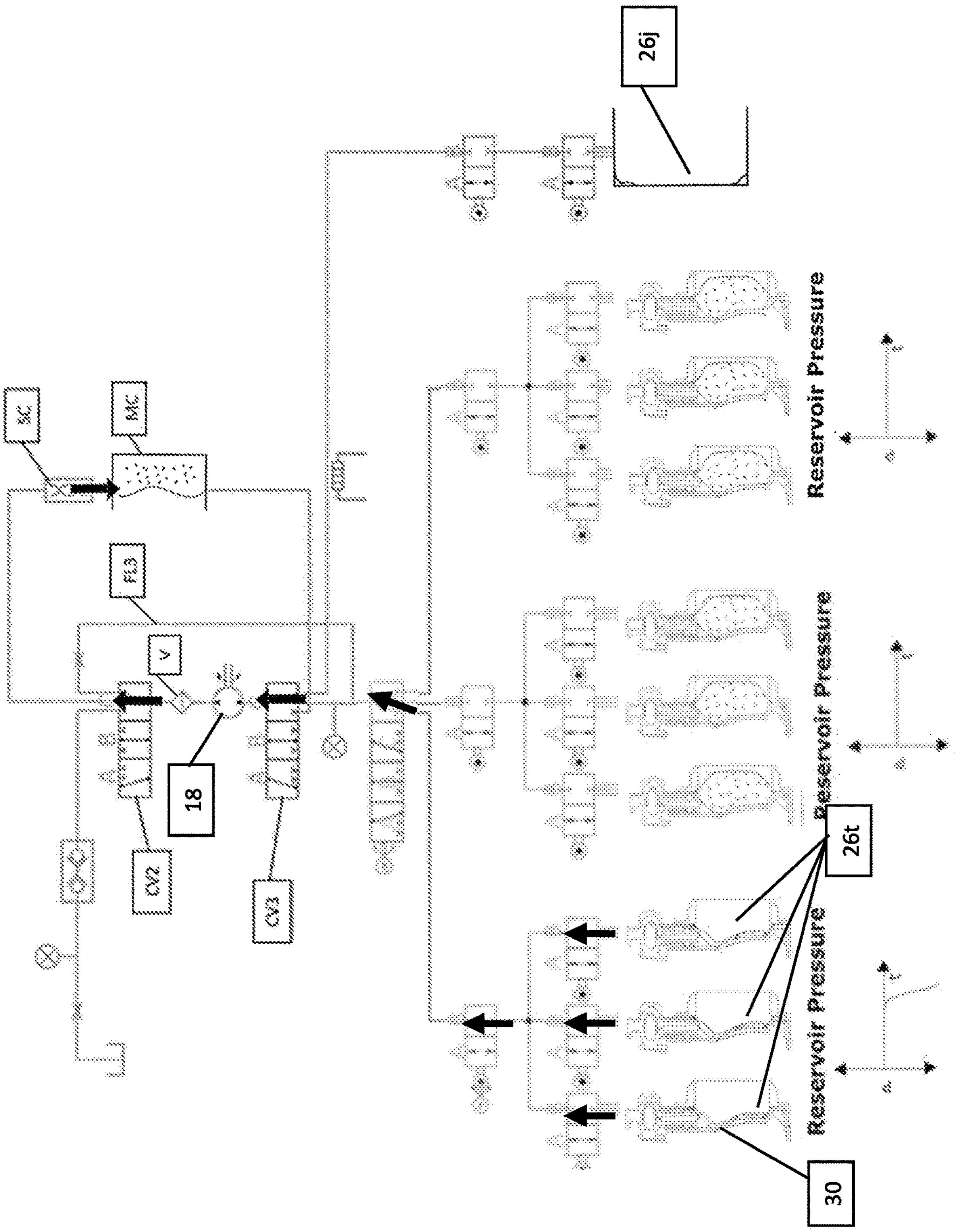
Figure 107N:
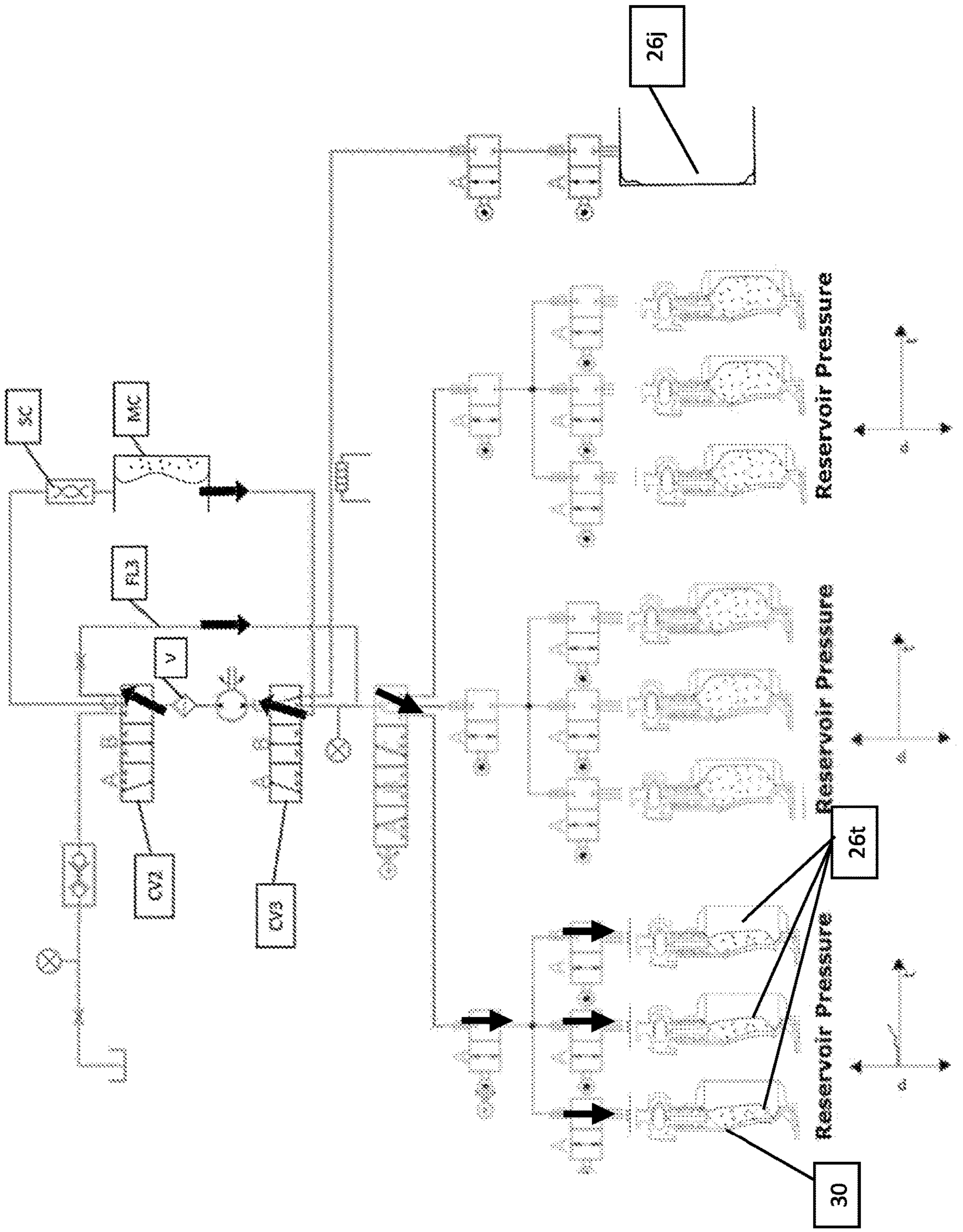
Figure 107O:
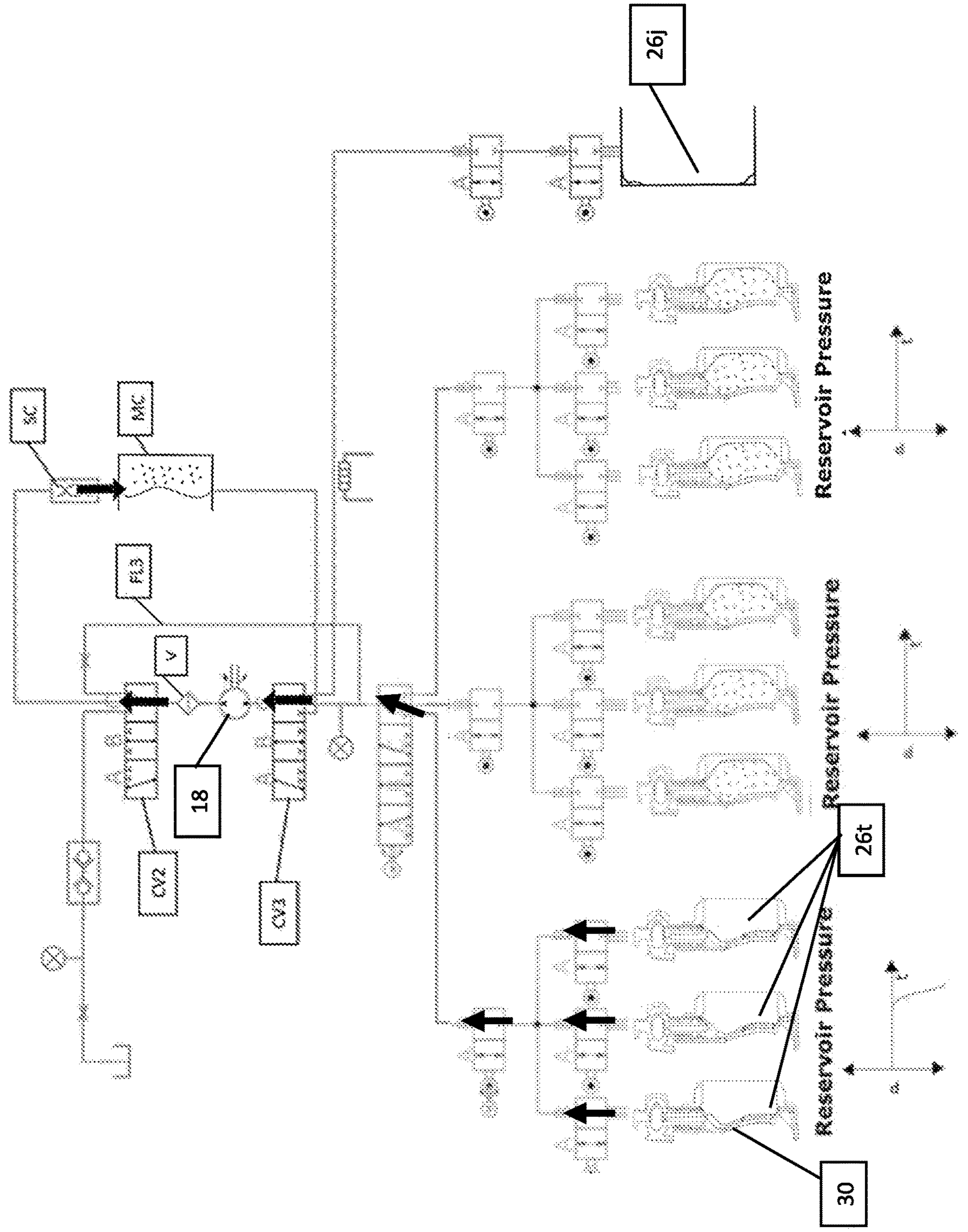
Figure 107P:
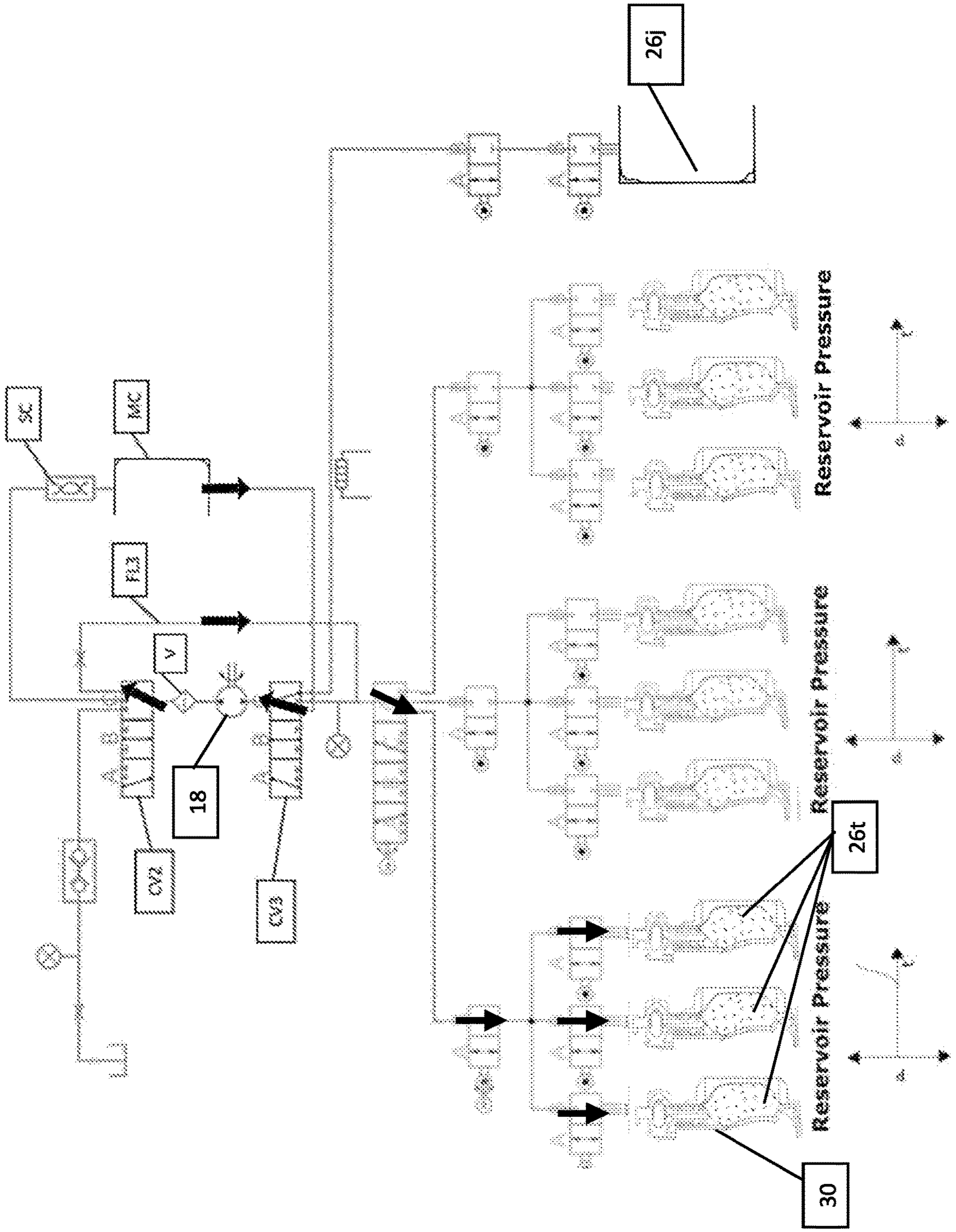

As will be appreciated by those skilled in the art, as shown in FIGS. 107A-107P, the mixing container MC may be utilized in addition to, or in place of, the diluent reservoir 26*j*, to temporarily house the intermediate mixture. FIGS. 107A-107P show similar processing to FIGS. 106A-106F, but with a mixing container MC being utilized to collect and retain the withdrawn intermediate mixture in providing an ultimate mixture for delivery to a patient. Advantageously, the mixing container MC may be connected in a manner which facilitates sequential reconstitution of more than one group of target reservoirs 26*t*, as illustrated in FIGS. 107A-107P. As will be appreciated by those skilled in the art, the diluent reservoir 26*j* may be located in various locations in the system. Depending on the location of the diluent reservoir 26*j*, one or more additional reservoirs 26*d* may be located in the location of the diluent reservoir 26*j* from FIGS. 105A-105D and FIGS. 106A-106F.

It is noted that the fluidics of FIGS. 107A-107P may be based on that discussed above in connection with FIG. 94A.

Gas trapped in the drug or diluent may affect reconstitution by defining unwanted pockets of compressibility. One or more of the vents V may be in-line in the flow path between the diluent reservoir 26*j* and target reservoir 26*t* to allow for removal of trapped gases. FIGS. 113-117 show an embodiment of a vent V useable with the subject invention. The vent V may include a base plate 700 in which is formed a channel 702 which extends between a first opening 704 and a second opening 706. As shown in FIG. 115, the channel 702 may be generally straight between the first opening 704 and the second opening 706. Alternatively, as shown in FIGS. 116 and 117, the channel 702 may define a tortious pathway between the first opening 704 and the second opening 706, including a plurality of bends 708 joined by connecting sections 710. As shown in FIGS. 116A-116C, the plurality of bends 708 may be disposed to create vertical changes in direction with the connecting sections 710 being disposed along a common longitudinal axis but in vertically spaced apart planes. A first set of the connecting sections 710 may be collinearly aligned with a second set of connecting sections 710 also being collinearly aligned but spaced from the linear axis of the first set. Further, as shown in FIG. 117, the channel 702 may include one or more enlarged portions 714, particularly along straight connecting sections 710, to provide areas for gas to collect and coalesce. As shown in FIGS. 117A-117B, the enlarged portions 714 may be diamond shaped having a diverging section 714A, receiving flow, and a converging section 714B, directing flow. Any quantity of the enlarged portions 714 may be utilized.

A gas permeable layer 712 is mounted to the base plate 700 to cover the channel 702, the channel 702 being direct contact with the gas permeable layer 712. Gas may permeate through the gas permeable layer 712 from the channel 702. It is preferred that the channel 702 act as a restriction, e.g., being narrow, thereby acting to urge the gas therefrom. The tortious pathway and the enlarged portions may further enhance this effect. It is also noted that this vent configuration is equally effective with flow in either direction, thus, providing venting with flow in either direction between the first and second openings 704, 706.

With reference to FIGS. 105C and 106C, the drug cartridge 14 may have the reservoir 26*t* support by outwardly concave portion of the rigid shell 30. The concave portion imparts an outwardly curved surface against which the drug may be spread across. In addition, it is preferred that the filling port 38 be arranged in define a flow path impinging on the concave portion. This allows for flow of the diluent to press the drug against this surface in causing compression thereof, thus, increasing "de-clumping" and wetting of the drug. As shown in FIG. 107C, the rigid shell 30 may be provided with an inward convex portion in place of the concave portion. The same considerations apply to the convex surface, which may define a larger surface for the drug to spread across.

Figure 108:
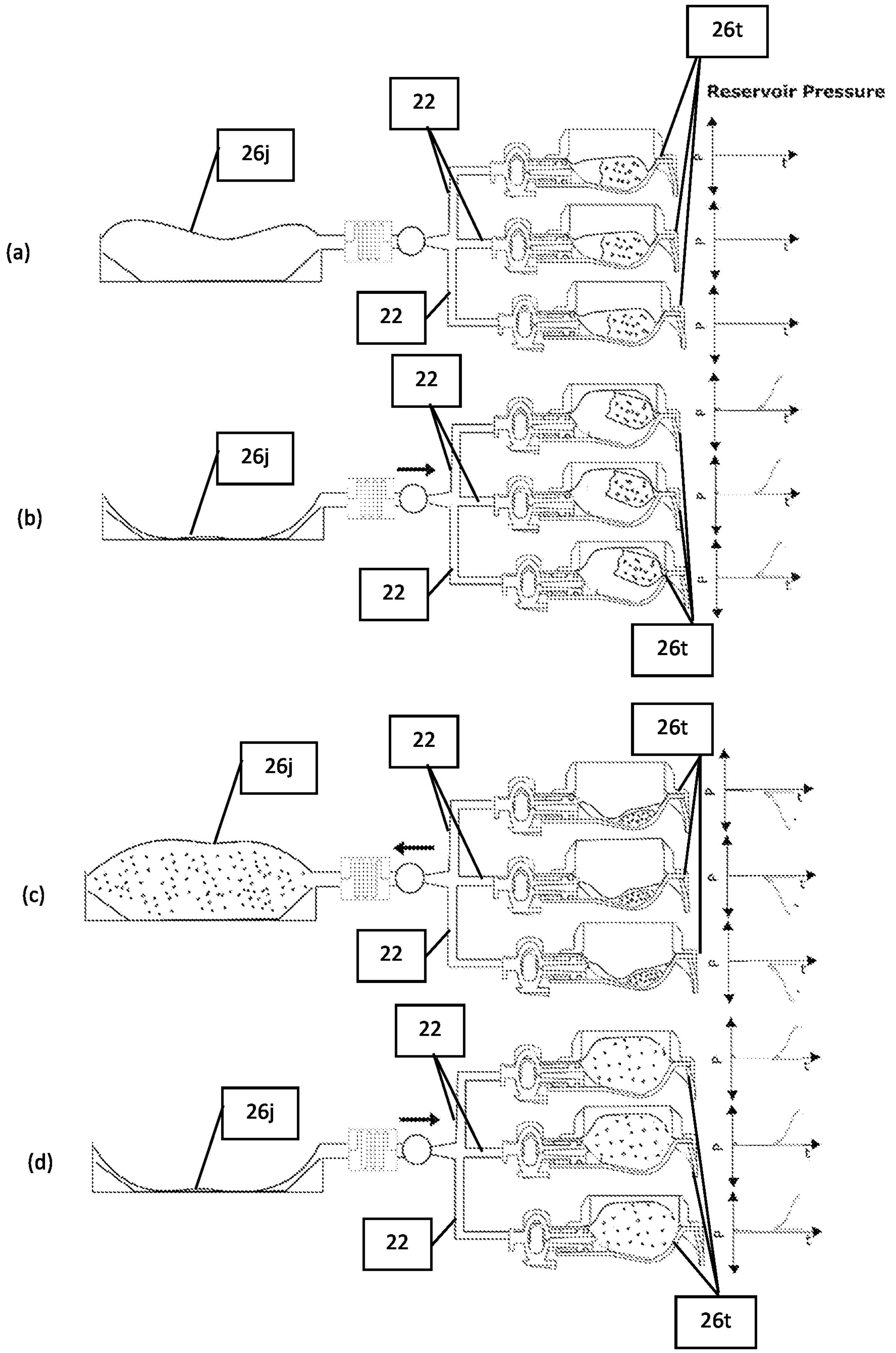

FIG. 108 shows a plurality of target reservoirs 26*t* being manifolded for simultaneous cycling. This allows for mixing of drugs from the various target reservoirs 26*t* in the manifolded fluid ducts 22 and the diluent reservoir 26*j*, in addition to reconstitution. The pressure of each of the target reservoirs 26*t* may be monitored to determine the fill levels thereof.

Figure 109:
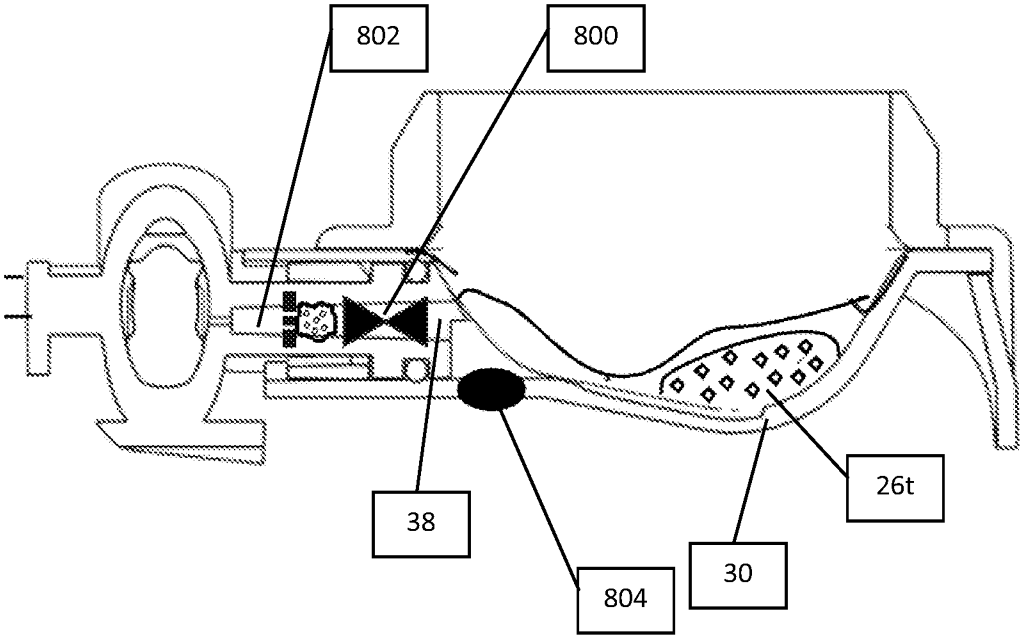

As shown in FIG. 109, each of the reservoirs 26, including the target reservoirs 26*t*, may be provided with a static mixer 800, for example in the filling port 38, adjacent to the respective reservoir 26. This provides improved mixing with withdrawal of drug from the respective reservoir 26. In addition, optionally, a filter 802 may be provided, e.g., along the filling port 38, for entrapping excessively large solid particles. Further, optionally, a reservoir pressure sensor 804 may be provided on the rigid shell 30 to detect the pressure of the respective reservoir 26. The reservoir pressure sensor 804 is located to be pressed against by the respective reservoir 26, with filling thereof.

Figure 110:
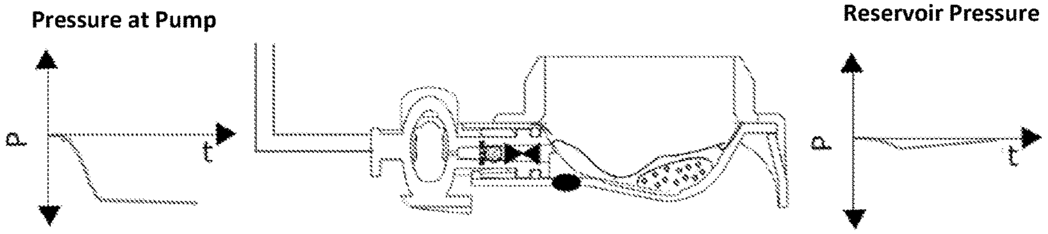
Figure 111:
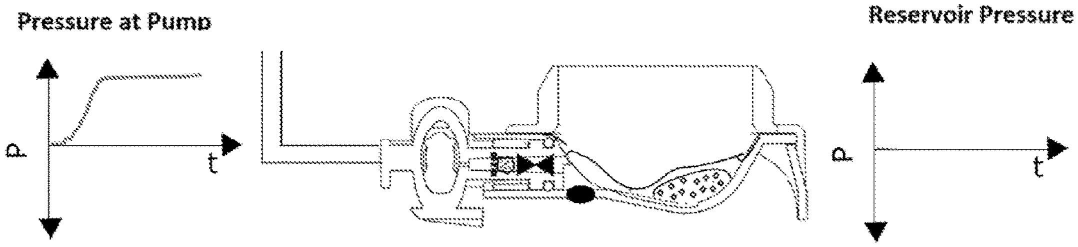
Figure 112:
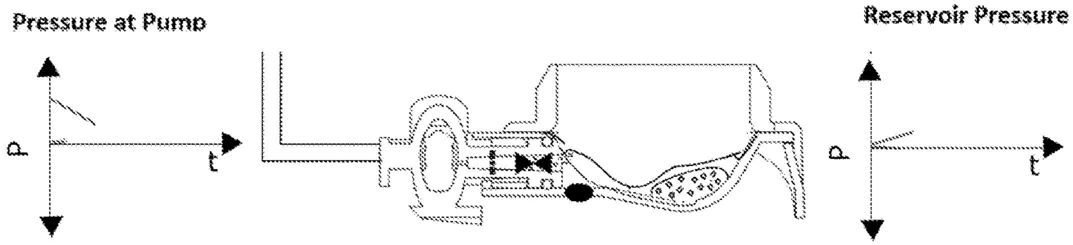

As shown in FIGS. 110-112, with the reservoir pressure sensor 804 being utilized, comparisons may be made of pressures at the pump 18 and the respective reservoir 26 to determine any differential therebetween. This may be utilized to identify a clog or blockage resulting from solid particles of drug obstructing a portion of the flow path. As shown in FIG. 110, with detection of a pressure differential, particularly during withdrawal of mixture from the target reservoir 26*t*, flow may be reversed to loosen the obstruction (FIG. 111). With removal of the obstruction, the pressure differential may dissipate (FIG. 112).

In use, the drug delivery device 10 may be actuated for use in various manners. For example, the drug delivery device 10 may be pre-actuated before use to allow for reconstitution, prior to the patient mounting the drug delivery device 10. In addition, one or more skin sensors (e.g., capacitative skin sensor(s)) may be provided on the drug delivery device 10 as a safety to detect proper mounting prior to activation and drug delivery. With activation, the needle 15 may be caused to be inserted into the patient, and the pump 18 activated to delivery drug therethrough. Pressure of flow and timing may be monitored to evaluate the state of drug delivery. Status indicators, such as lights, may be provided on the drug delivery device 10 to provide the patient with the status of drug delivery. A single dose may be considered depletion of all of the drug cartridges 14. Once the drug delivery is completed, the drug delivery device 10 may be removed from the patient and disposed of in accordance with applicable regulations.

With reference to FIGS. 118A-148B, by way of non-limiting example, a network of reversible valves may be used to selectively direct flow across various flow paths, e.g., as shown in FIGS. 90-94B, as described above. As shown in FIGS. 131 and 135, a plurality of flexible valves 900 may be provided, each having a flexible body 902 supported by its edge 904. Preferably, the edge 904 defines a circular shape. In addition, it is preferred that the body 902 be dome-shaped in an at-rest, unbiased state, as shown in FIGS. 131 and 135. The body 902 is formed from a resilient material, e.g., an elastomeric and/or polymeric material, which allows the body 902 to be reversibly, inwardly deflected under load. The body 902 may be formed to have inherent memory in the unbiased state, so that with removal of the load, the body 902, in a deflected state, returns towards its unbiased state. This allows for the body 902 to be reversibly deflected under force, with return to the unbiased state.

The body 902 may include a protruding, downwardly depending valve face 906. Preferably, the valve face 906 is generally planar. As shown in comparing FIGS. 135 and 136, the valve face 906 preferably moves straight downwardly, with deflection of the body 902, so that the valve face 906 is oriented generally parallel between the deflected state (FIG. 136) and the unbiased state (FIG. 135).

The valves 900 are each located at the intersections of flow paths and/or to act as a connection between flow paths, to selectively regulate flow therebetween. As shown in FIGS. 135 and 136, the valves 900 may be each located above an opening 908 to a flow path 910. It is preferred that the valve face 906 be formed with a larger area than the corresponding opening 908 so that the valve face 906 may fully cover the opening 908. As shown in FIG. 136, with the valve 900 in a deflected state, the valve face 906 is in pressing engagement with a seal face 912 about the opening 908 such that the opening 908 is fully covered by the valve face 906, thus, shutting off the flow path 910. To facilitate the formation of a good seal, the seal face 912 is generally planar and shaped and configured to have face-to-face engagement with the valve face 906 about the opening 908 to form an annular seal. As shown in FIGS. 135 and 136, the seal face 912 may be raised.

To control the opening and closing of the valves 900, the valves 900 may be each provided with a leaf spring 914 clipped to a boss 916 extending upwardly from the body 902. The leaf spring 914 may have an at-rest, unbiased state as shown in FIGS. 131 and 135, with the body 902 being unbiased. The leaf spring 914 provides additional restoration force to the valve 900 when returning to an unbiased state (FIG. 135) from a deflected state (FIG. 136). As shown in FIG. 136, the leaf spring 914 is deflected with the body 902 being deflected. The leaf spring 914 is formed from a material with inherent memory, e.g., metallic and/or polymeric material, which urges the leaf spring 914 towards its unbiased state when not under load. The return force of the leaf spring 914 acts on the body 902 to assist in returning to the unbiased state.

Various arrangements may be utilized to cause selective opening and closing of the valves 900. The deflected state of the valves 900 may correspond to a closed state (i.e., restricting flow), while the unbiased state may correspond to an open state (i.e., allowing flow). With a network of the valves 900, flow through multiple flow paths may be selectively controlled. By way of non-limiting example, an actuator gear 918 may be provided fixed to rotate above one or more of the valves 900. The actuator gear 918 may include a lower face 920, configured to be aligned with the valve(s) 900 over an arc of rotation of the actuator gear 918. As shown in FIG. 136, the lower face 920 is vertically positioned above the valve(s) 900 so as to be in interfering engagement with the valve(s) 900 to cause deflection thereof, with the valve(s) 900 being in the closed state. It is preferred that the lower face 920 be generally planar to allow for continuous engagement with the valve(s) 900.

The actuator gear 918 may be also provided with one or radial recesses 922 which may be rotated into alignment with one or more of the valve(s) 900. Each of the radial recesses 922 defines a relief allowing the valve(s) 900 to return towards the unbiased state, thereby providing an open state for the valve(s) 900. The radial recesses 922 may be located on the actuator gear(s) 918 to coordinate opening and closing of one or more valve(s) 900. For example, a plurality of the recesses 922 may be provided on the actuator gear 918 positioned to accommodate opening of different combinations of the valve(s) 900 (one of the radial recesses 922 be located for engagement with a single valve 900, with two or more of the radial recesses 922 being separately positioned to simultaneously open two of more of the valves 900 for coordinated action).

The valves 900 may be provided with a sliding contact 924, which may be generally planar to slide along the lower face 920 with rotation thereof. The sliding contact 924 may be formed integrally with the leaf spring 914, e.g., being formed from a single bent piece of metal. As will be appreciated by those skilled in the art, the sliding contact 924 may be omitted, with the lower face 920 interferingly engaging the boss 916 and/or the body 902 to causing deflection of the respective valve 900.

To allow reversible transition between the lower face 920 and the radial recess(es) 922, as shown in FIG. 134, ramped surfaces 926 may be located at radial ends of each of the radial recesses 922 to allow gradual, rather than step, transitions between the lower face 920 and the radial recess(es) 922. The radial recess(es) 922 may be each provided with a ceiling 928 for limiting upward movement of the valve(s) 900. As shown in FIG. 135, it is preferred that the ceiling 928 be located to restrict the valve(s) 900 from full return to the unbiased state. This allows for the valve(s) 900 to be in pressing engagement with the respective ceiling 928. For each of the radial recesses 922, the ramped surfaces 926 may be defined as angled surfaces extending between the respective ceiling 928 and the lower face 920.

As shown in FIG. 118A, the actuator gear 918 may be provided with teeth 930 formed to meshingly engage with worm gear 932. The worm gear 932 may be rotatably driven by a motor, preferably, reversibly to allow reversible rotation of the actuator gear 918. The motor may be the same motor to drive the pump 18 and/or the gear plate 510. FIG. 118B shows an alternate arrangement of the actuator gear 918 engaging with the worm gear 932. Shown as a block connection, the actuator gear 918 meshingly engages the worm gear 932 in similar fashion to that shown in FIG. 118A.

As shown in FIG. 119, a plurality of the valves 900 may be radially aligned to be overlapped by the actuator gear 918. This allows for the actuator gear 918 to selectively engage a plurality of the valves 900 in causing selectively opening/closing thereof. The configurations of the lower face 920 and the radial recess(es) 922 allows for various permissible configurations of open and closed valves 900. For example, as shown in FIG. 134, a first actuator gear 918A may be utilized which includes three radially spaced-apart radial recesses 922 about the lower face 920, whereas, a second actuator gear 918B may be utilized which includes a single radial recess 922. In addition, the radial length of the radial recess(es) 922 allows for simultaneous opening of a plurality of the valves 900. For example, as shown with the first actuator gear 918A, one of the radial recesses 922A includes a radial length sufficient to span across two of the valves 900. As shown in FIG. 118A, each of the first and second actuator gears 918A, 918B may be meshingly engaged by first and second worm gears 932A, 932B to allow for independent control thereof. This allows for further variability in regulating fluid flow. FIG. 118A shows the first and second worm gears 932A, 932B to be generally parallel on opposing sides of the first and second actuator gears 918A, 918B. As will be appreciated by those skilled in the art, the first and second worm gears 932A, 932B may be arranged in various positions. For example, as shown in FIG. 118B, the first and second worm gears 932A, 932B may be arranged transverse to, and/or adjacent to, one another.

FIGS. 132 and 133 show the leaf springs 914 superimposed over the first and second actuator gears 918A, 918B. As shown, a different quantity of the leaf springs 914 may be associated with each of the first and second actuator gears 918A, 918B, thereby allowing for different quantities of the valves 900 to be controlled by each.

The valves 900 may be supported by a valve module 934, as shown in FIG. 119. On the valve module 934, a first set of valves 900A may be radially aligned with the actuator gear 918A and a second set of valves 900B may be radially aligned with the actuator gear 918B. The leaf springs 914 of each of the sets of valves 900A, 900B may radiate from a central disc 936 (936A, 936B) mounted to center post 938 (938A, 938B). The leaf springs 914 and the respective central disc 936A, 936B may be integrally formed from a single piece, such as die-cut metal. The first and second actuator gears 918A, 918B are mounted to the center posts 938A, 938B, respectively, to be rotatable thereabout.

As shown in FIGS. 121A-131, the valve module 934 is preferably formed as a multi-layered structure, with various passageways defined therein. As shown in FIG. 131, the valve module 934 may be a four-layer structure with top layer 934A, first intermediate layer 934B, second intermediate layer 934C, and base layer 934D. The top layer 934A includes a plurality of apertures 940, each corresponding to one of the valves 900. As shown in FIG. 119, the bosses 916 may extend through the apertures 940 to be engaged by the leaf springs 914.

As shown in FIGS. 121A-121B, the body 902 of each of the valves 900 is exposed through a respective one of the apertures 940. The top layer 934A is atop first intermediate layer 934B, as shown in FIGS. 135-136. It is preferred that the edge 904 of each of the valves 900 be sandwiched between the top layer 934A and the first intermediate layer 934B so as to be fixed therebetween. Notches 935 may be formed in the top layer 934A and/or the first intermediate layer 934B to accommodate the edges 904. Each of the notches 935 may be annular, positioned to circumscribe the respective aperture 940. The edges 904 may be fixed by friction fit, welding, adhesion, fusion and so forth.

As shown in FIGS. 122A-123B, wells 937 may be defined in the first intermediate layer 934B, in one-to-one correspondence, and alignment, with the apertures 940. As shown in FIGS. 135 and 136, the seal face 912 of the respective valve 900 is defined on lower surface 939 of the respective well 937. As discussed above, the seal face 912 may be raised from the lower surface 939 (FIG. 122B). Alternatively, as shown in FIG. 122A, the seal face 912 may be generally co-planar with the lower surface 939. In addition, the openings 908 may be formed in the first intermediate layer 934B to extend from each of the wells 937 to a lower face 941 of the first intermediate layer 934B. In addition, for each of the wells 937, a secondary opening 943 is formed to extend from the respective lower surface 939 to the lower face 941.

As shown in FIGS. 125-130, the second intermediate layer 934C may be plated-shaped with upper face 942 and opposing, lower face 944. First fluid channels 946A may be formed in the upper face 942 to define flow channels. The first fluid channels 946A may extend from first openings 948A formed in edge 950 of the second intermediate layer 934C and terminate at locations in axial alignment with the wells 937. Thus, with the first intermediate layer 934B atop the second intermediate layer 934C, as shown in FIG. 124, closed flow paths may be defined from locations along the edge 950 to various of the wells 937. For example, as shown in FIG. 124, the first fluid channel 946A1 extends from the first opening 948A1 and terminates in alignment with the opening 908A of the well 937A. The interface between the opening 908A and the first fluid channel 946A1 is defined at the lower face 941 of the first intermediate layer 934B.

In addition, second fluid channels 946B may be formed in the lower face 944 to define flow channels. In addition, one or more through holes 952 may be formed in the second intermediate layer 934C to extend between the upper and lower faces 942, 944. The through holes 952 allow for vertical flow through the second intermediate layer 934C. The second fluid channels 946B may extend from second openings 948B formed in the edge 950. As shown in FIG. 125, the first openings 948B are formed in the edge 950, along the upper face 942, while the second openings 948B are formed in the edge 950, along the lower face 944. The base layer 934D covers the second fluid channels 946B to define closed fluid paths through the second fluid channels 946B.

As shown in FIG. 124, pairs of the first fluid channels 946A, the second fluid channels 946B, and/or the through holes 952 may be aligned with each of the wells 937 to allow the valves 900 to selectively control flow therebetween. The opening 908 and the secondary opening 943, of each of the valves 900, are aligned with the first fluid channels 946A and/or the through holes 952 to control flow between the pair thereof. With a respective one of the valves 900 open (as shown in FIG. 135), the respective opening 908 and the respective secondary opening 943 are unobstructed in the respective well 937 to allow flow therebetween. With the valve 900 closed (as shown in FIG. 136), the respective opening 908 is obstructed and flow through the respective well 937 is restricted. FIGS. 137 and 138 illustrate flow paths to the valves 900.

With selective opening and closing of the valves 900, flow between the first and second fluid channels 946A, 946B may be controlled. The through holes 952 allow for communication with the second fluid channels 946B to regulate flow therethrough. For example, as shown in FIG. 124, the through hole 952A may be aligned with the secondary opening 943A of the well 937A. In turn, the through hole 952A may extend to second fluid channel 946B1, which extends to through hole 952B, which in turn, is in alignment with the secondary opening 943B of the well 937B. First fluid channel 946A2 may extend from the first opening 948A2 to the opening 908B. This circuit allows selective flow between the first openings 948A1 and 948A2 with opening and closing of the valves 900 associated with the wells 937A, 937B.

The module 934 may be formed as a unitary structure with its layers being bonded, or otherwise fixed, together. It is preferred that each of the layers have a plate-shape with generally parallel opposing faces. It is also preferred that all features formed on each of the layers be formed recessed within (i.e., not protrude from) the faces. This allows for the layers to be stacked with full face-to-face engagement between the layers. This allows for fluid tightness in sealing about flow channels. The layers may be formed of polymeric and/or metallic material and joined in a stack by any known means, including, but not limited to, bonding, adhesion, fusion, and, mechanical fastening (e.g., interlocking elements, fasteners, etc.). The layers may be formed with the features defined therein (e.g., molded, 3d printing), and/or may be formed as plate-shaped blanks which are subsequently worked upon with material removal to define the features (e.g., milling, drilling, laser cutting, etching, etc.). Further, although the module 934 is described with four layers, as will be appreciated by those skilled in the art, various quantities of layers may be utilized in which the features described above may be partially or wholly formed. For example, a third intermediate layer may be provided defining further fluid channels and/or through holes, thereby allowing for further three-dimensional variability (e.g., allowing for fluid paths to cross without intersecting).

As will be appreciated by those skilled in the art, the valves 900 may be arranged to coordinate flow control over various flow paths, to allow for different functions to be achieved. For example, as discussed above, the valves 900 may be used within the drug delivery device 10 to regulate flow between the reservoirs 26, the pump 18, and the needle 15, to allow for reconstitution (with or without cycling), and drug delivery to the patient.

As discussed above, the valves 900 may be provided in various quantities, in separately controlled sub-sets, to allow for separate, but coordinated control. For example, with the first and second actuator gears 918A, 918B, as described above, a first set of six valves 900A is separately controlled from a second set of three valves 900B. FIG. 139C is a copy of FIG. 124, but marked to show schematically possible placement of the first and second sets of valves 900A, 900B, each valve being individually numbered (900A1-900A6 and 900B1-900B3). This arrangement allows for operation as multi-position valves, such as the control valves CV, secondary valves SV, and primary valves PV, discussed above in connection with FIGS. 90-94.

For example, with reference to FIG. 94, the first and second sets of valves 900A, 900B may be used as the control CV, the second control valve CV2, and the third control CV3. In particular, the first set of valves 900A (900A1-900A6) may act as the second control valve CV2 and the third control valve CV3, combined. The second set of valves 900B (900B1-900B3) may act as the control valve CV. FIGS. 139A and 139B show schematically the first set of valves 900A and to which feature each is fluidically coupled with. In addition, the first actuator gear 918A is schematically shown with "clock hands" representing the radial recesses 922 to permit both a connection between the valves 900A located 180 degrees apart (e.g., the valves 900A2 and 900A3), as well as, a connection between adjacent valves 900A (e.g., between the valves 900A5 and 900A1, and between the valves 900A4 and 900A6). FIG. 134 shows the radial recesses 922 in an arrangement on the first actuator gear 918A which permits the "clock hand" connections shown in FIG. 139A.

With the arrangement of the first set of valves 900A1, the first and second fluid channels 946A, 946B may be formed in the second intermediate layer 934C, as shown in FIGS. 139D and 139E. FIGS. 139D and 139E are copies of FIGS. 129 and 130, but marked up to show fluidic connections with the first and second sets of valves 900A, 900B and with various features of the drug delivery device 10. It is additionally noted that fluidic connections are made to, and from, the pump 18. With the pump 18 being unidirectional, flow can be directed in one direction throughout the system, e.g., through a closed loop with the pump 18 being located therealong. This is a slightly different arrangement than shown in FIG. 94. With the first set of valves 900A being arranged as shown in FIGS. 139D and 139E, and in the context of FIG. 94, diluent can be first drawn from the reservoir 26*j*, through the secondary valve SVd, to cause to pass through the pump 18; the diluent can be directed to the second set of valves 900B through a fluid channel designated as CV, to be delivered to a target reservoir 26; the pump 18 may then draw a mixture from the target reservoir 26, through the pump 18, to be directed to the mixing chamber MC; and, the pump 18 may draw the mixture from the mixing chamber MC and direct the flow to the needle 15 for delivery to a patient. In all, this process involves three passes through the pump 18. The process may be varied to include more passes through the pump 18, e.g., for cycling of the drug mixture. Rotational adjustment of the first actuator gear 918A allows for the valves 900A1-900A6 to be selectively opened to permit flow to achieve desired processing. It is noted that flow shall not be continuous, but rather in fixed allotments. It is desired to keep the diameter of fluid channels to a minimum to best ensure suction generated by the pump 18 can properly draw fluid as required, avoiding issues with compressibility of any pockets of air or other residual gases.

As shown in FIGS. 140A-140B, the second set of valves 900B (900B1-900B3) allow for selectively directing flow to a further valving, such as the second control valves SVa, SVb, SVc, to be directed to one or more of the target reservoirs 26. The second actuator gear 918B, as shown in FIG. 134, may be formed with one of the radial recesses 922, thereby allowing for each of the valves 900B1-900B3 be individually selected, as represented by the single "clock hand," in FIG. 140A. The second set of valves 900B may perform the function of the control valve CV shown in FIG. 94. FIG. 139D shows possible flows between the first set of valves 900A and the second set of valves 900B.

The module 934 may be provided as a stand-alone element coupleable to adjacent elements as part of the drug delivery device 10. As shown in FIGS. 141-148B, the module 934 may be formed integrally with portions of the drug delivery device 10, such as being coupled to, or formed integrally with, portions of the body 12. As shown in FIGS. 142 and 147, the actuator gear(s) 918 (918A, 918B) may be located interiorly of the module 934 so as to be fully within the drug delivery device 10. In this manner, as shown in FIGS. 148A-148B, the valves 900 may be configured to deflect in a downward (towards the interior) direction in opening (FIG. 148B). The module 934 may be formed multi-layered, as described above, with the first fluid channels 946A and/or the second fluid channels 946B being in fluid communication with one or more of the fluid ducts 22 and/or the outlet ducts 25. The reservoir 26*j* for the diluent may be provided in similar form to that shown in FIG. 104, and discussed relevant thereto, to overlie portions of the body 12, including the module 934. A printed circuit board 1000, or the like, may be also provided to overlie portions of the body 12. The printed circuit board 1000 may provide electrical connections between various components and support components, such as control elements (such as EEPROM's, microcontrollers, and the like) and/or power storage and regulating elements (such as power storage, voltage regulation, and the like). The overlaid arrangement of the elements provides the drug delivery device 10 with a compact profile.

FIG. 142 shows the drug delivery device 10 of FIG. 141, but with the reservoir 26*j* removed. FIG. 143 shows the drug delivery device 10 of FIG. 141, but with the reservoir 26*j* removed and the barrier 102 removed from the body 12. FIG. 144 shows FIG. 143 in transparency to show internal passageways.

FIGS. 145 and 146 show the module 934 useable with the drug delivery device 10 of FIG. 141. As shown, the multi-layer structure of the module 934 provides rigidity thereto. Elements such as the control 20, the pump 18, and one or more motors may be mounted to the module 934, to be supported thereby. This allows for pre-fabrication with later assembly to form the drug delivery device 10.

With reference to FIG. 146, flow paths, formed by the fluid ducts 22, between the first and second valves 900A, 900B, as described above, and the reservoirs 26, are configured in the module as shown schematically in FIGS. 91-94. The reservoirs 26 are not shown in FIG. 146, but locations of valving (primary valves PV and secondary valves SV) used to control flow to and from the reservoirs 26 are marked. These locations in the drug delivery device 10 may be formed as valve seats, as described above.

As will be appreciated by those skilled in the art, the module 934 may be formed with various configurations, including footprints, to overlie, and provide fluidic connections, between various components of the drug delivery device 10. FIGS. 149-155 show an alternate exemplary embodiment of the module 934. As shown in FIG. 151, the module 934 may be configured to overlie the diluent reservoir 26*j*, formed as a low-profile, collapsible reservoir as described above, the first and second actuator gears 918A, 918B, mixing container MC, and the pump 18. As shown in FIGS. 152-154, the module 934 may define the fluid ducts 22 to fluidically connect components, as described above. As shown in FIG. 155, one or more of the fluid ducts may be defined by a tube 22'.

Figure 156:
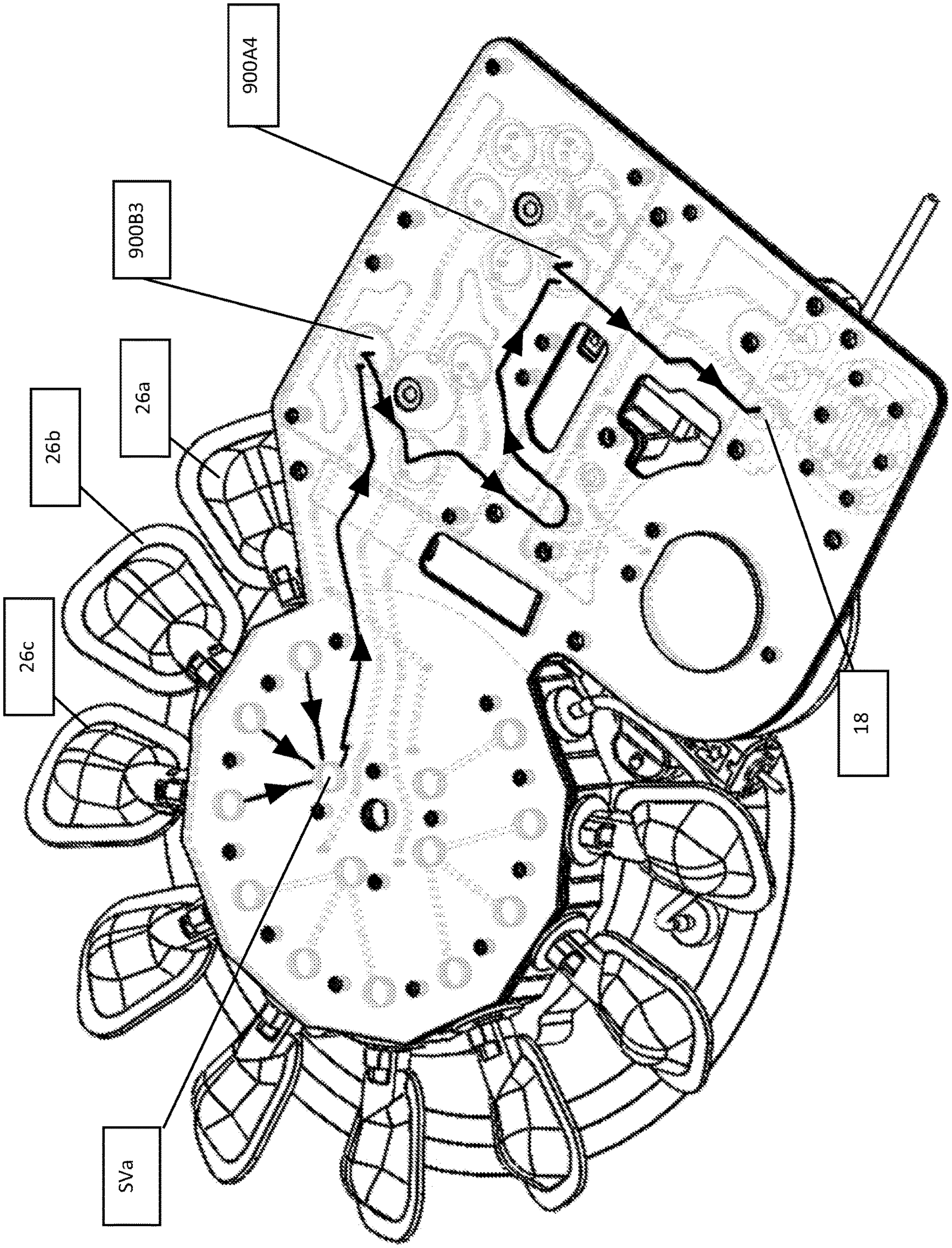
Figure 157:
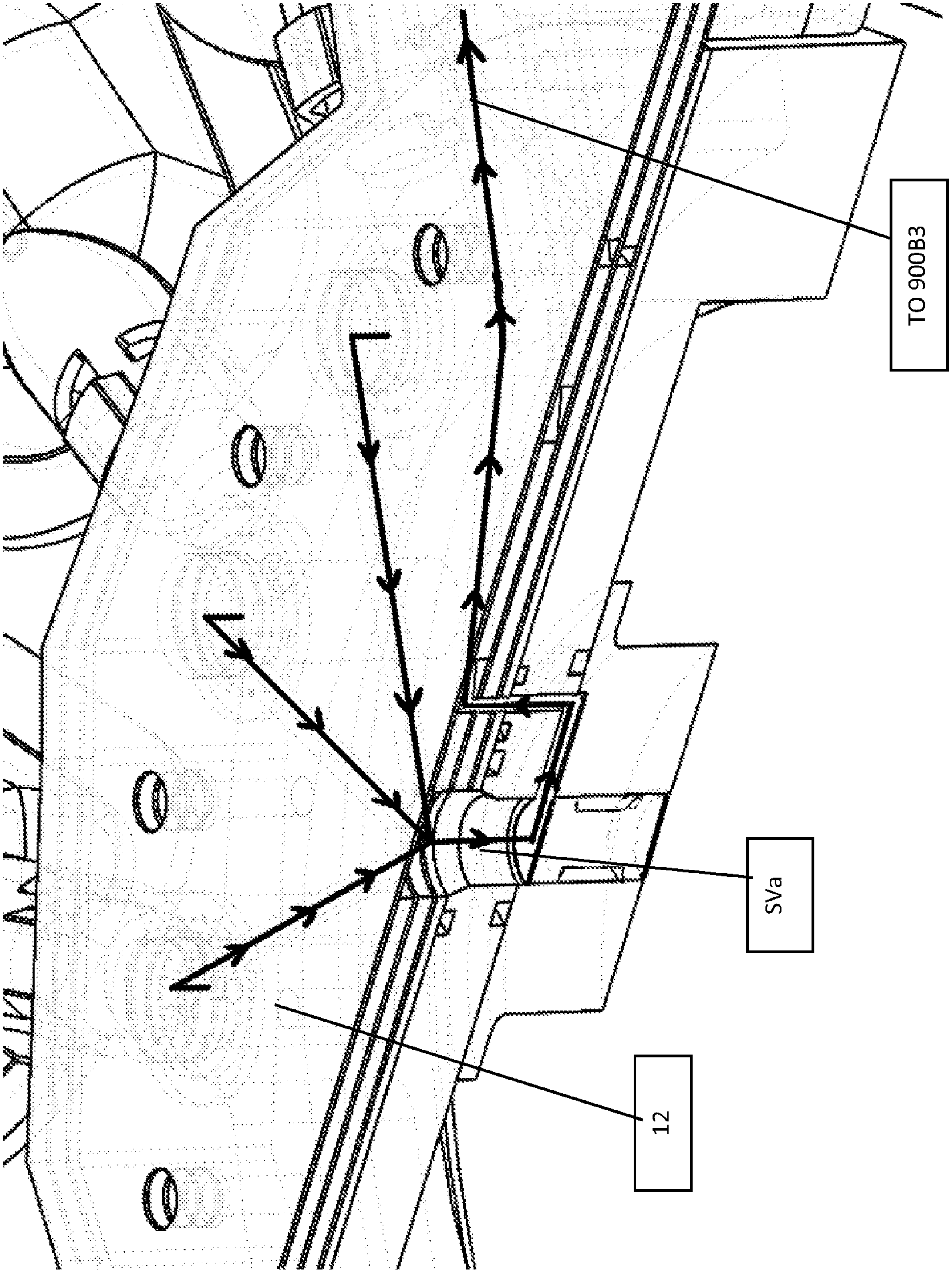
Figure 158:
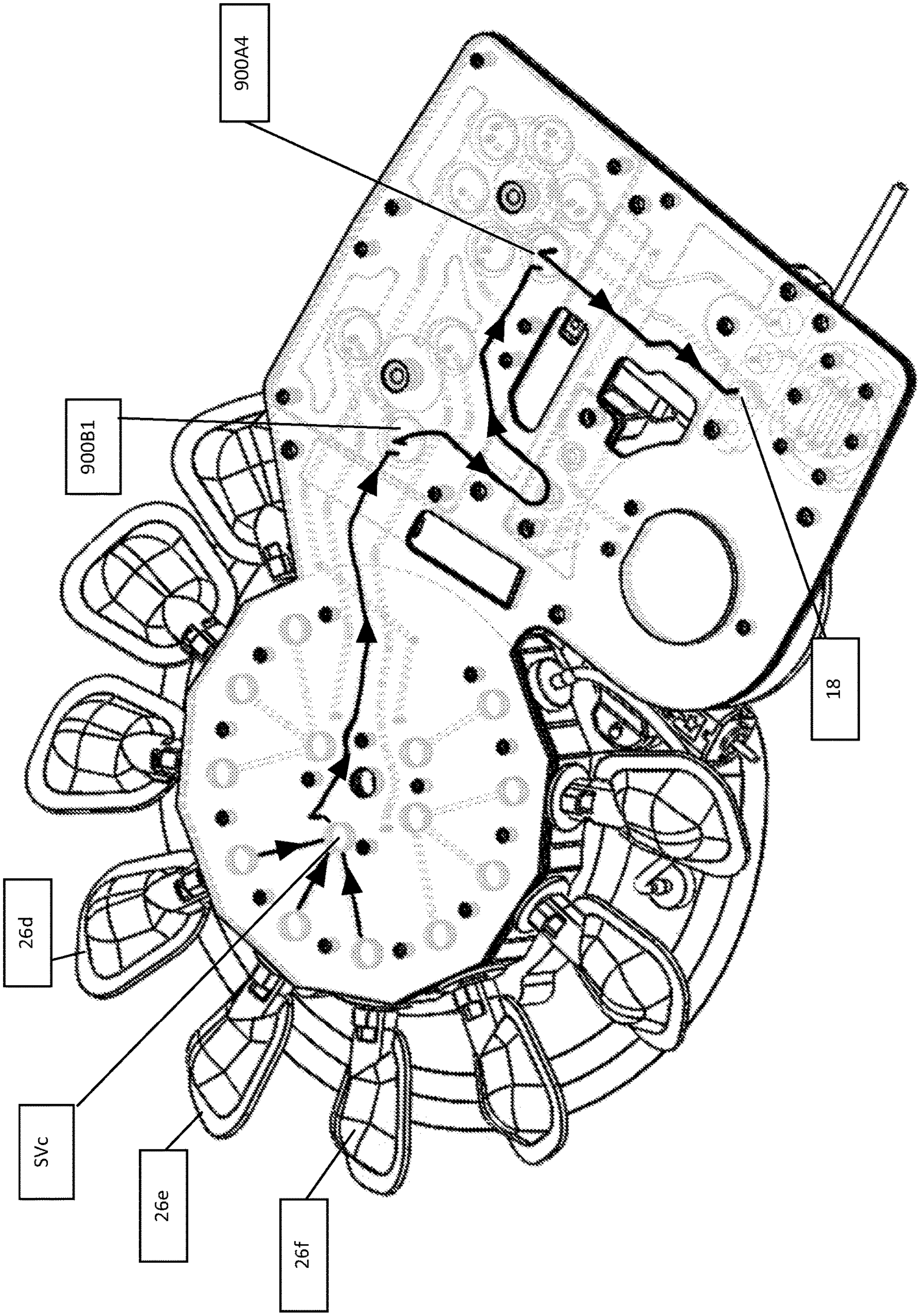
Figure 159:
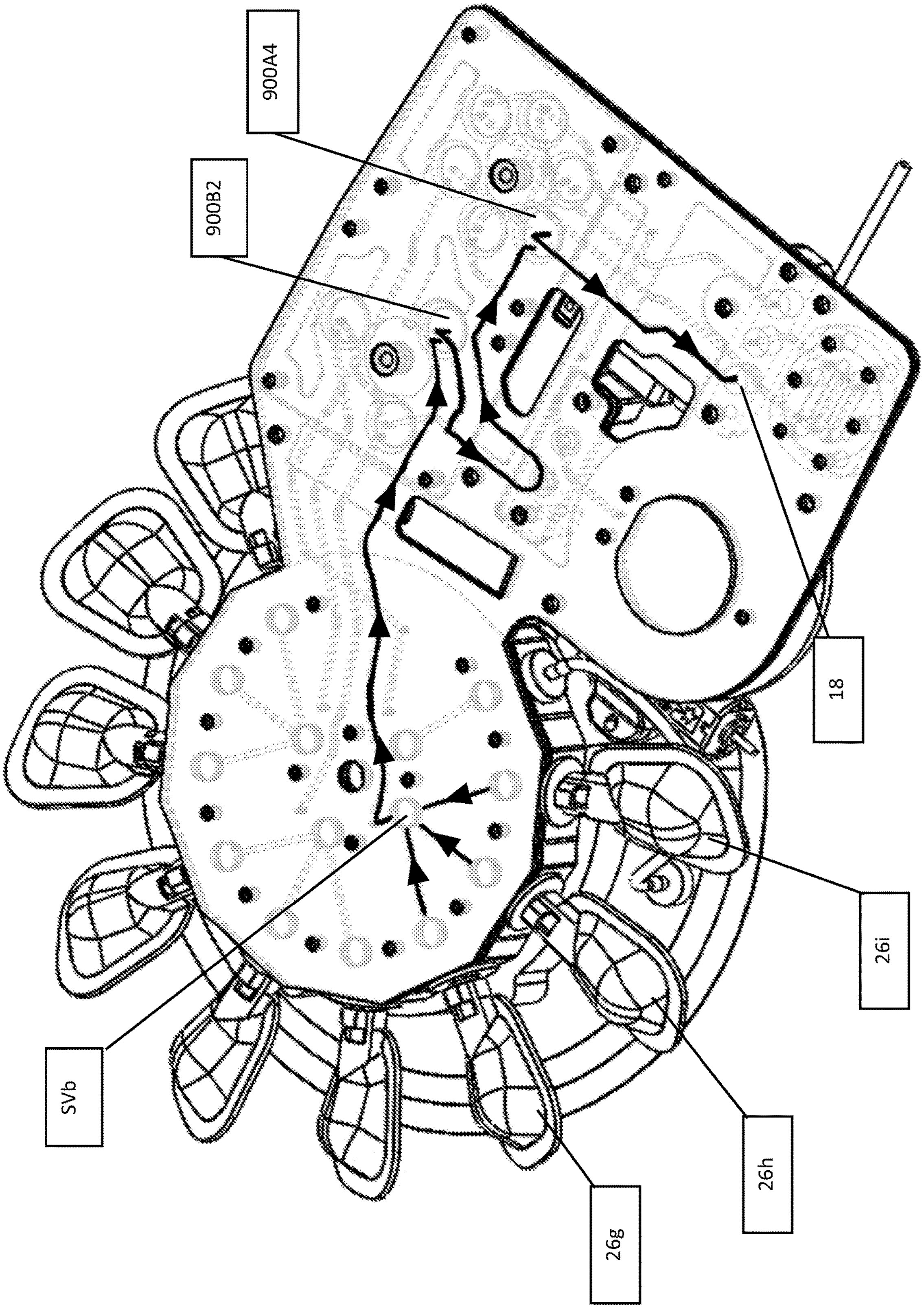
Figure 160:
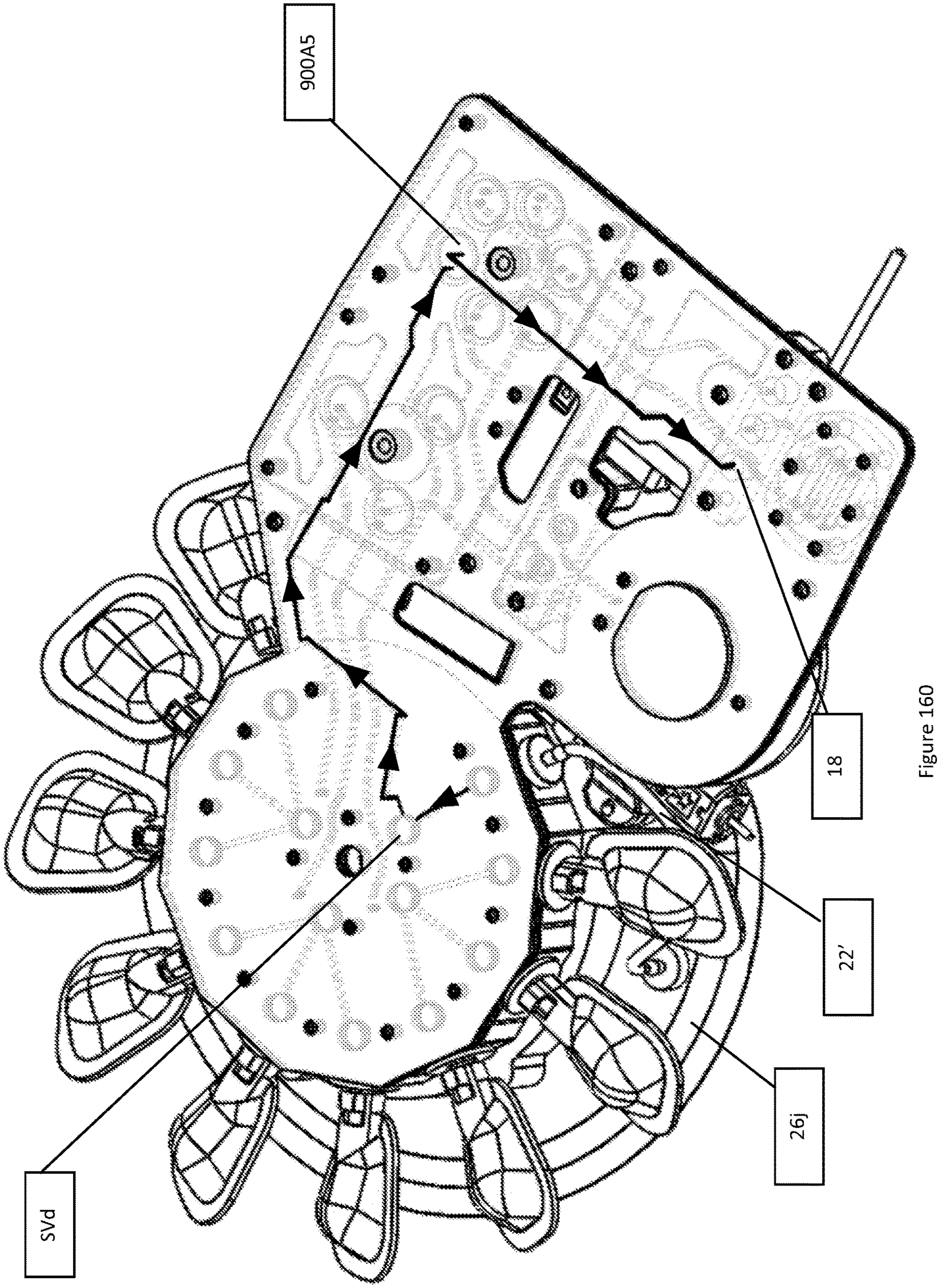

FIGS. 156-167 show exemplary fluid flows of the drug delivery device 10, in accordance with the description above. FIGS. 156-159 show fluid being drawn from the reservoirs under negative pressure of the pump 18. FIGS. 156-157 show fluid being drawn from the reservoirs 26*a*, 26*b*, 26*c* to the pump 18, via the secondary valve SVa, the second valve 900B3, and the first valve 900A4. As shown in FIG. 158, fluid may be drawn from the reservoirs 26*d*, 26*e*, 26*f* to the pump 18, via the secondary valve SVc, the second valve 900B1, and the first valve 900A4. Further, as shown in FIG. 159, fluid may be drawn from the reservoirs 26*g*, 26*h*, 26*i* to the pump 18, via the secondary valve SVb, the second valve 900B2, and the first valve 900A4. As discussed above, use of the primary valves (PVa-Pvi) allows control of flow from individual reservoirs. FIG. 160 shows fluid (diluent) being drawn from the diluent reservoir 26*j* to the pump 18, via the fluid duct 22', the secondary valve SVd, and the first valve 900A5.

Figure 161:
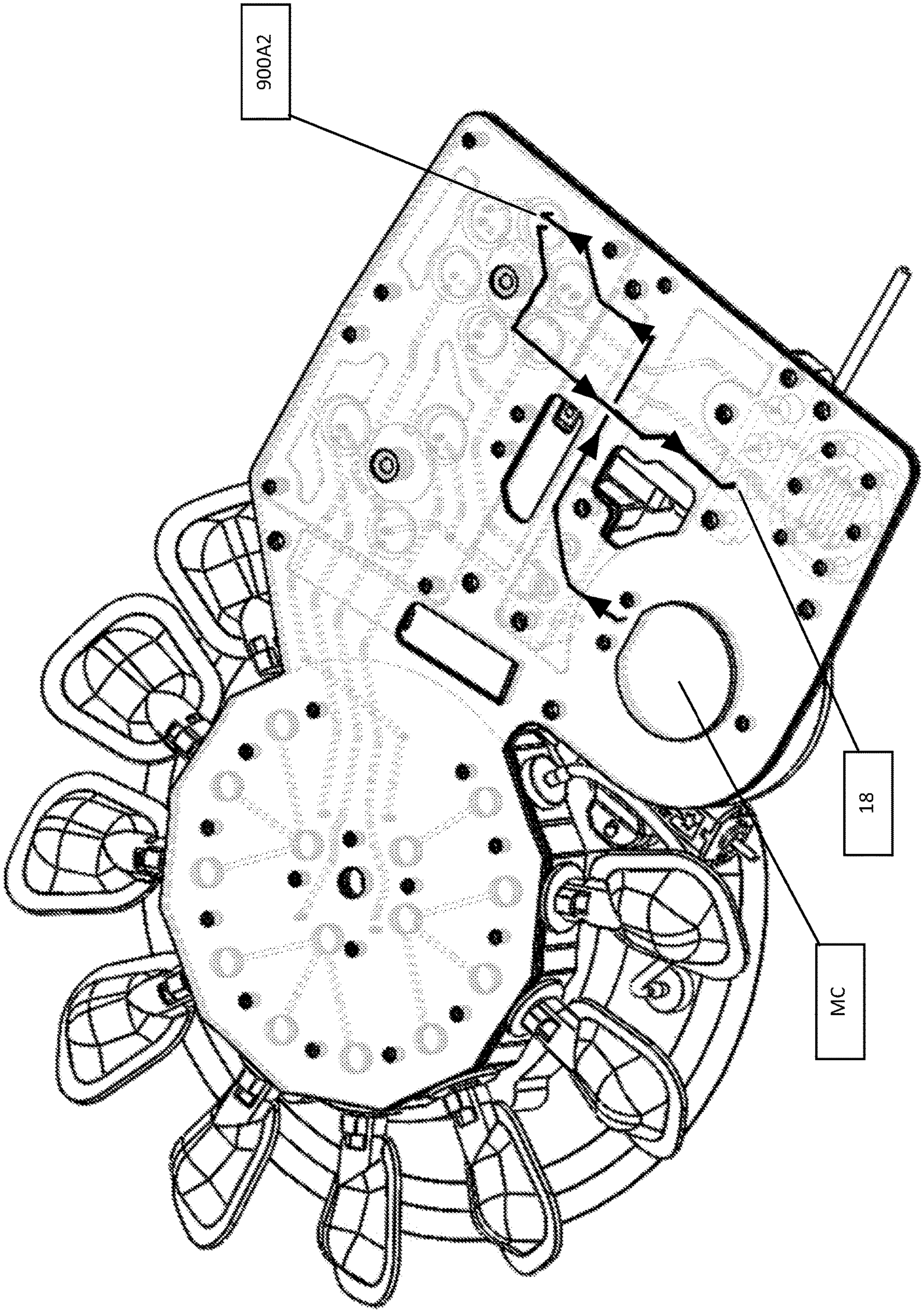

As shown in FIG. 161, fluid may be drawn from the mixing container MC to the pump 18, via the first valve 900A2.

Figure 162:
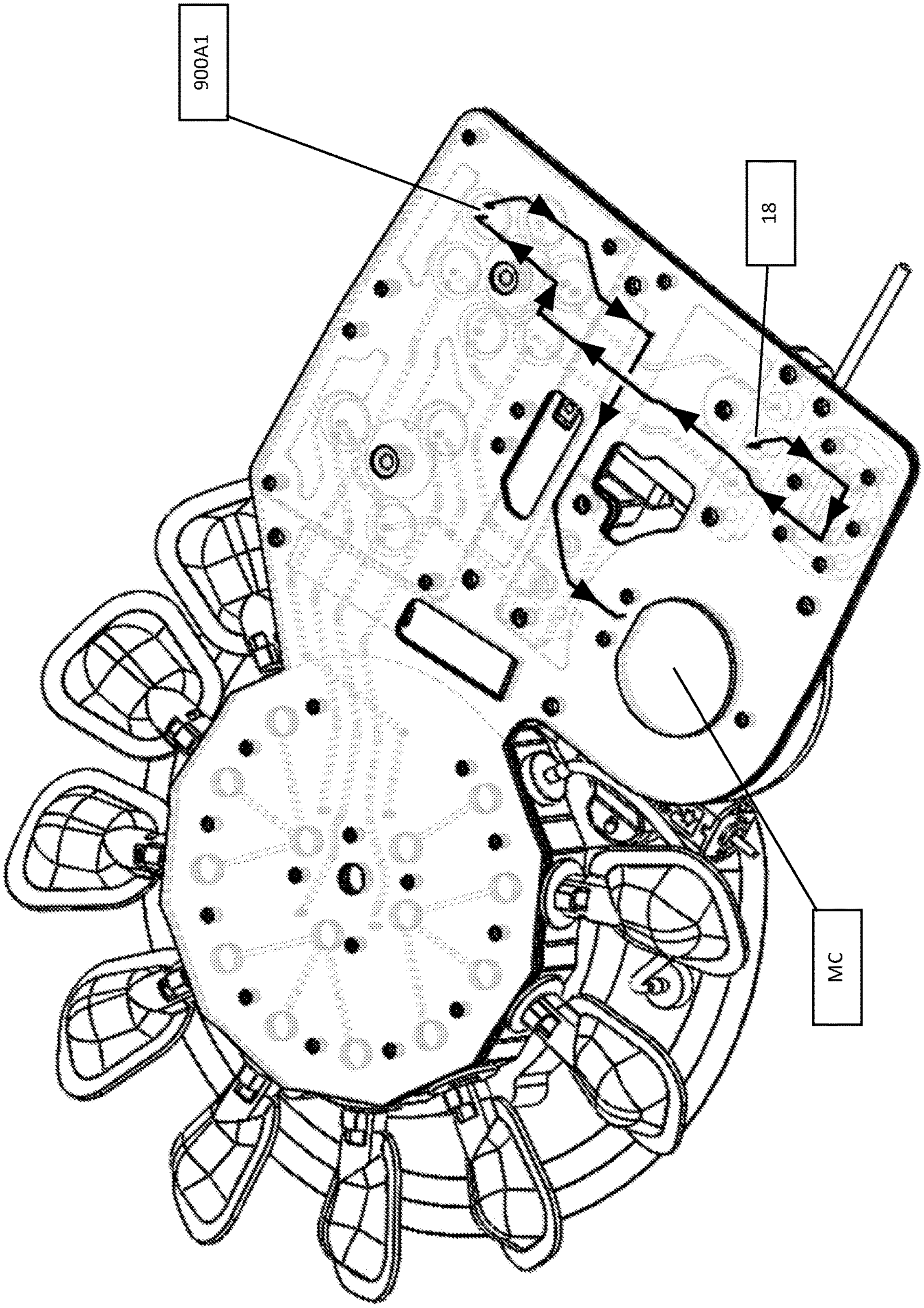

FIGS. 156-161 show flows in the negative, or suction, side of the pump 18. In other words, these flows are all drawn to the pump 18. Once drawn to the pump 18, the fluid may be urged, under positive pressure of the pump 18, to a target location, as directed by adjusted valving. For example, FIG. 162 shows fluid being urged from the pump 18 to the mixing container MC, via the first valve 900A1. Thus, by combining any of the fluid flows of FIGS. 156-160 with the flow of FIG. 162, fluid may be drawn from any of the reservoirs 26*a*-26*i* and the diluent reservoir 26*j* and urged to the mixing container MC.

Figure 163:
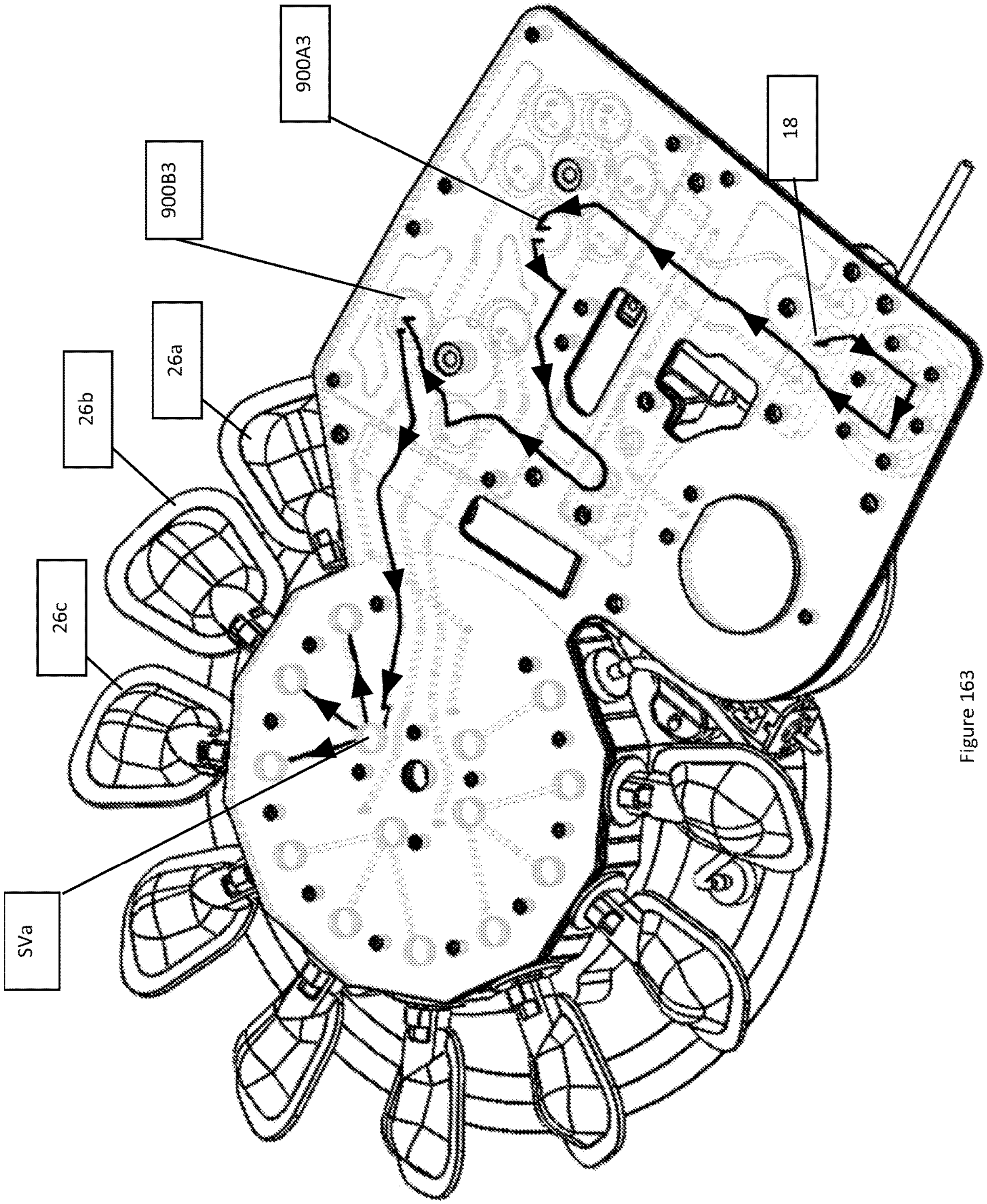
Figure 164:
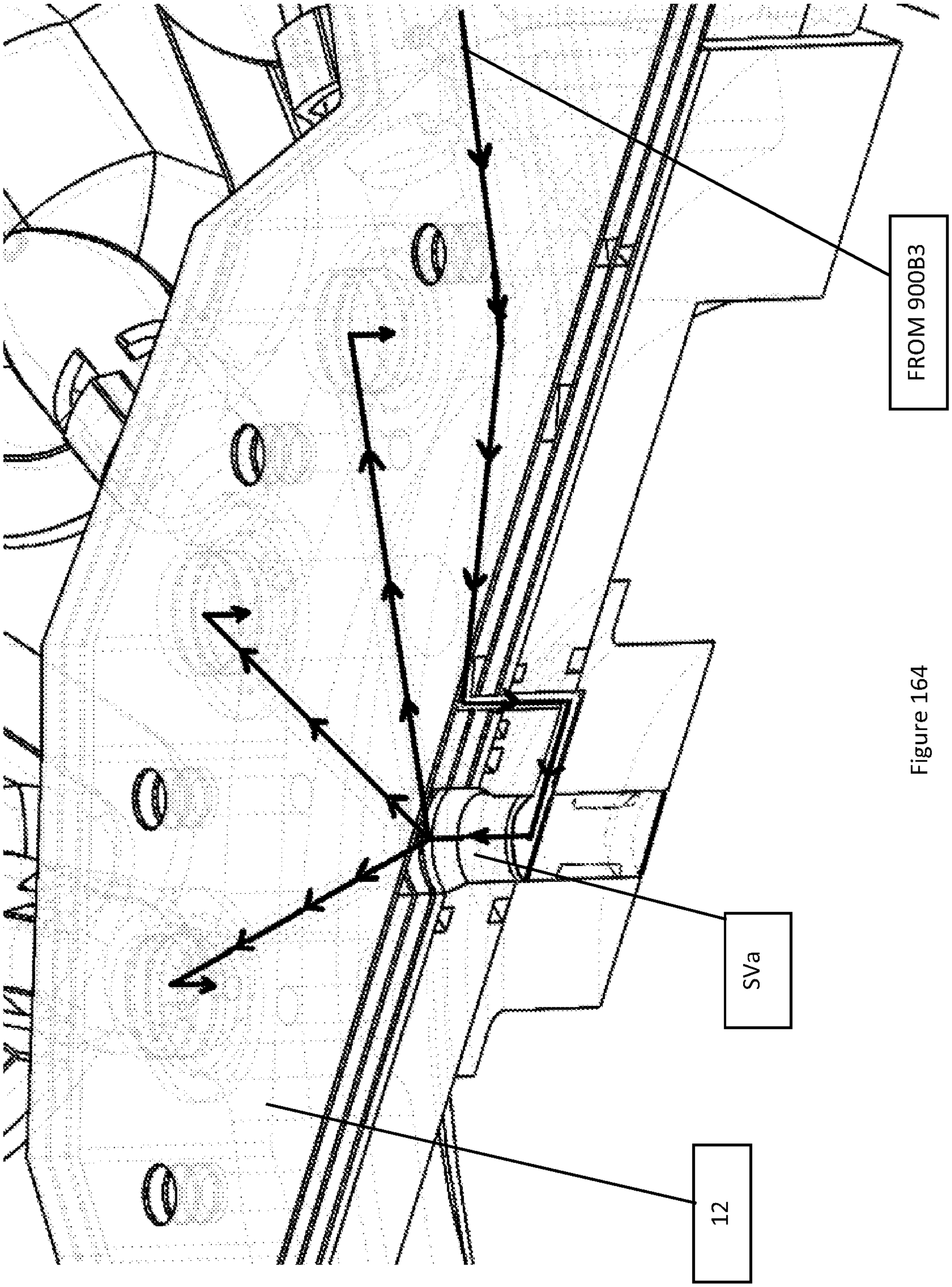
Figure 165:
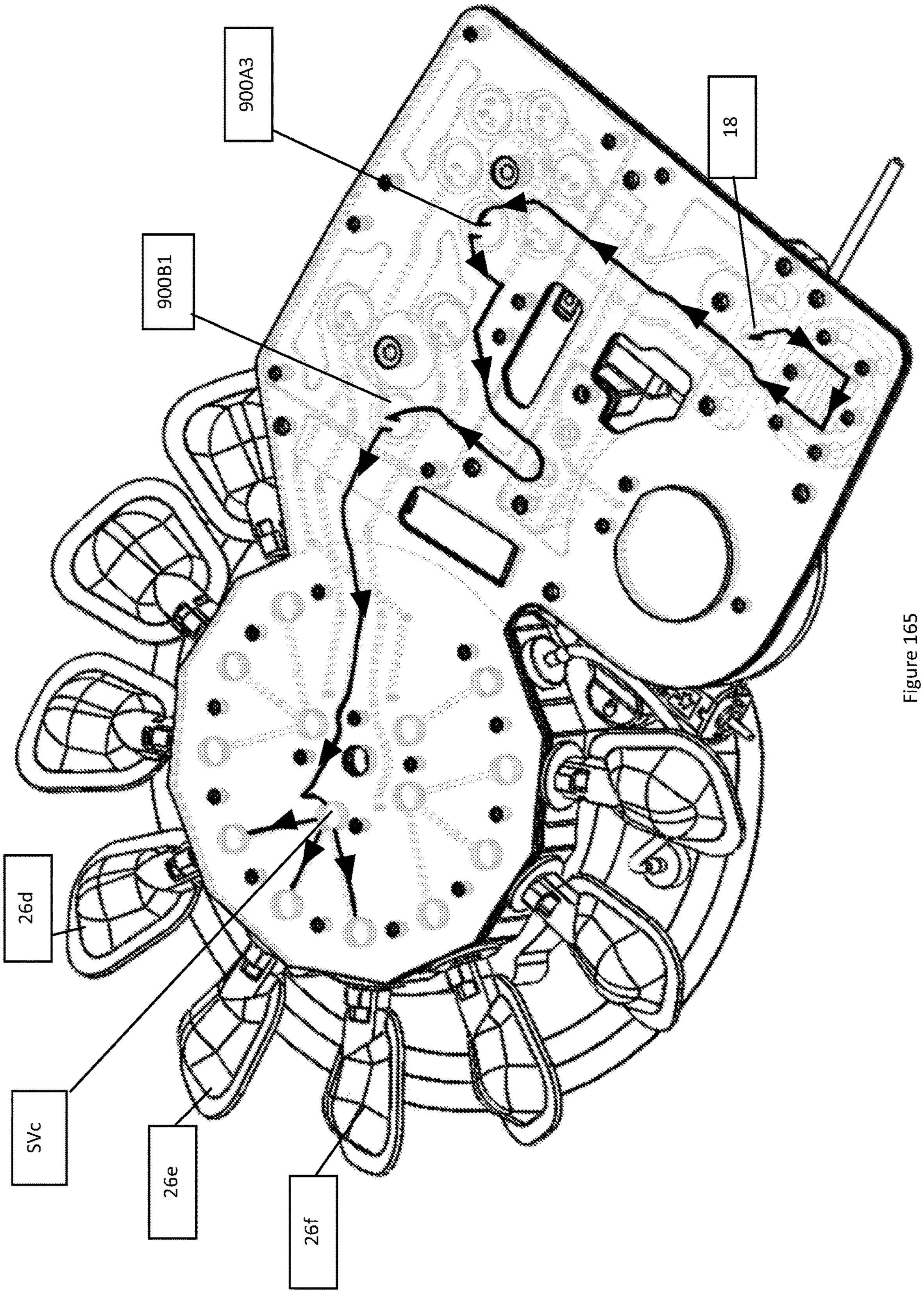
Figure 166:
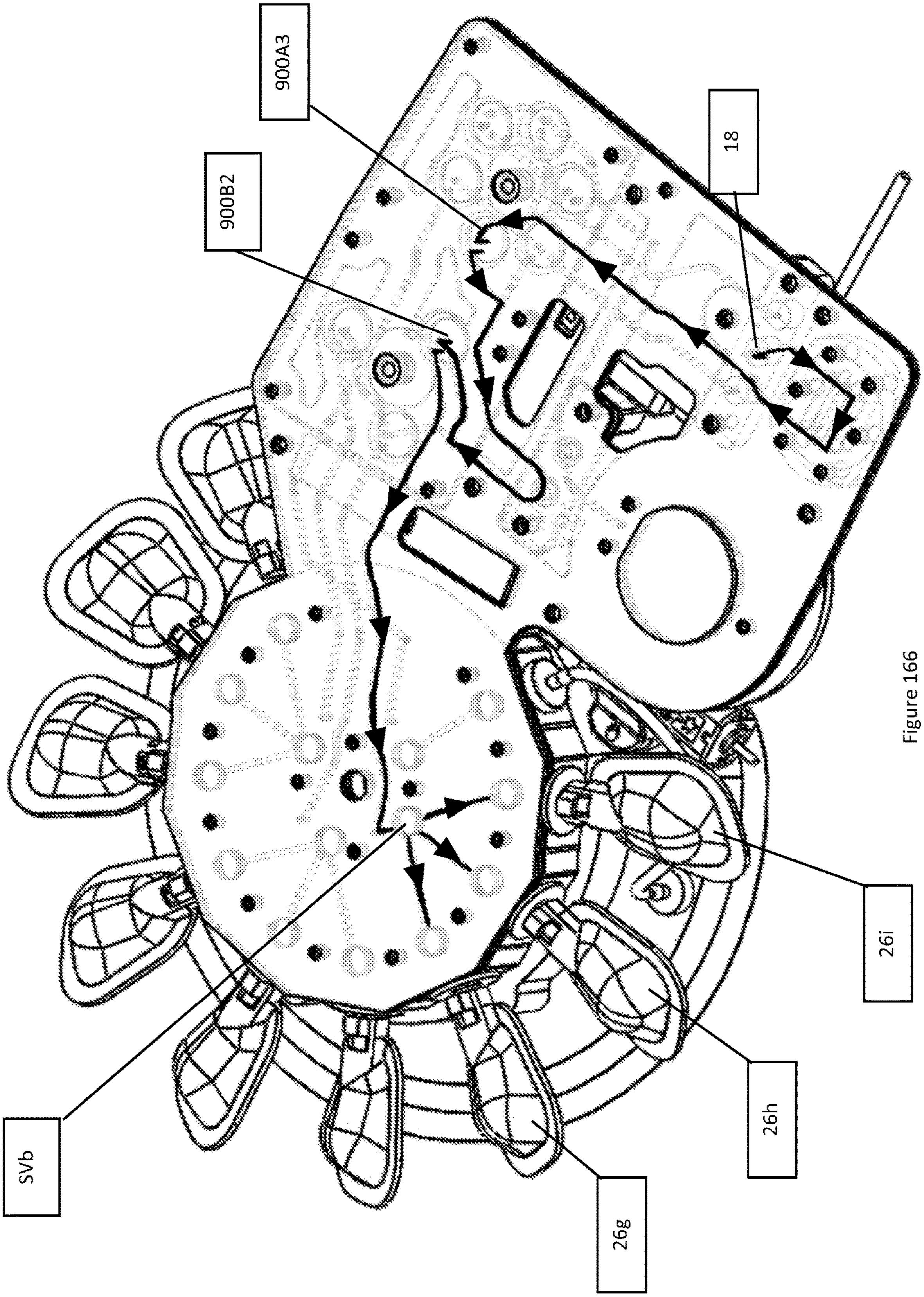

The pump 18 may also urge fluid to any of the reservoirs 26*a*-26*i*. For example, as shown in FIGS. 163-164, fluid may be urged from the pump 18 to any of the reservoirs 26*a*, 26*b*, 26*c*, via the first valve 900A3, the second valve 900B, and the secondary valve SVa. Likewise, fluid may be urged from the pump 18 to any of the reservoirs 26*d*, 26*e*, 26*f* (FIG. 165; via the first valve 900A3, the second valve 900B1, and the secondary valve SVc) and the reservoirs 26*g*, 26*h*, 26*i* (FIG. 166; via the first valve 900A3, the second valve 900B2, and the secondary valve SVb). Thus, by combining any of the fluid flows of FIGS. 163-166 with the fluid flow of FIG. 161, fluid may be drawn from the mixing chamber MC and urged to any of the reservoirs 26*a*-26*i*, e.g., to facilitate cycling of the drug, as described above. Again, the primary valves PVa-PVi may be utilized to control flow to individual reservoirs.

Figure 167:
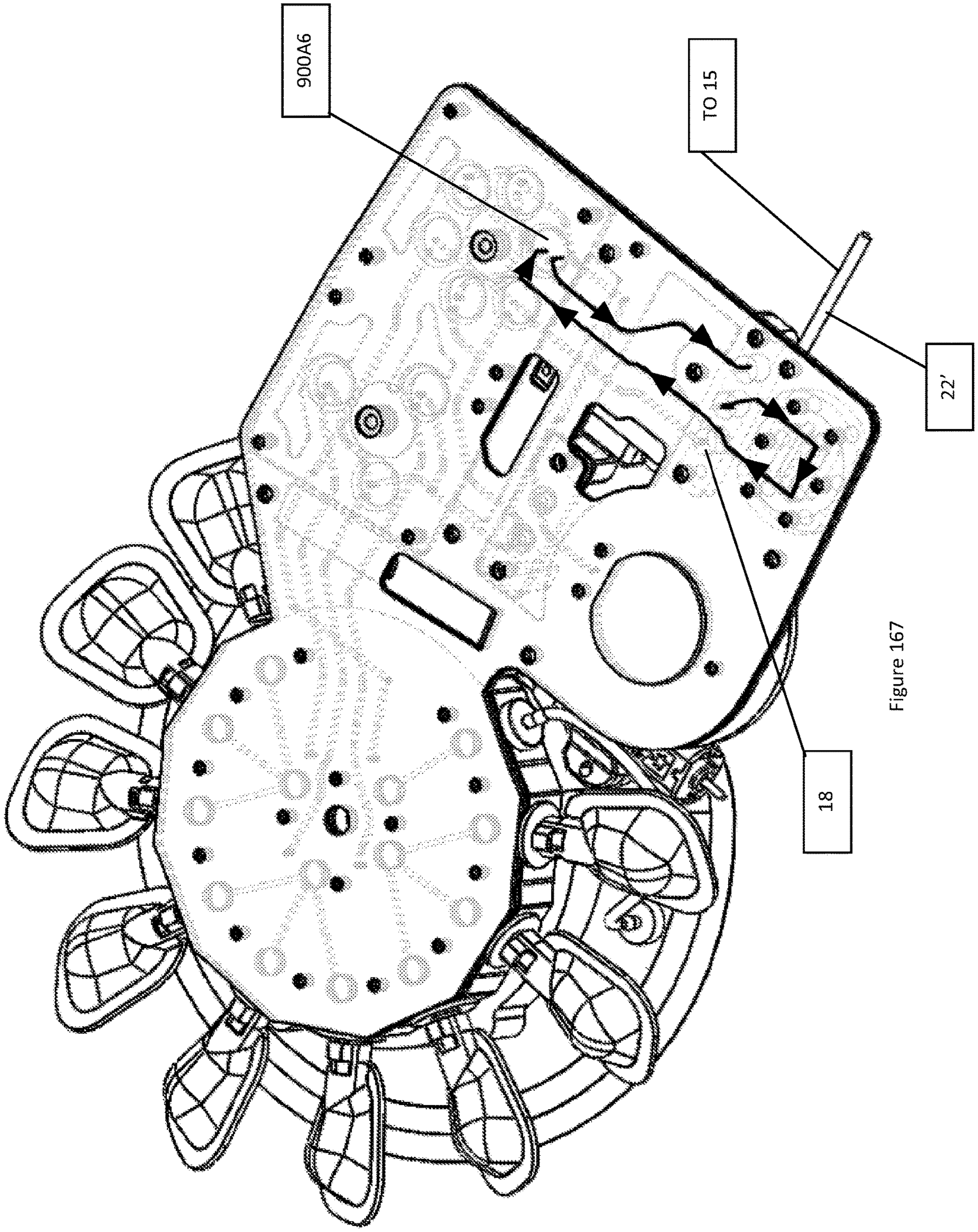

The flows described above allows for accessing drug and diluent, with mixing and cycling, as necessary. Once the drug is ready for administration, the drug may be drawn to the pump 18, and, as shown in FIG. 167, may be urged from the pump 18 to the needle 15, via the first valve 900A6, and the fluid duct 22'. The needle 15 is utilized to deliver the drug to a patient.

Figure 168:
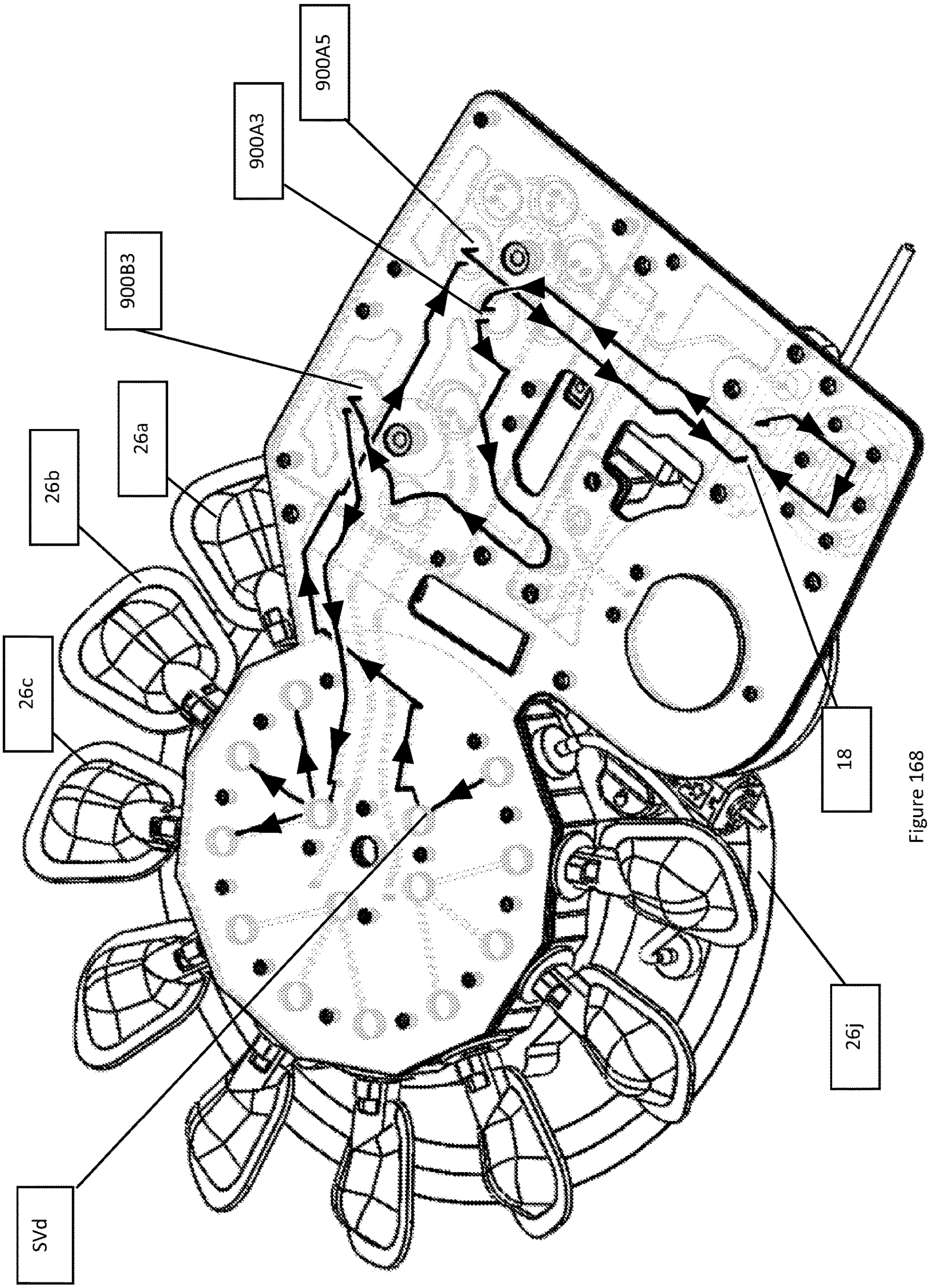

FIGS. 168-172 show examples of complete flows, both showing the drawing in, from a initial location, and urging to a target location, by the pump 18. FIG. 168 shows diluent being drawn from the diluent reservoir 26*j* and urged to any of the reservoirs 26*a*, 26*b*, 26*c*. This allows for introduction of the diluent as an initial step where drug is initially in solid or slurry form in any of the reservoirs. Similar flows may be used to provide diluent to any of the reservoirs 26*d*-26*i*.

Figure 169:
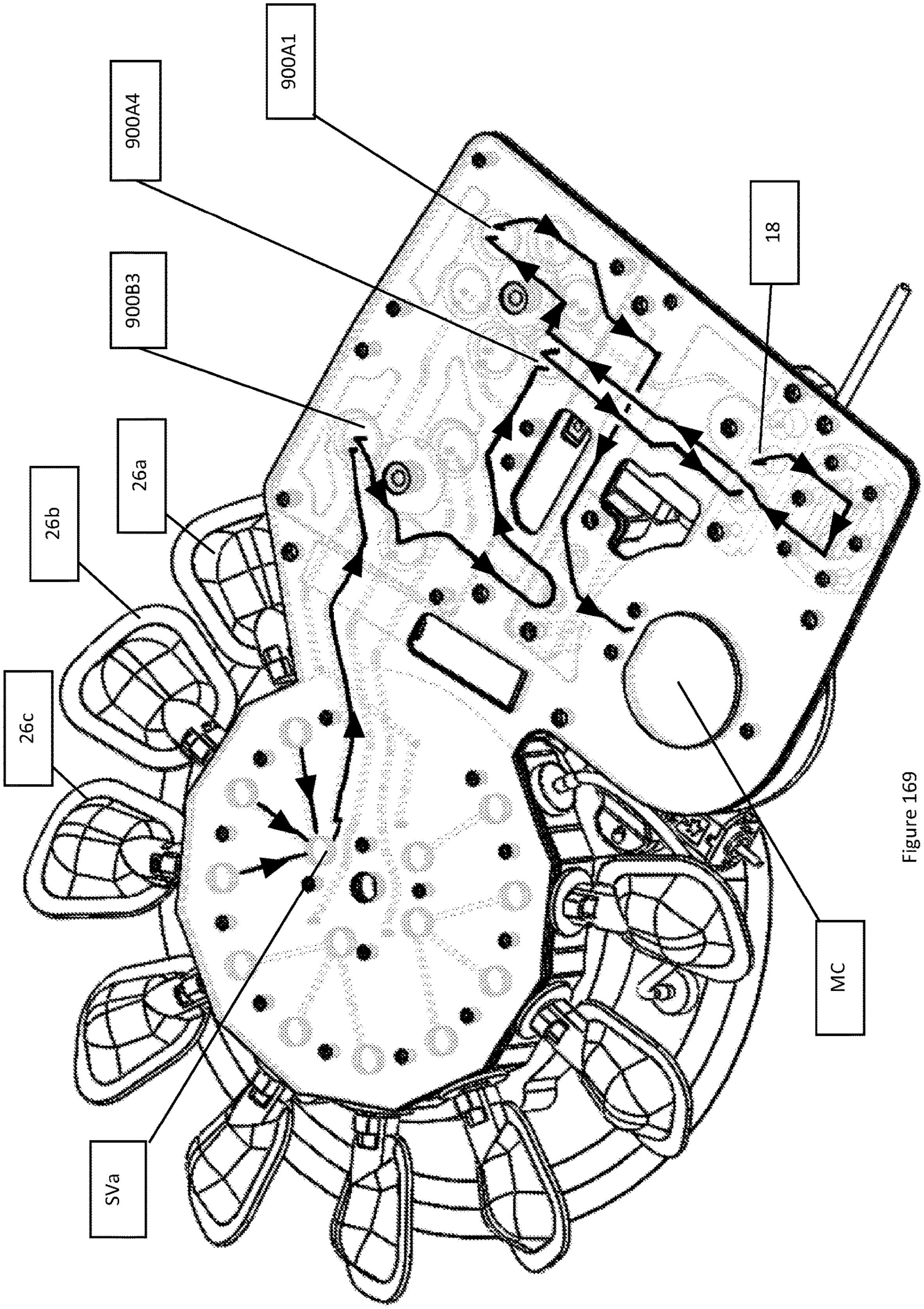

FIG. 169 shows fluid being drawn from any of the reservoirs 26*a*, 26*b*, 26*c* and urged to the mixing container MC. Similar flows may be used to draw fluid from any of the reservoirs 26*d*-26*i* and urged to the mixing container MC.

Figure 170:
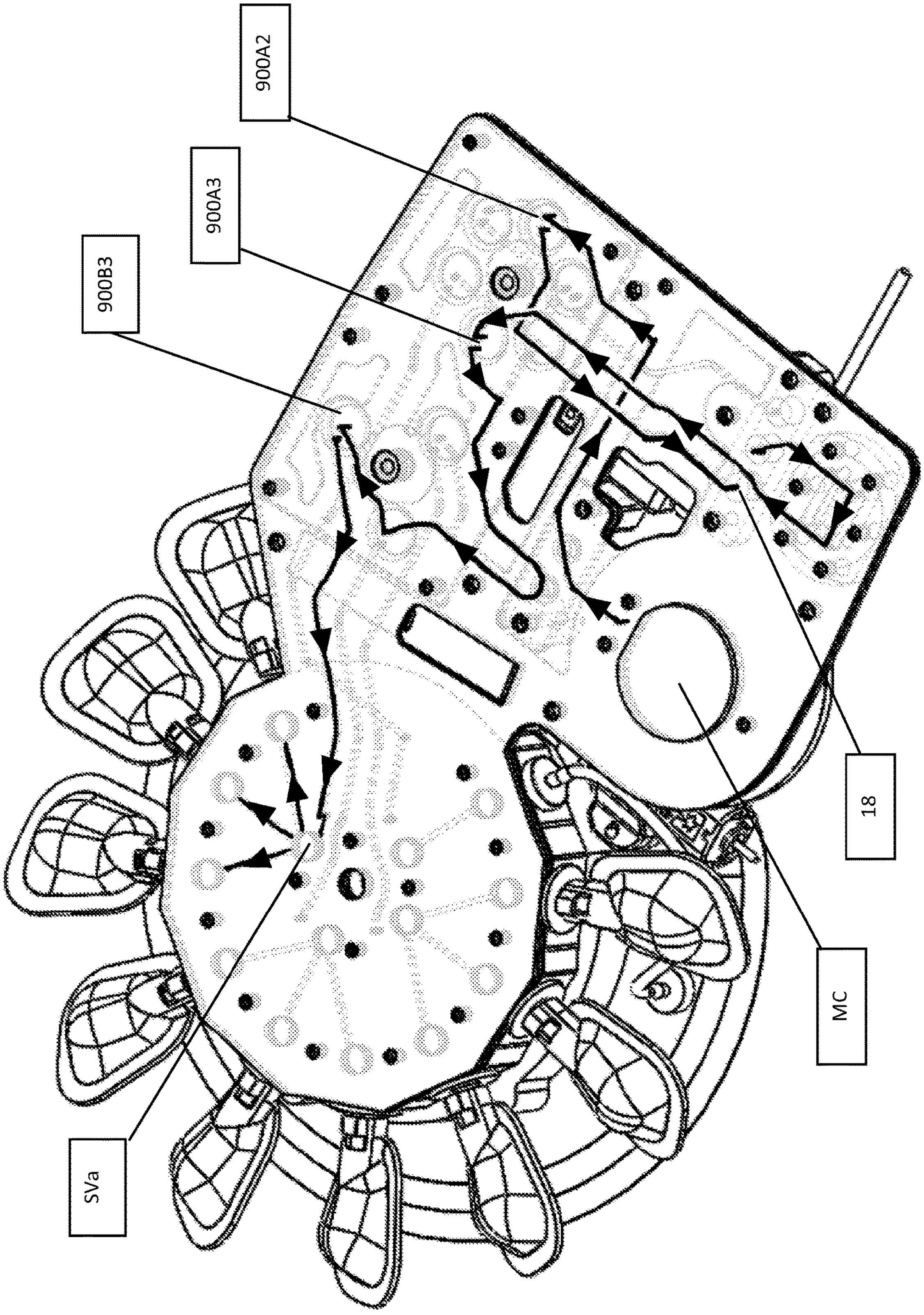

FIG. 170 shows reverse flow from FIG. 169. Here, fluid is drawn from the mixing container MC and urged to any of the reservoirs 26, 26*b*, 26. Again, similar flows may be used to draw fluid from the mixing container and urged to any of the reservoirs 26*d*-26*i*.

Figure 171:
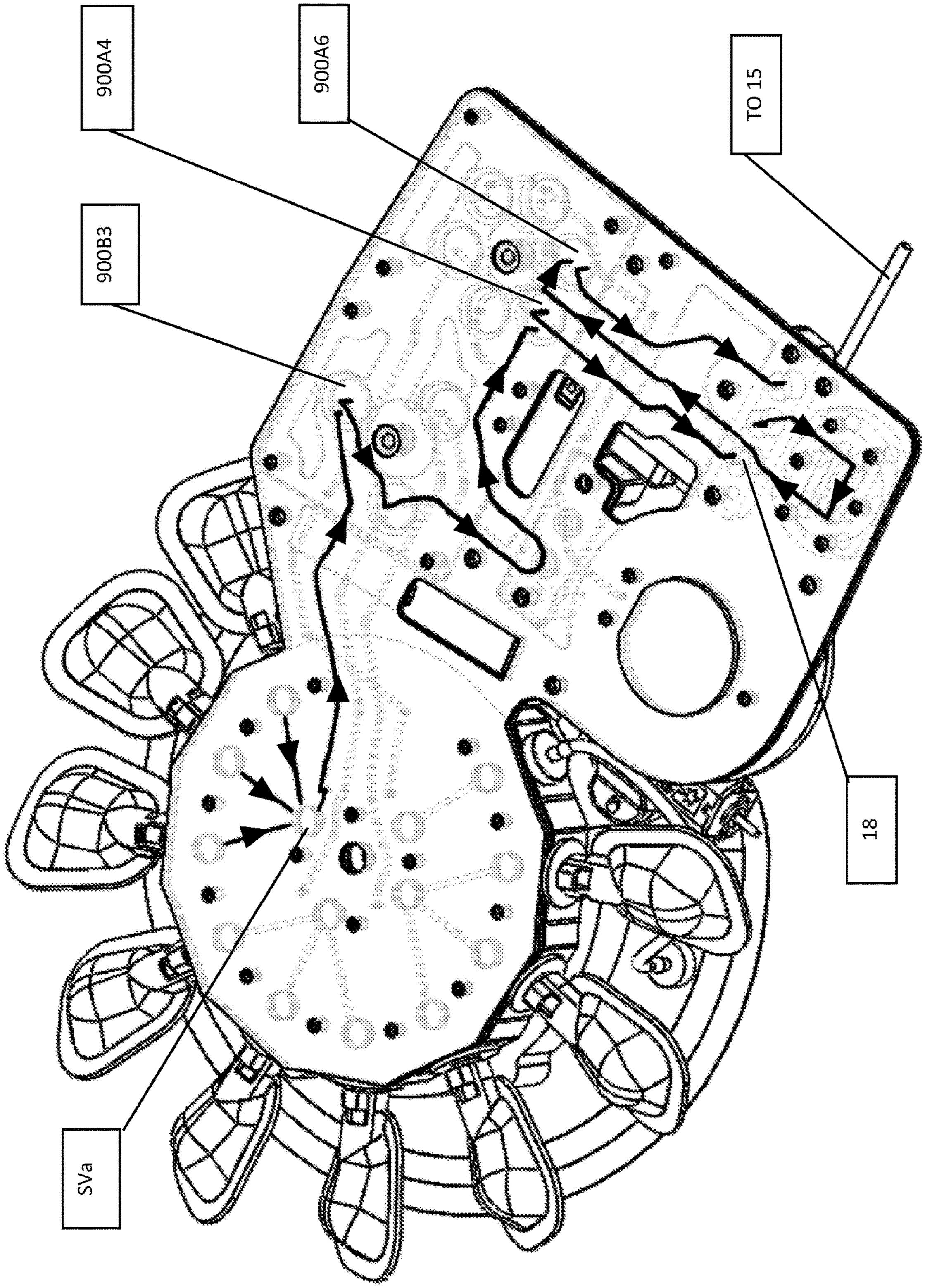

FIG. 171 shows fluid being drawn from any of the reservoirs 26*a*, 26*b*, 26*c* and urged to the needle 15. Here, drug is ready for administration. Similar flows may be used to draw fluid from any of the reservoirs 26*d*-26 and urged to the needle 15.

Figure 172:
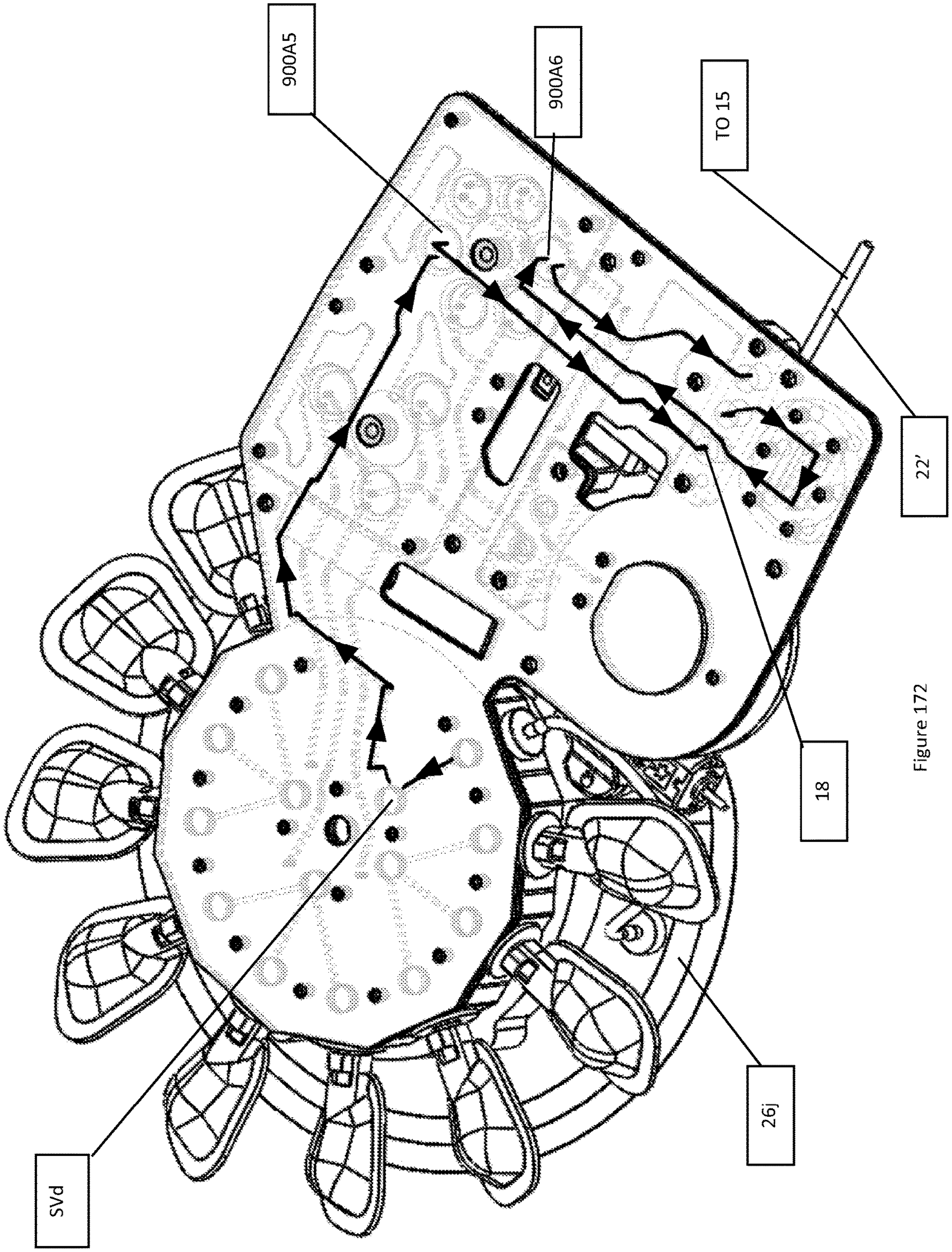

FIG. 172 shows fluid (diluent) being drawn from the diluent reservoir 26*j* and urged to the needle 15. This allows for flushing of the fluid duct 22' leading to the needle 15 and of the needle 15 itself. This also allows for establishment of priming, if necessary.

What is claimed is:

1. A drug delivery device comprising:

a body having a plurality of fluid ducts and at least one outlet duct formed therein; and, a plurality of drug cartridges attached to the body, the drug cartridges each including a reservoir for accommodating at least one drug, wherein, a first of the drug cartridges includes a fluid outlet, wherein, a first of the fluid ducts, is aligned to extend from the fluid outlet, wherein, an adjustable seal, formed by a sealing sheet joined to a sealing surface, selectively seals the fluid outlet, the seal being adjustable from a first state, where the fluid outlet is sealed, to a second state, where the fluid outlet is not sealed, wherein the sealing sheet is secured to a shiftable sealing element, and, wherein displacement of the shiftable sealing element causes delamination of the sealing sheet from the sealing surface and results in adjustment of the seal from the first state to the second state.

2. The drug delivery device of claim 1, wherein the shiftable sealing element includes multiple open passageways which come into alignment with the fluid outlet with the seal being in the second state.

3. The drug delivery device of claim 2, wherein the open passageways are provided at multiple radial locations about the shiftable sealing element.

4. The drug delivery device of claim 1, wherein the shiftable sealing element is displaced in response to pressure being applied thereto.

5. The drug delivery device of claim 1, wherein the shiftable sealing element is initially seated in a well, the sealing surface being located about the well.

6. The drug delivery device of claim 5, wherein the shiftable sealing element is displaced to protrude from the well in causing the sealing sheet to delaminate from the sealing surface.

7. The drug delivery device of claim 5, wherein the fluid outlet includes a divergent portion leading into the well and a convergent portion leading out of the well.

8. The drug delivery device of claim 1, wherein the sealing sheet is a thermoformable film.

* * * * *